US011787780B2

(12) United States Patent
Hunt et al.

(10) Patent No.: US 11,787,780 B2
(45) Date of Patent: Oct. 17, 2023

(54) QUATERNARY INDAZOLE GLUCOCORTICOID RECEPTOR ANTAGONISTS

(71) Applicant: CORCEPT THERAPEUTICS INCORPORATED, Menlo Park, CA (US)

(72) Inventors: Hazel Hunt, Storrington (GB); Lorna Duffy, Nottingham (GB); Ian Strutt, Nottingham (GB); Morgan Jouanneau, Nottingham (GB); Thomas Hornsby, Nottingham (GB); Mark Mills, Nottingham (GB); Andrew William Phillips, Nottingham (GB); Jon-Paul Ward, Nottingham (GB)

(73) Assignee: Corcept Therapeutics Incorporated, Menlo Park, CA (US)

( * ) Notice: Subject to any disclaimer, the term of this patent is extended or adjusted under 35 U.S.C. 154(b) by 65 days.

(21) Appl. No.: 17/353,567

(22) Filed: Jun. 21, 2021

(65) Prior Publication Data
US 2023/0032612 A1 Feb. 2, 2023

Related U.S. Application Data

(60) Provisional application No. 63/042,188, filed on Jun. 22, 2020.

(51) Int. Cl.
| | | |
|---|---|---|
| *C07D 401/14* | (2006.01) | |
| *C07D 403/04* | (2006.01) | |
| *C07D 403/12* | (2006.01) | |
| *C07D 403/14* | (2006.01) | |
| *C07D 231/56* | (2006.01) | |
| *C07D 409/14* | (2006.01) | |
| *C07D 413/14* | (2006.01) | |
| *C07D 487/04* | (2006.01) | |

(52) U.S. Cl.
CPC ......... *C07D 401/14* (2013.01); *C07D 231/56* (2013.01); *C07D 403/04* (2013.01); *C07D 403/12* (2013.01); *C07D 403/14* (2013.01); *C07D 409/14* (2013.01); *C07D 413/14* (2013.01); *C07D 487/04* (2013.01)

(58) Field of Classification Search
CPC .. C07D 401/14; C07D 403/04; C07D 403/12; C07D 403/14
See application file for complete search history.

(56) References Cited

U.S. PATENT DOCUMENTS

| | | | |
|---|---|---|---|
| 7,238,696 | B2 | 7/2007 | Wyeth |
| 7,678,813 | B2 | 3/2010 | Clark et al. |
| 7,928,237 | B2 | 4/2011 | Clark et al. |
| 8,324,203 | B2 | 12/2012 | Clark et al. |
| 8,557,839 | B2 | 10/2013 | Williams et al. |
| 8,598,154 | B2 | 12/2013 | Clark et al. |
| 8,859,774 | B2 | 10/2014 | Hunt et al. |
| 9,273,047 | B2 | 3/2016 | Hunt et al. |
| 9,707,223 | B2 | 7/2017 | Hunt et al. |
| 9,956,216 | B2 | 5/2018 | Hunt et al. |
| 10,047,082 | B2 | 8/2018 | Hunt et al. |
| 10,323,034 | B2 | 6/2019 | Hunt et al. |
| 10,456,392 | B2 | 10/2019 | Hunt et al. |
| 10,464,927 | B2 | 11/2019 | Zheng et al. |
| 10,787,449 | B2 | 9/2020 | Hunt et al. |
| 10,793,576 | B2 | 10/2020 | Li et al. |
| 10,973,813 | B2 | 4/2021 | Hunt et al. |
| 11,370,789 | B2 | 6/2022 | Hunt et al. |
| 2004/0138286 | A1 | 7/2004 | Imazaki et al. |
| 2007/0142438 | A1 | 6/2007 | Arista et al. |
| 2012/0165320 | A1 | 6/2012 | Jain et al. |
| 2015/0291604 | A1 | 10/2015 | Chen et al. |
| 2018/0093991 | A1 | 4/2018 | Thompson et al. |
| 2018/0228776 | A1* | 8/2018 | Saitoh ............... A61P 13/12 |
| 2019/0016721 | A1 | 1/2019 | Chen et al. |
| 2019/0185470 | A1 | 6/2019 | Jakob et al. |
| 2021/0169872 | A1 | 6/2021 | Hunt et al. |
| 2021/0369701 | A1 | 12/2021 | Hunt et al. |

FOREIGN PATENT DOCUMENTS

| | | | | |
|---|---|---|---|---|
| WO | 2009115427 | A1 | 9/2009 | |
| WO | WO-2009115427 | A1 * | 9/2009 | ........... C07D 401/14 |
| WO | 2020254552 | A2 | 12/2020 | |
| WO | WO-2022072512 | A1 * | 4/2022 | |

OTHER PUBLICATIONS

Clark et al., (Mar. 2008), "1H-Pyrazolo[3,4-g] hexahydro-isoquinolines as selective glucocorticoid receptor antagonists with high functional activity", Bioorganic & Medicinal Chemistry Letters, 18(4):1312-1317.

Clark et al., (Nov. 2007), "2-Benzenesulfonyl-8a-benzyl-hexahydro-2H-isoquinolin-6-ones as selective glucocorticoid receptor antagonists", Bioorganic & Medicinal Chemistry Letters, 17(20):5704-5708.

(Continued)

*Primary Examiner* — Matthew P Coughlin

(74) *Attorney, Agent, or Firm* — Mintz, Levin, Cohn, Ferris, Glovsky and Popeo, P.C.

(57) ABSTRACT

The present disclosure provides compounds of Formula I or II. Compounds of Formula I or II may be used in pharmaceutical formulations, and may be used for modulating glucocorticoid receptors.

28 Claims, No Drawings

(56) References Cited

OTHER PUBLICATIONS

Hunt et al., (2015), "1H-Pyrazolo[3,4-g]hexahydro-isoquinolines as potent GR antagonists with reduced hERG inhibition and an improved pharmacokinetic profile", Bioorganic & Medicinal Chemistry Letters, 25(24):5720-5725.

Hunt et al., Apr. 27, 2017, "Identification of the Clinical Candidate (R)-(1-(4-Fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone (CORT125134): A Selective Glucocorticoid Receptor", Journal of Medicinal Chemistry, 60(8):3405-3421.

ISRWO, "International Search Report and Written Opinion for PCT/US2021/038218", dated Oct. 12, 2021, 10 pages.

International Search Report and Written Opinion for PCT/US2022/082027, dated Apr. 17, 2023, 16 pages.

International Search Report and Written Opinion for PCT/US2022/082034, dated Apr. 26, 2023, 12 pages.

\* cited by examiner

QUATERNARY INDAZOLE GLUCOCORTICOID RECEPTOR ANTAGONISTS

CROSS-REFERENCES TO RELATED APPLICATIONS

This application claims priority to U.S. Provisional Application No. 63/042,188, filed Jun. 22, 2020, which is incorporated herein in its entirety for all purposes.

BACKGROUND OF THE INVENTION

In most species, including man, the physiological glucocorticoid is cortisol (hydrocortisone). In rodents, the physiological glucocorticoid is corticosterone. Glucocorticoids are secreted in response to ACTH (corticotropin), which shows both circadian rhythm variation and elevations in response to stress and food. Cortisol levels are responsive within minutes to many physical and psychological stresses, including trauma, surgery, exercise, anxiety and depression. Cortisol is a steroid and acts by binding to an intracellular, glucocorticoid receptor (GR). In man, glucocorticoid receptors are present in two forms: a ligand-binding GR-alpha of 777 amino acids; and, a GR-beta isoform which lacks the 50 carboxy terminal residues. Since these residues include the ligand binding domain, GR-beta is unable to bind the natural ligand, and is constitutively localized in the nucleus.

The biologic effects of cortisol, including those caused by hypercortisolemia, can be modulated at the GR level using receptor modulators, such as agonists, partial agonists and antagonists. Several different classes of agents are able to block the physiologic effects of GR-agonist binding. These antagonists include compositions which, by binding to GR, block the ability of an agonist to effectively bind to and/or activate the GR. One such known GR antagonist, mifepristone, has been found to be an effective anti-glucocorticoid agent in humans (Bertagna (1984) *J. Clin. Endocrinol. Metab.* 59:25). Mifepristone binds to the GR with high affinity, with a dissociation constant ($K_d$) of $10^{-9}$ M (Cadepond (1997) *Annu. Rev. Med.* 48:129).

Cortisol (and corticosterone) also bind to the mineralocorticoid receptor, MR. Cortisol has higher affinity for MR than it does for GR, and MR is usually considered to be fully occupied under normal physiological conditions. Under conditions of stress, cortisol concentrations are increased and GR becomes occupied. MR also binds to aldosterone and aldosterone and cortisol have similar affinity for MR. However, glucocorticoids circulate at roughly 100 times the level of mineralocorticoids. An enzyme (11-β hydroxsteroid dehydrogenase 1) exists in mineralocorticoid target tissues to prevent overstimulation by glucocorticoids.

When administered to subjects in need thereof, steroids can provide both intended therapeutic effects as well as negative side effects. What is needed in the art are new compositions and methods for selectively modulating GR. Surprisingly, the present invention meets these and other needs.

BRIEF SUMMARY OF THE INVENTION

In one embodiment, the present invention provides a compound of Formula I:

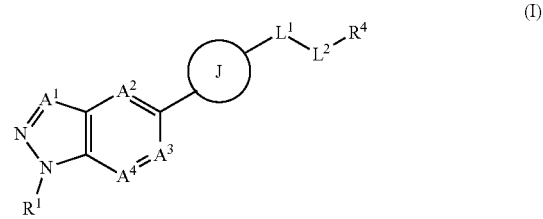

or a pharmaceutically acceptable salt thereof, wherein
$R^1$ is heterocycloalkyl having 3 to 8 ring members and 1 to 4 heteroatoms each N, O or S, phenyl or heteroaryl having 5 to 10 ring members and 1 to 5 heteroatoms each N, O or S, each independently substituted with 1 to 5 $R^{1a}$ groups;
each $R^{1a}$ is independently hydrogen, $C_{1-6}$ alkyl, $C_{1-6}$ deuteroalkyl, $C_{1-6}$ alkoxy, $C_{1-6}$ alkoxyalkyl, $C_{1-6}$ hydroxyalkyl, halogen, $C_{1-6}$ haloalkyl, $C_{1-6}$ haloalkoxy, —OH, oxo, —CN, —C(O)N($R^{1b}$)($R^{1c}$), $C_{3-10}$ cycloalkyl, or heterocycloalkyl having 3 to 8 ring members and 1 to 4 heteroatoms each N, O or S;
each $R^{1b}$ and $R^{1c}$ is independently hydrogen, $C_{1-6}$ alkyl or a 3 to 8 membered heterocycloalkyl having 1 to 3 heteroatoms each independently N, O or S;
$A^1$, $A^2$, $A^3$ and $A^4$ are each independently =$CR^2$— or =N—;
each $R^2$ is independently hydrogen, $C_{1-6}$ alkyl, $C_{1-6}$ alkoxy, $C_{2-6}$ alkoxyalkyl, halogen, $C_{1-6}$ haloalkyl, $C_{1-6}$ haloalkoxy, hydroxy or —CN;
ring J is a 3 to 10 membered heterocycloalkyl having 1 to 3 heteroatoms each independently N, O or S, wherein at least one heteroatom is N, and wherein ring J is optionally substituted with 1 to 13 $R^{3a}$ and $R^{3b}$ groups;
each $R^{3a}$ is independently hydrogen, $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, —C(O)$R^{3a1}$, —C(O)O$R^{3a1}$, —C(O)N($R^{3a1}$)($R^{3a2}$), —OH, oxo, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each alkenyl and alkynyl is optionally substituted with $C_{6-12}$ aryl or heteroaryl, wherein each heterocycloalkyl has 3 to 8 ring members and 1 to 3 heteroatoms each independently N, O or S, and wherein each heteroaryl has 5 to 10 ring members and 1 to 5 heteroatoms each independently N, O or S;
each $R^{3a1}$ and $R^{3a2}$ is independently hydrogen or $C_{1-6}$ alkyl;
alternatively, two $R^{3a}$ groups attached to the same atom can be combined with the atom to which they are attached to form a $C_{3-6}$ cycloalkyl;
alternatively, two $R^{3a}$ groups attached to different atoms can be combined with the atoms to which they are attached to form a $C_{3-10}$ cycloalkyl or 3 to 10 membered heterocycloalkyl having 1 to 4 heteroatoms each independently N, O or S, each substituted with 1 to 4 $R^{3a3}$ groups;
each $R^{3a3}$ is independently hydrogen or $C_{1-6}$ alkyl;
each $R^{3b}$ is independently hydrogen, $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, —C(O)$R^{3b1}$, —C(O)O$R^{3b1}$, —C(O)N($R^{3b1}$)($R^{3b2}$), $C_{3-8}$ cycloalkyl, $C_{1-6}$ alkyl-$C_{3-8}$ cycloalkyl, $C_{2-6}$ alkynyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, $C_{2-6}$ alkenyl-$C_{6-12}$ aryl, $C_{2-6}$ alkynyl-$C_{6-12}$ aryl, $C_{1-6}$ alkyl-O—$C_{6-12}$ aryl, $C_{1-6}$ alkoxyalkyl-$C_{6-12}$ aryl, —C(O)—$C_{6-12}$ aryl, heteroaryl, or $C_{1-6}$ alkyl-heteroaryl, wherein each heterocycloalkyl has 3 to 8 ring members and 1 to 3 heteroatoms each independently N, O or S, wherein each heteroaryl has 5 to ring members and 1 to 5 heteroatoms each independently N, O or S, and wherein each aryl and heteroaryl are substituted with 1 to 3 $R^{3b3}$ groups;

$R^{3b1}$ and $R^{3b2}$ are each independently hydrogen or $C_{1-6}$ alkyl;

alternatively $R^{3b1}$ and $R^{3b2}$ are combined with the atom to which they are attached to form a 3 to 6 membered heterocycloalkyl having 1 to 2 additional heteroatoms each independently N, O or S;

each $R^{3b3}$ is hydrogen, $C_{1-6}$ alkyl, $C_{1-6}$ alkoxy, $C_{2-6}$ alkoxyalkyl, $C_{1-6}$ hydroxyalkyl, halogen, $C_{1-6}$ haloalkyl, or $C_{1-6}$ haloalkoxy;

alternatively, $R^{3b}$ is combined with the $R^{3a}$ on an adjacent ring atom and the atoms to which each is attached to form a $C_{3-6}$ cycloalkyl substituted with 0 to 4 halogens;

$R^4$ is $C_{1-6}$ alkyl, $C_{2-6}$ alkenyl, $C_{2-6}$ alkynyl, $C_{1-6}$ haloalkyl, —CN, $C_{3-8}$ cycloalkyl, 3 to 8 membered heterocycloalkyl having 1 to 3 heteroatoms each independently N, O or S, $C_{6-12}$ aryl, or 5 to 10 membered heteroaryl having 1 to 5 heteroatoms each independently N, O or S, wherein the cycloalkyl, heterocycloalkyl, aryl and heteroaryl are each independently substituted with 1 to 5 $R^{4a}$ groups;

each $R^{4a}$ is hydrogen, $C_{1-6}$ alkyl, $C_{1-6}$ deuteroalkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, —OH, oxo, —C(O)$R^{4b}$, —C(O)O$R^{4b}$, —C(O)N($R^{4b}$)($R^{4c}$), —S(O)$_2R^{4b}$, —S(O)$_2$N($R^{4b}$)($R^{4c}$), $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, —O—$C_{6-12}$ aryl, heteroaryl, $C_{1-6}$ alkyl-heteroaryl, wherein each heterocycloalkyl independently has 3 to 8 ring members and 1 to 3 heteroatoms each independently N, O or S, wherein each heteroaryl independently has 5 to 8 ring members and 1 to 4 heteroatoms each independently N, O or S, and wherein each cycloalkyl, heterocycloalkyl, aryl and heteroaryl is optionally substituted with $C_{1-6}$ alkoxy;

each $R^{4b}$ and $R^{4c}$ is hydrogen or $C_{1-6}$ alkyl;

$L^1$ is absent or —N($R^{5a}$)—;

$L^2$ is absent, $C_{1-6}$ alkylene, —C(O)—, —C(O)—$C_{1-6}$ alkylene-, C(O)—$C_{1-6}$ alkylene-O—, —C(O)O—, —C(O)N($R^{5b}$)—, —S(O)$_2$—, or —S(O)$_2$N($R^{5b}$)—; and $R^{5a}$ and $R^{5b}$ are each independently hydrogen, $C_{1-6}$ alkyl or $C_{2-6}$ alkoxyalkyl;

wherein when $L^2$ is absent, then $R^{3b}$ is not hydrogen, and wherein when $A^1$, $A^2$, $A^3$ and $A^4$ are each —CH—, ring J is

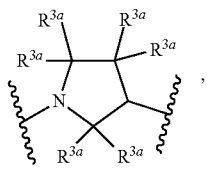

$L^1$ is —NH—, and $L^2$ is —C(O)—, —C(O)O— or —S(O)$_2$—, then each $R^{3a}$ is H.

In another embodiment, the present invention provides a compound of Formula I:

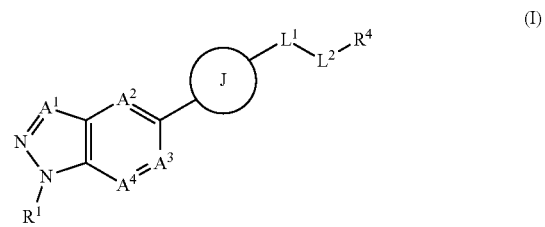

or a pharmaceutically acceptable salt thereof, wherein $R^1$ is phenyl or pyridyl, each independently substituted with 1 to 5 $R^{1a}$ groups each independently hydrogen, $C_{1-6}$ alkoxy, halogen, —OH and —C(O)N($R^{1b}$)($R^{1c}$);

each $R^{1b}$ and $R^{1c}$ is independently hydrogen, $C_{1-6}$ alkyl or a 3 to 8 membered heterocycloalkyl having 1 to 3 heteroatoms each independently N, O or S;

$A^1$, $A^2$, $A^3$ and $A^4$ are each independently =CR$^2$— or =N—;

each $R^2$ is independently hydrogen, $C_{1-6}$ alkyl, $C_{1-6}$ alkoxy, $C_{2-6}$ alkoxy alkyl, halogen, $C_{1-6}$ haloalkyl, $C_{1-6}$ haloalkoxy, hydroxy or —CN;

ring J is a 3 to 10 membered heterocycloalkyl having 1 to 3 heteroatoms each independently N, O or S, wherein at least one heteroatom is N, and wherein ring J is optionally substituted with 1 to 13 $R^{3a}$ and $R^{3b}$ groups;

each $R^{3a}$ is hydrogen, $C_{1-6}$ alkyl, $C_{2-6}$ alkenyl, $C_{2-6}$ alkynyl, $C_{1-6}$ alkoxy, $C_{2-6}$ alkoxy alkyl, $C_{1-6}$ hydroxyalkyl, —C(O)$R^{3a1}$, —C(O)O$R^{3a1}$, —C(O)N($R^{3a1}$)($R^{3a2}$), oxo, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each alkenyl and alkynyl is optionally substituted with $C_{6-12}$ aryl or heteroaryl, wherein each heterocycloalkyl has 3 to 8 ring members and 1 to 3 heteroatoms each independently N, O or S, and wherein each heteroaryl has 5 to 10 ring members and 1 to 5 heteroatoms each independently N, O or S;

each $R^{3a1}$ and $R^{3a2}$ is independently hydrogen or $C_{1-6}$ alkyl;

alternatively, two $R^{3a}$ groups attached to the same atom can be combined with the atom to which they are attached to form a $C_{3-6}$ cycloalkyl;

alternatively, two $R^{3a}$ groups attached to different atoms can be combined with the atoms to which they are attached to form a $C_{3-10}$ cycloalkyl or 3 to 10 membered heterocycloalkyl having 1 to 4 heteroatoms each independently N, O or S, each substituted with 1 to 4 $R^{3a3}$ groups;

each $R^{3a3}$ is independently hydrogen or $C_{1-6}$ alkyl;

each $R^{3b}$ is independently hydrogen, $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, —C(O)$R^{3b1}$, —C(O)O$R^{3b1}$, —C(O)N($R^{3b1}$)($R^{3b2}$), $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl has 3 to 8 ring members and 1 to 3 heteroatoms each independently N, O or S, wherein each heteroaryl has 5 to 10 ring members and 1 to 5 heteroatoms each independently N, O or S, and wherein each aryl and heteroaryl are substituted with 1 to 3 $R^{3b3}$ groups;

$R^{3b1}$ and $R^{3b2}$ are each independently hydrogen or $C_{1-6}$ alkyl;

alternatively $R^{3b1}$ and $R^{3b2}$ are combined with the atom to which they are attached to form a 3 to 6 membered heterocycloalkyl having 1 to 2 additional heteroatoms each independently N, O or S;

each $R^{3b3}$ is hydrogen, $C_{1-6}$ alkyl, $C_{1-6}$ alkoxy, $C_{2-6}$ alkoxyalkyl, $C_{1-6}$ hydroxyalkyl, halogen, $C_{1-6}$ haloalkyl, or $C_{1-6}$ haloalkoxy;

alternatively, $R^{3b}$ is combined with the $R^{3a}$ on an adjacent ring atom and the atoms to which each is attached to form a $C_{3-6}$ cycloalkyl substituted with 0 to 4 halogens;

$R^4$ is $C_{1-6}$ alkyl, $C_{2-6}$ alkenyl, $C_{2-6}$ alkynyl, —CN, $C_{3-8}$ cycloalkyl, 3 to 8 membered heterocycloalkyl having 1 to 3 heteroatoms each independently N, O or S, $C_{6-12}$ aryl, or 5 to 10 membered heteroaryl having 1 to 5 heteroatoms each independently N, O or S, wherein the heterocycloalkyl, aryl and heteroaryl are each independently substituted with 1 to 5 $R^{4a}$ groups;

each $R^{4a}$ is hydrogen, $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, oxo, —C(O)$R^{4b}$, —C(O)O$R^{4b}$, —C(O)N($R^{4b}$)($R^{4c}$), —S(O)$_2$ $R^{4b}$, —S(O)$_2$N($R^{4b}$)($R^{4c}$), $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl or —O—$C_{6-12}$ aryl, wherein each heterocycloalkyl independently has 3 to 8 ring members and 1 to 3 heteroatoms each independently N, O or S, and wherein each aryl is optionally substituted with $C_{1-6}$ alkoxy;

each $R^{4b}$ and $R^{4c}$ is hydrogen or $C_{1-6}$ alkyl;

$L^1$ is absent or —N($R^{5a}$)—;

$L^2$ is absent, —C(O)—, —C(O)—$C_{1-6}$ alkylene C(O)—$C_{1-6}$ alkylene-O—, —C(O)O—, —C(O)N($R^{5b}$)—, —S(O)$_2$—, or —S(O)$_2$N($R^{5b}$)—; and $R^{5a}$ and $R^{5b}$ are each independently hydrogen, $C_{1-6}$ alkyl or $C_{2-6}$ alkoxyalkyl.

In another embodiment, the present invention provides a pharmaceutical composition comprising a compound of the present invention and a pharmaceutically acceptable excipient.

In another embodiment, the present invention provides a method of treating a disorder or condition through modulating a glucocorticoid receptor, the method comprising administering to a subject in need of such treatment, a therapeutically effective amount of a compound or a pharmaceutical composition of the present invention, thereby treating the disorder or condition.

In another embodiment, the present invention provides a method of treating a disorder or condition through antagonizing a glucocorticoid receptor, the method comprising administering to a subject in need of such treatment, an effective amount of the compound or a pharmaceutical composition of the present invention.

In another embodiment, the present invention provides a compound or pharmaceutical composition for use in a method of treating a disorder or condition through modulating a glucocorticoid receptor.

In another embodiment, the present invention provides a compound or pharmaceutical composition for use in a method of treating a disorder or condition through antagonizing the glucocorticoid receptor.

In another embodiment, the present invention provides use of a compound or pharmaceutical composition of the present invention in the manufacture of a medicament for treating a disorder or condition through modulating a glucocorticoid receptor.

In another embodiment, the present invention provides a use of a compound or pharmaceutical composition of the present invention in the manufacture of a medicament for treating a disorder or condition through antagonizing a glucocorticoid receptor.

DETAILED DESCRIPTION OF THE INVENTION

I. General

The present invention provides compounds of Formula I capable of modulating and/or antagonizing a glucocorticoid receptor, and thereby providing beneficial therapeutic effects. The present invention also provides methods of treating disorders and conditions by modulating a glucocorticoid receptor or by antagonizing a glucocorticoid receptor. The present invention also provides use of a compound of the present invention in the manufacture of a medicament for treating a disorder or condition through modulating a glucocorticoid receptor, agonizing a glucocorticoid receptor or antagonizing a glucocorticoid receptor.

II. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

"A," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

"Alkylene" refers to a straight or branched, saturated, aliphatic radical having the number of carbon atoms indicated (i.e., $C_{1-6}$ means one to six carbons), and linking at least two other groups, i.e., a divalent hydrocarbon radical. The two moieties linked to the alkylene can be linked to the same atom or different atoms of the alkylene group. For instance, a straight chain alkylene can be the bivalent radical of —(CH$_2$)$_n$—, where n is 1, 2, 3, 4, or 6. Representative $C_{1-4}$ alkylene groups include, but are not limited to, methylene, ethylene, propylene, isopropylene, butylene, isobutylene, and sec-butylene.

"Alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted.

"Alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be substituted or unsubstituted.

"Deuteroalkyl" refers to an alkyl group, as defined above, where at least one of the hydrogen atoms is replaced with a deuterium. As for the alkyl group, deuteroalkyl groups can have any suitable number of carbon atoms, such as $C_{1-6}$. Exemplary Cm deuteroalkyl groups include, but are not limited to, $-CH_2D$, $-CHD_2$, $-CD_3$, $-CH_2CH_2D$, $-CH_2CHD_2$, $-CH_2CD_3$, and the like.

"Alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Alkoxyalkyl" refers to a radical having an alkyl component and an alkoxy component, where the alkyl component links the alkoxy component to the point of attachment. The alkyl component is as defined above, except that the alkyl component is at least divalent, an alkylene, to link to the alkoxy component and to the point of attachment. The alkyl component can include any number of carbons, such as $C_{1-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The alkoxy component is as defined above. Examples of the alkyl-alkoxy group include, but are not limited to, 2-ethoxy-ethyl and methoxymethyl.

"Hydroxyalkyl" or "alkylhydroxy" refers to an alkyl group, as defined above, where at least one of the hydrogen atoms is replaced with a hydroxy group. As for the alkyl group, hydroxyalkyl or alkylhydroxy groups can have any suitable number of carbon atoms, such as $C_{1-6}$. Exemplary $C_{1-4}$ hydroxyalkyl groups include, but are not limited to, hydroxymethyl, hydroxy ethyl (where the hydroxy is in the 1- or 2-position), hydroxypropyl (where the hydroxy is in the 1-, 2- or 3-position), hydroxybutyl (where the hydroxy is in the 1-, 2-, 3- or 4-position), 1,2-dihydroxy ethyl, and the like.

"Halogen" refers to fluorine, chlorine, bromine and iodine.

"Haloalkyl" refers to alkyl, as defined above, where some or all of the hydrogen atoms are replaced with halogen atoms. As for alkyl group, haloalkyl groups can have any suitable number of carbon atoms, such as $C_{1-6}$. For example, haloalkyl includes trifluoromethyl, fluoromethyl, etc. In some instances, the term "perfluoro" can be used to define a compound or radical where all the hydrogens are replaced with fluorine. For example, perfluoromethyl refers to 1,1,1-trifluoromethyl.

"Haloalkoxy" refers to an alkoxy group where some or all of the hydrogen atoms are substituted with halogen atoms. As for an alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, perfluoroethoxy, etc.

"Amino" refers to an $-N(R)_2$ group where the R groups can be hydrogen, alkyl, alkenyl, alkynyl, cycloalkyl, heterocycloalkyl, aryl, or heteroaryl, among others. The R groups can be the same or different. The amino groups can be primary (each R is hydrogen), secondary (one R is hydrogen) or tertiary (each R is other than hydrogen).

"Alkylamine" refers to an alkyl group as defined within, having one or more amino groups. The amino groups can be primary, secondary or tertiary. The alkyl amine can be further substituted with a hydroxy group to form an amino-hydroxy group. Alkyl amines useful in the present invention include, but are not limited to, ethyl amine, propyl amine, isopropyl amine, ethylene diamine and ethanolamine. The amino group can link the alkyl amine to the point of attachment with the rest of the compound, be at the omega position of the alkyl group, or link together at least two carbon atoms of the alkyl group. One of skill in the art will appreciate that other alkyl amines are useful in the present invention.

"Heteroalkyl" refers to an alkyl group of any suitable length and having from 1 to 3 heteroatoms such as N, O and S. Heteroalkyl groups have the indicated number of carbon atoms where at least one non-terminal carbon is replaced with a heteroatom. Additional heteroatoms can also be useful, including, but not limited to, B, Al, Si and P. The heteroatoms can also be oxidized, such as, but not limited to, $-S(O)-$ and $-S(O)_2-$. For example, heteroalkyl can include ethers, thioethers and alkyl-amines. Heteroalkyl groups do not include peroxides (—O—O—) or other consecutively linked heteroatoms. The heteroatom portion of the heteroalkyl can replace a hydrogen of the alkyl group to form a hydroxy, thio or amino group. Alternatively, the heteroatom portion can be the connecting atom, or be inserted between two carbon atoms.

"Oxo" refers to a carbonyl group, =O.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2]bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted.

"Alkyl-cycloalkyl" refers to a radical having an alkyl component and a cycloalkyl component, where the alkyl component links the cycloalkyl component to the point of attachment. The alkyl component is as defined above, except that the alkyl component is at least divalent, an alkylene, to link to the cycloalkyl component and to the point of attachment. In some instances, the alkyl component can be absent. The alkyl component can include any number of carbons, such as $C_{1-6}$, $C_{1-2}$, $C_{1-3}$, CM, $C_{1-5}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The cycloalkyl component is as defined within. Exemplary alkyl-cycloalkyl groups include, but are not limited to, methyl-cyclopropyl, methyl-cyclobutyl, methyl-cyclopentyl and methyl-cyclohexyl.

"Alkenyl-cycloalkyl" refers to a radical having an alkenyl component and a cycloalkyl component, where the alkenyl component links the cycloalkyl component to the point of attachment. The alkenyl component is as defined above, except that the alkenyl component is at least divalent, an alkenylene, to link to the cycloalkyl component and to the point of attachment. The alkenyl component can include any number of carbons, such as $C_{2-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The cycloalkyl component is as defined within. Exemplary alkenylene-cycloalkyl groups include, but are not limited to, ethenylene-cyclopropyl, ethenylene-cyclobutyl, ethenylene-cyclopentyl and ethenylene-cyclohexyl.

"Alkynyl-cycloalkyl" refers to a radical having an alkynyl component and a cycloalkyl component, where the alkynyl component links the cycloalkyl component to the point of attachment. The alkynyl component is as defined above, except that the alkynyl component is at least divalent, an alkynylene, to link to the cycloalkyl component and to the point of attachment. The alkynyl component can include any number of carbons, such as $C_{2-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The cycloalkyl component is as defined within. Exemplary alkynylene-cycloalkyl groups include, but are not limited to, ethynyl-cyclopropyl, propynyl-cyclopropyl, ethynyl-cyclobutyl, ethynyl-cyclopentyl and ethynyl-cyclohexyl.

"Heterocycloalkyl" refers to a saturated ring system having from 3 to 12 ring members and from 1 to 5 heteroatoms of N, O and S. The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, 4, or 5, or 1 to 2, 1 to 3, 1 to 4, 1 to 5, 2 to 3, 2 to 4, 2 to 5, 3 to 4 or 3 to 5. The heterocycloalkyl group can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. The heterocycloalkyl group can include groups such as aziridine, azetidine, pyrrolidine, piperidine, azepane, diazepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. The heterocycloalkyl groups can also form spiro structures such as, but not limited to, diazabicycloheptane, diazabicyclooctane, diazaspirooctane or diazaspirononane. Heterocycloalkyl groups can be unsubstituted or substituted. For example, heterocycloalkyl groups can be substituted with $C_{1-6}$ alkyl or oxo (=O), among many others. Heterocycloalkyl groups can also include a double bond or a triple bond, such as, but not limited to dihydropyridine or 1,2,3,6-tetrahydropyridine.

The heterocycloalkyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazobdine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxzoalidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Alkyl-heterocycloalkyl" refers to a radical having an alkyl component and a heterocycloalkyl component, where the alkyl component links the heterocycloalkyl component to the point of attachment. The alkyl component is as defined above, except that the alkyl component is at least divalent, an alkylene, to link to the heterocycloalkyl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The heterocycloalkyl component is as defined above. Alkyl-heterocycloalkyl groups can be substituted or unsubstituted.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

"Alkyl-aryl" refers to a radical having an alkyl component and an aryl component, where the alkyl component links the aryl component to the point of attachment. The alkyl component is as defined above, except that the alkyl component is at least divalent, an alkylene, to link to the aryl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The aryl component is as defined above. Examples of alkyl-aryl groups include, but are not limited to, benzyl and ethyl-benzene. Alkyl-aryl groups can be substituted or unsubstituted.

"Alkenyl-aryl" refers to a radical having both an alkenyl component and a aryl component, where the alkenyl component links the aryl component to the point of attachment. The alkenyl component is as defined above, except that the alkenyl component is at least divalent, an alkenylene, to link to the aryl component and to the point of attachment. The alkenyl component can include any number of carbons, such as $C_{2-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The aryl component is as defined above. Alkenyl-aryl groups can be substituted or unsubstituted.

"Alkynyl-aryl" refers to a radical having both an alkynyl component and a aryl component, where the alkynyl component links the aryl component to the point of attachment. The alkynyl component is as defined above, except that the alkynyl component is at least divalent, an alkynylene, to link to the aryl component and to the point of attachment. The alkynyl component can include any number of carbons, such as $C_{2-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The aryl component is as defined above, alkynyl-aryl groups can be substituted or unsubstituted.

"Alkoxyalkyl-aryl" refers to a radical having an alkoxyalkyl component and an aryl component, where the alkoxyalkyl component links the aryl component to the point of attachment. The alkoxyalkyl component is as defined above, except that the alkoxyalkyl component is at least divalent to link to the aryl component and to the point of attachment. The alkoxyalkyl component can include any number of carbons, such as $C_{2-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The aryl component is as defined above. Alkoxyalkyl-aryl groups can be substituted or unsubstituted.

"Heteroaryl" refers to a monocyclic or fused bicyclic or tricyclic aromatic ring assembly containing 5 to 16 ring atoms, where from 1 to 5 of the ring atoms are a heteroatom such as N, O or S. The heteroatoms can also be oxidized, such as, but not limited to, —S(O)— and —S(O)$_2$—. Heteroaryl groups can include any number of ring atoms, such as, to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O or S, such as pyrrole, pyridine, imidazole, pyrazole, pyrazine, pyrimidine, pyridazine, thiophene, furan, thiazole, isothiazole, oxazole, and isoxazole.

"Alkyl-heteroaryl" refers to a radical having an alkyl component and a heteroaryl component, where the alkyl component links the heteroaryl component to the point of attachment. The alkyl component is as defined above, except that the alkyl component is at least divalent, an alkylene, to link to the heteroaryl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The heteroaryl component is as defined within. Alkyl-heteroaryl groups can be substituted or unsubstituted.

"Pharmaceutically acceptable excipient" refers to a substance that aids the administration of an active agent to and absorption by a subject. Pharmaceutical excipients useful in the present invention include, but are not limited to, binders, fillers, disintegrants, lubricants, surfactants, coatings, sweeteners, flavors and colors. One of skill in the art will recognize that other pharmaceutical excipients are useful in the present invention.

"Treat", "treating" and "treatment" refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

"Administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

"Therapeutically effective amount" refers to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

"Glucocorticoid receptor" ("GR") refers to one of the family of intracellular receptors which specifically bind to cortisol and/or cortisol analogs such as dexamethasone (See, e.g., Turner & Muller, J. Mol. Endocrinol. Oct. 1, 2005 35 283-292). The glucocorticoid receptor is also referred to as the cortisol receptor. The term includes isoforms of GR, recombinant GR and mutated GR.

A cortisol receptor is a glucocorticoid receptor (GR), specifically the type II GR, which specifically binds cortisol and/or cortisol analogs such as dexamethasone (See, e.g, Turner & Muller, J. Mol. Endocrinol. Oct. 1, 2005 35 283-292).

"Mineralocorticoid receptor" (MR) refers to a type I glucocorticoid receptor (GR I), which is activated by aldosterone in humans.

"Glucocorticoid receptor modulator" (GRM) refers to any compound which modulates any biological response associated with the binding of a glucocorticoid receptor to an agonist. As used herein, with respect to a GRM, the glucocorticoid receptor may be GR, or both. For example, a GRM that acts as an agonist, such as dexamethasone, increases the activity of tyrosine aminotransferase (TAT) in HepG2 cells (a human liver hepatocellular carcinoma cell line; ECACC, UK). A GRM that acts as an antagonist, such as mifepristone, inhibits the agonist-induced increase in the activity of tyrosine aminotransferase (TAT) in HepG2 cells. TAT activity can be measured as outlined in the literature by A. Ah el al, J. Med. Chem., 2004, 47, 2441-2452.

"Glucocorticoid receptor antagonist" (GRA) refers to any compound which inhibits any biological response associated with the binding of a glucocorticoid receptor to an agonist. As used herein, with respect to a GRA, the glucocorticoid receptor may be GR. Accordingly, GR antagonists can be identified by measuring the ability of a compound to inhibit the effect of dexamethasone. TAT activity can be measured as outlined in the literature by A. Ah et al., J. Med. Chem., 2004, 47, 2441-2452. An inhibitor is a compound with an $IC_{50}$ (half maximal inhibition concentration) of less than 10 micromolar. See Example 1 of U.S. Pat. No. 8,685,973, the entire contents of which is hereby incorporated by reference in its entirety.

"Modulate" and "modulating" are used in accordance with its plain ordinary meaning and refer to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

"Modulator" refers to a composition that increases or decreases the level of a target molecule or the function of a target molecule or the physical state of the target of the molecule.

"Antagonize' and "antagonizing" refer to inhibiting the binding of an agonist at a receptor molecule or to inhibiting the signal produced by a receptor-agonist. A receptor antagonist inhibits or dampens agonist-mediated responses, such as gene expression.

"Antagonist" refers to a substance capable of detectably lowering expression or activity of a given gene or protein. The antagonist can inhibit expression or activity 10%, 20%, 30%, 40%, 50%, 60%, 70%, 80%, 90%, 100% or less in comparison to a control in the absence of the antagonist. In some embodiments, the inhibition is 1.5-fold, 2-fold, 3-fold, 4-fold, 5-fold, 10-fold, or more than the expression or activity in the absence of the antagonist.

"Inhibition", "inhibits" and "inhibitor" refer to a compound that prohibits or a method of prohibiting, a specific action or function.

"Disorder" or "condition" refers to a state of being or health status of a patient or subject capable of being treated with the glucocorticoid receptor modulators of the present invention. In some embodiments, examples of disorders or conditions include, but are not limited to, obesity, hypertension, depression, anxiety, and Cushing's Syndrome. In some embodiments, the disorders or conditions include nonalcoholic liver disease and/or nonalcoholic steatohepatitis. In some embodiments, the disorders or conditions include addiction disorders. In some embodiments, the disorders or conditions include cancer.

"Medicament" refers to a composition or substance used for treatment of a disease or condition.

"Subject" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, horse, and other non-mammalian animals. In some embodiments, the patient is human.

III. Compounds

In some embodiments, the present invention provides a compound of Formula I:

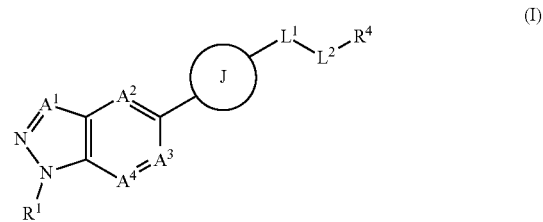

or a pharmaceutically acceptable salt thereof, wherein $R^1$ is heterocycloalkyl having 3 to 8 ring members and 1 to 4 heteroatoms each N, O or S, phenyl or heteroaryl having 5 to 10 ring members and 1 to 5 heteroatoms each N, O or S, each independently substituted with 1 to 5 $R^{1a}$ groups;

each $R^{1a}$ is independently hydrogen, $C_{1-6}$ alkyl, $C_{1-6}$ deuteroalkyl, $C_{1-6}$ alkoxy, $C_{1-6}$ alkoxyalkyl, $C_{1-6}$ hydroxyalkyl, halogen, $C_{1-6}$ haloalkyl, $C_{1-6}$ haloalkoxy, —OH, oxo, —CN, —C(O)N($R^{1b}$)($R^{1c}$), $C_{3-10}$ cycloalkyl, or heterocycloalkyl having 3 to 8 ring members and 1 to 4 heteroatoms each N, O or S;

each $R^{1b}$ and $R^{1c}$ is independently hydrogen, $C_{1-6}$ alkyl or a 3 to 8 membered heterocycloalkyl having 1 to 3 heteroatoms each independently N, O or S;

$A^1$, $A^2$, $A^3$ and $A^4$ are each independently =CR$^2$— or =N—;

each $R^2$ is independently hydrogen, $C_{1-6}$ alkyl, $C_{1-6}$ alkoxy, $C_{2-6}$ alkoxyalkyl, halogen, $C_{1-6}$ haloalkyl, $C_{1-6}$ haloalkoxy, hydroxy or —CN;

ring J is a 3 to 10 membered heterocycloalkyl having 1 to 3 heteroatoms each independently N, O or S, wherein at least one heteroatom is N, and wherein ring J is optionally substituted with 1 to 13 $R^{3a}$ and $R^{3b}$ groups;

each $R^{3a}$ is independently hydrogen, $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, —C(O)$R^{3a1}$, —C(O)O$R^{3a1}$, —C(O)N($R^{3a1}$)($R^{3a2}$), —OH, oxo, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each alkenyl and alkynyl is optionally substituted with $C_{6-12}$ aryl or heteroaryl, wherein each heterocycloalkyl has 3 to 8 ring members and 1 to 3 heteroatoms each independently N, O or S, and wherein each heteroaryl has 5 to 10 ring members and 1 to 5 heteroatoms each independently N, O or S;

each $R^{3a1}$ and $R^{3a2}$ is independently hydrogen or $C_{1-6}$ alkyl;

alternatively, two $R^{3a}$ groups attached to the same atom can be combined with the atom to which they are attached to form a $C_{3-6}$ cycloalkyl;

alternatively, two $R^{3a}$ groups attached to different atoms can be combined with the atoms to which they are attached to form a $C_{3-10}$ cycloalkyl or 3 to 10 membered heterocycloalkyl having 1 to 4 heteroatoms each independently N, O or S, each substituted with 1 to 4 $R^{3a3}$ groups;

each $R^{3a3}$ is independently hydrogen or $C_{1-6}$ alkyl;

each $R^{3b}$ is independently hydrogen, $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, —C(O)$R^{3b1}$, —C(O)O$R^{3b1}$, —C(O)N($R^{3b1}$)($R^{3b2}$), $C_{3-8}$ cycloalkyl, $C_{1-6}$ alkyl-$C_{3-8}$ cycloalkyl, $C_{2-6}$ alkynyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, $C_{2-6}$ alkenyl-$C_{6-12}$ aryl, $C_{2-6}$ alkynyl-$C_{6-12}$ aryl, $C_{1-6}$ alkyl-O—$C_{6-12}$ aryl, $C_{1-6}$ alkoxyalkyl-$C_{6-12}$ aryl, —C(O)—$C_{6-12}$ aryl, heteroaryl, or $C_{1-6}$ alkyl-heteroaryl, wherein each heterocycloalkyl has 3 to 8 ring members and 1 to 3 heteroatoms each independently N, O or S, wherein each heteroaryl has 5 to ring members and 1 to 5 heteroatoms each independently N, O or S, and wherein each aryl and heteroaryl are substituted with 1 to 3 $R^{3b3}$ groups;

$R^{3b1}$ and $R^{3b2}$ are each independently hydrogen or $C_{1-6}$ alkyl;

alternatively $R^{3b1}$ and $R^{3b2}$ are combined with the atom to which they are attached to form a 3 to 6 membered heterocycloalkyl having 1 to 2 additional heteroatoms each independently N, O or S;

each $R^{3b3}$ is hydrogen, $C_{1-6}$ alkyl, $C_{1-6}$ alkoxy, $C_{2-6}$ alkoxyalkyl, $C_{1-6}$ hydroxyalkyl, halogen, $C_{1-6}$ haloalkyl, or $C_{1-6}$ haloalkoxy;

alternatively, $R^{3b}$ is combined with the $R^{3a}$ on an adjacent ring atom and the atoms to which each is attached to form a $C_{3-6}$ cycloalkyl substituted with 0 to 4 halogens;

$R^4$ is $C_{1-6}$ alkyl, $C_{2-6}$ alkenyl, $C_{2-6}$ alkynyl, $C_{1-6}$ haloalkyl, —CN, $C_{3-8}$ cycloalkyl, 3 to 8 membered heterocycloalkyl having 1 to 3 heteroatoms each independently N, O or S, $C_{6-12}$ aryl, or 5 to 10 membered heteroaryl having 1 to 5 heteroatoms each independently N, O or S, wherein the cycloalkyl, heterocycloalkyl, aryl and heteroaryl are each independently substituted with 1 to 5 $R^{4a}$ groups;

each $R^{4a}$ is hydrogen, $C_{1-6}$ alkyl, $C_{1-6}$ deuteroalkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, —OH, oxo, —C(O)$R^{4b}$, —C(O)O$R^{4b}$, —C(O)N($R^{4b}$)($R^{4c}$), —S(O)$_2$$R^{4b}$, —S(O)$_2$N($R^{4b}$)($R^{4c}$), $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, —O—$C_{6-12}$ aryl, heteroaryl, $C_{1-6}$ alkyl-heteroaryl, wherein each heterocycloalkyl independently has 3 to 8 ring members and 1 to 3 heteroatoms each independently N, O or S, wherein each heteroaryl independently has 5 to 8 ring members and 1 to 4 heteroatoms each independently N, O or S, and wherein each cycloalkyl, heterocycloalkyl, aryl and heteroaryl is optionally substituted with $C_{1-6}$ alkoxy;

each $R^{4b}$ and $R^{4c}$ is hydrogen or $C_{1-6}$ alkyl;

$L^1$ is absent or —N($R^{5a}$)—;

$L^2$ is absent, $C_{1-6}$ alkylene, —C(O)—, —C(O)—$C_{1-6}$ alkylene-, C(O)—$C_{1-6}$ alkylene-O—, —C(O)O—, —C(O)N($R^{5b}$)—, —S(O)$_2$—, or —S(O)$_2$N($R^{5b}$)—; and $R^{5a}$ and $R^{5b}$ are each independently hydrogen, $C_{1-6}$ alkyl or $C_{2-6}$ alkoxyalkyl;

wherein when $L^2$ is absent, then $R^{3b}$ is not hydrogen, and wherein when $A^1$, $A^2$, $A^3$ and $A^4$ are each —CH—, ring J is

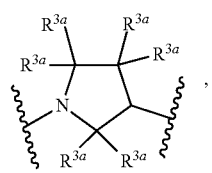

$L^1$ is —NH—, and $L^2$ is —C(O)—, —C(O)O— or —S(O)$_2$—, then each $R^{3a}$ is H.

In some embodiments, the present invention provides a compound of Formula I:

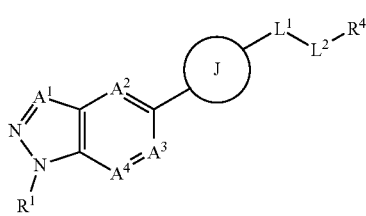

or a pharmaceutically acceptable salt thereof, wherein
$R^1$ is phenyl or pyridyl, each independently substituted with 1 to 5 $R^{1a}$ groups each independently hydrogen, $C_{1-6}$ alkoxy, halogen, —OH and —C(O)N($R^{1b}$)($R^{1c}$);
each $R^{1b}$ and $R^{1c}$ is independently hydrogen, $C_{1-6}$ alkyl or a 3 to 8 membered heterocycloalkyl having 1 to 3 heteroatoms each independently N, O or S;
$A^1$, $A^2$, $A^3$ and $A^4$ are each independently =CR$^2$— or =N—;
each $R^2$ is independently hydrogen, $C_{1-6}$ alkyl, $C_{1-6}$ alkoxy, $C_{2-6}$ alkoxy alkyl, halogen, $C_{1-6}$ haloalkyl, $C_{1-6}$ haloalkoxy, hydroxy or —CN;
ring J is a 3 to 10 membered heterocycloalkyl having 1 to 3 heteroatoms each independently N, O or S, wherein at least one heteroatom is N, and wherein ring J is optionally substituted with 1 to 13 $R^{3a}$ and $R^{3b}$ groups;
each $R^{3a}$ is hydrogen, $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, —C(O)$R^{3a1}$, —C(O)O$R^{3a1}$, —C(O)N($R^{3a1}$)($R^{3a2}$), oxo, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each alkenyl and alkynyl is optionally substituted with $C_{6-12}$ aryl or heteroaryl, wherein each heterocycloalkyl has 3 to 8 ring members and 1 to 3 heteroatoms each independently N, O or S, and wherein each heteroaryl has 5 to 10 ring members and 1 to 5 heteroatoms each independently N, O or S;
each $R^{3a1}$ and $R^{3a2}$ is independently hydrogen or $C_{1-6}$ alkyl;
alternatively, two $R^{3a}$ groups attached to the same atom can be combined with the atom to which they are attached to form a $C_{3-6}$ cycloalkyl;
alternatively, two $R^{3a}$ groups attached to different atoms can be combined with the atoms to which they are attached to form a $C_{3-10}$ cycloalkyl or 3 to 10 membered heterocycloalkyl having 1 to 4 heteroatoms each independently N, O or S, each substituted with 1 to 4 $R^{3a3}$ groups;
each $R^{3a3}$ is independently hydrogen or $C_{1-6}$ alkyl;
each $R^{3b}$ is independently hydrogen, $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, —C(O)$R^{3b1}$, —C(O)O$R^{3b1}$, —C(O)N($R^{3b1}$)($R^{3b2}$), $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl has 3 to 8 ring members and 1 to 3 heteroatoms each independently N, O or S, wherein each heteroaryl has 5 to 10 ring members and 1 to 5 heteroatoms each independently N, O or S, and wherein each aryl and heteroaryl are substituted with 1 to 3 $R^{3b3}$ groups;
$R^{3b1}$ and $R^{3b2}$ are each independently hydrogen or $C_{1-6}$ alkyl;
alternatively $R^{3b1}$ and $R^{3b2}$ are combined with the atom to which they are attached to form a 3 to 6 membered heterocycloalkyl having 1 to 2 additional heteroatoms each independently N, O or S;
each $R^{3b3}$ is hydrogen, $C_{1-6}$ alkyl, $C_{1-6}$ alkoxy, $C_{2-6}$ alkoxyalkyl, $C_{1-6}$ hydroxyalkyl, halogen, $C_{1-6}$ haloalkyl, or $C_{1-6}$ haloalkoxy;
alternatively, $R^{3b}$ is combined with the $R^{3a}$ on an adjacent ring atom and the atoms to which each is attached to form a $C_{3-6}$ cycloalkyl substituted with 0 to 4 halogens;
$R^4$ is $C_{1-6}$ alkyl, $C_{2-6}$ alkenyl, $C_{2-6}$ alkynyl, —CN, $C_{3-8}$ cycloalkyl, 3 to 8 membered heterocycloalkyl having 1 to 3 heteroatoms each independently N, O or S, $C_{6-12}$ aryl, or 5 to 10 membered heteroaryl having 1 to 5 heteroatoms each independently N, O or S, wherein the heterocycloalkyl, aryl and heteroaryl are each independently substituted with 1 to 5 $R^{4a}$ groups;
each $R^{4a}$ is hydrogen, $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, oxo, —C(O)$R^{4b}$, —C(O)O$R^{4b}$, —C(O)N($R^{4b}$)($R^{4c}$), —S(O)$_2$ $R^{4b}$, —S(O)$_2$N($R^{4b}$)($R^{4c}$), $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl or —O—$C_{6-12}$ aryl, wherein each heterocycloalkyl independently has 3 to 8 ring members and 1 to 3 heteroatoms each independently N, O or S, and wherein each aryl is optionally substituted with $C_{1-6}$ alkoxy;
each $R^{4b}$ and $R^{4c}$ is hydrogen or $C_{1-6}$ alkyl;
$L^1$ is absent or —N($R^{5a}$)—;
$L^2$ is absent, —C(O)—, —C(O)—$C_{1-6}$ alkylene-, C(O)—$C_{1-6}$ alkylene-O—, —C(O)O—, —C(O)N($R^{5b}$)—, —S(O)$_2$—, or —S(O)$_2$N($R^{5b}$)—; and
$R^{5a}$ and $R^{5b}$ are each independently hydrogen, $C_{1-6}$ alkyl or $C_{2-6}$ alkoxyalkyl.

In some embodiments, the compound of Formula I, II, III, IIIa, IIIb, IV, IVa, V, VI or VII, or a pharmaceutically acceptable salt thereof, is the compound wherein $R^1$ is phenyl or pyridyl, each independently substituted with 1 to 5 $R^{1a}$ groups each independently hydrogen, $C_{1-6}$ alkoxy, halogen, —OH and —C(O)N($R^{1b}$)($R^{1c}$), and each $R^{1b}$ and $R^{1c}$ can independently be hydrogen, $C_{1-6}$ alkyl or a 3 to 8 membered heterocycloalkyl having 1 to 3 heteroatoms each independently N, O or S.

In some embodiments, the compound of Formula I, II, III, IIIa, IIIb, IV, IVa, V, VI or VII, or a pharmaceutically acceptable salt thereof, is the compound wherein $R^1$ is phenyl substituted with 1 to 5 $R^{1a}$ groups each independently hydrogen, $C_{1-6}$ alkoxy, halogen or —C(O)N($R^{1b}$)($R^{1c}$), wherein each $R^{1b}$ and $R^{1c}$ can independently be hydrogen or a 4 to 6 membered heterocycloalkyl having 1 to 3 heteroatoms each independently N, O or S. In some embodiments, the compound of Formula I or II, or a pharmaceutically acceptable salt thereof, is the compound wherein $R^1$ is phenyl substituted with halogen. In some embodiments, the compound of Formula I or II, or a pharmaceutically acceptable salt thereof, is the compound wherein $R^1$ is phenyl substituted with fluoro. In some embodiments, the compound of Formula I or II, or a pharmaceutically acceptable salt thereof, is the compound wherein $R^1$ is 4-fluoro-phenyl.

In some embodiments, the compound of Formula I, II, III, IIIa, IIIb, IV, IVa, IVg, V, VI or VII, or a pharmaceutically acceptable salt thereof, is the compound wherein $R^1$ is

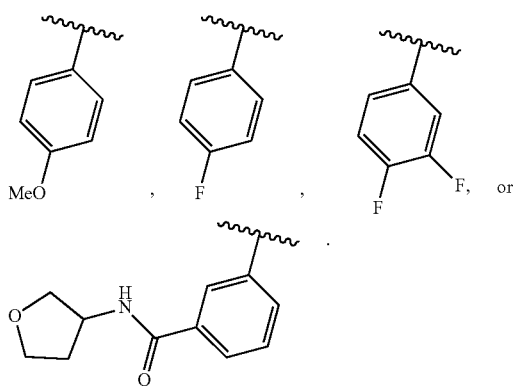

In some embodiments, the compound of Formula I, II, III, IIIa, IIIb, IV, IVa, IVg, V, VI or VII, or a pharmaceutically acceptable salt thereof, is the compound wherein $R^1$ is

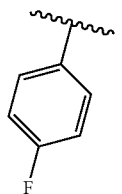

In some embodiments, the compound of Formula I, II, III, IIIa, IIIb, IV, IVa, IVb, V, VI or VII, or a pharmaceutically acceptable salt thereof, is the compound wherein $A^1$, $A^2$, $A^3$ and $A^4$ are each independently =$CR^2$— or =N—; and each $R^2$ is independently hydrogen, $C_{1-6}$ alkyl, $C_{1-6}$ alkoxy, $C_{2-6}$ alkoxyalkyl, halogen, $C_{1-6}$ haloalkyl, $C_{1-6}$ haloalkoxy, hydroxy or —CN.

In some embodiments, the compound of Formula I, II, III, IIIa, IIIb, IV, IVa, IVb, V, VI or VII, or a pharmaceutically acceptable salt thereof, is the compound wherein each of $A^1$, $A^2$, $A^3$ and $A^4$ can independently be =$CR^2$— or =N—. In some embodiments, the compound of Formula I, II, III, IIIa, IIIb, IV, IVa, IVb, V, VI or VII, or a pharmaceutically acceptable salt thereof, is the compound wherein each of $A^1$, $A^2$, $A^3$, and $A^4$ can be =$CR^2$—. In some embodiments, the compound of Formula I, II, III, IIIa, IIIb, IV, IVa, IVb, V, VI or VII, or a pharmaceutically acceptable salt thereof, is the compound wherein one of $A^1$, $A^2$, $A^3$, and $A^4$ can be =N—. In some embodiments, the compound of Formula I, II, III, IIIa, IIIb, IV, IVa, IVb, V, VI or VII, or a pharmaceutically acceptable salt thereof, is the compound wherein $A^1$ can be =N— and each of $A^2$, $A^3$, and $A^4$ can be =$CR^2$—. In some embodiments, the compound of Formula I, II, III, IIIa, IIIb, IV, IVa, IVb, V, VI or VII, or a pharmaceutically acceptable salt thereof, is the compound wherein each of $A^1$, $A^3$, and $A^4$ can be =$CR^2$— and $A^2$ can be =N—. In some embodiments, the compound of Formula I, II, III, IIIa, IIIb, IV, IVa, IVb, V, VI or VII, or a pharmaceutically acceptable salt thereof, is the compound wherein each of $A^1$, $A^2$, and $A^4$ can be =$CR^2$— and $A^3$ can be =N—. In some embodiments, the compound of Formula I, II, III, IIIa, IIIb, IV, IVa, IVb, V, VI or VII, or a pharmaceutically acceptable salt thereof, is the compound wherein each of $A^1$, $A^2$, and $A^3$ can be =$CR^2$— and $A^4$ can be =N—.

In some embodiments, the compound of Formula I, II, IIa-1, IIa-2, IIb-1, IIb-2, IIc-1, IIc-2, III, IIIa, IIIb, IV, IVa, IVb, IVg, V, VI or VII, or a pharmaceutically acceptable salt thereof, is the compound wherein each $R^2$ can independently be hydrogen, $C_{1-6}$ alkyl, $C_{1-6}$ alkoxy, halogen, or $C_{1-6}$ haloalkoxy. In some embodiments, the compound of Formula I, II, IIa-1, IIa-2, IIb-1, IIb-2, IIc-1, IIc-2, III, IIIa, IIIb, IV, IVa, IVb, IVg, V, VI or VII, or a pharmaceutically acceptable salt thereof, is the compound wherein at least one $R^2$ is $C_{1-6}$ alkyl, $C_{1-6}$ alkoxy, halogen, or $C_{1-6}$ haloalkoxy. In some embodiments, the compound of Formula I, II, IIa-1, IIa-2, IIb-1, IIb-2, IIc-1 or IIc-2, or a pharmaceutically acceptable salt thereof, is the compound wherein each $R^2$ is independently hydrogen, $C_{1-3}$ alkyl, $C_{1-3}$ alkoxy, halogen, or $C_{1-3}$ haloalkoxy. In some embodiments, the compound of Formula I, II, IIa-1, IIa-2, IIb-1, IIb-2, IIc-1, IIc-2, III, IIIa, IIIb, IV, IVa, IVb, IVg, V, VI or VII, or a pharmaceutically acceptable salt thereof, is the compound wherein $R^2$ is independently hydrogen, methyl, ethyl, n-propyl, iso-propyl, methoxy, ethoxy, n-propoxy, iso-propoxy, F, Cl, Br, —$OCH_2F$, —$OCHF_2$, or —$OCF_3$. In some embodiments, the compound of Formula I, II, IIa-1, IIa-2, IIb-1, IIb-2, IIc-1, IIc-2, III, IIIa, IIIb, IV, IVa, IVb, IVg, V, VI or VII, or a pharmaceutically acceptable salt thereof, is the compound wherein $R^2$ is independently hydrogen, methyl, ethyl, n-propyl, iso-propyl, methoxy, ethoxy, n-propoxy, iso-propoxy, F, Cl, Br, —$OCH_2F$, —$OCHF_2$, —$OCF_3$ or —CN.

In some embodiments, the compound of Formula I, II, III, IIIa, IIIb, IV, IVa, IVb, V, VI or VII, or a pharmaceutically acceptable salt thereof, is the compound wherein $A^1$, $A^2$, $A^3$ and $A^4$ are each independently =$CR^2$— or =N—; and each $R^2$ is independently hydrogen, $C_{1-6}$ alkyl, $C_{1-6}$ alkoxy, halogen, or $C_{1-6}$ haloalkoxy. In some embodiments, the compound of Formula I or II, or a pharmaceutically acceptable salt thereof, is the compound wherein each of $A^1$, $A^2$, $A^3$, and $A^4$ is —$CR^2$—.

In some embodiments, the compound of Formula I, II, III, IIIa, IIIb, IV, IVa, IVb, V, VI or VII, or a pharmaceutically acceptable salt thereof, is the compound wherein $A^1$ is =CH— or =N—; $A^2$ and $A^4$ are each independently =CH—, =C(Me)- or =N—; and $A^3$ is =CH—, =C(Me)-, =C(iPr)—, =C(OMe)-, =C(F)— =C(Cl)—, =C($OCHF_2$)— or =N—. In some embodiments, the compound of Formula I, II, III, IIIa, IIIb, IV, IVa, IVb, V, VI or VII, or a pharmaceutically acceptable salt thereof, is the compound wherein $A^1$, $A^2$ and $A^4$ are each =CH—; and $A^3$ is =CH—, =C(Me)-, =C(iPr)—, =C(OMe)-, =C(F)— =C(Cl)— or =C($OCHF_2$). In some embodiments, the compound of Formula I, II, III, IIIa, IIIb, IV, IVa, IVb, V, VI or VII, or a pharmaceutically acceptable salt thereof, is the compound wherein $A^1$ is =CH— or =N—; $A^2$ and $A^4$ are each independently =CH—, =C(Me)- or =N—; and $A^3$ is =CH—, =C(Me)-, =C(iPr)—, =C(OMe)-, =C(Cl)—, =C($OCHF_2$)— or =N—.

In some embodiments, the compound of Formula I, II, III, IIIa, IIIb, IV, IVa, IVb, V, VI or VII, or a pharmaceutically acceptable salt thereof, is the compound wherein $A^1$ is =CH— or =N—; $A^2$ and $A^4$ are each =CH—; and $A^3$ is =CH—, =C(Me)-, =C(iPr)—, =C(OMe)-, or =C(F)—. In some embodiments, the compound of Formula I, II, III, IIIa, IIIb, IV, IVa, IVb, V, VI or VII, or a pharmaceutically acceptable salt thereof, is the compound wherein $A^1$, $A^2$ and $A^4$ are each =CH—; and $A^3$ is =CH—, =C(Me)-, =C(iPr)—, =C(OMe)-, or =C(F)—.

In some embodiments, the compound of Formula I or II, or a pharmaceutically acceptable salt thereof, is the compound wherein ring J is a 3 to 10 membered heterocycloalkyl having 1 to 3 heteroatoms each independently N, O or S, wherein at least one heteroatom is N, and wherein ring J is optionally substituted with 1 to 13 $R^{3a}$ and $R^{3b}$ groups;

each $R^{3a}$ is hydrogen, $C_{1-6}$ alkyl, $C_{2-6}$ alkenyl, $C_{2-6}$ alkynyl, $C_{1-6}$ alkoxy, $C_{2-6}$ alkoxy alkyl, $C_{1-6}$ hydroxyalkyl, —C(O)$R^{3a1}$, —C(O)O$R^{3a1}$, —C(O)N($R^{3a1}$)($R^{3a2}$), oxo, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each alkenyl and alkynyl is optionally substituted with $C_{6-12}$ aryl or heteroaryl, wherein each heterocycloalkyl has 3 to 8 ring members and 1 to 3 heteroatoms each independently N, O or S, and wherein each heteroaryl has 5 to 10 ring members and 1 to 5 heteroatoms each independently N, O or S;

each $R^{3a1}$ and $R^{3a2}$ is independently hydrogen or $C_{1-6}$ alkyl;

alternatively, two $R^{3a}$ groups attached to the same atom can be combined with the atom to which they are attached to form a $C_{3-6}$ cycloalkyl;

alternatively, two $R^{3a}$ groups attached to different atoms can be combined with the atoms to which they are attached to form a $C_{3-10}$ cycloalkyl or 3 to 10 membered heterocycloalkyl having 1 to 4 heteroatoms each independently N, O or S, each substituted with 1 to 4 $R^{3a3}$ groups;

each $R^{3a3}$ is independently hydrogen or $C_{1-6}$ alkyl;

each $R^{3b}$ is independently hydrogen, $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, —C(O)$R^{3b1}$, —C(O)O$R^{3b1}$, —C(O)N($R^{3b1}$)($R^{3b2}$), $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each heterocycloalkyl has 3 to 8 ring members and 1 to 3 heteroatoms each independently N, O or S, wherein each heteroaryl has 5 to 10 ring members and 1 to 5 heteroatoms each independently N, O or S, and wherein each aryl and heteroaryl are substituted with 1 to 3 $R^{3b3}$ groups;

$R^{3b1}$ and $R^{3b2}$ are each independently hydrogen or $C_{1-6}$ alkyl;

alternatively $R^{3b1}$ and $R^{3b2}$ are combined with the atom to which they are attached to form a 3 to 6 membered heterocycloalkyl having 1 to 2 additional heteroatoms each independently N, O or S;

each $R^{3b3}$ is hydrogen, $C_{1-6}$ alkyl, $C_{1-6}$ alkoxy, $C_{2-6}$ alkoxyalkyl, $C_{1-6}$ hydroxyalkyl, halogen, $C_{1-6}$ haloalkyl, or $C_{1-6}$ haloalkoxy;

alternatively, $R^{3b}$ is combined with the $R^{3a}$ on an adjacent ring atom and the atoms to which each is attached to form a $C_{3-6}$ cycloalkyl substituted with 0 to 4 halogens;

In some embodiments, the compound of Formula I or II, or a pharmaceutically acceptable salt thereof, is the compound wherein ring J can be a $C_{3-8}$ heterocycloalkyl having 1 to 3 nitrogen ring atoms, wherein ring J can be optionally substituted with 1 to 13 $R^{3a}$ and $R^{3b}$ groups. In some embodiments, the compound of Formula I or II, or a pharmaceutically acceptable salt thereof, is the compound wherein ring J can be a $C_{5-8}$ heterocycloalkyl having 1 to 2 nitrogen ring atoms, wherein ring J can be optionally substituted with 1 to 13 $R^{3a}$ and $R^{3b}$ groups. In some embodiments, the compound of Formula I or II, or a pharmaceutically acceptable salt thereof, is the compound wherein ring J can be aziridine, azetidine, pyrrolidine, imidazolidine, piperidine, 1,2,3,6-tetrahydropyridine, piperazine, azepane, diazepane, azocane, diazabicycloheptane, diazabicyclooctane, diazaspirooctane or diazaspirononane, wherein ring J can be optionally substituted with 1 to 13 $R^{3a}$ and $R^{3b}$ groups. In some embodiments, the compound of Formula I or II, or a pharmaceutically acceptable salt thereof, is the compound wherein ring J can be pyrrolidine, imidazolidine, piperidine, 1,2,3,6-tetrahydropyridine, piperazine, azepane, diazepane, azocane, diazabicycloheptane, diazabicyclooctane, diazaspirooctane or diazaspirononane, wherein ring J can be optionally substituted with 1 to 13 $R^{3a}$ and $R^{3b}$ groups.

In some embodiments, the compound of Formula I or II, or a pharmaceutically acceptable salt thereof, is the compound wherein Ring J has the structure:

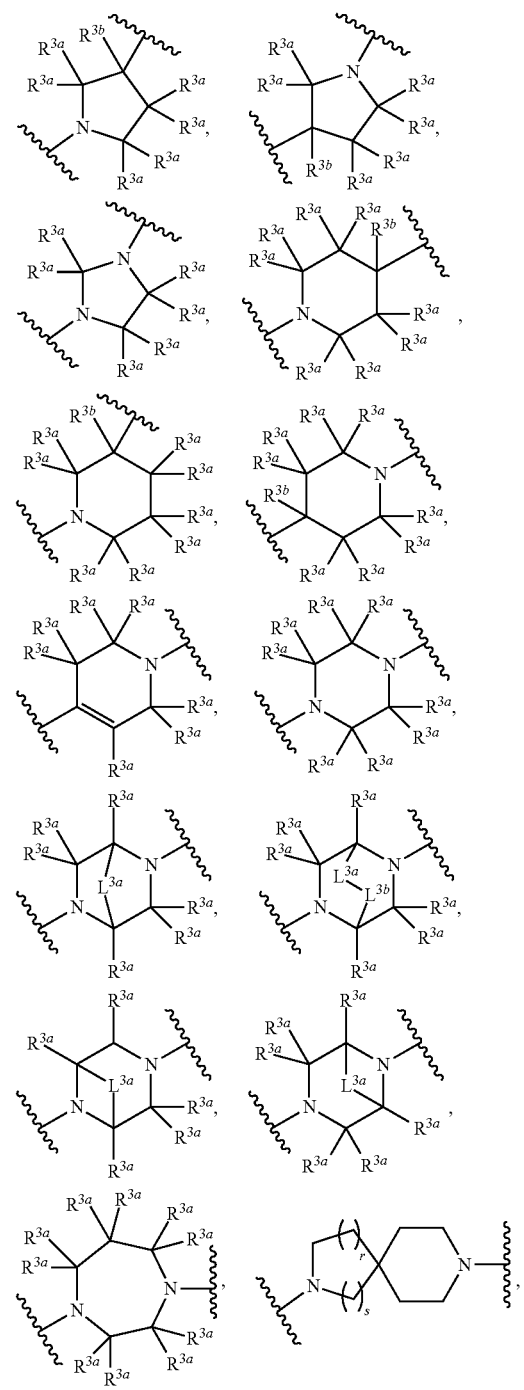

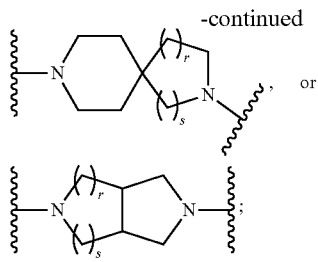

wherein $L^{3a}$ and $L^{3b}$ are each —C($R^{3a3}$)($R^{3a3}$)—; each $R^{3a3}$ is independently hydrogen or $C_{1-6}$ alkyl; and subscripts r and s are each independently 0, 1 or 2, such that the sum of r and s is 2.

In some embodiments, the compound of Formula I or II, or a pharmaceutically acceptable salt thereof, is the compound wherein each $R^{3a}$ is hydrogen, $C_{1-6}$ alkyl, $C_{2-6}$ alkoxyalkyl, $C_{1-6}$ hydroxyalkyl, —C(O)O$R^{3a1}$, oxo, $C_{6-12}$ aryl, or $C_{1-6}$ alkyl-$C_{6-12}$ aryl; alternatively, two $R^{3a}$ groups attached to the same atom can be combined with the atom to which they are attached to form a $C_{3-6}$ cycloalkyl; $R^{3a1}$ is hydrogen or $C_{1-6}$ alkyl; $R^{3b}$ is hydrogen, $C_{1-6}$ alkyl, $C_{2-6}$ alkynyl, $C_{2-6}$ alkoxyalkyl, $C_{1-6}$ hydroxyalkyl, —C(O)O$R^{3b1}$, —C(O)N($R^{3b1}$)($R^{3b2}$), $C_{1-6}$ alkyl-$C_{6-12}$ aryl, $C_{1-6}$ alkyl-heteroaryl, wherein each heteroaryl has 5 to 10 ring members and 1 to 5 heteroatoms each independently N, O or S, and wherein each aryl and heteroaryl are substituted with 1 to 3 $R^{3b3}$ groups; $R^{3b1}$ and $R^{3b2}$ are each independently hydrogen or $C_{1-6}$ alkyl; alternatively $R^{3b1}$ and $R^{3b2}$ are combined with the atom to which they are attached to form a 3 to 6 membered heterocycloalkyl having 1 to 2 additional heteroatoms each independently N, O or S; each $R^{3b3}$ is hydrogen, $C_{1-6}$ alkyl, halogen, or $C_{1-6}$ haloalkyl; and alternatively, $R^{3b}$ is combined with the $R^{3a}$ on an adjacent ring atom and the atoms to which each is attached to form a $C_{3-6}$ cycloalkyl substituted with 0 to 4 halogens.

In some embodiments, the compound of Formula I or a pharmaceutically acceptable salt thereof, is the compound wherein Ring J has the structure:

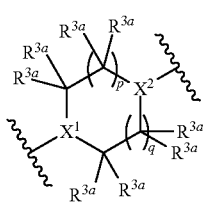

wherein $X^1$ and $X^2$ are each independently —C$R^{3b}$— or —N—, wherein at least one of $X^1$ and $X^2$ is —N—; and subscripts p and q are each independently 0, 1 or 2.

In some embodiments, the compound of Formula I, or a pharmaceutically acceptable salt thereof, is the compound wherein the compound of Formula I is the compound of Formula II:

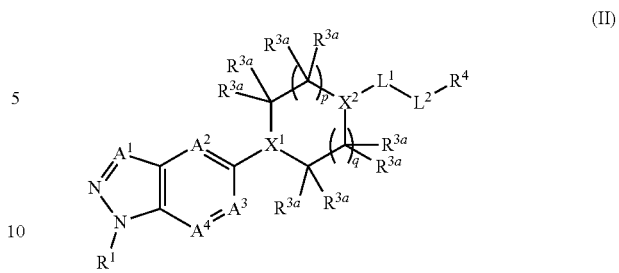

wherein $X^1$ and $X^2$ are each independently —C$R^{3b}$— or —N—, wherein at least one of $X^1$ and $X^2$ is —N—; and subscripts p and q are each independently 0, 1 or 2.

In some embodiments, the compound of Formula I, or a pharmaceutically acceptable salt thereof, is the compound wherein the compound of Formula I is the compound of Formula II:

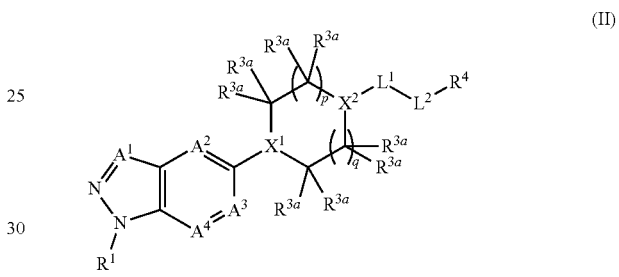

wherein $X^1$ and $X^2$ are each independently —C$R^{3b}$— or —N—, wherein at least one of $X^1$ and $X^2$ is —N—; and subscripts p and q are each independently 0, 1 or 2, and wherein when $A^1$, $A^2$, $A^3$ and $A^4$ are each —CH—, $X^1$ is N, $X^2$ is —CH—, the sum of subscripts p and q is 1, $L^1$ is —NH—, and $L^2$ is —C(O)—, —C(O)O— or —S(O)$_2$—, then each $R^{3a}$ is H.

In some embodiments, the compound of Formula I or II, or a pharmaceutically acceptable salt thereof, is the compound wherein the compound of Formula I or II, or a pharmaceutically acceptable salt thereof, is the compound wherein $X^1$ can be —C$R^{3b}$— and $X^2$ can be —N—. In some embodiments, the compound of Formula I or II, or a pharmaceutically acceptable salt thereof, is the compound wherein the compound of Formula I or II, or a pharmaceutically acceptable salt thereof, is the compound wherein $X^1$ can be —N— and $X^2$ can be —C$R^{3b}$. In some embodiments, the compound of Formula I or II, or a pharmaceutically acceptable salt thereof, is the compound wherein the compound of Formula I or II, or a pharmaceutically acceptable salt thereof, is the compound wherein $X^1$ and $X^2$ can both be —N—.

In some embodiments, the compound of Formula I or II, or a pharmaceutically acceptable salt thereof, is the compound wherein Ring J has the structure:

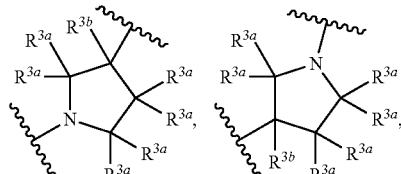

-continued

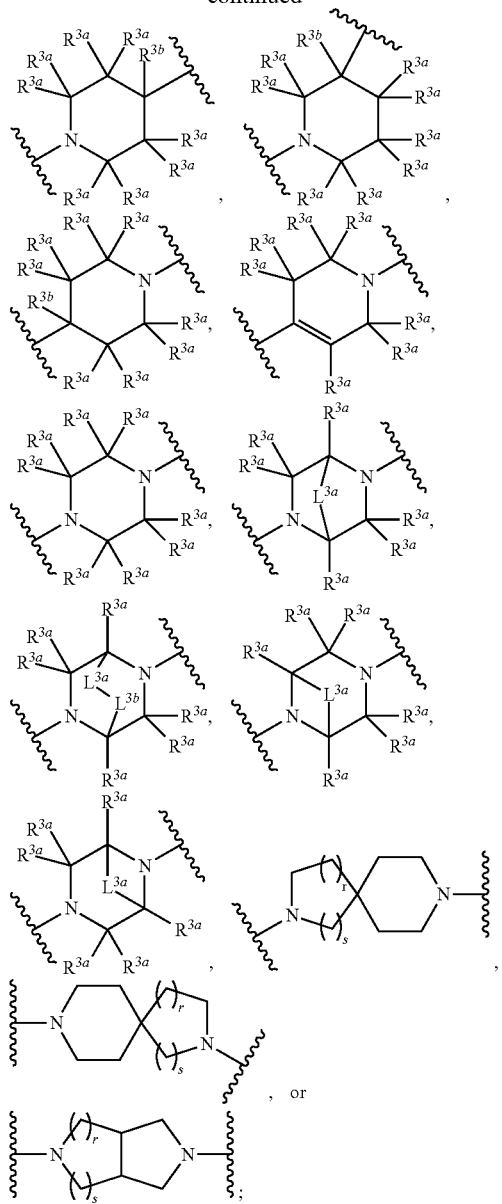

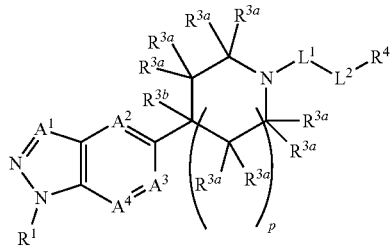

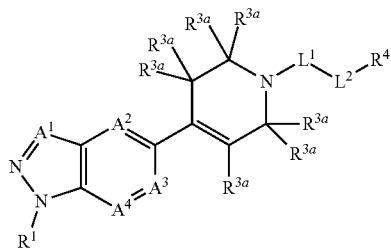

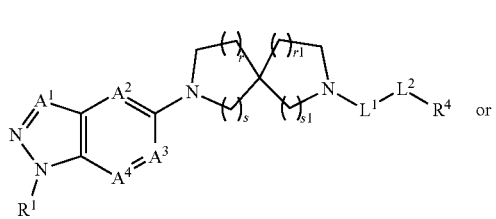

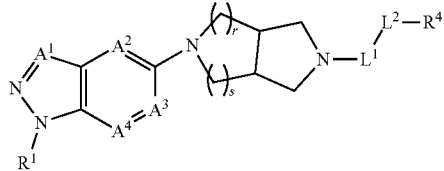

wherein $L^{3a}$ and $L^{3b}$ are each —C($R^{3a3}$)($R^{3a3}$)—; each $R^{3a3}$ is independently hydrogen or $C_{1-6}$ alkyl; and subscripts r and s are each independently 0, 1 or 2, such that the sum of r and s is 2.

In some embodiments, the compound, or a pharmaceutically acceptable salt thereof, has the structure of:

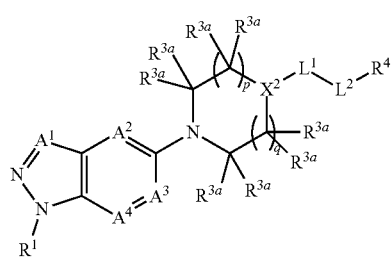
(III)

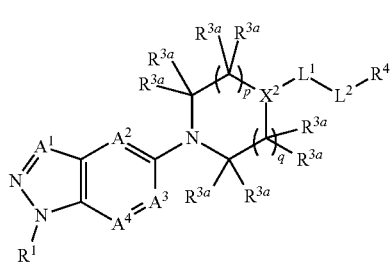
(III)

wherein $X^2$ is —$CR^{3b}$— or —N—; and subscripts p, q, r, r1, s and s1 are each independently 0, 1 or 2, such that the sum of r and s is 2 or 3, and the sum of r1 and s1 is 2 or 3, wherein when $A^1$, $A^2$, $A^3$ and $A^4$ are each —CH—, $X^2$ is —CH—, the sum of subscripts p and q is 1, $L^1$ is —NH—, and $L^2$ is —C(O)—, —C(O)O— or —S(O)$_2$—, then each $R^{3a}$ is H.

In some embodiments, the present invention provides a compound of Formula III, Formula IV, Formula V, Formula VI, or Formula VII:

-continued

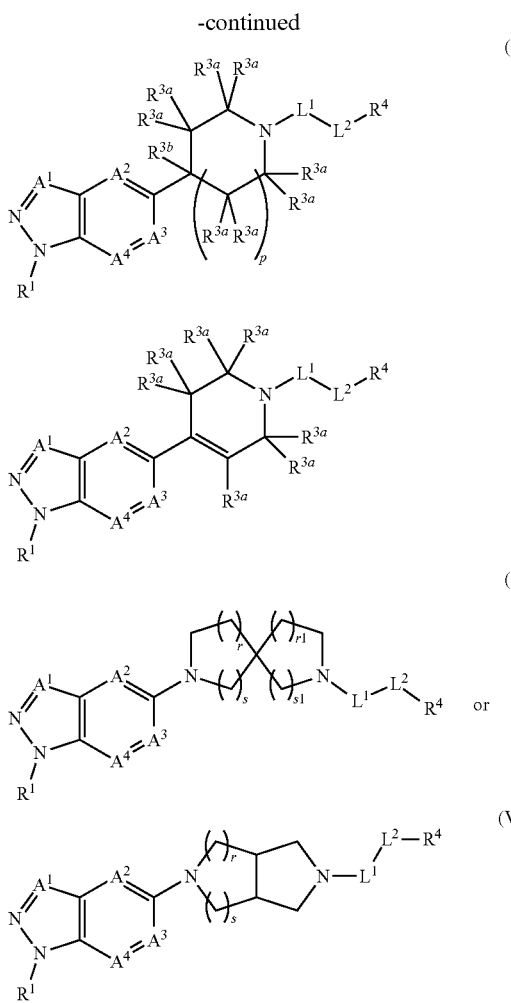

or a pharmaceutically acceptable salt thereof, wherein R$^1$ is heterocycloalkyl having 3 to 8 ring members and 1 to 4 heteroatoms each N, O or S, phenyl or heteroaryl having 5 to 10 ring members and 1 to 5 heteroatoms each N, O or S, each independently substituted with 1 to 5 R$^{1a}$ groups;

each R$^{1a}$ is independently hydrogen, $C_{1-6}$ alkyl, $C_{1-6}$ deuteroalkyl, $C_{1-6}$ alkoxy, $C_{1-6}$ alkoxyalkyl, $C_{1-6}$ hydroxyalkyl, halogen, $C_{1-6}$ haloalkyl, $C_{1-6}$ haloalkoxy, —OH, oxo, —CN, —C(O)N(R$^{1b}$)(R$^{1c}$), $C_{3-10}$ cycloalkyl, or heterocycloalkyl having 3 to 8 ring members and 1 to 4 heteroatoms each N, O or S;

each R$^{1b}$ and R$^{1c}$ is independently hydrogen, $C_{1-6}$ alkyl or a 3 to 8 membered heterocycloalkyl having 1 to 3 heteroatoms each independently N, O or S;

A$^1$, A$^2$, A$^3$ and A$^4$ are each independently =CR$^2$— or =N—;

each R$^2$ is independently hydrogen, $C_{1-6}$ alkyl, $C_{1-6}$ alkoxy, $C_{2-6}$ alkoxyalkyl, halogen, $C_{1-6}$ haloalkyl, $C_{1-6}$ haloalkoxy, hydroxy or —CN;

each R$^{3a}$ is independently hydrogen, $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, —C(O)R$^{3a1}$, —C(O)OR$^{3a1}$, —C(O)N(R$^{3a1}$)(R$^{3a2}$), —OH, oxo, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each alkenyl and alkynyl is optionally substituted with $C_{6-12}$ aryl or heteroaryl, wherein each heterocycloalkyl has 3 to 8 ring members and 1 to 3 heteroatoms each independently N, O or S, and wherein each heteroaryl has 5 to 10 ring members and 1 to 5 heteroatoms each independently N, O or S;

each R$^{3a1}$ and R$^{3a2}$ is independently hydrogen or $C_{1-6}$ alkyl;

alternatively, two R$^{3a}$ groups attached to the same atom can be combined with the atom to which they are attached to form a $C_{3-6}$ cycloalkyl;

alternatively, two R$^{3a}$ groups attached to different atoms can be combined with the atoms to which they are attached to form a $C_{3-10}$ cycloalkyl or 3 to 10 membered heterocycloalkyl having 1 to 4 heteroatoms each independently N, O or S, each substituted with 1 to 4 R$^{3a3}$ groups;

each R$^{3a3}$ is independently hydrogen or $C_{1-6}$ alkyl;

each R$^{3b}$ is independently hydrogen, $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, —C(O)R$^{3b1}$, —C(O)OR$^{3b1}$, —C(O)N(R$^{3b1}$)(R$^{3b2}$), $C_{3-8}$ cycloalkyl, $C_{1-6}$ alkyl-$C_{3-8}$ cycloalkyl, $C_{2-6}$ alkynyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, $C_{2-6}$ alkenyl-$C_{6-12}$ aryl, $C_{2-6}$ alkynyl-$C_{6-12}$ aryl, $C_{1-6}$ alkyl-O—$C_{6-12}$ aryl, $C_{1-6}$ alkoxyalkyl-$C_{6-12}$ aryl, —C(O)—$C_{6-12}$ aryl, heteroaryl, or $C_{1-6}$ alkyl-heteroaryl, wherein each heterocycloalkyl has 3 to 8 ring members and 1 to 3 heteroatoms each independently N, O or S, wherein each heteroaryl has 5 to ring members and 1 to 5 heteroatoms each independently N, O or S, and wherein each aryl and heteroaryl are substituted with 1 to 3 R$^{3b3}$ groups;

R$^{3b1}$ and R$^{3b2}$ are each independently hydrogen or $C_{1-6}$ alkyl;

alternatively R$^{3b1}$ and R$^{3b2}$ are combined with the atom to which they are attached to form a 3 to 6 membered heterocycloalkyl having 1 to 2 additional heteroatoms each independently N, O or S;

each R$^{3b3}$ is hydrogen, $C_{1-6}$ alkyl, $C_{1-6}$ alkoxy, $C_{2-6}$ alkoxyalkyl, $C_{1-6}$ hydroxyalkyl, halogen, $C_{1-6}$ haloalkyl, or $C_{1-6}$ haloalkoxy;

alternatively, R$^{3b}$ is combined with the R$^{3a}$ on an adjacent ring atom and the atoms to which each is attached to form a $C_{3-6}$ cycloalkyl substituted with 0 to 4 halogens;

X$^2$ is —CR$^{3b}$— or —N—;

subscripts p, q, r, r1, s and s1 are each independently 0, 1 or 2, such that the sum of r and s is 2 or 3, and the sum of r1 and s1 is 2 or 3;

R$^4$ is $C_{1-6}$ alkyl, $C_{2-6}$ alkenyl, $C_{2-6}$ alkynyl, $C_{1-6}$ haloalkyl, —CN, $C_{3-8}$ cycloalkyl, 3 to 8 membered heterocycloalkyl having 1 to 3 heteroatoms each independently N, O or S, $C_{6-12}$ aryl, or 5 to 10 membered heteroaryl having 1 to 5 heteroatoms each independently N, O or S, wherein the cycloalkyl, heterocycloalkyl, aryl and heteroaryl are each independently substituted with 1 to 5 R$^{4a}$ groups;

each R$^{4a}$ is hydrogen, $C_{1-6}$ alkyl, $C_{1-6}$ deuteroalkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, —OH, oxo, —C(O)R$^{4b}$, —C(O)OR$^{4b}$, —C(O)N(R$^{4b}$)(R$^{4c}$), —S(O)$_2$R$^{4b}$, —S(O)$_2$N(R$^{4b}$)(R$^{4c}$), $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, —O—$C_{6-12}$ aryl, heteroaryl, $C_{1-6}$ alkyl-heteroaryl, wherein each heterocycloalkyl independently has 3 to 8 ring members and 1 to 3 heteroatoms each independently N, O or S, wherein each heteroaryl independently has 5 to 8 ring members and 1 to 4 heteroatoms each independently N, O or S, and wherein each cycloalkyl, heterocycloalkyl, aryl and heteroaryl is optionally substituted with $C_{1-6}$ alkoxy;

each $R^{4b}$ and $R^{4c}$ is hydrogen or $C_{1-6}$ alkyl;

$L^1$ is absent or —N($R^{5a}$)—;

$L^2$ is absent, $C_{1-6}$ alkylene, —C(O)—, —C(O)—$C_{1-6}$ alkylene-, C(O)—$C_{1-6}$ alkylene-O—, —C(O)O—, —C(O)N($R^{5b}$)—, —S(O)$_2$—, or —S(O)$_2$N($R^{5b}$)—; and $R^{5a}$ and $R^{5b}$ are each independently hydrogen, $C_{1-6}$ alkyl or $C_{2-6}$ alkoxyalkyl;

wherein when $L^2$ is absent, then $R^{3b}$ is not hydrogen, and wherein when $A^1$, $A^2$, $A^3$ and $A^4$ are each —CH—, $X^2$ is —CH—, the sum of subscripts p and q is 1, $L^1$ is —NH—, and $L^2$ is —C(O)—, —C(O)O— or —S(O)$_2$—, then each $R^{3a}$ is H.

In some embodiments, the compound, or a pharmaceutically acceptable salt thereof, has the structure of:

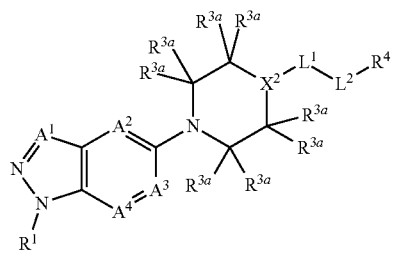
(IIIa)

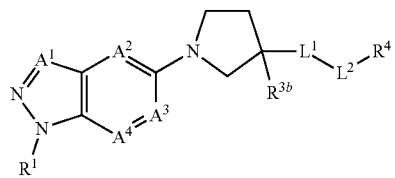
(IIIb)

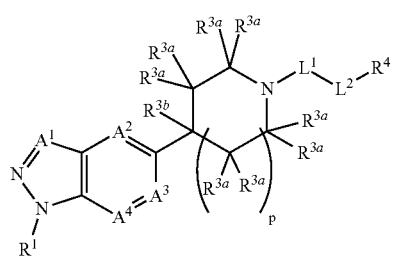
(IV)

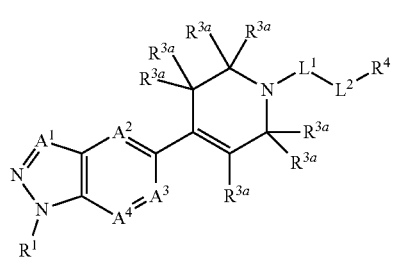
(V)

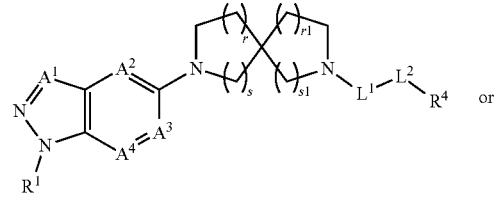
(VI)

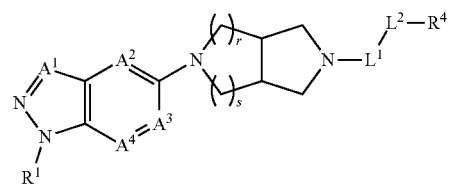
(VII)

wherein $X^2$ is —$CR^{3b}$— or —N—; and subscripts p, q, r, r1, s and s1 are each independently 0, 1 or 2, such that the sum of r and s is 2 or 3, and the sum of r1 and s1 is 2 or 3.

In some embodiments, the present invention provides a compound of Formula IIIa, Formula IIIb, Formula IV, Formula V, Formula VI, or Formula VII:

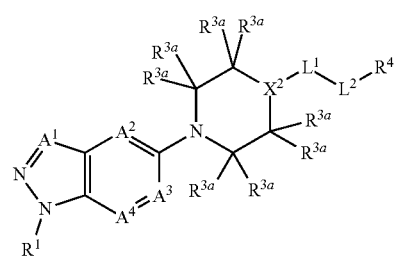
(IIIa)

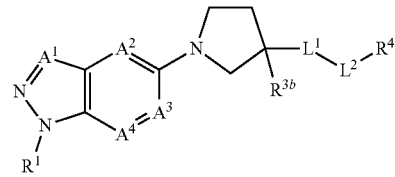
(IIIb)

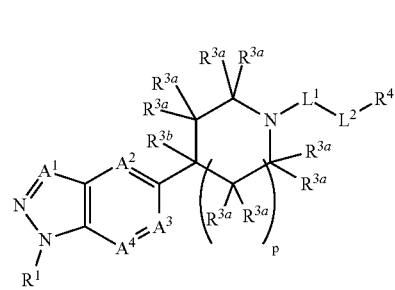
(IV)

-continued

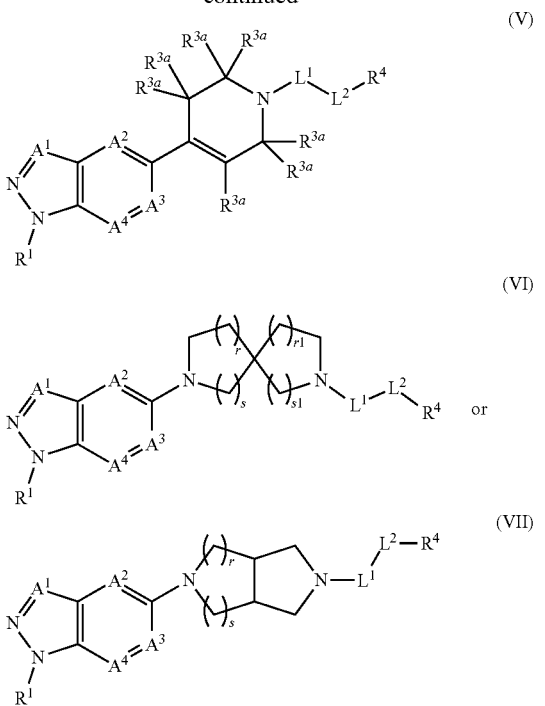

or a pharmaceutically acceptable salt thereof, wherein
$R^1$ is heterocycloalkyl having 3 to 8 ring members and 1 to 4 heteroatoms each N, O or S, phenyl or heteroaryl having 5 to 10 ring members and 1 to 5 heteroatoms each N, O or S, each independently substituted with 1 to 5 $R^{1a}$ groups;
each $R^{1a}$ is independently hydrogen, $C_{1-6}$ alkyl, $C_{1-6}$ deuteroalkyl, $C_{1-6}$ alkoxy, $C_{1-6}$ alkoxyalkyl, $C_{1-6}$ hydroxyalkyl, halogen, $C_{1-6}$ haloalkyl, $C_{1-6}$ haloalkoxy, —OH, oxo, —CN, —C(O)N($R^{1b}$)($R^{1c}$), $C_{3-10}$ cycloalkyl, or heterocycloalkyl having 3 to 8 ring members and 1 to 4 heteroatoms each N, O or S;
each $R^{1b}$ and $R^{1c}$ is independently hydrogen, $C_{1-6}$ alkyl or a 3 to 8 membered heterocycloalkyl having 1 to 3 heteroatoms each independently N, O or S;
$A^1$, $A^2$, $A^3$ and $A^4$ are each independently =$CR^2$— or =N—;
each $R^2$ is independently hydrogen, $C_{1-6}$ alkyl, $C_{1-6}$ alkoxy, $C_{2-6}$ alkoxyalkyl, halogen, $C_{1-6}$ haloalkyl, $C_{1-6}$ haloalkoxy, hydroxy or —CN;
each $R^{3a}$ is independently hydrogen, $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, —C(O)$R^{3a1}$, —C(O)O$R^{3a1}$, —C(O)N($R^{3a1}$)($R^{3a2}$), —OH, oxo, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each alkenyl and alkynyl is optionally substituted with $C_{6-12}$ aryl or heteroaryl, wherein each heterocycloalkyl has 3 to 8 ring members and 1 to 3 heteroatoms each independently N, O or S, and wherein each heteroaryl has 5 to 10 ring members and 1 to 5 heteroatoms each independently N, O or S;
each $R^{3a1}$ and $R^{3a2}$ is independently hydrogen or $C_{1-6}$ alkyl;
alternatively, two $R^{3a}$ groups attached to the same atom can be combined with the atom to which they are attached to form a $C_{3-6}$ cycloalkyl;
alternatively, two $R^{3a}$ groups attached to different atoms can be combined with the atoms to which they are attached to form a $C_{3-10}$ cycloalkyl or 3 to 10 membered heterocycloalkyl having 1 to 4 heteroatoms each independently N, O or S, each substituted with 1 to 4 $R^{3a3}$ groups;
each $R^{3a3}$ is independently hydrogen or $C_{1-6}$ alkyl;
each $R^{3b}$ is independently hydrogen, $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, —C(O)$R^{3b1}$, —C(O)O$R^{3b1}$, —C(O)N($R^{3b1}$)($R^{3b2}$), $C_{3-8}$ cycloalkyl, $C_{1-6}$ alkyl-$C_{3-8}$ cycloalkyl, $C_{2-6}$ alkynyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, $C_{2-6}$ alkenyl-$C_{6-12}$ aryl, $C_{2-6}$ alkynyl-$C_{6-12}$ aryl, $C_{1-6}$ alkyl-O—$C_{6-12}$ aryl, $C_{1-6}$ alkoxyalkyl-$C_{6-12}$ aryl, —C(O)—$C_{6-12}$ aryl, heteroaryl, or $C_{1-6}$ alkyl-heteroaryl, wherein each heterocycloalkyl has 3 to 8 ring members and 1 to 3 heteroatoms each independently N, O or S, wherein each heteroaryl has 5 to ring members and 1 to 5 heteroatoms each independently N, O or S, and wherein each aryl and heteroaryl are substituted with 1 to 3 $R^{3b3}$ groups;
$R^{3b1}$ and $R^{3b2}$ are each independently hydrogen or $C_{1-6}$ alkyl;
alternatively $R^{3b1}$ and $R^{3b2}$ are combined with the atom to which they are attached to form a 3 to 6 membered heterocycloalkyl having 1 to 2 additional heteroatoms each independently N, O or S;
each $R^{3b3}$ is hydrogen, $C_{1-6}$ alkyl, $C_{1-6}$ alkoxy, $C_{2-6}$ alkoxyalkyl, $C_{1-6}$ hydroxyalkyl, halogen, $C_{1-6}$ haloalkyl, or $C_{1-6}$ haloalkoxy;
alternatively, $R^{3b}$ is combined with the $R^{3a}$ on an adjacent ring atom and the atoms to which each is attached to form a $C_{3-6}$ cycloalkyl substituted with 0 to 4 halogens;
$X^2$ is —$CR^{3b}$— or —N—;
subscripts p, q, r, r1, s and s1 are each independently 0, 1 or 2, such that the sum of r and s is 2 or 3, and the sum of r1 and s1 is 2 or 3;
$R^4$ is $C_{1-6}$ alkyl, $C_{2-6}$ alkenyl, $C_{2-6}$ alkynyl, $C_{1-6}$ haloalkyl, —CN, $C_{3-8}$ cycloalkyl, 3 to 8 membered heterocycloalkyl having 1 to 3 heteroatoms each independently N, O or S, $C_{6-12}$ aryl, or 5 to 10 membered heteroaryl having 1 to 5 heteroatoms each independently N, O or S, wherein the cycloalkyl, heterocycloalkyl, aryl and heteroaryl are each independently substituted with 1 to 5 $R^{4a}$ groups;
each $R^{4a}$ is hydrogen, $C_{1-6}$ alkyl, $C_{1-6}$ deuteroalkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, —OH, oxo, —C(O)$R^{4b}$, —C(O)O$R^{4b}$, —C(O)N($R^{4b}$)($R^{4c}$), —S(O)$_2R^{4b}$, —S(O)$_2$N($R^{4b}$)($R^{4c}$), $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, —O—$C_{6-12}$ aryl, heteroaryl, $C_{1-6}$ alkyl-heteroaryl, wherein each heterocycloalkyl independently has 3 to 8 ring members and 1 to 3 heteroatoms each independently N, O or S, wherein each heteroaryl independently has 5 to 8 ring members and 1 to 4 heteroatoms each independently N, O or S, and wherein each cycloalkyl, heterocycloalkyl, aryl and heteroaryl is optionally substituted with $C_{1-6}$ alkoxy;
each $R^{4b}$ and $R^{4c}$ is hydrogen or $C_{1-6}$ alkyl;
$L^1$ is absent or —N($R^{5a}$)—;

$L^2$ is absent, $C_{1-6}$ alkylene, —C(O)—, —C(O)—$C_{1-6}$ alkylene-, C(O)—$C_{1-6}$ alkylene-O—, —C(O)O—, —C(O)N($R^{5b}$)—, —S(O)$_2$—, or —S(O)$_2$N($R^{5b}$)—; and $R^{5a}$ and $R^{5b}$ are each independently hydrogen, $C_{1-6}$ alkyl or $C_{2-6}$ alkoxyalkyl;

wherein when $L^2$ is absent, then $R^{3b}$ is not hydrogen.

In some embodiments, the compound of Formula I or II, or a pharmaceutically acceptable salt thereof, is the compound wherein the compound of Formula I or II, or a pharmaceutically acceptable salt thereof, is the compound wherein $L^{3a}$ and $L^{3b}$ can each independently be —CH$_2$—, —CH(Me)- or —C(Me)$_2$-. In some embodiments, the compound of Formula I or II, or a pharmaceutically acceptable salt thereof, is the compound wherein the compound of Formula I or II, or a pharmaceutically acceptable salt thereof, is the compound wherein $L^{3a}$ and $L^{3b}$ can each be —CH$_2$—.

In some embodiments, the compound of Formula III, III, IIIa, IIIb, IV, IVa, IVb, IVc, or V, or a pharmaceutically acceptable salt thereof, is the compound wherein each $R^{3a}$ is hydrogen, $C_{1-6}$ alkyl, $C_{2-6}$ alkoxyalkyl, $C_{1-6}$ hydroxyalkyl, —C(O)O$R^{3a1}$, $C_{6-12}$ aryl, or $C_{1-6}$ alkyl-$C_{6-12}$ aryl; $R^{3a1}$ is hydrogen or $C_{1-6}$ alkyl; $R^{3b}$ is hydrogen, $C_{1-6}$ alkyl, $C_{2-6}$ alkynyl, $C_{2-6}$ alkoxyalkyl, $C_{1-6}$ hydroxyalkyl, —C(O)O$R^{3b1}$, —C(O)N($R^{3b1}$)($R^{3b2}$), $C_{1-6}$ alkyl-$C_{6-12}$ aryl, $C_{1-6}$ alkyl-heteroaryl, wherein each heteroaryl has 5 to 10 ring members and 1 to 5 heteroatoms each independently N, O or S, and wherein each aryl and heteroaryl are substituted with 1 to 3 $R^{3b3}$ groups; $R^{3b1}$ and $R^{3b2}$ are each independently hydrogen or $C_{1-6}$ alkyl; alternatively $R^{3b1}$ and $R^{3b2}$ are combined with the atom to which they are attached to form a 3 to 6 membered heterocycloalkyl having 1 to 2 additional heteroatoms each independently N, O or S; and each $R^{3b3}$ is hydrogen, $C_{1-6}$ alkyl, halogen, or $C_{1-6}$ haloalkyl; alternatively, $R^{3b}$ is combined with the $R^{3a}$ on an adjacent ring atom and the atoms to which each is attached to form a $C_{3-6}$ cycloalkyl substituted with 0 to 4 halogens.

In some embodiments, the compound of Formula I or II, or a pharmaceutically acceptable salt thereof, is the compound wherein Ring J has the structure:

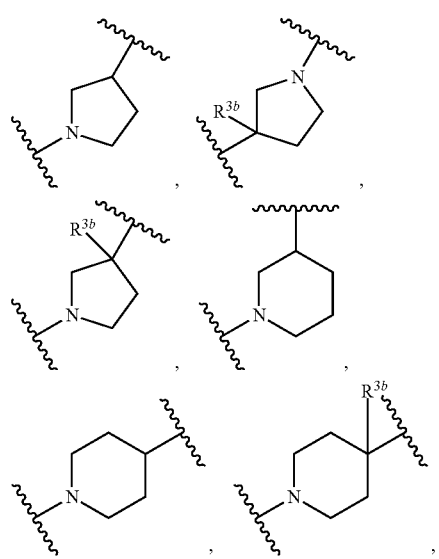

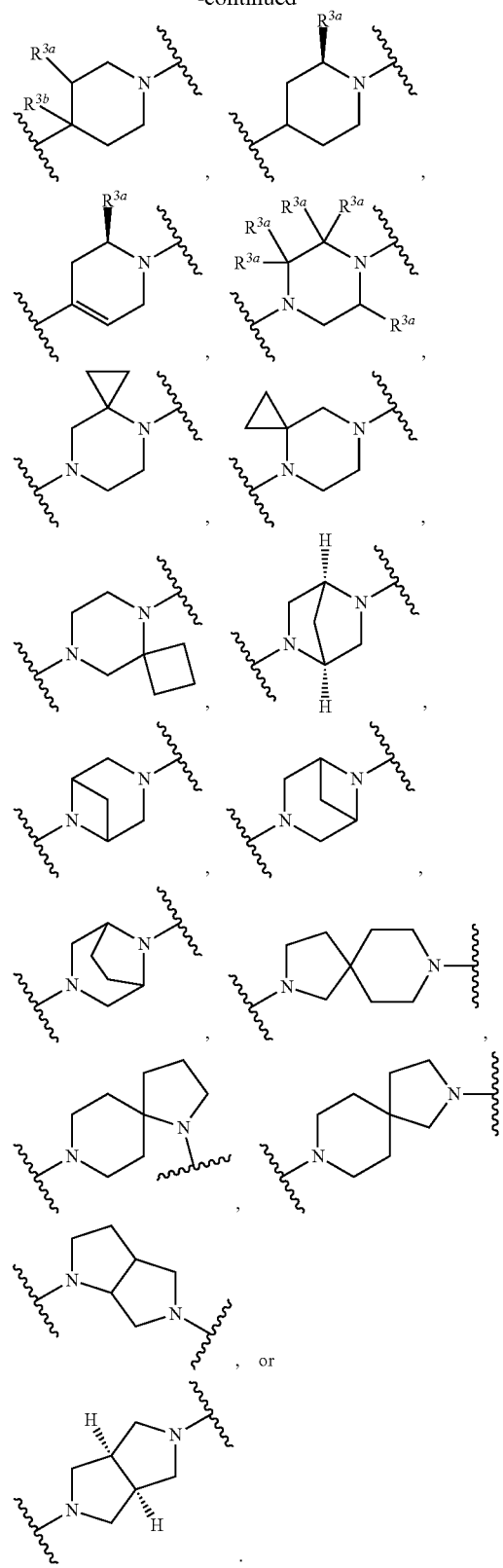

In some embodiments, the compound of Formula III, III, IIIa, IIIb, IV, IVa, IVb, IVc, or V, or a pharmaceutically acceptable salt thereof, is the compound wherein each $R^{3a}$ is hydrogen, $C_{1-6}$ alkyl, $C_{2-3}$ alkoxyalkyl, $C_{1-3}$ hydroxyalkyl, —C(O)OR$^{3a1}$, oxo, C$_{6-12}$ aryl, or C$_{1-2}$ alkyl-C$_{6-12}$ aryl; alternatively, two R$^{3a}$ groups attached to the same atom can be combined with the atom to which they are attached to form a C$_{3-4}$ cycloalkyl; R$^{3a1}$ is hydrogen or C$_{1-3}$ alkyl; and R$^{3b}$ is hydrogen. In some embodiments, the compound of Formula III, III, IIIa, IIIb, IV, IVa, IVb, IVc, or V, or a pharmaceutically acceptable salt thereof, is the compound wherein each R$^{3a}$ is independently hydrogen, methyl, ethyl, n-propyl, iso-propyl, n-butyl, iso-butyl, sec-butyl, tert-butyl, pentyl, hexyl, —CH$_2$OMe, —CH$_2$OEt, —CH$_2$OPr, —CH$_2$OH, —CH$_2$CH$_2$OH, —CH$_2$CH$_2$CH$_2$OH, oxo, —C(O)OMe, —C(O)OEt, —C(O)O$^n$Pr, phenyl, or benzyl; alternatively, two R$^{3a}$ groups attached to the same atom can be combined to form a cyclopropyl, cyclobutyl or cyclopentyl. In some embodiments, the compound of Formula I II, III, IIIa, IIIb, IV, IVa, IVb, IVc, or V, or a pharmaceutically acceptable salt thereof, is the compound wherein each R$^{3a}$ is hydrogen, methyl, iso-butyl, —CH$_2$OMe, —CH$_2$OH, oxo, —C(O)OMe, phenyl, or benzyl; alternatively, two R$^{3a}$ groups attached to the same atom can be combined with the atom to which they are attached to form a C$_{3-4}$ cycloalkyl; and R$^{3b}$ is hydrogen.

In some embodiments, the compound of Formula I or II, or a pharmaceutically acceptable salt thereof, is the compound wherein Ring J has the structure:

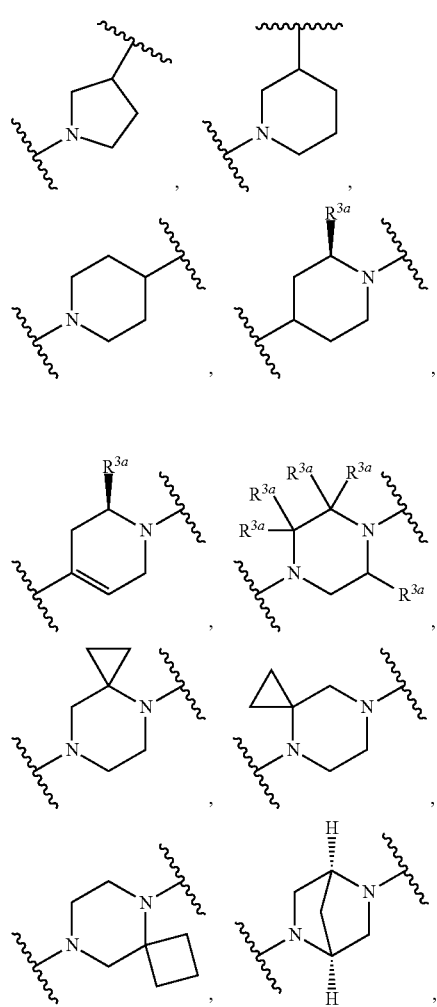

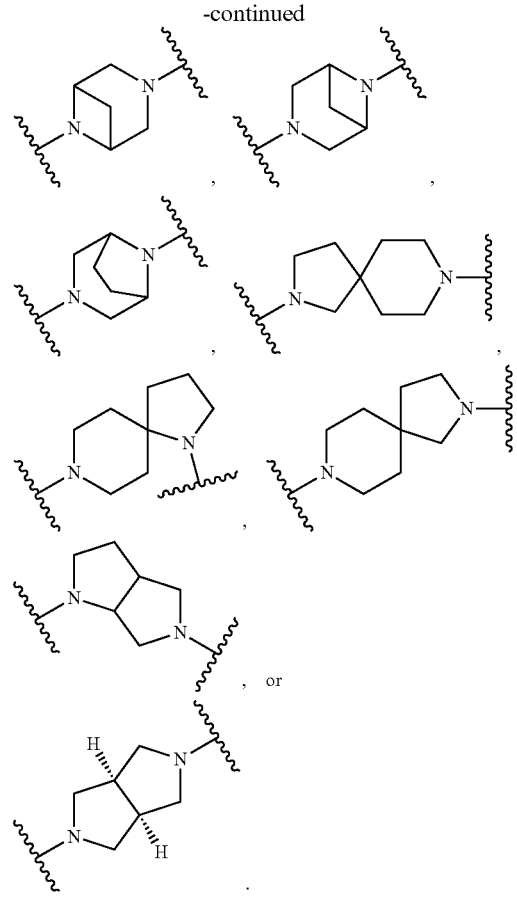

wherein each R$^{3a}$ is hydrogen, methyl, iso-butyl, —CH$_2$OMe, —CH$_2$OH, oxo, —C(O)OMe, phenyl, or benzyl.

In some embodiments, the compound of Formula III, III, IIIa, IIIb, or V, or a pharmaceutically acceptable salt thereof, is the compound wherein each R$^{3a}$ is hydrogen or methyl; and R$^{3b}$ is hydrogen.

In some embodiments, the compound of Formula I or II, or a pharmaceutically acceptable salt thereof, is the compound wherein Ring J has the structure:

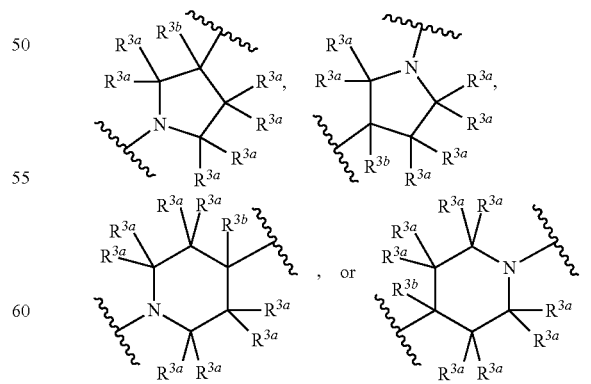

In some embodiments, the compound of Formula I or II, or a pharmaceutically acceptable salt thereof, is the compound wherein Ring J has the structure:

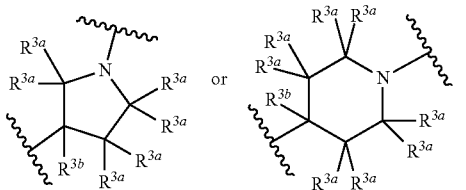

In some embodiments, the compound of Formula I or II, or a pharmaceutically acceptable salt thereof, is the compound wherein Ring J has the structure:

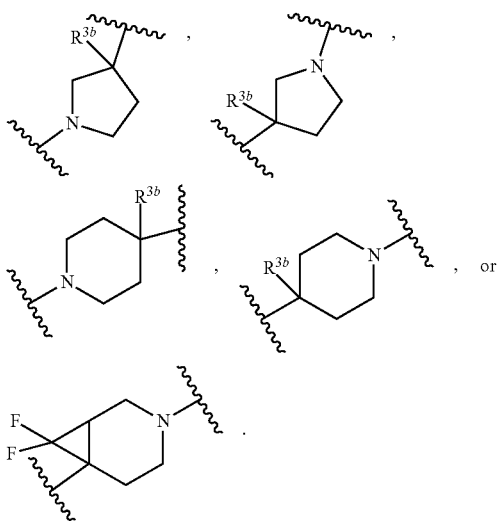

In some embodiments, the compound of Formula I or II, or a pharmaceutically acceptable salt thereof, is the compound wherein Ring J has the structure:

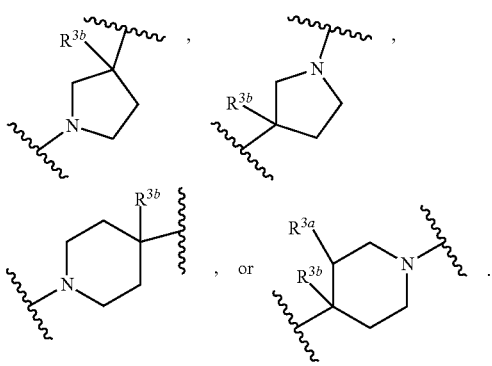

In some embodiments, the compound of Formula I, II, IIa-1, IIa-2, IIb-1, IIb-2, IIc-1, IIc-2, III, IIIa, IIIb, IV, IVa, IVb, IVc, IVd, or IVg, or a pharmaceutically acceptable salt thereof, is the compound wherein
each $R^{3a}$ is hydrogen;
$R^{3b}$ is $C_{1-6}$ alkyl, $C_{2-6}$ alkynyl, $C_{2-6}$ alkoxyalkyl, $C_{1-6}$ hydroxyalkyl, —C(O)OR$^{3b1}$, —C(O)N(R$^{3b1}$)(R$^{3b2}$), $C_{2-6}$ alkynyl-$C_{3-6}$ cycloalkyl, $C_{1-6}$ alkyl-$C_{6-12}$ aryl, $C_{2-6}$ alkenyl-$C_{6-12}$ aryl, $C_{2-6}$ alkynyl-$C_{6-12}$ aryl, $C_{1-6}$ alkyl-O—$C_{6-12}$ aryl, $C_{1-6}$ alkoxyalkyl-$C_{6-12}$ aryl, —C(O)—$C_{6-12}$ aryl, or $C_{1-6}$ alkyl-heteroaryl, wherein each heteroaryl has 5 to 10 ring members and 1 to 5 heteroatoms each independently N, O or S, wherein each aryl and heteroaryl are substituted with 1 to 3 R$^{3b3}$ groups;
$R^{3b1}$ and $R^{3b2}$ are each independently hydrogen or $C_{1-6}$ alkyl;
alternatively $R^{3b1}$ and $R^{3b2}$ are combined with the atom to which they are attached to form a 3 to 6 membered heterocycloalkyl having 1 to 2 additional heteroatoms each independently N, O or S; and
each $R^{3b3}$ is hydrogen, $C_{1-6}$ alkyl, $C_{1-6}$ hydroxyalkyl, halogen, or $C_{1-6}$ haloalkyl;
alternatively, $R^{3b}$ is combined with the $R^{3a}$ on an adjacent ring atom and the atoms to which each is attached to form a $C_{3-6}$ cycloalkyl substituted with 1 to 4 halogens.

In some embodiments, the compound of Formula I, II, IIa-1, IIa-2, IIb-1, IIb-2, IIc-1, IIc-2, III, IIIa, IIIb, IV, IVa, IVb, IVc, IVd, or IVg, or a pharmaceutically acceptable salt thereof, is the compound wherein each $R^{3a}$ is hydrogen; $R^{3b}$ is $C_{1-6}$ alkyl, $C_{2-6}$ alkynyl, $C_{2-6}$ alkoxyalkyl, $C_{1-6}$ hydroxyalkyl, —C(O)OR$^{3b1}$, —C(O)N(R$^{3b1}$)(R$^{3b2}$), $C_{1-6}$ alkyl-$C_{6-12}$ aryl, $C_{1-6}$ alkyl-heteroaryl, wherein each heteroaryl has 5 to 10 ring members and 1 to 5 heteroatoms each independently N, O or S, wherein each aryl and heteroaryl are substituted with 1 to 3 R$^{3b3}$ groups; R$^{3b1}$ and R$^{3b2}$ are each independently hydrogen or $C_{1-6}$ alkyl; alternatively R$^{3b1}$ and R$^{3b2}$ are combined with the atom to which they are attached to form a 3 to 6 membered heterocycloalkyl having 1 to 2 additional heteroatoms each independently N, O or S; and each R$^{3b3}$ is hydrogen, $C_{1-6}$ alkyl, halogen, or $C_{1-6}$ haloalkyl; alternatively, $R^{3b}$ is combined with the $R^{3a}$ on an adjacent ring atom and the atoms to which each is attached to form a $C_{3-6}$ cycloalkyl substituted with 1 to 4 halogens.

In some embodiments, the compound of Formula I, II, IIa-1, IIa-2, IIb-1, IIb-2, IIc-1, IIc-2, III, IIIa, IIIb, IV, IVa, IVb, IVc, IVd, or IVg, or a pharmaceutically acceptable salt thereof, is the compound wherein
each $R^{3a}$ is hydrogen;
$R^{3b}$ is $C_{1-3}$ alkyl, $C_{2-3}$ alkynyl, $C_{2-3}$ alkoxyalkyl, $C_{2-3}$ alkynyl-$C_{3-6}$ cycloalkyl, $C_{1-3}$ alkyl-$C_{6-12}$ aryl, $C_{2-3}$ alkenyl-$C_{6-12}$ aryl, $C_{2-3}$ alkynyl-$C_{6-12}$ aryl, $C_{1-3}$ alkyl-O—$C_{6-12}$ aryl, $C_{1-3}$ alkoxyalkyl-$C_{6-12}$ aryl, —C(O)—$C_{6-12}$ aryl, or $C_{1-3}$ alkyl-heteroaryl, wherein each heteroaryl has 5 to 10 ring members and 1 to 3 heteroatoms each independently N, O or S, wherein each aryl and heteroaryl are substituted with 1 to 3 R$^{3b3}$ groups; and
each R$^{3b3}$ is hydrogen, $C_{1-3}$ alkyl, $C_{1-3}$ hydroxyalkyl, halogen, or $C_{1-3}$ haloalkyl;
alternatively, $R^{3b}$ is combined with the $R^{3a}$ on an adjacent ring atom and the atoms to which each is attached to form a $C_{3-4}$ cycloalkyl substituted with 1 to 2 halogens.

In some embodiments, the compound of Formula I, II, IIa-1, IIa-2, IIb-1, IIb-2, IIc-1, IIc-2, III, IIIa, IIIb, IV, IVa, IVb, IVc, IVd, or IVg, or a pharmaceutically acceptable salt thereof, is the compound wherein each $R^{3a}$ is hydrogen; $R^{3b}$ is $C_{1-3}$ alkyl, benzyl, or $C_{1-2}$ alkyl-heteroaryl, wherein each heteroaryl has 5 to 10 ring members and 1 to 3 heteroatoms each independently N or S, wherein each aryl and heteroaryl are substituted with 1 to 3 R$^{3b3}$ groups; and each R$^{3b3}$ is hydrogen, $C_{1-3}$ alkyl, halogen, or $C_{1-3}$ haloalkyl; alternatively, $R^{3b}$ is combined with the $R^{3a}$ on an adjacent ring atom and the atoms to which each is attached to form a $C_{3-4}$ cycloalkyl substituted with 1 to 2 halogens.

In some embodiments, the compound of Formula I, II, IIa-1, IIa-2, IIb-1, IIb-2, IIc-1, IIc-2, III, IIIa, IIIb, IV, IVa, IVb, IVc, IVd, or IVg, or a pharmaceutically acceptable salt thereof, is the compound wherein $R^{3b}$ is methyl, ethyl, —CH$_2$C≡CH, —CH$_2$OMe, —CH$_2$OH, —C(O)OEt,

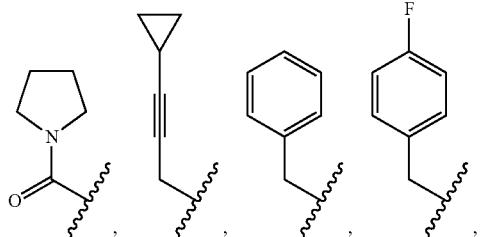

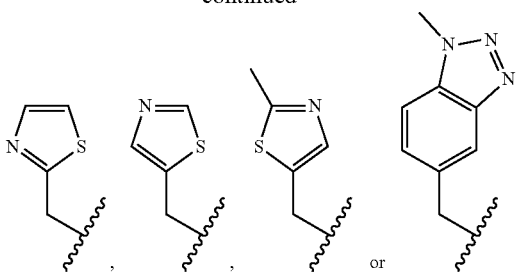

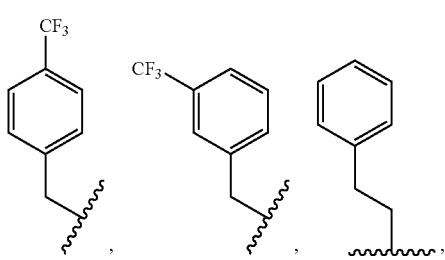

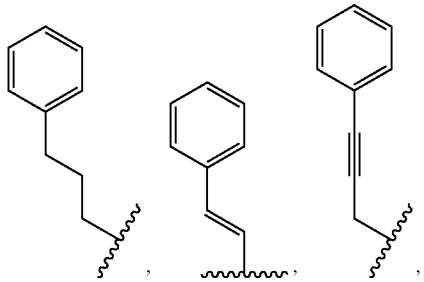

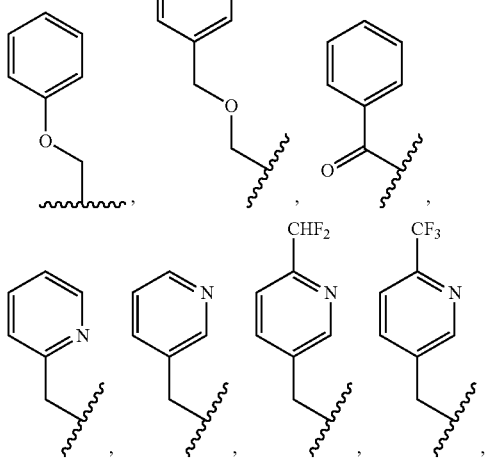

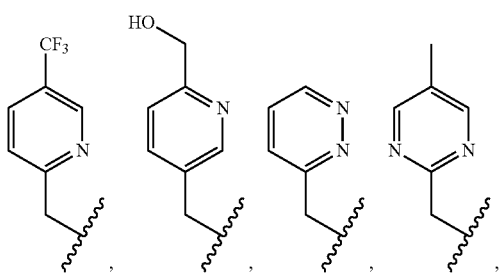

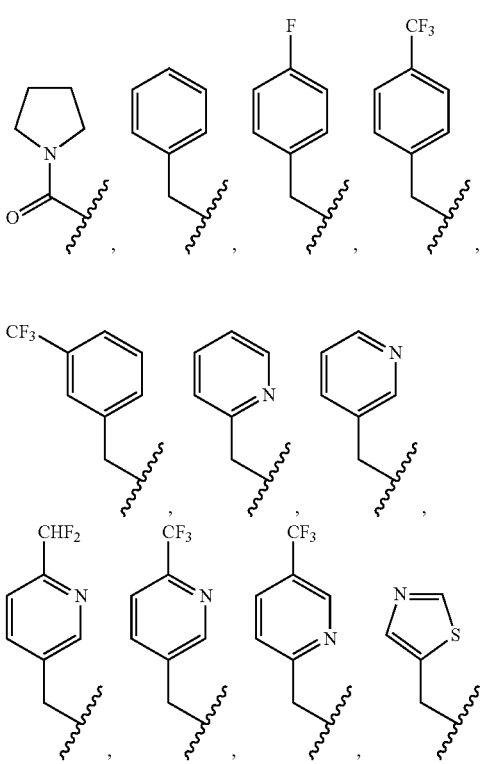

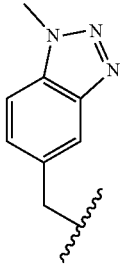

In some embodiments, the compound of Formula I, II, IIa-1, IIa-2, IIb-1, IIb-2, IIc-1, IIc-2, III, IIIa, IIIb, IV, IVa, IVb, IVc, IVd, or IVg, or a pharmaceutically acceptable salt thereof, is the compound wherein $R^{3b}$ is methyl, ethyl, —CH$_2$C≡CH, —CH$_2$OMe, —CH$_2$OH, —C(O)OEt, In some embodiments, the compound of Formula I, II, IIa-1, IIa-2, IIb-1, IIb-2, IIc-1, IIc-2, III, IIIa, IIIb, IV, IVa, IVb, IVc, IVd, or IVg, or a pharmaceutically acceptable salt thereof, is the compound wherein $R^{3b}$ is methyl,

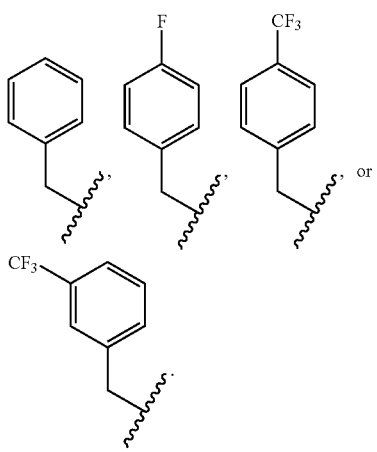

In some embodiments, the compound of Formula I, II, III, IIIa, IV, IVa, IVb, IVg, or V, or a pharmaceutically acceptable salt thereof, is the compound wherein each $R^{3a}$ is hydrogen, methyl, iso-butyl, oxo, —CH$_2$OMe, —CH$_2$OH, —C(O)OMe, phenyl, or benzyl; and $R^{3b}$ is methyl, ethyl, —CH$_2$C≡CH, —CH$_2$OMe, —CH$_2$OH, —C(O)OEt,

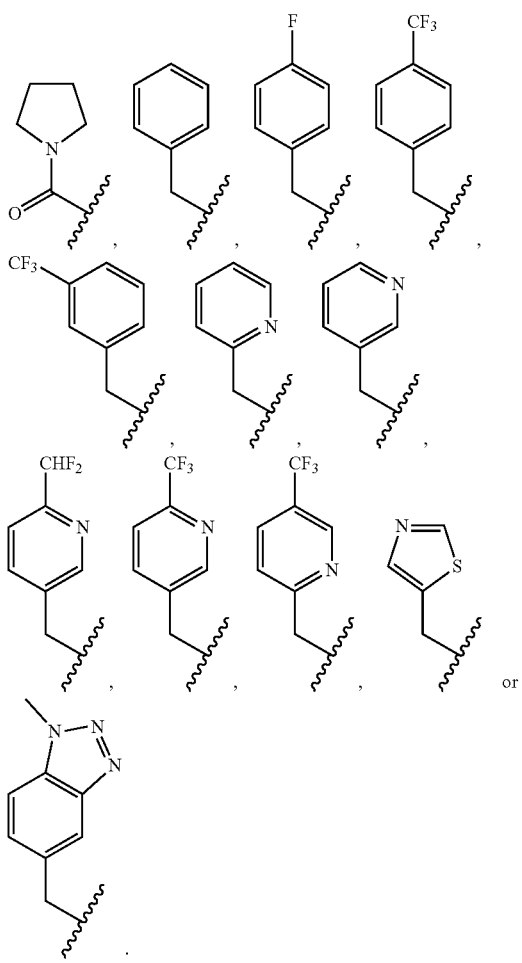

In some embodiments, the compound of Formula I, II, IIa-1, IIa-2, IIb-1, IIb-2, IIc-1, IIc-2, III, IIIa, IV, IVa, IVb, IVg, or V, or a pharmaceutically acceptable salt thereof, is the compound wherein $R^{3b}$ is methyl, ethyl, —CH$_2$C≡CH, —CH$_2$OMe, —CH$_2$OH, —C(O)OEt,

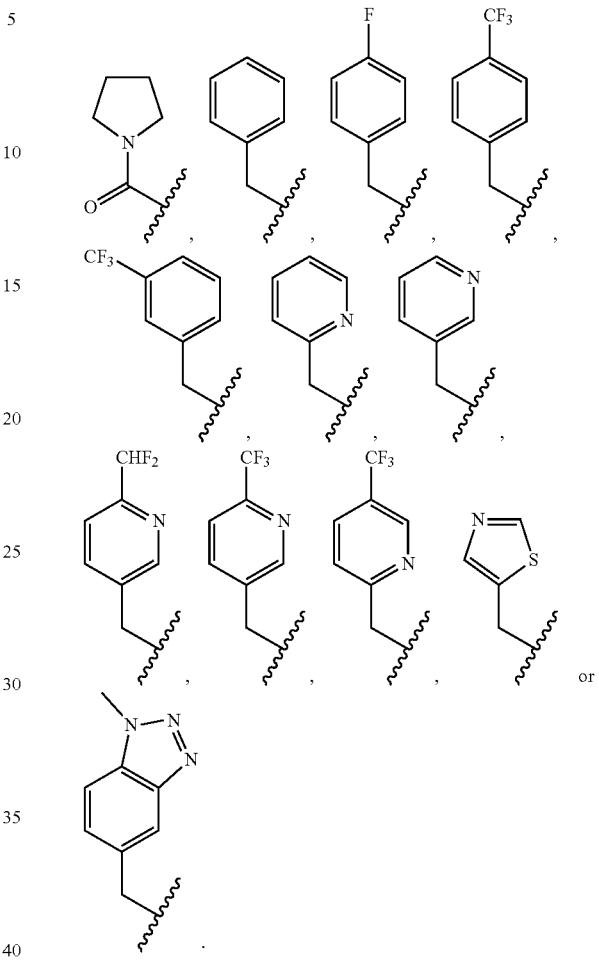

In some embodiments, the compound of Formula I, II, IIa-1, IIa-2, IIb-1, IIb-2, IIc-1 IIc-2, III, IIIa, IIIb, IV, IVa, IVb, IVc, IVd, IVe, or IVf, or a pharmaceutically acceptable salt thereof, is the compound wherein $R^4$ is $C_{1-6}$ alkyl, $C_{2-6}$ alkenyl, $C_{2-6}$ alkynyl, —CN, $C_{3-8}$ cycloalkyl, 3 to 8 membered heterocycloalkyl having 1 to 3 heteroatoms each independently N, O or S, $C_{6-12}$ aryl, or 5 to 10 membered heteroaryl having 1 to 5 heteroatoms each independently N, O or S, wherein the heterocycloalkyl, aryl and heteroaryl are each independently substituted with 1 to 5 $R^{4a}$ groups; each $R^{4a}$ is hydrogen, $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, oxo, —C(O)$R^{4b}$, —C(O)O$R^{4b}$, —C(O)N($R^{4b}$)($R^{4c}$), —S(O)$_2R^{4b}$, —S(O)$_2$N($R^{4b}$)($R^{4c}$), $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl or —O—$C_{6-12}$ aryl, wherein each heterocycloalkyl independently has 3 to 8 ring members and 1 to 3 heteroatoms each independently N, O or S, and wherein each aryl is optionally substituted with $C_{1-6}$ alkoxy; and each $R^{4b}$ and $R^{4c}$ is hydrogen or $C_{1-6}$ alkyl.

In some embodiments, the compound of Formula I, II, IIa-1, IIa-2, IIb-1, IIb-2, IIc-1 IIc-2, III, IIIa, IIIb, IV, IVa, IVb, IVc, IVd, IVe, or IVf, or a pharmaceutically acceptable salt thereof, is the compound wherein $R^4$ is $C_{1-6}$ alkyl, —CN, $C_{3-8}$ cycloalkyl, 3 to 8 membered heterocycloalkyl having 1 to 3 heteroatoms each independently N, O or S, $C_{6-12}$ aryl, or 5 to membered heteroaryl having 1 to 5 heteroatoms each independently N, O or S, wherein the heterocycloalkyl, aryl and heteroaryl are each independently substituted with 1 to 5 $R^{4a}$ groups; and each $R^{4a}$ is hydrogen, $C_{1-6}$ alkyl, $C_{2-6}$ alkoxyalkyl, $C_{1-6}$ hydroxyalkyl, $C_{1-6}$ haloalkyl, $C_{3-8}$ cycloalkyl, $C_{1-6}$ alkyl-$C_{3-8}$ cycloalkyl, a 3 to 8 membered heterocycloalkyl having 1 to 3 heteroatoms each independently N, O or S, $C_{6-12}$ aryl or —O—$C_{6-12}$ aryl, wherein each aryl is optionally substituted with $C_{1-6}$ alkoxy.

In some embodiments, the compound of Formula I, II, IIa-1, IIa-2, IIb-1, IIb-2, IIc-1 IIc-2, III, IIIa, IIIb, IV, IVa, IVb, IVc, IVd, IVe, or IVf, or a pharmaceutically acceptable salt thereof, is the compound wherein $R^4$ is $C_{1-4}$ alkyl, —CN, $C_{3-6}$ cycloalkyl, 5 to 6 membered heterocycloalkyl having 1 heteroatom N or O, $C_{6-12}$ aryl, or 5 to 10 membered heteroaryl having 1 to 4 heteroatoms each independently N, O or S, wherein the heterocycloalkyl, aryl and heteroaryl are each independently substituted with 1 to 2 $R^{4a}$ groups; and each $R^{4a}$ is hydrogen, $C_{1-4}$ alkyl, $C_{2-4}$ alkoxyalkyl, $C_{1-3}$ hydroxy alkyl, $C_{1-3}$ haloalkyl, $C_{3-6}$ cycloalkyl, $C_{1-2}$ alkyl-$C_{3-5}$ cycloalkyl, a 4 to 6 membered heterocycloalkyl having 1 heteroatom N, O or S, or $C_{6-12}$ aryl, wherein each aryl is optionally substituted with $C_{1-3}$ alkoxy.

In some embodiments, the compound of Formula I, II, IIa-1, IIa-2, IIb-1, IIb-2, IIc-1 IIc-2, III, IIIa, IIIb, IV, IVa, IVb, IVc, IVd, IVe, or IVf, or a pharmaceutically acceptable salt thereof, is the compound wherein
   $R^4$ is $C_{1-3}$ alkyl, $C_{1-3}$ haloalkyl, —CN, $C_{3-6}$ cycloalkyl, 4 to 6 membered heterocycloalkyl having 1 heteroatoms each N or O, $C_{6-12}$ aryl, or 5 to 10 membered heteroaryl having 1 to 4 heteroatoms each independently N, O or S, wherein the cycloalkyl, heterocycloalkyl, aryl and heteroaryl are each independently substituted with 1 to 2 $R^{4a}$ groups; and
   each $R^{4a}$ is hydrogen, $C_{1-3}$ alkyl, $C_{1-3}$ deuteroalkyl, $C_{1-3}$ alkoxy, $C_{2-3}$ alkoxyalkyl, $C_{1-3}$ hydroxyalkyl, halogen, $C_{1-3}$ haloalkyl, —CN, —OH, oxo, —S(O)$_2$R$^{4b}$, —S(O)$_2$ N(R$^{4b}$)(R$^{4c}$), $C_{3-6}$ cycloalkyl, $C_{1-2}$ alkyl-$C_{3-6}$ cycloalkyl, $C_{6-12}$ aryl, or —O—$C_{6-12}$ aryl, wherein each aryl is optionally substituted with $C_{1-6}$ alkoxy.

In some embodiments, the compound of Formula I, II, IIa-1, IIa-2, IIb-1, IIb-2, IIc-1 or IIc-2, or a pharmaceutically acceptable salt thereof, is the compound wherein each $R^{4a}$ is each $R^{4a}$ is hydrogen, $C_{1-6}$ alkyl, $C_{2-6}$ alkoxyalkyl, $C_{1-6}$ hydroxyalkyl, $C_{1-6}$ haloalkyl, $C_{3-8}$ cycloalkyl, $C_{1-6}$ alkyl-$C_{3-8}$ cycloalkyl, a 3 to 8 membered heterocycloalkyl having 1 to 3 heteroatoms each independently N, O or S, $C_{6-12}$ aryl or —O—$C_{6-12}$ aryl, wherein each aryl is optionally substituted with $C_{1-6}$ alkoxy. In some embodiments, the compound of Formula I, II, IIa-1, IIa-2, IIb-1, IIb-2, IIc-1 or IIc-2, or a pharmaceutically acceptable salt thereof, is the compound wherein each $R^{4a}$ is hydrogen, $C_{1-4}$ alkyl, $C_{2-4}$ alkoxyalkyl, $C_{1-3}$ hydroxyalkyl, $C_{1-3}$ haloalkyl, $C_{3-6}$ cycloalkyl, $C_{1-2}$ alkyl-$C_{3-5}$ cycloalkyl, a 4 to 6 membered heterocycloalkyl having 1 heteroatom N, O or S, or $C_{6-12}$ aryl, wherein each aryl is optionally substituted with $C_{1-3}$ alkoxy. In some embodiments, the compound of Formula I, II, IIa-1, IIa-2, IIb-1, IIb-2, IIc-1 or IIc-2, or a pharmaceutically acceptable salt thereof, is the compound wherein each $R^{4a}$ is hydrogen, methyl, n-propyl, iso-propyl, iso-butyl, —OCH$_3$, —CH$_2$CH$_2$OCH$_3$, —CH$_2$OH, F, —CF$_3$, —CH$_2$CF$_3$, cyclopentyl, —CH$_2$-cyclopropyl, tetrahydrofuranyl, or 2-methoxyphenyl.

In some embodiments, the compound of Formula I, II, IIa-1, IIa-2, III, IIIa, IIIb, IV, IVa, IVb, IVc, IVd, IVe, or IVf, or a pharmaceutically acceptable salt thereof, is the compound wherein $R^4$ is methyl, ethyl, n-propyl, iso-propyl, t-butyl, —CN,

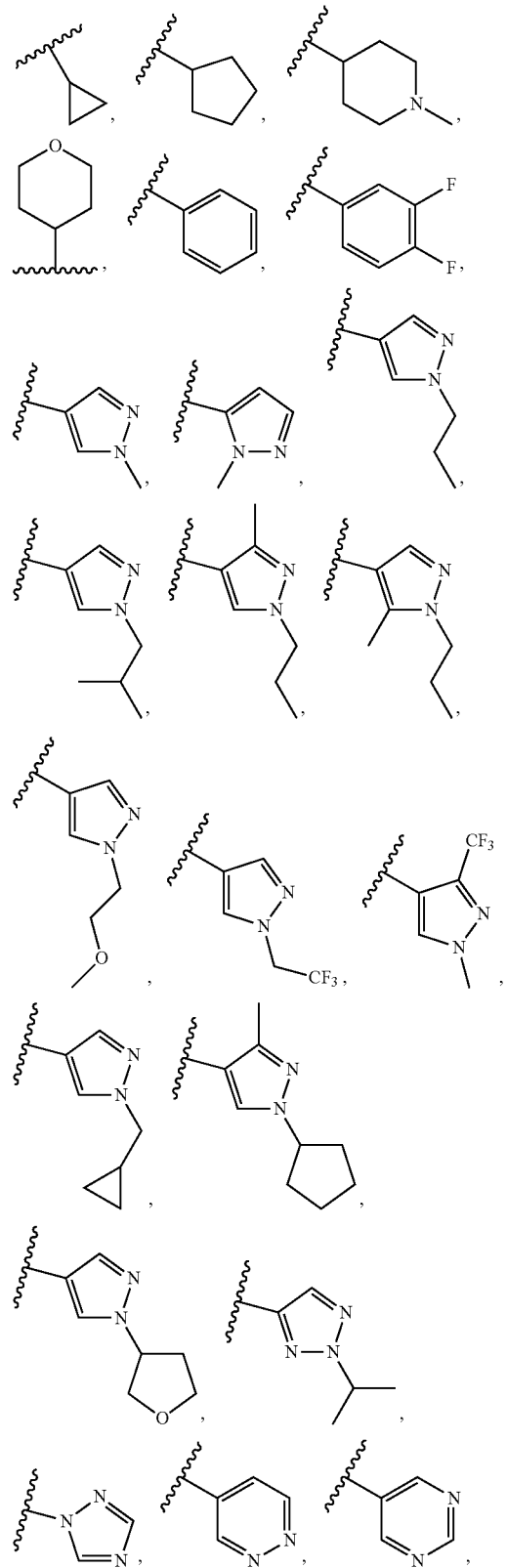

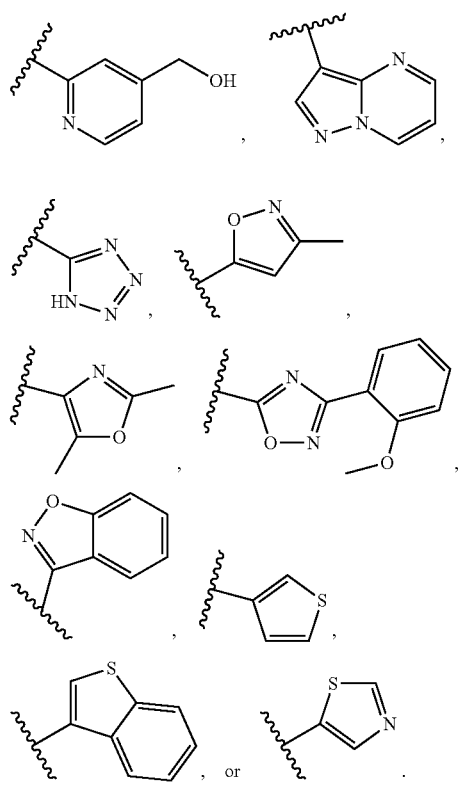

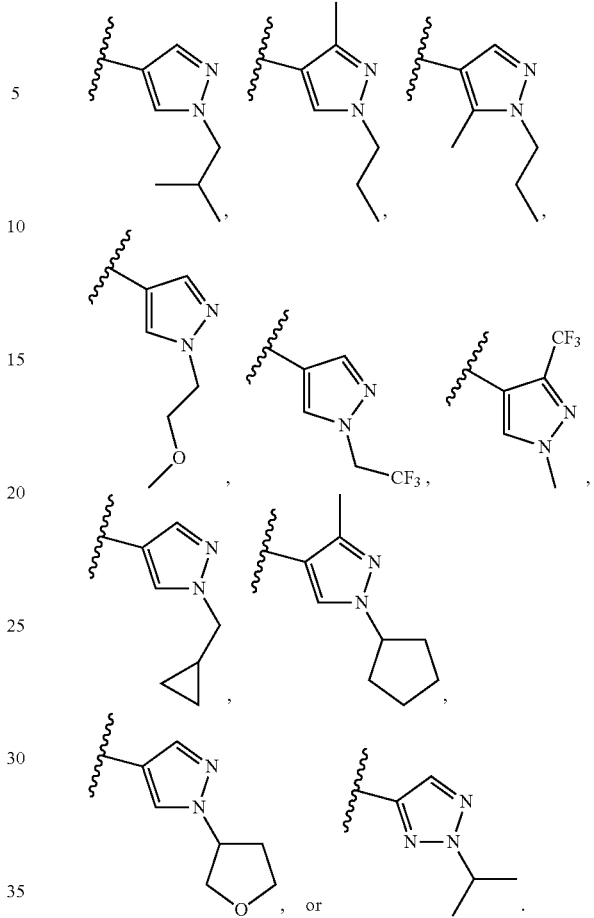

In some embodiments, the compound of Formula I, II, IIa-1, IIa-2, IIb-1, IIb-2, IIc-1 or IIc-2, or a pharmaceutically acceptable salt thereof, is the compound wherein each $R^{4a}$ is hydrogen, $C_{1-4}$ alkyl, $C_{2-4}$ alkoxyalkyl, $C_{1-3}$ haloalkyl, $C_{3-6}$ cycloalkyl, $C_{1-2}$ alkyl-$C_{3-5}$ cycloalkyl, or a 4 to 6 membered heterocycloalkyl having 1 heteroatom N, O or S. In some embodiments, the compound of Formula I, II, IIa-1, IIa-2, IIb-1, IIb-2, IIc-1 or IIc-2, or a pharmaceutically acceptable salt thereof, is the compound wherein each $R^{4a}$ is hydrogen, methyl, n-propyl, iso-propyl, iso-butyl, —CH$_2$CH$_2$OCH$_3$, F, —CF$_3$, —CH$_2$CF$_3$, cyclopentyl, —CH$_2$-cyclopropyl, or tetrahydrofuranyl.

In some embodiments, the compound of Formula I, II, IIa-1, IIa-2, III, IIIa, IIIb, IV, IVa, IVb, IVc, IVd, IVe, or IVf, or a pharmaceutically acceptable salt thereof, is the compound wherein $R^4$ is methyl, ethyl, n-propyl, iso-propyl, t-butyl,

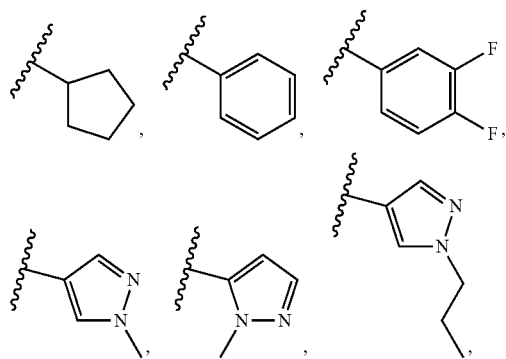

In some embodiments, the compound of Formula I, II, IIa-1, IIa-2, IIb-1, IIb-2, IIc-1 IIc-2, III, IIIa, IIIb, IV, IVa, IVb, IVc, IVd, IVe, or IVf, or a pharmaceutically acceptable salt thereof, is the compound wherein $R^4$ is $C_{1-3}$ alkyl, —CN, $C_{3-6}$ cycloalkyl, 4 to 6 membered heterocycloalkyl having 1 heteroatoms each N or O, $C_{6-12}$ aryl, or 5 to 10 membered heteroaryl having 1 to 4 heteroatoms each independently N, O or S, wherein the heterocycloalkyl, aryl and heteroaryl are each independently substituted with 1 to 2 $R^{4a}$ groups; and each $R^{4a}$ is hydrogen, $C_{1-3}$ alkyl, $C_{1-3}$ hydroxyalkyl, $C_{3-6}$ cycloalkyl, $C_{1-2}$ alkyl-$C_{3-6}$ cycloalkyl, or $C_{6-12}$ aryl, wherein each aryl is optionally substituted with $C_{1-6}$ alkoxy.

In some embodiments, the compound of Formula I, II, IIa-1, IIa-2, IIb-1, IIb-2, IIc-1 IIc-2, III, IIIa, IIIb, IV, IVa, IVb, IVc, IVd, IVe, or IVf, or a pharmaceutically acceptable salt thereof, is the compound wherein each $R^{4a}$ is hydrogen, $C_{1-3}$ alkyl, $C_{1-3}$ hydroxyalkyl, $C_{3-6}$ cycloalkyl, $C_{1-2}$ alkyl-$C_{3-6}$ cycloalkyl, or $C_{6-12}$ aryl, wherein each aryl is optionally substituted with $C_{1-6}$ alkoxy. In some embodiments, the compound of Formula I, II, IIa-1, IIa-2, IIb-1, IIb-2, IIc-1 IIc-2, III, IIIa, IIIb, IV, IVa, IVb, IVc, IVd, IVe, or IVf, or a pharmaceutically acceptable salt thereof, is the compound wherein each $R^{4a}$ is hydrogen, methyl, n-propyl, —OCH$_3$, —CH$_2$OH, —CH$_2$-cyclopropyl, or 2-methoxyphenyl.

In some embodiments, the compound of Formula I, II, IIa-1, IIa-2, IIb-1, IIb-2, IIc-1 IIc-2, III, IIIa, IIIb, IV, IVa, IVb, IVc, IVd, IVe, or IVf, or a pharmaceutically acceptable salt thereof, is the compound wherein $R^4$ is methyl, ethyl, —$CF_2CH_3$, —CN, cyclopropyl, cyclobutyl, piperidinyl, tetrahydropyranyl, pyrimidinedione, phenyl, pyrazolyl, imidazolyl, triazolyl, tetrazolyl, pyridinyl, pyridin-2-one, pyridazinyl, pyrimidinyl, indazolyl, pyrazolo-pyrimidine, oxazolyl, isoxazolyl, oxadiazolyl, benzoisoxazolyl, thiophenyl, benzothiophenyl or thiazolyl; and each $R^{4a}$ is hydrogen, methyl, ethyl, n-propyl, iso-butyl, —$CD_3$, methoxy, —$CH_2CH_2OCH_3$, hydroxymethyl, F, Cl, —$CHF_2$, —$CF_3$, —$CH_2CF_3$, —CN, —OH, oxo, —$S(O)_2Me$, —$S(O)_2NHMe$, cyclobutyl, cyclopropylmethyl, 2-methoxyphenyl or -OPh.

In some embodiments, the compound of Formula I, II, IIa-1, IIa-2, IIb-1, IIb-2, IIc-1 IIc-2, III, IIIa, IIIb, IV, IVa, IVb, IVc, IVd, IVe, or IVf, or a pharmaceutically acceptable salt thereof, is the compound wherein $R^4$ is methyl, —CN, cyclopropyl, piperidinyl, tetrahydropyranyl, phenyl, pyrazolyl, triazolyl, tetrazolyl, pyridinyl, pyridazinyl, pyrimidinyl, pyrazolo-pyrimidine, oxazolyl, isoxazolyl, oxadiazolyl, benzoisoxazolyl, thiophenyl, benzothiophenyl or thiazolyl; and each $R^{4a}$ is hydrogen, methyl, n-propyl, methoxy, hydroxymethyl, cyclopropylmethyl, or 2-methoxyphenyl.

In some embodiments, the compound of Formula I, II, IIa-1, IIa-2, IIb-1, IIb-2, IIc-1 IIc-2, III, IIIa, IIIb, IV, IVa, IVb, IVc, IVd, IVe, or IVf, or a pharmaceutically acceptable salt thereof, is the compound wherein $R^4$ is methyl, ethyl, —$CF_2CH_3$, —CN,

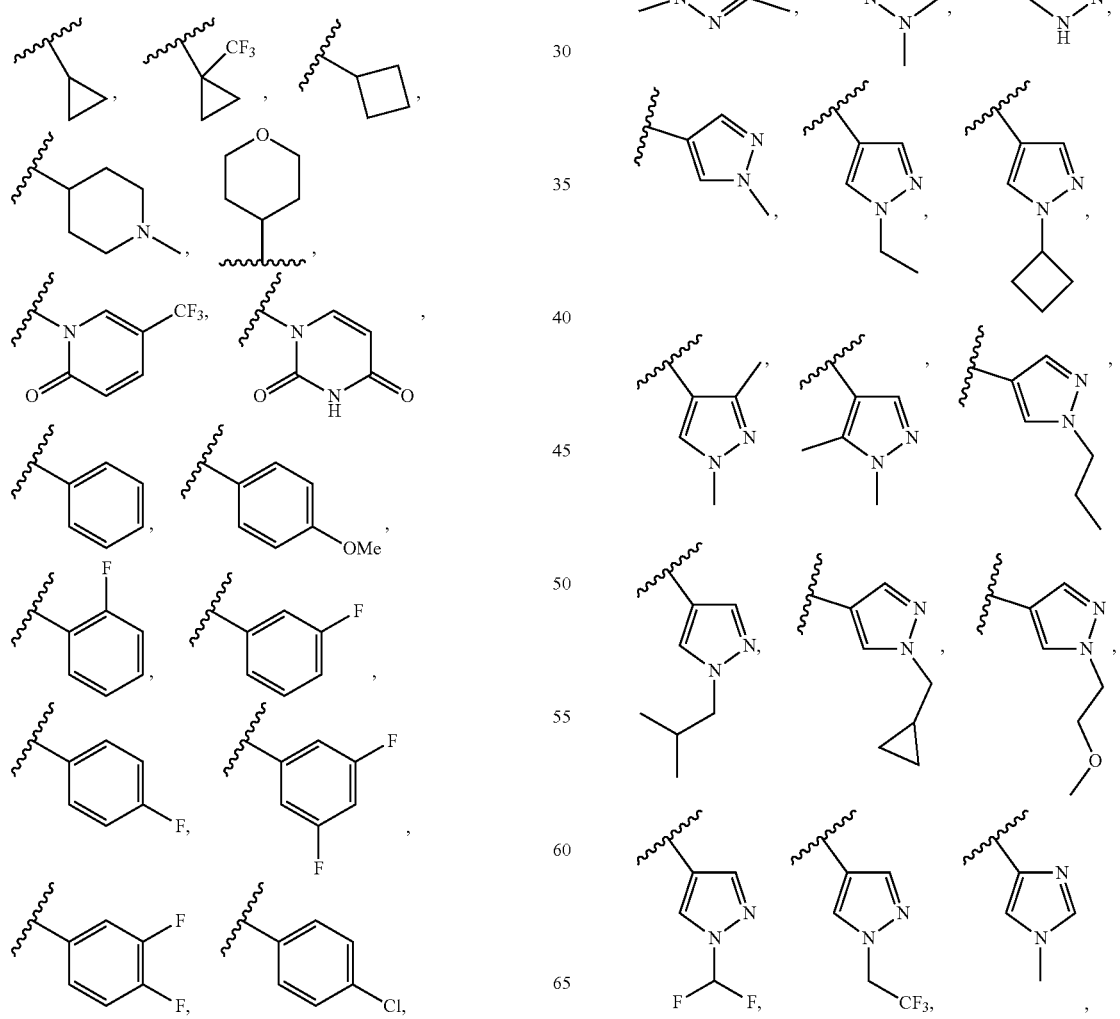
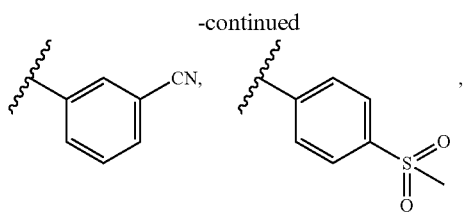
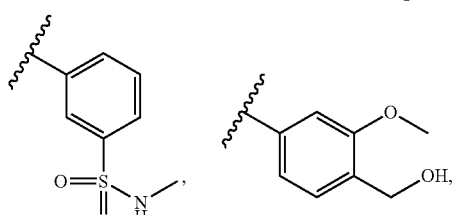
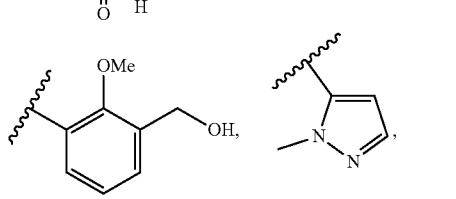
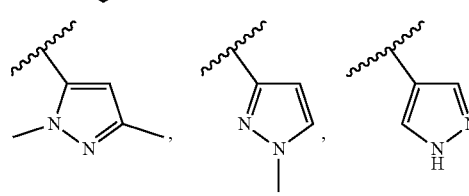
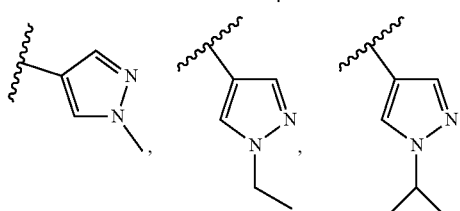
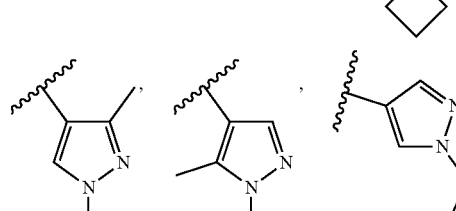
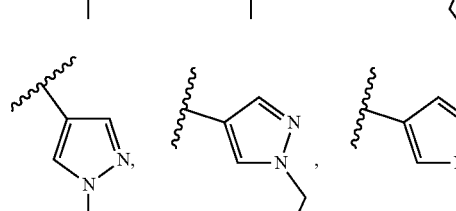
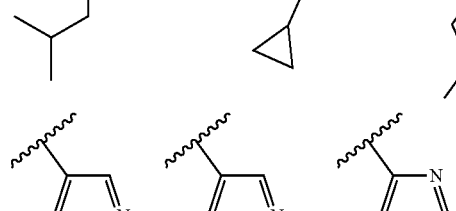
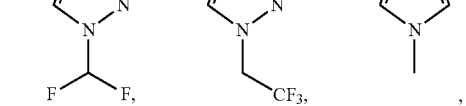

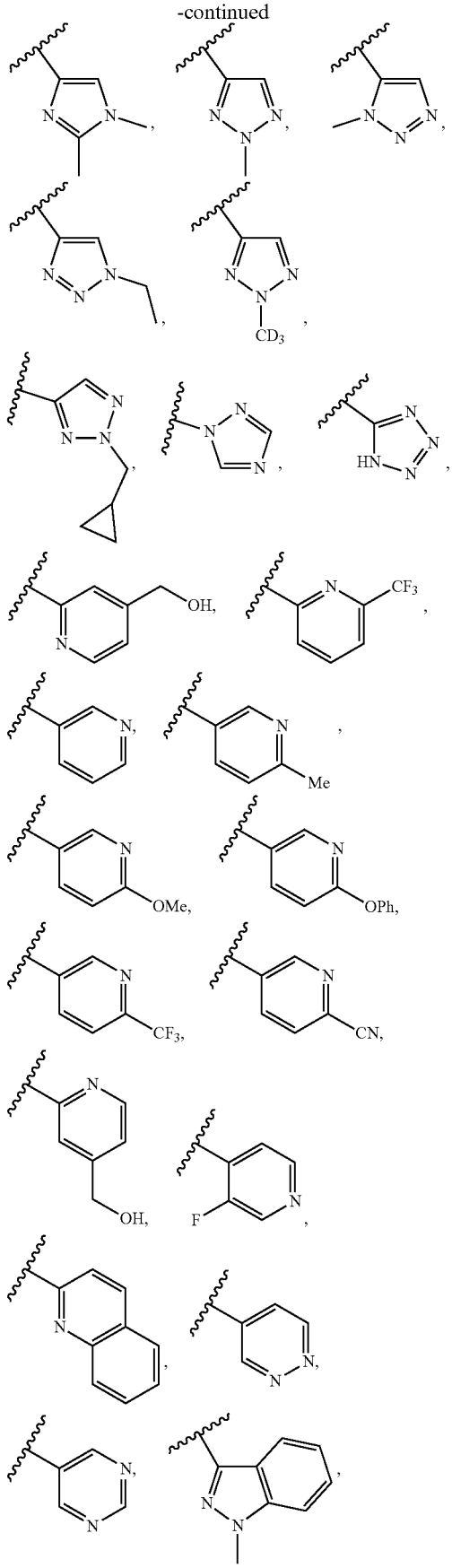
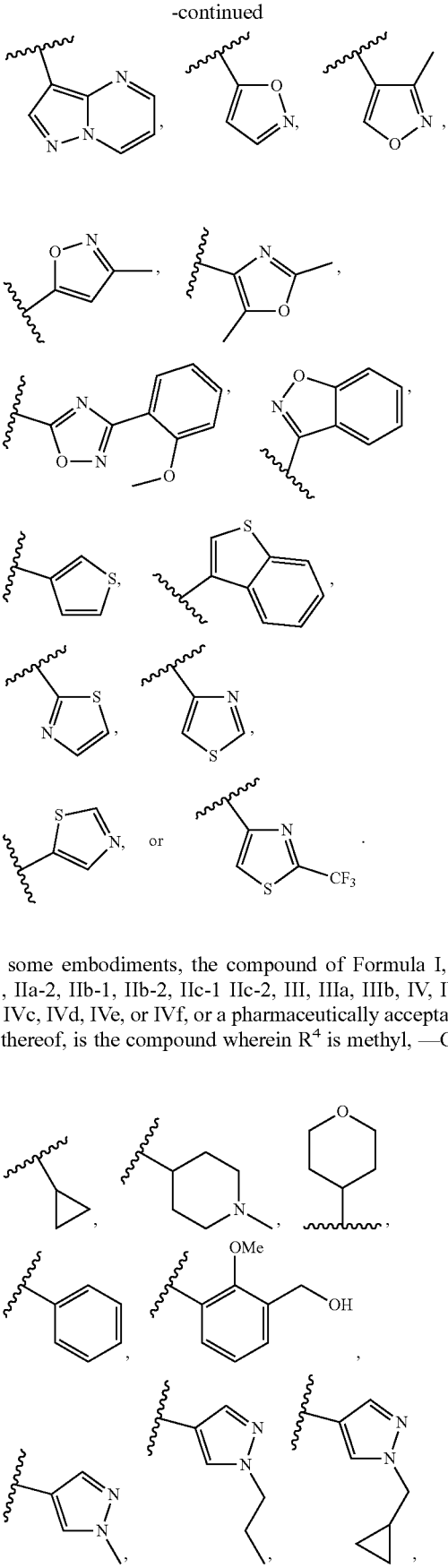
In some embodiments, the compound of Formula I, II, IIa-1, IIa-2, IIb-1, IIb-2, IIc-1 IIc-2, III, IIIa, IIIb, IV, IVa, IVb, IVc, IVd, IVe, or IVf, or a pharmaceutically acceptable salt, thereof, is the compound wherein $R^4$ is methyl, —CN, -continued

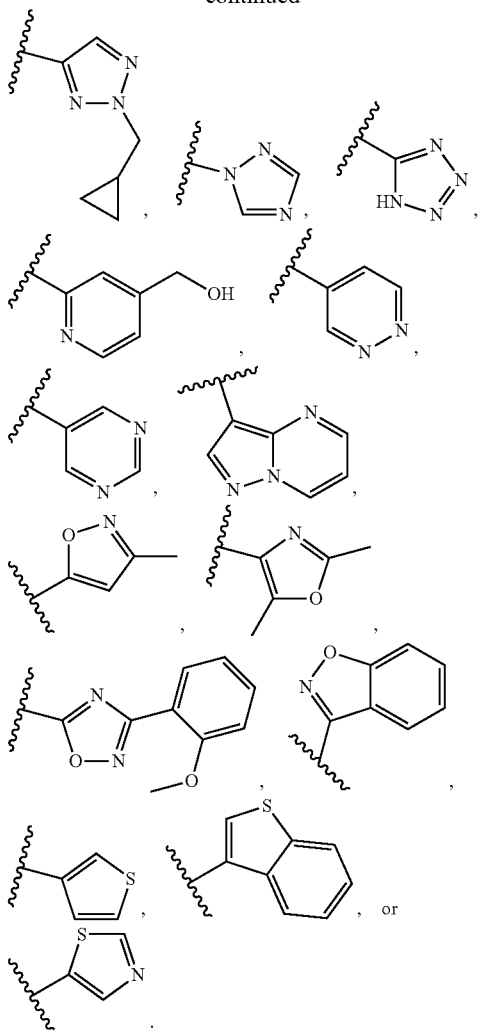

In some embodiments, the compound of Formula I, II, IIa-1, IIa-2, IIb-1, IIb-2, IIc-1 IIc-2, III, IIIa, IIIb, IV, IVa, IVb, IVc, IVd, IVe, or IVf, or a pharmaceutically acceptable salt thereof, is the compound wherein $R^4$ is methyl,

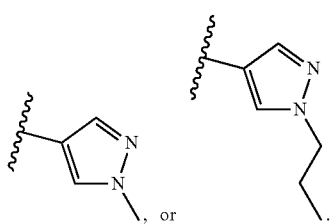

In some embodiments, the compound of Formula I, II, IIa-1, IIa-2, IIb-1, IIb-2, IIc-1 IIc-2, III, IIIa, IIIb, IV, IVa, IVb, IVc, IVd, or IVe, or a pharmaceutically acceptable salt thereof, is the compound wherein $L^1$ is absent or —N($R^{5a}$)—; $L^2$ is absent, —C(O)—, —C(O)—$C_{1-6}$ alkylene-, C(O)—$C_{1-6}$ alkylene-O—, —C(O)O—, —C(O)N($R^{5b}$)—, —S(O)$_2$—, or —S(O)$_2$N($R^{5b}$)—; and $R^{5a}$ and $R^{5b}$ are each independently hydrogen, $C_{1-6}$ alkyl or $C_{2-6}$ alkoxyalkyl.

In some embodiments, the compound of Formula I, II, IIa-1, IIa-2, IIb-1 IIb-2, III, IIIa, IIIb, IV, IVa, IVb, IVc, IVd, or IVe, or a pharmaceutically acceptable salt thereof, is the compound wherein $L^1$ is absent, -NMe-, or —NH—. In some embodiments, the compound of Formula I, II, IIa-1, IIa-2, IIb-1, IIb-2, III, IIIa, IIIb, IV, IVa, IVb, IVc, IVd, or IVe, or a pharmaceutically acceptable salt thereof, is the compound wherein $L^1$ is absent. In some embodiments, the compound of Formula I, II, IIa-1, IIa-2, IIb-1, IIb-2, III, IIIa, IIIb, IV, IVa, IVb, IVc, IVd, or IVe, or a pharmaceutically acceptable salt thereof, is the compound wherein $L^1$ is -NMe- or —NH—. In some embodiments, the compound of Formula I, II, IIa-1, IIa-2, IIb-1, IIb-2, III, IIIa, IIIb, IV, IVa, IVb, IVc, IVd, or IVe, or a pharmaceutically acceptable salt thereof, is the compound wherein $L^1$ is -NMe-. In some embodiments, the compound of Formula I, II, IIa-1, IIa-2, IIb-1, IIb-2, III, IIIa, IIIb, IV, IVa, IVb, IVc, IVd, or IVe, or a pharmaceutically acceptable salt thereof, is the compound wherein $L^1$ is —NH—. In some embodiments, the compound of Formula I, II, IIa-1, IIa-2, III, IIIa, IIIb, IV, IVa, IVb, IVc, IVd, or IVe, or a pharmaceutically acceptable salt thereof, is the compound wherein $L^2$ is absent, —C(O)—, —C(O)O—, —C(O)NR$^{5b}$—, —S(O)$_2$—, or —S(O)$_2$—NR$^{5b}$—. In some embodiments, the compound of Formula I, II, IIa-1, IIa-2, III, IIIa, IIIb, IV, IVa, IVb, IVc, IVd, or IVe, or a pharmaceutically acceptable salt thereof, is the compound wherein $L^2$ is absent, —C(O)—, —C(O)CH$_2$—, —C(O)CH$_2$CH$_2$—, —C(O)(CH$_2$)$_3$O—, —C(O)O—, —C(O)NH—, —S(O)$_2$—, —S(O)$_2$—NH— or —S(O)$_2$—N(Me)-. In some embodiments, the compound of Formula I, II, IIa-1, IIa-2, III, IIIa, IIIb, IV, IVa, IVb, IVc, IVd, or IVe, or a pharmaceutically acceptable salt thereof, is the compound wherein $L^2$ is —S(O)$_2$—, —S(O)$_2$—NH— or —S(O)$_2$ —N(Me)-.

In some embodiments, the compound of Formula I, II, IIa-1, IIa-2, III, IIIa, IIIb, IV, IVa, IVb, IVc, IVd, or IVe, or a pharmaceutically acceptable salt thereof, is the compound wherein $L^1$ and $L^2$ together are absent, —CH$_2$—, —C(O)—, —C(O)CH$_2$—, —C(O)CH$_2$CH$_2$—, —C(O)CH$_2$O—, —C(O)(CH$_2$)$_3$O—, —C(O)O—, —C(O)NH—, —S(O)$_2$—, —NH—S(O)$_2$—, —N(Me)S(O)$_2$—, —N(CH$_2$CH$_2$OCH$_3$)S(O)$_2$—, —S(O)$_2$—NH— or —S(O)$_2$—N(Me)-. In some embodiments, the compound of Formula I, II, IIa-1, IIa-2, III, IIIa, IIIb, IV, IVa, IVb, IVc, IVd, or IVe, or a pharmaceutically acceptable salt thereof, is the compound wherein $L^1$ and $L^2$ together are absent, —C(O)—, —C(O)CH$_2$—, —C(O)CH$_2$CH$_2$—, —C(O)(CH$_2$)$_3$O—, —C(O)O—, —C(O)NH—, —S(O)$_2$—, —NH—S(O)$_2$—, —N(Me)S(O)$_2$ —, —N(CH$_2$CH$_2$OCH$_3$)S(O)$_2$—, —S(O)$_2$—NH— or —S(O)$_2$—N(Me)-. In some embodiments, the compound of Formula I, II, IIa-1, IIa-2, III, IIIa, IIIb, IV, IVa, IVb, IVc, IVd, or IVe, or a pharmaceutically acceptable salt thereof, is the compound wherein $L^1$ and $L^2$ together are —C(O)—, —C(O)O—, —C(O)NH—, —S(O)$_2$—, —NH—S(O)$_2$—, —N(Me)S(O)$_2$—, —N(CH$_2$CH$_2$OCH$_3$)S(O)$_2$—, —S(O)$_2$—NH— or —S(O)$_2$—N(Me)- In some embodiments, the compound of Formula I, II, IIa-1, IIa-2, III, IIIa, IIIb, IV, IVa, IVb, IVc, IVd, or IVe, or a pharmaceutically acceptable salt thereof, is the compound wherein $L^1$ and $L^2$ together are absent, —CH$_2$—, —C(O)—, —C(O)CH$_2$—, —C(O)CH$_2$CH$_2$—, —C(O)CH$_2$O—, —C(O)(CH$_2$)$_3$O—, —S(O)$_2$—, —NH—S(O)$_2$—, or —N(Me)S(O)$_2$—. In some embodiments, the compound of Formula I, II, IIa-1, IIa-2, III, IIIa, IIIb, IV, IVa, IVb, IVc, IVd, or IVe, or a pharmaceutically acceptable salt thereof, is the compound wherein $L^1$ and $L^2$ together are absent, —C(O)—, —C(O)CH$_2$—, —C(O)CH₂CH₂—, —C(O)(CH₂)₃O—, —S(O)₂—, —NH—S(O)₂—, or —N(Me)S(O)₂—.

In some embodiments, the compound of Formula I, II, or IIa-1, or a pharmaceutically acceptable salt thereof, is the compound wherein Ring J has the structure:

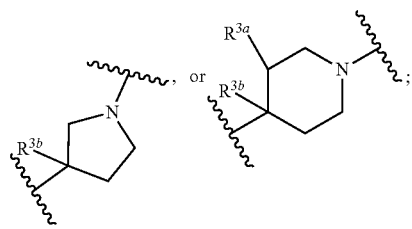

$L^1$ is absent; and $L^2$ is —C(O)—, —C(O)—C$_{1-6}$ alkylene-, C(O)—C$_{1-6}$ alkylene-O—, —C(O)O—, or —S(O)₂—. In some embodiments, the compound of Formula I, II, or IIa-1, or a pharmaceutically acceptable salt thereof, is the compound wherein $L^1$ and $L^2$ together are —C(O)—, —C(O)CH₂—, —C(O)CH₂CH₂—, —C(O)(CH₂)₃O—, or —S(O)₂—.

In some embodiments, the compound of Formula I, II, or IIa-2, or a pharmaceutically acceptable salt thereof, is the compound wherein Ring J has the structure:

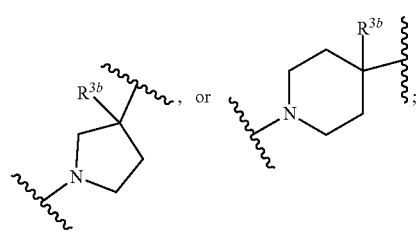

and $L^1$ is —N(R$^{5a}$)—; $L^2$ is —C(O)—, —C(O)—C$_{1-6}$ alkylene-, C(O)—C$_{1-6}$ alkylene-O—, or —S(O)₂—; and R$^{5a}$ is hydrogen or C$_{1-6}$ alkyl. In some embodiments, the compound of Formula I, II, or IIa-2, or a pharmaceutically acceptable salt thereof, is the compound wherein $L^1$ and $L^2$ together are —NHS(O)₂— or —N(Me)S(O)₂—.

In some embodiments, the compound of Formula I or II, or a pharmaceutically acceptable salt thereof, is the compound of Formula IIa-1 or IIa-2:

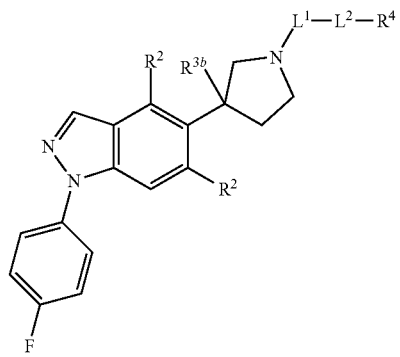

(IIa-1)

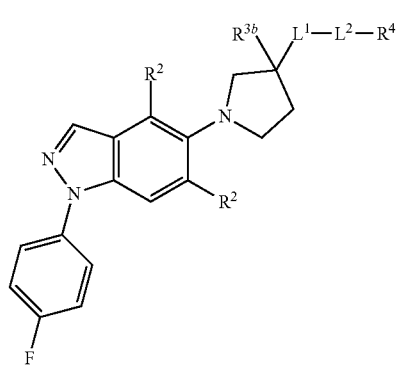

(IIa-2)

wherein each R², R$^{3b}$, L¹, L², and R⁴ are as defined within.

In some embodiments, the compound of Formula I, II, IIa-1 or IIa-2, or a pharmaceutically acceptable salt thereof, is the compound of Formula IIb-1 or IIb-2:

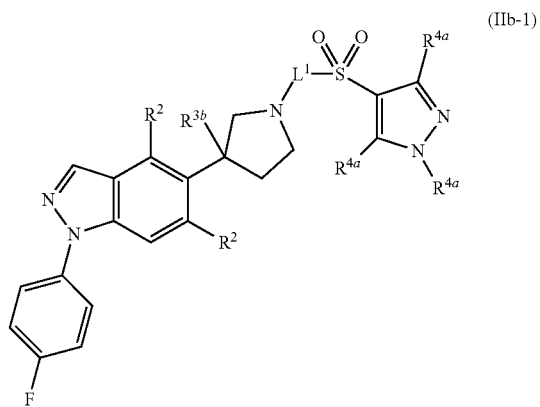

(IIb-1)

-continued

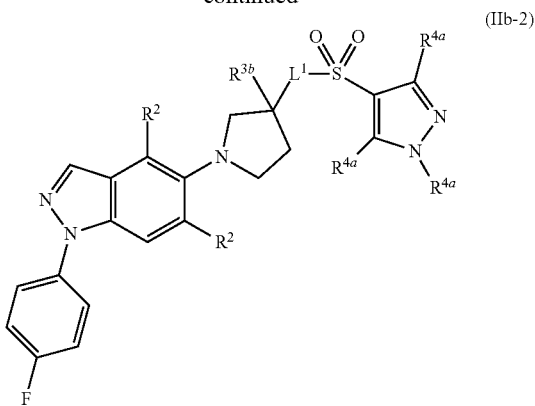

(IIb-2)

wherein each $R^2$, $R^{3b}$, $L^1$, and $R^{4a}$ are as defined within.

In some embodiments, the compound of Formula I, II, IIa-1, IIa-2, IIb-1 or IIb-2, or a pharmaceutically acceptable salt thereof, is the compound of Formula IIc-1 or IIc-2:

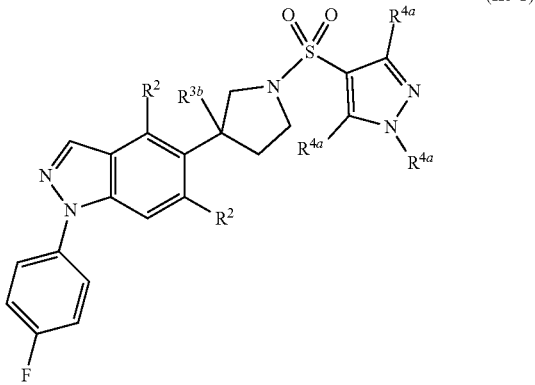

(IIc-1)

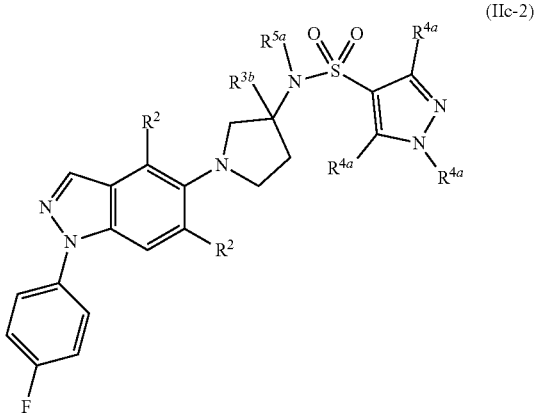

(IIc-2)

wherein each $R^2$, $R^{3b}$, $R^{4a}$, and $R^{5a}$ are as defined within.

In some embodiments, the compound of Formula I or II, or a pharmaceutically acceptable salt thereof, is the compound wherein $R^1$ is phenyl substituted with 1 to 5 $R^{1a}$ groups each independently hydrogen, $C_{1-6}$ alkoxy, halogen or —C(O)N($R^{1b}$)($R^{1c}$), wherein each $R^{1b}$ and $R^{1c}$ is independently hydrogen or a 4 to 6 membered heterocycloalkyl having 1 to 3 heteroatoms each independently N, O or S;

$A^1$, $A^2$, $A^3$ and $A^4$ are each independently =CR²— or =N—;

each $R^2$ is independently hydrogen, $C_{1-6}$ alkyl, $C_{1-6}$ alkoxy, halogen, or $C_{1-6}$ haloalkoxy;

Ring J has the structure:

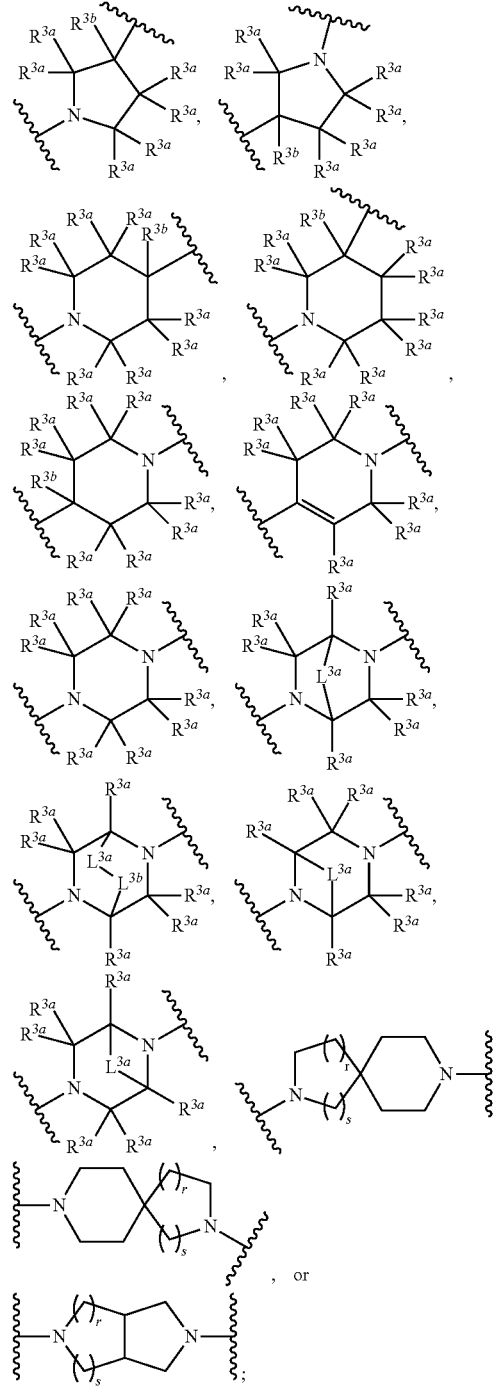

each $R^{3a}$ is hydrogen, $C_{1-6}$ alkyl, $C_{2-6}$ alkoxyalkyl, $C_{1-6}$ hydroxyalkyl, —C(O)O$R^{3a1}$, $C_{6-12}$ aryl, or $C_{1-6}$ alkyl-$C_{6-12}$ aryl;

$R^{3a1}$ is hydrogen or $C_{1-6}$ alkyl;

$R^{3b}$ is hydrogen, $C_{1-6}$ alkyl, $C_{2-6}$ alkynyl, $C_{2-6}$ alkoxyalkyl, $C_{1-6}$ hydroxyalkyl, —C(O)O$R^{3b1}$, —C(O)N($R^{3b1}$)

($R^{3b2}$), $C_{1-6}$ alkyl-$C_{6-12}$ aryl, $C_{1-6}$ alkyl-heteroaryl, wherein each heteroaryl has 5 to 10 ring members and 1 to 5 heteroatoms each independently N, O or S, and wherein each aryl and heteroaryl are substituted with 1 to 3 $R^{3b3}$ groups;

$R^{3b1}$ and $R^{3b2}$ are each independently hydrogen or $C_{1-6}$ alkyl;

alternatively $R^{3b1}$ and $R^{3b2}$ are combined with the atom to which they are attached to form a 3 to 6 membered heterocycloalkyl having 1 to 2 additional heteroatoms each independently N, O or S;

each $R^{3b3}$ is hydrogen, $C_{1-6}$ alkyl, halogen, or $C_{1-6}$ haloalkyl;

alternatively, $R^{3b}$ is combined with the $R^{3a}$ on an adjacent ring atom and the atoms to which each is attached to form a $C_{3-6}$ cycloalkyl substituted with 0 to 4 halogens;

$L^{3a}$ and $L^{3b}$ are each —C($R^{3a3}$)($R^{3a3}$)—;

each $R^{3a3}$ is independently hydrogen or $C_{1-6}$ alkyl;

$R^4$ is $C_{1-6}$ alkyl, —CN, $C_{3-8}$ cycloalkyl, 3 to 8 membered heterocycloalkyl having 1 to 3 heteroatoms each independently N, O or S, $C_{6-12}$ aryl, or 5 to 10 membered heteroaryl having 1 to 5 heteroatoms each independently N, O or S, wherein the heterocycloalkyl, aryl and heteroaryl are each independently substituted with 1 to 5 $R^{4a}$ groups;

each $R^{4a}$ is hydrogen, $C_{1-6}$ alkyl, $C_{2-6}$ alkoxyalkyl, $C_{1-6}$ hydroxyalkyl, $C_{1-6}$ haloalkyl, $C_{3-8}$ cycloalkyl, $C_{1-6}$ alkyl-$C_{3-8}$ cycloalkyl, a 3 to 8 membered heterocycloalkyl having 1 to 3 heteroatoms each independently N, O or S, $C_{6-12}$ aryl or —O—$C_{6-12}$ aryl, wherein each aryl is optionally substituted with $C_{1-6}$ alkoxy;

$L^1$ is absent or —N($R^{5a}$)—;

$L^2$ is absent, —C(O)—, —C(O)—$C_{1-6}$ alkylene-, C(O)—$C_{1-6}$ alkylene-O—, —C(O)O—, —C(O)N($R^{5b}$)—, —S(O)$_2$—, or —S(O)$_2$N($R^{5b}$)—;

$R^{5a}$ and $R^{5b}$ are each independently hydrogen, $C_{1-6}$ alkyl or $C_{2-6}$ alkoxyalkyl; and subscripts r and s are each independently 0, 1 or 2, such that the sum of r and s is 2.

In some embodiments, the compound of Formula I or II, or a pharmaceutically acceptable salt thereof, is the compound wherein $R^1$ is

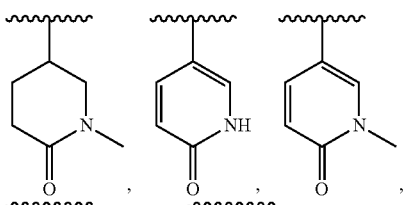

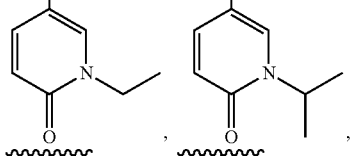

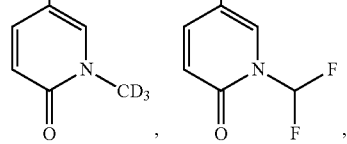

-continued

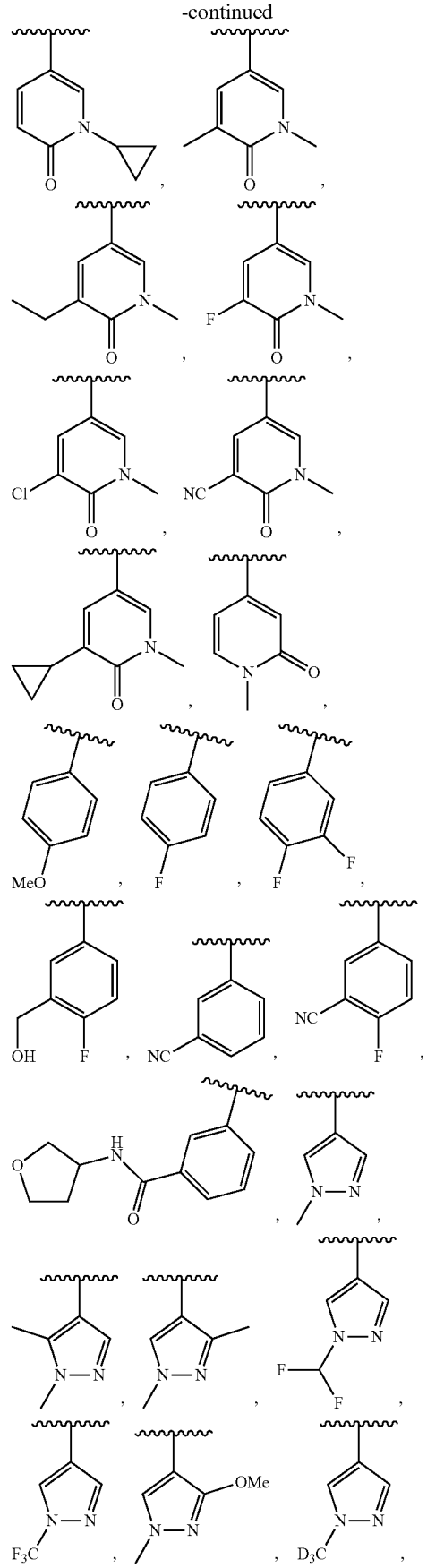

-continued
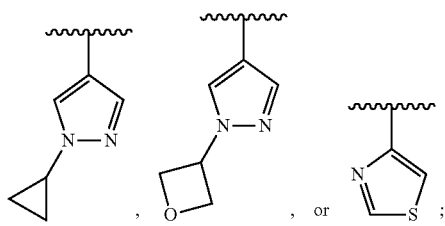
A¹ is =CH— or =N—;
A² and A⁴ are each independently =CH—, =C(Me)- or =N—;
A³ is =CH—, =C(Me)-, =C(Et)-, =C(iPr)—, =C(OMe)-, =C(F)— =C(Cl)—, =C(OCHF$_2$)—, =C(CN)— or =N—;
Ring J has the structure:
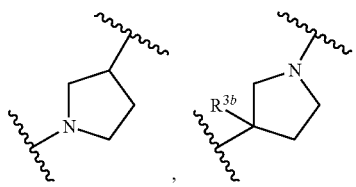
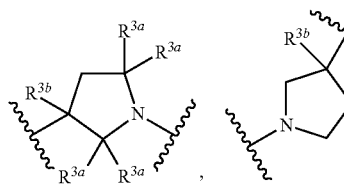
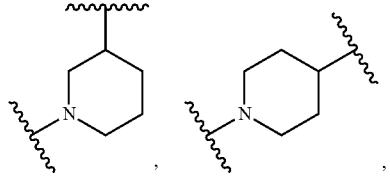
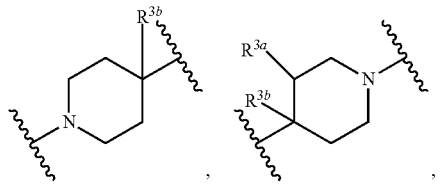
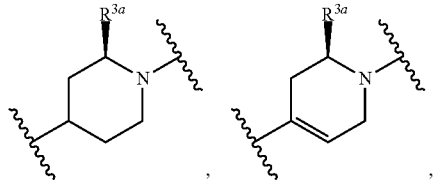
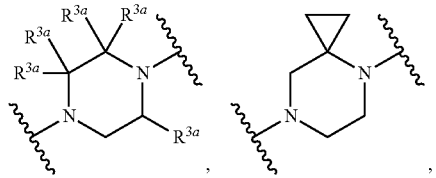
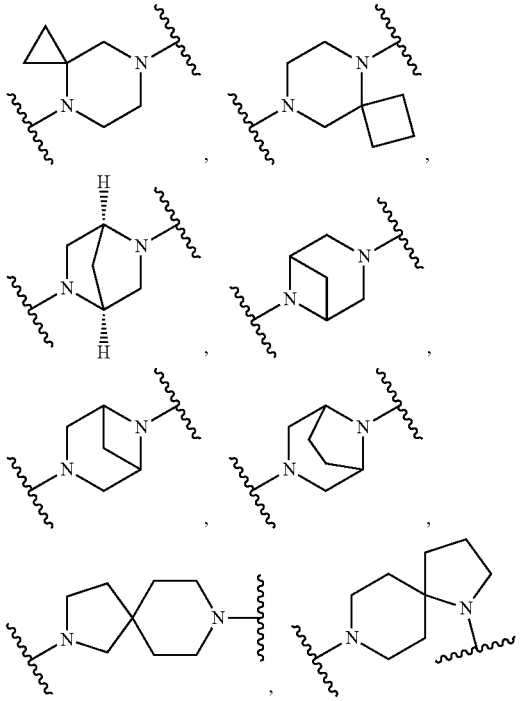
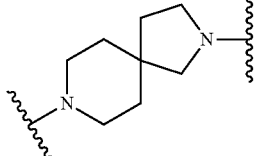
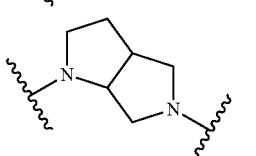
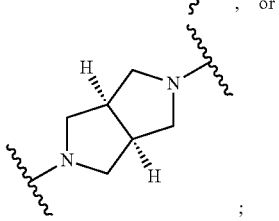, or
each $R^{3a}$ is hydrogen, methyl, iso-butyl, —OH, oxo, —CH$_2$OMe, —CH$_2$OH, —C(O)OMe, phenyl, or benzyl;
$R^{3b}$ is methyl, ethyl, —CH$_2$C≡CH, —CH$_2$OMe, —CH$_2$OH, —C(O)OEt,
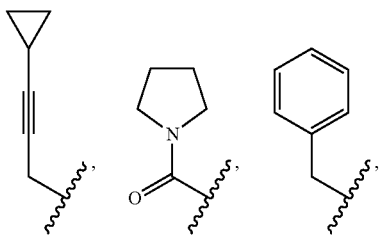

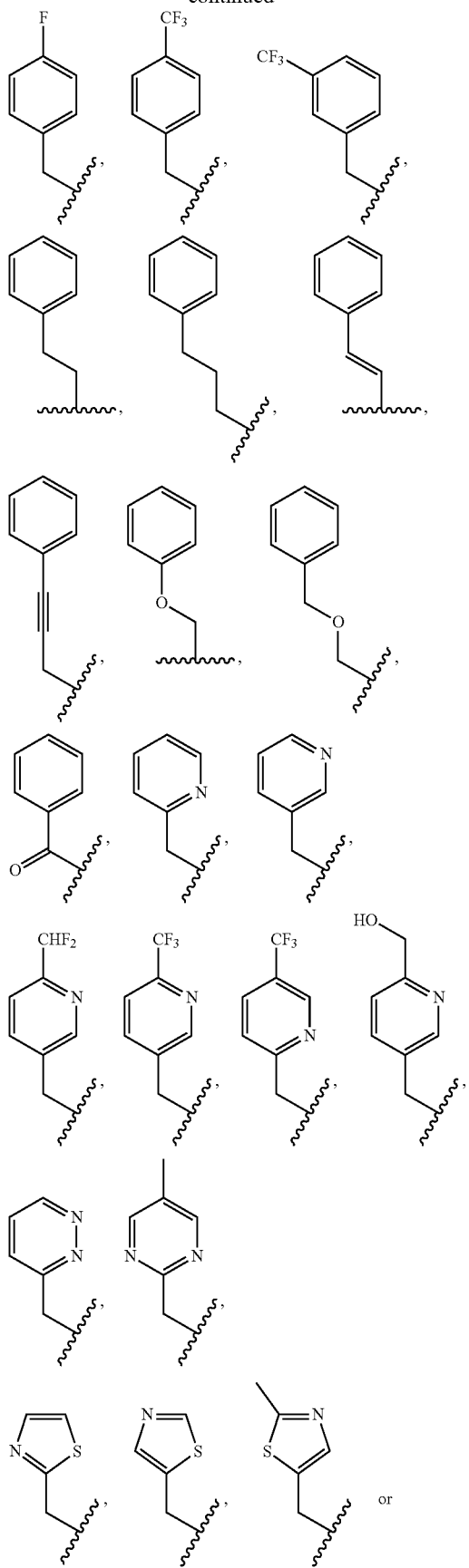
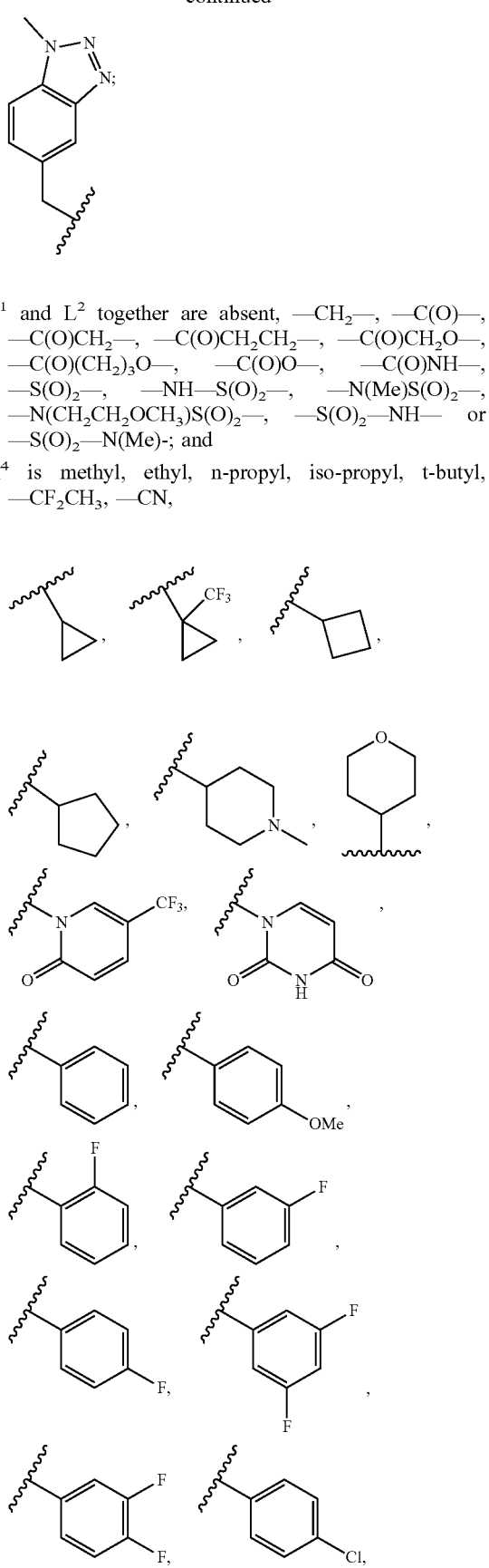
$L^1$ and $L^2$ together are absent, —CH$_2$—, —C(O)—, —C(O)CH$_2$—, —C(O)CH$_2$CH$_2$—, —C(O)CH$_2$O—, —C(O)(CH$_2$)$_3$O—, —C(O)O—, —C(O)NH—, —S(O)$_2$—, —NH—S(O)$_2$—, —N(Me)S(O)$_2$—, —N(CH$_2$CH$_2$OCH$_3$)S(O)$_2$—, —S(O)$_2$—NH— or —S(O)$_2$—N(Me)-; and
$R^4$ is methyl, ethyl, n-propyl, iso-propyl, t-butyl, —CF$_2$CH$_3$, —CN, -continued
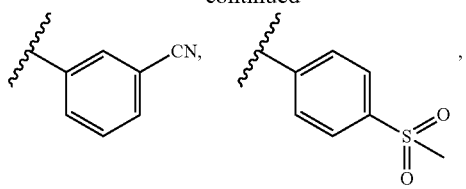
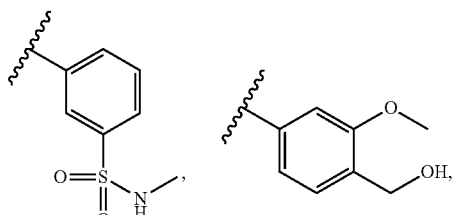
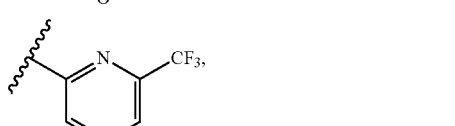
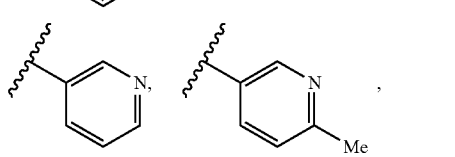
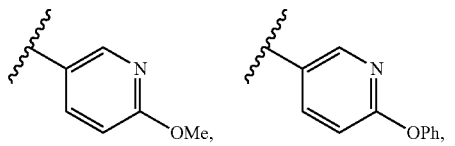
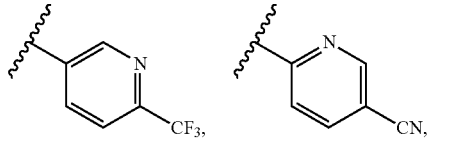
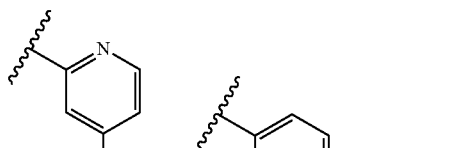
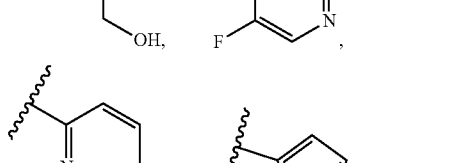
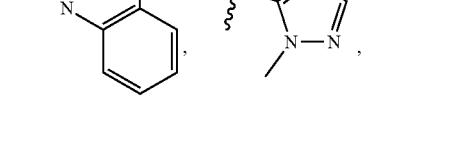
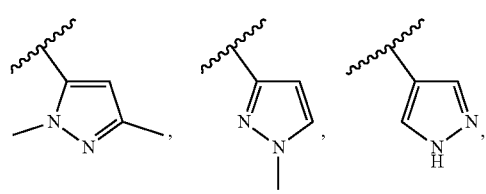
-continued
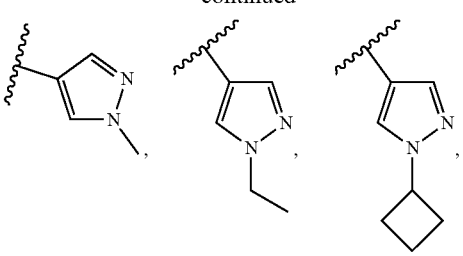
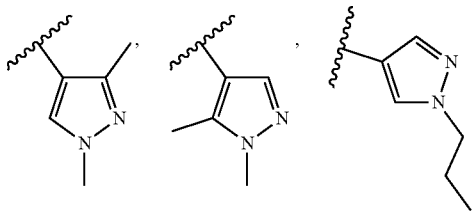
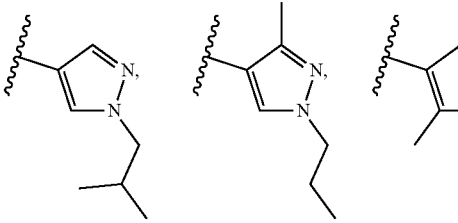
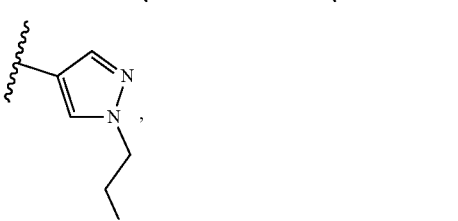
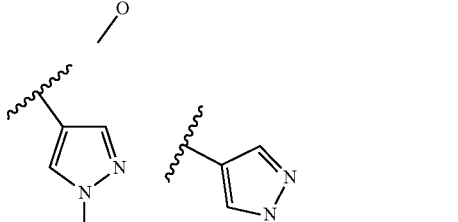
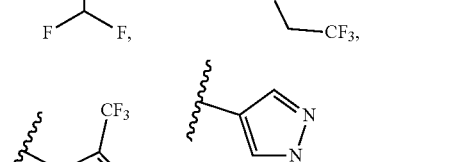
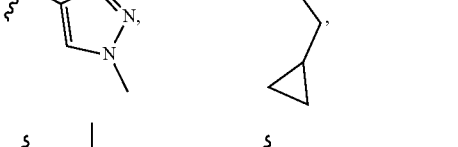
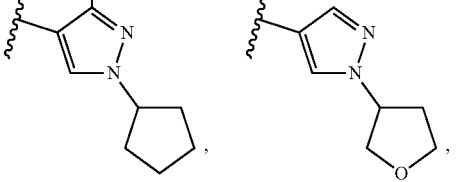

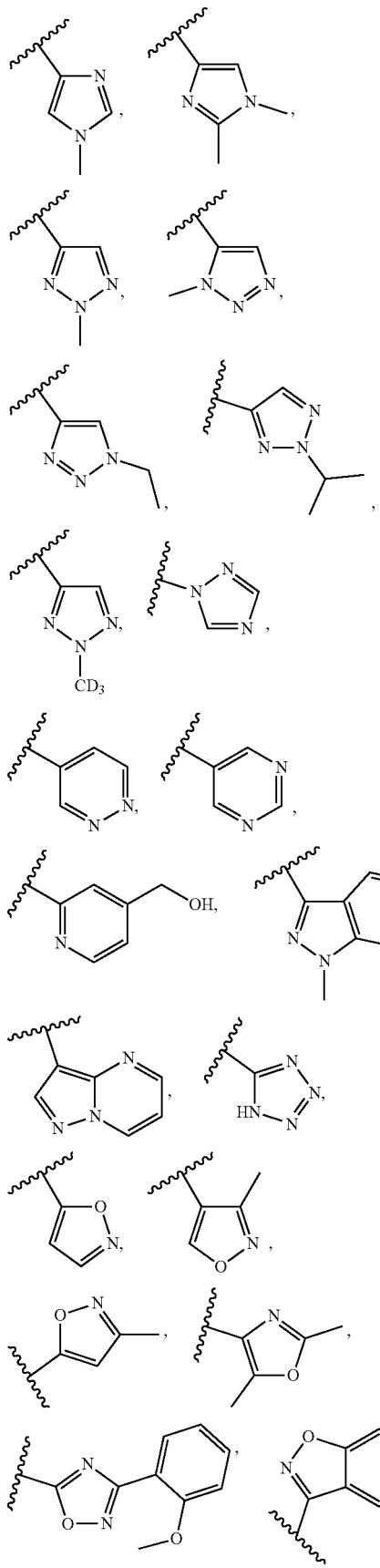
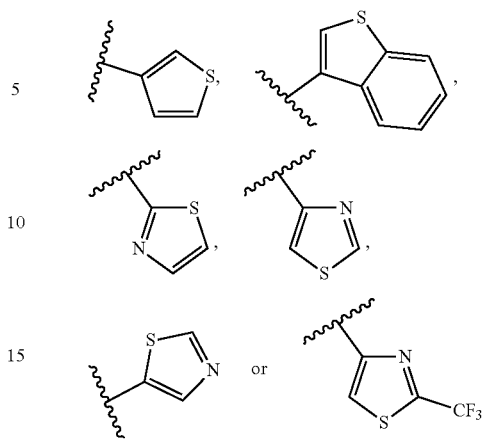
In some embodiments, the compound of Formula I or II, or a pharmaceutically acceptable salt thereof, is the compound wherein
R¹ is
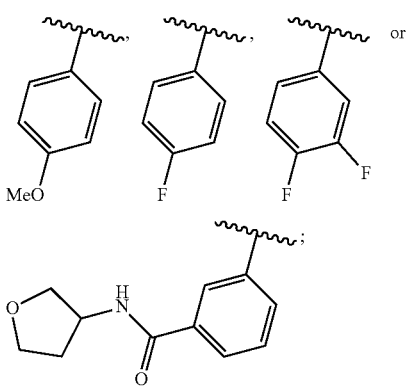
A¹ is =CH— or =N—;
A² and A⁴ are each independently =CH—, =C(Me)- or =N—;
A³ is =CH—, =C(Me)-, =C(iPr)—, =C(OMe)-, =C(F)— =C(Cl)—, =C(OCHF₂)— or =N—;
Ring J has the structure:
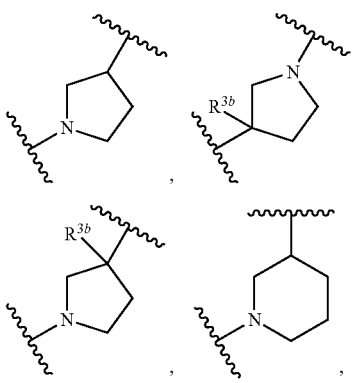

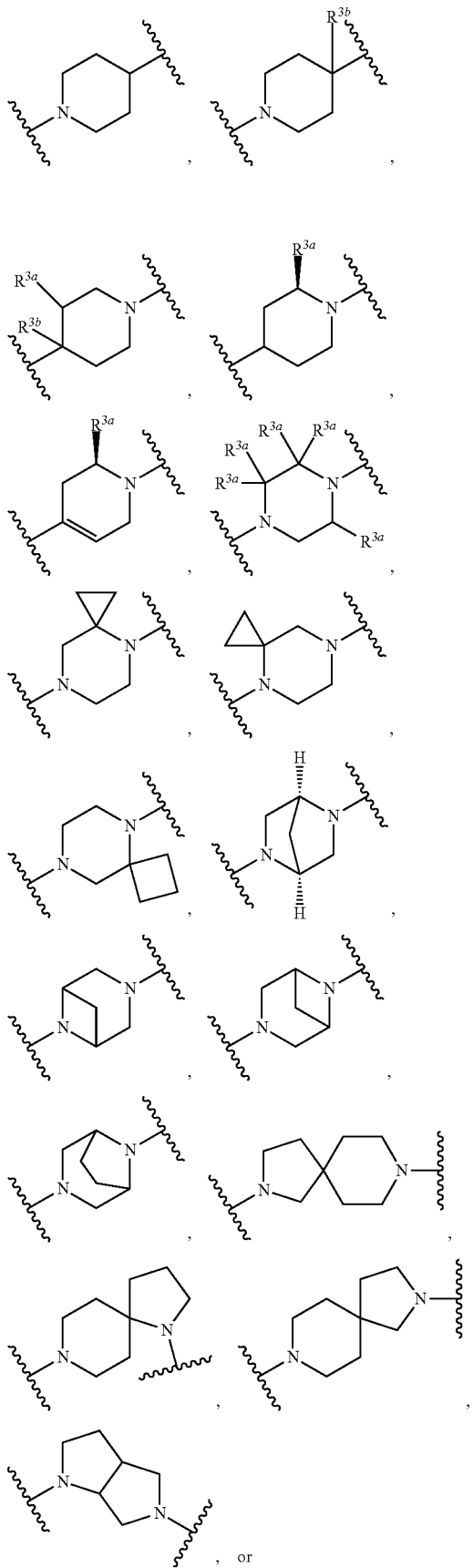
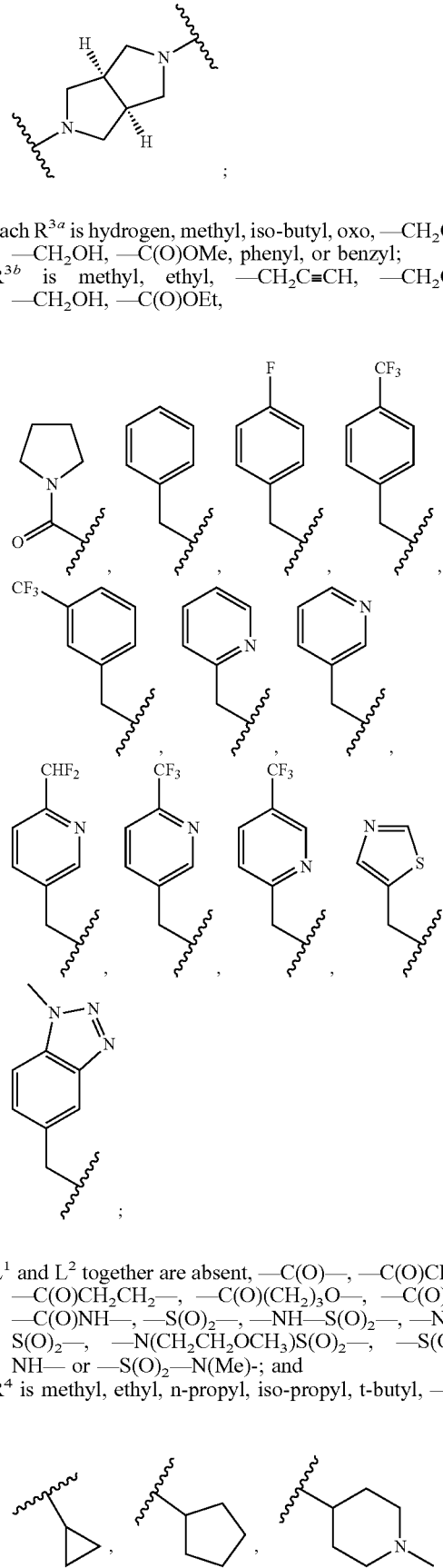
each R³ᵃ is hydrogen, methyl, iso-butyl, oxo, —CH₂OMe, —CH₂OH, —C(O)OMe, phenyl, or benzyl;
R³ᵇ is methyl, ethyl, —CH₂C≡CH, —CH₂OMe, —CH₂OH, —C(O)OEt,
L¹ and L² together are absent, —C(O)—, —C(O)CH₂—, —C(O)CH₂CH₂—, —C(O)(CH₂)₃O—, —C(O)O—, —C(O)NH—, —S(O)₂—, —NH—S(O)₂—, —N(Me)S(O)₂—, —N(CH₂CH₂OCH₃)S(O)₂—, —S(O)₂—NH— or —S(O)₂—N(Me)-; and
R⁴ is methyl, ethyl, n-propyl, iso-propyl, t-butyl, —CN, -continued
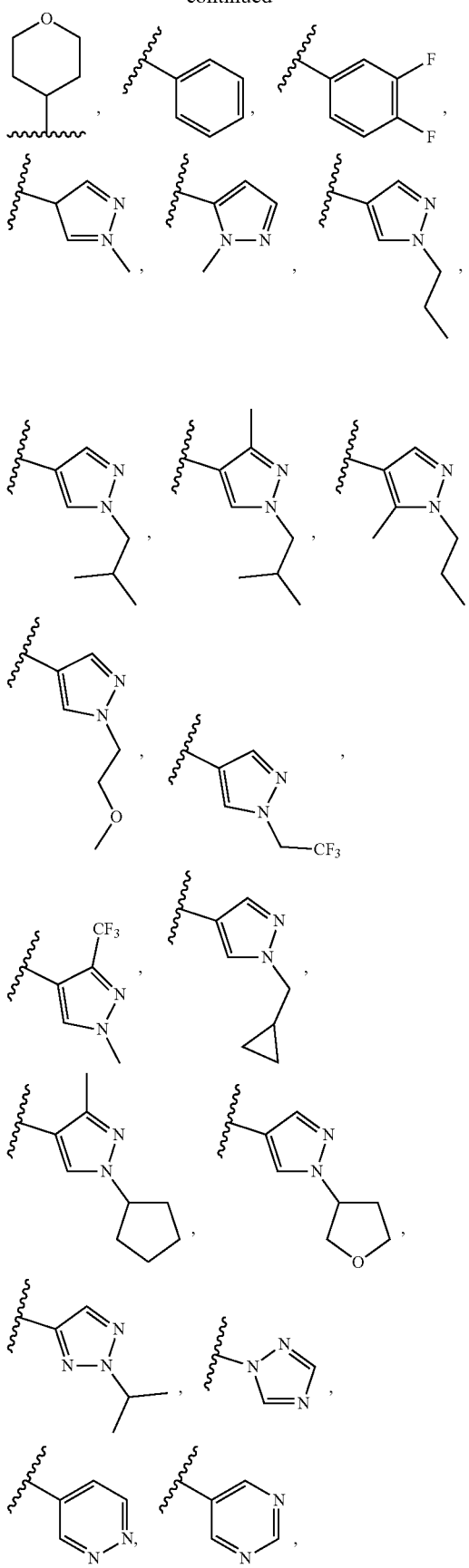
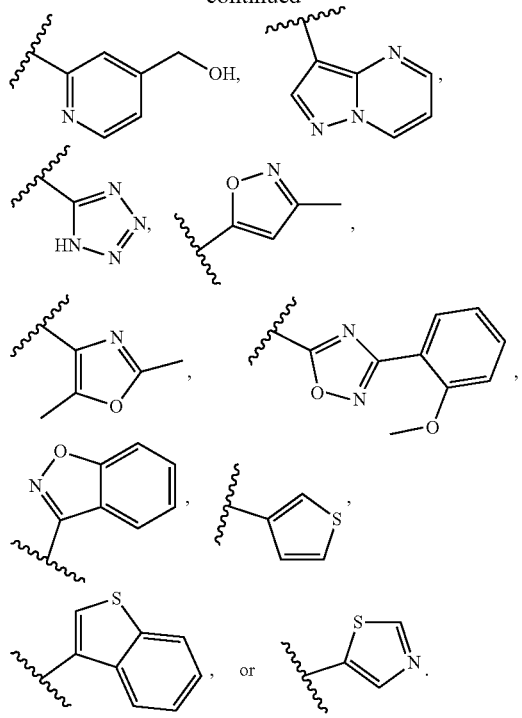
In some embodiments, the compound of Formula I or II, or a pharmaceutically acceptable salt thereof, is the compound wherein
R¹ is
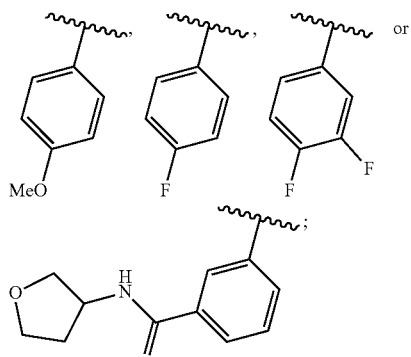
A¹ is =CH— or =N—;
A² and A⁴ are each independently =CH—, =C(Me)- or =N—;
A³ is =CH—, =C(Me)-, =C(iPr)—, =C(OMe)—, =C(Cl)—, =C(OCHF₂)— or =N—;
Ring J has the structure:
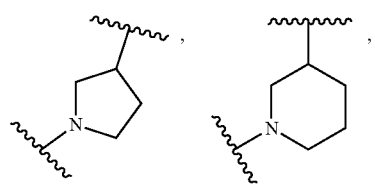

-continued
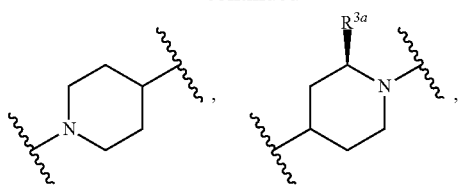
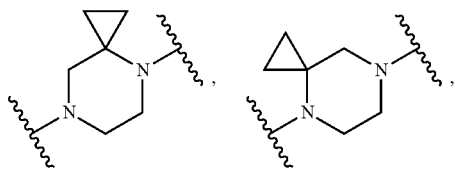
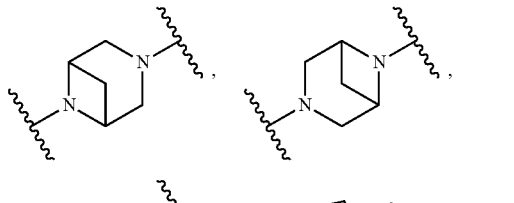
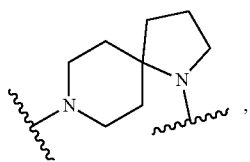, or
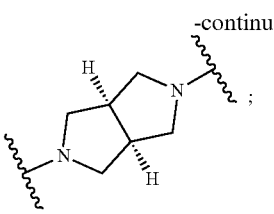;
each R³ᵃ is hydrogen, methyl, iso-butyl, —CH₂OMe, —CH₂OH, oxo, —C(O)OMe, phenyl, or benzyl;
L¹ and L² together are —C(O)—, —C(O)O—, —C(O)NH—, —S(O)₂—, —NH—S(O)₂—, —N(Me)S(O)₂—, —N(CH₂CH₂OCH₃)S(O)₂—, —S(O)₂—NH— or —S(O)₂—N(Me)-; and
R⁴ is methyl, ethyl, n-propyl, iso-propyl, t-butyl,
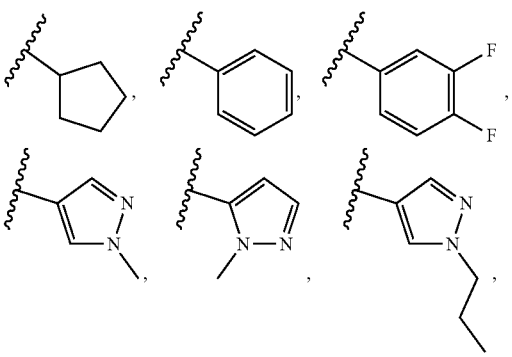
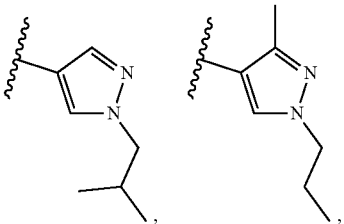
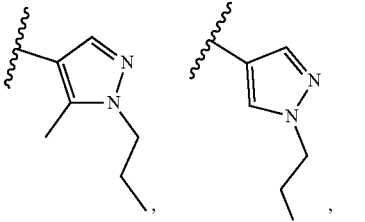
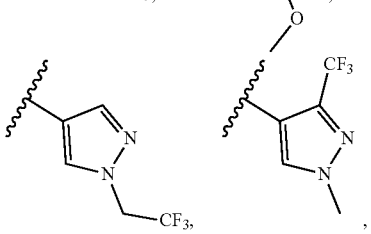
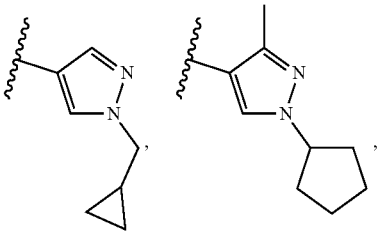

-continued

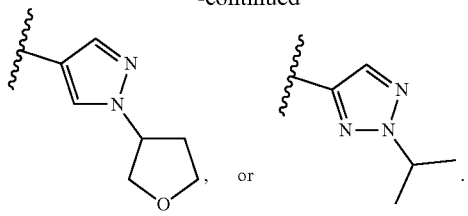

In some embodiments, the compound of Formula I or II, or a pharmaceutically acceptable salt thereof, is the compound wherein
R[1] is

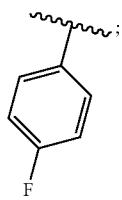 [SMILES: *c1ccc(F)cc1]

$A^1$ is =CH— or =N—;
$A^2$ and $A^4$ are each =CH—;
$A^3$ is =CH—, =C(Me)-, =C(iPr)—, =C(OMe)-, or =C(F)—;
Ring J has the structure:

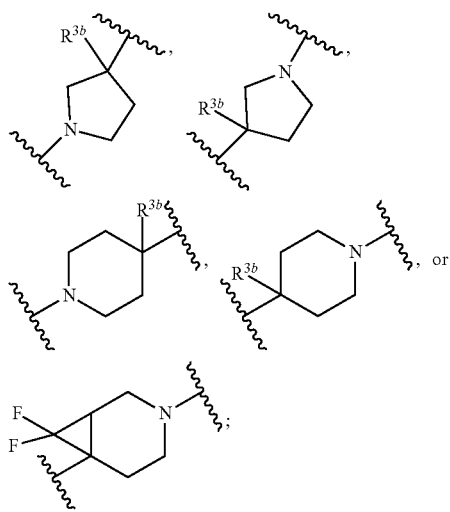

$R^{3b}$ is methyl, ethyl, —CH$_2$C≡CH, —CH$_2$OMe, —CH$_2$OH, —C(O)OEt,

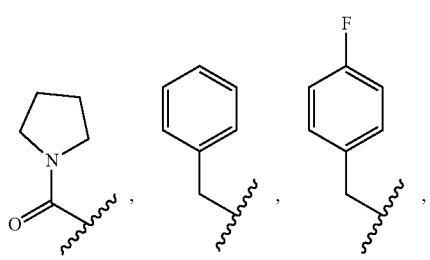

-continued

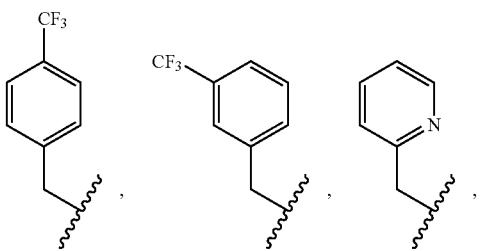

$L^1$ and $L^2$ together are absent, —C(O)—, —C(O)CH$_2$—, —C(O)CH$_2$CH$_2$—, —C(O)(CH$_2$)$_3$O—, —S(O)$_2$—, —NH—S(O)$_2$—, or —N(Me)S(O)$_2$—; and
$R^4$ is methyl, —CN,

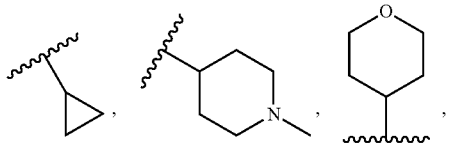

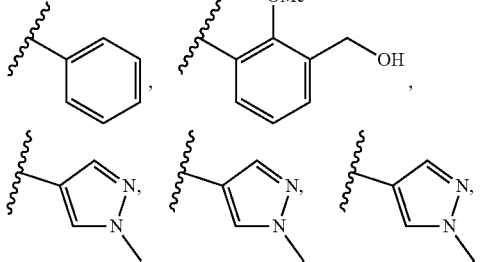

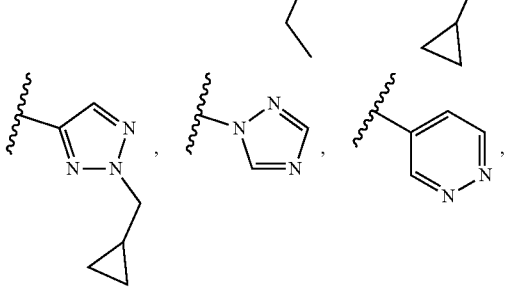

-continued

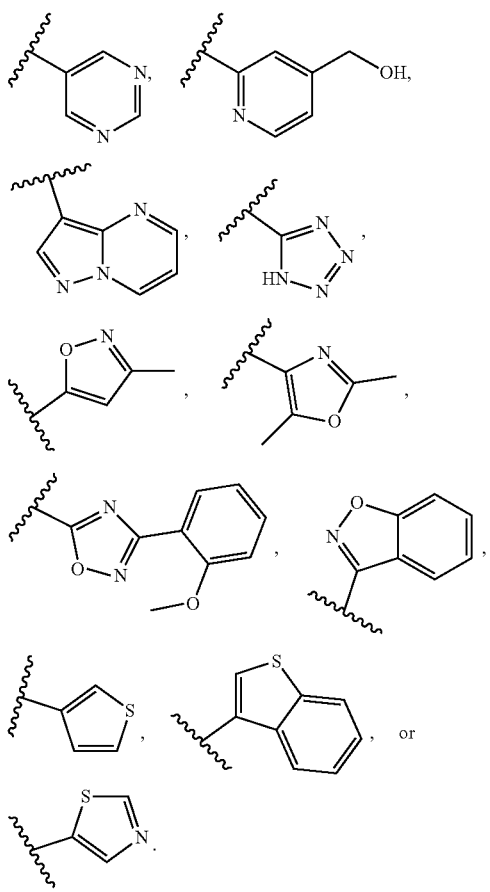

In some embodiments, the compound of Formula I, or a pharmaceutically acceptable salt thereof, is the compound wherein Ring J has the structure:

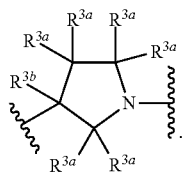

In some embodiments, the compound of Formula I, or a pharmaceutically acceptable salt thereof, is the compound wherein Ring J has the structure:

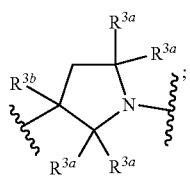

In some embodiments, the compound of Formula I, II or IV, or a pharmaceutically acceptable salt thereof, is the compound having the structure:

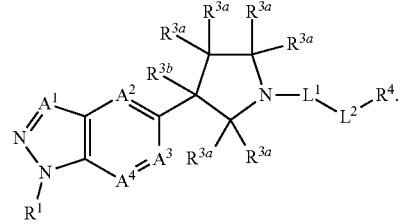

In some embodiments, the present invention provides a compound of Formula IVa:

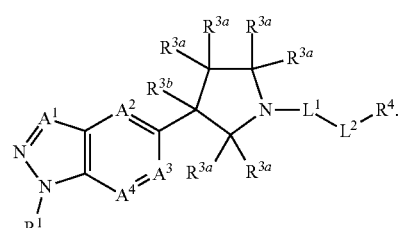

or a pharmaceutically acceptable salt thereof, wherein
$R^1$ is heterocycloalkyl having 3 to 8 ring members and 1 to 4 heteroatoms each N, O or S, phenyl or heteroaryl having 5 to 10 ring members and 1 to 5 heteroatoms each N, O or S, each independently substituted with 1 to 5 $R^{1a}$ groups;
each $R^{1a}$ is independently hydrogen, $C_{1-6}$ alkyl, $C_{1-6}$ deuteroalkyl, $C_{1-6}$ alkoxy, $C_{1-6}$ alkoxyalkyl, $C_{1-6}$ hydroxyalkyl, halogen, $C_{1-6}$ haloalkyl, $C_{1-6}$ haloalkoxy, —OH, oxo, —CN, —C(O)N($R^{1b}$)($R^{1c}$), $C_{3-10}$ cycloalkyl, or heterocycloalkyl having 3 to 8 ring members and 1 to 4 heteroatoms each N, O or S;
each $R^{1b}$ and $R^{1c}$ is independently hydrogen, $C_{1-6}$ alkyl or a 3 to 8 membered heterocycloalkyl having 1 to 3 heteroatoms each independently N, O or S;
$A^1$, $A^2$, $A^3$ and $A^4$ are each independently =$CR^2$— or =N—; each $R^2$ is independently hydrogen, $C_{1-6}$ alkyl, $C_{1-6}$ alkoxy, $C_{2-6}$ alkoxyalkyl, halogen, $C_{1-6}$ haloalkyl, $C_{1-6}$ haloalkoxy, hydroxy or —CN;
each $R^{3a}$ is independently hydrogen, $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, —C(O)$R^{3a1}$, —C(O)O$R^{3a1}$, —C(O)N($R^{3a1}$)($R^{3a2}$), —OH, oxo, $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, heteroaryl, or $C_{1-6}$ alkyl-heteroaryl, wherein each alkenyl and alkynyl is optionally substituted with $C_{6-12}$ aryl or heteroaryl, wherein each heterocycloalkyl has 3 to 8 ring members and 1 to 3 heteroatoms each independently N, O or S, and wherein each heteroaryl has 5 to 10 ring members and 1 to 5 heteroatoms each independently N, O or S;
each $R^{3a1}$ and $R^{3a2}$ is independently hydrogen or $C_{1-6}$ alkyl;
alternatively, two $R^{3a}$ groups attached to the same atom can be combined with the atom to which they are attached to form a $C_{3-6}$ cycloalkyl;
alternatively, two $R^{3a}$ groups attached to different atoms can be combined with the atoms to which they are attached to form a $C_{3-10}$ cycloalkyl or 3 to 10 membered heterocycloalkyl having 1 to 4 heteroatoms each independently N, O or S, each substituted with 1 to 4 $R^{3a3}$ groups;

each $R^{3a3}$ is independently hydrogen or $C_{1-6}$ alkyl;

each $R^{3b}$ is independently $C_{1-6}$ alkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, —C(O)$R^{3b1}$, —C(O)O$R^{3b1}$, —C(O)N($R^{3b1}$)($R^{3b2}$), $C_{3-8}$ cycloalkyl, $C_{1-6}$ alkyl-$C_{3-8}$ cycloalkyl, $C_{2-6}$ alkynyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, $C_{2-6}$ alkenyl-$C_{6-12}$ aryl, $C_{2-6}$ alkynyl-$C_{6-12}$ aryl, $C_{1-6}$ alkyl-O—$C_{6-12}$ aryl, $C_{1-6}$ alkoxyalkyl-$C_{6-12}$ aryl, —C(O)—$C_{6-12}$ aryl, heteroaryl, or $C_{1-6}$ alkyl-heteroaryl, wherein each heterocycloalkyl has 3 to 8 ring members and 1 to 3 heteroatoms each independently N, O or S, wherein each heteroaryl has 5 to 10 ring members and 1 to 5 heteroatoms each independently N, O or S, and wherein each aryl and heteroaryl are substituted with 1 to 3 $R^{3b3}$ groups;

$R^{3b1}$ and $R^{3b2}$ are each independently hydrogen or $C_{1-6}$ alkyl;

alternatively $R^{3b1}$ and $R^{3b2}$ are combined with the atom to which they are attached to form a 3 to 6 membered heterocycloalkyl having 1 to 2 additional heteroatoms each independently N, O or S;

each $R^{3b3}$ is hydrogen, $C_{1-6}$ alkyl, $C_{1-6}$ alkoxy, $C_{2-6}$ alkoxy alkyl, $C_{1-6}$ hydroxyalkyl, halogen, $C_{1-6}$ haloalkyl, or $C_{1-6}$ haloalkoxy;

$R^4$ is $C_{1-6}$ alkyl, $C_{2-6}$ alkenyl, $C_{2-6}$ alkynyl, $C_{1-6}$ haloalkyl, —CN, $C_{3-8}$ cycloalkyl, 3 to 8 membered heterocycloalkyl having 1 to 3 heteroatoms each independently N, O or S, $C_{6-12}$ aryl, or 5 to 10 membered heteroaryl having 1 to 5 heteroatoms each independently N, O or S, wherein the cycloalkyl, heterocycloalkyl, aryl and heteroaryl are each independently substituted with 1 to 5 $R^{4a}$ groups;

each $R^{4a}$ is hydrogen, $C_{1-6}$ alkyl, $C_{1-6}$ deuteroalkyl, $C_{2-6}$ alkenyl, $C_{2-6}$ alkynyl, $C_{1-6}$ alkoxy, $C_{2-6}$ alkoxyalkyl, $C_{1-6}$ hydroxyalkyl, halogen, $C_{1-6}$ haloalkyl, $C_{1-6}$ haloalkoxy, —CN, —OH, oxo, —C(O)$R^{4b}$, —C(O)O$R^{4b}$, —C(O)N($R^{4b}$)($R^{4c}$), —S(O)$_2R^{4b}$, —S(O)$_2$N($R^{4b}$)($R^{4c}$), $C_{3-8}$ cycloalkyl, $C_{1-6}$ alkyl-$C_{3-8}$ cycloalkyl, heterocycloalkyl, $C_{1-6}$ alkyl-heterocycloalkyl, $C_{6-12}$ aryl, $C_{1-6}$ alkyl-$C_{6-12}$ aryl, —O—$C_{6-12}$ aryl, heteroaryl, $C_{1-6}$ alkyl-heteroaryl, wherein each heterocycloalkyl independently has 3 to 8 ring members and 1 to 3 heteroatoms each independently N, O or S, wherein each heteroaryl independently has 5 to 8 ring members and 1 to 4 heteroatoms each independently N, O or S, and wherein each cycloalkyl, heterocycloalkyl, aryl and heteroaryl is optionally substituted with $C_{1-6}$ alkoxy;

each $R^{4b}$ and $R^{4c}$ is hydrogen or $C_{1-6}$ alkyl;

$L^1$ is absent or —N($R^{5a}$)—;

$L^2$ is absent, $C_{1-6}$ alkylene, —C(O)—, —C(O)—$C_{1-6}$ alkylene-, C(O)—$C_{1-6}$ alkylene-O—, —C(O)O—, —C(O)N($R^{5b}$)—, —S(O)$_2$—, or —S(O)$_2$N($R^{5b}$)—; and $R^{5a}$ and $R^{5b}$ are each independently hydrogen, $C_{1-6}$ alkyl or $C_{2-6}$ alkoxyalkyl.

In some embodiments, the compound of Formula I, II, III, IIIa, IV or IVa, or a pharmaceutically acceptable salt thereof, is the compound wherein $R^1$ is heterocycloalkyl having 5 to 6 ring members and 1 to 2 heteroatoms each N, phenyl or a heteroaryl having 5 to 6 ring members and 1 to 2 heteroatoms each N or S, each substituted with 1 to 3 $R^{1a}$ groups; and each $R^{1a}$ is independently hydrogen, $C_{1-3}$ alkyl, $C_{1-3}$ deuteroalkyl, $C_{1-3}$ alkoxy, $C_{1-3}$ hydroxyalkyl, halogen, $C_{1-3}$ haloalkyl, oxo, —CN, $C_{3-6}$ cycloalkyl, or heterocycloalkyl having 3 to 5 ring members and 1 to 2 heteroatoms each N or O. In some embodiments, the compound of Formula I, II, III, IIIa, IV or IVa, or a pharmaceutically acceptable salt thereof, is the compound wherein $R^1$ is piperidine, pyrdin-2-one, phenyl, pyridine, pyrazole, or thiazole, each substituted with 1 to 3 $R^{1a}$ groups; and each $R^{1a}$ is hydrogen, methyl, ethyl, iso-propyl, —CD$_3$, methoxy, —CH$_2$OH, F, Cl, —CHF$_2$, —CF$_3$, oxo, —CN, cyclopropyl, or oxetane.

In some embodiments, the compound of Formula I, II, III, IIIa, IIIb, IV or IVa, or a pharmaceutically acceptable salt thereof, is the compound wherein $R^1$ is

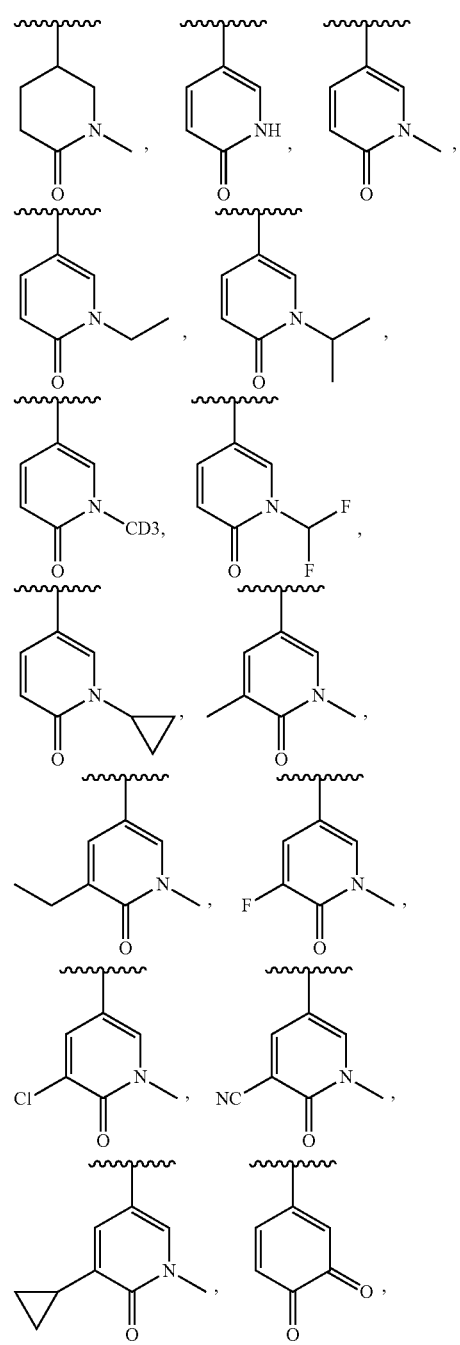

In some embodiments, the compound of Formula I, II, III, IIIa, IIIb, IV or IVa, or a pharmaceutically acceptable salt thereof, is the compound having the structure:

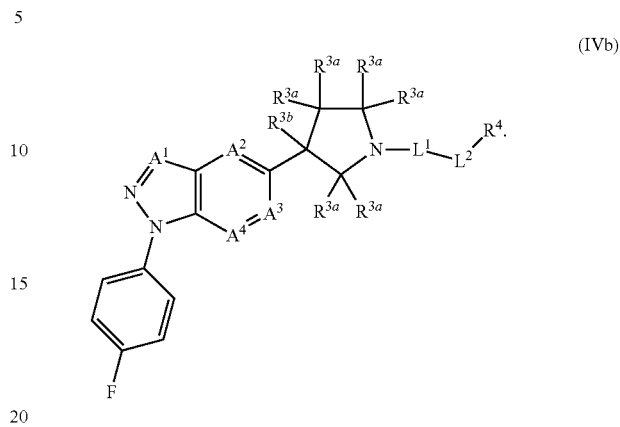

(IVb)

In some embodiments, the compound of Formula I, II, III, IIIa, IIIb, IV, IVa or IVb, or a pharmaceutically acceptable salt thereof, is the compound wherein $A^1$, $A^2$, $A^3$ and $A^4$ are each independently =CR²— or =N—; and each R² is independently hydrogen, $C_{1-4}$ alkyl, $C_{1-4}$ alkoxy, halogen, or —CN. In some embodiments, the compound of Formula I, II, IIa-1, IIb-1, IIc-1, III, III, IIIa, IIIb, IV, IVa or IVb, or a pharmaceutically acceptable salt thereof, is the compound wherein each R² is independently hydrogen, methyl, ethyl, iso-propyl, methoxy, F, Cl, or —CN. In some embodiments, the compound of Formula I, II, III, IIIa, IIIb, IV, IVa or IVb, or a pharmaceutically acceptable salt thereof, is the compound wherein $A^1$, $A^2$, $A^3$ and $A^4$ are each independently =CH—, =C(Me)-, =C(Et)-, =C(iPr)—, =C(OMe)-, =C(F)—, =C(Cl)—, =C(CN)— or =N—. In some embodiments, the compound of Formula I, II, III, IIIa, IIIb, IV, IVa or IVb, or a pharmaceutically acceptable salt thereof, is the compound wherein $A^1$ is =CH— or =N—; $A^2$ and $A^4$ are each =CH—; and $A^3$ is =CH—, =C(Me)-, =C(Et)-, =C(iPr)—, =C(OMe)-, =C(F)—, =C(Cl)—, or =C(CN)—. In some embodiments, the compound of Formula I, II, III, IIIa, IIIb, IV, IVa or IVb, or a pharmaceutically acceptable salt thereof, is the compound wherein $A^1$, $A^2$ and $A^4$ are each =CH—; and $A^3$ is =C(Me)-.

In some embodiments, the compound of Formula I, II, III, IIIa, IV, IVa or IVb, or a pharmaceutically acceptable salt thereof, is the compound having the structure:

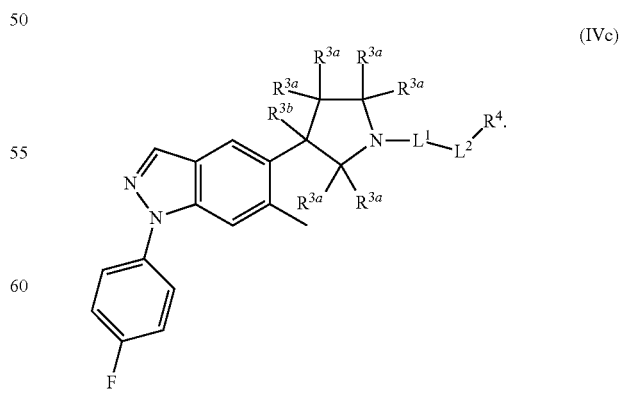

(IVc)

In some embodiments, the compound of Formula I, II, III, IIIa, IV, IVa, IVb or IVc, or a pharmaceutically acceptable

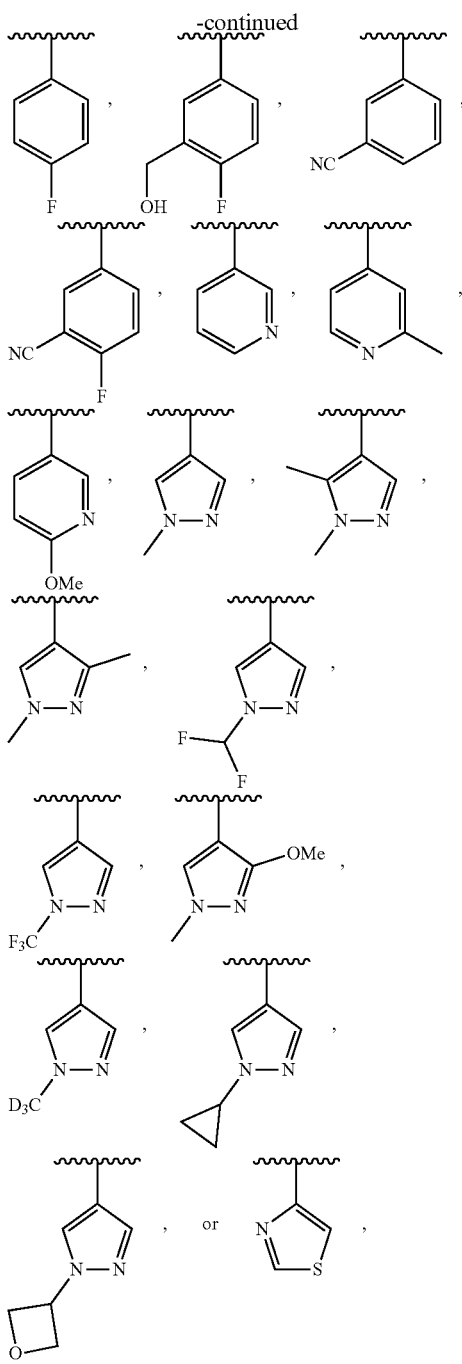

In some embodiments, the compound of Formula I, II, III, IIIa, IIIb, IV or IVa, or a pharmaceutically acceptable salt thereof, is the compound wherein R¹ is

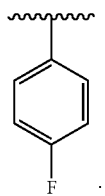 [SMILES: *c1ccc(F)cc1]

.

salt thereof, is the compound wherein each $R^{3a}$ is independently hydrogen, —OH, or oxo. In some embodiments, the compound of Formula I, II, III, IIIa, IV, IVa, IVb or IVc, or a pharmaceutically acceptable salt thereof, is the compound wherein each $R^{3a}$ is hydrogen.

In some embodiments, the compound of Formula I, II, IIa-1, III, IIIa, IV, IVa, IVb or IVc, or a pharmaceutically acceptable salt thereof, is the compound having the structure:

(IVd)

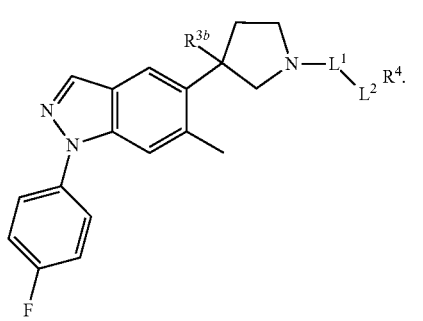

In some embodiments, the compound of Formula I, II, IIa-1, IIb-1, IIc-1, III, IIIa, IIIb, IV, IVa, IVb, IVc or IVd, or a pharmaceutically acceptable salt thereof, is the compound wherein $R^{3b}$ is $C_{1-6}$ alkyl, $C_{2-6}$ alkynyl, $C_{2-6}$ alkoxyalkyl, $C_{2-6}$ alkynyl-$C_{3-6}$ cycloalkyl, $C_{1-6}$ alkyl-$C_{6-12}$ aryl, $C_{2-6}$ alkenyl-$C_{6-12}$ aryl, $C_{2-6}$ alkynyl-$C_{6-12}$ aryl, $C_{1-6}$ alkyl-O—$C_{6-12}$ aryl, $C_{1-6}$ alkoxyalkyl-$C_{6-12}$ aryl, —C(O)—$C_{6-12}$ aryl, or $C_{1-6}$ alkyl-heteroaryl, wherein each heteroaryl has 5 to 10 ring members and 1 to 3 heteroatoms each independently N, O or S, and wherein each aryl and heteroaryl is substituted with 1 to 3 $R^{3b3}$ groups; and each $R^{3b3}$ is hydrogen, $C_{1-6}$ alkyl, $C_{1-6}$ hydroxyalkyl, halogen, or $C_{1-6}$ haloalkyl.

In some embodiments, the compound of Formula I, II, IIa-1, IIb-1, IIc-1, III, IIIa, IIIb, IV, IVa, IVb, IVc or IVd, or a pharmaceutically acceptable salt thereof, is the compound wherein $R^{3b}$ is $C_{1-3}$ alkyl, $C_{2-3}$ alkynyl, $C_{2-3}$ alkoxyalkyl, $C_{2-3}$ alkynyl-$C_{3-6}$ cycloalkyl, $C_{1-3}$ alkyl-$C_{6-12}$ aryl, $C_{2-3}$ alkenyl-$C_{6-12}$ aryl, $C_{2-3}$ alkynyl-$C_{6-12}$ aryl, $C_{1-3}$ alkyl-O—$C_{6-12}$ aryl, $C_{1-3}$ alkoxyalkyl-$C_{6-12}$ aryl, —C(O)—$C_{6-12}$ aryl, or $C_{1-3}$ alkyl-heteroaryl, wherein each heteroaryl has 5 to 10 ring members and 1 to 3 heteroatoms each independently N, O or S, and wherein each aryl and heteroaryl is substituted with 1 to 3 $R^{3b3}$ groups; and each $R^{3b3}$ is hydrogen, $C_{1-3}$ alkyl, $C_{1-3}$ hydroxyalkyl, halogen, or $C_{1-3}$ haloalkyl.

In some embodiments, the compound of Formula I, II, IIa-1, IIb-1, IIc-1, III, IIIa, IIIb, IV, IVa, IVb, IVc or IVd, or a pharmaceutically acceptable salt thereof, is the compound wherein $R^{3b3}$ is hydrogen, methyl, —CH$_2$OH, F, —CHF$_2$, or —CF$_3$. In some embodiments, the compound of Formula I, II, IIa-1, IIb-1, IIc-1, III, IIIa, IIIb, IV, IVa, IVb, IVc or IVd, or a pharmaceutically acceptable salt thereof, is the compound wherein $R^{3b}$ is ethyl, —CH$_2$C≡CH, —CH$_2$OMe,

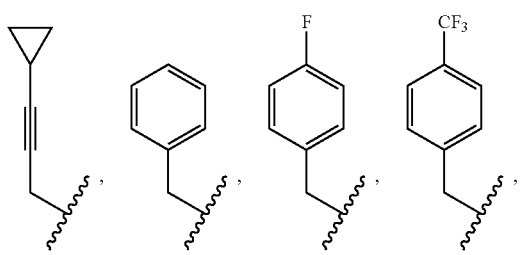

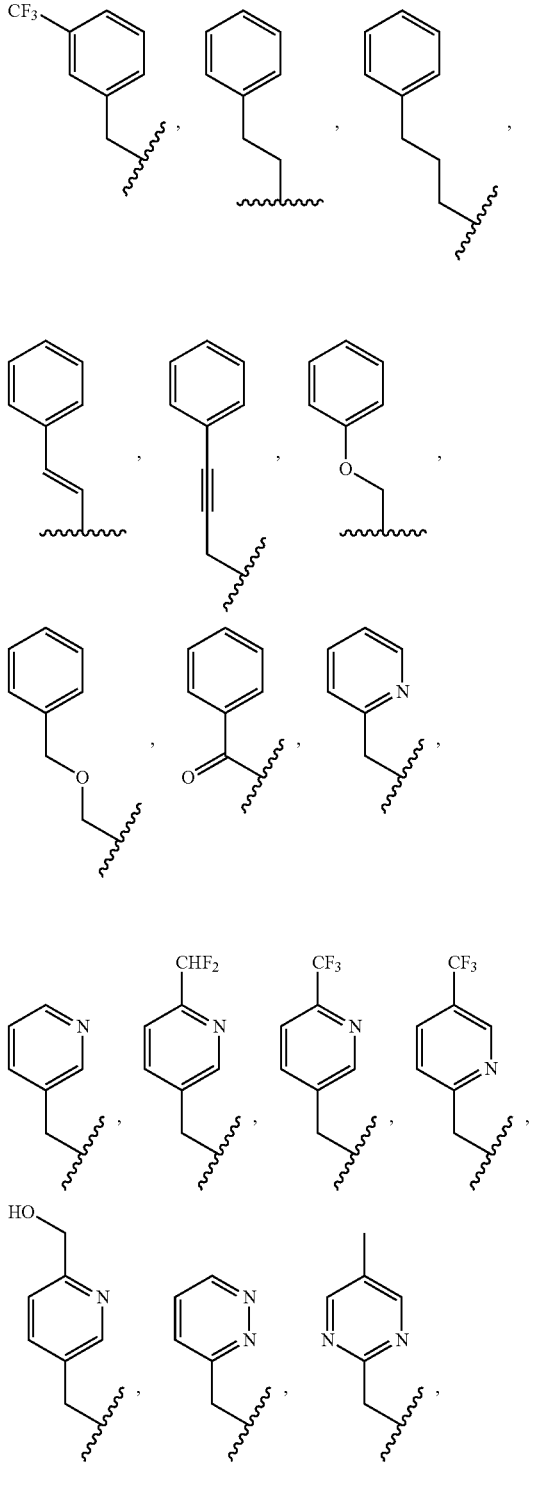

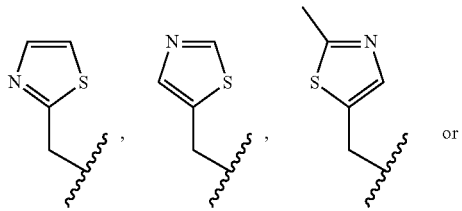

or

-continued

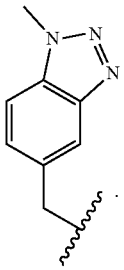

In some embodiments, the compound of Formula I, II, IIa-1, IIb-1, IIc-1, III, IIIa, IIIb, IV, IVa, IVb, IVc or IVd, or a pharmaceutically acceptable salt thereof, is the compound wherein $R^{3b}$ is

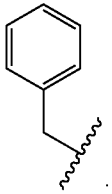

In some embodiments, the compound of Formula I, II, IIa-1, III, IIIa, IV, IVa, IVb, IVc or IVd, or a pharmaceutically acceptable salt thereof, is the compound having the structure:

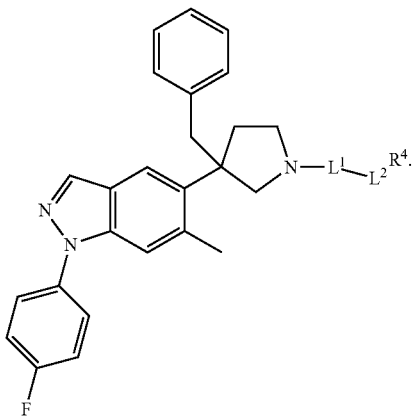

(IVe)

In some embodiments, the compound of Formula I, II, IIa-1, III, IIIa, IIIb, IV, IVa, IVb, IVc, IVd or IVe, or a pharmaceutically acceptable salt thereof, is the compound wherein $L^1$ is absent; and $L^2$ is absent, $C_{1-4}$ alkylene, —C(O)—, —C(O)—$C_{1-4}$ alkylene-, C(O)—$C_{1-4}$ alkylene-O—, or —S(O)$_2$—. In some embodiments, the compound of Formula I, II, IIa-1, III, IIIa, IIIb, IV, IVa, IVb, IVc, IVd or IVe, or a pharmaceutically acceptable salt thereof, is the compound wherein $L^1$ is absent; and $L^2$ is absent, —CH$_2$—, —C(O)—, —C(O)CH$_2$—, —C(O)CH$_2$CH$_2$—, —C(O)CH$_2$O—, —C(O)(CH$_2$)$_3$O—, or —S(O)$_2$—. In some embodiments, the compound of Formula I, II, IIa-1, III, IIIa, IIIb, IV, IVa, IVb, IVc, IVd or IVe, or a pharmaceutically acceptable salt thereof, is the compound wherein $L^2$ is —CH$_2$—, —C(O)—, —C(O)CH$_2$—, —C(O)CH$_2$CH$_2$—, —C(O)CH$_2$O—, —C(O)(CH$_2$)$_3$O—, or —S(O)$_2$—. In some embodiments, the compound of Formula I, II, IIa-1, III, IIIa, IIIb, IV, IVa, IVb, IVc, IVd or IVe, or a pharmaceutically acceptable salt thereof, is the compound wherein $L^2$ is —C(O)— or —S(O)$_2$—.

In some embodiments, the compound of Formula I, II, IIa-1, III, IIIa, IIIb, IV, IVa, IVb, IVc, IVd or IVe, or a pharmaceutically acceptable salt thereof, is the compound having the structure:

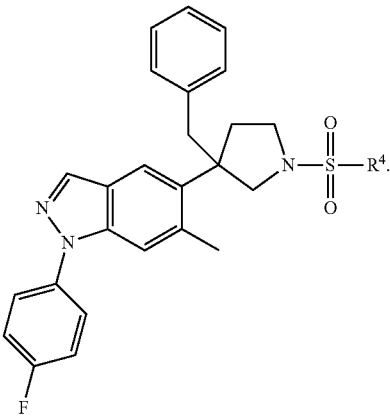

(IVf)

In some embodiments, the compound of Formula I, II, IIa-1, III, IIIa, IIIb, IV, IVa, IVb, IVc, IVd, IVe or IVf, or a pharmaceutically acceptable salt thereof, is the compound wherein $R^4$ is $C_{1-6}$ alkyl, $C_{1-6}$ haloalkyl, —CN, $C_{3-8}$ cycloalkyl, 3 to 8 membered heterocycloalkyl having 1 to 3 heteroatoms each independently N, O or S, $C_{6-12}$ aryl, or 5 to membered heteroaryl having 1 to 5 heteroatoms each independently N, O or S, wherein the cycloalkyl, heterocycloalkyl, aryl and heteroaryl are each independently substituted with 1 to 5 $R^{4a}$ groups; each $R^{4a}$ is hydrogen, $C_{1-6}$ alkyl, $C_{1-6}$ deuteroalkyl, $C_{1-6}$ alkoxy, $C_{2-6}$ alkoxyalkyl, $C_{1-6}$ hydroxyalkyl, halogen, $C_{1-6}$ haloalkyl, —CN, —OH, oxo, —S(O)$_2$R$^{4b}$, —S(O)$_2$N(R$^{4b}$)(R$^{4c}$), $C_{3-6}$ cycloalkyl, $C_{6-12}$ aryl, or —O—$C_{6-12}$ aryl, wherein each aryl is optionally substituted with $C_{1-6}$ alkoxy; and each $R^{4b}$ and $R^{4c}$ is hydrogen or $C_{1-6}$ alkyl.

In some embodiments, the compound of Formula I, II, IIa-1, III, IIIa, IIIb, IV, IVa, IVb, IVc, IVd, IVe or IVf, or a pharmaceutically acceptable salt thereof, is the compound wherein $R^4$ is $C_{1-3}$ alkyl, $C_{1-3}$ haloalkyl, —CN, $C_{3-6}$ cycloalkyl, 4 to 6 membered heterocycloalkyl having 1 heteroatoms each N or O, $C_{6-12}$ aryl, or 5 to 10 membered heteroaryl having 1 to 4 heteroatoms each independently N, O or S, wherein the cycloalkyl, heterocycloalkyl, aryl and heteroaryl are each independently substituted with 1 to 2 $R^{4a}$ groups; each $R^{4a}$ is hydrogen, $C_{1-3}$ alkyl, $C_{1-3}$ deuteroalkyl, $C_{1-3}$ alkoxy, $C_{2-3}$ alkoxyalkyl, $C_{1-3}$ hydroxyalkyl, halogen, $C_{1-3}$ haloalkyl, —CN, —OH, oxo, —S(O)$_2$R$^{4b}$, —S(O)$_2$N(R$^{4b}$)(R$^{4c}$), $C_{3-6}$ cycloalkyl, $C_{6-12}$ aryl, or —O—$C_{6-12}$ aryl, wherein each aryl is optionally substituted with $C_{1-3}$ alkoxy; and each $R^{4b}$ and $R^{4c}$ is hydrogen or $C_{1-3}$ alkyl.

In some embodiments, the compound of Formula I, II, IIa-1, III, IIIa, IIIb, IV, IVa, IVb, IVc, IVd, IVe or IVf, or a pharmaceutically acceptable salt thereof, is the compound wherein $R^4$ is methyl, ethyl, —CF$_2$CH$_3$, —CN, cyclopropyl, cyclobutyl, piperidinyl, tetrahydropyranyl, pyrimidine-dione, phenyl, pyridinyl, pyridin-2-one, quinolinyl, pyrazolyl, imidazolyl, pyridazinyl, pyrimidinyl, indazolyl, triazolyl, pyrazolo-pyrimidine, tetrazolyl, oxazolyl, isoxazolyl, benzoisoxazolyl, oxadiazolyl, thiophenyl, benzothiophenyl, or thiazolyl; and each $R^{4a}$ is hydrogen, methyl, ethyl, n-propyl, iso-butyl, —CD$_3$, methoxy, —CH$_2$CH$_2$OCH$_3$, hydroxymethyl, F, Cl, —CHF$_2$, —CF$_3$, —CH$_2$CF$_3$, —CN, —OH, oxo, —S(O)$_2$Me, —S(O)$_2$NHMe, cyclobutyl, 2-methoxyphenyl or -OPh.

In some embodiments, the compound of Formula I, II, IIa-1, III, IIIa, IIIb, IV, IVa, IVb, IVc, IVd, IVe or IVf, or a pharmaceutically acceptable salt thereof, is the compound wherein $R^4$ is methyl, —CF$_2$CH$_3$, —CN,

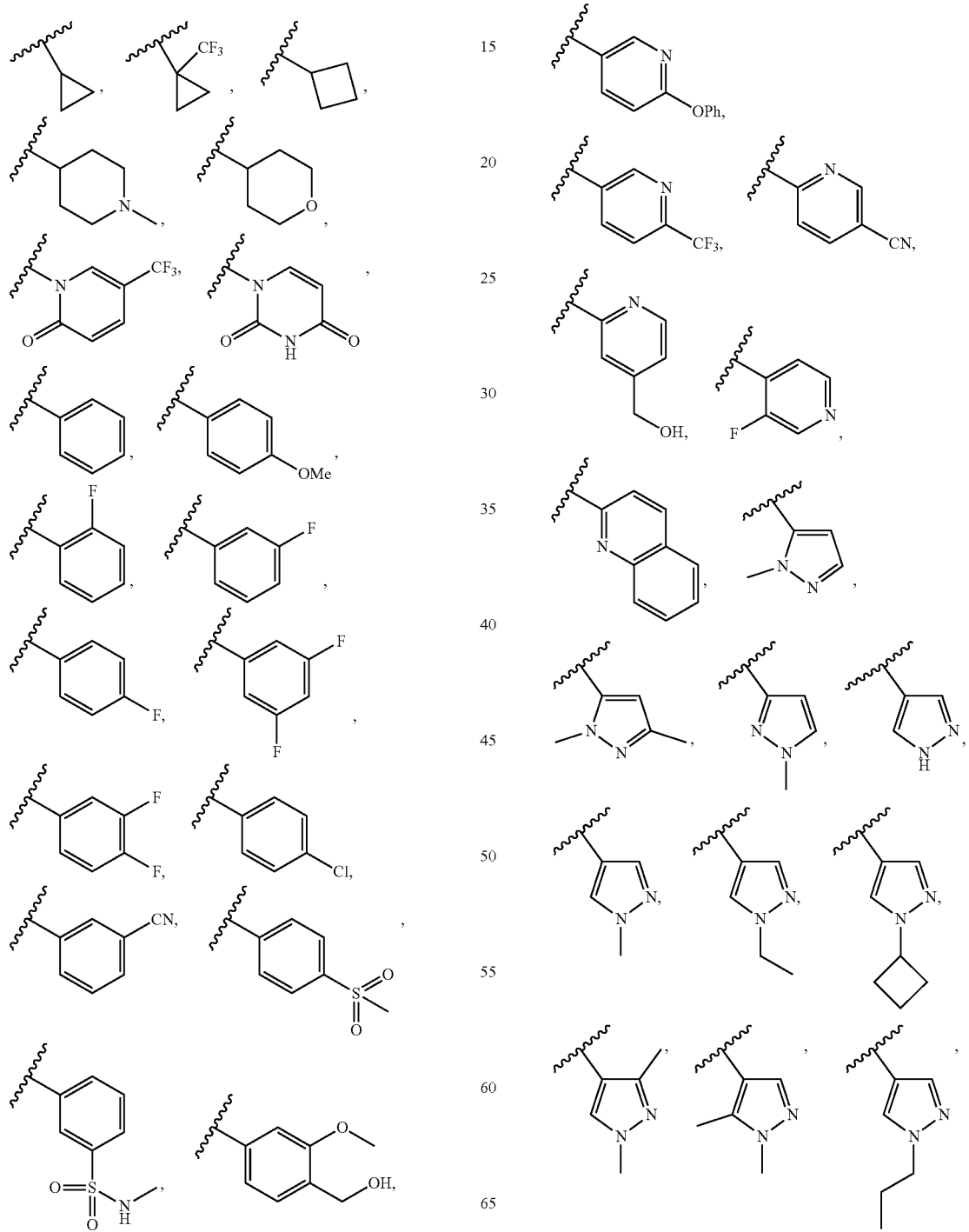

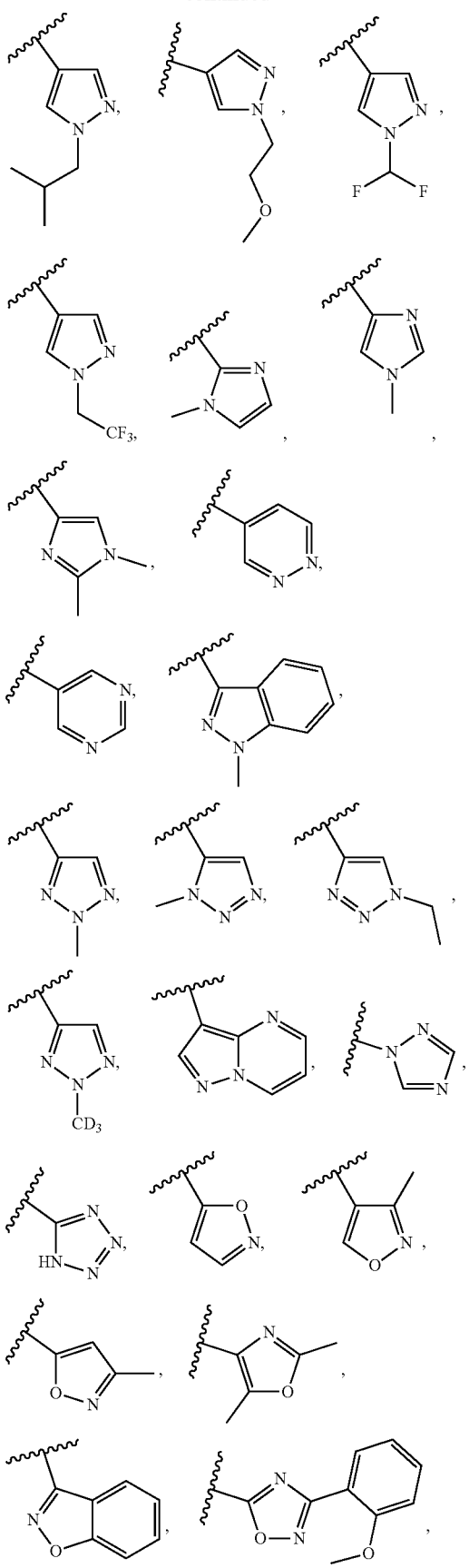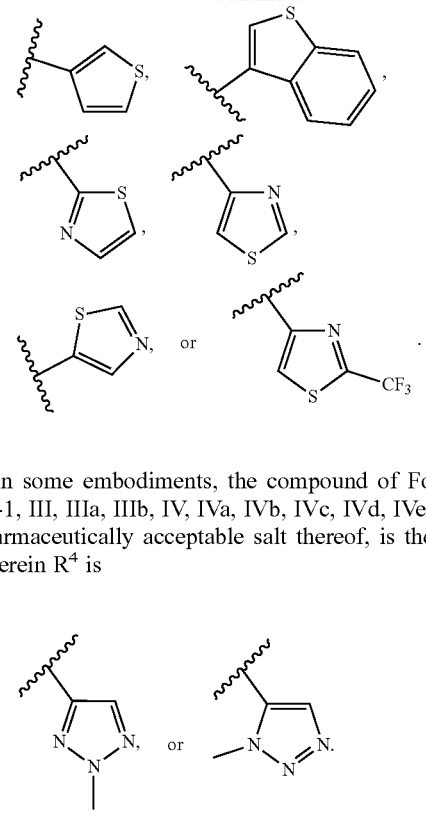

In some embodiments, the compound of Formula I, II, IIa-1, III, IIIa, IIIb, IV, IVa, IVb, IVc, IVd, IVe or IVf, or a pharmaceutically acceptable salt thereof, is the compound wherein R⁴ is

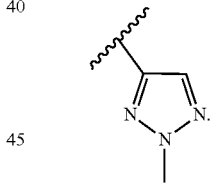

In some embodiments, the compound of Formula I, II, IIa-1, III, IIIa, IIIb, IV, IVa, IVb, IVc, IVd, IVe or IVf, or a pharmaceutically acceptable salt thereof, is the compound wherein R⁴ is In some embodiments, the compound of Formula I, II, IV, or IVa, or a pharmaceutically acceptable salt thereof, is the compound having the structure:

(IVg)

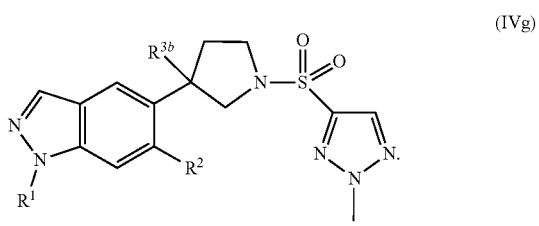

In some embodiments, the compound of Formula I, II, IIa-1, III, IIIa, IIIb, IV, IVa, IVb, IVc, IVd, IVe or IVf, or a pharmaceutically acceptable salt thereof, is the compound wherein R⁴ is

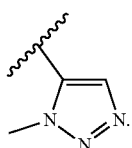
In some embodiments, the compound of Formula I, II, IV or IVa, or a pharmaceutically acceptable salt thereof, is the compound wherein
R[1] is
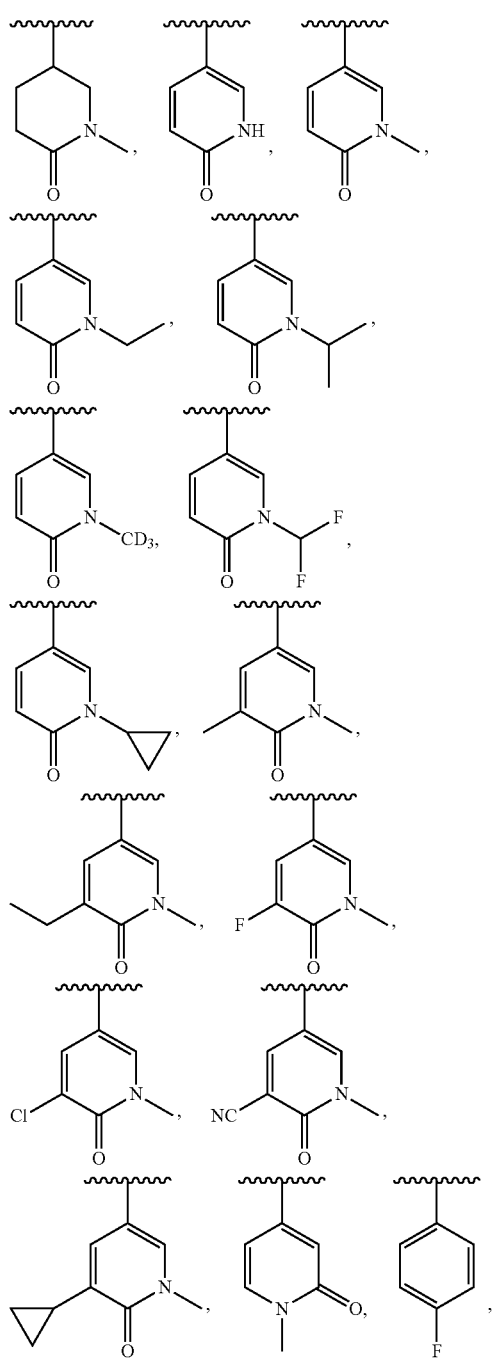
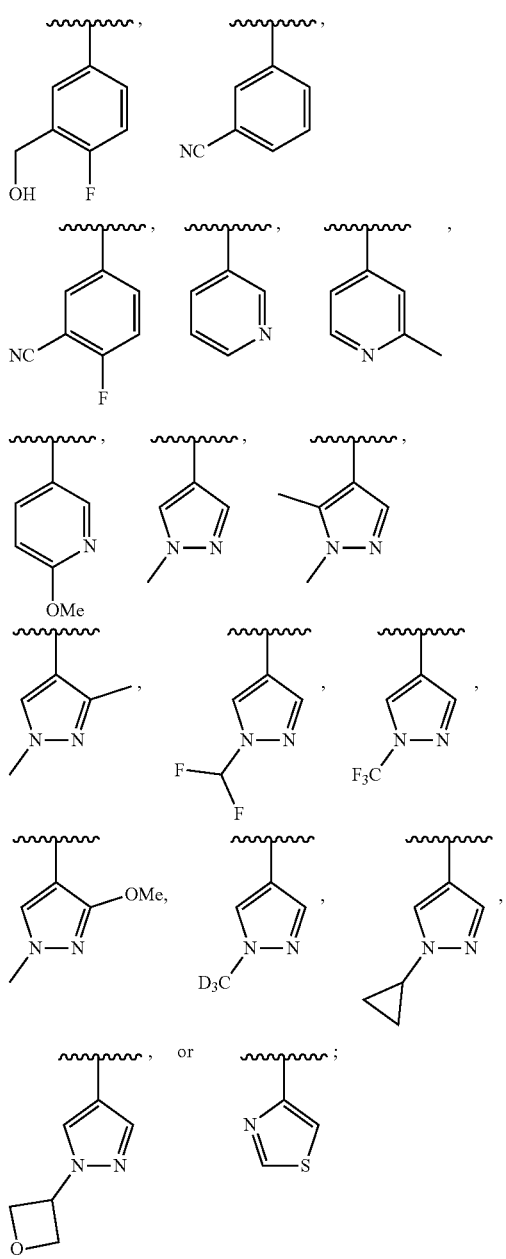
A[1] is =CH— or =N—;
A[2] and A[4] are each =CH—;
A[3] is =CH—, =C(Me)-, =C(Et)-, =C(iPr)—, =C(OMe)-, =C(F)—, =C(Cl)—, or =C(CN)—;
Ring J has the structure:
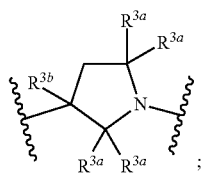

each $R^{3a}$ is hydrogen, —OH, or oxo;
$R^{3b}$ is ethyl, —CH$_2$C≡CH, —CH$_2$OMe,
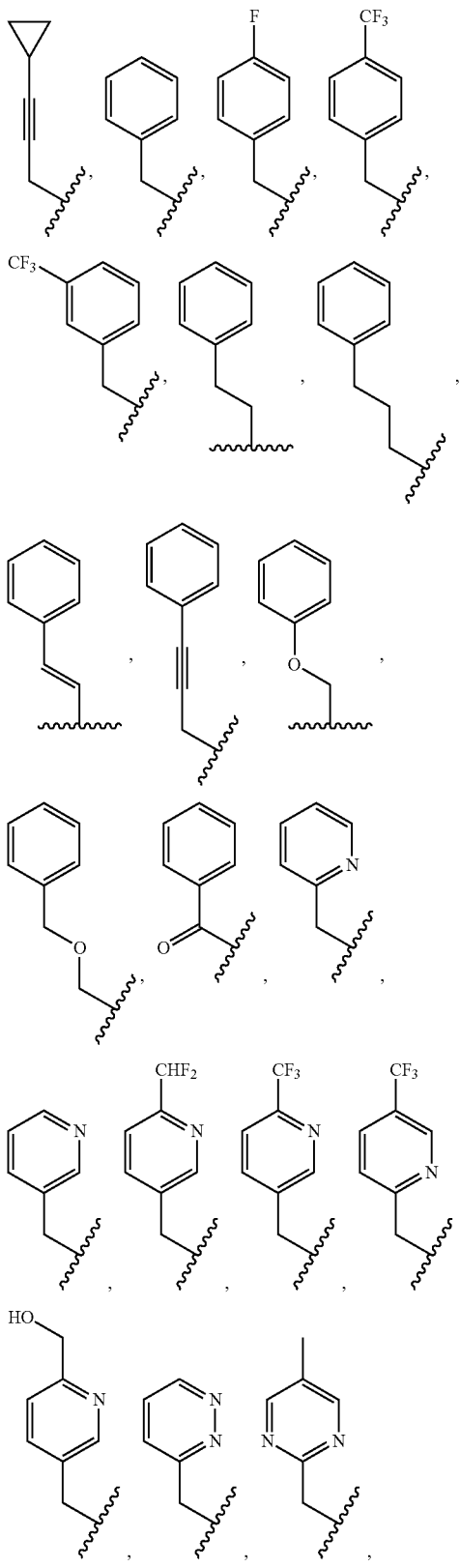
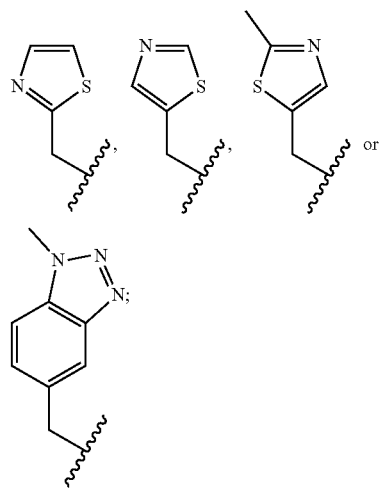
$L^1$ and $L^2$ together are absent, —CH$_2$—, —C(O)—, —C(O)CH$_2$—, —C(O)CH$_2$CH$_2$—, —C(O)CH$_2$O—, —C(O)(CH$_2$)$_3$O—, or —S(O)$_2$—; and
$R^4$ is methyl, —CF$_2$CH$_3$, —CN,
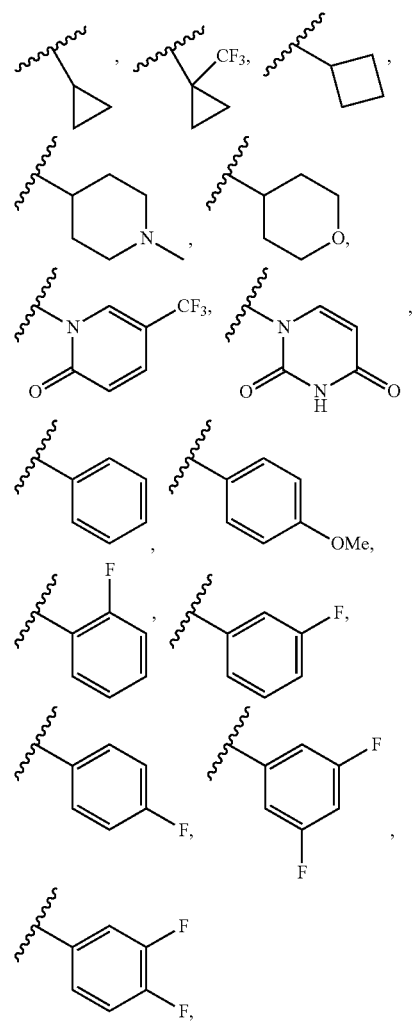

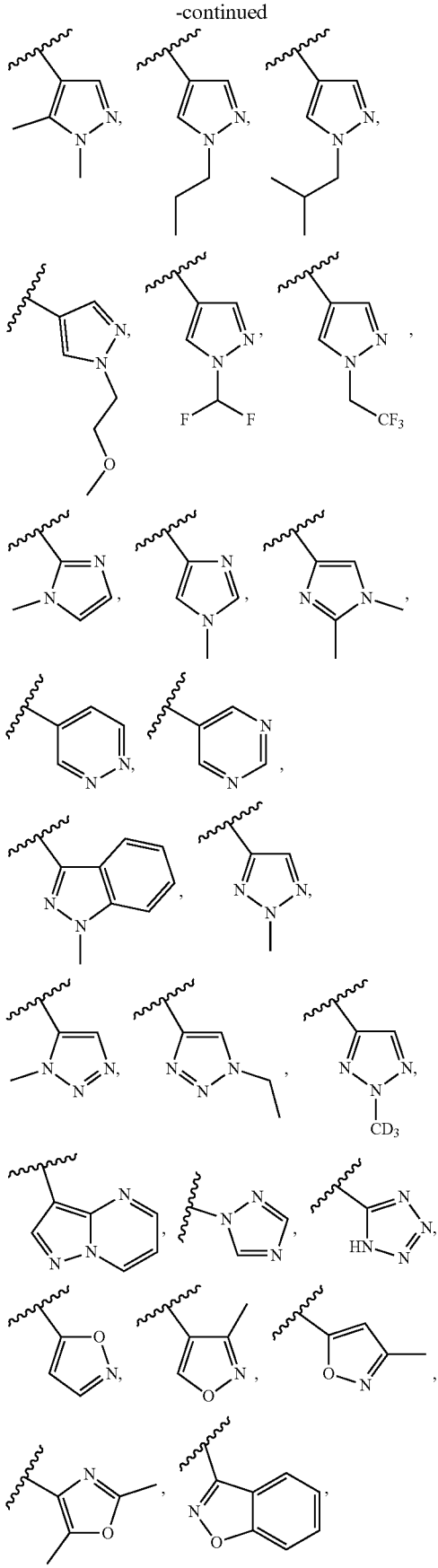

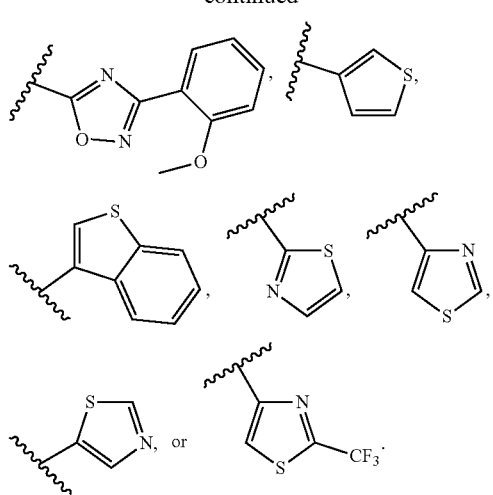
In some embodiments, the compound of Formula I, II, IV or IVa, or a pharmaceutically acceptable salt thereof, is the compound wherein
R¹ is
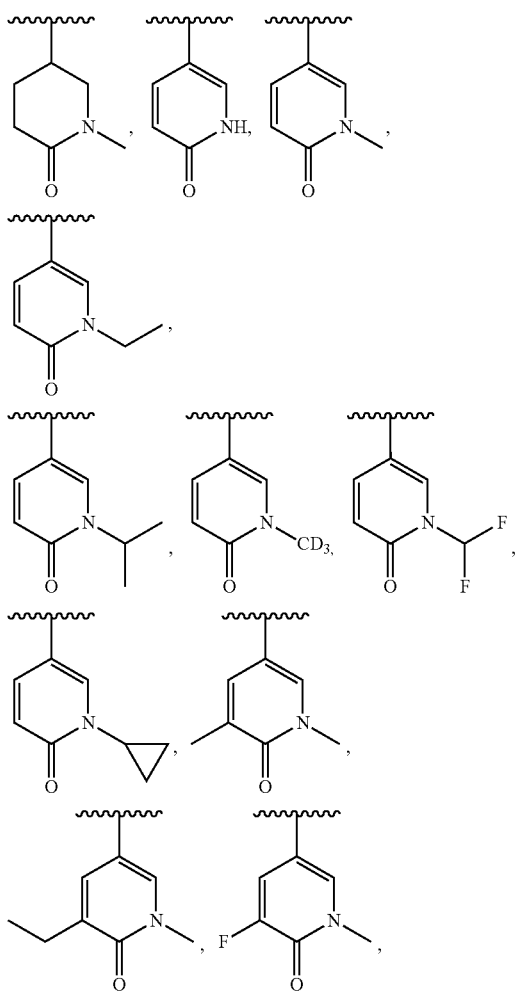
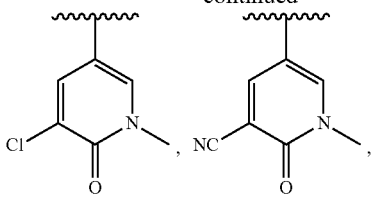
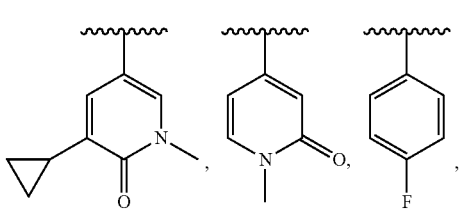
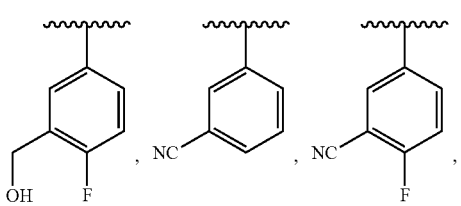
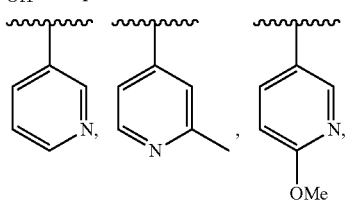
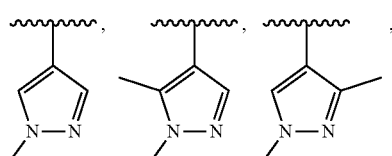
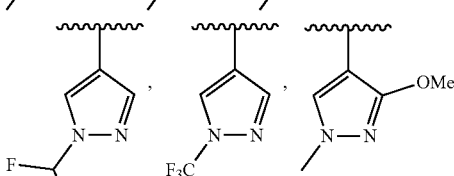
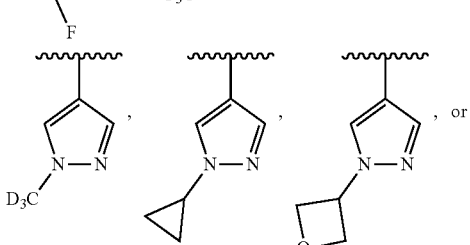
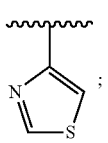

$A^1$ is =CH—
$A^2$ and $A^4$ are each =CH—;
$A^3$ is =CH—, =C(Me)-, =C(Et)-, =C(OMe)-, =C(Cl)—, or =C(CN)—;
Ring J has the structure:
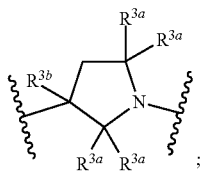
each $R^{3a}$ is hydrogen, —OH, or oxo;
$R^{3b}$ is —CH$_2$OMe.
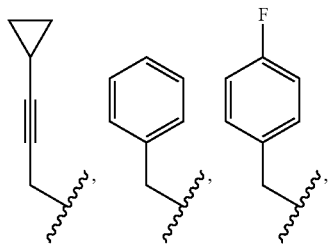
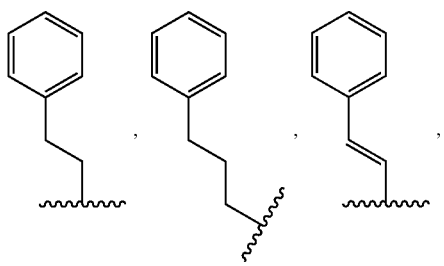
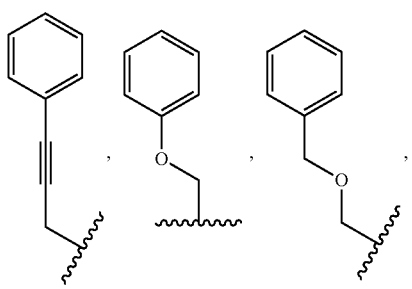
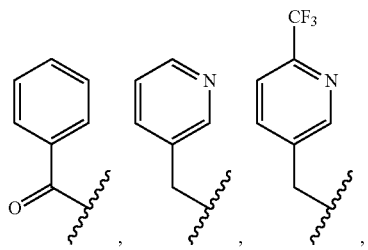
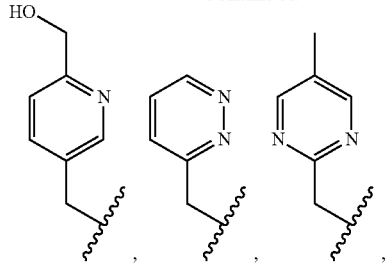
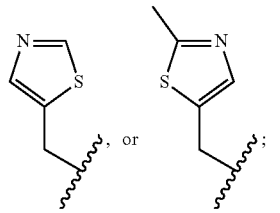
$L^1$ and $L^2$ together are —CH$_2$—, —C(O)—, —C(O)CH$_2$—, —C(O)CH$_2$CH$_2$—, —C(O)CH$_2$O—, or —S(O)$_2$—; and
$R^4$ is methyl, —CF$_2$CH$_3$,
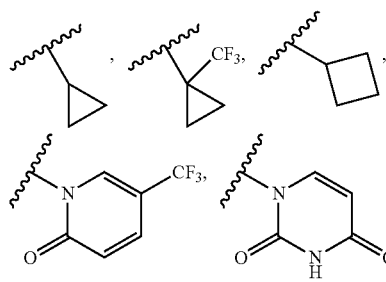
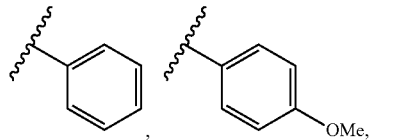
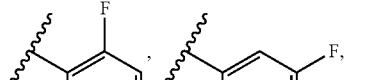
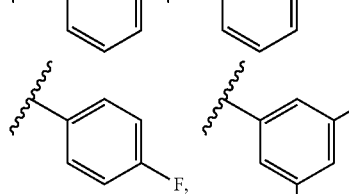
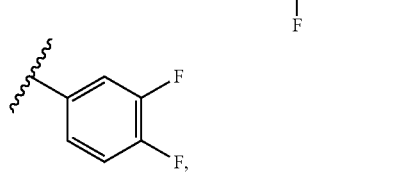
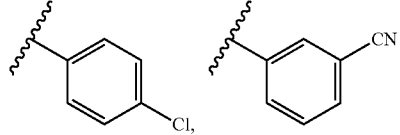

99
-continued
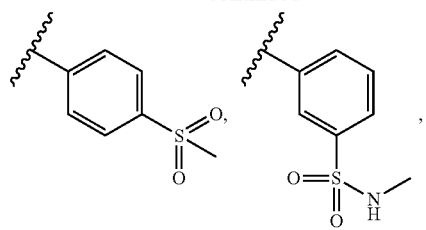
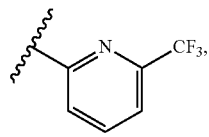
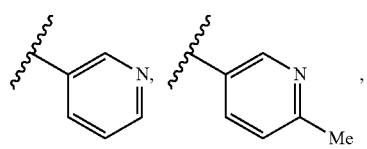
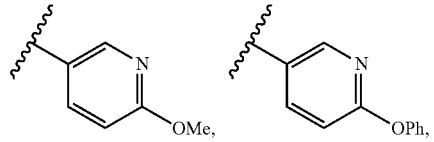
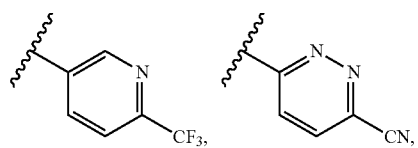
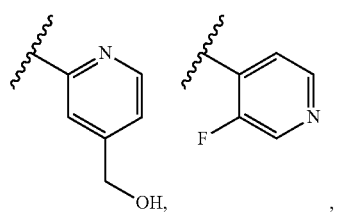
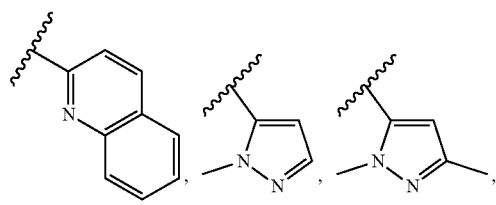
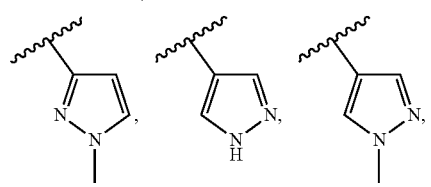
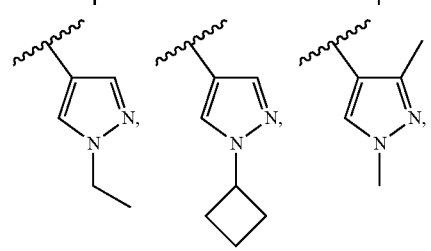
100
-continued
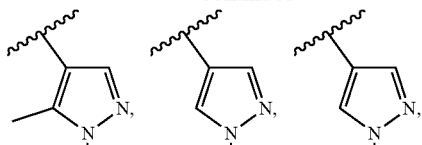
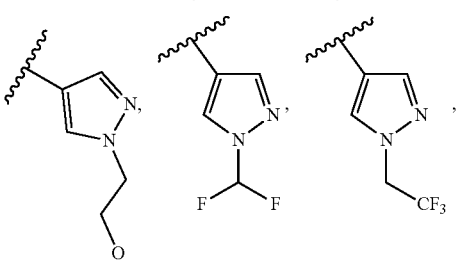
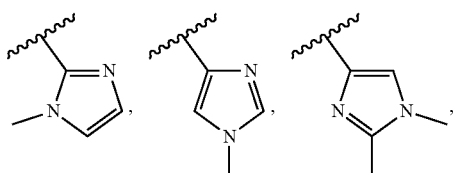
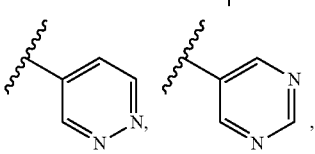
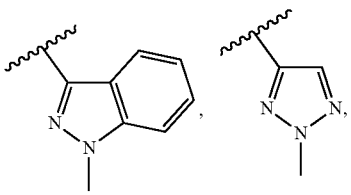
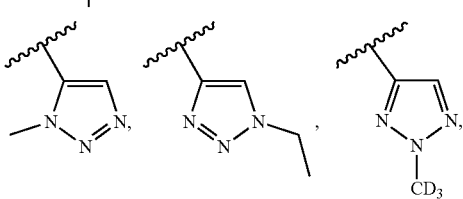
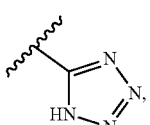
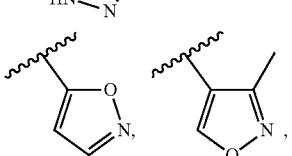
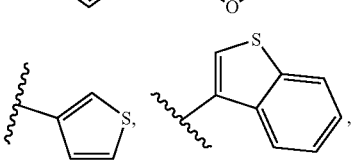

101
-continued
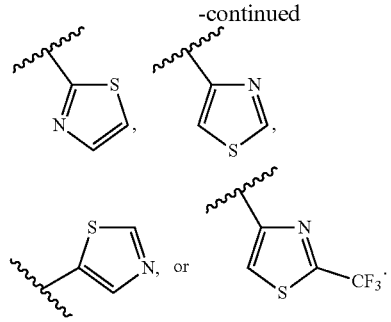
102
-continued
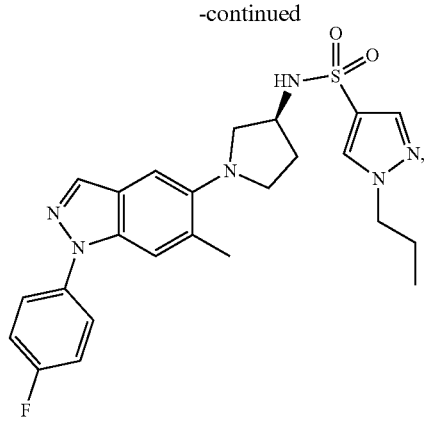
In some embodiments, the compound of Formula I or II, or a pharmaceutically acceptable salt thereof, is a compound in Table 1A:
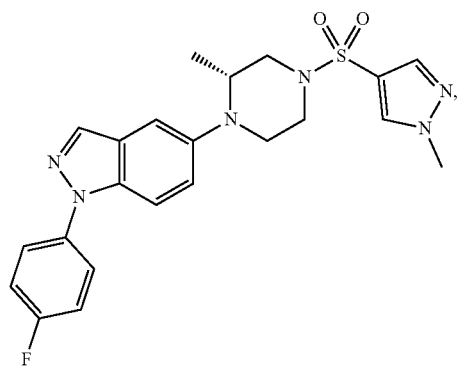
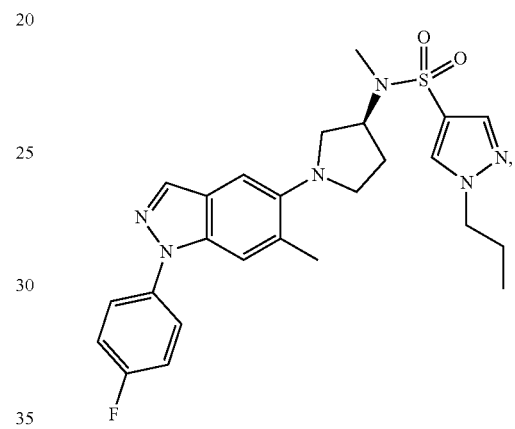
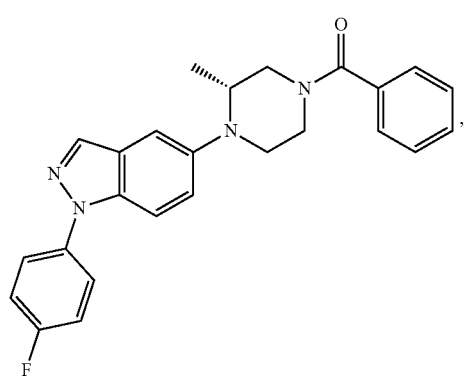
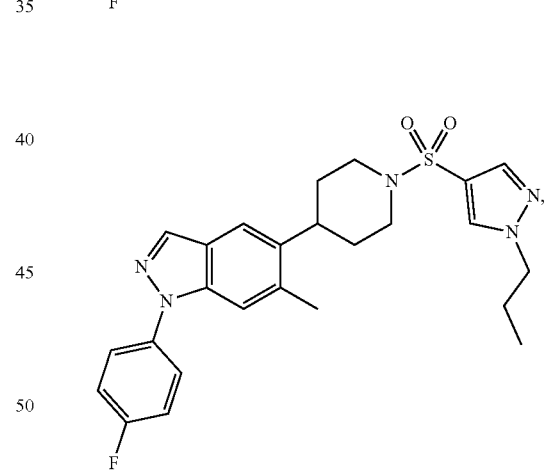
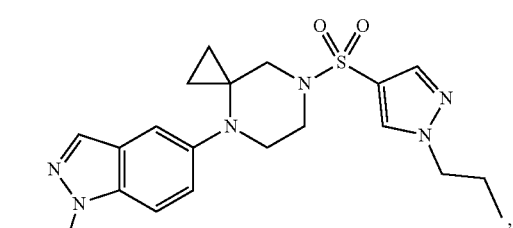
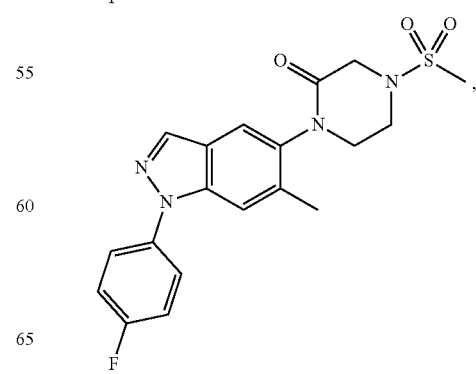

103
-continued
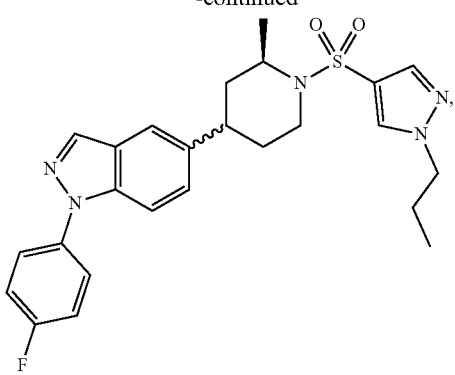
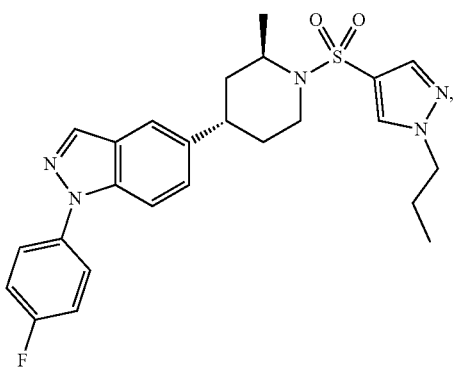
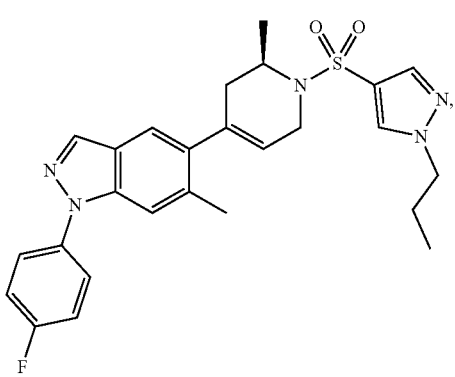
104
-continued
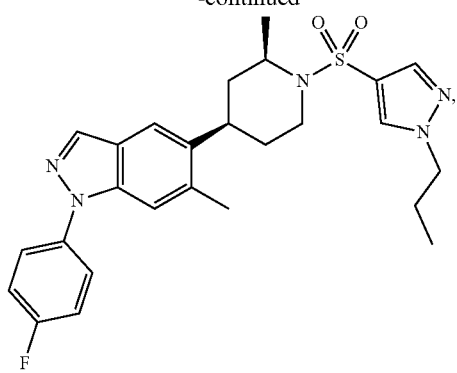
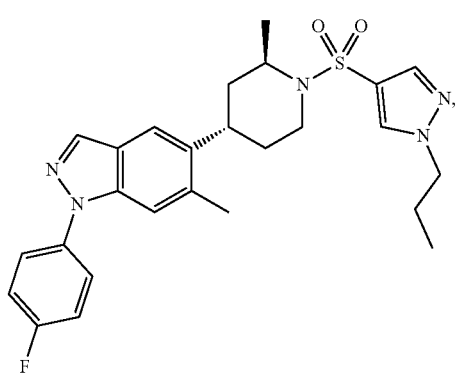
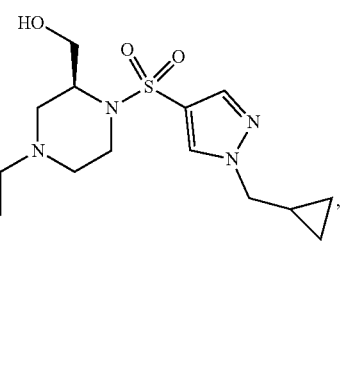
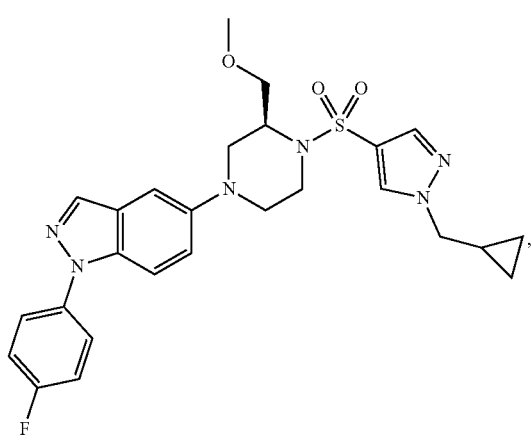

105
-continued
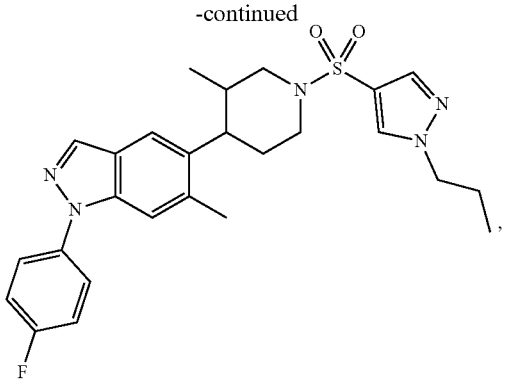
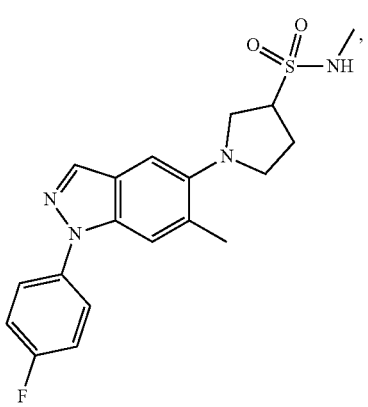
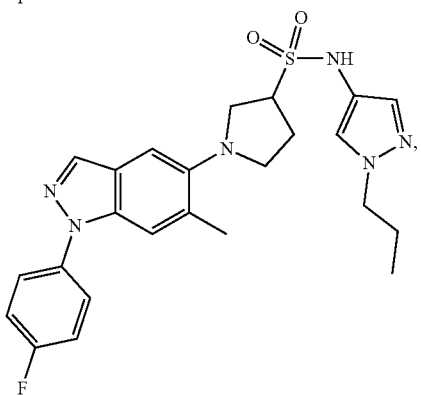
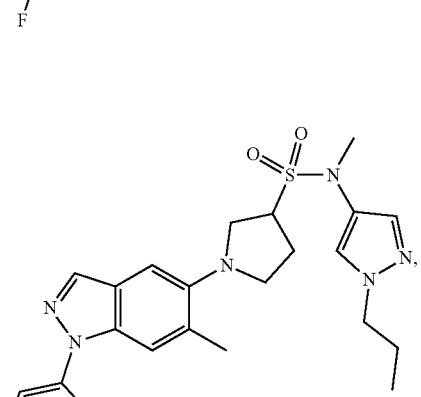
106
-continued
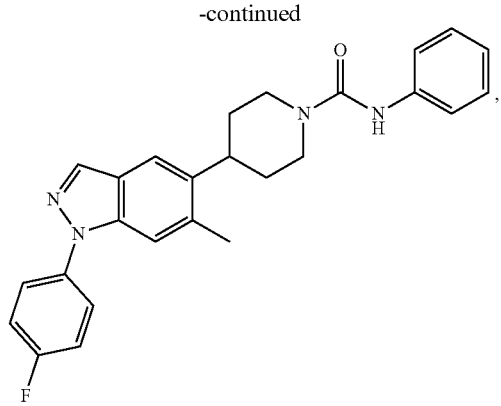
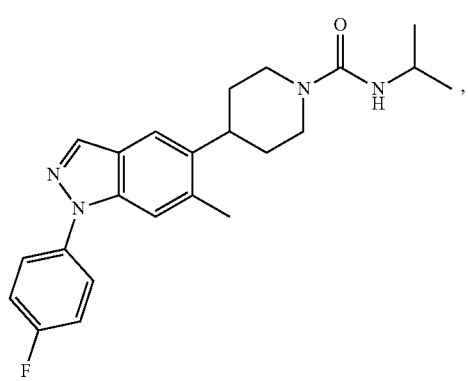
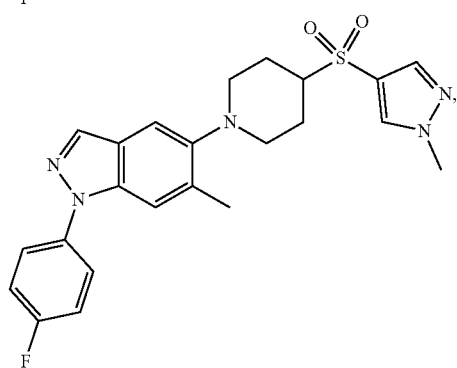
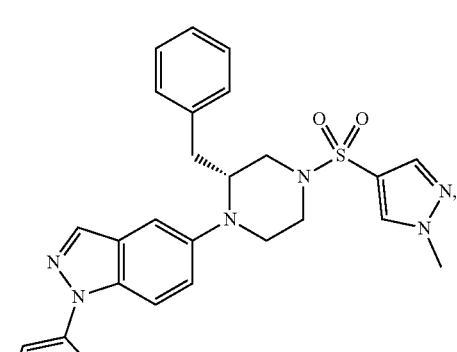

107
-continued
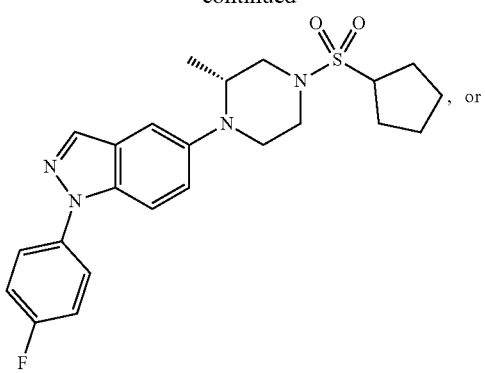
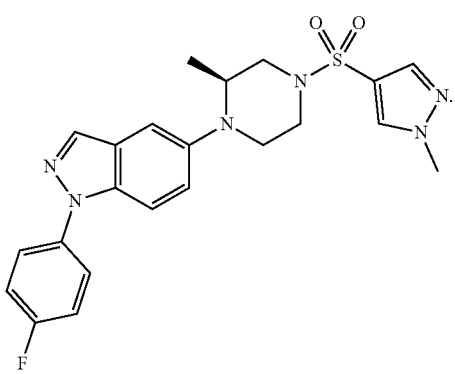 [SMILES: C[C@H]1CN(S(=O)(=O)c2cnn(C)c2)CCN1c1ccc2c(cnn2-c2ccc(F)cc2)c1]
In some embodiments, the compound of Formula I or II, or a pharmaceutically acceptable salt thereof, is a compound in Table 1B:
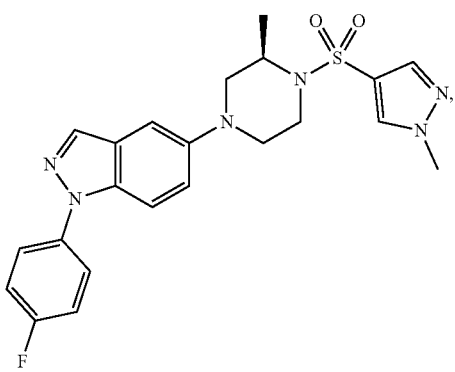
108
-continued
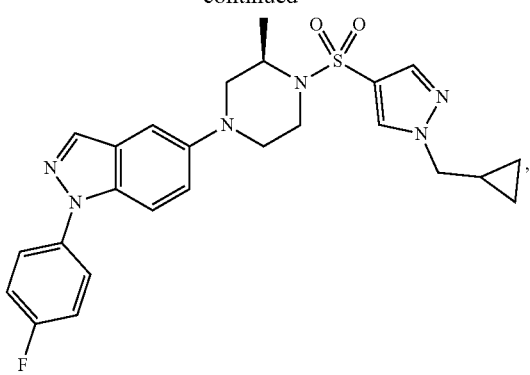
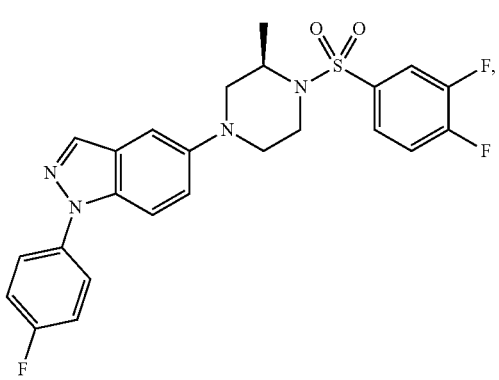
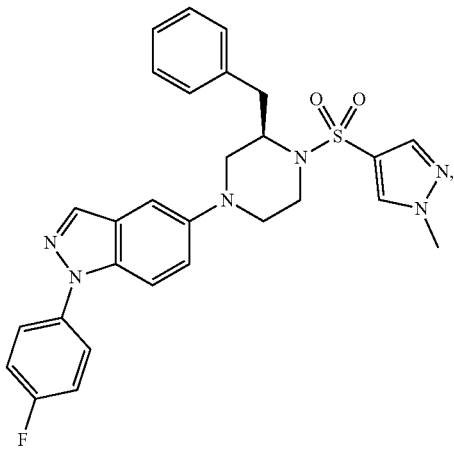
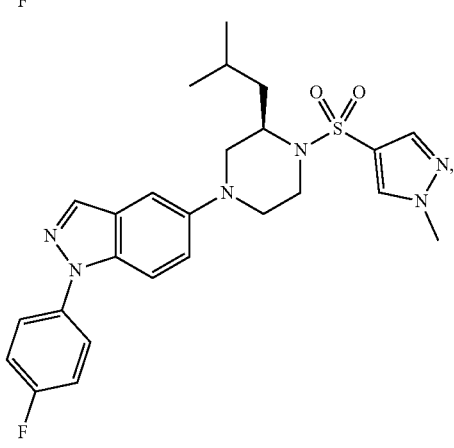

109
-continued
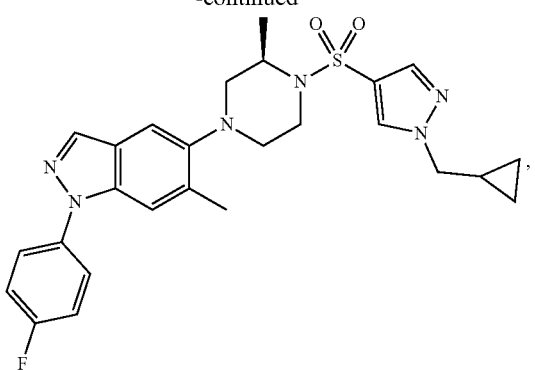
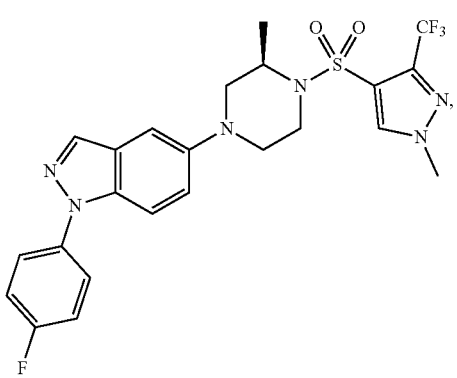 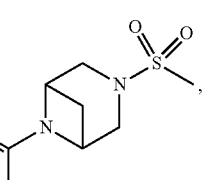
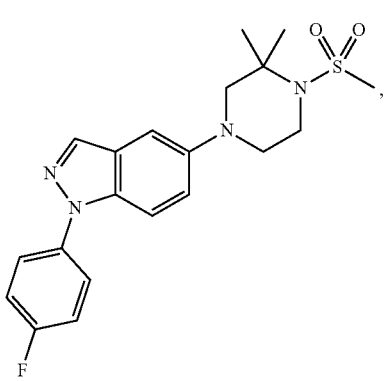
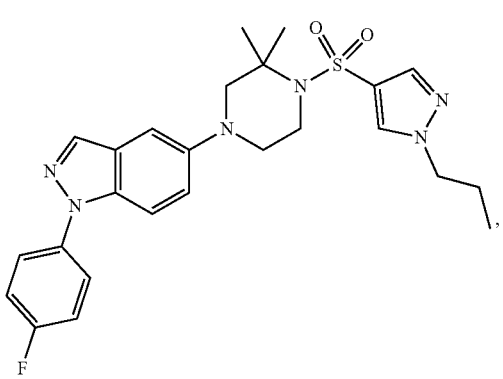
110
-continued
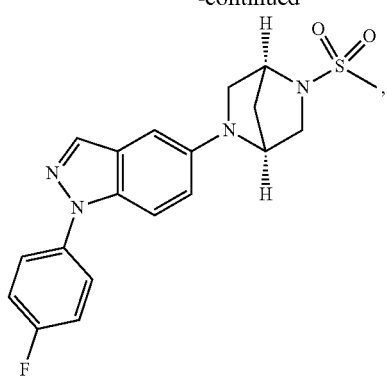
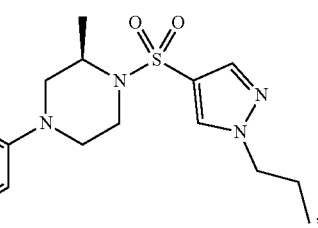
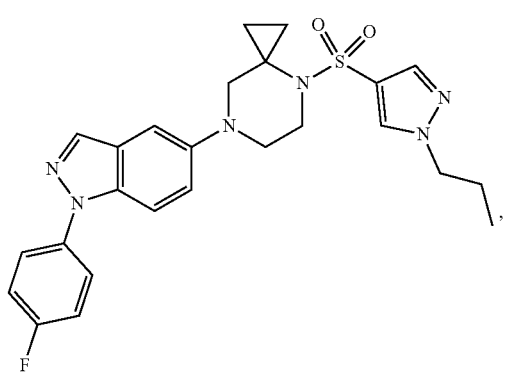

111
-continued
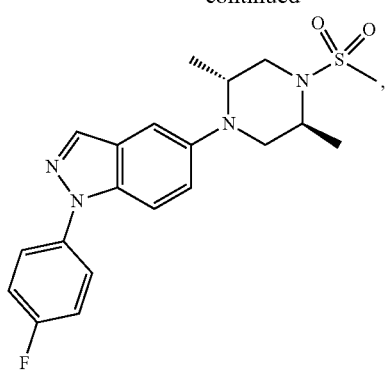
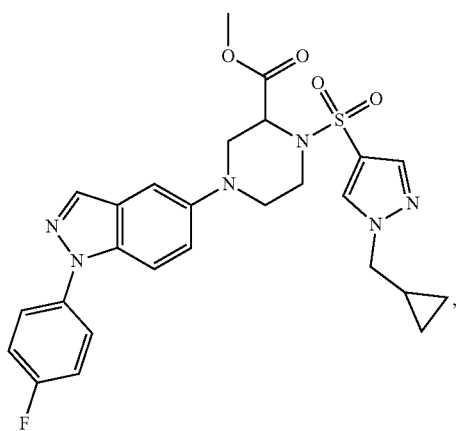
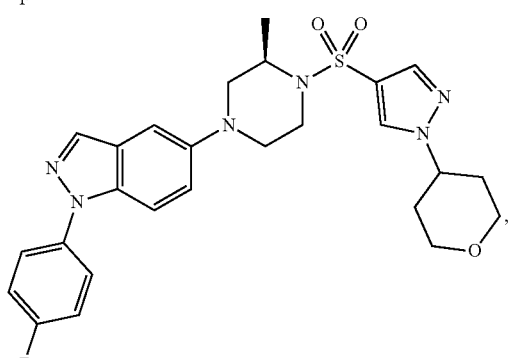
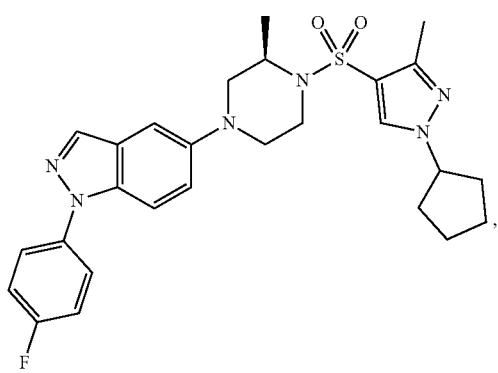
112
-continued
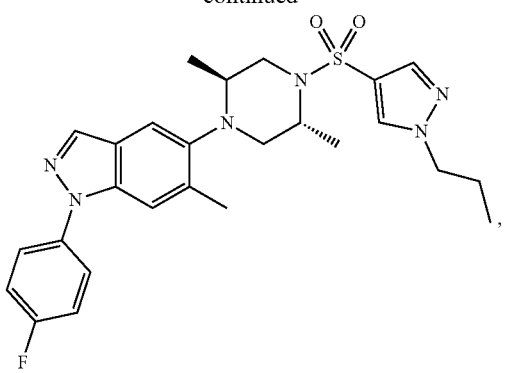
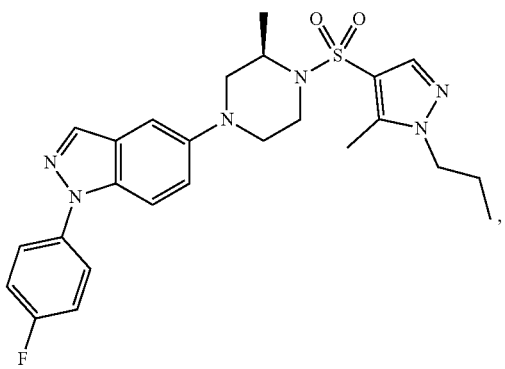
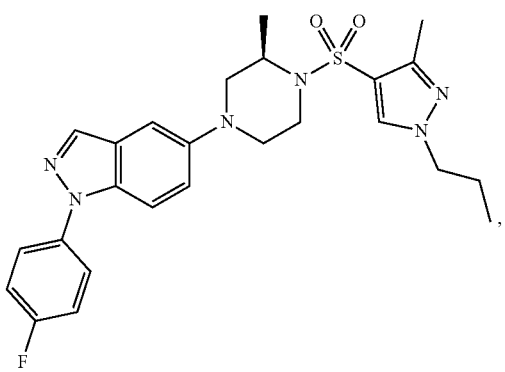
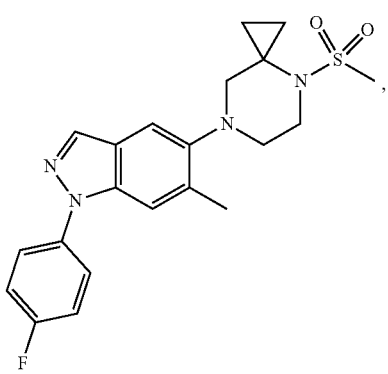

113
-continued
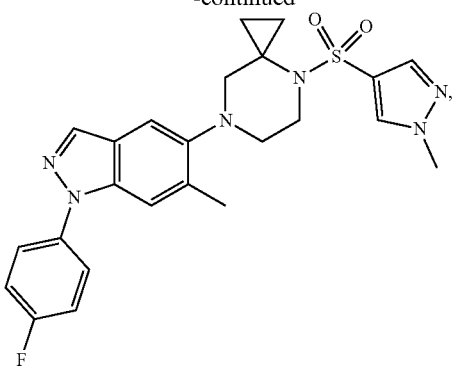
114
-continued
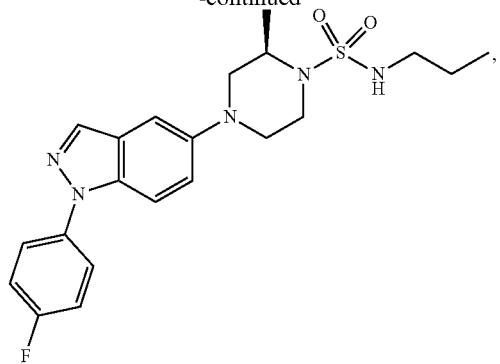
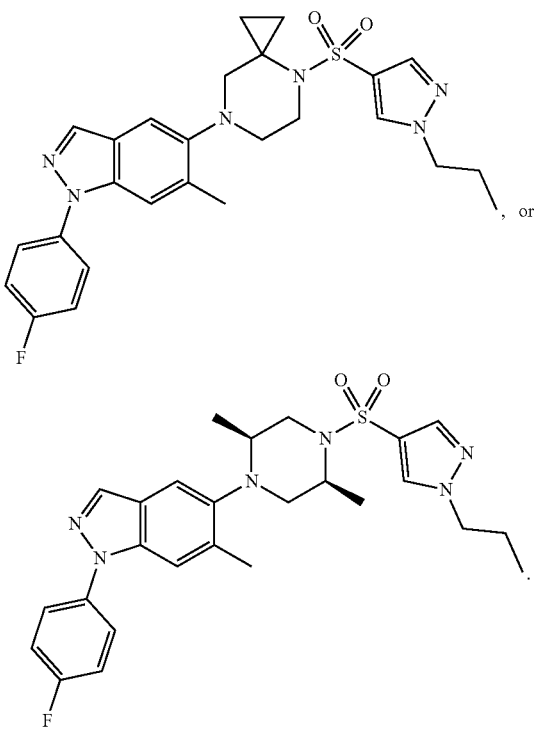
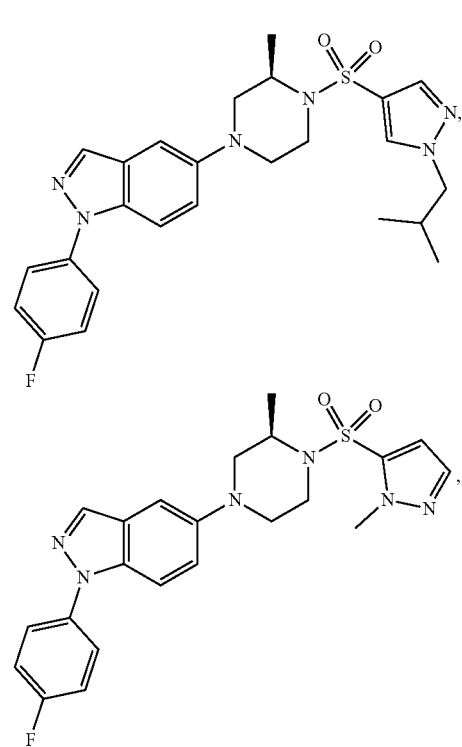
In some embodiments, the compound of Formula I or II, or a pharmaceutically acceptable salt thereof, is a compound in Table 1C:
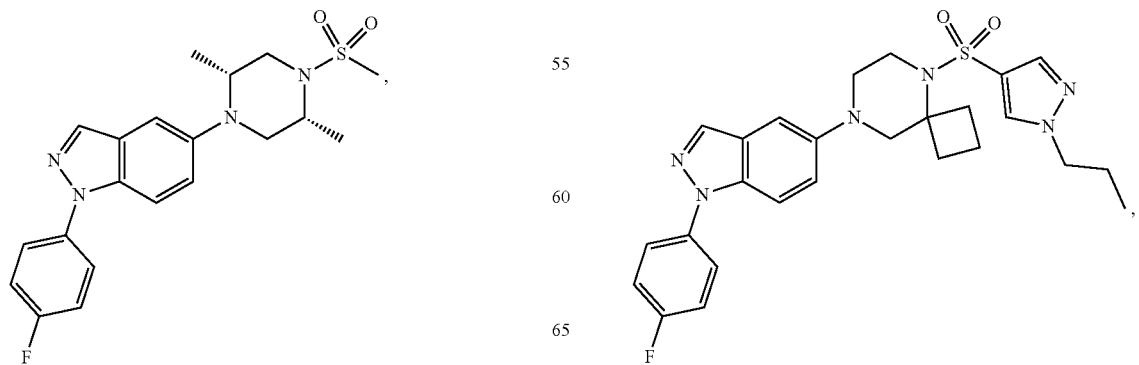

115
-continued
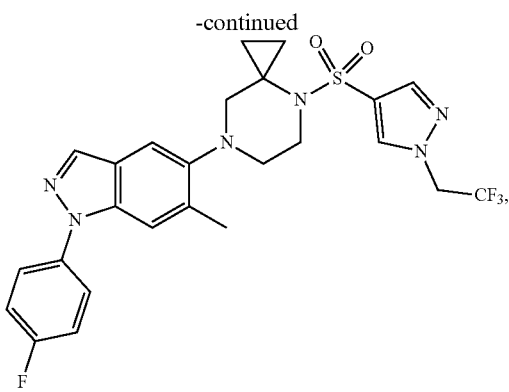
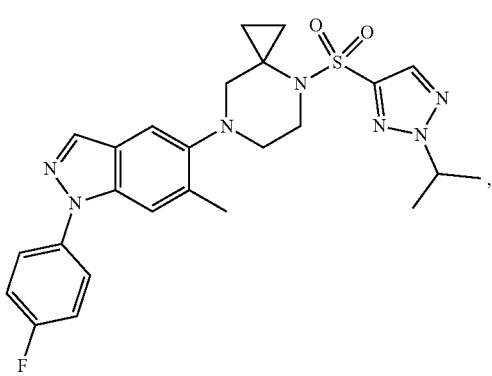
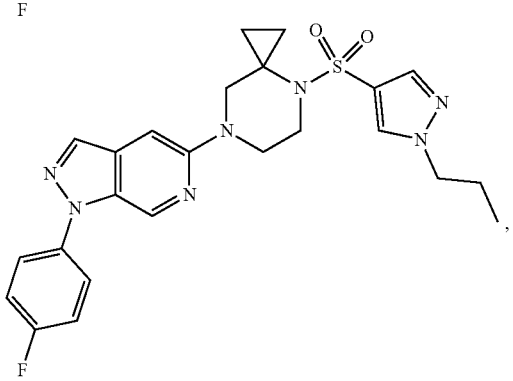
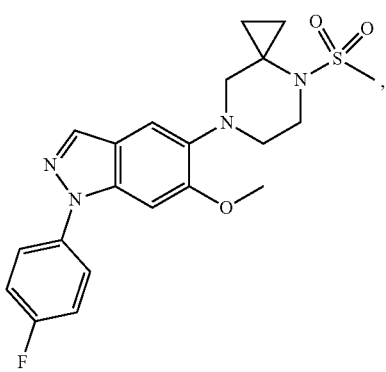
116
-continued
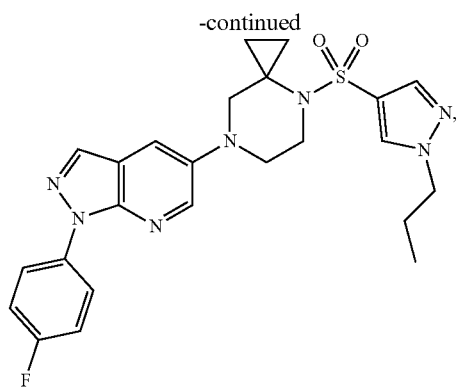
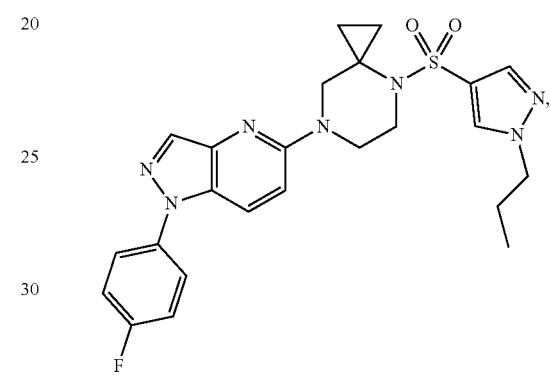
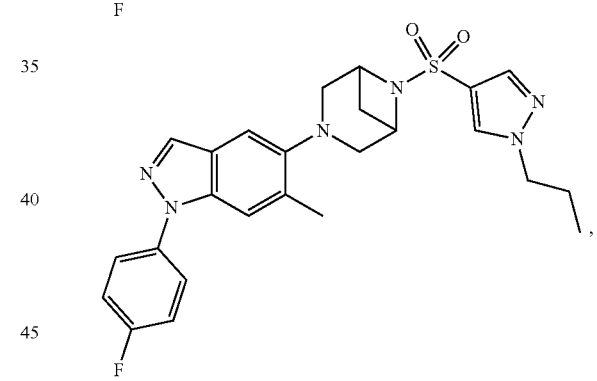
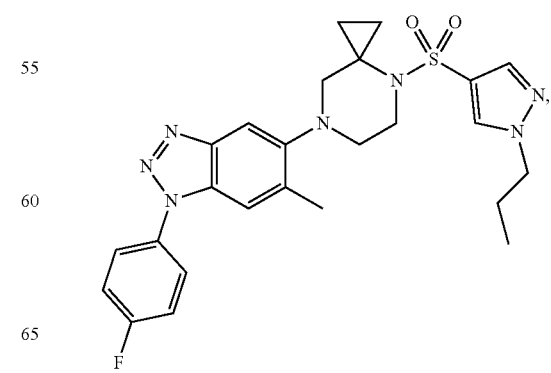

117 -continued
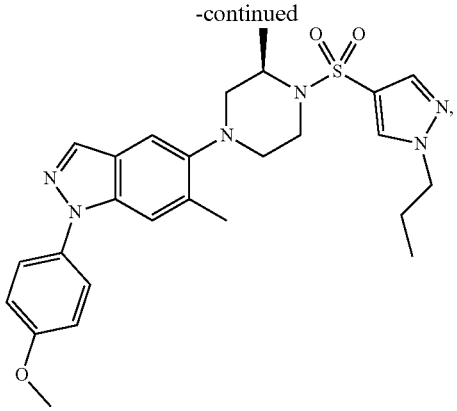
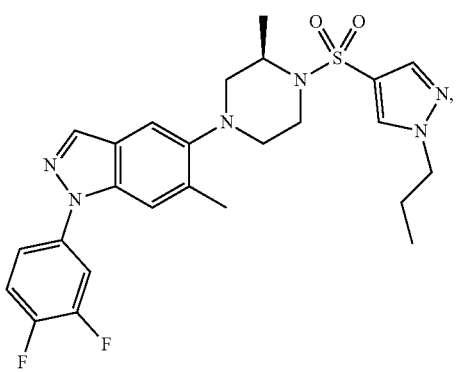
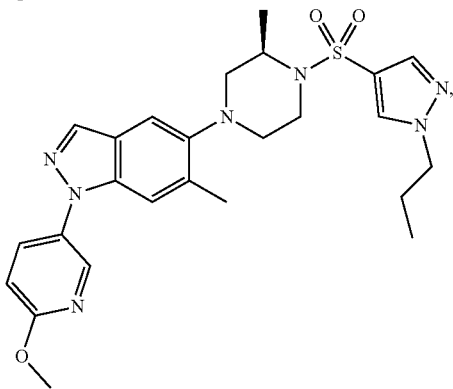
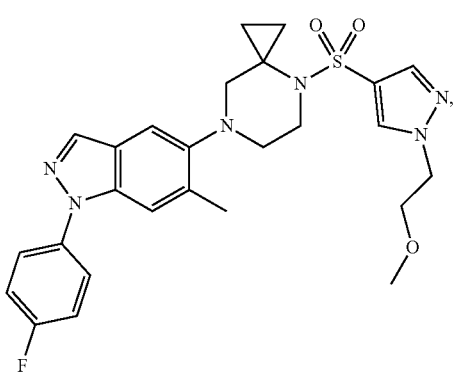
118 -continued
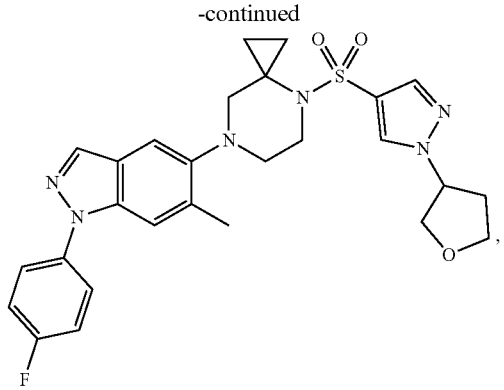
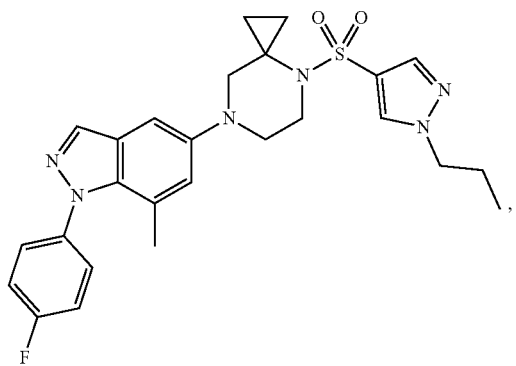
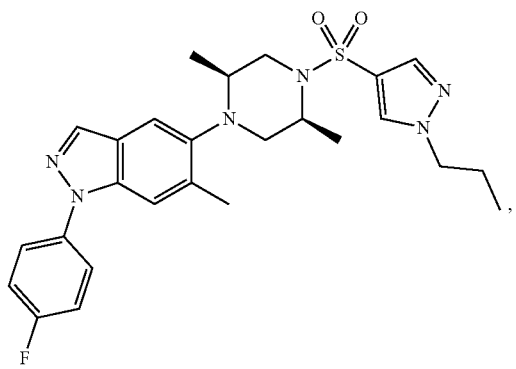
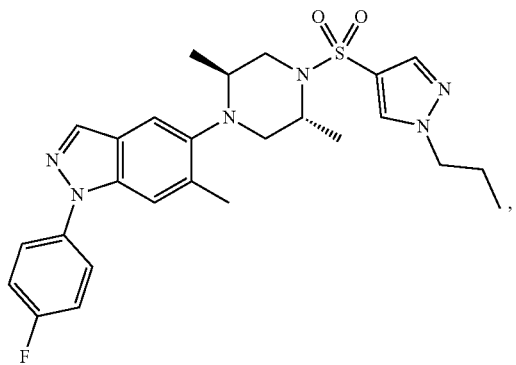

119
-continued
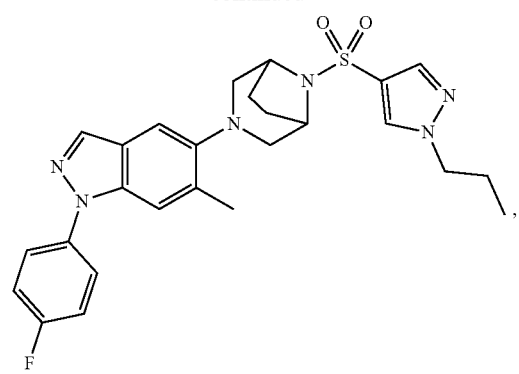
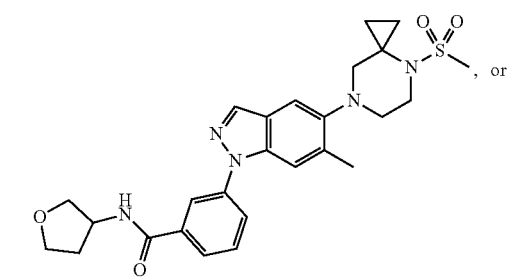
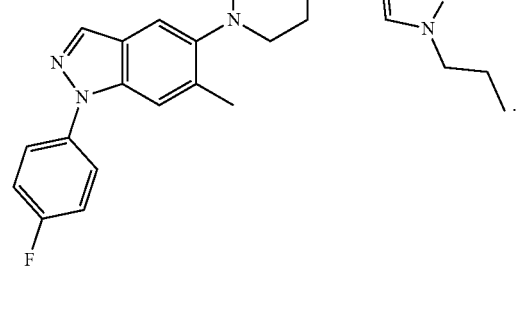
, or
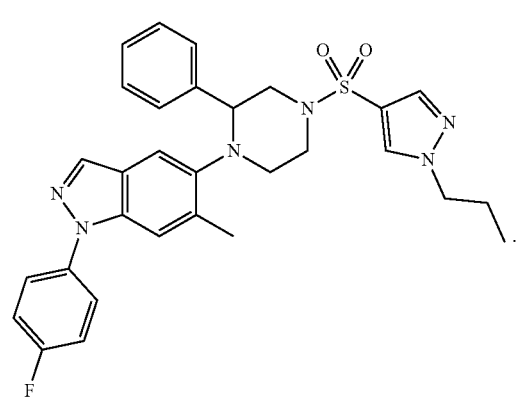
.
120
In some embodiments, the compound of Formula I or II, or a pharmaceutically acceptable salt thereof, is a compound in Table 1D:
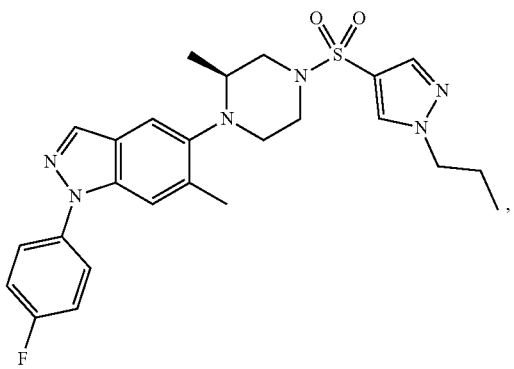
,
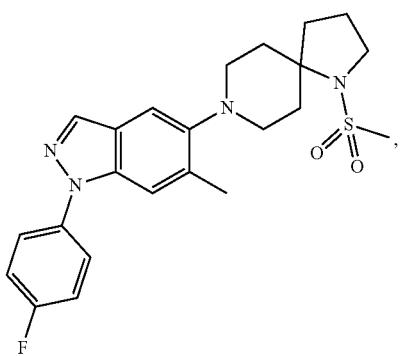
,
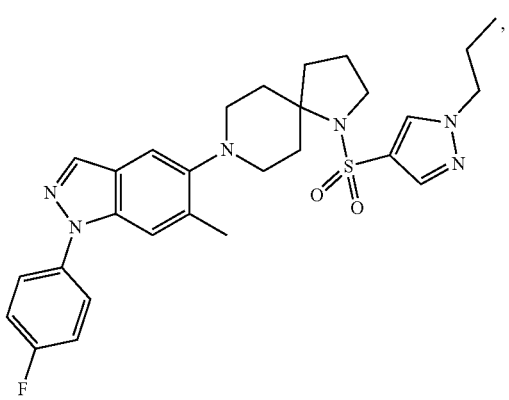
,
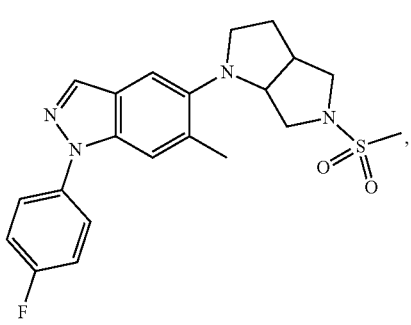
, 121
-continued
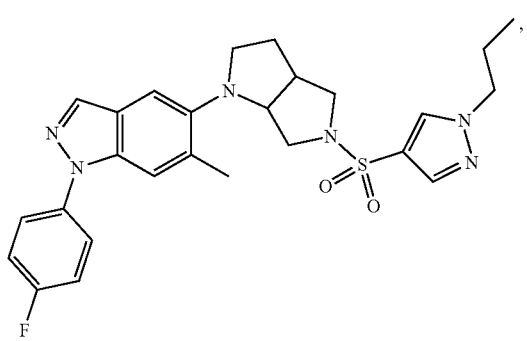
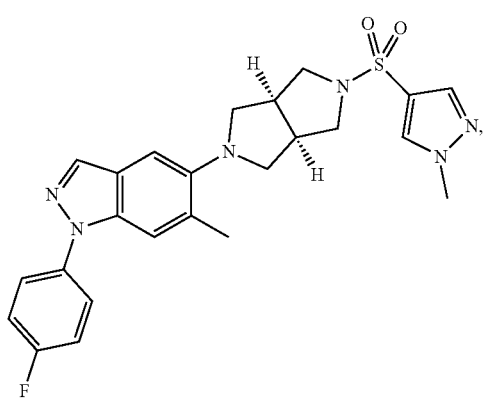
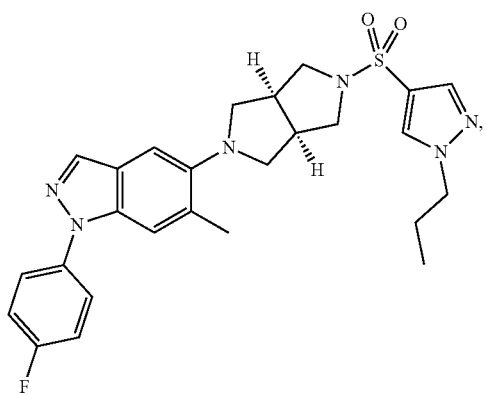
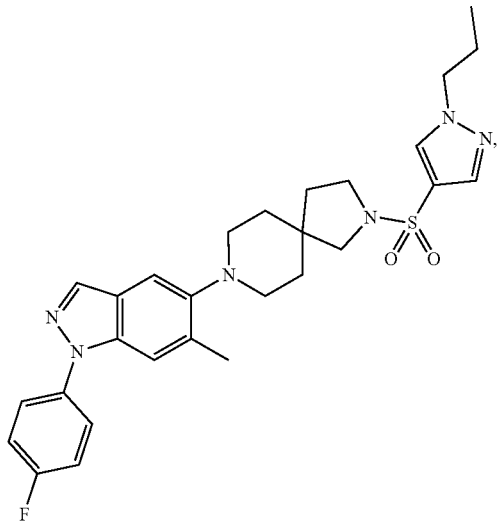
122
-continued
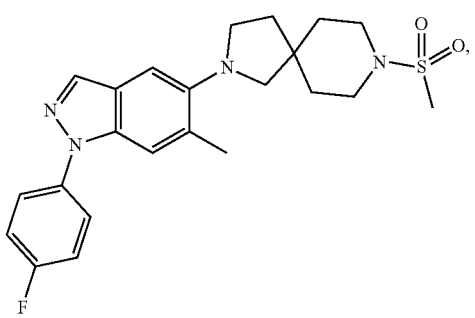
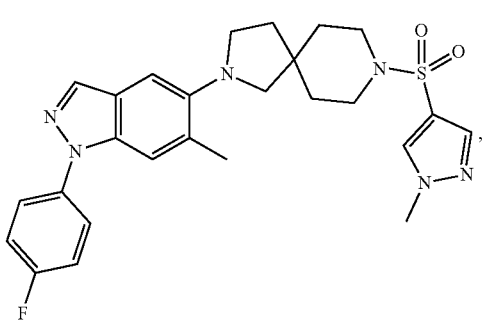
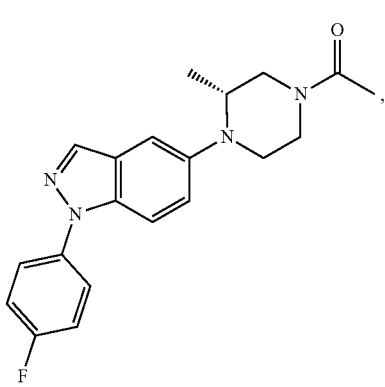
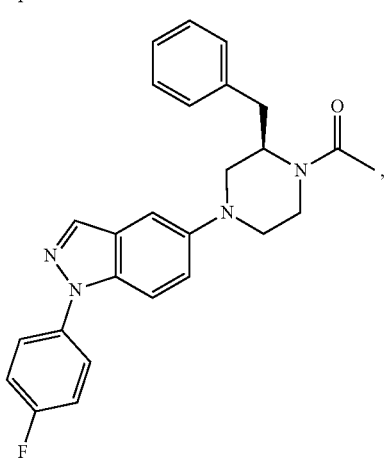

123
-continued
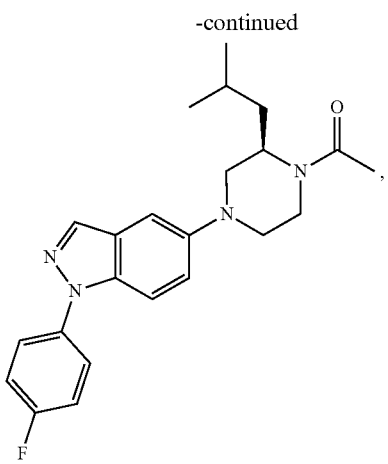
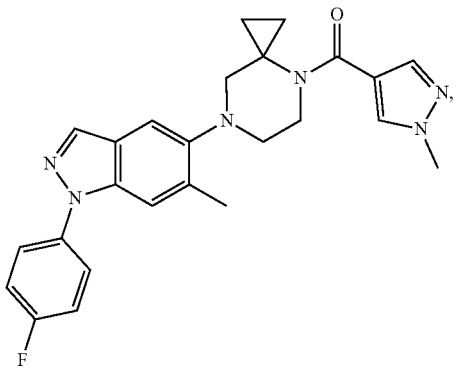
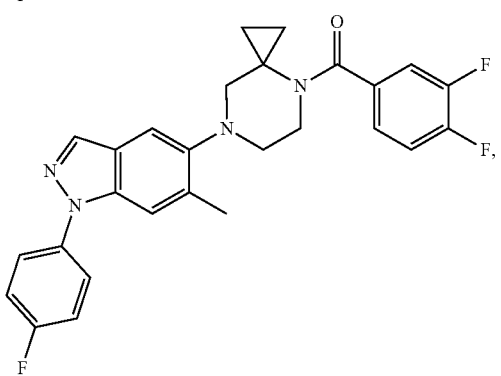
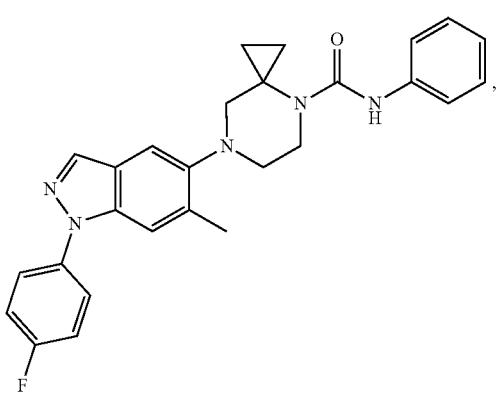
124
-continued
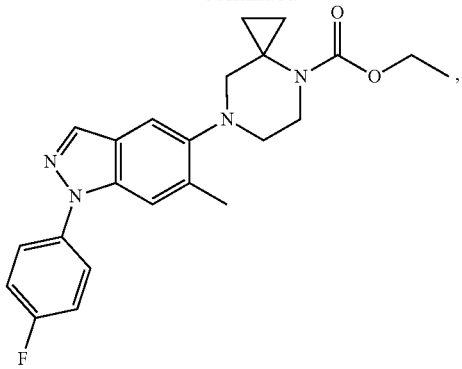
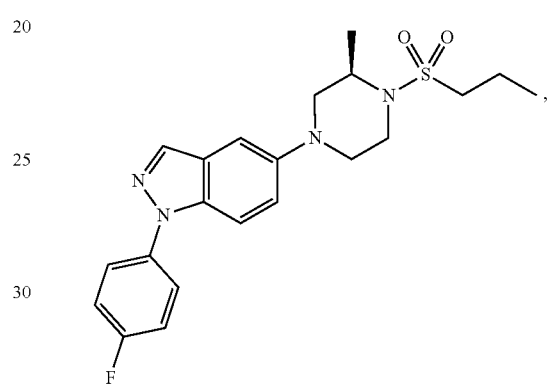
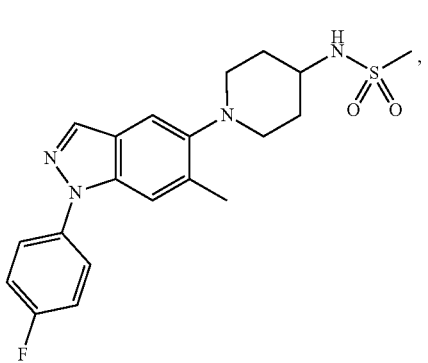

125
-continued
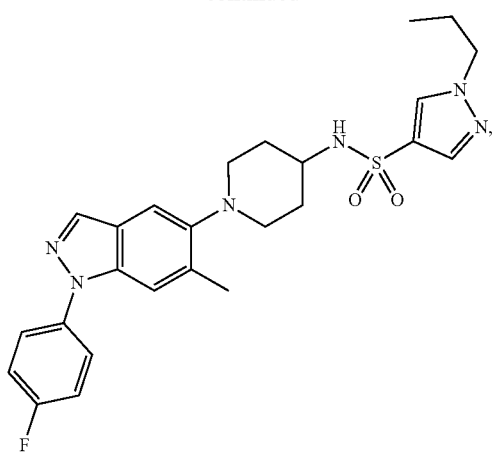
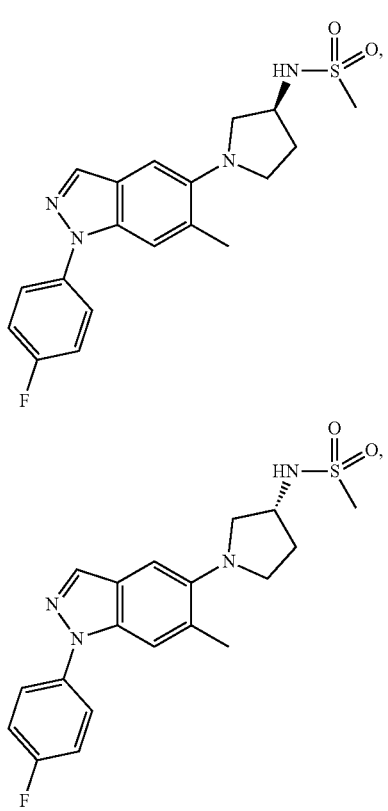
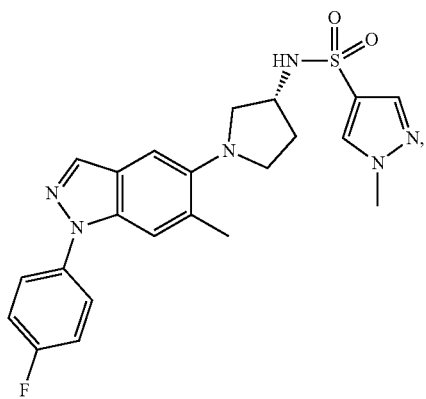
126
-continued
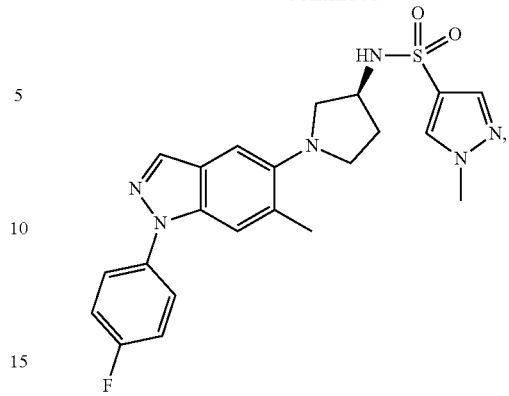
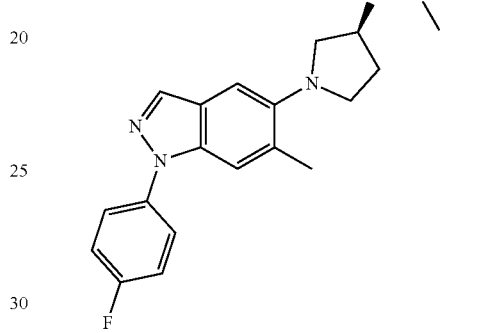, or
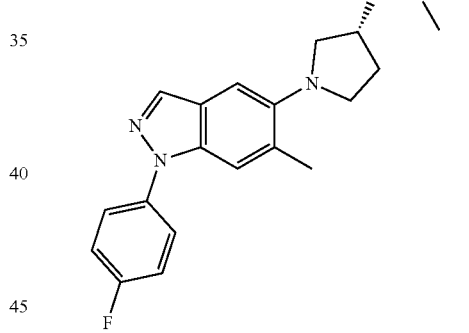
In some embodiments, the compound of Formula I or II, or a pharmaceutically acceptable salt thereof, is a compound in Table 1E:
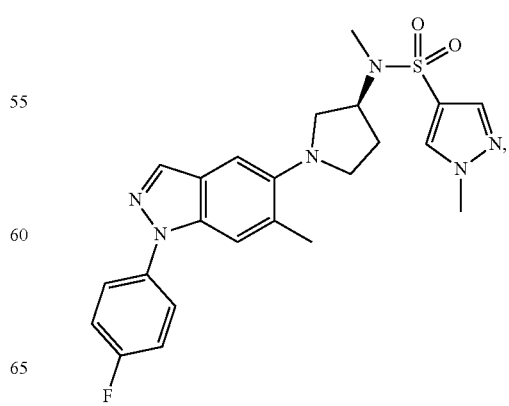

127
-continued
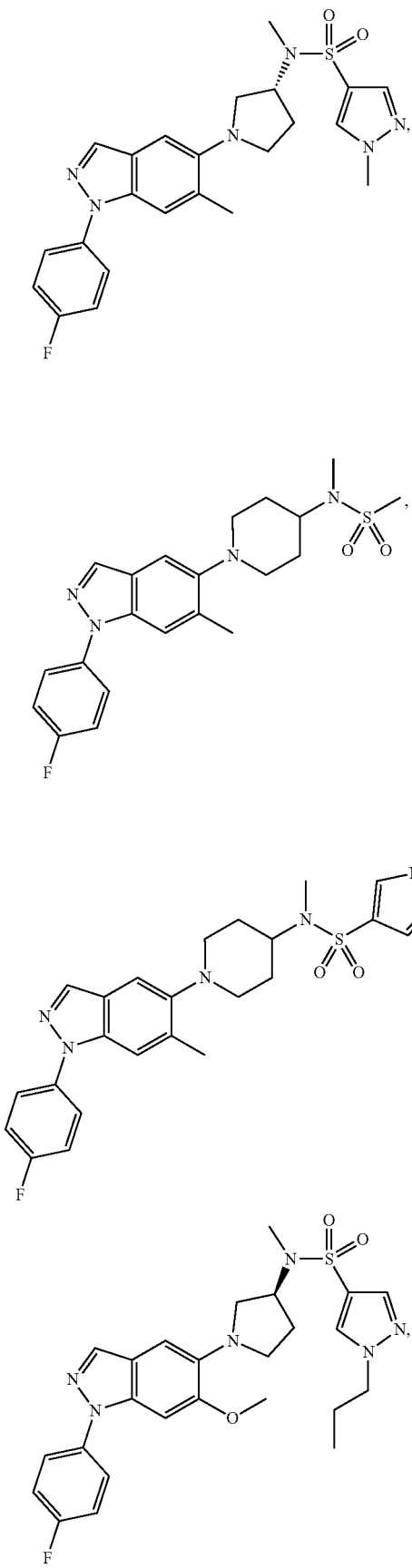
128
-continued
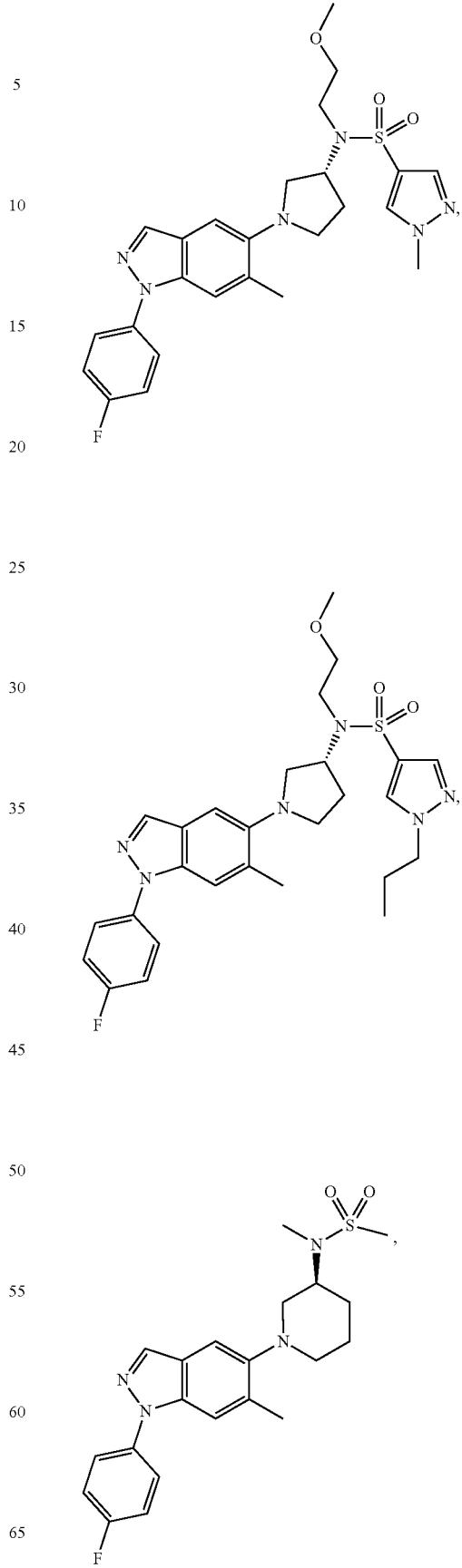

129
-continued
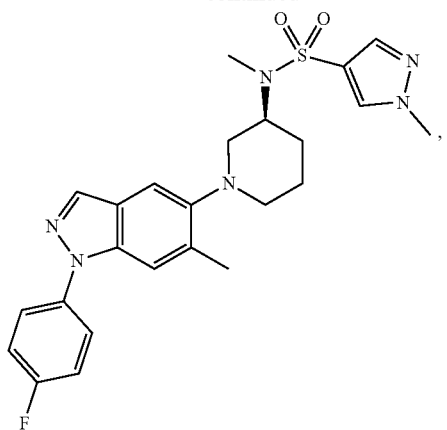
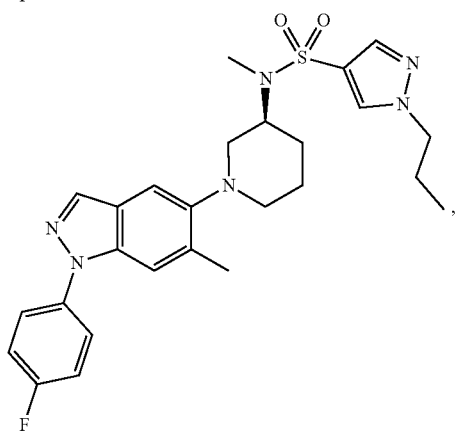
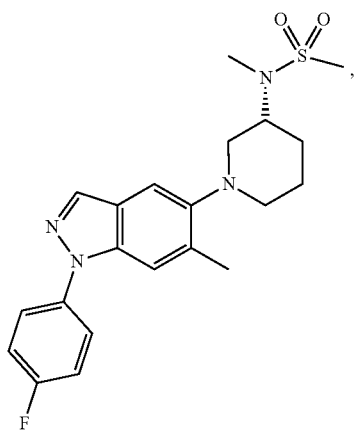
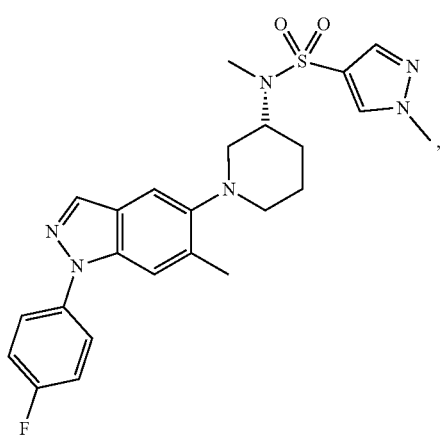
130
-continued
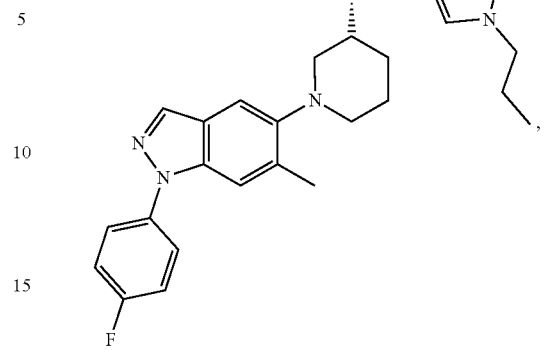
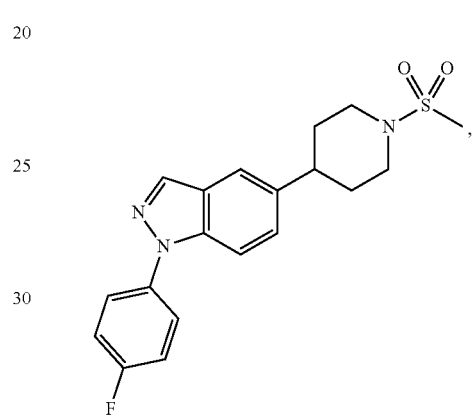
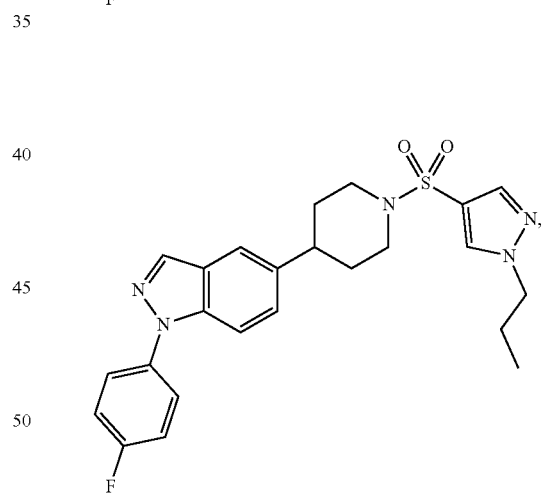
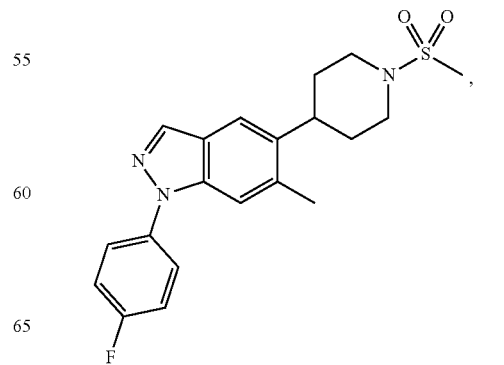

131
-continued
132
-continued
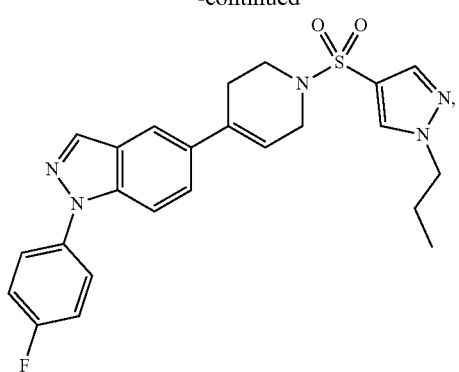
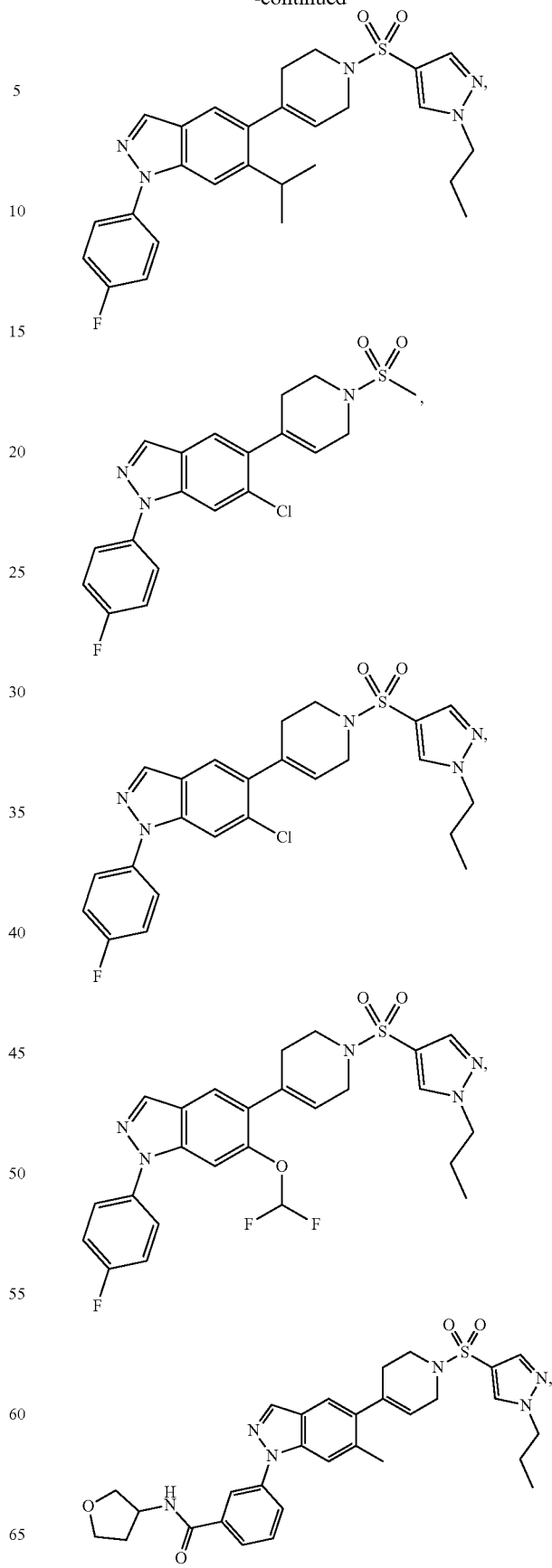

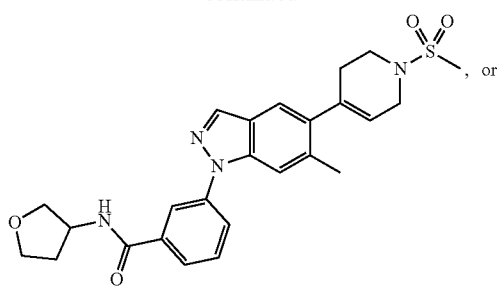
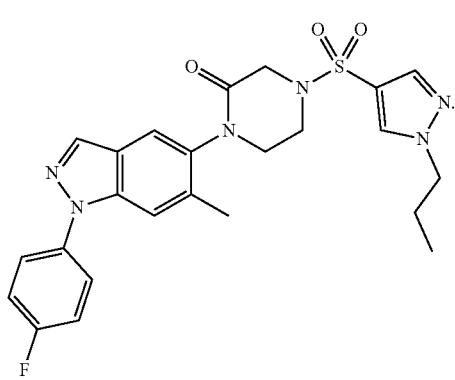
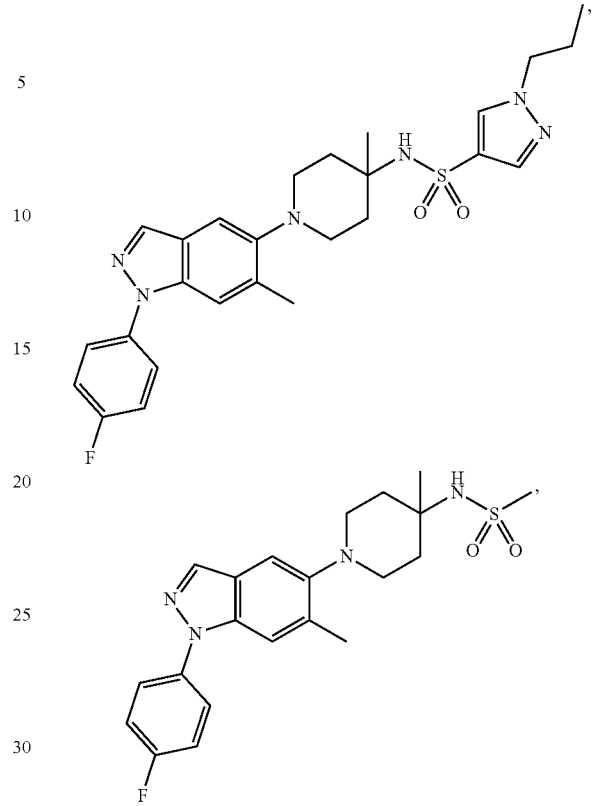
In some embodiments, the compound of Formula I or II, or a pharmaceutically acceptable salt thereof, is a compound in Table 1F:
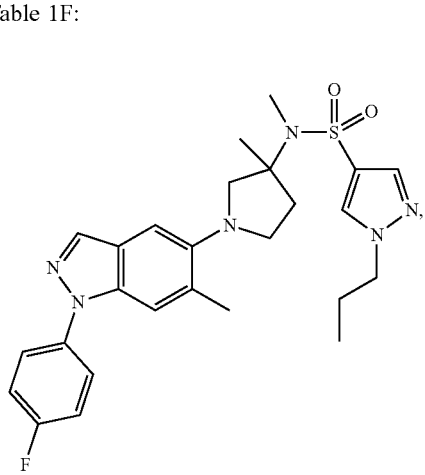
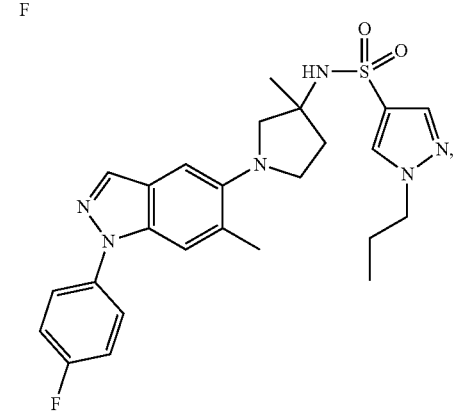
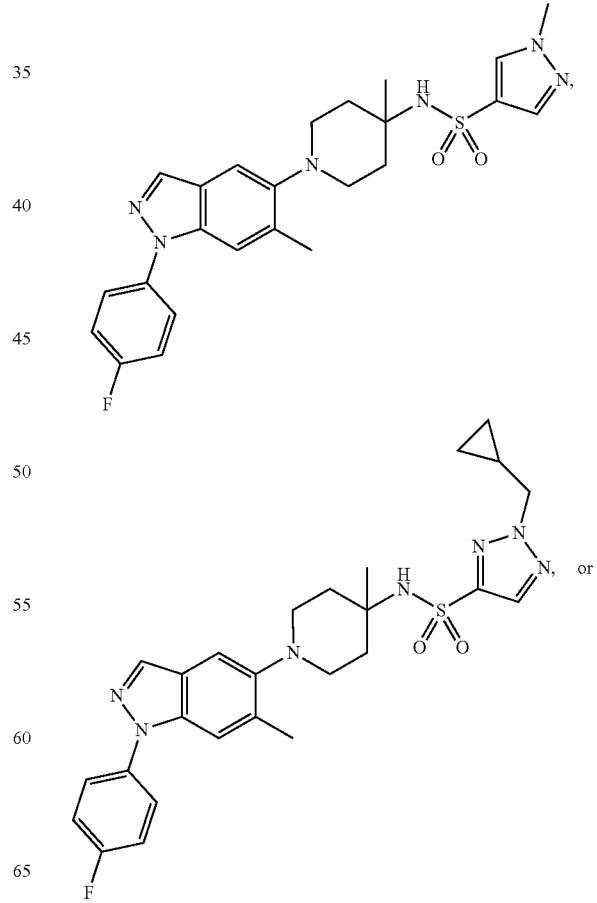

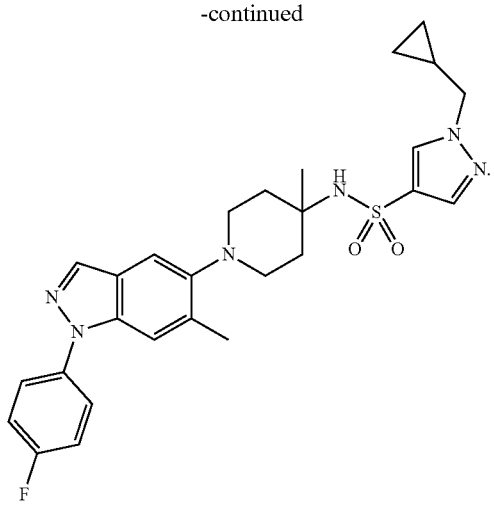
In some embodiments, the compound of Formula I or II, or a pharmaceutically acceptable salt thereof, is a compound in Table 1G:
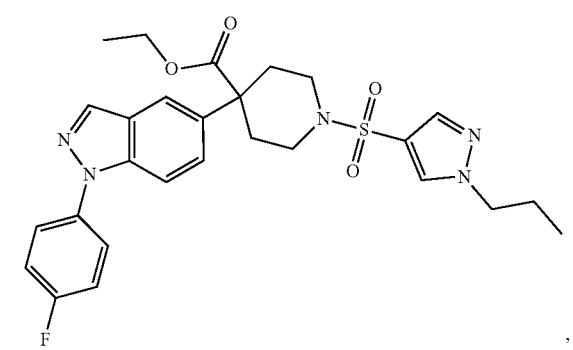
,
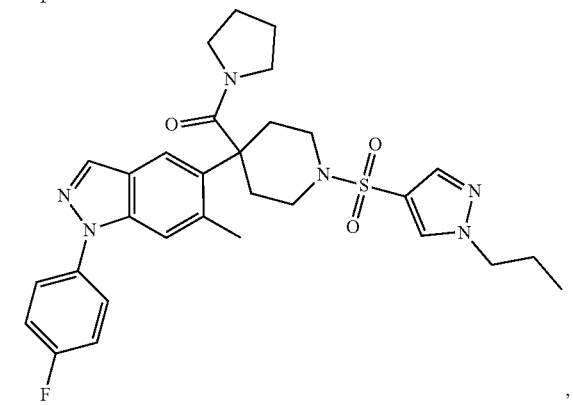
,
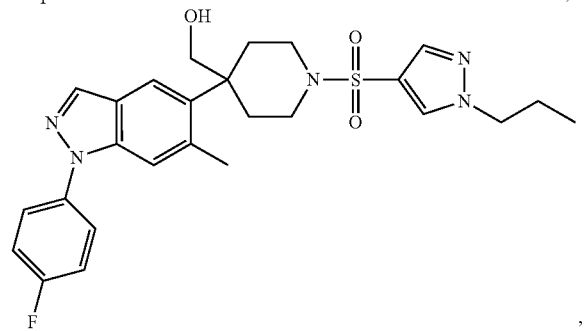
,
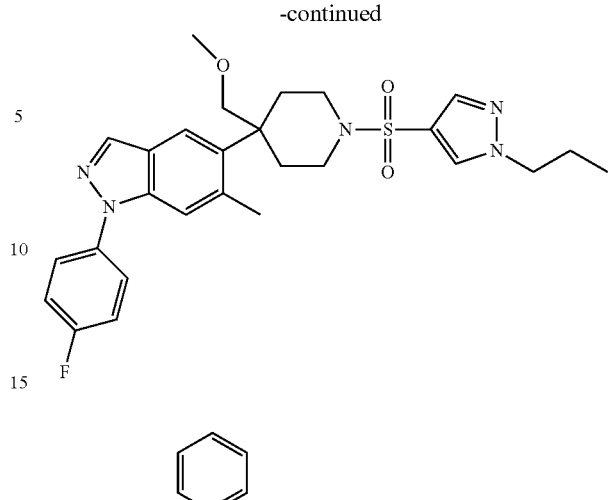
,
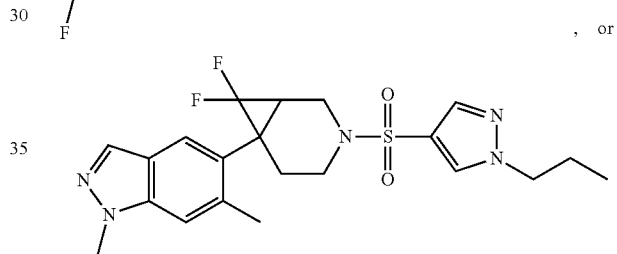
, or
.
In some embodiments, the compound of Formula I or II, or a pharmaceutically acceptable salt thereof, is a compound in Table 1H:
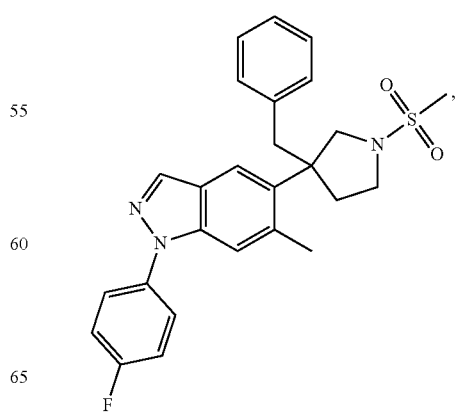
,

137
-continued
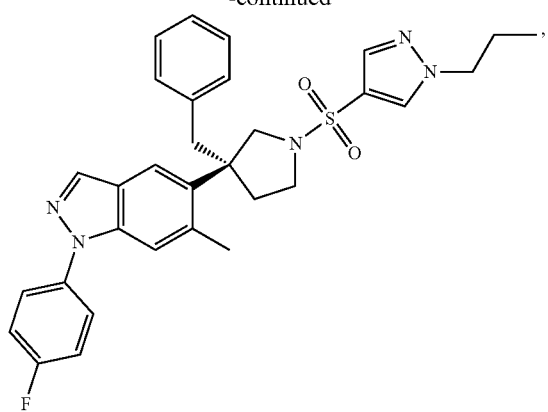
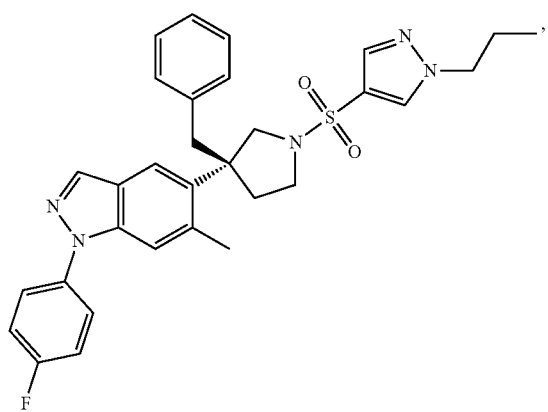
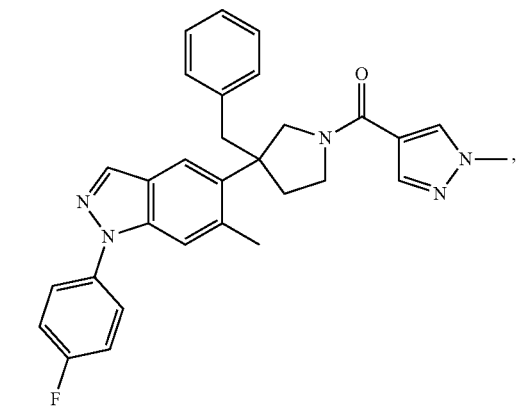
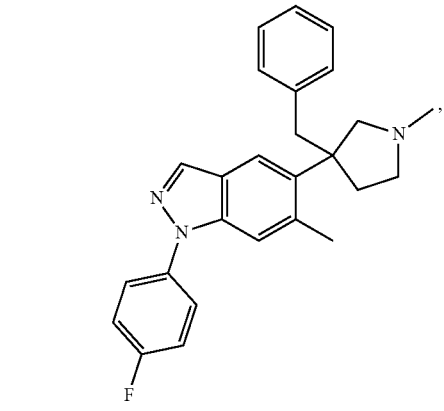
138
-continued
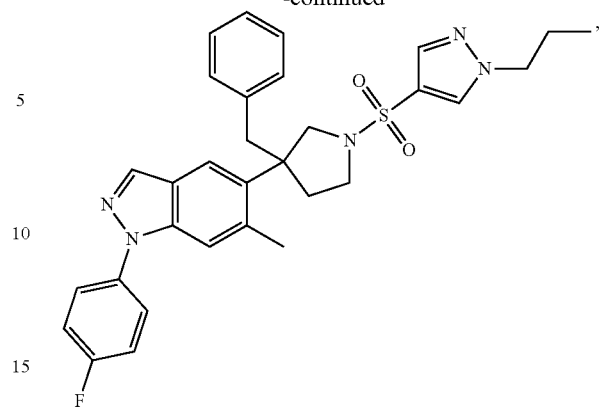
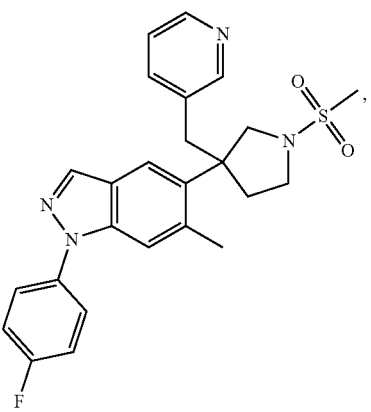
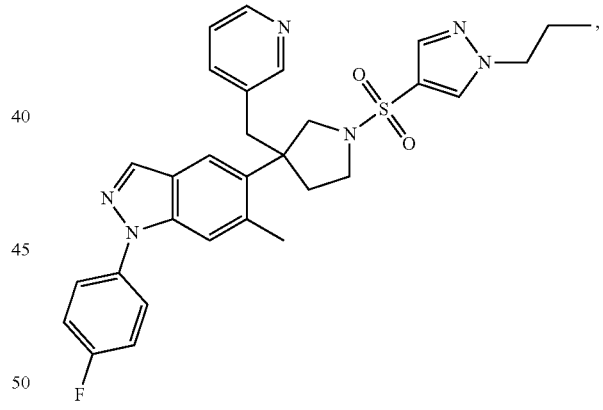
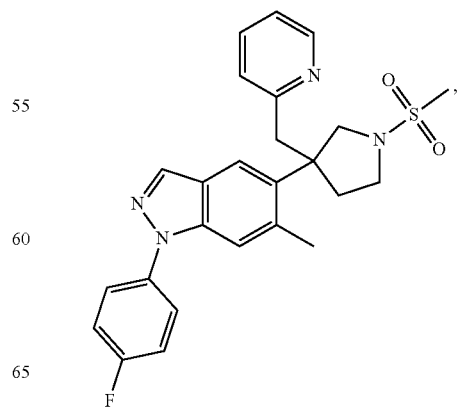

139
-continued
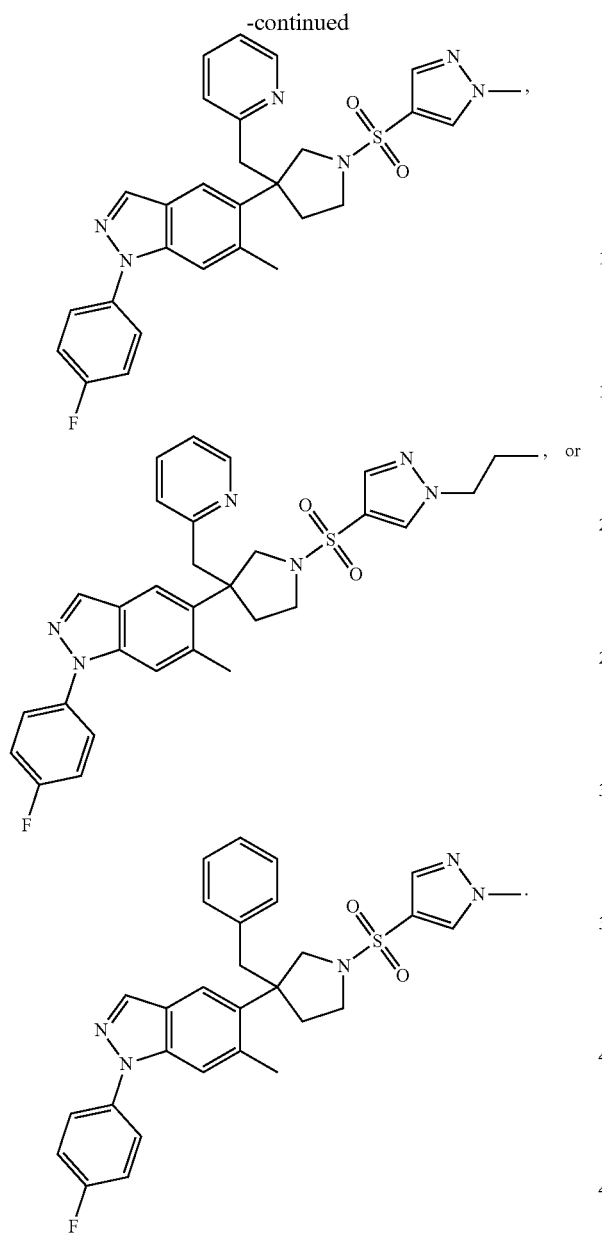
140
-continued
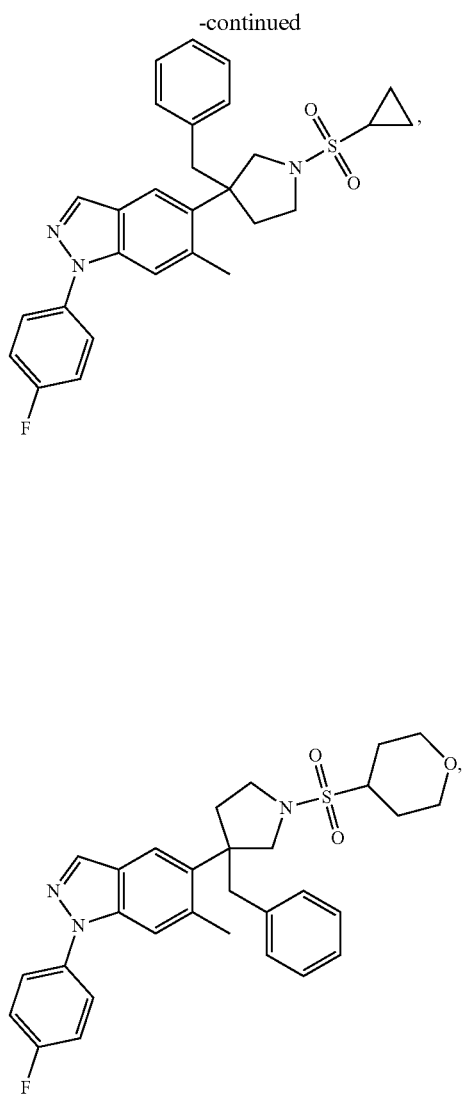
In some embodiments, the compound of Formula I or II, or a pharmaceutically acceptable salt thereof, is a compound in Table 1I:
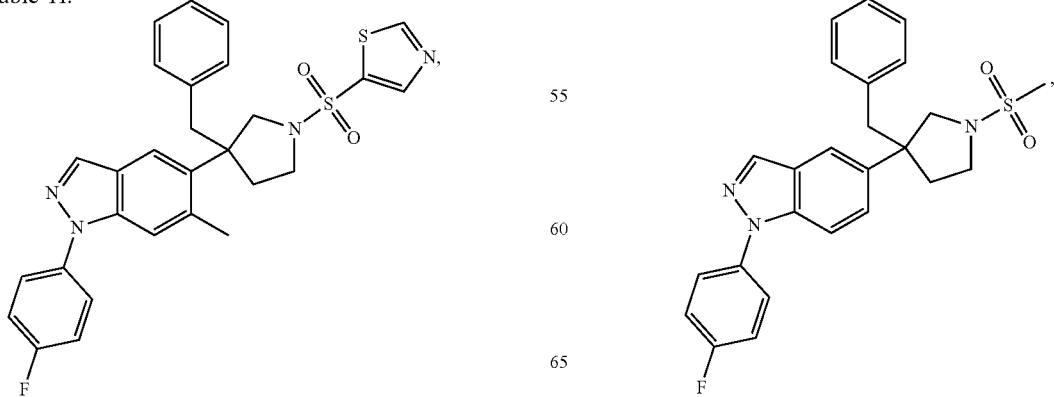

141
-continued
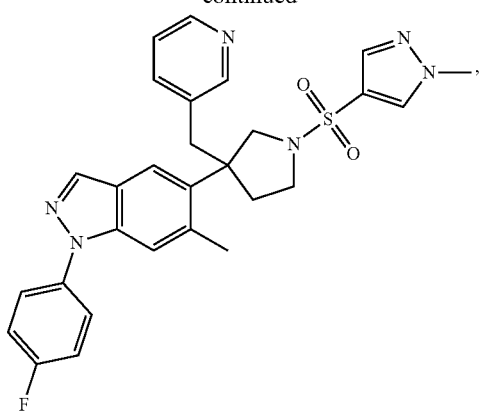
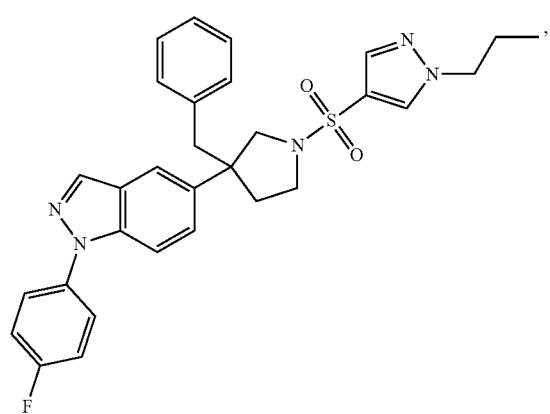
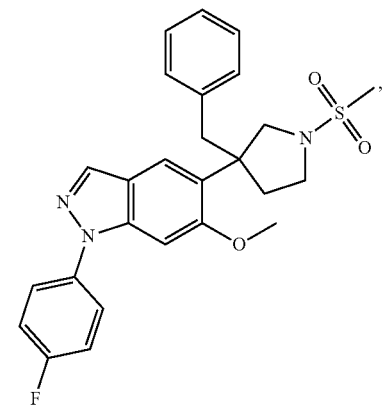
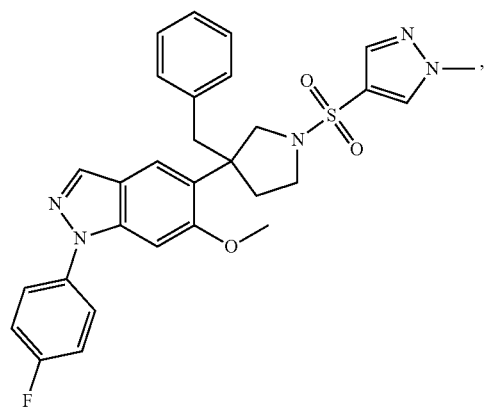
142
-continued
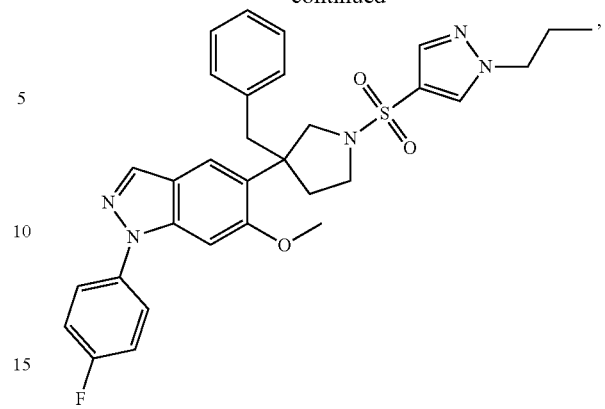
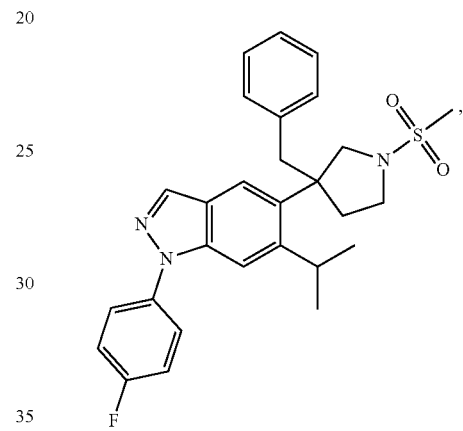
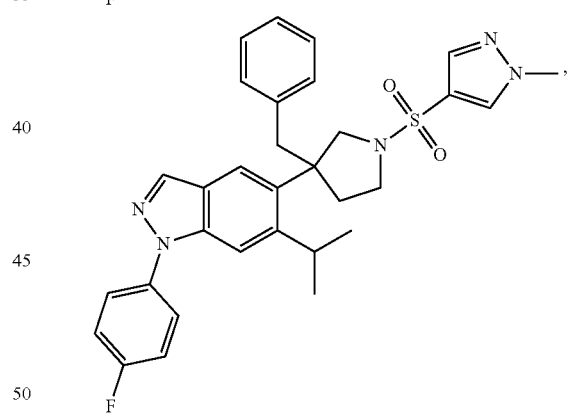
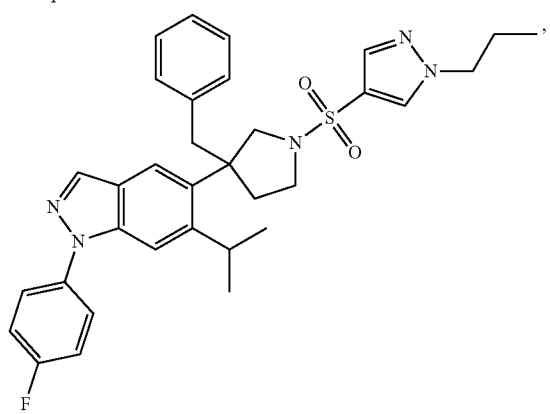

143
-continued
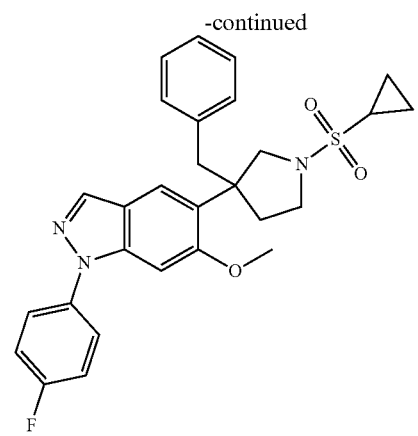
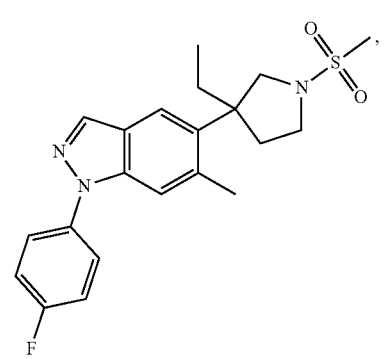
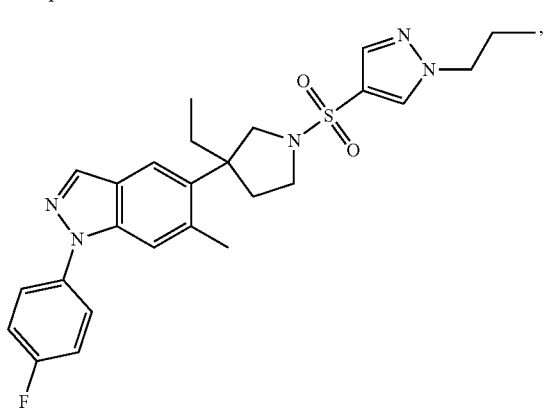
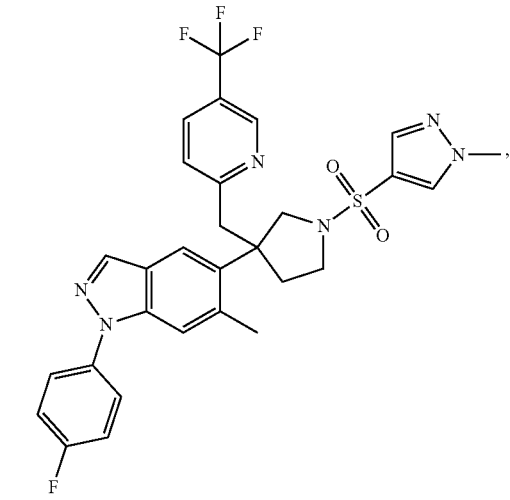
144
-continued
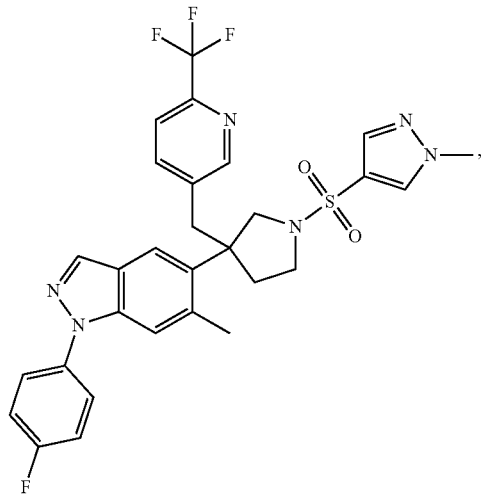
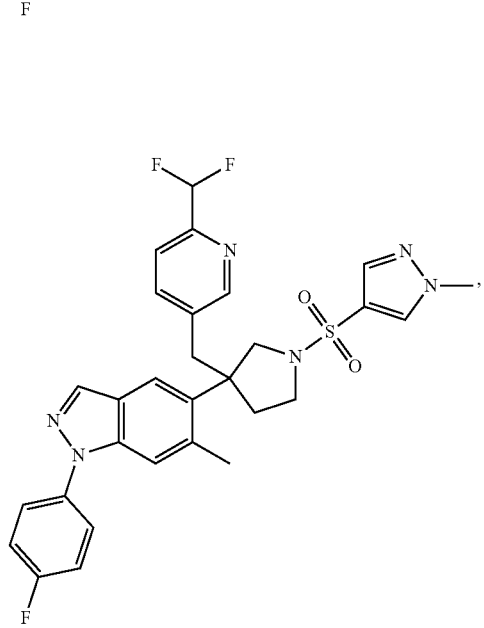
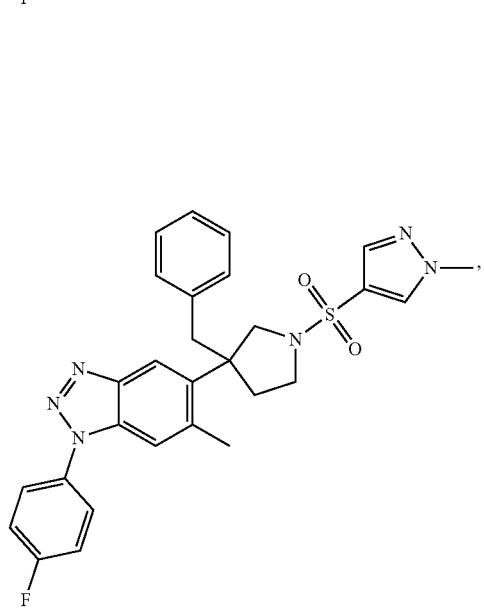

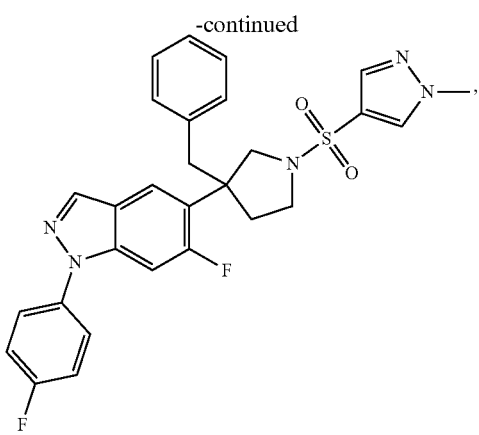
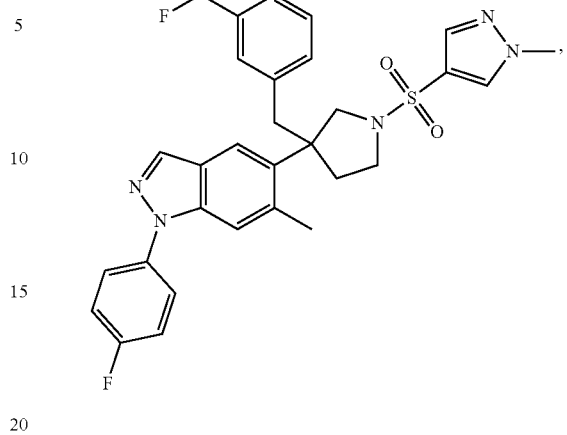
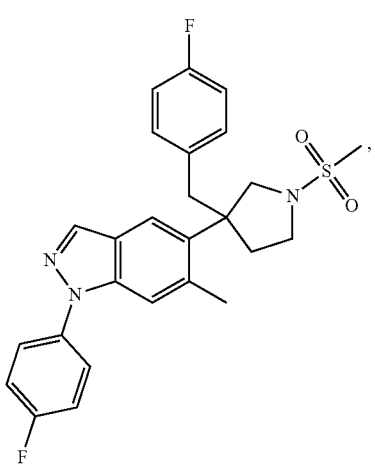
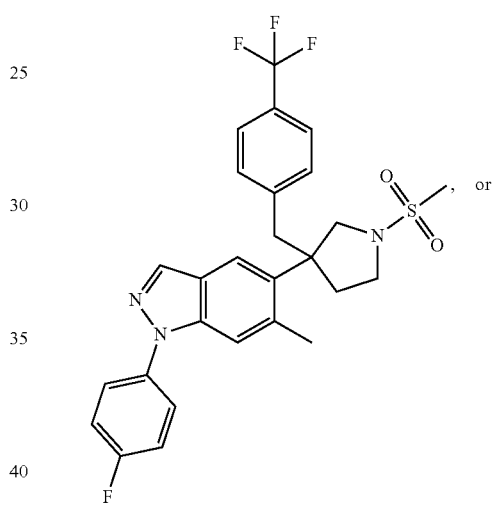
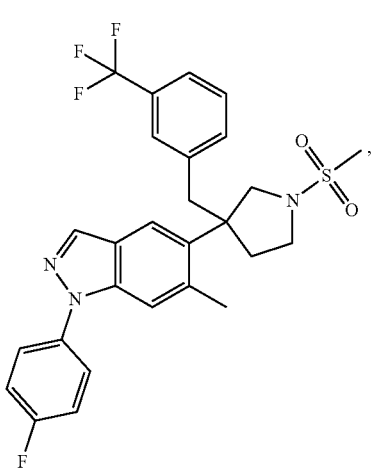
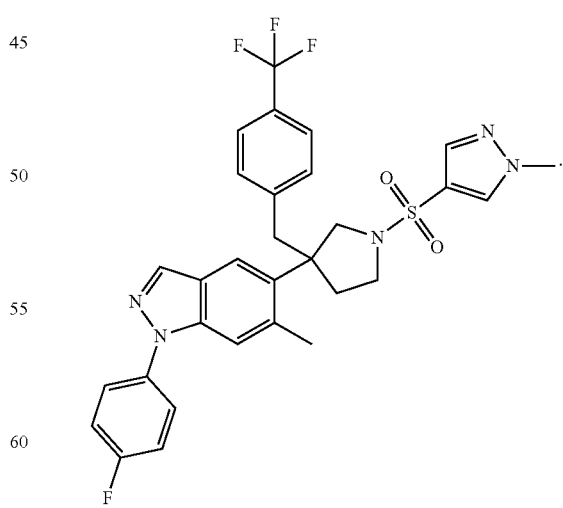
In some embodiments, the compound of Formula I or II, or a pharmaceutically acceptable salt thereof, is a compound in Table 1J:

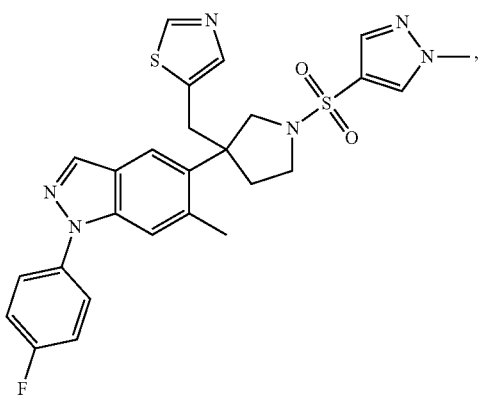
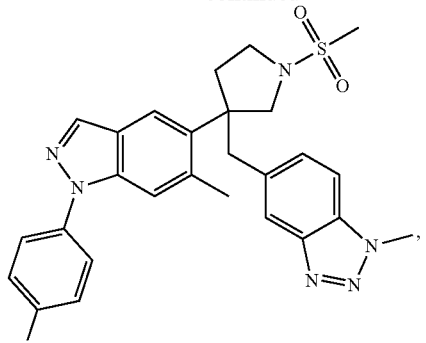
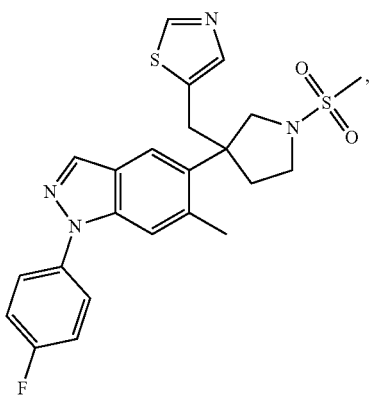
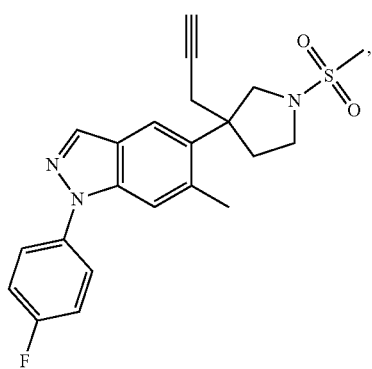
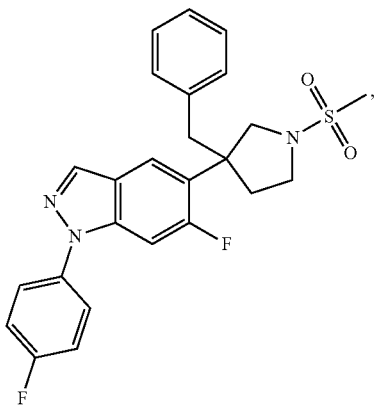
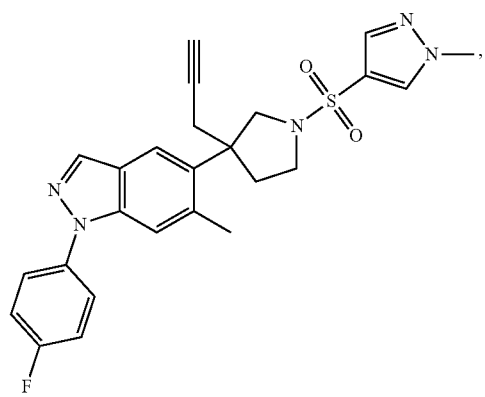
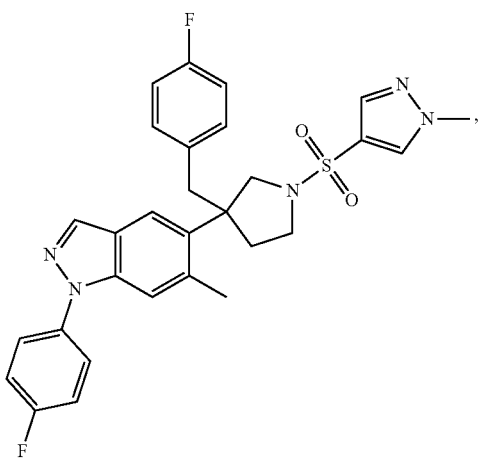
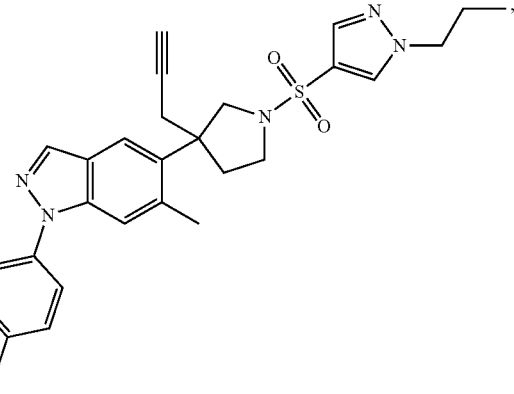

149
-continued
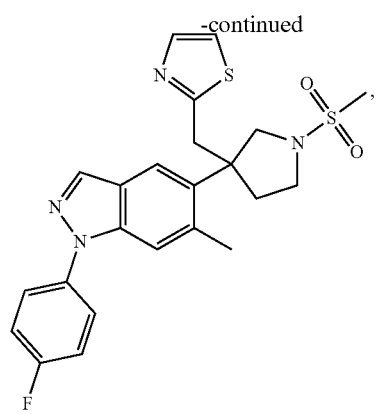
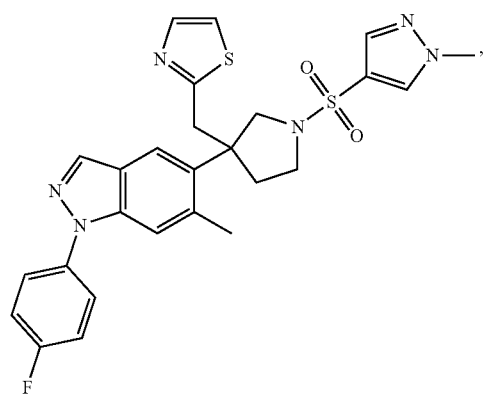
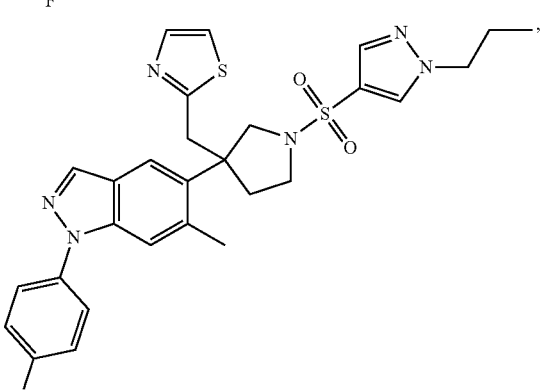
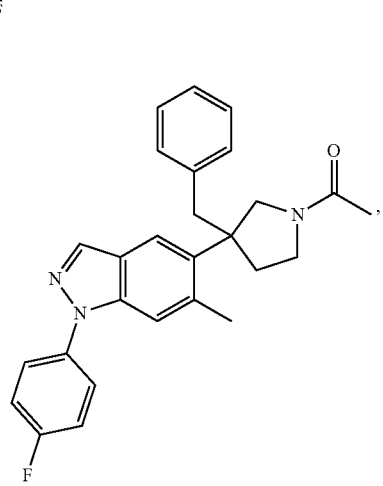
150
-continued
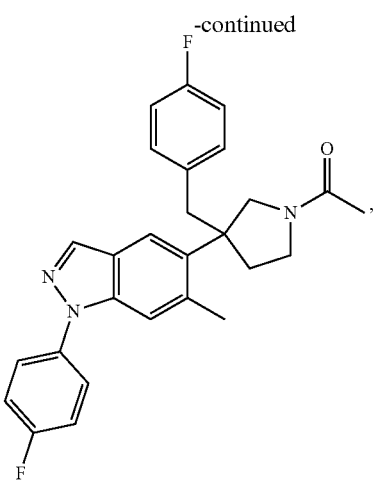
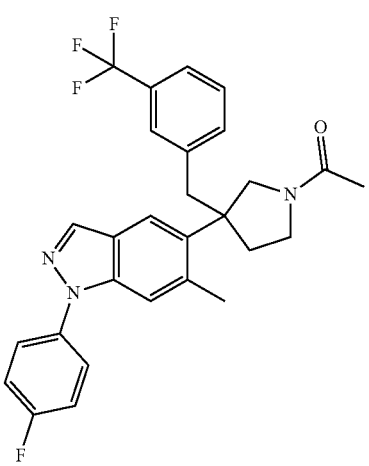
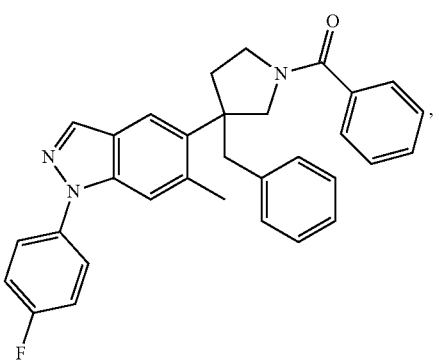

151
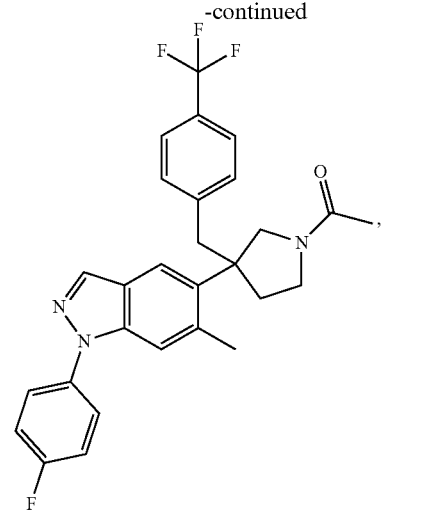
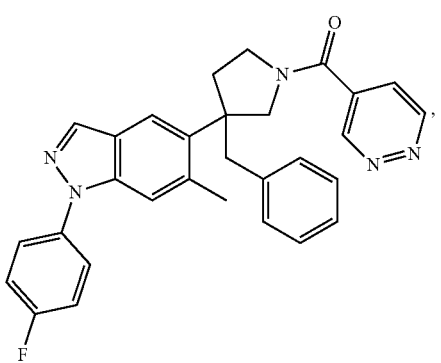
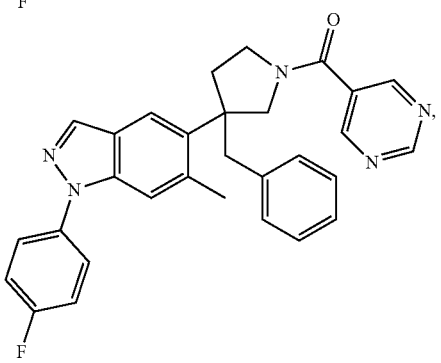
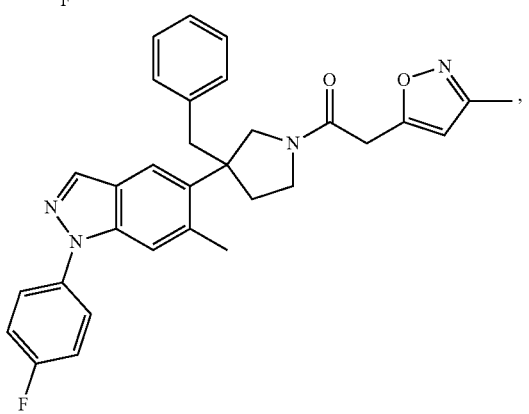
152
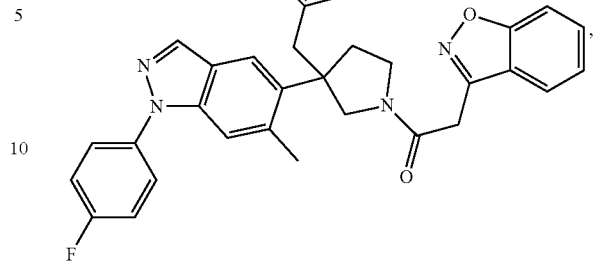
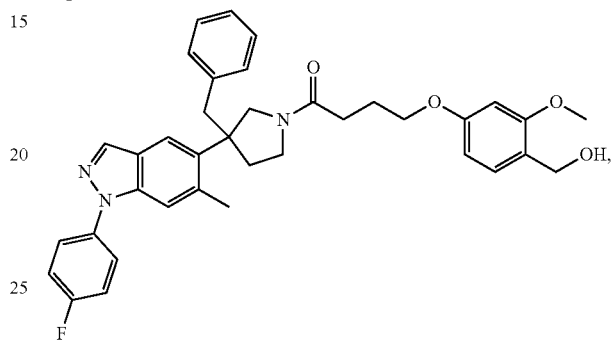
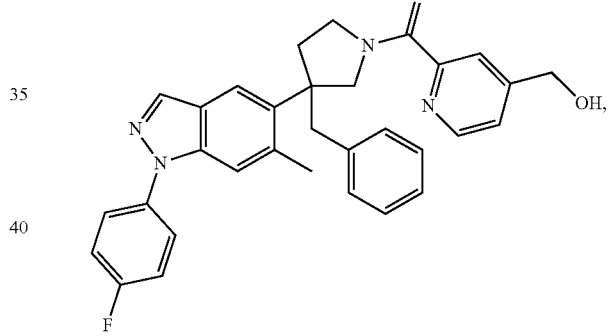
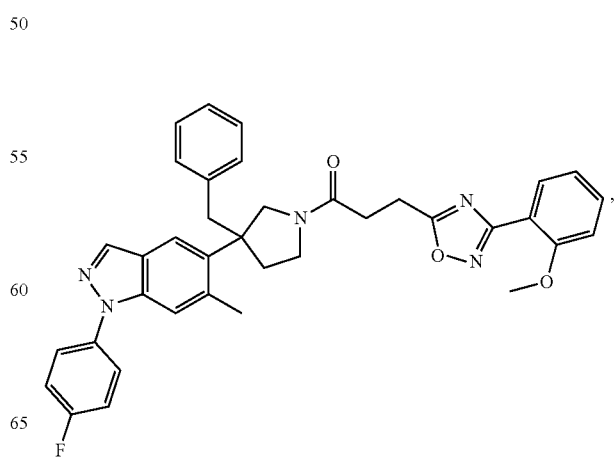

-continued
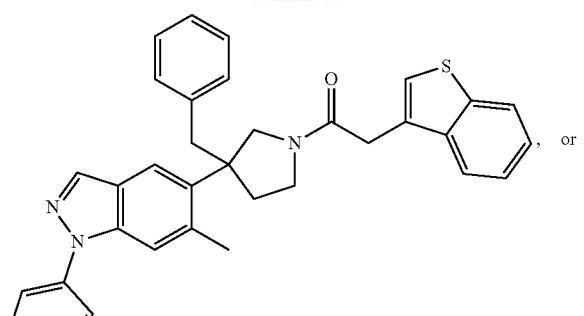
, or
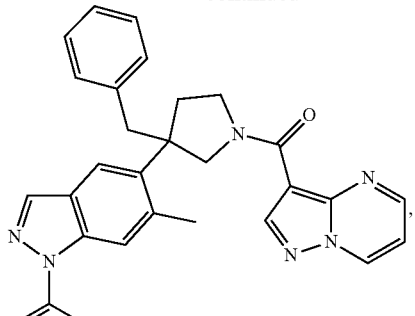
,
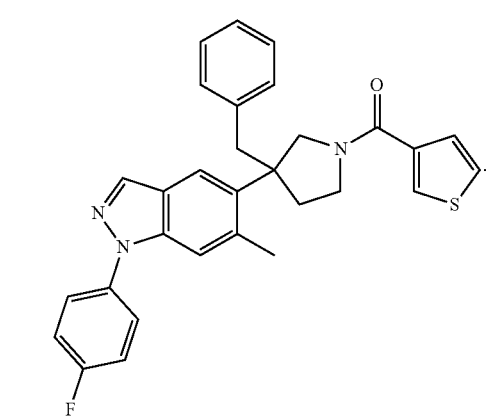
;
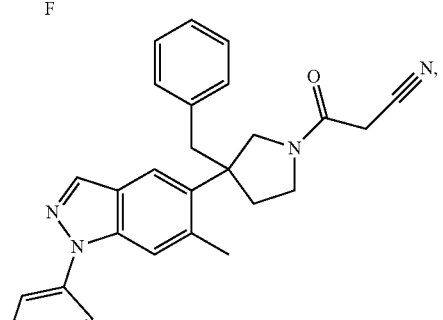
,
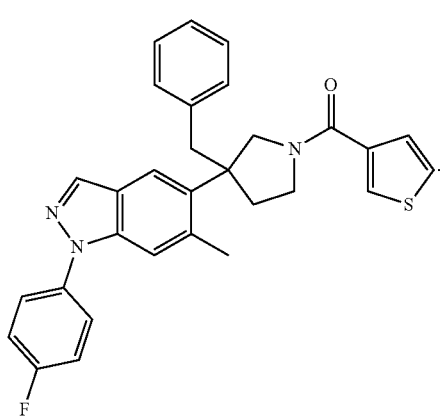
;
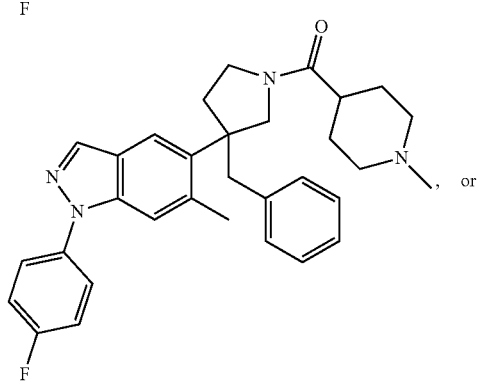
, or
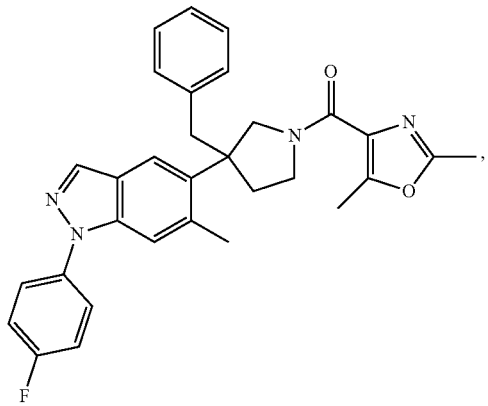
In some embodiments, the compound of Formula I or II, or a pharmaceutically acceptable salt thereof, is a compound in Table 1K:

.
In some embodiments, the compound of Formula I or II, or a pharmaceutically acceptable salt thereof, is a compound in Table 1A, Table 1B, Table 1C, Table 1D, Table 1E, Table 1F, Table 1G, Table 1H, Table 1I, Table 1J, or Table 1K. In some embodiments, the compound of Formula I or II, or a pharmaceutically acceptable salt thereof, is a compound in Table 1A, Table 1B, Table 1C, Table 1D, or Table 1E. In some embodiments, the compound of Formula I or II, or a pharmaceutically acceptable salt thereof, is a compound in Table 1F, Table 1G, Table 1H, Table 1I, Table 1J, or Table 1K. In some embodiments, the compound of Formula I, II, IV or IVa, or a pharmaceutically acceptable salt thereof, is a compound in Table 1H, Table 1I, Table 1J, or Table 1K. In some embodiments, the compound of Formula I, II, IV or IVa, or a pharmaceutically acceptable salt thereof, is a compound in Table 1H. In some embodiments, the compound of Formula I, II, IV or IVa, or a pharmaceutically acceptable salt thereof, is a compound in Table 1I. In some embodiments, the compound of Formula I, II, IV or IVa, or a pharmaceutically acceptable salt thereof, is a compound in Table 1J. In some embodiments, the compound of Formula I, II, IV or IVa, or a pharmaceutically acceptable salt thereof, is a compound in Table 1K.

In some embodiments, the compound of Formula I, II, IV or IVa, or a pharmaceutically acceptable salt thereof, is a compound in Table 2A:

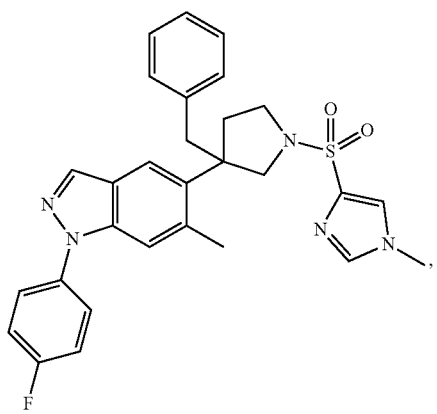

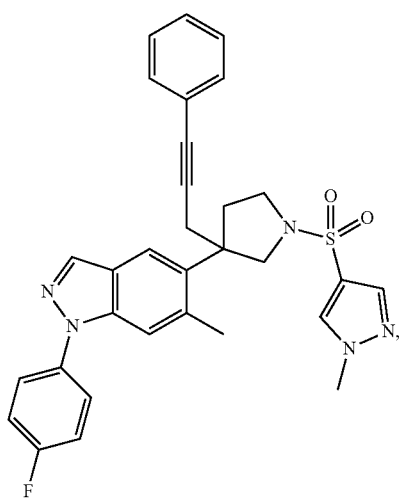

-continued

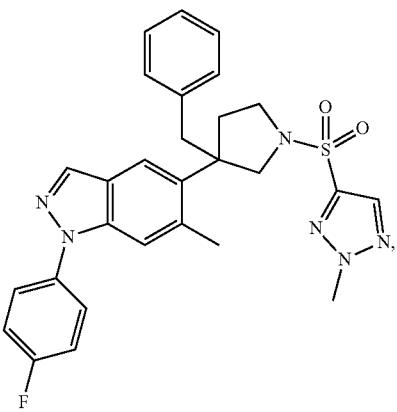

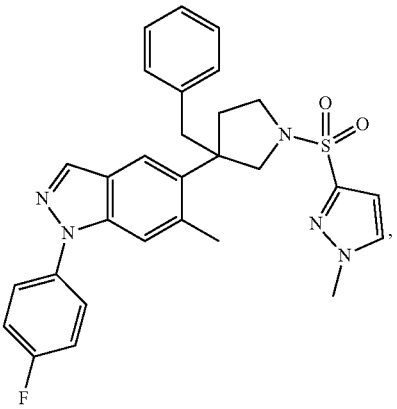

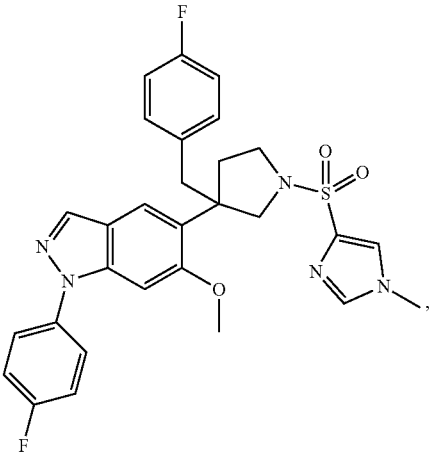

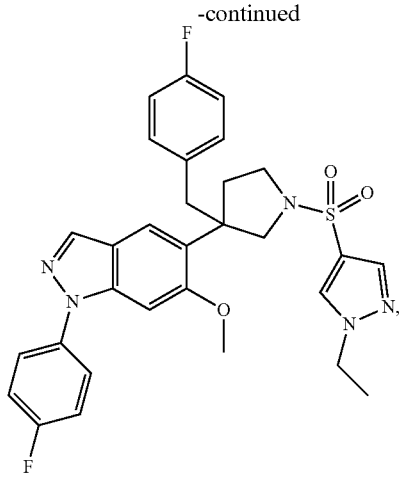
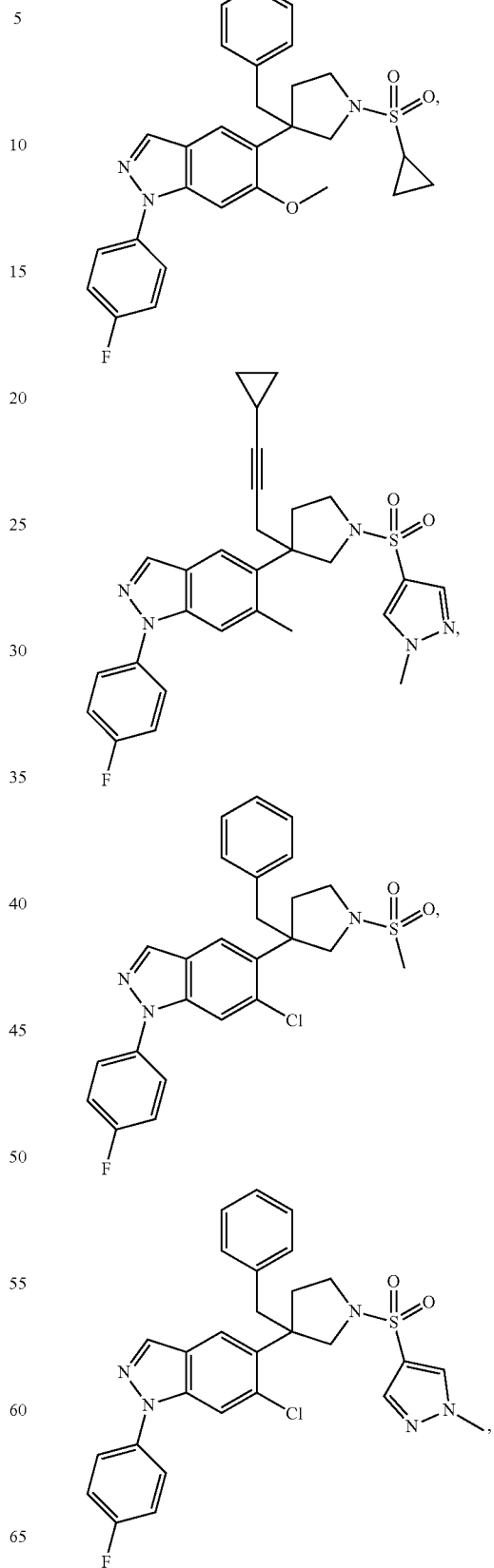

159
-continued
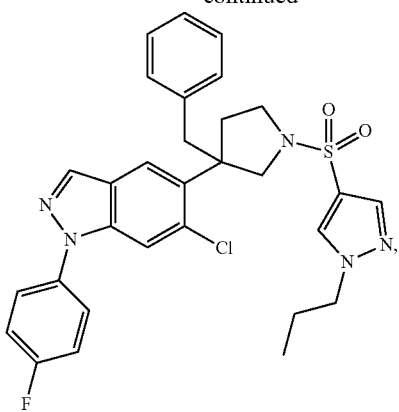
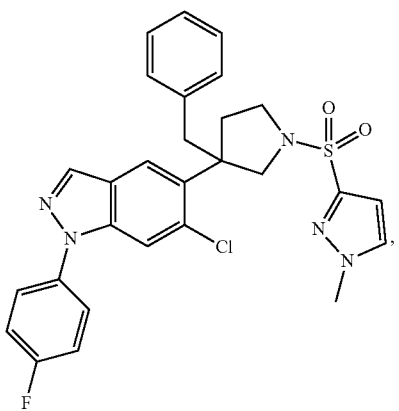
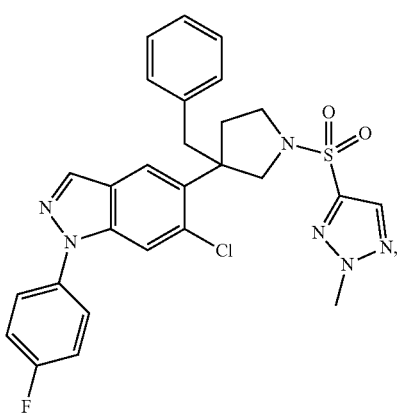
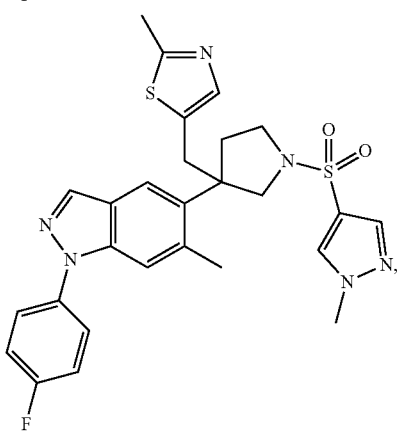
160
-continued
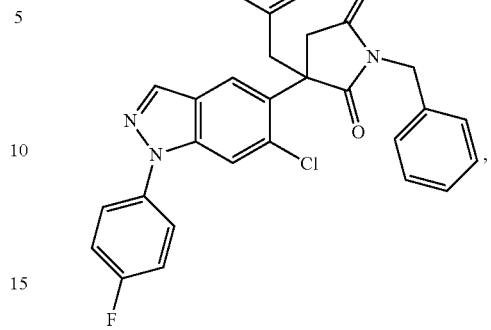
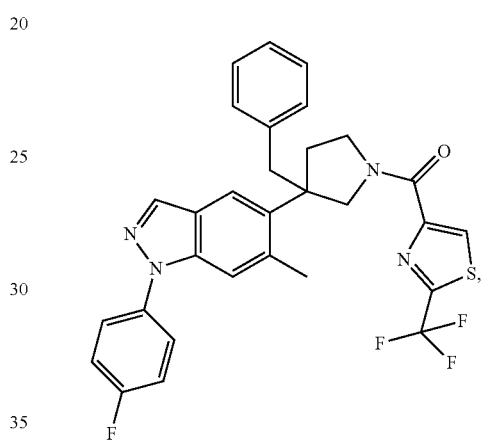
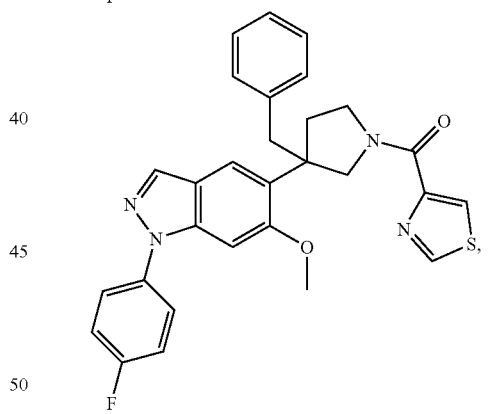
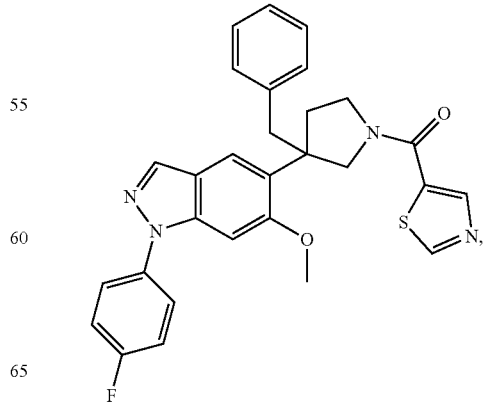

-continued
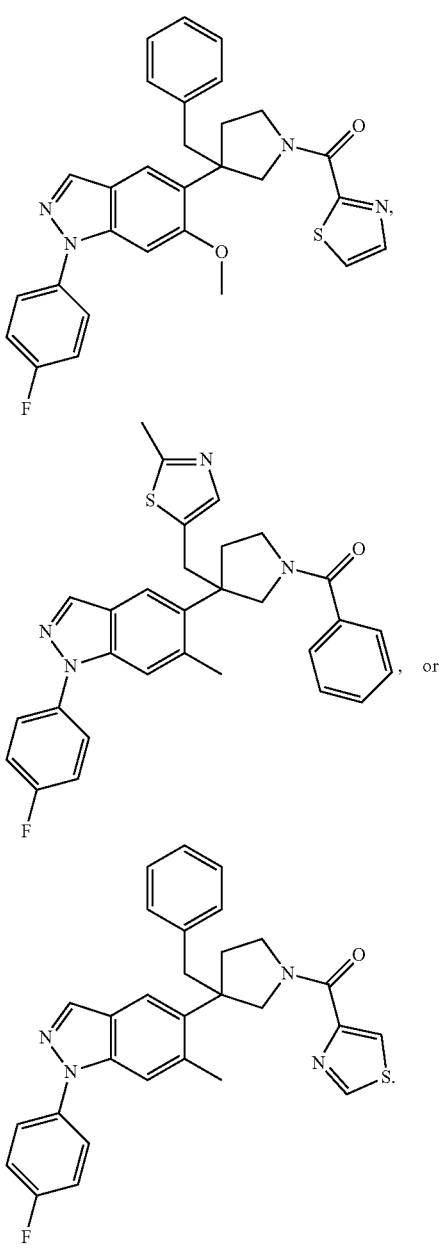
In some embodiments, the compound of Formula I, II, IV or IVa, or a pharmaceutically acceptable salt thereof, is a compound in Table 2B:
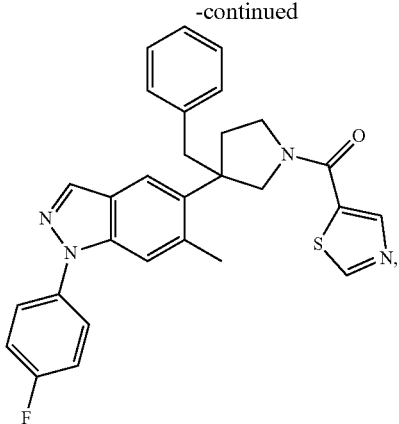

163
-continued
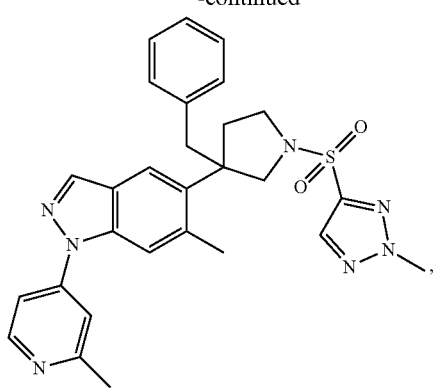
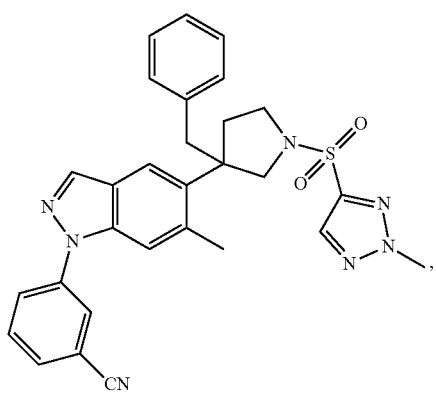
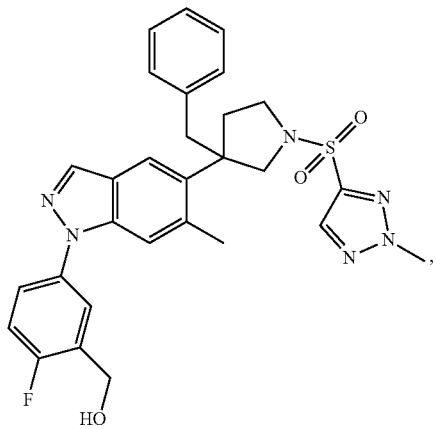
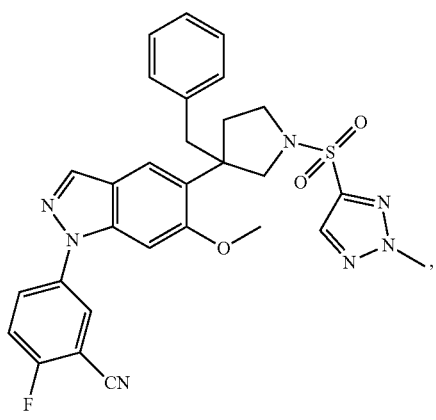
164
-continued
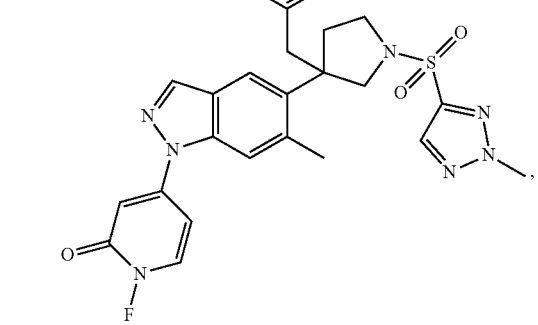
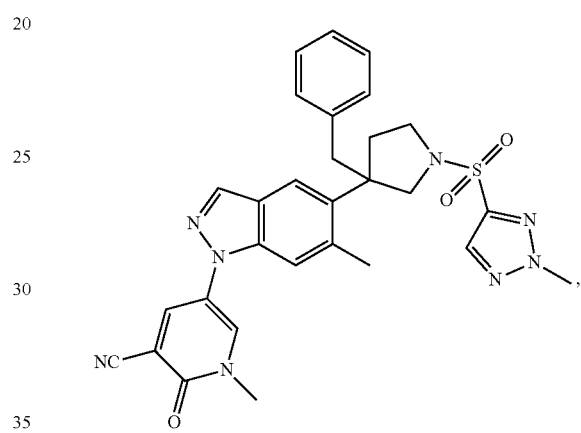
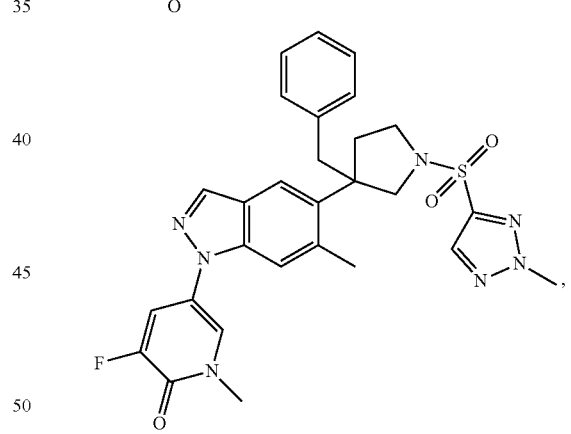
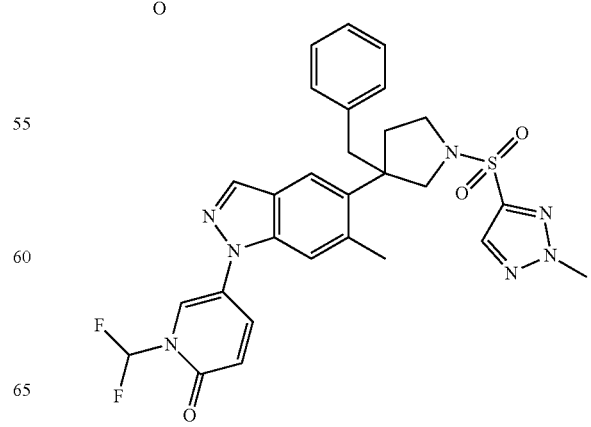

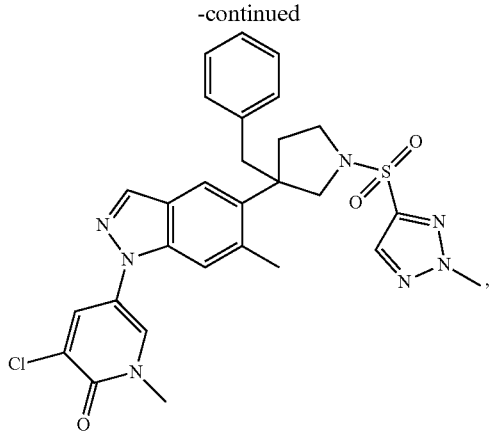
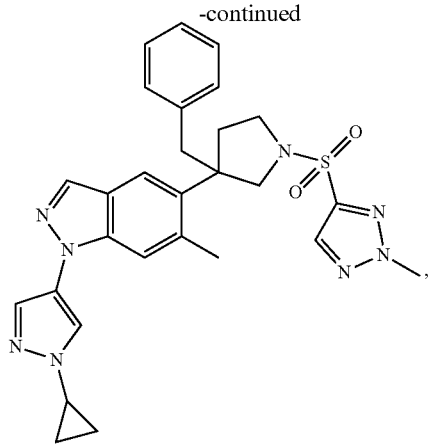
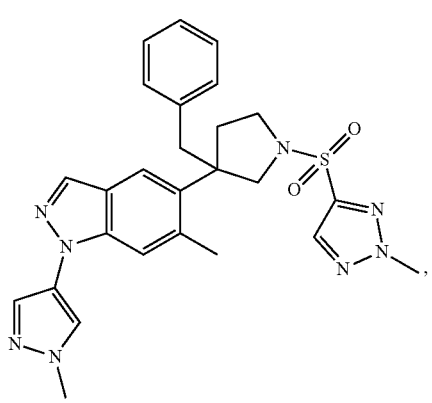
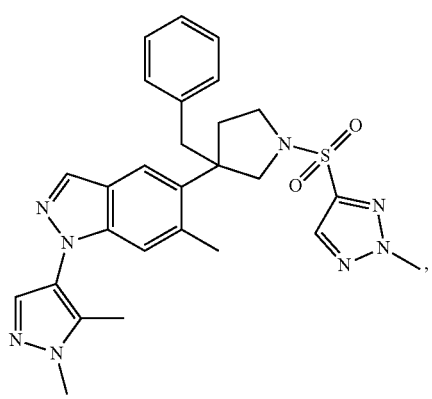
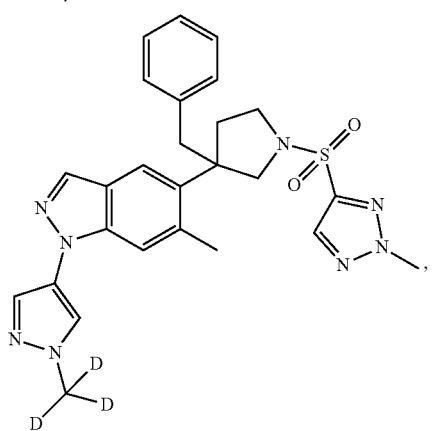
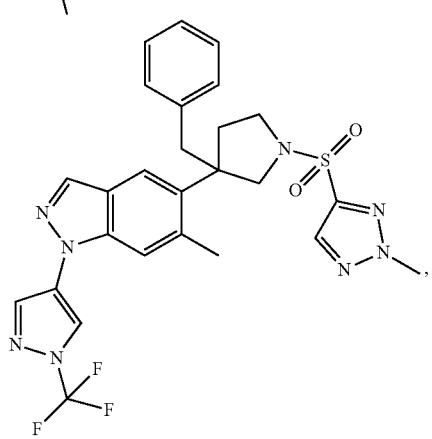
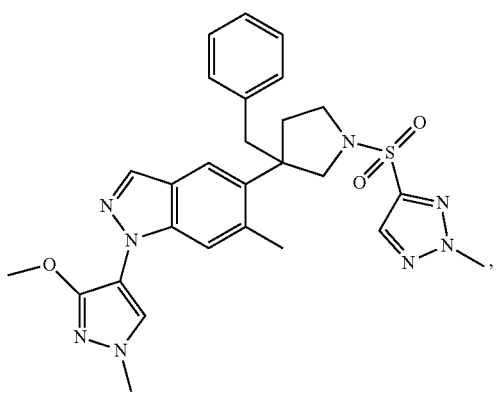
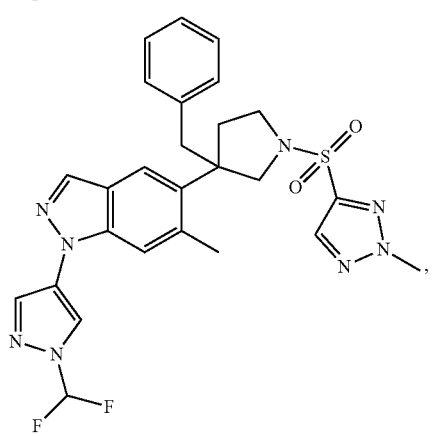

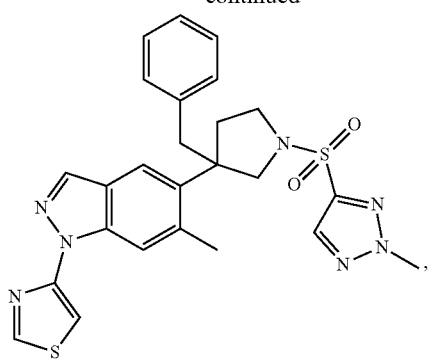
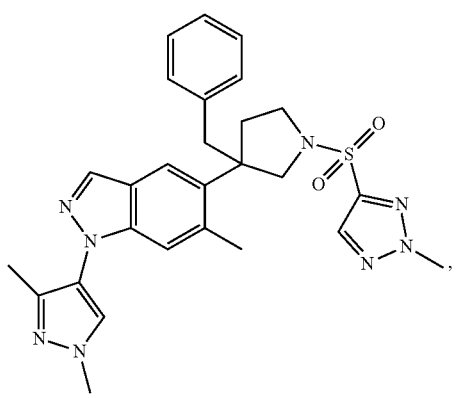
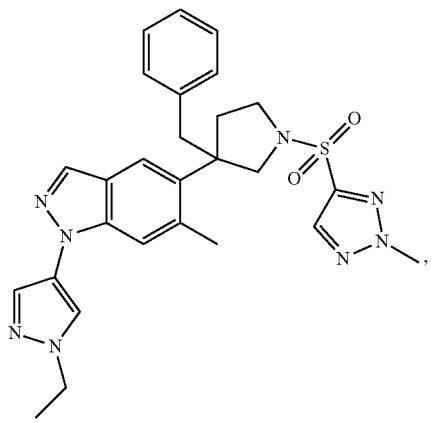
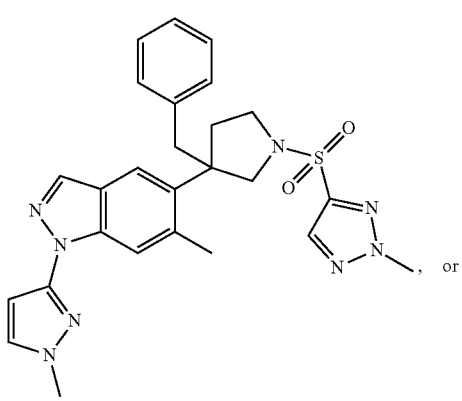
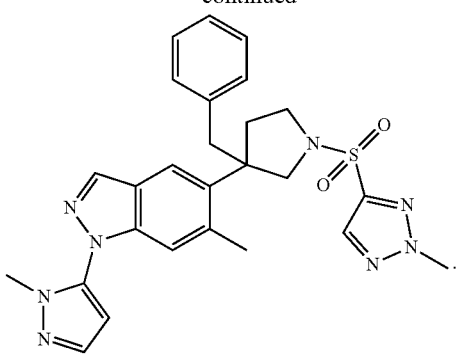
In some embodiments, the compound of Formula I, II, IV or IVa, or a pharmaceutically acceptable salt thereof, is a compound in Table 2C:
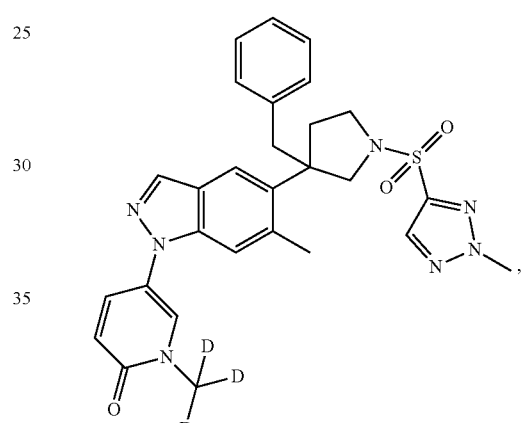
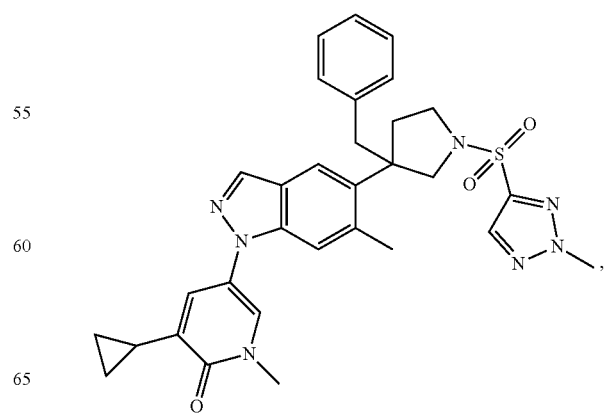

169
-continued
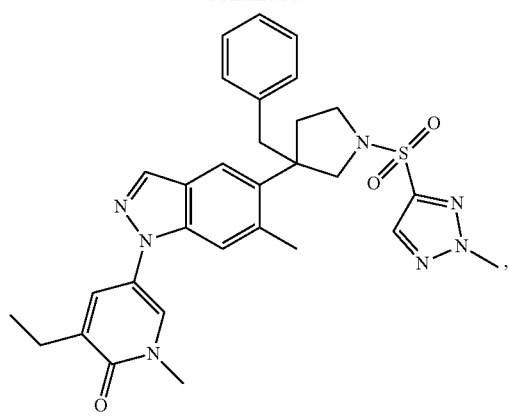
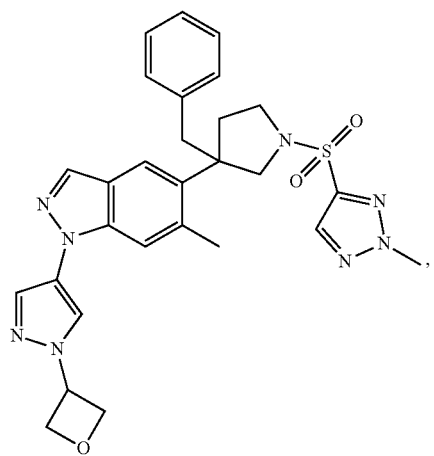
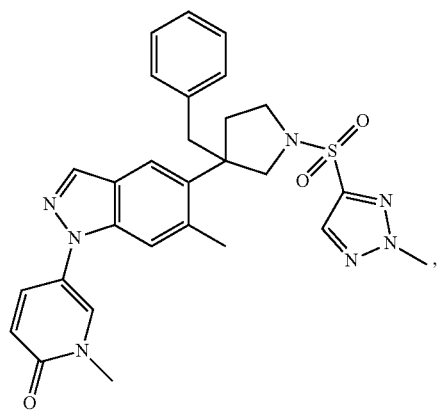
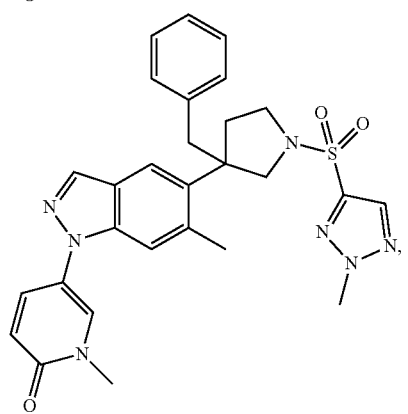
170
-continued
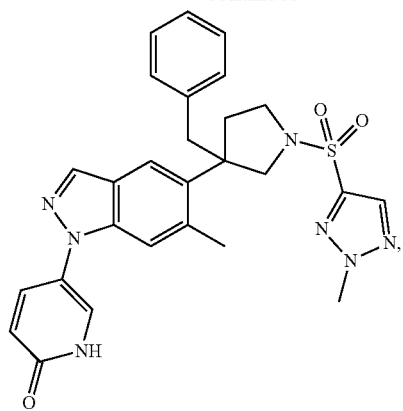
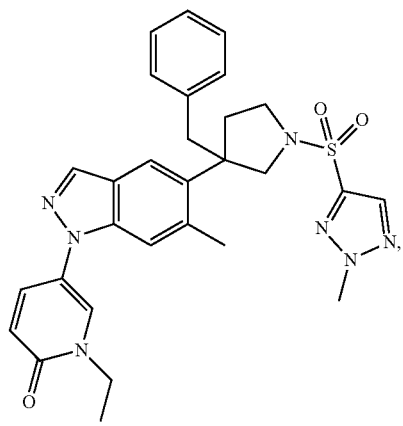
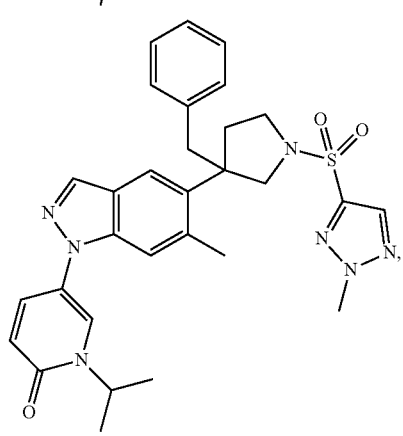
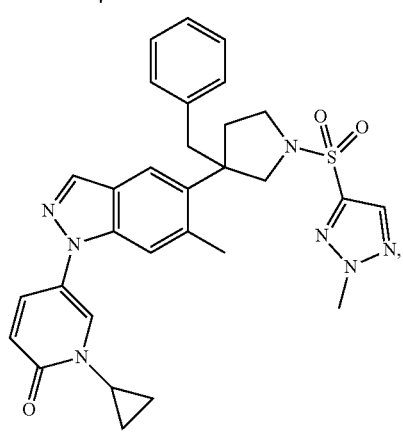

-continued
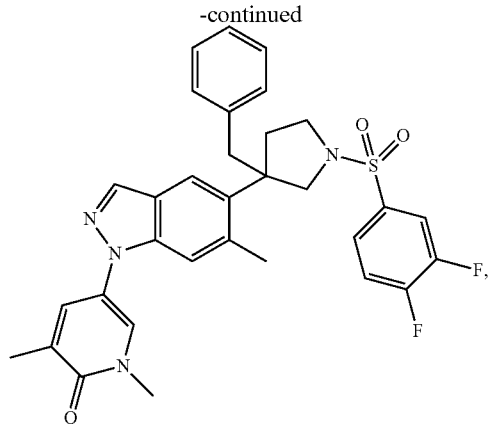
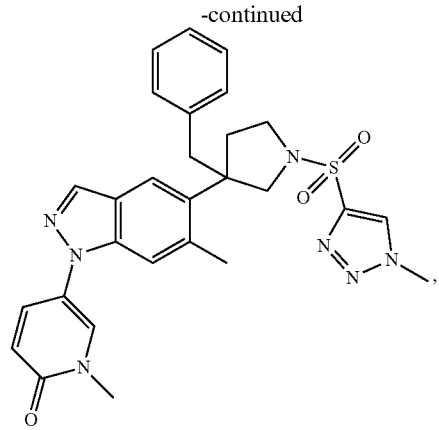
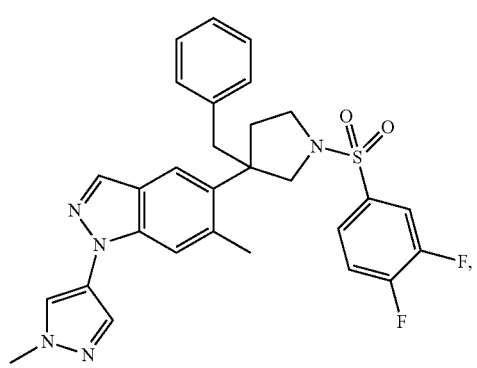
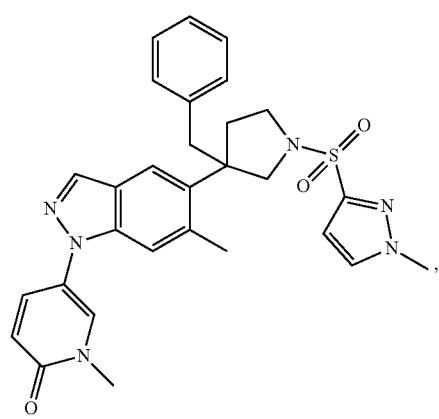
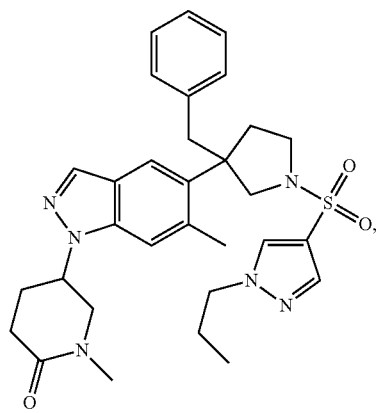
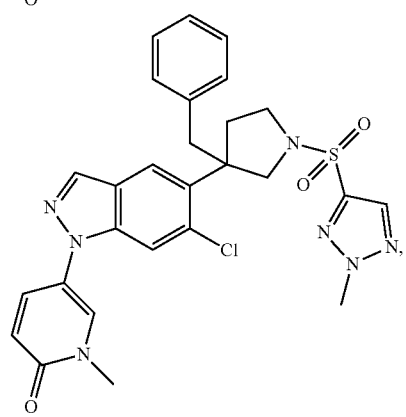
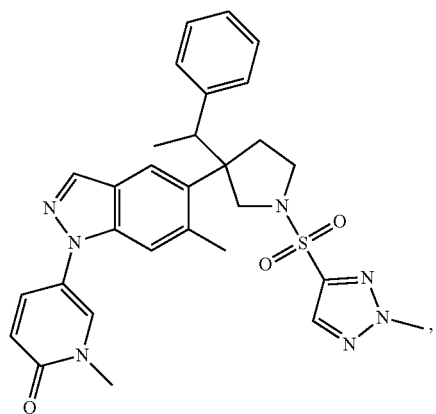
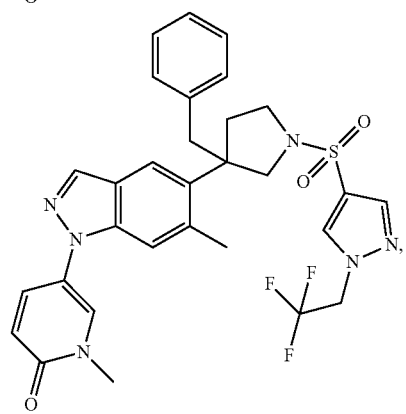

173
-continued
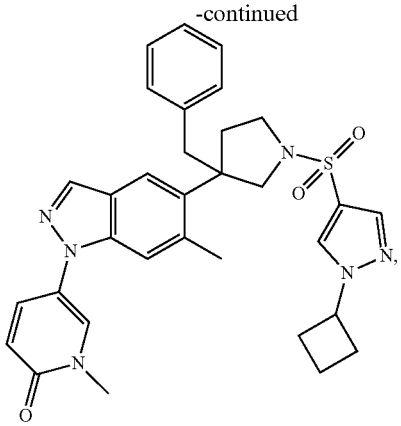
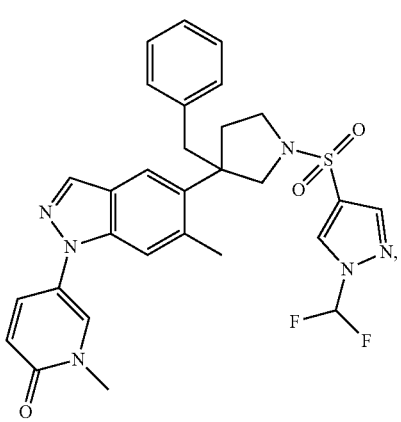
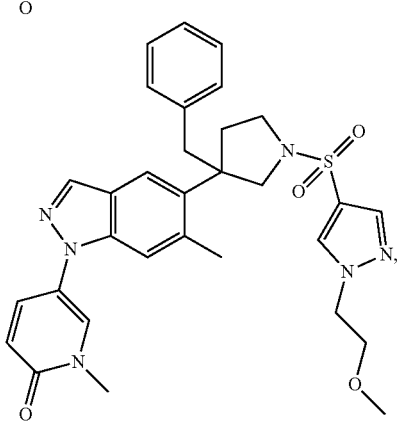
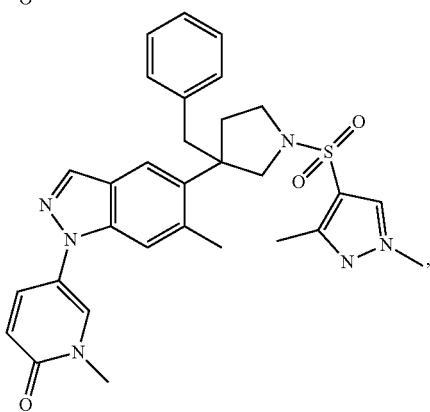
174
-continued
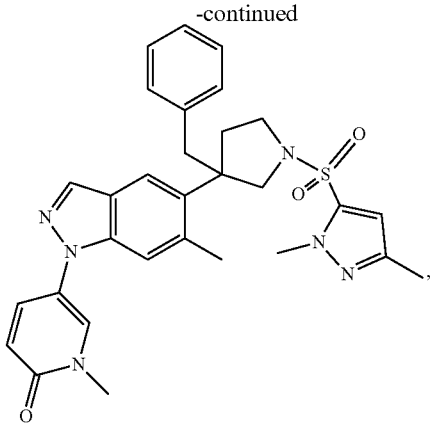
, or
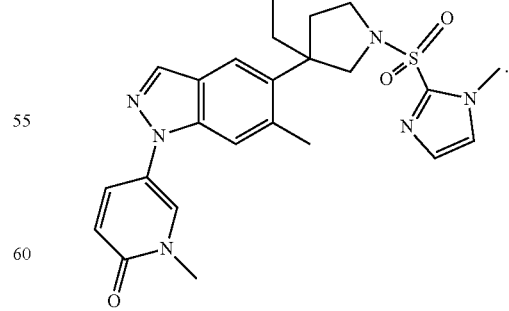
In some embodiments, the compound of Formula I, II, IV or IVa, or a pharmaceutically acceptable salt thereof, is a compound in Table 2D:

175
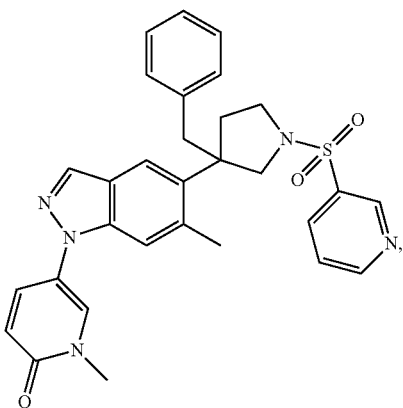
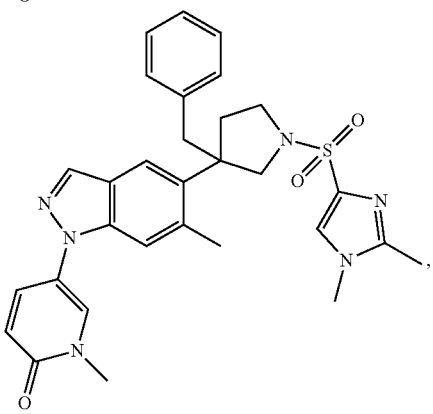
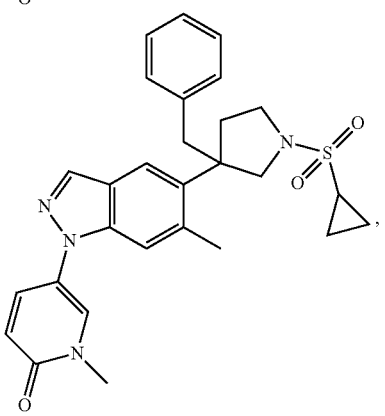
176
-continued
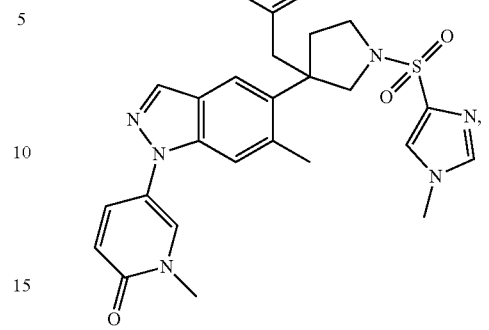
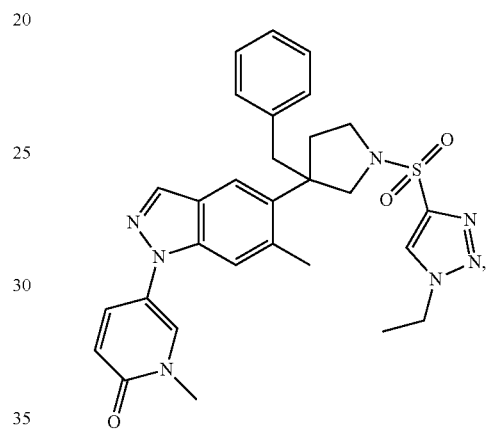
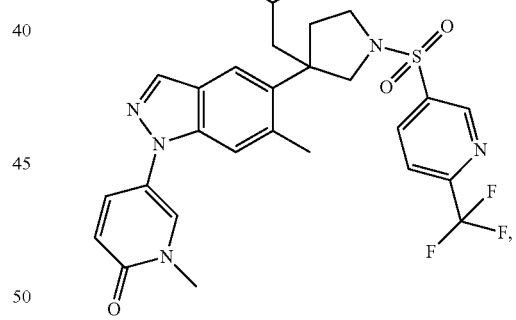
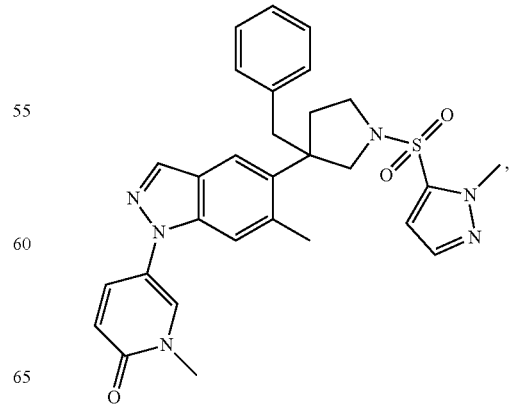

177
-continued
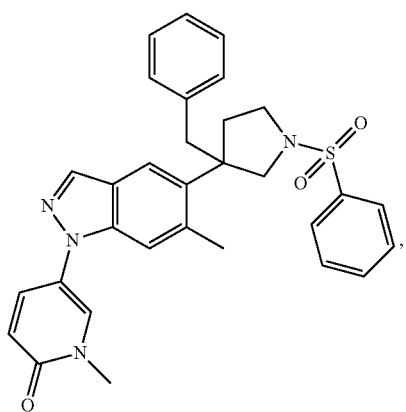
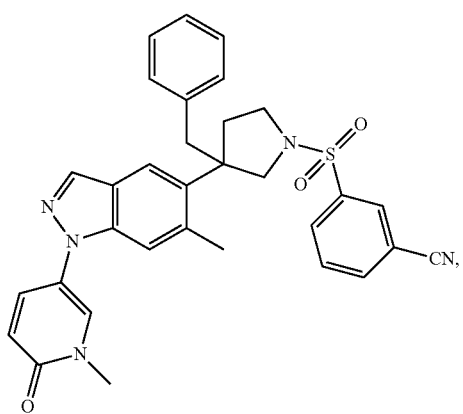
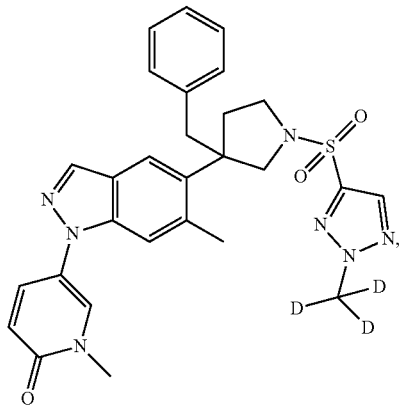
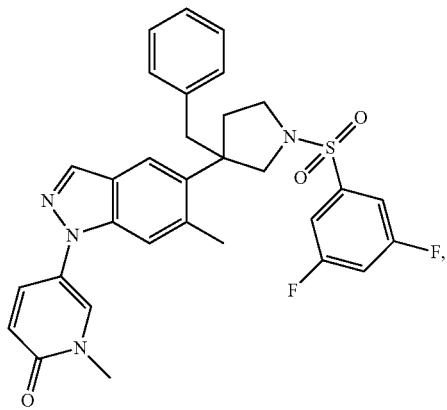
178
-continued
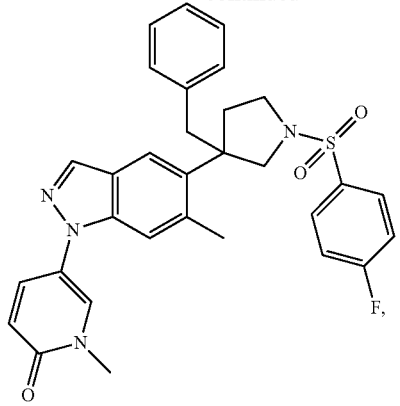
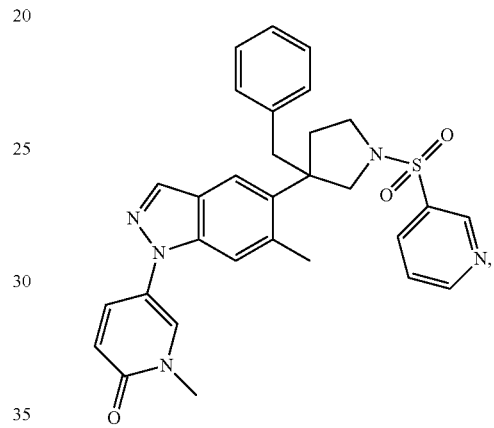
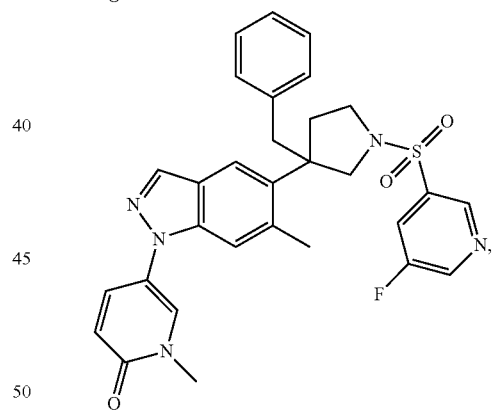
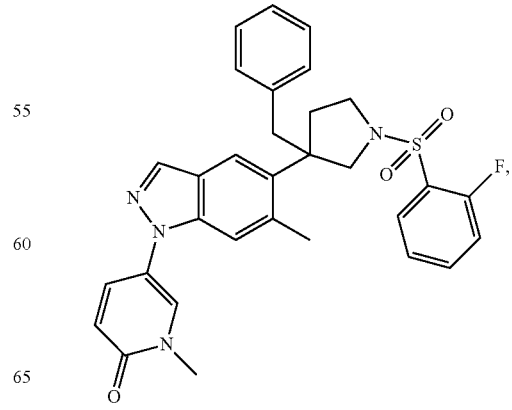

179
-continued
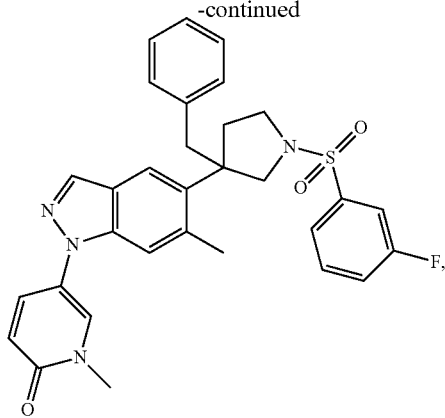
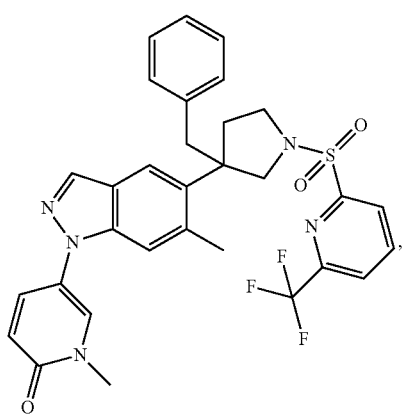
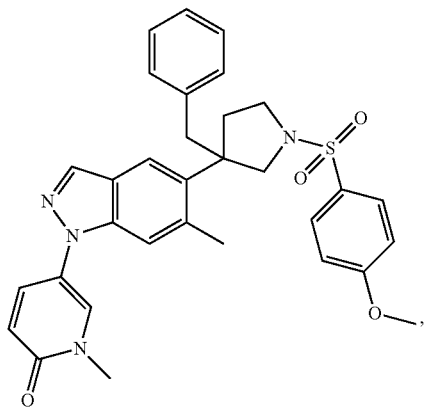
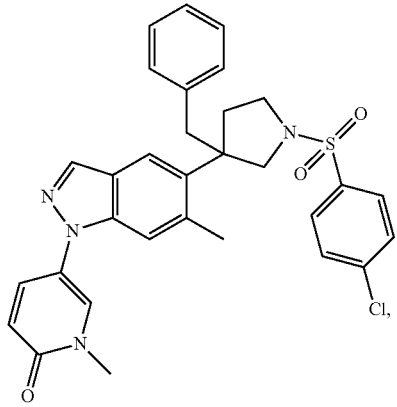
180
-continued
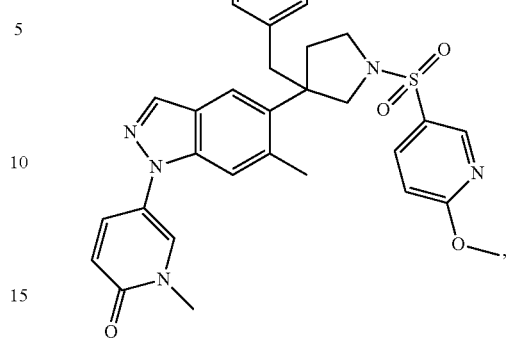
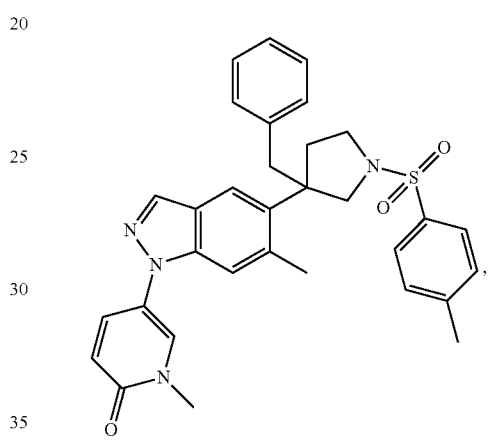
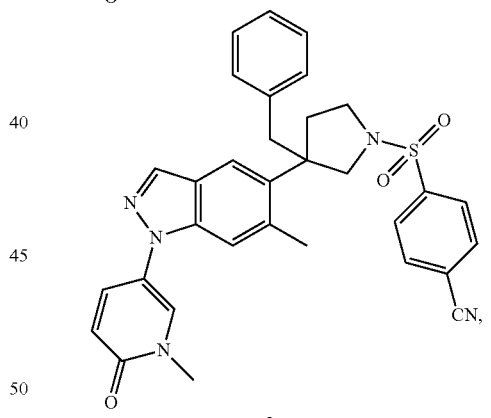
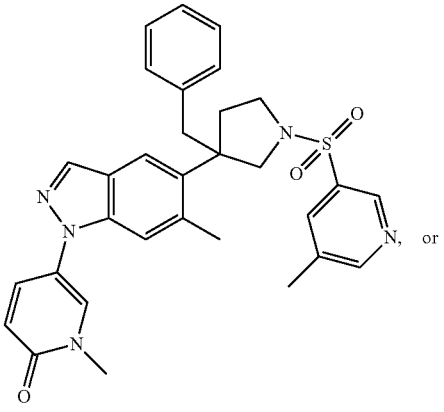

181
-continued
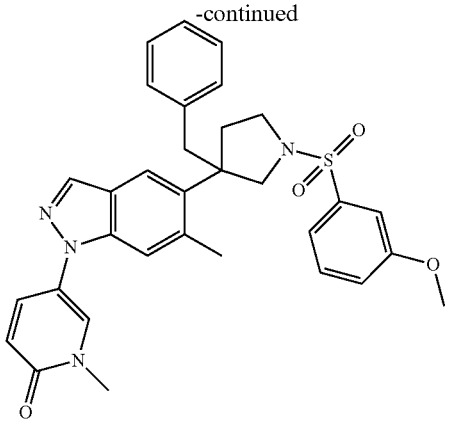
182
-continued
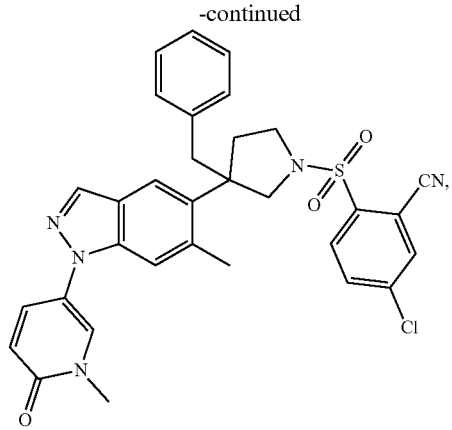
In some embodiments, the compound of Formula I, II, IV or IVa, or a pharmaceutically acceptable salt thereof, is a compound in Table 2E:
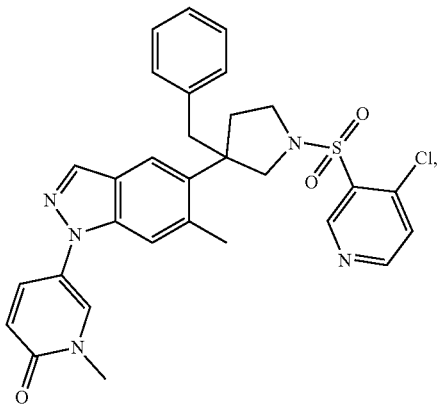
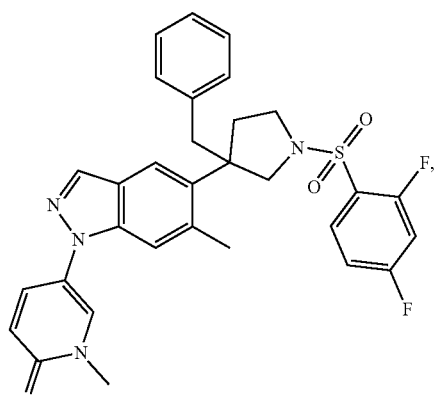
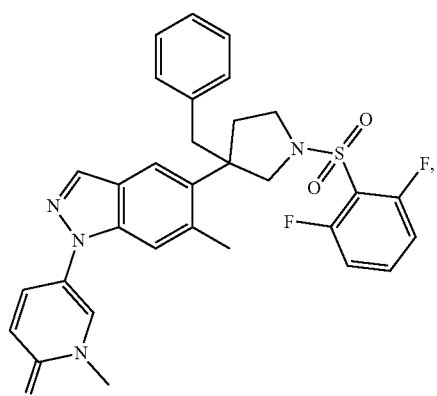
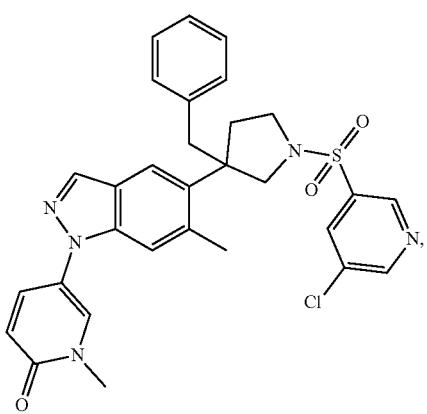
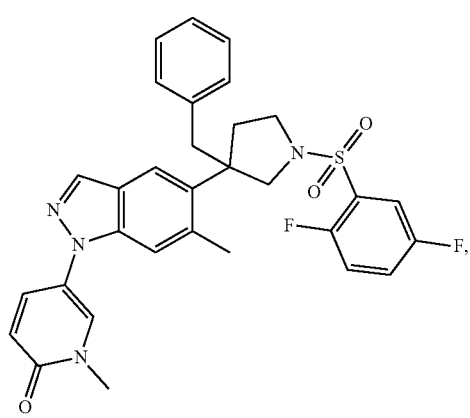

183
-continued
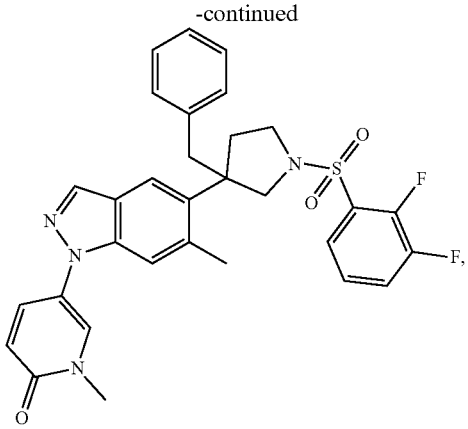
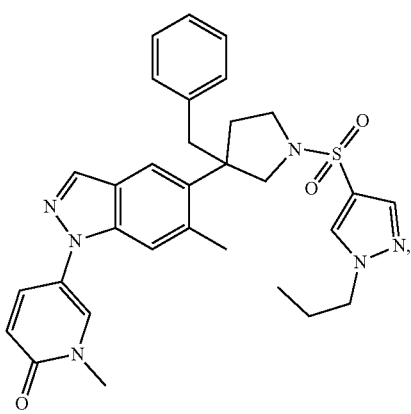
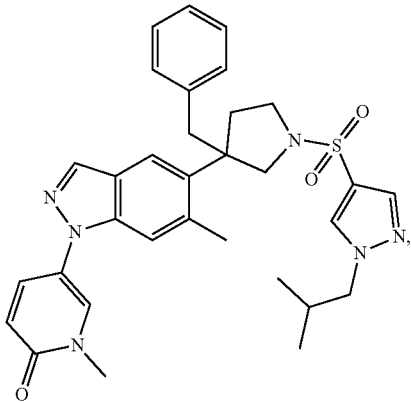
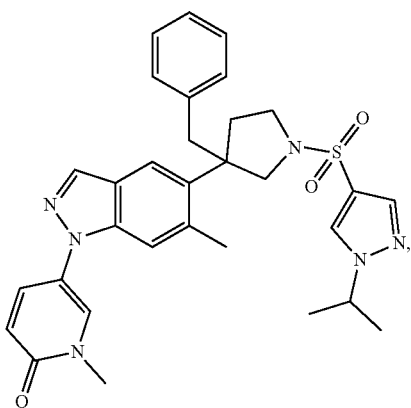
184
-continued
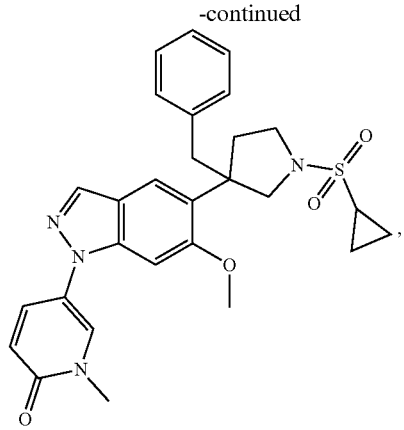
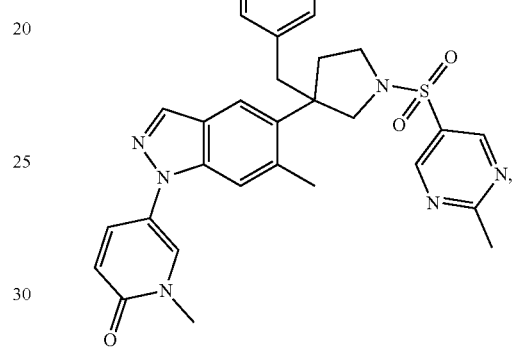
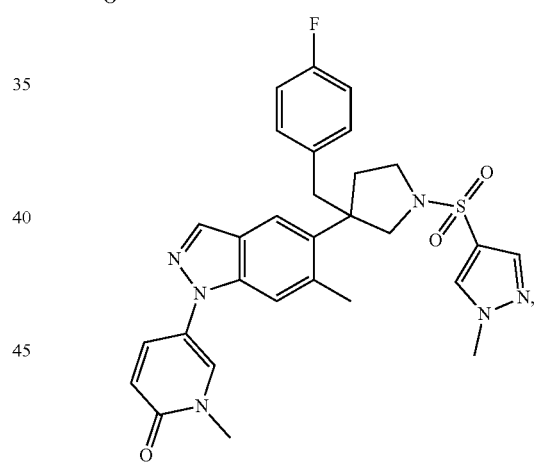
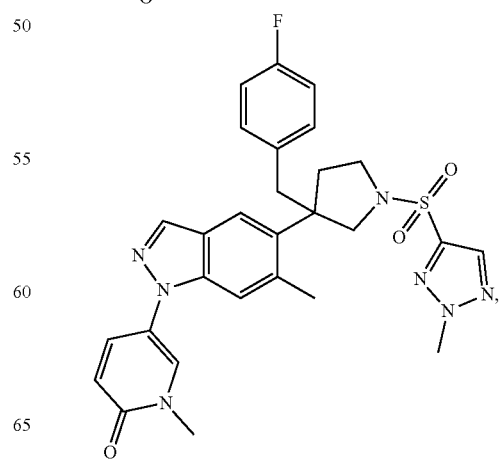

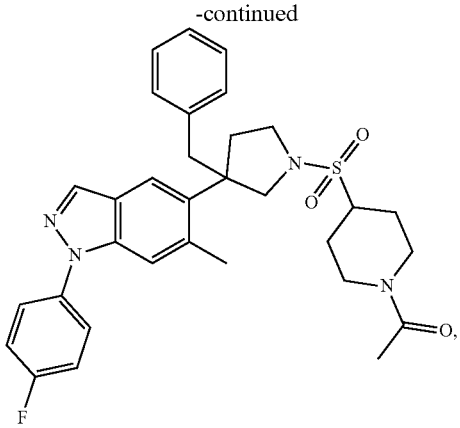
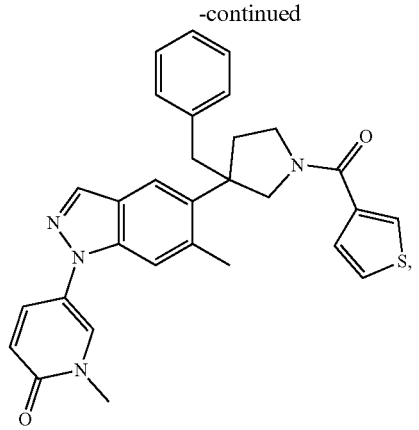
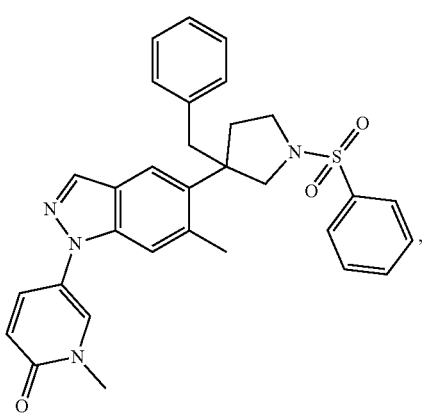
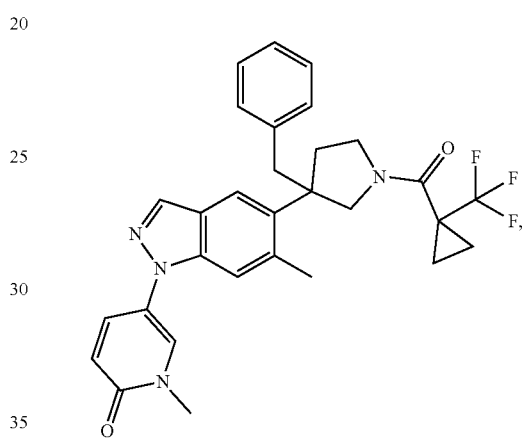
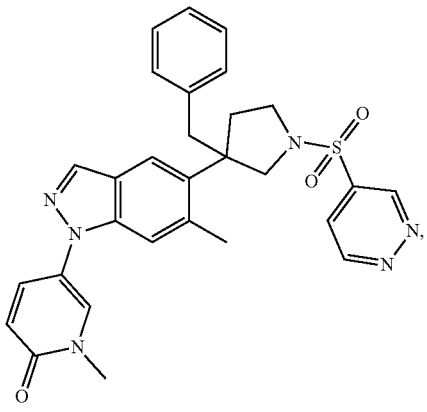
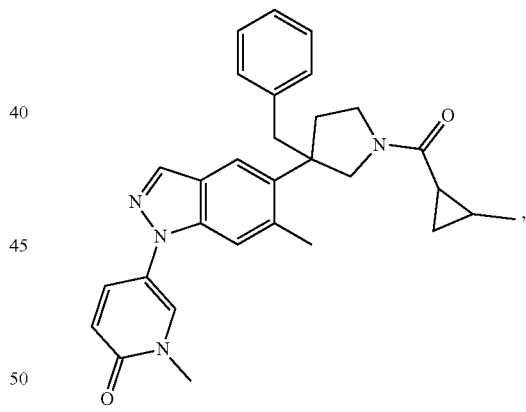
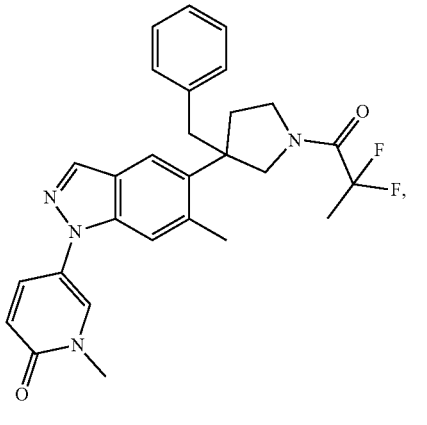
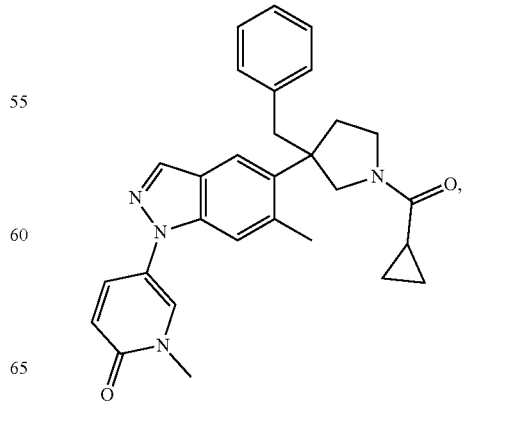

-continued
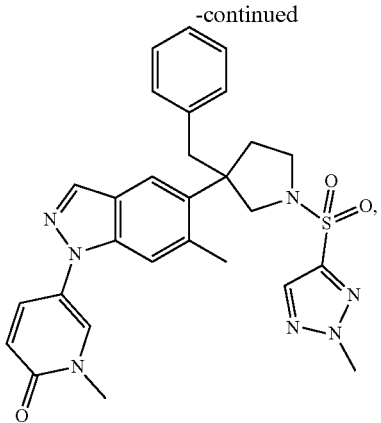
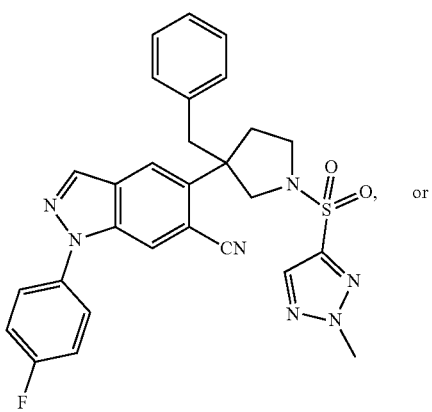  or
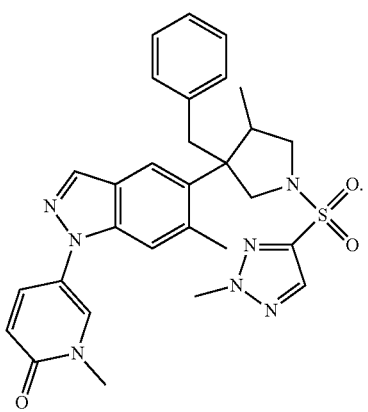 [SMILES: Cc1cc2c(cnn2-c2ccc(=O)n(C)c2)cc1C1(Cc2ccccc2)CN(S(=O)(=O)c2cnn(C)n2)CC1C]
In some embodiments, the compound of Formula I, II, IV or IVa, or a pharmaceutically acceptable salt thereof, is a compound in Table 2F:
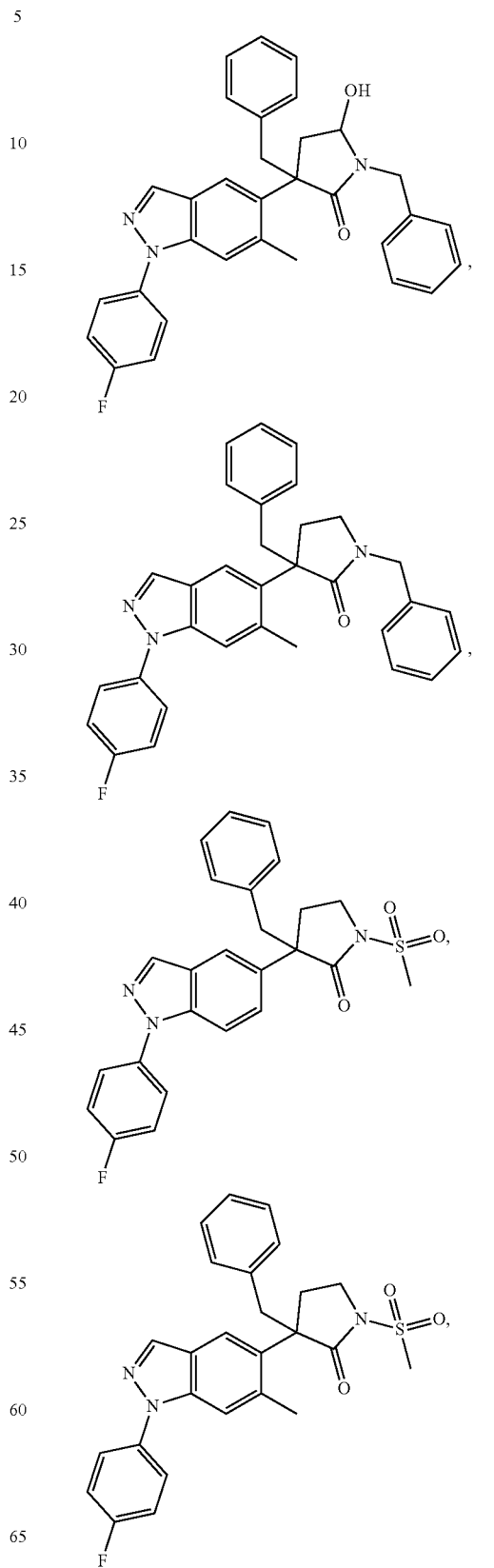

189
-continued

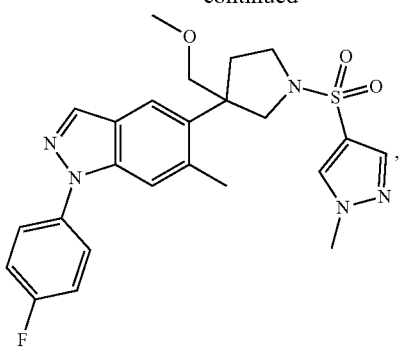

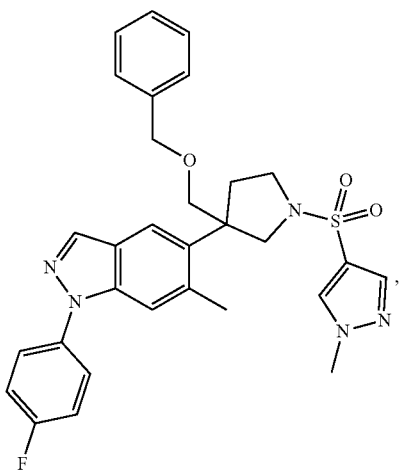

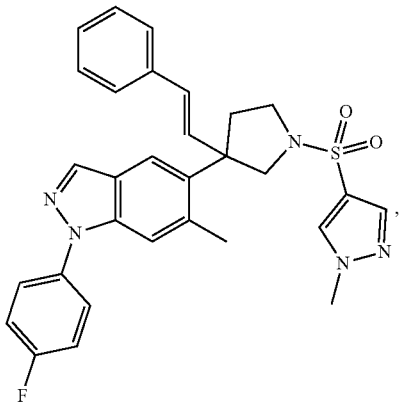

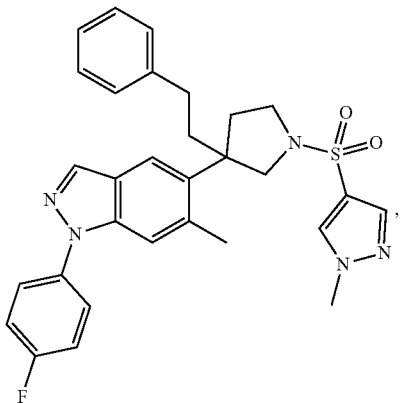

190
-continued

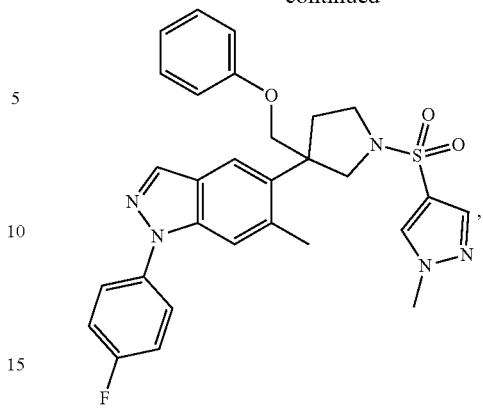

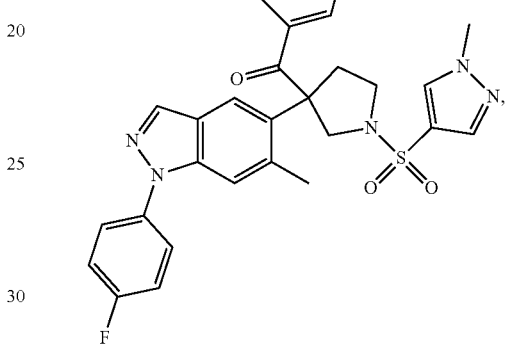

or

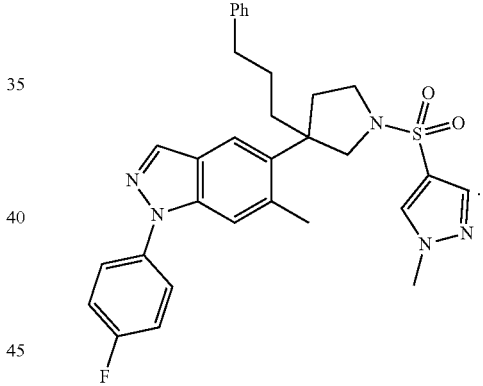

In some embodiments, the compound of Formula I, II, IV or IVa, or a pharmaceutically acceptable salt thereof, is a compound in Table 2A, Table 2B, Table 2C, Table 2D, Table 2E or Table 2F. In some embodiments, the compound of Formula I, II, IV or IVa, or a pharmaceutically acceptable salt thereof, is a compound in Table 2A. In some embodiments, the compound of Formula I, II, IV or IVa, or a pharmaceutically acceptable salt thereof, is a compound in Table 2B. In some embodiments, the compound of Formula I, II, IV or IVa, or a pharmaceutically acceptable salt thereof, is a compound in Table 2C. In some embodiments, the compound of Formula I, II, IV or IVa, or a pharmaceutically acceptable salt thereof, is a compound in Table 2D. In some embodiments, the compound of Formula I, II, IV or IVa, or a pharmaceutically acceptable salt thereof, is a compound in Table 2E. In some embodiments, the compound of Formula I, II, IV or IVa, or a pharmaceutically acceptable salt thereof, is a compound in Table 2F.

In some embodiments, the compound of Formula I or II, or a pharmaceutically acceptable salt thereof, is a compound in Table 1A, Table 1B, Table 1C, Table 1D, Table 1E, Table 1F, Table 1G, Table 1H, Table 1I, Table 1J, Table 1K, Table 2A, Table 2B, Table 2C, Table 2D, Table 2E or Table 2F. In some embodiments, the compound of Formula I or II, or a pharmaceutically acceptable salt thereof, is a compound in Table 1F, Table 1G, Table 1H, Table 1I, Table 1J, Table 1K, Table 2A, Table 2B, Table 2C, Table 2D, Table 2E or Table 2F. In some embodiments, the compound of Formula I or II, or a pharmaceutically acceptable salt thereof, is a compound in Table 1H, Table 1I, Table 1J, Table 1K, Table 2A, Table 2B, Table 2C, Table 2D, Table 2E or Table 2F.

The compounds of the present invention may exist as salts. The present invention includes such salts, which can be pharmaceutically acceptable salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention contain both basic and acidic functionalities that allow the compounds to be converted into either base or acid addition salts.

Other salts include acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, and quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically acceptable salts includes salts of the active compounds which are prepared with relatively non-toxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques.

Isomers include compounds having the same number and kind of atoms, and hence the same molecular weight, but differing in respect to the structural arrangement or configuration of the atoms.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, the compounds of the present invention may also contain unnatural proportions of atomic isotopes at one or more of the atoms that constitute such compounds. For example, the compounds of the present invention may be labeled with radioactive or stable isotopes, such as for example deuterium ($^2$H), tritium ($^3$H), iodine-125 ($^{125}$I), fluorine-18 ($^{18}$F), nitrogen-15 ($^{15}$N), oxygen-17

($^{17}$O), oxygen-18 ($^{18}$O), carbon-13 ($^{13}$C), or carbon-14 ($^{14}$C). All isotopic variations of the compounds of the present invention, whether radioactive or not, are encompassed within the scope of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

IV. Compositions

In some embodiments, the present invention provides a pharmaceutical composition comprising a compound of any one of the compounds of the present invention and a pharmaceutically acceptable excipient.

The compounds of the present invention can be prepared and administered in a wide variety of oral, parenteral and topical dosage forms. Oral preparations include tablets, pills, powder, dragees, capsules, liquids, lozenges, gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. The compounds of formula I of this invention can also be administered by in intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Accordingly, the present invention also provides pharmaceutical compositions including one or more pharmaceutically acceptable carriers and/or excipients and either a compound of formula I, or a pharmaceutically acceptable salt of a compound of formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, surfactants, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton PA ("Remington's").

In powders, the carrier is a finely divided solid, which is in a mixture with the finely divided active component. In tablets, the active component is mixed with the carrier having the necessary binding properties and additional excipients as required in suitable proportions and compacted in the shape and size desired.

The powders, capsules and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other excipients, is surrounded by a carrier, which is thus in association with it. Similarly, cachets and lozenges are included. Tablets, powders, capsules, pills, cachets, and lozenges can be used as solid dosage forms suitable for oral administration.

Suitable solid excipients are carbohydrate or protein fillers including, but not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain the compounds of formula I mixed with a filler or binders such as lactose or starches, lubricants such as talc or magnesium stearate, and, optionally, stabilizers. In soft capsules, the compounds of formula I may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the compound of formula I in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compounds of formula I of the invention can be delivered by transdermally, by a topical route, formulated as applicator sticks, solutions, suspensions, emulsions, gels, creams, ointments, pastes, jellies, paints, powders, and aerosols.

The compounds of formula I and compositions of the invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The pharmaceutical formulations of the compounds of formula I of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

The pharmaceutical formulations of the compounds of formula I of the invention can be provided as a salt and can be formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

In some embodiments, the formulations of the compounds of formula I of the invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the GR modulator into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

The dosage regimen also takes into consideration pharmacokinetics parameters well known in the art, i.e., the rate of absorption, bioavailability, metabolism, clearance, and the like (see, e.g., Hidalgo-Aragones (1996) *J. Steroid Biochem. Mol. Biol.* 58:611-617; Groning (1996) *Pharmazie* 51:337-341; Fotherby (1996) *Contraception* 54:59-69; Johnson (1995) *J. Pharm. Sci.* 84:1144-1146; Rohatagi (1995) *Pharmazie* 50:610-613; Brophy (1983) *Eur. J. Clin. Pharmacol.* 24:103-108; the latest Remington's, supra). The state of the art allows the clinician to determine the dosage regimen for each individual patient, GR and/or MR modulator and disease or condition treated.

Single or multiple administrations of the compound of formula I formulations can be administered depending on the dosage and frequency as required and tolerated by the patient. The formulations should provide a sufficient quantity of active agent to effectively treat the disease state. Thus, in one embodiment, the pharmaceutical formulations for oral administration of the compound of formula I is in a daily amount of between about 0.5 to about 30 mg per kilogram of body weight per day. In an alternative embodiment, dosages are from about 1 mg to about 20 mg per kg of body weight per patient per day are used. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing formulations including the compound of formula I for parenteral administration are known or apparent to those skilled in the art and are described in more detail in such publications as Remington's, supra. See also Nieman, In "Receptor Mediated Antisteroid Action," Agarwal, et al., eds., De Gruyter, New York (1987).

The compounds described herein can be used in combination with one another, with other active agents known to be useful in modulating a glucocorticoid receptor, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In some embodiments, the active agents can be formulated separately. In some embodiments, the active and/or adjunctive agents may be linked or conjugated to one another.

After a pharmaceutical composition including a compound of formula I of the invention has been formulated in one or more acceptable carriers, it can be placed in an appropriate container and labeled for treatment of an indicated condition. For administration of the compounds of formula I, such labeling would include, e.g., instructions concerning the amount, frequency and method of administration.

In some embodiments, the compositions of the present invention are useful for parenteral administration, such as intravenous (IV) administration or administration into a body cavity or lumen of an organ. The formulations for administration will commonly comprise a solution of the compositions of the present invention dissolved in one or more pharmaceutically acceptable carriers. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, tonicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In some embodiments, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

V. Methods & Use

In some embodiments, the present invention provides a method of treating a disorder or condition through modulating a glucocorticoid receptor, the method comprising administering to a subject in need of such treatment, a therapeutically effective amount of any one of the compounds of the present invention, or a pharmaceutical composition of the present invention, thereby treating the disorder or condition.

In an exemplary embodiment, the GR modulator is an antagonist of GR activity (also referred to herein as "a glucocorticoid receptor antagonist"). A glucocorticoid receptor antagonist, as used herein, refers to any composition or compound which partially or completely inhibits (antagonizes) the binding of a glucocorticoid receptor (GR) agonist (e.g. cortisol and synthetic or natural cortisol analog) to a GR thereby inhibiting any biological response associated with the binding of a GR to the agonist.

In some embodiments, the GR modulator is a specific glucocorticoid receptor antagonist. As used herein, a specific glucocorticoid receptor antagonist refers to a composition or compound which inhibits any biological response associated with the binding of a GR to an agonist by preferentially binding to the GR rather than another nuclear receptor (NR). In some embodiments, the specific glucocorticoid receptor antagonist binds preferentially to GR rather than the mineralocorticoid receptor (MR), aldosterone receptor (AR) or progesterone receptor (PR). In an exemplary embodiment, the specific glucocorticoid receptor antagonist binds preferentially to GR rather than the mineralocorticoid receptor (MR). In another exemplary embodiment, the specific glucocorticoid receptor antagonist binds preferentially to GR rather than the progesterone receptor (PR). In another exemplary embodiment, the specific glucocorticoid antagonist binds preferentially to GR rather than to the aldosterone receptor (AR).

In some embodiments, the specific glucocorticoid receptor antagonist binds to the GR with an association constant (Kd) that is at least 10-fold less than the Kd for any other NR. In some embodiments, the specific glucocorticoid receptor antagonist binds to the GR with an association constant (Kd) that is at least 100-fold less than the Kd for any other NR. In some embodiments, the specific glucocorticoid receptor antagonist binds to the GR with an association constant (Kd) that is at least 1000-fold less than the Kd for any other NR.

In some embodiments, the present invention provides a method of treating a disorder or condition through antagonizing a glucocorticoid receptor, the method comprising administering to a subject in need of such treatment, an effective amount of any one of the compounds of the present invention, or a pharmaceutical composition of the present invention.

In some embodiments, the disorder or condition is selected from the group consisting of amyotrophic lateral sclerosis (ALS), obesity, diabetes, cardiovascular disease, hypertension, Syndrome X, depression, anxiety, glaucoma, neurodegeneration, Alzheimer's disease, Parkinson's disease, Cushing's Syndrome, Cushing Disease, cancer, liver disease, osteoporosis, muscle frailty, a disorder caused by adrenal disease-related cortisol excess, addiction, psychosis, anorexia, cachexia, post-traumatic stress syndrome, post-surgical bone fracture, a GR-related metabolic disorders, major psychotic depression, mild cognitive impairment, dementia, hyperglycemia, a stress disorder, antipsychotic induced weight gain, delirium, cognitive impairment in depressed patients, postpartum psychosis, postpartum depression, and a neurological disorder in a premature infant.

In some embodiments, the method includes administering one or more second agents (e.g. therapeutic agents). In some embodiments, the method includes administering one or more second agents (e.g. therapeutic agents) in a therapeutically effective amount. In some embodiments, the second agent is an agent known to be useful in modulating a glucocorticoid receptor. In some embodiments, the second agent is an agent for treating amyotrophic lateral sclerosis (ALS), obesity, diabetes, cardiovascular disease, hypertension, Syndrome X, depression, anxiety, glaucoma, neurodegeneration, Alzheimer's disease, Parkinson's disease, Cushing's Syndrome, Cushing Disease, cancer, liver disease, osteoporosis, muscle frailty, a disorder caused by adrenal disease-related cortisol excess, addiction, psychosis, anorexia, cachexia, post-traumatic stress syndrome, post-surgical bone fracture, a GR-related metabolic disorders, major psychotic depression, mild cognitive impairment, dementia, hyperglycemia, a stress disorder, antipsychotic induced weight gain, delirium, cognitive impairment in depressed patients, postpartum psychosis, postpartum depression, and a neurological disorder in a premature infant. In some embodiments, the second agent is an agent for treating major psychotic depression, stress disorders or antipsychotic induced weight gain. In some embodiments, the second agent is an agent for treating nonalcoholic fatty liver disease and/or nonalcoholic steatohepatitis. In some embodiments, the second agent is an agent for treating an addiction disorder. In some embodiments, the second agent is an agent for treating cancer. In some embodiments, the second agent is an anti-cancer agent. In some embodiments, the second agent is a chemotherapeutic.

In some embodiments, any one of the compounds of the present invention, or a pharmaceutical composition of the present invention can be used for a method of treating a disorder or condition through modulating a glucocorticoid receptor.

In some embodiments, any one of the compounds of the present invention, or a pharmaceutical composition of the present invention can be used for a method of treating a disorder or condition through antagonizing a glucocorticoid receptor.

In some embodiments, any one of the compounds of the present invention, or a pharmaceutical composition of the present invention, can be used in the manufacture of a medicament for treating a disorder or condition through modulating a glucocorticoid receptor.

In some embodiments, any one of the compounds of the present invention, or a pharmaceutical composition of the present invention, can be used in the manufacture of a medicament for treating a disorder or condition through antagonizing a glucocorticoid receptor.

VI. Examples

General Procedures

All starting materials and solvents were obtained either from commercial sources or prepared according to the literature citation. Unless otherwise stated all reactions were stirred. Organic solutions were routinely dried over anhydrous magnesium sulfate. Hydrogenations were performed on a Thales H-cube flow reactor under the conditions stated or under pressure in a gas autoclave (bomb).

Column chromatography was performed on pre-packed silica (230-400 mesh, 40-63 µm) cartridges using the amount indicated. SCX was purchased from Supelco and treated with 1 M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 1% $NH_3$ in MeOH.

Analytical Methods

Reverse Phase High Performance Liquid Chromatography. Method 1: Waters XSelect CSH UPLC C18 1.7 µm (2.1×30 mm) at 40° C.; flow rate 0.77 mL·min$^{-1}$ eluted with a $H_2O$-MeCN gradient containing 0.1% v/v formic acid over 3 min employing UV detection between 210 and 400 nm. Gradient information: 0-0.11 min, held at 95% $H_2O$-5% MeCN, 0.11-2.15 min ramped from 95% $H_2O$-5% MeCN to 5% $H_2O$-95% MeCN; 2.15-2.49 min, held at 5% $H_2O$-95% MeCN, 2.49-2.56 min, ramped from 5% $H_2O$-95% MeCN to 95% $H_2O$-5% MeCN; 2.56-3.00 min, held at 95% $H_2O$-5% MeCN.

Method 2: Waters XSelect CSH C18 2.5 µm (4.6×30 mm) at 40° C.; flow rate 2.5-4.5 mL min$^{-1}$ eluted with a $H_2O$-MeCN gradient containing 0.1% v/v formic acid over 4 min employing UV detection at 254 and 215 nm. Gradient information: 0-3.00 min, ramped from 95% $H_2O$-5% MeCN to 5% $H_2O$-95% MeCN; 3.00-3.01 min, held at 5% $H_2O$-95% MeCN, flow rate increased to 4.5 mL min$^{-1}$; 3.01-3.50 min, held at 5% $H_2O$-95% MeCN; 3.50-3.60 min, returned to 95% $H_2O$-5% MeCN, flow rate reduced to 3.50 mL min$^{-1}$; 3.60-3.90 min, held at 95% $H_2O$-5% MeCN; 3.90-4.00 min, held at 95% $H_2O$-5% MeCN, flow rate reduced to 2.5 mL min$^{-1}$.

Method 3: Waters XBridge BEH C18, 1.7 µm (2.1×30 mm) at 40° C.; flow rate 2.5-4.5 mL min$^{-1}$ eluted with a $H_2O$-MeCN gradient containing 10 mM ammonium bicarbonate over 4 min employing UV detection at 254 nm. Gradient information: 0-0.11 min, held at 95% $H_2O$-5% MeCN, 0.11-2.15 min ramped from 95% $H_2O$-5% MeCN to 5% $H_2O$-95% MeCN; 2.15-2.49 min, held at 5% $H_2O$-95% MeCN, 2.49-2.56 min, ramped from 5% $H_2O$-95% MeCN to 95% $H_2O$-5% MeCN; 2.56-3.00 min, held at 95% $H_2O$-5% MeCN.

Method 4: Waters XSelect BEH C18 1.7 µm (2.1×30 mm) at 40° C.; flow rate 0.77 mL·min$^{-1}$ eluted with a $H_2O$-MeCN gradient containing 10 mM ammonium bicarbonate over 3 min employing UV detection between 210 and 400 nm. Gradient information: 0-0.11 min, held at 95% $H_2O$-5% MeCN, 0.11-2.15 min ramped from 95% $H_2O$-5% MeCN to 5% $H_2O$-95% MeCN; 2.15-2.49 min, held at 5% $H_2O$-95% MeCN, 2.49-2.56 min, ramped from 5% $H_2O$-95% MeCN to 95% $H_2O$-5% MeCN; 2.56-3.00 min, held at 95% $H_2O$-5% MeCN.

Method 5: Waters XSelect CSH UPLC C18 1.7 µm (2.1×30 mm) at 40° C.; flow rate 0.77 mL·min$^{-1}$ eluted with a $H_2O$-MeCN gradient containing 0.1% v/v formic acid over 10 min employing UV detection between 210 and 400 nm.

Gradient information: 0.-9.52 min ramped from 95% H$_2$O-5% MeCN to 5% H$_2$O-95% MeCN; 9.52-9.93 min, held at 5% H$_2$O-95% MeCN, 9.93-10.00 min, ramped from 5% H$_2$O-95% MeCN to 95% H$_2$O-5% MeCN; 10.00-10.20 min, held at 95% H$_2$O-5% MeCN.

Method 6: Waters HClass; Binary Solvent Pump, SM-FTN, CMA, PDA:210-400 nm, QDa: ACQ-QDaESI; Column: Waters CSH C18, 30×2.1 mm, 1.7 μm, Temp: 40° C., Flow: 0.77 mL/min, Gradient: t0=2% B, t2.5 min=100% B, t3.0 min=100% B, Eluent A: 0.1% Formic acid in water, Eluent B: acetonitrile.

Method 7: Waters HClass; Quaternary Solvent Pump, SM-FTN, CMA, PDA:210-400 nm, QDa: ACQ-QDa ESI; Column: Waters CSH C18, 30×2.1 mm, 1.7 μm, Temp: 40° C., Flow: 0.77 mL/min, Gradient: t0=2% B, t2.5 min=100% B, t3.0 min=100% B, Eluent A: 0.1% Formic acid in water, Eluent B: acetonitrile.

Method 8: UPLC_Basic, Apparatus: Waters HClass; Binary Solvent Pump, SM-FTN, CMA, PDA:210-400 nm, QDa: ACQ-QDa ESI; Column: Waters BEH C18, 30×2.1 mm, 1.7 μm, Temp: 40° C., Flow: 0.77 mL/min, Gradient: t0=2% B, t2.5 min=100% B, t3.0 min=100% B, Eluent A: 0.1% NH3 in water, Eluent B: Acetonitrile.

NMR spectra were recorded using a Bruker 400 MHz Avance Neo spectrometer fitted with a Bruker 5 mm iProbe, or a Bruker 500 MHz Avance III HD spectrometer equipped with a Bruker 5 mm SmartProbe™. Spectra were measured at 298 K, unless indicated otherwise, and were referenced relative to the solvent resonance. The chemical shifts are reported in parts per million. Data were acquired using Bruker TopSpin software and processed using MestreNova software.

All chemical names have been generated using ChemDraw.

INTERMEDIATES

Intermediate A:
4-bromo-N-(4-fluorophenyl)-5-methyl-2-nitroaniline

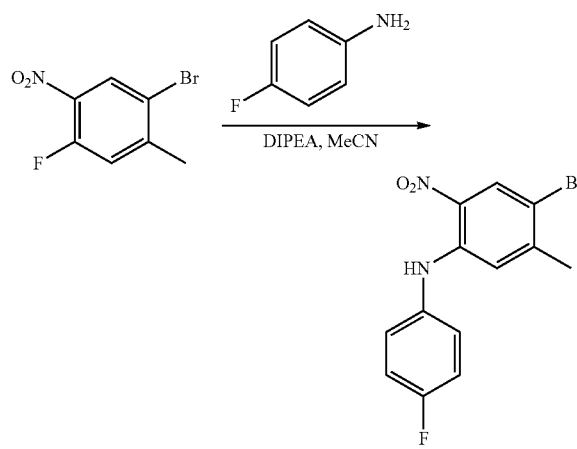

N,N-Diisopropylethylamine (1.642 ml, 9.40 mmol) was added to a solution of 4-fluoroaniline (0.810 ml, 8.55 mmol) and 1-bromo-4-fluoro-2-methyl-5-nitrobenzene (2 g, 8.55 mmol) in acetonitrile (10 mL) and the reaction mixture heated to 90° C. overnight. The reaction was allowed to cool to room temperature and concentrated in vacuo. The crude product was purified by chromatography on silica gel (40 g cartridge, 0-20% EtOAc/isohexane) to provide 4-bromo-N-(4-fluorophenyl)-5-methyl-2-nitroaniline (Intermediate A) (2.6 g, 5.68 mmol, 66.4% yield) as an orange oil which solidified on standing; $\delta_H$ (CDCl$_3$, 500 MHz) 9.34 (s, 1H), 8.40 (s, 1H), 7.28-7.23 (m, 2H), 7.16 (t, 8.5, 2H), 6.91 (s, 1H), 2.33 (s, 3H).

Intermediate B: 4-bromo-N1-(4-fluorophenyl)-5-methylbenzene-1,2-diamine

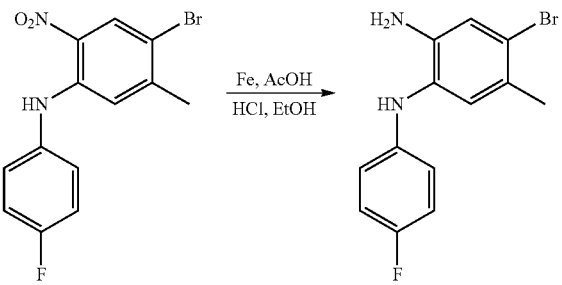 [SMILES: Cc1cc(Nc2ccc(F)cc2)c([N+](=O)[O-])cc1Br ; Cc1cc(Nc2ccc(F)cc2)c(N)cc1Br]

Iron (2.070 g, 37.1 mmol) followed by aqueous HCl (2 M, 7.41 ml, 14.82 mmol) was added to a solution of 4-bromo-N-(4-fluorophenyl)-5-methyl-2-nitroaniline (Intermediate A) (2.41 g, 7.41 mmol) in ethanol (5 mL) and acetic acid (21 ml) and stirred overnight at room temperature. The reaction mixture was diluted with water (100 mL) and extracted with ethyl acetate (3×100 mL). The combined organics were washed with sat. aqueous NaHCO$_3$ (100 mL) filtered through celite, washing with EtOAc (50 mL). The filtrate was concentrated in vacuo to give 4-bromo-N1-(4-fluorophenyl)-5-methylbenzene-1,2-diamine (Intermediate B) (2.23 g, 6.80 mmol, 92% yield) as a brown solid; (CDCl$_3$, 500 MHz) 7.04 (s, 1H), 6.97-6.92 (m, 3H), 6.73 (dd, J 8.9, 4.5, 2H), 2.27 (s, 3H). No exchangeable protons observed.

Intermediate C: 5-bromo-1-(4-fluorophenyl)-6-methyl-1H-benzo[d][1,2,3]triazole

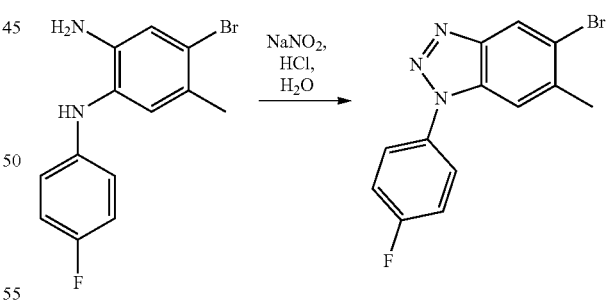

37% HCl (6.12 ml, 74.5 mmol) was added to a stirred 0° C. suspension of 4-bromo-N1-(4-fluorophenyl)-5-methyl-benzene-1,2-diamine (Intermediate B) (2.2 g, 7.45 mmol) in water (13 mL). After 5 minutes a solution of sodium nitrite (0.599 g, 8.68 mmol) in water (13 mL) was added dropwise and the reaction mixture stirred for 2 hours. The reaction mixture was basified by the addition of 2 M NaOH$_{(aq)}$ and the resultant precipitate collected by filtration and purified by chromatography on silica gel (80 g cartridge, 0-20% EtOAc/isohexane) to afford 5-bromo-1-(4-fluorophenyl)-6-methyl-1H-benzo[d][1,2,3]triazole (Intermediate C) (502 mg, 1.607 mmol, 21.56% yield) as a brown solid; δ$_H$ (CDCl$_3$, 500 MHz) 8.38 (s, 1H), 7.75 (dd, J 8.9, 4.6, 2H), 7.58 (s, 1H), 7.35 (dd, J 9.0, 8.0, 2H), 2.61 (s, 3H).

Example 1: (R)-1-(4-fluorophenyl)-5-(2-methyl-4-((1-methyl-1H-pyrazol-4-yl)sulfonyl)piperazin-1-yl)-1H-indazole Intermediate D: 5-bromo-1-(4-fluorophenyl)-1H-indazole

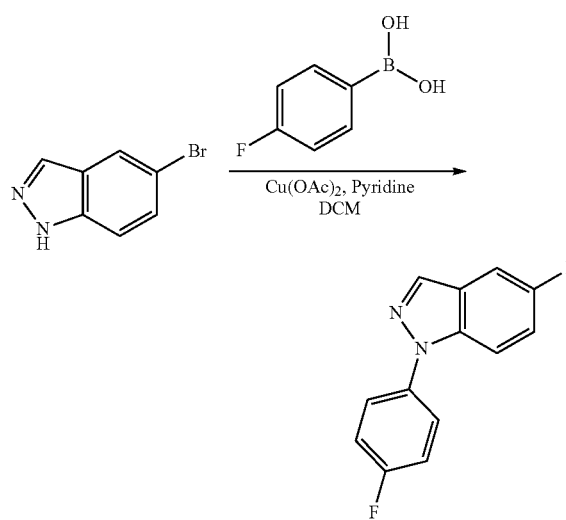

Pyridine (0.877 ml, 10.84 mmol) was added to a solution of 5-bromo-1H-indazole (1.068 g, 5.42 mmol), (4-fluorophenyl)boronic acid (1.517 g, 10.84 mmol) and copper (II) acetate (1.477 g, 8.13 mmol) in dichloromethane (75 mL) and stirred, open to air, via a punctured septum overnight. The reaction was filtered through a pad of celite which was washed with dichloromethane (30 mL) and concentrated in vacuo. The crude product was purified by chromatography on silica gel (80 g cartridge, 0-10% EtOAc/isohexane) to afford 5-bromo-1-(4-fluorophenyl)-1H-indazole (Intermediate D) (610 mg, 2.074 mmol, 38.3% yield) as a white solid; R$^t$ 1.76 min (Method 1); m/z 291.63 and 293.46 (M+H)$^+$ (ES$^+$).

Intermediate E: tert-butyl (R)-4-(1-(4-fluorophenyl)-1H-indazol-5-yl)-3-methylpiperazine-1-carboxylate

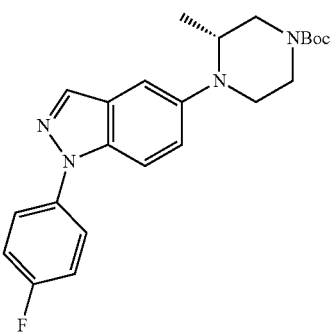

A solution of 5-bromo-1-(4-fluorophenyl)-1H-indazole (Intermediate D) (1.0 g, 3.44 mmol), (R)-tert-butyl 3-methylpiperazine-1-carboxylate (688 mg, 3.44 mmol) and sodium tert-butoxide (528 mg, 5.50 mmol) in 1,4-dioxane (10 mL) was degassed by bubbling through with nitrogen for 5 minutes. Chloro(crotyl)(tri-tert-butylphosphine)palladium (II) (69 mg, 0.172 mmol) was then added and the solution was degassed for a further 5 minutes. The solution was then heated to 80° C. and stirred overnight. The reaction mixture was allowed to cool to room temperature and partitioned between EtOAc (50 mL) and water (80 mL), the layers were separated and the aqueous layer extracted with EtOAc (2×50 mL). The combined organics were dried over MgSO$_4$, filtered and concentrated in vacuo. The crude product was purified by chromatography on silica gel (40 g cartridge, 0-30% EtOAc/isohexane) to afford (R)-tert-butyl 4-(1-(4-fluorophenyl)-1H-indazol-5-yl)-3-methylpiperazine-1-carboxylate (Intermediate E) (800 mg, 1.929 mmol, 56.2% yield) as a white solid; R$^t$ 1.72 min (Method 1); m/z 411.85 (M+H)$^+$ (ES$^+$).

Example 1: (R)-1-(4-fluorophenyl)-5-(2-methyl-4-((1-methyl-1H-pyrazol-4-yl)sulfonyl)piperazin-1-yl)-1H-indazole

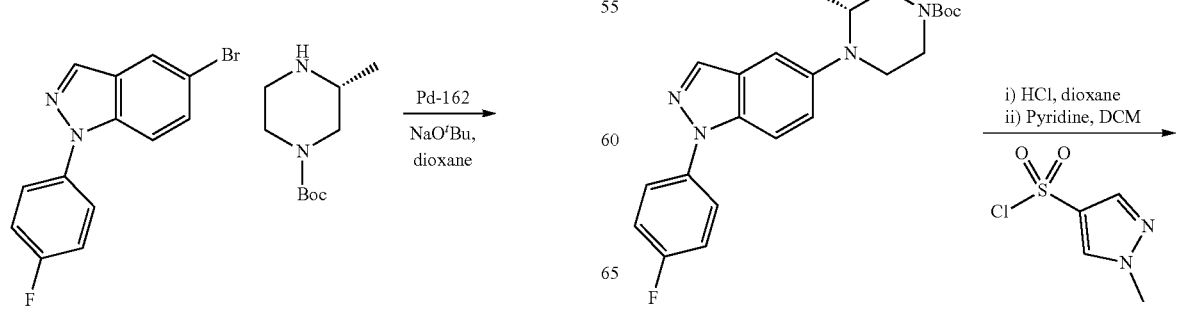

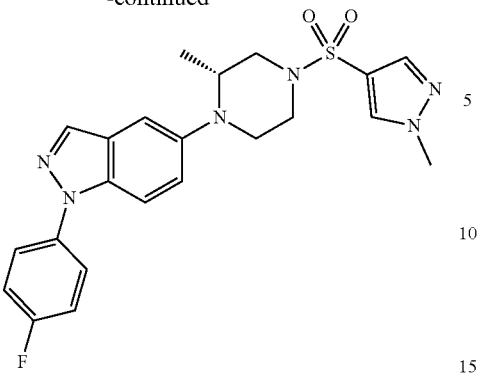

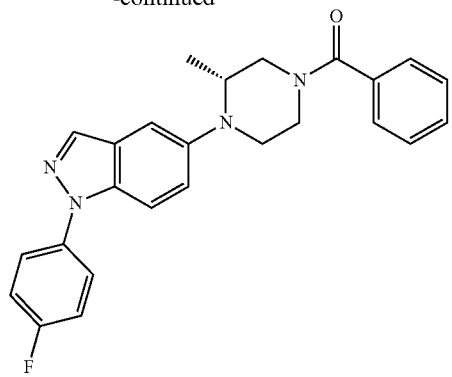

HCl (4M in 1,4-dioxane) (886 μl, 3.54 mmol) was added to a solution of (R)-tert-butyl 4-(1-(4-fluorophenyl)-1H-indazol-5-yl)-3-methylpiperazine-1-carboxylate (Intermediate E) (97 mg, 0.236 mmol) in 1,4-dioxane (1 ml), the reaction was stirred at room temperature for 3 hours and then concentrated to dryness.

A solution of 1-methyl-1H-pyrazole-4-sulfonyl chloride (64.0 mg, 0.354 mmol) in dichloromethane (1 ml) was added to a solution of (R)-1-(4-fluorophenyl)-5-(2-methylpiperazin-1-yl)-1H-indazole and pyridine (96 μl, 1.182 mmol) in dichloromethane (2 ml) and the mixture was stirred overnight at room temperature. Water (10 ml) and dichloromethane (10 ml) were added and the layers were separated and the organic layer was washed with water (10 mL), dried over MgSO$_4$, filtered and concentrated in vacuo. The crude product was purified by chromatography on silica gel (12 g cartridge, 0-50% EtOAc/isohexane) to afford (R)-1-(4-fluorophenyl)-5-(2-methyl-4-((1-methyl-1H-pyrazol-4-yl)sulfonyl)piperazin-1-yl)-1H-indazole Example 1 (70 mg, 0.152 mmol, 64.5% yield) as a colourless solid; R$^t$ 1.49 min (Method 1); m/z 455.11 (M+H)$^+$ (ES$^+$); δ$_H$ (DMSO-d6, 500 MHz) 8.38 (s, 1H), 8.22 (d, J 0.9, 1H), 7.83 (d, J 0.7, 1H), 7.78 (dd, J 9.0, 4.8, 2H), 7.73-7.67 (m, 1H), 7.41 (t, J 8.8, 2H), 7.29 (m, 2H), 3.94 (s, 3H), 3.90 (dt, J 7.3, 4.1, 1H), 3.31-3.26 (m, 1H), 3.24-3.15 (m, 2H), 3.04 (dd, J 11.0, 4.7, 1H), 2.88 (dd, J 11.1, 3.3, 1H), 2.73 (ddd, J 11.2, 8.2, 3.7, 1H), 0.95 (d, J 6.4, 3H).

Example 2: (R)-(4-(1-(4-fluorophenyl)-1H-indazol-5-yl)-3-methylpiperazin-1-yl)(phenyl)methanone HCl (4M in 1,4-dioxane) (685 μl, 2.74 mmol) was added to a solution of (R)-tert-butyl 4-(1-(4-fluorophenyl)-1H-indazol-5-yl)-3-methylpiperazine-1-carboxylate (Intermediate E) (75 mg, 0.183 mmol) in 1,4-dioxane (1 ml), the reaction was stirred at room temperature for 3 hours and then concentrated to dryness.

A solution of benzoyl chloride (31.6 μl, 0.274 mmol) in dichloromethane (1 ml) was added to a solution of (R)-1-(4-fluorophenyl)-5-(2-methylpiperazin-1-yl)-1H-indazole and pyridine (73.9 μl, 0.914 mmol) in dichloromethane (2 ml) and the mixture was stirred overnight at room temperature. Water (10 ml) and dichloromethane (10 ml) were added and the layers were separated and the organic layer was washed with water (10 mL), dried over MgSO$_4$, filtered and concentrated in vacuo. The crude product was purified by chromatography on silica gel (12 g cartridge, 0-50% EtOAc/isohexane) to afford (R)-(4-(1-(4-fluorophenyl)-1H-indazol-5-yl)-3-methylpiperazin-1-yl)(phenyl)methanone Example 2 (62 mg, 0.147 mmol, 80% yield) as a dark yellow solid; R$^t$ 1.55 min (Method 1); m/z 415.19 (M+H)$^+$ (ES$^+$); δ$_H$ (DMSO-d6, 500 MHz) 8.22 (d, J 0.9, 1H), 7.79 (dd, J 9.0, 4.8, 2H), 7.72 (d, J 9.1, 1H), 7.51-7.43 (m, 5H), 7.41 (dd, J 9.8, 7.8, 2H), 7.33 (s, 1H), 7.28 (d, J 2.2, 1H), 4.26 (br. s, 0.5H), 4.07-3.91 (m, 1H), 3.83 (br. s, 0.5H), 3.59 (s, 1.5H), 3.44-3.34 (m, 1.5H), 3.23 (br. s, 0.5H), 3.11 (br. s, 1.5H), 0.93 (br.s, 1.5H), 0.80 (br. s, 1.5H). Compound exists as a 1:1 mixture of conformers/rotamers.

Example 3: 1-(4-fluorophenyl)-5-(7-((1-propyl-1H-pyrazol-4-yl)sulfonyl)-4,7-diazaspiro[2.5]octan-4-yl)-1H-indazole Intermediate F: tert-butyl 7-((1-propyl-1H-pyrazol-4-yl)sulfonyl)-4,7-diazaspiro[2.5]octane-4-carboxylate

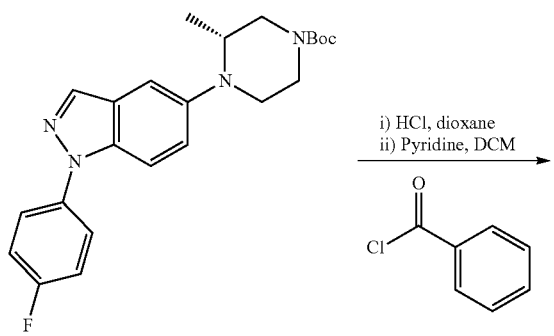

i) HCl, dioxane
ii) Pyridine, DCM

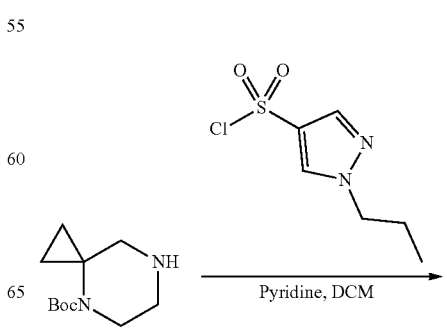

Pyridine, DCM

-continued

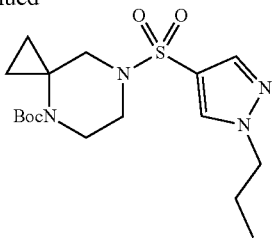

A solution of 1-propyl-1H-pyrazole-4-sulfonyl chloride (211 µl, 1.413 mmol) in dichloromethane (1 ml) was added to a solution of tert-butyl 4,7-diazaspiro[2.5]octane-4-carboxylate (200 mg, 0.942 mmol) and pyridine (381 µl, 4.71 mmol) in dichloromethane (10 ml) and the mixture was stirred overnight at room temperature. Water (10 ml) and dichloromethane (10 ml) were added and the layers separated. The organic layer was washed with water (10 mL), dried over MgSO$_4$, filtered and concentrated in vacuo. The crude product was purified by chromatography on silica gel (24 g cartridge, 0-50% EtOAc/isohexane) to afford tert-butyl 7-((1-propyl-1H-pyrazol-4-yl)sulfonyl)-4,7-diazaspiro[2.5] octane-4-carboxylate (Intermediate F) (301 mg, 0.775 mmol, 82% yield) as a white powder; δ$_H$ (CDCl$_3$, 500 MHz) 7.74 (s, 1H), 7.72 (d, J 0.7, 1H), 4.14 (t, J 7.0, 2H), 3.65 (t, J 5.0, 2H), 2.99 (s, 2H), 2.83 (s, 2H), 1.94 (h, J 7.3, 2H), 1.41 (s, 9H), 1.05 (m, 2H), 0.94 (t, J 7.4, 3H), 0.93-0.89 (m, 2H).

Example 3: 1-(4-fluorophenyl)-5-(7-((1-propyl-1H-pyrazol-4-yl)sulfonyl)-4,7-diazaspiro[2.5]octan-4-yl)-1H-indazole

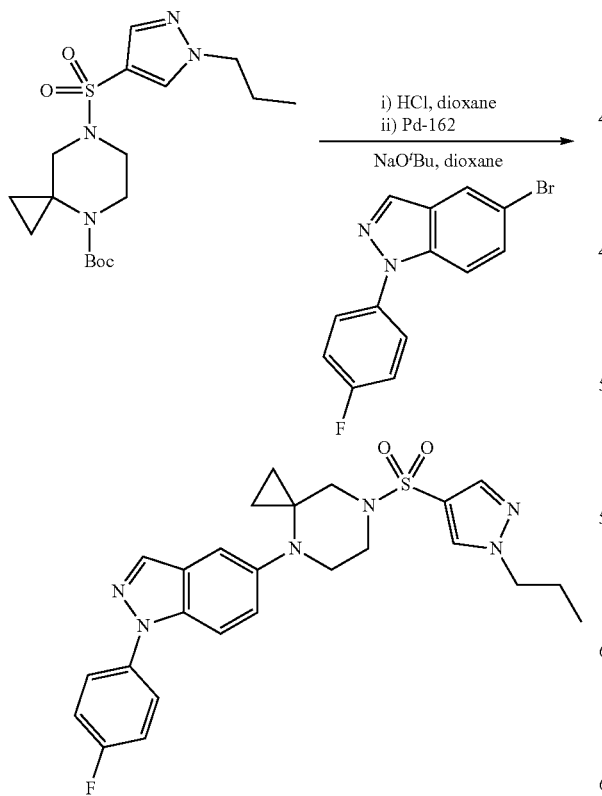

HCl (4M in 1,4-dioxane) (1288 µl, 5.15 mmol) was added to a solution of tert-butyl 7-((1-propyl-1H-pyrazol-4-yl)sulfonyl)-4,7-diazaspiro[2.5]octane-4-carboxylate (Intermediate F) (132 mg, 0.344 mmol) in 1,4-dioxane (1 ml), the reaction was stirred at room temperature for 3 hours and then concentrated to dryness.

5-Bromo-1-(4-fluorophenyl)-1H-indazole (Intermediate D) (100 mg, 0.344 mmol), sodium tert-butoxide (52.8 mg, 0.550 mmol) and 1,4-dioxane (1 mL) were added, and the solution was degassed by bubbling through with nitrogen for 5 minutes. Chloro(crotyl)(tri-tert-butylphosphine)palladium (II) (6.86 mg, 0.017 mmol) was added and the solution further degassed for 5 minutes and then heated to 80° C. and stirred overnight. The reaction mixture was allowed to cool to room temperature and partitioned between ethyl acetate (15 mL) and water (20 mL), the layers were separated and the aqueous layer extracted with ethyl acetate (2×15 mL). The combined organics were dried over MgSO$_4$, filtered and concentrated in vacuo. The crude product was purified by chromatography on silica gel (12 g cartridge, 0-50% EtOAc/isohexane) to afford 1-(4-fluorophenyl)-5-(7-((1-propyl-1H-pyrazol-4-yl)sulfonyl)-4,7-diazaspiro[2.5]octan-4-yl)-1H-indazole Example 3 (15 mg, 0.029 mmol, 8.39% yield) as a light brown solid; R$^t$ 1.67 min (Method 1); m/z 495.73 (M+H)$^+$ (ES$^+$); (DMSO-d6, 500 MHz) 8.30 (d, J 0.8, 1H), 8.13 (d, J 0.9, 1H), 7.76-7.72 (m, 3H), 7.62 (dt, J 9.3, 0.9, 1H), 7.40 (t, J 8.8, 2H), 7.28 (d, J 2.2, 1H), 7.22 (dd, J 9.2, 2.3, 1H), 4.03 (t, J 6.8, 2H), 3.78 (br. s, 2H), 2.92 (s, 2H), 2.54-2.52 (obs. m, 2H), 1.63 (h, J 7.2, 2H), 0.89-0.79 (m, 4H), 0.49 (t, J 7.3, 3H).

Example 4: (S)—N-(1-(1-(4-fluorophenyl)-6-methyl-1H-indazol-5-yl)pyrrolidin-3-yl)-1-propyl-1H-pyrazole-4-sulfonamide Intermediate G. tert-butyl (S)-(1-(1-(4-fluorophenyl)-6-methyl-1H-indazol-5-yl)pyrrolidin-3-yl)carbamate

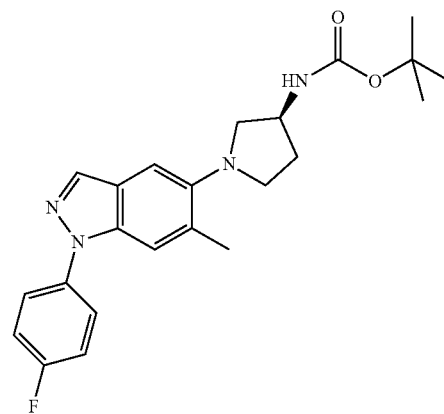 [SMILES: Cc1cc2c(cnn2-c2ccc(F)cc2)cc1N1CC[C@H](NC(=O)OC(C)(C)C)C1]

A vial containing 5-bromo-1-(4-fluorophenyl)-6-methyl-1H-indazole (prepared via method for Intermediate D) (800 mg, 2.62 mmol), (S)-tert-butyl pyrrolidin-3-ylcarbamate (977 mg, 5.24 mmol), RuPhos G3 Precatalyst (219 mg, 0.262 mmol) and cesium carbonate (2.56 g, 7.87 mmol) was evacuated and back filled with nitrogen (×3). 1,4-Dioxane (15 mL) was added and the resultant pale green suspension was heated at 80° C. for 3 days. The reaction mixture was quenched with a saturated solution of sodium bicarbonate (10 mL) and extracted with ethyl acetate (3×10 mL). The organic layers were combined and passed through a hydrophobic frit. The solvent was removed under reduced pressure to afford a dark yellow residue. The crude product was purified by chromatography on silica gel (liquid loading with DCM, 120 g cartridge, 0-50% EtOAc/isohexane) to afford (S)-tert-butyl (1-(1-(4-fluorophenyl)-6-methyl-1H-indazol-5-yl)pyrrolidin-3-yl)carbamate (Intermediate G) (976 mg, 2.347 mmol, 90% yield) as an off-white solid; $R^t$ 1.76 min (Method 1); m/z 411.4 (M+H)$^+$ (ES$^+$); $\delta_H$ (DMSO-d6, 500 MHz) 8.17 (d, J 0.9, 1H), 7.80-7.75 (m, 2H), 7.60 (s, 1H), 7.44-7.37 (m, 2H), 7.30 (s, 1H), 7.17 (br d, J 7.1, 1H), 4.11 (obs. br. d, J 6.3, 1H), 3.31-3.25 (m, 1H), 3.20-3.08 (m, 2H), 2.95 (dd, J 9.4, 5.4, 1H), 2.41 (d, J 0.9, 3H), 2.24-2.13 (m, 1H), 1.85-1.75 (m, 1H), 1.40 (s, 9H).

(S)—N-(1-(1-(4-fluorophenyl)-6-methyl-1H-indazol-5-yl)pyrrolidin-3-yl)-1-propyl-1H-pyrazole-4-sulfonamide

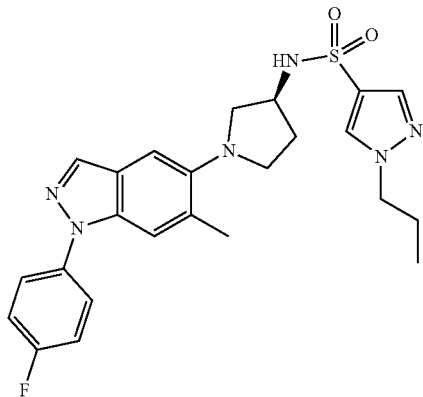 [SMILES: CCCn1cc(S(=O)(=O)N[C@H]2CCN(c3cc4cnn(-c5ccc(F)cc5)c4cc3C)C2)cn1]

To a solution of (S)-tert-butyl (1-(1-(4-fluorophenyl)-6-methyl-1H-indazol-5-yl)pyrrolidin-3-yl)carbamate (Intermediate G) (500 mg, 1.218 mmol) in dichloromethane (10 mL) was added HCl (3.5 M in 1,4-dioxane) (3480 µl, 12.18 mmol). The resultant cloudy solution was stirred at room temperature for 18 hours. The solvent was removed under reduced pressure and the resultant solid was triturated with tert-butyl methyl ether (5 mL), filtered, rinsing with tert-butyl methy ether (2×5 mL), and dried in vacuo to afford (S)-1-(1-(4-fluorophenyl)-6-methyl-1H-indazol-5-yl)pyrrolidin-3-amine hydrochloride as a white solid which was used without further purification.

To a solution of (S)-1-(1-(4-fluorophenyl)-6-methyl-1H-indazol-5-yl)pyrrolidin-3-amine hydrochloride (160 mg, 0.461 mmol) in dichloromethane (4 mL) were added pyridine (187 µl, 2.307 mmol) and 1-propyl-1H-pyrazole-4-sulfonyl chloride (193 mg, 0.923 mmol). The resultant white suspension was stirred at room temperature for 4 days. The reaction mixture was quenched with a saturated solution of aqueous NaHCO$_3$ (10 mL) and extracted with ethyl acetate (3×10 mL). The organic layers were combined and passed through a hydrophobic frit. The solvent was removed under reduced and the crude product was purified by chromatography on silica gel (liquid loading, 40 g cartridge, 0-50% EtOAc/isohexane) to afford (S)—N-(1-(1-(4-fluorophenyl)-6-methyl-1H-indazol-5-yl)pyrrolidin-3-yl)-1-propyl-1H-pyrazole-4-sulfonamide (Example 4) (58 mg, 0.118 mmol, 25.6% yield) as a yellow solid; $R^t$ 1.60 min (Method 1); m/z 483.4 (M+H)$^+$ (ES$^+$); $\delta_H$ (DMSO-d6, 500 MHz) 8.31 (s, 1H), 8.17 (d, J=0.9 Hz, 1H), 7.78 (dd, J=9.01, 4.8 Hz, 2H), 7.60 (s, 1H), 7.41 (app. t, J=8.8 Hz, 2H), 7.30 (s, 1H), 4.12 (t, J=6.9 Hz, 2H), 3.85 (q, J=6.7 Hz, 1H), 3.17-3.05 (m, 3H), 2.95 (dd, J=9.5, 5.5 Hz, 1H), 2.37-2.32 (m, 3H), 2.13 (d, J=6.5 Hz, 1H), 1.78 (ddd, J=12.1, 9.6, 6.2 Hz, 4H), 0.79 (t, J=7.4 Hz, 3H).

Example 5: (S)—N-(1-(1-(4-fluorophenyl)-6-methyl-1H-indazol-5-yl)pyrrolidin-3-yl)-N-methyl-1-propyl-1H-pyrazole-4-sulfonamide

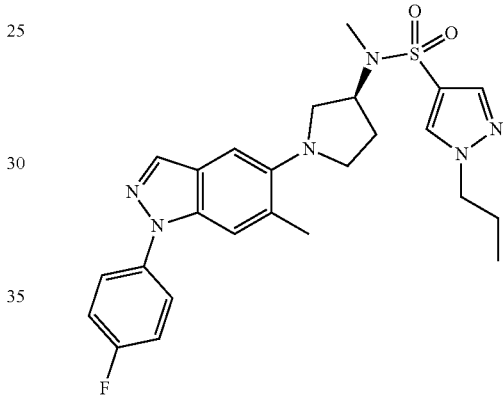

To a solution of (S)—N-(1-(1-(4-fluorophenyl)-1H-indazol-5-yl)pyrrolidin-3-yl)-1-propyl-1H-pyrazole-4-sulfonamide (Example 4) (48 mg, 0.099 mmol) in dimethylformamide (3 mL) at 0° C. was added sodium hydride (60% in mineral oil) (4.77 mg, 0.119 mmol) in one portion. The resultant yellow solution was stirred at 0° C. for 30 min and methyl iodide (12.44 µl, 0.199 mmol) was added. The resultant white solution was stirred at room temperature for 1 hour. The reaction mixture was quenched with a saturated solution of bicarbonate (10 mL) and extracted with ethyl acetate (3×10 mL). The organic layers were combined and passed through a hydrophobic frit. The solvent was removed under reduced pressure and the crude product purified by chromatography on silica gel (24 g cartridge, 0-50% EtOAc/isohexane) to afford (S)—N-(1-(1-(4-fluorophenyl)-6-methyl-1H-indazol-5-yl)pyrrolidin-3-yl)-N-methyl-1-propyl-1H-pyrazole-4-sulfonamide (Example 5) (42 mg, 0.084 mmol, 84% yield) as a yellow solid; $R^t$ 1.76 min (Method 1); m/z 497.4 (M+H)$^+$ (ES$^+$); $\delta_H$ (DMSO-d6, 500 MHz) 8.44 (d, J 0.7, 1H), 8.18 (d, J 0.9, 1H), 7.88 (d, J 0.7, 1H), 7.77 (dd, J 9.0, 4.8, 2H), 7.60 (s, 1H), 7.41 (app. t, J 8.8, 2H), 7.34 (s, 1H), 4.66-4.55 (m, 1H), 4.13 (t, J 6.8, 2H), 3.13 (td, J 8.5, 3.3, 1H), 2.91 (m, 3H), 2.80 (s, 3H), 2.34 (s, 3H), 2.16-2.05 (m, 1H), 1.85-1.73 (m, 3H), 0.78 (t, J 7.4, 3H).

Example 6: 1-(4-fluorophenyl)-6-methyl-5-(1-((1-propyl-1H-pyrazol-4-yl)sulfonyl)piperidin-4-yl)-1H-indazole Intermediate H: tert-butyl 4-(1-(4-fluorophenyl)-6-methyl-1H-indazol-5-yl)-5,6-dihydropyridine-1(2H)-carboxylate

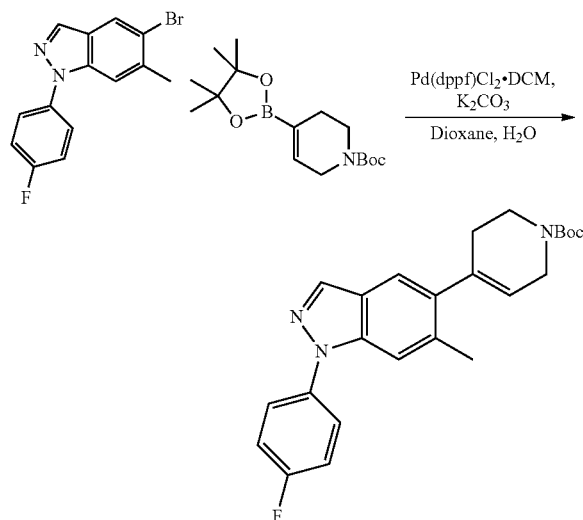

5-Bromo-1-(4-fluorophenyl)-6-methyl-1H-indazole (Prepared using the method described for Intermediate D) (0.262 g, 0.859 mmol), tert-butyl 4-(4,4,5,5-tetramethyl-1,3,2-dioxaborolan-2-yl)-5,6-dihydropyridine-1(2H)-carboxylate (0.4 g, 1.294 mmol), potassium carbonate (0.4 g, 2.89 mmol), and Pd(dppf)Cl2·DCM (0.140 g, 0.172 mmol) were suspended in a mixture of 1,4-dioxane (5 mL) and water (1 mL). The vial was evacuated and backfilled with nitrogen three times then heated to reflux for 16 hours. The mixture was cooled to room temperature, diluted with ethyl acetate (10 mL), filtered through Celite then absorbed directly onto silica gel and purified by chromatography on silica gel (24 g cartridge, 0-100% EtOAc/isohexane) to afford tert-butyl 4-(1-(4-fluorophenyl)-6-methyl-1H-indazol-5-yl)-5,6-dihydropyridine-1(2H)-carboxylate (Intermediate H) (329 mg, 0.783 mmol, 91% yield) as a pale yellow tar; $R^t$ 1.99 min (Method 1); m/z 408.7 (M+H)$^+$ (ES$^+$).

Intermediate I: tert-butyl 4-(1-(4-fluorophenyl)-6-methyl-1H-indazol-5-yl)piperidine-1-carboxylate

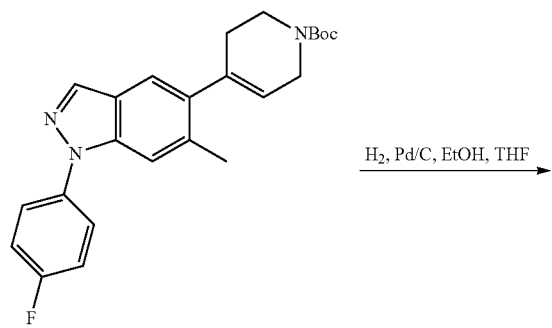

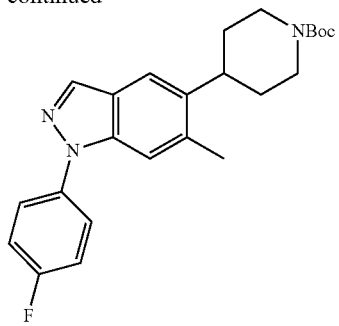

tert-Butyl 4-(1-(4-fluorophenyl)-6-methyl-1H-indazol-5-yl)-5,6-dihydropyridine-1(2H)-carboxylate (Intermediate H) (329 mg, 0.783 mmol) was dissolved in a mixture of ethanol/tetrahydrofuran (5:1, 6 mL) and palladium on carbon (type 39, 10% loading, 50% w/w water) (150 mg, 0.070 mmol) was added. The mixture was stirred under 5 bar hydrogen pressure for 4 hours. The mixture was filtered through Celite, eluting with ethanol (3×5 mL) and ethyl acetate (3×5 mL). After concentration of the filtrate, tert-butyl 4-(1-(4-fluorophenyl)-6-methyl-1H-indazol-5-yl)piperidine-1-carboxylate (Intermediate I) (281 mg, 0.672 mmol, 86% yield) was isolated as a pale yellow solid foam; $R^t$ 1.97 min (Method 1); m/z 410.3 (M+H)$^+$ (ES$^+$).

Example 6: 1-(4-fluorophenyl)-6-methyl-5-(1-((1-propyl-1H-pyrazol-4-yl)sulfonyl)piperidin-4-yl)-1H-indazole

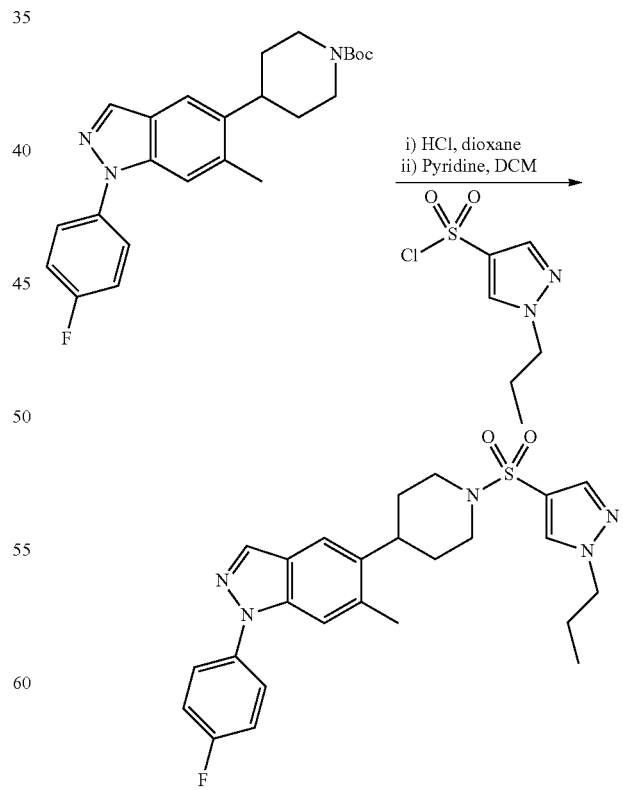

tert-Butyl 4-(1-(4-fluorophenyl)-6-methyl-1H-indazol-5-yl)piperidine-1-carboxylate (Intermediate I) (0.05 g, 0.122 mmol) was dissolved in HCl (4M in 1,4-dioxane) (2 mL, 8.00 mmol) and stirred at room temperature for 1 hour. The solvent was removed in vacuo and the residue was suspended in dichloromethane (2 mL). Pyridine (50 μl, 0.618 mmol) and methanesulfonyl chloride (20 μl, 0.258 mmol) were added and the mixture was warmed to 35° C. (bath temperature) for 3 days. The mixture was allowed to reach room temperature then quenched with 1M HCl$_{(aq)}$ (1 mL). The organic phase was separated by passing through a hydrophobic frit then concentrated in vacuo. The crude product was purified by chromatography on silica gel (4 g cartridge, 0-100% EtOAc/isohexane) to afford 1-(4-fluorophenyl)-6-methyl-5-(1-(methylsulfonyl)piperidin-4-yl)-1H-indazole (Example 6) (36 mg, 0.092 mmol, 76% yield) as a colourless solid; R$^t$ 1.74 min (Method 1); m/z 482.3 (M+H)$^+$ (ES$^+$); δ$_H$ (DMSO-d6, 500 MHz) 8.43 (s, 1H), 8.24 (s, 1H), 7.85 (s, 1H), 7.78 (dd, J 8.9, 4.9, 2H), 7.70 (s, 1H), 7.60 (s, 1H), 7.42 (app. t, J 8.6, 2H), 4.17 (t, J 6.9, 2H), 3.75 (d, J 11.3, 2H), 2.79 (tt, J 11.9, 3.5, 1H), 2.42 (s, 3H), 2.42-2.35 (m, 2H), 1.91-1.81 (m, 4H), 1.81-1.70 (m, 2H), 0.84 (t, J 7.4, 3H).

Example 7: 1-(1-(4-fluorophenyl)-6-methyl-1H-indazol-5-yl)-4-(methylsulfonyl)piperazin-2-one Intermediate J: tert-butyl 4-(1-(4-fluorophenyl)-6-methyl-1H-indazol-5-yl)-3-oxopiperazine-1-carboxylate

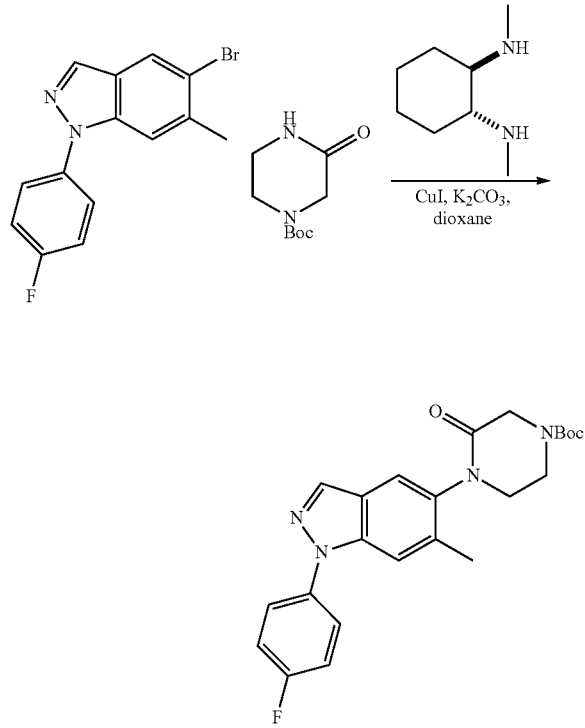

5-Bromo-1-(4-fluorophenyl)-6-methyl-1H-indazole (prepared using the method described for Intermediate D) (0.25 g, 0.819 mmol), tert-butyl 3-oxopiperazine-1-carboxylate (0.246 g, 1.229 mmol), copper iodide (0.031 g, 0.164 mmol), and potassium carbonate (0.340 g, 2.458 mmol) were suspended in 1,4-dioxane (3 mL) under nitrogen. The mixture was evacuated and back filled with nitrogen three times. Trans-N1,N2-dimethylcyclohexane-1,2-diamine (0.039 ml, 0.246 mmol) was added and the mixture was heated to reflux overnight. The mixture was cooled to room temperature and filtered through a plug of Celite and the solvent was removed in vacuo. The crude product was purified by chromatography on silica gel (12 g cartridge, 0-100% EtOAc/isohexane) to afford tert-butyl 4-(1-(4-fluorophenyl)-6-methyl-1H-indazol-5-yl)-3-oxopiperazine-1-carboxylate (Intermediate J) (0.05 g, 0.110 mmol, 13.37% yield) as a yellow solid; R$^t$ 1.53 min (Method 1); m/z 425.3 (M+H)$^+$ (ES$^+$).

Example 7: 1-(1-(4-fluorophenyl)-6-methyl-1H-indazol-5-yl)-4-(methylsulfonyl)piperazin-2-one

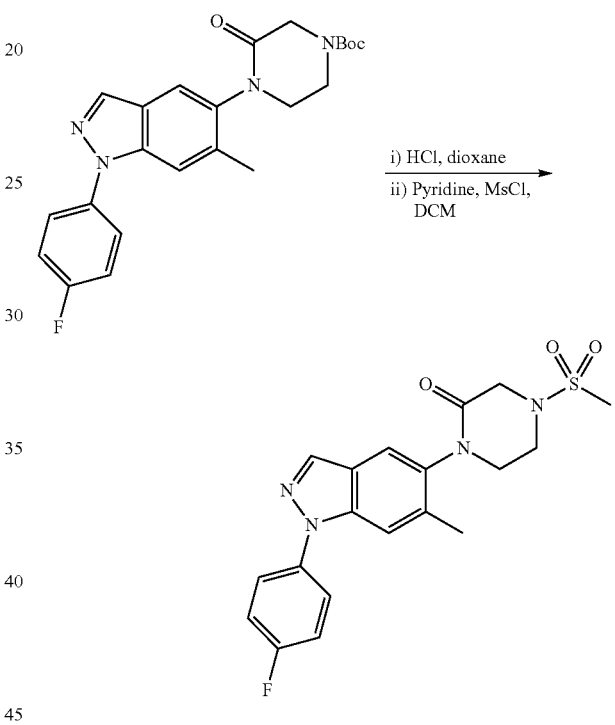

tert-Butyl 4-(1-(4-fluorophenyl)-6-methyl-1H-indazol-5-yl)-3-oxopiperazine-1-carboxylate (Intermediate J) (0.025 g, 0.059 mmol) was dissolved in HCl (4 M in 1,4-dioxane) (3 mL) and stirred at room temperature for 3 hours. The solvent was removed in vacuo and the residue was suspended in dichloromethane (3 mL). Methanesulfonyl chloride (10 μl, 0.129 mmol) was added followed by triethylamine (0.04 ml, 0.287 mmol). The mixture was stirred at room temperature overnight. The solvent was removed in vacuo and the residue was dissolved in dimethyl sulfoxide (2 mL). The mixture was filtered then purified directly by preparative HPLC (Method A, 20-50% MeCN in Water). After concentration of product-containing fractions (Genevac), 1-(1-(4-fluorophenyl)-6-methyl-1H-indazol-5-yl)-4-(methylsulfonyl)piperazin-2-one (Example 7) (10 mg, 0.025 mmol, 42.2% yield) was isolated as a colourless oil; R$^t$ 1.21 min (Method 1); m/z 403.1 (M+H)$^+$ (ES$^+$); δ$_H$ (DMSO-d6, 500 MHz) 8.34 (d, J 0.9, 1H), 7.87-7.77 (m, 3H), 7.73 (s, 1H), 7.45 (app. t, J 8.8, 2H), 4.04 (d, J 16.7, 1H), 3.97 (d, J 16.8, 1H), 3.88-3.78 (m, 1H), 3.73-3.65 (m, 1H), 3.63-3.51 (m, 2H), 3.10 (s, 3H), 2.30 (s, 3H).

Example 8: 1-(4-fluorophenyl)-5-((2R)-2-methyl-1-((1-propyl-1H-pyrazol-4-yl)sulfonyl)piperidin-4-yl)-1H-indazole Intermediate K: (2R)-tert-butyl 4-(1-(4-fluorophenyl)-1H-indazol-5-yl)-4-hydroxy-2-methylpiperidine-1-carboxylate Intermediate L: (R)-1-(4-fluorophenyl)-5-(6-methyl-1,2,3,6-tetrahydropyridin-4-yl)-1H-indazole hydrochloride and (R)-1-(4-fluorophenyl)-5-(2-methyl-1,2,3,6-tetrahydropyridin-4-yl)-1H-indazole hydrochloride

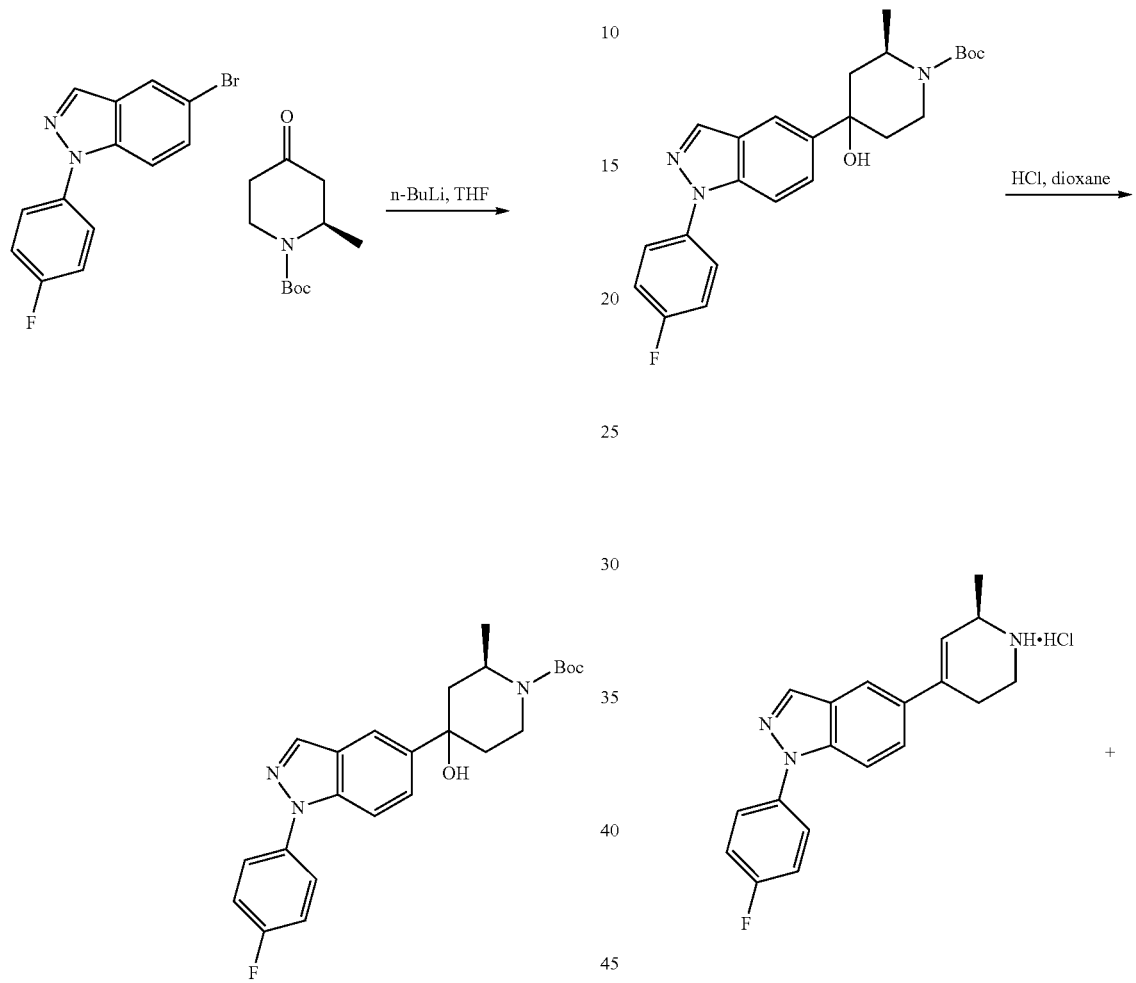

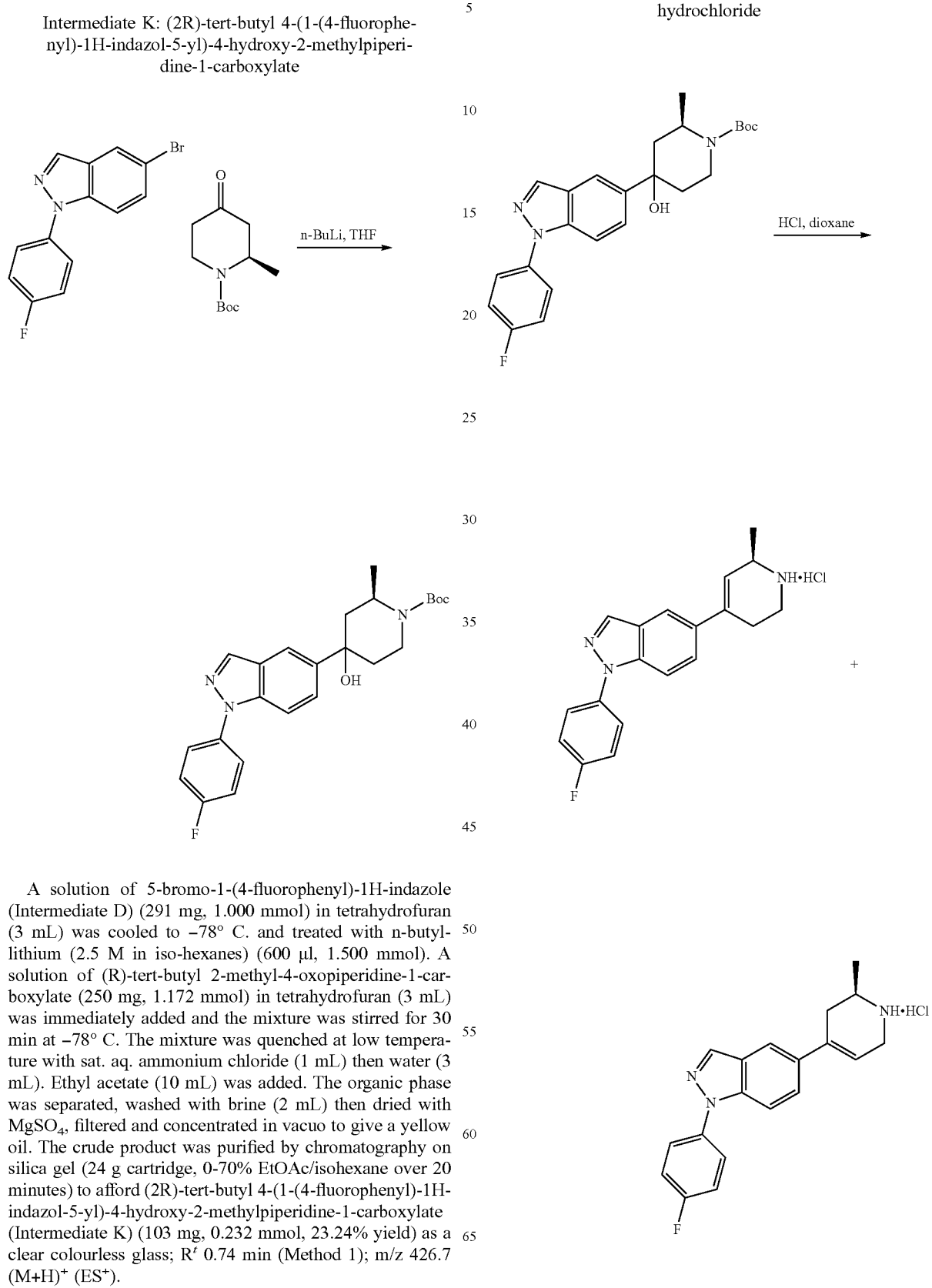

A solution of 5-bromo-1-(4-fluorophenyl)-1H-indazole (Intermediate D) (291 mg, 1.000 mmol) in tetrahydrofuran (3 mL) was cooled to −78° C. and treated with n-butyl-lithium (2.5 M in iso-hexanes) (600 µl, 1.500 mmol). A solution of (R)-tert-butyl 2-methyl-4-oxopiperidine-1-carboxylate (250 mg, 1.172 mmol) in tetrahydrofuran (3 mL) was immediately added and the mixture was stirred for 30 min at −78° C. The mixture was quenched at low temperature with sat. aq. ammonium chloride (1 mL) then water (3 mL). Ethyl acetate (10 mL) was added. The organic phase was separated, washed with brine (2 mL) then dried with MgSO$_4$, filtered and concentrated in vacuo to give a yellow oil. The crude product was purified by chromatography on silica gel (24 g cartridge, 0-70% EtOAc/isohexane over 20 minutes) to afford (2R)-tert-butyl 4-(1-(4-fluorophenyl)-1H-indazol-5-yl)-4-hydroxy-2-methylpiperidine-1-carboxylate (Intermediate K) (103 mg, 0.232 mmol, 23.24% yield) as a clear colourless glass; R$^t$ 0.74 min (Method 1); m/z 426.7 (M+H)$^+$ (ES$^+$).

217

(2R)-tert-Butyl 4-(1-(4-fluorophenyl)-1H-indazol-5-yl)-4-hydroxy-2-methylpiperidine-1-carboxylate (Intermediate K) (100 mg, 0.226 mmol) was dissolved in HCl (4 M in 1,4-dioxane) (3 mL, 12.00 mmol) and stirred at room temperature for 15 minutes. The yellow oily suspension was concentrated in vacuo to give a 1:1 mixture of (R)-1-(4-fluorophenyl)-5-(6-methyl-1,2,3,6-tetrahydropyridin-4-yl)-1H-indazole hydrochloride and (R)-1-(4-fluorophenyl)-5-(2-methyl-1,2,3,6-tetrahydropyridin-4-yl)-1H-indazole hydrochloride (Intermediate L) (87 mg, 100%) which was used without further purification; $R^t$ 0.39 and 0.44 min (Method 1); m/z 308.2 (M+H)$^+$ (ES$^+$).

Intermediate M: (R)-1-(4-fluorophenyl)-5-(6-methyl-1-((1-propyl-1H-pyrazol-4-yl)sulfonyl)-1,2,3,6-tetrahydropyridin-4-yl)-1H-indazole and (R)-1-(4-fluorophenyl)-5-(2-methyl-1-((1-propyl-1H-pyrazol-4-yl)sulfonyl)-1,2,3,6-tetrahydropyridin-4-yl)-1H-indazole

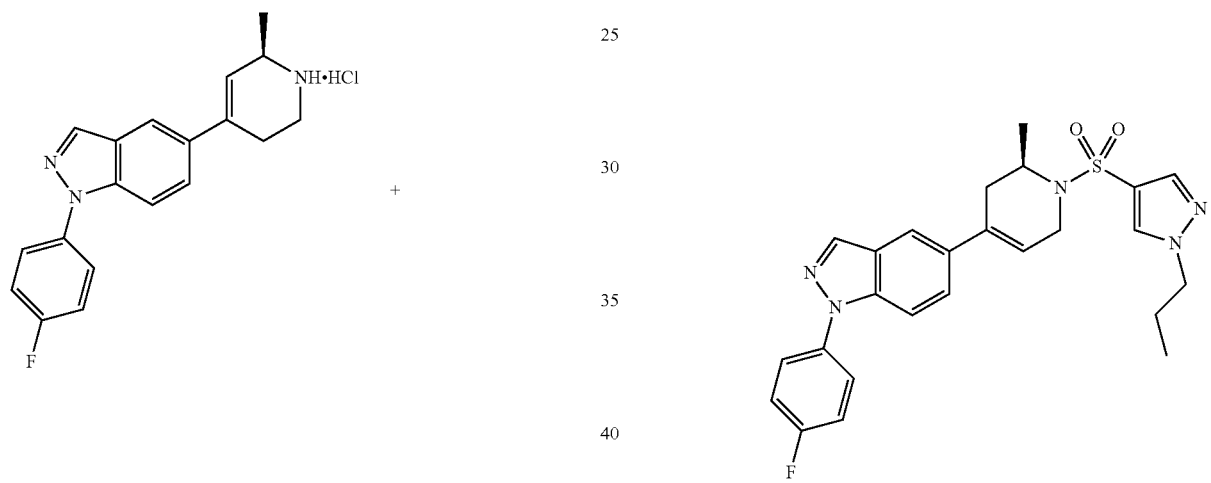

A 1:1 mixture of (R)-1-(4-fluorophenyl)-5-(6-methyl-1,2,3,6-tetrahydropyridin-4-yl)-1H-indazole hydrochloride and (R)-1-(4-fluorophenyl)-5-(2-methyl-1,2,3,6-tetrahydropyridin-4-yl)-1H-indazole hydrochloride (Intermediate L) (87 mg, 0.226 mmol) was suspended in dichloromethane (3 mL). 1-Propyl-1H-pyrazole-4-sulfonyl chloride (70.7 mg, 0.339 mmol) was added followed by triethylamine (0.1 ml, 0.717 mmol). The mixture was heated to reflux for 1 hour. Dichloromethane (10 mL) and water (5 mL) were added. The organic phase was separated, dried by passing through a hydrophobic frit and concentrated in vacuo. The crude product was purified by chromatography on silica gel (12 g cartridge, 0-100% EtOAc/isohexane) to afford a 1:1 mixture of (R)-1-(4-fluorophenyl)-5-(6-methyl-1-((1-propyl-1H-pyrazol-4-yl)sulfonyl)-1,2,3,6-tetrahydropyridin-4-yl)-1H-indazole and (R)-1-(4-fluorophenyl)-5-(2-methyl-1-((1-propyl-1H-pyrazol-4-yl)sulfonyl)-1,2,3,6-tetrahydropyridin-4-yl)-1H-indazole (Intermediate M) (53 mg, 0.103 mmol, 45.5% yield) as a clear colourless oil; $R^t$ 0.75 min (Method 1); m/z 480.3 (M+H)$^+$ (ES$^+$).

Example 8: 1-(4-fluorophenyl)-5-((2R)-2-methyl-1-((1-propyl-1H-pyrazol-4-yl)sulfonyl)piperidin-4-yl)-1H-indazole
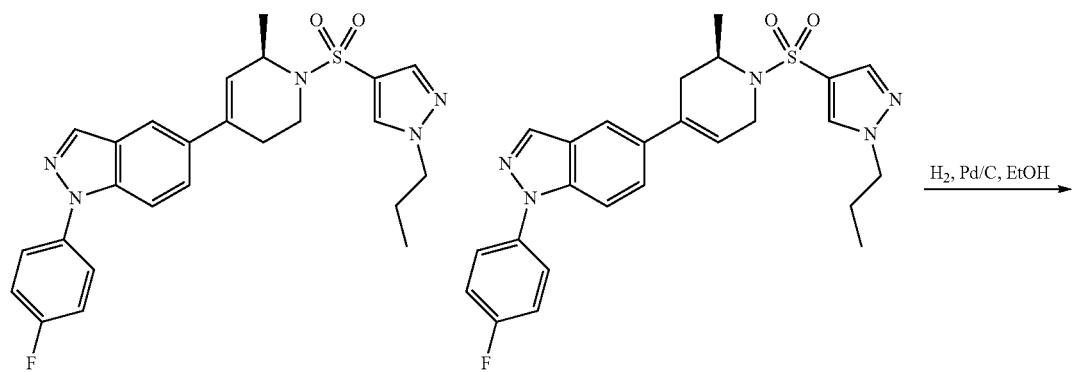
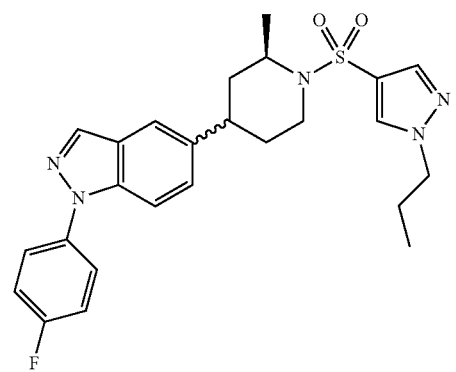

A 1:1 mixture of (R)-1-(4-fluorophenyl)-5-(2-methyl-1-((1-propyl-1H-pyrazol-4-yl)sulfonyl)-1,2,3,6-tetrahydropyridin-4-yl)-1H-indazole (25 mg, 0.048 mmol) and (R)-1-(4-fluorophenyl)-5-(6-methyl-1-((1-propyl-1H-pyrazol-4-yl)sulfonyl)-1,2,3,6-tetrahydropyridin-4-yl)-1H-indazole (Intermediate M) (25 mg, 0.048 mmol) was dissolved in ethanol (2 mL) and tetrahydrofuran (1 mL). Palladium on carbon (type 39, 10% Pd, 50 wt % water) (10 mg, 4.70 µmol) was added and the mixture was stirred under 5 bar hydrogen pressure for 4 hours. The mixture was filtered through Celite and concentrated in vacuo. The crude product was purified by chromatography on silica gel (12 g cartridge, 0-100% EtOAc/isohexane) to give (R)-1-(4-fluorophenyl)-5-(2-methyl-1-((1-propyl-1H-pyrazol-4-yl)sulfonyl)piperidin-4-yl)-1H-indazole (Example 8) (43 mg, 0.089 mmol, 92% yield) as a 1.4:1 mixture of diastereoisomers; $R^t$ 1.74 and 1.76 min (Method 1); m/z 482.3 (M+H)$^+$ (ES$^+$).

Example 9: 1-(4-fluorophenyl)-5-((2R,4R)-2-methyl-1-((1-propyl-1H-pyrazol-4-yl)sulfonyl)piperidin-4-yl)-1H-indazole and Example 10: 1-(4-fluorophenyl)-5-((2R)-2-methyl-1-((1-propyl-1H-pyrazol-4-yl)sulfonyl)piperidin-4-yl)-1H-indazole 4R)-2-methyl-1-((1-propyl-1H-pyrazol-4-yl)sulfonyl)piperidin-4-yl)-1H-indazole (Example 9) (10.5 mg, 0.022 mmol) as a colourless glass; $R^t$ 1.77 min (Method 1); m/z 482.3 (M+H)$^+$ (ES$^+$); $\delta_H$ (DMSO-d6, 500 MHz) 8.47 (s, 1H), 8.30 (d, J 0.9, 1H), 7.89 (d, J 0.8, 1H), 7.79 (dd, J 9.0, 4.8, 2H), 7.73 (d, J 8.8, 1H), 7.67 (s, 1H), 7.46-7.39 (m, 2H), 7.38 (dd, J 8.9, 1.7, 1H), 4.18 (t, J 6.9, 2H), 3.90 (dt, J 12.2, 4.2, 1H), 2.84-2.63 (m, 3H), 2.01-1.91 (m, 1H), 1.89-1.80 (m, 3H), 1.80-1.71 (m, 1H), 1.70-1.59 (m, 1H), 1.37 (d, J 6.3, 3H), 0.83 (t, J 7.4, 3H); and 1-(4-fluorophenyl)-5-((2R, 4S)-2-methyl-1-((1-propyl-1H-pyrazol-4-yl)sulfonyl)piperidin-4-yl)-1H-indazole (Example 10) (15.1 mg, 0.031 mmol) as a colourless glass; $R^t$ 1.74 min (Method 1); m/z 482.3 (M+H)$^+$ (ES$^+$); $\delta_H$ (DMSO-d6, 500 MHz) 8.43 (s, 1H), 8.29 (d, J 0.9, 1H), 7.87 (d, J 0.7, 1H), 7.79 (dd, J 9.0, 4.8, 2H), 7.72 (d, J 8.8, 1H), 7.62 (s, 1H), 7.43 (app. t, J 8.8, 2H), 7.33 (dd, J 8.9, 1.7, 1H), 4.35-4.26 (m, 1H), 4.15 (t, J 6.8, 2H), 3.81-3.70 (m, 1H), 3.20-3.02 (m, 2H), 1.88-1.70 (m, 4H), 1.70-1.63 (m, 1H), 1.53 (qd, J 12.7, 4.6, 1H), 1.18 (d, J 6.9, 3H), 0.80 (t, J 7.4, 3H).

Example 11: (R)-1-(4-fluorophenyl)-6-methyl-5-(2-methyl-1-((1-propyl-1H-pyrazol-4-yl)sulfonyl)-1,2,3,6-tetrahydropyridin-4-yl)-1H-indazole

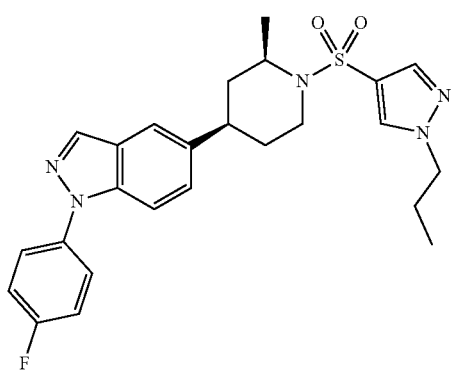

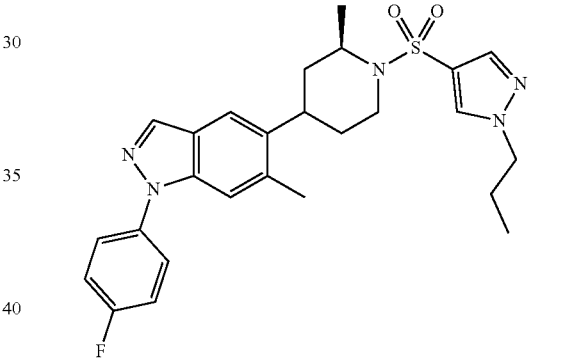

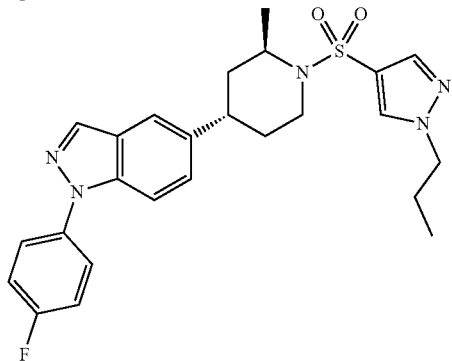 [SMILES: CCCn1cc(S(=O)(=O)N2CCC(c3cc4cnn(-c5ccc(F)cc5)c4cc3C)C[C@H]2C)cn1]

(R)-1-(4-Fluorophenyl)-5-(2-methyl-1-((1-propyl-1H-pyrazol-4-yl)sulfonyl)piperidin-4-yl)-1H-indazole (Example 8) (32 mg, 0.066 mmol) as a 1.4:1 mixture of diastereoisomers was dissolved to 20 mg/mL in ethanol without the need to sonicate or heat and was then separated by chiral SFC on a Waters prep 15 with UV detection by DAD at 210-400 nm, 40° C., 120 bar on a Chiralpak® IA, Column (1×25 cm, 5 µm particle size) flow rate 15 mL/min$^{-1}$ using 25% ethanol. Combined fractions were then concentrated in vacuo to give 1-(4-fluorophenyl)-5-((2R, A mixture of (R)-1-(4-fluorophenyl)-6-methyl-5-(6-methyl-1-((1-propyl-1H-pyrazol-4-yl)sulfonyl)-1,2,3,6-tetrahydropyridin-4-yl)-1H-indazole and (R)-1-(4-fluorophenyl)-6-methyl-5-(2-methyl-1-((1-propyl-1H-pyrazol-4-yl)sulfonyl)-1,2,3,6-tetrahydropyridin-4-yl)-1H-indazole (41 mg, 0.128 mmol), prepared by similar methods to those described for Intermediate M, was dissolved in 50 mg/mL in MeOH without the need to sonicate or heat, filtered and was then separated by chiral SFC on a Waters prep 15 with UV detection by DAD at 210-400 nm, 40° C., 120 bar on a LUX C4, Column (1×25 cm, 5 µm particle size) flow rate 15 mL/min-1 using 35% MeOH. Combined fractions were then concentrated in vacuo to give (R)-1-(4-fluorophenyl)-6-methyl-5-(2-methyl-1-((1-propyl-1H-pyrazol-4-yl)sulfonyl)-1,2,3,6-tetrahydropyridin-4-yl)-1H-indazole (Example 11) (10.5 mg, 0.021 mmol) as a colourless tar; $R^t$ 1.80 min (Method 1); m/z 494.3 (M+H)$^+$ (ES$^+$); $\delta_H$ (DMSO-d6, 500 MHz) 8.45 (s, 1H), 8.26 (s, 1H), 7.90 (s, 1H), 7.78 (dd, J 9.0, 4.8, 1H), 7.62-7.56 (m, 1H), 7.42 (app. t, J 8.8, 1H), 7.33 (s, 1H), 5.60-5.55 (m, 1H), 4.32 (p, J 6.6, 1H), 4.24-4.11 (m, 4H), 3.78-3.68 (m, 1H), 2.27 (s, 3H), 1.94 (br. d, J 17.11H), 1.82 (h, J 7.2, 2H), 1.16 (d, J 6.8, 3H), 0.80 (t, J 7.4, 3H). The other regioisomer was not isolated cleanly.

Example 12: 1-(4-fluorophenyl)-6-methyl-5-((2R,4R)-2-methyl-1-((1-propyl-1H-pyrazol-4-yl)sulfonyl)piperidin-4-yl)-1H-indazole and Example 13: 1-(4-fluorophenyl)-6-methyl-5-((2R,4S)-2-methyl-1-(1-propyl-1H-pyrazol-4-yl)sulfonyl)piperidin-4-yl)-1H-indazole

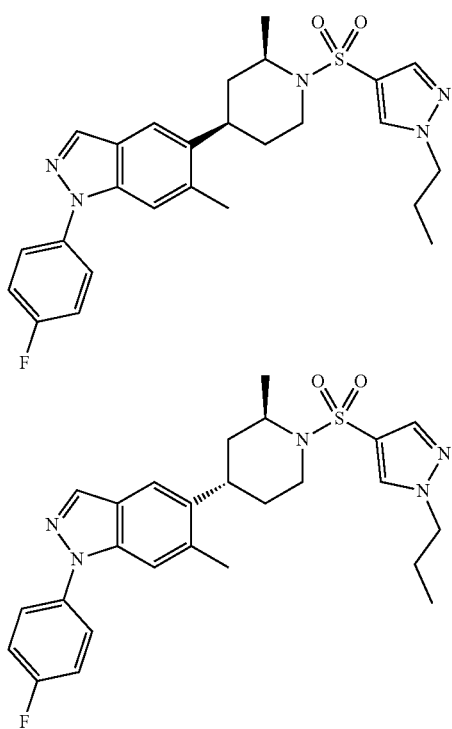

Example 14: (S)-(1-((1-(cyclopropylmethyl)-1H-pyrazol-4-yl)sulfonyl)-4-(1-(4-fluorophenyl)-1H-indazol-5-yl)piperazin-2-yl)methanol

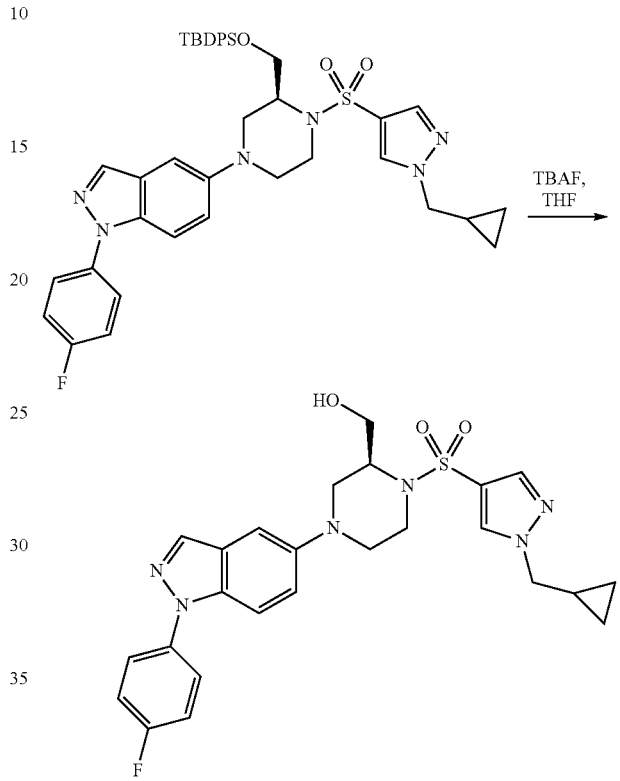

A mixture of 1-(4-fluorophenyl)-6-methyl-5-((2R,4R)-2-methyl-1-((1-propyl-1H-pyrazol-4-yl)sulfonyl)piperidin-4-yl)-1H-indazole and 1-(4-fluorophenyl)-6-methyl-5-((2R,4S)-2-methyl-1-((1-propyl-1H-pyrazol-4-yl)sulfonyl)piperidin-4-yl)-1H-indazole (22 mg, 0.045 mmol), prepared by similar methods to those described for Example 7, was dissolved in 50 mg/mL in MeOH without the need to sonicate or heat, filtered and was then separated by chiral SFC on a Waters prep 15 with UV detection by DAD at 210-400 nm, 40° C., 120 bar on a Chiralpak® IA, Column (1×25 cm, 5 μm particle size) flow rate 15 mL/min-1 using 25% ethanol. Combined fractions were then concentrated in vacuo to give 1-(4-fluorophenyl)-6-methyl-5-((2R,4R)-2-methyl-1-((1-propyl-1H-pyrazol-4-yl)sulfonyl)piperidin-4-yl)-1H-indazole (Example 12) (10.2 mg, 0.020 mmol) as a colourless glass; $R^t$ 1.80 min (Method 1); m/z 496.3 (M+H)$^+$ (ES$^+$); $\delta_H$ (DMSO-d6, 500 MHz) 8.47 (s, 1H), 8.23 (s, 1H), 7.91 (s, 1H), 7.81-7.72 (m, 2H), 7.68 (s, 1H), 7.58 (s, 1H), 7.45-7.30 (m, 2H), 4.17 (t, J=6.8 Hz, 2H), 3.92-3.84 (m, 1H), 2.97-2.69 (m, 3H), 2.35 (s, 3H), 2.01-1.88 (m, 1H), 1.88-1.72 (m, 3H), 1.72-1.58 (m, 2H), 1.38 (d, J=6.3 Hz, 3H), 0.83 (t, J=7.5 Hz, 3H); and 1-(4-fluorophenyl)-6-methyl-5-((2R,4S)-2-methyl-1-((1-propyl-1H-pyrazol-4-yl)sulfonyl)piperidin-4-yl)-1H-indazole (10.1 mg, 0.020 mmol) (Example 13) as a colourless glass; $R^t$ 1.79 min (Method 1); m/z 496.4 (M+H)$^+$ (ES$^+$); $\delta_H$ (DMSO-d6, 500 MHz) 8.44 (s, 1H), 8.21 (s, 1H), 7.88 (s, 1H), 7.78 (dd, J 9.0, 4.8, 2H), 7.61 (s, 1H), 7.51 (s, 1H), 7.42 (t, J 8.8, 2H), 4.36-4.25 (m, 1H), 4.16 (t, J=6.8 Hz, 2H), 3.84-3.72 (m, 1H), 3.24-3.10 (m, 2H), 2.46 (s, 3H), 1.83 (h, J 7.2, 2H), 1.77-1.55 (m, 4H), 1.22 (d, J 6.9, 3H), 0.81 (t, J 7.4, 3H).

To a solution of (S)-5-(3-(((tert-butyldiphenylsilyl)oxy)methyl)-4-((1-(cyclopropylmethyl)-1H-pyrazol-4-yl)sulfonyl)piperazin-1-yl)-1-(4-fluorophenyl)-1H-indazole (135 mg, 0.180 mmol), prepared by similar methods to those described for Example 3, in tetrahydrofuran (2 mL) at 0° C. was added tetrabutylammonium fluoride (1M in THF) (360 μl, 0.360 mmol) dropwise. The resultant pale yellow solution was stirred at 0° C. for 1 hour. The reaction mixture was quenched with a solution of sodium bicarbonate (10 mL) and extracted with ethyl acetate (3×10 mL). The organic layers were combined and washed with brine (1×5 mL) and passed through a hydrophobic frit. The solvent was removed under reduced pressure to afford a residue. The crude product was purified by chromatography on silica gel (24 g cartridge, 0-100% EtOAc/isohexane) to afford (S)-(1-((1-(cyclopropylmethyl)-1H-pyrazol-4-yl)sulfonyl)-4-(1-(4-fluorophenyl)-1H-indazol-5-yl)piperazin-2-yl)methanol (Example 14) (80 mg, 0.155 mmol, 86% yield) as a sticky colourless gum; $R^t$ 1.49 min (Method 1); m/z 511.5 (M+H)$^+$ (ES$^+$); $\delta_H$ (DMSO-d6, 500 MHz) 8.44 (s, 1H), 8.20 (d, J 0.9, 1H), 7.88 (s, 1H), 7.77 (app. dd, J 9.0, 4.8, 2H), 7.70 (d, J 9.2, 1H), 7.41 (t, J 8.8, 2H), 7.25 (dd, J 9.3, 2.3, 1H), 7.18 (d, J 2.2, 1H), 5.02 (obs. br. t, J 5.5, 1H), 4.02 (d, J 7.2, 2H), 3.95-3.90 (m, 1H), 3.79 (td, J 9.9, 5.6, 1H), 3.70 (dd, J 12.5, 8.8, 2H), 3.52-3.46 (m, 1H), 3.43 (br. d, J 11.8, 1H), 3.31-3.26 (obs. m, 1H), 2.63-2.56 (m, 2H), 1.25 (m, 1H), 0.53-0.47 (m, 2H), 0.39-0.33 (m, 2H).

Example 15: (S)-5-(4-((1-(cyclopropylmethyl)-1H-pyrazol-4-yl)sulfonyl)-3-(methoxymethyl)piperazin-1-yl)-1-(4-fluorophenyl)-1H-indazole

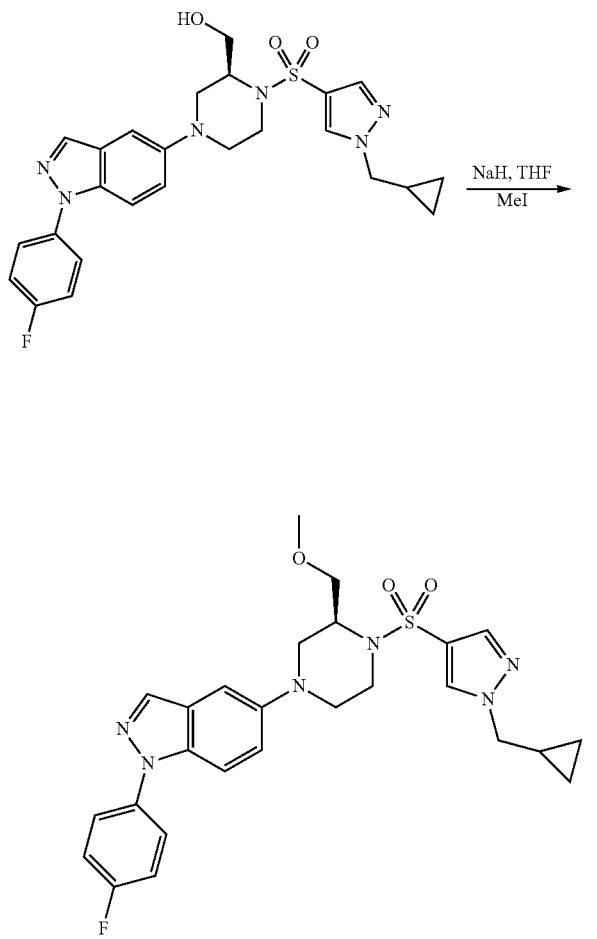

To a solution of (S)-(1-((1-(cyclopropylmethyl)-1H-pyrazol-4-yl)sulfonyl)-4-(1-(4-fluorophenyl)-1H-indazol-5-yl)piperazin-2-yl)methanol (Example 14) (60 mg, 0.118 mmol) in tetrahydrofuran (2 mL) at 0° C. was added sodium hydride (60% in mineral oil) (7.05 mg, 0.176 mmol) in one portion. The resultant white suspension was stirred at 0° C. for 30 minutes. Methyl iodide (9.55 µl, 0.153 mmol) was added and the resultant solution was stirred at room temperature for 15 hours. The reaction mixture was quenched with a saturated solution of sodium bicarbonate (10 mL) and extracted with ethyl acetate (3×10 mL). The organic layers were combined, washed with brine (5 mL), passed through a hydrophobic frit and the solvent was removed under reduced pressure to afford a yellow residue. The crude product was purified by chromatography on silica gel (12 g cartridge, 0-100% EtOAc/isohexane) to afford (S)-5-(4-((1-(cyclopropylmethyl)-1H-pyrazol-4-yl)sulfonyl)-3-(methoxymethyl)piperazin-1-yl)-1-(4-fluorophenyl)-1H-indazole (Example 15) (20 mg, 0.037 mmol, 31.9% yield) as a sticky colourless oil; $R^t$ 1.69 min (Method 1); m/z 525.4 (M+H)$^+$ (ES$^+$); $\delta_H$ (DMSO-d6, 500 MHz) 8.44 (d, J=0.7 Hz, 1H), 8.20 (d, J=0.9 Hz, 1H), 7.89 (d, J=0.8 Hz, 1H), 7.77 (dd, J=9.0, 4.8 Hz, 2H), 7.71 (d, J=9.1 Hz, 1H), 7.41 (t, J=8.8 Hz, 2H), 7.20 (dd, J=9.2, 2.3 Hz, 1H), 7.17 (d, J=2.2 Hz, 1H), 4.16-4.11 (m, 1H), 4.02 (d, J=7.2 Hz, 2H), 3.75-3.66 (m, 2H), 3.58 (br. d, J=12.3 Hz, 1H), 3.48 (dd, J=9.6, 6.0 Hz, 1H), 3.45 (br. d, J=12.1 Hz, 1H), 3.33 (m, 1H, overlapped with H$_2$O signal), 3.28 (s, 3H), 2.67 (dd, J=12.3, 3.7 Hz, 1H), 2.60 (td, J=11.7, 3.5 Hz, 1H), 1.25 (m, 1H), 0.53-0.47 (m, 2H), 0.38-0.34 (m, 2H).

Example 16: 5-(3-benzyl-1-(methylsulfonyl)pyrrolidin-3-yl)-1-(4-fluorophenyl)-6-methyl-1H-indazole Intermediate N: 1-(4-fluorophenyl)-6-methyl-5-(4,4,5-trimethyl-1,3,2-dioxaborolan-2-yl)-1H-indazole

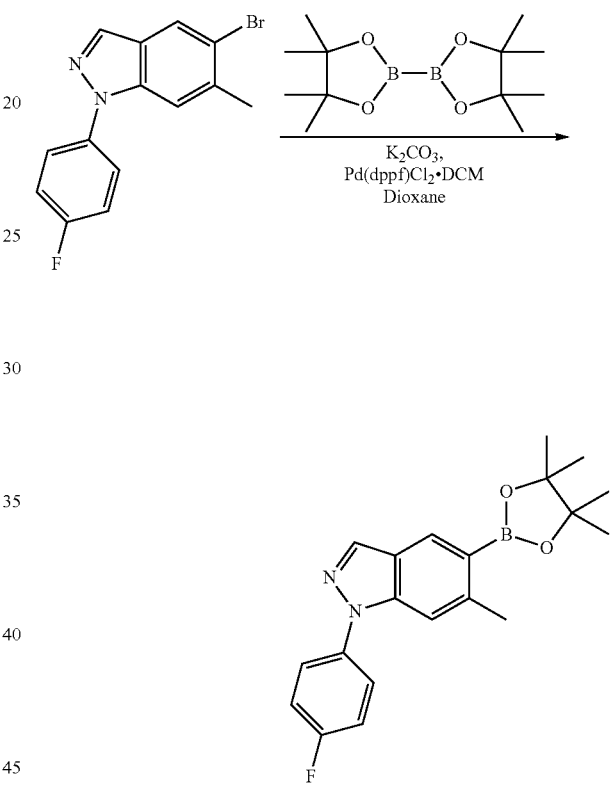

5-bromo-1-(4-fluorophenyl)-6-methyl-1H-indazole (Prepared using the method described for Intermediate D) (1.00 g, 3.27 mmol), 4,4,4',4',5,5,5',5'-octamethyl-2,2'-bi(1,3,2-dioxaborolane) (1.30 g, 5.12 mmol), potassium acetate (1.40 g, 14.27 mmol) and Pd(dppl)Cl$_2$·DCM (250 mg, 0.31 mmol) were suspended in 1,4-dioxane (15 mL). The mixture was evacuated and back filled with nitrogen (3×) then heated to 80° C. for 16 hours. The mixture was cooled to room temperature then filtered through Celite eluting with ethyl acteate (50 mL). The filtrate was washed with water (2×50 mL) and brine (50 mL) then dried over Na$_2$SO$_4$, filtered and concentrated in vacuo. The crude product was purified by chromatography on silica gel (80 g cartridge, 0-50% EtOAc/isohexane) to afford 1-(4-fluorophenyl)-6-methyl-5-(4,4,5,5-tetramethyl-1,3,2-dioxaborolan-2-yl)-1H-indazole (Intermediate N) (1.060 g, 2.4 mmol, 73%) as a pale yellow crystalline solid; $R^t$ 2.06 min (Method 1); m/z 353.4 (M+H)$^+$ (ES$^+$); $\delta_H$ (DMSO-d6, 500 MHz) δ 8.35 (s, 1H), 8.22 (s, 1H), 7.88-7.74 (m, 2H), 7.59-7.57 (m, 1H), 7.51-7.38 (m, 2H), 2.62 (s, 3H), 1.33 (s, 12H).

Intermediate O: 1-benzyl-3-(1-(4-fluorophenyl)-6-methyl-1H-indazol-5-yl)pyrrolidine-2,5-dione

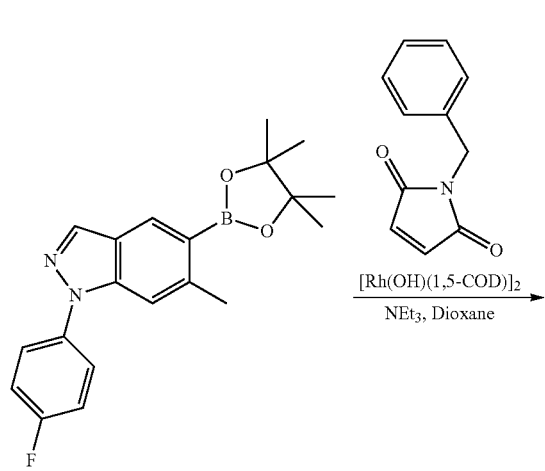

1-(4-fluorophenyl)-6-methyl-5-(4,4,5,5-tetramethyl-1,3,2-dioxaborolan-2-yl)-1H-indazole (Intermediate N) (1.060 g, 2.4 mmol), N-benzylmaleimide (0.50 g, 2.67 mmol) and hydroxy(cyclooctadiene)rhodium dimer (55 mg, 0.12 mmol) were suspended in a mixture of 1,4-dioxane (9 mL) and water (1 mL). Triethylamine (0.37 g, 3.6 mmol) was added and the mixture was evacuated and back-filled with nitrogen (3×). The dark brown mixture was heated to 50° C. overnight. The mixture was cooled to room temperature and concentrated in vacuo. The crude product was purified by chromatography on silica gel (80 g cartridge, 0-50% EtOAc/isohexane) to afford 1-benzyl-3-(1-(4-fluorophenyl)-6-methyl-1H-indazol-5-yl)pyrrolidine-2,5-dione (Intermediate O) (1.05 g, 2.0 mmol, 84%) as a pale yellow oil; R$^t$ 1.68 min (Method 1); m/z 414.5 (M+H)$^+$ (ES$^+$); $\delta_H$ (DMSO-d6, 500 MHz) δ 8.26 (s, 1H), 7.83-7.75 (m, 2H), 7.67 (s, 1H), 7.63 (s, 1H), 7.47-7.40 (m, 2H), 7.40-7.23 (m, 5H), 4.68 (s, 2H), 4.60 (dd, J=9.5, 5.1 Hz, 1H), 3.36 (dd, J=18.2, 9.5 Hz, 1H), 2.81 (dd, J=18.2, 5.2 Hz, 1H), 2.44 (s, 3H).

Intermediate P: 1,3-dibenzyl-3-(1-(4-fluorophenyl)-6-methyl-1H-indazol-5-yl)pyrrolidine-2,5-dione

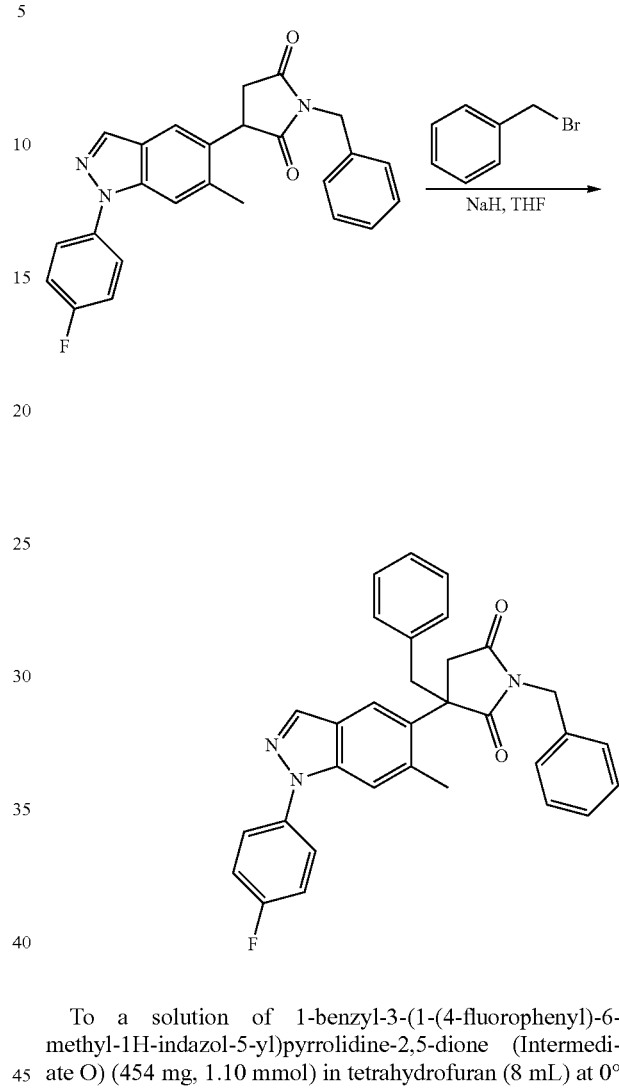

To a solution of 1-benzyl-3-(1-(4-fluorophenyl)-6-methyl-1H-indazol-5-yl)pyrrolidine-2,5-dione (Intermediate O) (454 mg, 1.10 mmol) in tetrahydrofuran (8 mL) at 0° C. was added sodium hydride (66 mg, 60% Wt, 1.65 mmol). The resultant dark purple solution was stirred for 30 minutes at 0° C., at which point benzyl bromide (376 mg, 2.20 mmol) was added and the resultant purple solution was stirred at room temperature for 2 hours. The reaction mixture was quenched at 0° C. by adding a saturated solution of sodium bicarbonate (30 mL) and extracted with ethyl acetate (3×25 mL). The organic layers were combined, washed with brine (10 mL) and passed through a hydrophobic frit. The solvent was removed to afford a colourless oil and the crude product was purified by chromatography on silica gel (40 g cartridge, 0-50% EtOAc/isohexane) to afford 1,3-dibenzyl-3-(1-(4-fluorophenyl)-6-methyl-1H-indazol-5-yl)pyrrolidine-2,5-dione (Intermediate P) (135 mg, 0.25 mmol, 23%) as a white solid; R$^t$ 1.99 min (Method 1); m/z 504.5 (M+H)$^+$ (ES$^+$); $\delta_H$ (DMSO-d6, 500 MHz) δ 8.35 (d, J=0.9 Hz, 1H), 8.11 (s, 1H), 7.83-7.77 (m, 2H), 7.68 (s, 1H), 7.47-7.39 (m, 2H), 7.31-7.20 (m, 8H), 7.15-7.11 (m, 2H), 4.33 (d, J=14.4 Hz, 1H), 4.25 (d, J=14.4 Hz, 1H), 3.62 (d, J=12.7 Hz, 1H), 3.40 (d, J=12.7 Hz, 1H), 3.22 (d, J=18.9 Hz, 1H), 3.05 (d, J=18.9 Hz, 1H), 2.21 (s, 3H).

229

Intermediate Q: 5-(1,3-dibenzylpyrrolidin-3-yl)-1-(4-fluorophenyl)-6-methyl-1H-indazole

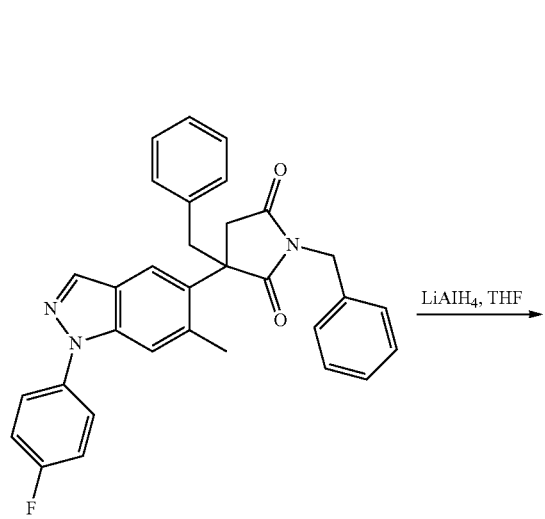

LiAlH₄, THF →

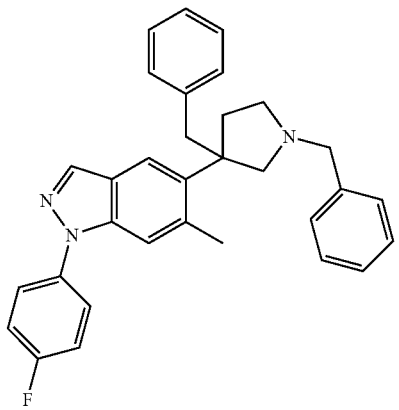

To a solution of 1,3-dibenzyl-3-(1-(4-fluorophenyl)-6-methyl-1H-indazol-5-yl)pyrrolidine-2,5-dione (Intermediate P) (135 mg, 0.26 mmol) in tetrahydrofuran (2 mL) was added lithium aluminum hydride (2 M in THF) (29 mg, 0.4 mL, 0.77 mmol) dropwise. The mixture was heated to 60° C. for 2 hours. After cooling to room temperature, the mixture was diluted with tetrahydrofuran (5 mL) then quenched carefully with water (0.2 mL), then 2 M aq. sodium hydroxide (0.2 mL), then water (0.4 mL). Na₂SO₄ was added and the mixture was filtered. After concentration of the filtrate 5-(1,3-dibenzylpyrrolidin-3-yl)-1-(4-fluorophenyl)-6-methyl-1H-indazole (Intermediate Q) (125 mg, 0.26 mmol, 102%) was isolated as a colourless oil; $R^t$ 1.23 min (Method 1); m/z 476.5 (M+H)⁺ (ES⁺); The product was used in the next step without further purification.

230

Intermediate R: 5-(3-benzylpyrrolidin-3-yl)-1-(4-fluorophenyl)-6-methyl-1H-indazole

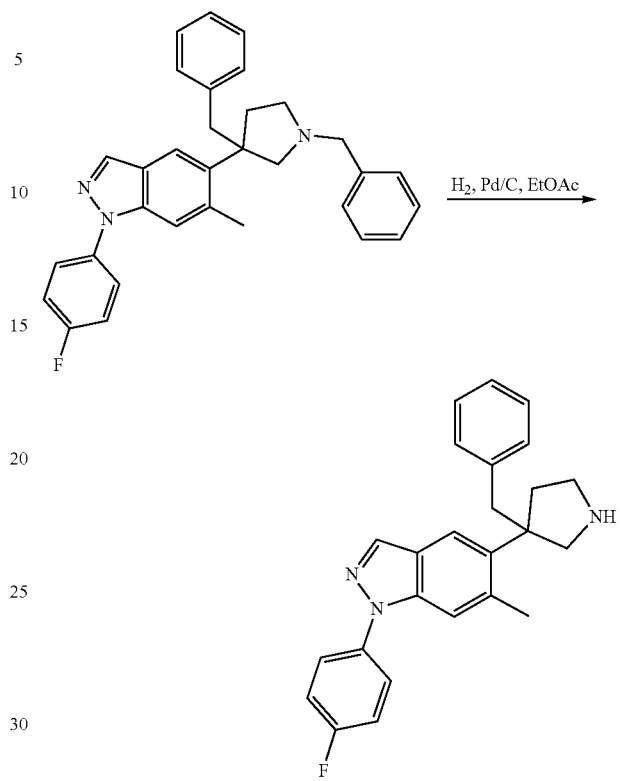

H₂, Pd/C, EtOAc →

5-(1,3-dibenzylpyrrolidin-3-yl)-1-(4-fluorophenyl)-6-methyl-1H-indazole (Intermediate Q) (130.0 mg, 0.25 mmol) was dissolved in ethyl acetate (5 mL). 10% Pd/C (type 39) (26 mg, 0.25 mmol) was added and the mixture was stirred at 50° C. under 5 bar hydrogen pressure overnight. The mixture was filtered through Celite eluting with ethyl acetate (3×5 mL) and methanol (3×5 mL). The combined filtrate was concentrated in vacuo to give 5-(3-benzylpyrrolidin-3-yl)-1-(4-fluorophenyl)-6-methyl-1H-indazole (Intermediate R) (100 mg, 0.21 mmol, 86%) as a colourless oil; $R^t$ 1.34 min (Method 4); m/z 386.5 (M+H)⁺ (ES⁺); $\delta_H$ (DMSO-d6, 500 MHz). The crude product was used in the next step without further purification.

Example 16: 5-(3-benzyl-1-(methylsulfonyl)pyrrolidin-3-yl)-1-(4-fluorophenyl)-6-methyl-1H-indazole

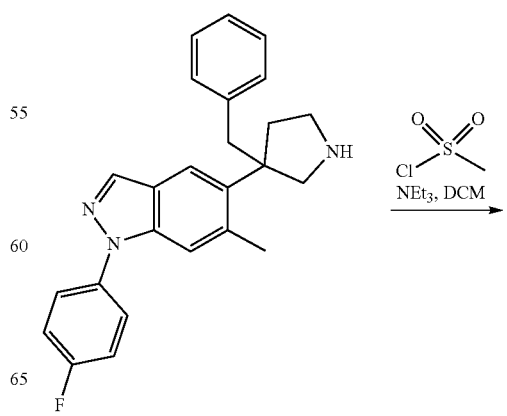

NEt₃, DCM →

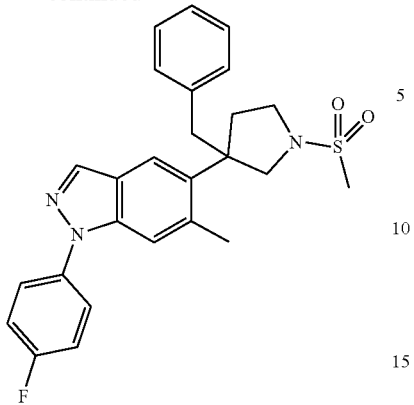

To a solution of 5-(3-benzylpyrrolidin-3-yl)-1-(4-fluorophenyl)-6-methyl-1H-indazole (Intermediate R) (30 mg, 0.63 mmol) in dichloromethane (2 mL) was added methanesulfonyl chloride (14 mg, 0.13 mmol) and triethylamine (32 mg, 0.32 mmol). The resultant yellow solution was stirred at room temperature for 18 hours. The reaction was quenched by adding a saturated solution of sodium bicarbonate (10 mL) and extracted with dichloromethane (3×10 mL). The organic layers were combined and passed through a hydrophobic frit. The solvent was removed under reduced pressure to afford a black residue. The crude product was purified by chromatography on silica gel (12 g cartridge, 0-50% EtOAc/isohexane) to afford 5-(3-benzyl-1-(methylsulfonyl)pyrrolidin-3-yl)-1-(4-fluorophenyl)-6-methyl-1H-indazole (Example 16) (5.0 mg, 11 μmol, 17%) as a white solid; $R^t$ 1.75 min (Method 1); m/z 464.1 (M+H)$^+$ (ES$^+$); $\delta_H$ (DMSO-d6, 500 MHz) δ 8.16 (s, 1H), 7.82 (dd, J=8.8, 4.8 Hz, 2H), 7.66 (s, 1H), 7.43 (t, J=8.7 Hz, 2H), 7.13-7.07 (m, 2H), 7.05 (t, J=7.3 Hz, 2H), 6.59 (d, J=7.4 Hz, 2H), 3.95 (br. d, J=9.4 Hz, 1H), 3.63 (br. q, J=9.0, 8.5 Hz, 1H), 3.50 (br. t, J=9.5 Hz, 1H), 3.44 (d, J=9.4 Hz, 1H), 3.14 (br. d, J=13.6 Hz, 1H), 3.02 (s, 3H) overlapped with 3.00 (m, 1H), 2.50 (m, 1H, hidden in DMSO signal),$^{(2)}$ 2.47 (s, 3H), 2.21 (q, J=10.6 Hz, 1H).

Example 17: (S)-5-(3-benzyl-1-((1-propyl-1H-pyrazol-4-yl)sulfonyl)pyrrolidin-3-yl)-1-(4-fluorophenyl)-6-methyl-1H-indazole Example 18: (R)-5-(3-benzyl-1-((1-propyl-1H-pyrazol-4-yl)sulfonyl)pyrrolidin-3-yl)-1-(4-fluorophenyl)-6-methyl-1H-indazole

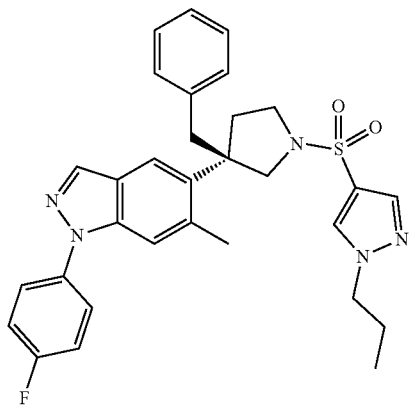

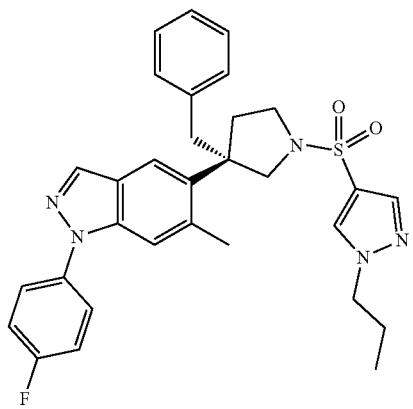

The racemic product was dissolved to 50 mg/mL in 1:1 dichloromethane: methanol by sonicating and heating, then filtered and separated by chiral SFC on a Waters prep 15 with UV detection by DAD at 210-400 nm, 40° C., 120 bar on a Chiralpak® IC (Daicel Ltd.) column (1×25 cm, 5 μm particle size), flow rate 15 mL/min-1 using 50% ethanol with 0.1% ammonia. The clean fractions were pooled, rinsed with ethanol and evaporated to dryness using a rotary evaporator. The residues were re-dissolved in ethanol, transferred into final vials and evaporated under a stream of nitrogen at 40° C. The samples were then further dried in a vacuum oven at 40° C./5 mbar over the weekend to afford (S)-5-(3-benzyl-1-((1-propyl-1H-pyrazol-4-yl)sulfonyl)pyrrolidin-3-yl)-1-(4-fluorophenyl)-6-methyl-1H-indazole (Example 17) (23 mg, 39 μmol, 27%) as a white solid; $R^t$ 1.89 min (Method 1); m/z 558.8 (M+H)$^+$ (ES$^+$); $\delta_H$ (DMSO-d6, 500 MHz) δ 8.53 (s, 1H), 8.13 (s, 1H), 7.97 (s, 1H), 7.84-7.77 (m, 2H), 7.63 (s, 1H), 7.43 (t, J=8.7 Hz, 2H), 7.11-7.00 (m, 4H), 6.48 (d, J=7.4 Hz, 2H), 4.07 (t, J=6.8 Hz, 2H), 3.90 (d, J=9.8 Hz, 1H), 3.54 (dd, J=16.2, 8.4 Hz, 1H), 3.36 (t, J=10.2 Hz, 1H), 3.21 (d, J=9.7 Hz, 1H), 2.97 (d, J=13.4 Hz, 1H), 2.65 (d, J=10.5 Hz, 1H), 2.44 (s, 3H), 2.37 (s, 1H), 1.98 (q, J=10.1 Hz, 1H), 1.71 (h, J=7.1 Hz, 2H), 0.67 (t, J=7.4 Hz, 3H) and (R)-5-(3-benzyl-1-((1-propyl-1H-pyrazol-4-yl)sulfonyl)pyrrolidin-3-yl)-1-(4-fluorophenyl)-6-methyl-1H-indazole (Example 18) (25 mg, 43 μmol, 29%) as a white solid. $R^t$ 1.88 min (Method 1); m/z 558.4 (M+H)$^+$ (ES$^+$); $\delta_H$ (DMSO-d6, 500 MHz) δ 8.53 (s, 1H), 8.13 (s, 1H), 7.97 (s, 1H), 7.83-7.76 (m, 2H), 7.63 (s, 1H), 7.43 (t, J=8.8 Hz, 2H), 7.11-7.00 (m, 4H), 6.48 (d, J=7.4 Hz, 2H), 4.07 (t, J=6.8 Hz, 2H), 3.90 (d, J=9.7 Hz, 1H), 3.60-3.49 (m, 1H), 3.36 (t, J=10.5 Hz, 1H), 3.21 (br. d, J=9.7 Hz, 1H), 2.97 (d, J=13.4 Hz, 1H), 2.65 (br. d, J=11.5 Hz, 1H), 2.44 (s, 3H), 2.37 (m, 1H), 1.98 (q, J=10.3 Hz, 1H), 1.71 (h, J=7.2 Hz, 2H), 0.67 (t, J=7.4 Hz, 3H).

Example 19: (3-benzyl-3-(1-(4-fluorophenyl)-6-methyl-1H-indazol-5-yl)pyrrolidin-1-yl)(1-methyl-1H-pyrazol-4-yl)methanone

Example 20: 5-(3-benzyl-1-methylpyrrolidin-3-yl)-1-(4-fluorophenyl)-6-methyl-1H-indazole

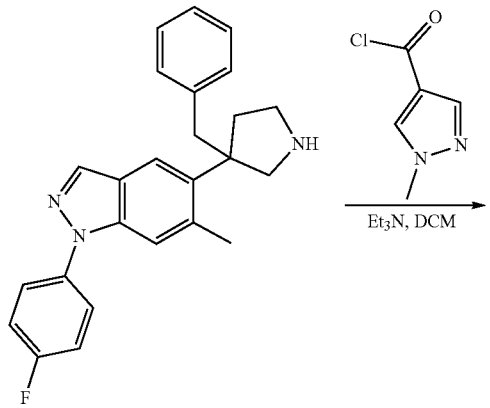

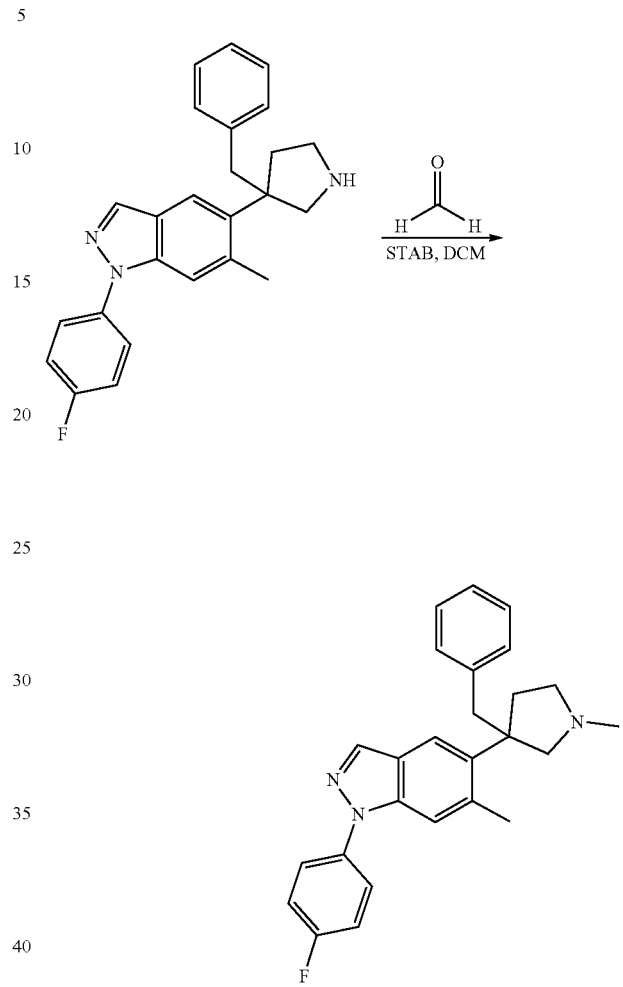

To a solution of 5-(3-benzylpyrrolidin-3-yl)-1-(4-fluorophenyl)-6-methyl-1H-indazole (Intermediate R) (30 mg, 78 µmol) and triethylamine (39 mg, 54 µL, 0.39 mmol) in dichloromethane (2 mL) was added 1-methyl-1H-pyrazole-4-carbonyl chloride (23 mg, 0.16 mmol). The resultant yellow solution was stirred for 16 hours. The reaction mixture was quenched with a saturated solution of sodium bicarbonate (10 mL) and extracted with dichloromethane (3×10 mL). The organic layers were combined and passed through a hydrophobic frit. The solvent was removed under reduced pressure to afford a yellow residue. The crude product was purified by chromatography on silica gel (12 g cartridge, 0-100% EtOAc/isohexane) and on silica gel (12 g cartridge, 0-10% MeOH/DCM) to afford (3-benzyl-3-(1-(4-fluorophenyl)-6-methyl-1H-indazol-5-yl)pyrrolidin-1-yl)(1-methyl-1H-pyrazol-4-yl)methanone (Example 19) (12 mg, 24 µmol, 31%) as a white solid; R$^r$ 1.60 min (Method 1); m/z 494.5 (M+H)$^+$ (ES$^+$); $\delta_H$ (DMSO-d6, 500 MHz, 363K) δ 8.16-8.12 (m, 2H), 7.84-7.79 (m, 3H), 7.62 (s, 1H), 7.43-7.37 (m, 2H), 7.27 (s, 1H), 7.10 (t, J=7.3 Hz, 1H), 7.04 (t, J=7.4 Hz, 2H), 6.63 (br. s, 2H), 4.38 (br. d, J=11.0 Hz, 1H), 3.91 (s, 3H), 3.81-3.65 (m, 2H), 3.08-3.02 (m, 2H), 2.62-2.55 (m, 1H), 2.53 (s, 4H), 2.35-2.25 (m, 1H).

To a solution of 5-(3-benzylpyrrolidin-3-yl)-1-(4-fluorophenyl)-6-methyl-1H-indazole (Intermediate R) (20 mg, 0.052 mmol) in dichloromethane (2 mL) was added a 37% solution of formaldehyde (8.4 mg, 0.10 mmol) in water (1 mL). The resultant solution was stirred at room temperature for 1 hour before sodium triacetoxyborohydride (33 mg, 0.16 mmol) was added. The resultant solution was stirred at room temperature overnight. The reaction was quenched by the addition of 10 mL of water and was extracted with dichloromethane (3×20 mL). The organic layers were combined and passed through a hydrophobic frit. The solvent was removed under reduced pressure to afford a colourless oil. The crude product was purified by chromatography on silica gel (12 g cartridge, 0-10% MeOH/DCM) to afford 5-(3-benzyl-1-methylpyrrolidin-3-yl)-1-(4-fluorophenyl)-6-methyl-1H-indazole (Example 20) (10 mg, 24 µmol, 47%) as a white solid; R$^r$ 1.69 min (Method 4); m/z 400.5 (M+H)$^+$ (ES$^+$); $\delta_H$ (DMSO-d6, 500 MHz) δ 8.11 (d, J=0.9 Hz, 1H), 7.86-7.77 (m, 2H), 7.64 (s, 1H), 7.46-7.39 (m, 2H), 7.07-6.99 (m, 3H), 6.98 (s, 1H), 6.54-6.49 (m, 2H), 3.19 (d, J=4.4 Hz, 1H), 3.17 (s, 1H), 3.12-3.06 (m, 2H), 2.53 (s, 3H), 2.45 (d, J=8.9 Hz, 1H), 2.38 (s, 3H) overlapped with 2.36-2.31 (m, 1H), (3) 2.30-2.23 (m, 1H), 2.20-2.13 (m, 1H).

Example 21: (4-(1-(4-fluorophenyl)-1H-indazol-5-yl)-1-((1-propyl-1H-pyrazol-4-yl)sulfonyl)piperidin-4-yl)(pyrrolidin-1-yl)methanone Intermediate S: 1-(tert-butyl) 4-methyl 4-(1-(4-fluorophenyl)-1H-indazol-5-yl)piperidine-1,4-dicarboxylate

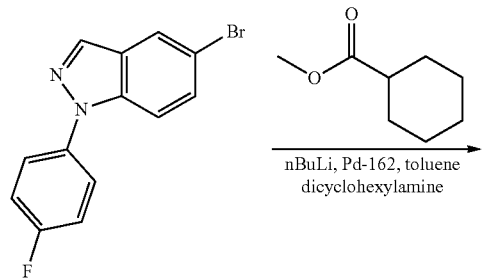

Example 21: Ethyl 4-(1-(4-fluorophenyl)-1H-indazol-5-yl)-1-((1-propyl-1H-pyrazol-4-yl)sulfonyl)piperidine-4-carboxylate

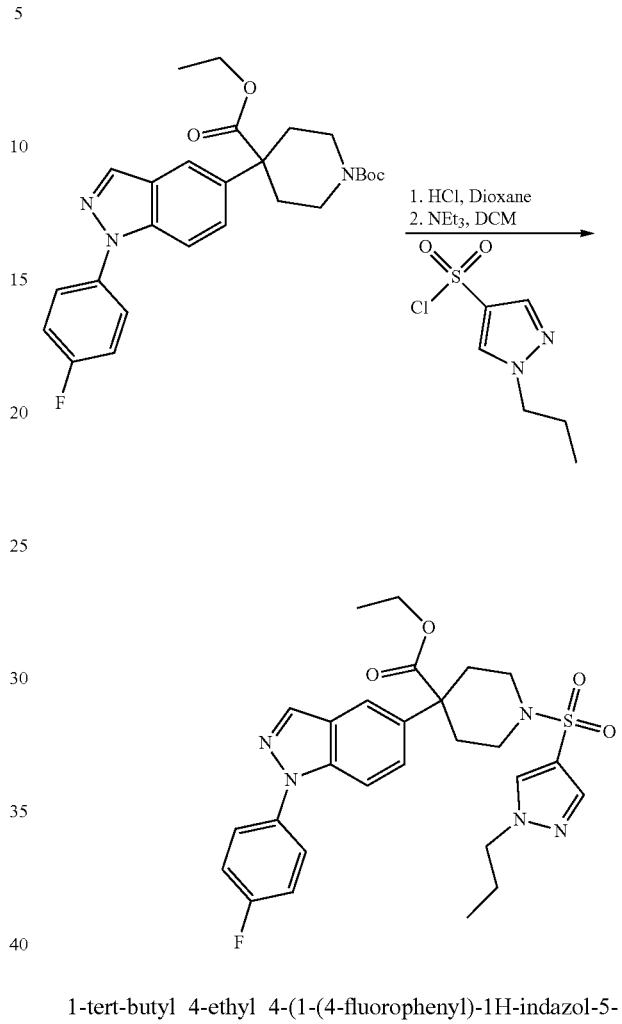

To a solution of dicyclohexylamine (0.6 ml, 3.02 mmol) in toluene (5 mL) which was cooled to 0° C. was added n-BuLi (2.5 M in hexanes) (1.1 ml, 2.75 mmol). The mixture was stirred at room temperature for 15 minutes before 1-tert-butyl 4-ethyl piperidine-1,4-dicarboxylate (0.685 ml, 2.79 mmol) was added. After stirring for a further 10 minutes, Pd-162 (33 mg, 0.082 mmol) and a solution of 5-bromo-1-(4-fluorophenyl)-1H-indazole (Intermediate D) (0.5 g, 1.718 mmol) in toluene (5 mL) was added. The mixture was heated to 100° C. for 20 minutes. The mixture was absorbed directly onto silica gel and purified by chromatography on silica gel (40 g cartridge, 0-50% EtOAc/isohexane) to afford 1-tert-butyl 4-ethyl 4-(1-(4-fluorophenyl)-1H-indazol-5-yl)piperidine-1,4-dicarboxylate (Intermediate S) (691 mg, 1.404 mmol, 82% yield) as a pale yellow glass that gradually crystallized on standing; $R^t$ 1.95 min (Method 1); m/z 468.4 (M+H)$^+$ (ES$^+$); $\delta_H$ (DMSO-d6, 500 MHz) δ 8.37 (s, 1H), 7.89 (d, J=1.8 Hz, 1H), 7.83-7.76 (m, 3H), 7.52 (dd, J=9.0, 1.8 Hz, 1H), 7.46-7.40 (m, 2H), 4.09 (q, J=7.1 Hz, 2H), 3.90-3.79 (m, 2H), 3.11-2.86 (m, 2H), 2.50-2.45 (m, 2H), 1.90-1.80 (m, 2H), 1.40 (s, 9H), 1.12 (t, J=7.1 Hz, 3H).

1-tert-butyl 4-ethyl 4-(1-(4-fluorophenyl)-1H-indazol-5-yl)piperidine-1,4-dicarboxylate (Intermediate S) (480 mg, 1.027 mmol) was dissolved in HCl (4M in dioxane) (5 mL, 20.00 mmol) and stirred at room temperature for 1 hour. The solvent was removed in vacuo and the residue was dissolved in dichloromethane (5 mL). 1-propyl-1H-pyrazole-4-sulfonyl chloride (257 mg, 1.232 mmol) was added as a solution in dichloromethane (1 mL) followed by addition of triethylamine (400 μl, 2.87 mmol). The mixture was stirred at room temperature overnight. The mixture was diluted with dichloromethane (10 mL), washed with 1 M aq. HCl (2×5 mL) and brine (5 mL) then dried by passing through a hydrophobic frit and concentrated in vacuo. The crude product was purified by chromatography on silica gel (24 g cartridge, 0-60% EtOAc/isohexane) to afford ethyl 4-(1-(4-fluorophenyl)-1H-indazol-5-yl)-1-((1-propyl-1H-pyrazol-4-yl)sulfonyl)piperidine-4-carboxylate (Example 21) (354 mg, 0.636 mmol, 62% yield) as a pale yellow solid foam; $R^t$ 1.72 min (Method 1); m/z 540.3 (M+H)$^+$ (ES$^+$); $\delta_H$ (DMSO-d6, 500 MHz) δ 8.41 (s, 1H), 8.36 (s, 1H), 7.87 (s, 1H), 7.82 (s, 1H), 7.80-7.73 (m, 3H), 7.51-7.46 (m, 1H), 7.46-7.39 (m, 2H), 4.12 (t, J=6.7 Hz, 2H), 3.98 (q, J=7.0 Hz, 2H), 3.53-3.43 (m, 2H), 2.62 (d, J=13.4 Hz, 2H), 2.41 (t, J=11.5 Hz, 2H), 2.12-2.03 (m, 2H), 1.75 (h, J=7.2 Hz, 2H), 0.98 (t, J=7.0 Hz, 3H), 0.69 (t, J=7.4 Hz, 3H).

Example 22: (4-(1-(4-fluorophenyl)-6-methyl-1H-indazol-5-yl)-1-((1-propyl-1H-pyrazol-4-yl)sulfonyl)piperidin-4-yl)(pyrrolidin-1-yl)methanone Intermediate T: 4-(1-(4-fluorophenyl)-1H-indazol-5-yl)-1-((1-propyl-1H-pyrazol-4-yl)sulfonyl)piperidine-4-carboxylic acid

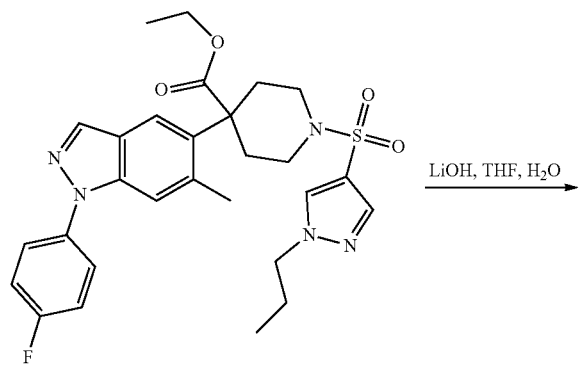

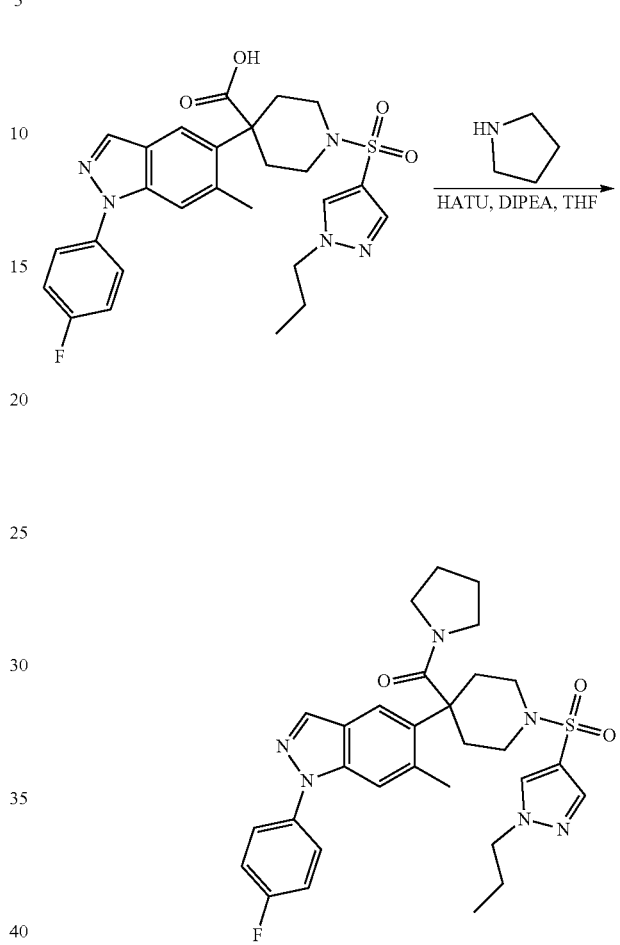

Ethyl 4-(1-(4-fluorophenyl)-6-methyl-1H-indazol-5-yl)-1-((1-propyl-1H-pyrazol-4-yl)sulfonyl)piperidine-4-carboxylate (Prepared using the same method as Example 21) (0.1 g, 0.181 mmol) was dissolved in a mixture of tetrahydrofuran and methanol (3:1, 4 mL). A solution of lithium hydroxide (0.022 g, 0.903 mmol) in water (0.5 mL) was added and the mixture was heated to 50° C. overnight. The mixture was concentrated in vacuo then suspended in a mixture of ethanol (5 mL) and 2 M aq. sodium hydroxide (5 mL). The mixture was heated to reflux for 3 days. The mixture was cooled to room temperature and the ethanol was removed in vacuo. The mixture was acidified with 1 M aq. HCl. The resulting solid formed was isolated and dried overnight at 50° C. in vacuo giving 4-(1-(4-fluorophenyl)-6-methyl-1H-indazol-5-yl)-1-((1-propyl-1H-pyrazol-4-yl)sulfonyl)piperidine-4-carboxylic acid (Intermediate T) (184 mg, 0.315 mmol, 174% yield) as a colourless solid; $R^t$ 0.66 min (Method 1); m/z 526.3 (M+H)$^+$ (ES$^+$); $\delta_H$ (DMSO-d6, 500 MHz) δ 12.68 (s, 1H), 8.41 (s, 1H), 8.28 (s, 1H), 7.88 (s, 1H), 7.83 (s, 1H), 7.81-7.76 (m, 2H), 7.59 (s, 1H), 7.45-7.39 (m, 2H), 4.14 (t, J=6.8 Hz, 2H), 3.45-3.37 (m, 2H), 2.82-2.75 (m, 2H), 2.49-2.46 (m, 2H), 2.44 (s, 3H), 2.12-2.04 (m, 2H), 1.78 (h, J=7.2 Hz, 2H), 0.75 (t, J=7.4 Hz, 3H).

Example 22: (4-(1-(4-fluorophenyl)-6-methyl-1H-indazol-5-yl)-1-((1-propyl-1H-pyrazol-4-yl)sulfonyl)piperidin-4-yl)(pyrrolidin-1-yl)methanone To a stirred suspension of 4-(1-(4-fluorophenyl)-6-methyl-1H-indazol-5-yl)-1-((1-propyl-1H-pyrazol-4-yl)sulfonyl)piperidine-4-carboxylic acid (Intermediate T) (40 mg, 0.076 mmol) in tetrahydrofuran (2 mL) was added HATU (50 mg, 0.131 mmol) and N,N-diisopropylethylamine (50 µl, 0.286 mmol). After stirring for 15 minutes at room temperature, pyrrolidine (10 µl, 0.122 mmol) was added and the mixture was stirred overnight at room temperature. The mixture was diluted with ethyl acetate (10 mL). The organic phase was washed with 1 M aq. HCl (10 mL), sat. aq. sodium bicarbonate (10 mL), and brine (10 mL) then dried over Na$_2$SO$_4$, filtered and concentrated in vacuo. The crude product was purified by chromatography on silica gel (12 g cartridge, 0-100% EtOAc/isohexane) to afford (4-(1-(4-fluorophenyl)-6-methyl-1H-indazol-5-yl)-1-((1-propyl-1H-pyrazol-4-yl)sulfonyl)piperidin-4-yl)(pyrrolidin-1-yl)methanone (Example 22) (17.3 mg, 0.029 mmol, 43% yield) as an amorphous colourless solid; $R^t$ 1.63 min (Method 1); m/z 579.3 (M+H)$^+$ (ES$^+$); $\delta_H$ (DMSO-d6, 500 MHz) δ 8.39 (s, 1H), 8.29 (s, 1H), 7.94 (s, 1H), 7.83-7.76 (m, 3H), 7.62 (s, 1H), 7.45-7.37 (m, 2H), 4.15 (t, J=6.8 Hz, 2H), 3.39 (s, 2H), 3.25 (t, J=6.9 Hz, 2H), 2.95 (br s, 2H), 2.49-2.42 (m, 4H), 2.32 (s, 3H), 2.03 (br s, 2H), 1.79 (h, J=7.1 Hz, 2H), 1.58-1.42 (m, 4H), 0.76 (t, J=7.4 Hz, 3H).

Example 23: 1-(4-fluorophenyl)-5-(4-(methoxymethyl)-1-((1-propyl-1H-pyrazol-4-yl)sulfonyl)piperidin-4-yl)-1H-indazole Intermediate U: (4-(1-(4-fluorophenyl)-1H-indazol-5-yl)-1-((1-propyl-1H-pyrazol-4-yl)sulfonyl)piperidin-4-yl)methanol

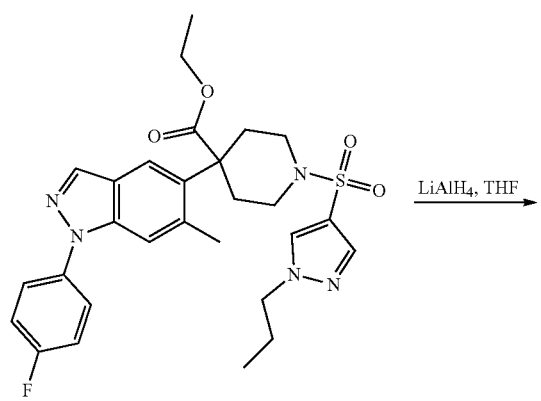

LiAlH₄, THF

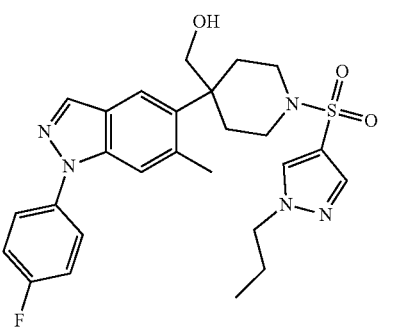

Example 24: 1-(4-fluorophenyl)-5-(4-(methoxymethyl)-1-((1-propyl-1H-pyrazol-4-yl)sulfonyl)piperidin-4-yl)-1H-indazole

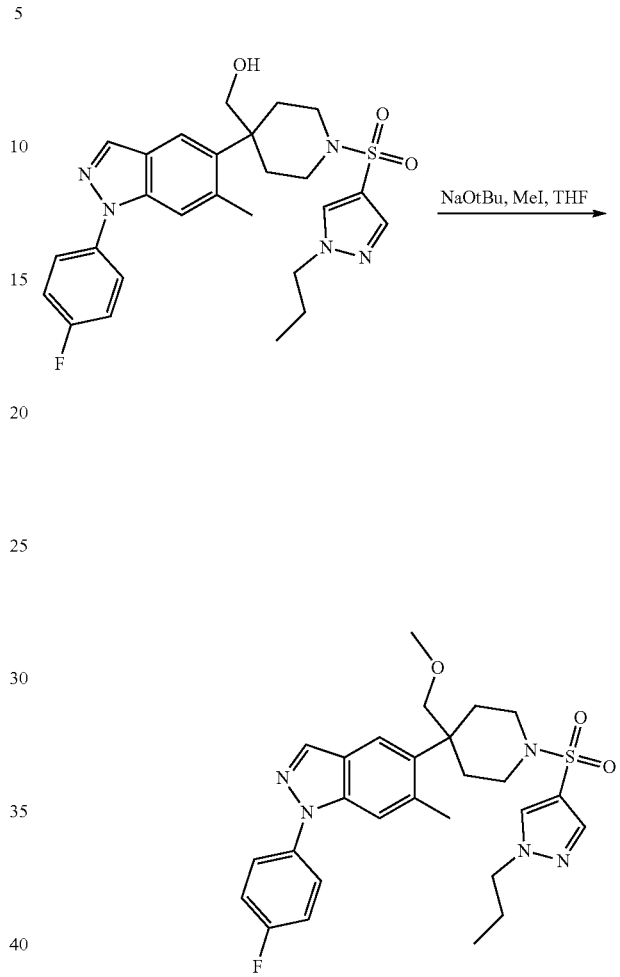

To a stirred solution of ethyl 4-(1-(4-fluorophenyl)-1H-indazol-5-yl)-1-((1-propyl-1H-pyrazol-4-yl)sulfonyl)piperidine-4-carboxylate (Prepared using the same method as Example 21) (150 mg, 0.278 mmol) in tetrahydrofuran (3 mL) was slowly added lithium aluminium hydride (2 M in THF) (0.3 mL, 0.60 mmol) over 5 minutes. The mixture was stirred at room temperature for 2 hours. Water (0.05 mL) was added, followed by 2 M aq. sodium hydroxide (0.05 mL) and then more water (0.15 mL). The mixture was stirred until gas evolution ceased then dried over Na₂SO₄ and filtered through Celite eluting with tetrahydrofuran (3×5 mL). The filtrate was concentrated in vacuo. The residue was dissolved in the minimum amount of dichloromethane then iso-hexane (5 mL) was added, resulting in a cloudy suspension. The solvent was removed in vacuo to give (4-(1-(4-fluorophenyl)-1H-indazol-5-yl)-1-((1-propyl-1H-pyrazol-4-yl)sulfonyl)piperidin-4-yl)methanol (Intermediate U) (130 mg, 0.259 mmol, 93% yield) as a colourless amorphous solid; R$^t$ 1.37 min (Method 1); m/z 498.4 (M+H)⁺ (ES⁺); δ$_H$ (DMSO-d6, 500 MHz) δ 8.27 (s, 1H), 8.22 (s, 1H), 7.80-7.72 (m, 3H), 7.69 (d, J=9.0 Hz, 1H), 7.67 (s, 1H), 7.48-7.39 (m, 3H), 4.69 (t, J=5.5 Hz, 1H), 3.98 (t, J=6.7 Hz, 2H), 3.35-3.28 (m, 4H), 2.39-2.27 (m, 4H), 2.03-1.93 (m, 2H), 1.53 (h, J=7.2 Hz, 2H), 0.32 (t, J=7.4 Hz, 3H).

To a stirred solution of (4-(1-(4-fluorophenyl)-6-methyl-1H-indazol-5-yl)-1-((1-propyl-1H-pyrazol-4-yl)sulfonyl)piperidin-4-yl)methanol (Intermediate U) (25 mg, 0.049 mmol) and methyl iodide (25 µl, 0.400 mmol) in tetrahydrofuran (1 mL) was added sodium tert-butoxide (2 M in THF) (40 µl, 0.080 mmol). The yellow mixture was stirred at room temperature for 1 hour then partitioned between dichloromethane (5 mL) and water (2 mL). The organic phase was separated, washed with brine (1 mL), dried by passing through a hydrophobic frit then concentrated in vacuo. The crude product was purified by chromatography on silica gel (12 g cartridge, 0-60% EtOAc/isohexane) to afford 1-(4-fluorophenyl)-5-(4-(methoxymethyl)-1-((1-propyl-1H-pyrazol-4-yl)sulfonyl)piperidin-4-yl)-6-methyl-1H-indazole (Example 24) (17.8 mg, 0.033 mmol, 67.9% yield) as an amorphous colourless solid. R$^t$ 1.67 min (Method 1); m/z 526.3 (M+H)⁺ (ES⁺); δ$_H$ (DMSO-d6, 500 MHz) δ 8.25 (s, 1H), 8.20 (d, J=0.9 Hz, 1H), 7.80-7.74 (m, 2H), 7.69 (d, J=5.2 Hz, 2H), 7.56 (s, 1H), 7.45-7.39 (m, 2H), 3.98 (t, J=6.7 Hz, 2H), 3.46 (s, 2H), 3.26-3.20 (m, 2H), 3.11 (s, 3H), 2.59 (s, 3H), 2.58-2.52 (m, 4H), 2.07-1.98 (m, 2H), 1.54 (h, J=7.2 Hz, 2H), 0.38 (t, J=7.4 Hz, 3H).

Example 25: 5-(4-benzyl-1-((1-propyl-1H-pyrazol-4-yl)sulfonyl)piperidin-4-yl)-1-(4-fluorophenyl)-1H-indazole Intermediate V: 4-(1-(4-fluorophenyl)-6-methyl-1H-indazol-5-yl)-1-((1-propyl-1H-pyrazol-4-yl)sulfonyl)piperidine-4-carbaldehyde

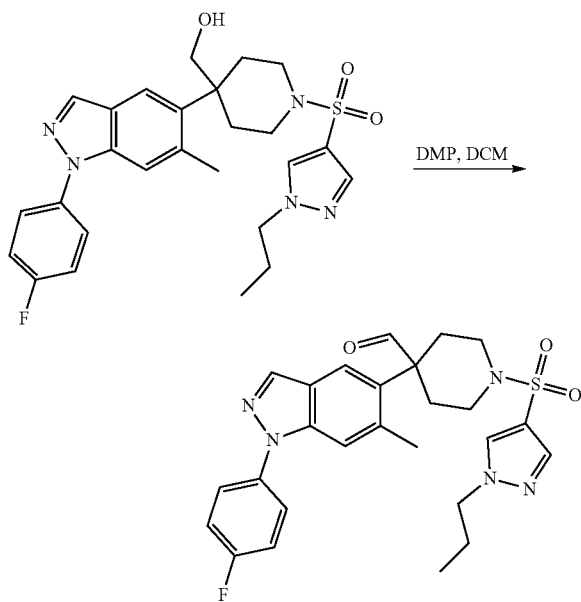

Dess-martinperiodinane (236 mg, 0.56 mmol) was added to a 0° C. solution of (4-(1-(4-fluorophenyl)-6-methyl-1H-indazol-5-yl)-1-((1-propyl-1H-pyrazol-4-yl)sulfonyl)piperidin-4-yl)methanol (Intermediate U) (237 mg, 0.46 mmol) in dichloromethane (3 mL). The reaction was allowed to warm to room temperature and left to stir overnight. The reaction was diluted with dichloromethane (10 mL) and washed with 2M $Na_2S_2O_3$ (20 mL) followed by saturated sodium carbonate (20 mL). The organic layer was dried over $MgSO_4$, filtered and concentrated in vacuo to afford 4-(1-(4-fluorophenyl)-6-methyl-1H-indazol-5-yl)-1-((1-propyl-1H-pyrazol-4-yl)sulfonyl)piperidine-4-carbaldehyde (Intermediate V) (277 mg, 0.46 mmol, 99%) as a white solid which was used in the next step without further purification; $R^t$ 0.73 min (Method 1); m/z 510.35 (M+H)$^+$ (ES$^+$).

Intermediate W: (4-(1-(4-fluorophenyl)-6-methyl-1H-indazol-5-yl)-1-((1-propyl-1H-pyrazol-4-yl)sulfonyl)piperidin-4-yl)(phenyl)methanol

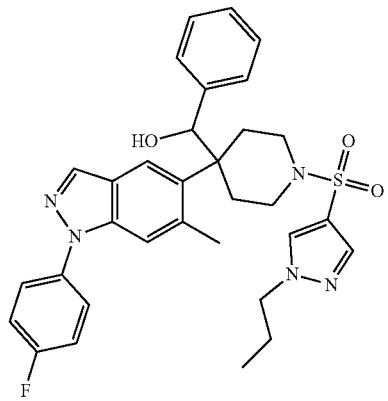

Phenylmagnesium chloride (2M in THF) (0.14 mL, 0.27 mmol) was added to a 0° C. solution of 4-(1-(4-fluorophenyl)-6-methyl-1H-indazol-5-yl)-1-((1-propyl-1H-pyrazol-4-yl)sulfonyl)piperidine-4-carbaldehyde (Intermediate V) (75 mg, 0.14 mmol) in tetrahydrofuran (1 mL). The reaction was allowed to warm to room temperature and stirred overnight. The reaction was quenched with water (10 mL) and the layers separated. The aqueous phase was extracted with dichloromethane (3×10 mL) and the combined organic layers were dried over $MgSO_4$, filtered and concentrated in vacuo. The crude product was purified by chromatography on silica gel (12 g cartridge, 0-50% EtOAc/isohexane) to afford (4-(1-(4-fluorophenyl)-6-methyl-1H-indazol-5-yl)-1-((1-propyl-1H-pyrazol-4-yl)sulfonyl)piperidin-4-yl)(phenyl)methanol (Intermediate W) (53 mg, 87 μmol, 63%) as a white powder. $R^t$ 1.68 min (Method 1); m/z 588.80 (M+H)$^+$ (ES$^+$).

Example 25: 5-(4-benzyl-1-((1-propyl-1H-pyrazol-4-yl)sulfonyl)piperidin-4-yl)-1-(4-fluorophenyl)-1H-indazole

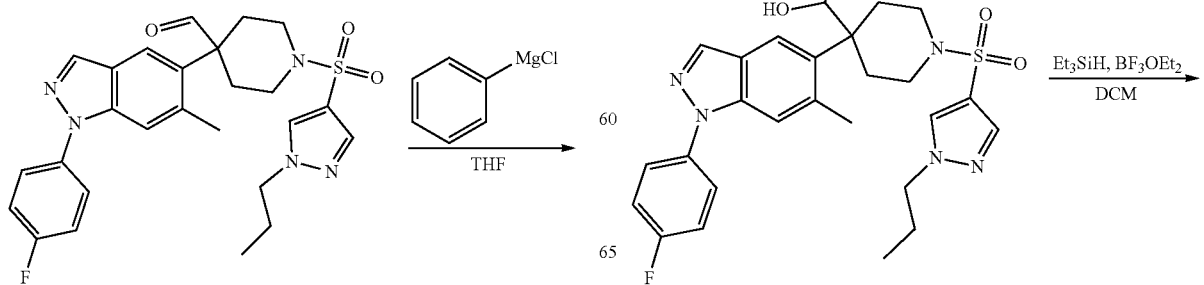

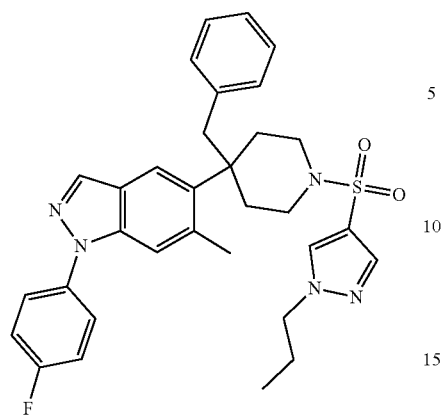

Boron trifluoride etherate (68 mg, 0.48 mmol) was added to a solution of (4-(1-(4-fluorophenyl)-6-methyl-1H-indazol-5-yl)-1-((1-propyl-1H-pyrazol-4-yl)sulfonyl)piperidin-4-yl)(phenyl)methanol (Intermediate W) (28 mg, 0.48 mmol) and triethylsilane (76 μL, 0.48 mmol) in dichloroethane (1 mL) and stirred at 80° C. for 4 hours. The reaction was quenched with water (10 mL) and the layers separated. The aqueous phase was extracted with dichloromethane (3×10 mL) and the combined organics dried over MgSO$_4$, filtered and concentrated in vacuo. The crude product was purified by chromatography on silica gel (12 g cartridge, 0-50% EtOAc/isohexane) to afford 5-(4-benzyl-1-((1-propyl-1H-pyrazol-4-yl)sulfonyl)piperidin-4-yl)-1-(4-fluorophenyl)-6-methyl-1H-indazole (Example 25) (2.00 mg, 0.33 mmol, 4%) as a white solid; R$^t$ 1.97 min (Method 1); m/z 572.50 (M+H)$^+$ (ES$^+$); (DMSO-d6, 500 MHz) δ 8.35 (d, J 0.8, 1H), 8.24 (d, J 0.9, 1H), 8.02 (s, 1H), 7.77 (d, J 0.7, 1H), 7.77-7.74 (m, 2H), 7.55 (s, 1H), 7.42-7.37 (m, 2H), 7.35-7.31 (m, 2H), 7.25 (t, J 7.6, 2H), 7.15-7.11 (m, 1H), 4.15 (t, J 7.0, 2H), 3.89 (d, J 11.0, 1H), 3.58-3.48 (m, 2H), 2.45 (s, 3H), 2.36-2.26 (m, 1H), 2.25-2.11 (m, 2H), 1.83 (h, J 7.2, 2H), 1.75-1.68 (m, 1H), 1.42-1.35 (m, 1H), 1.35-1.15 (m, 2H), 0.84 (t, J 7.4, 3H).

Example 26: 1-(4-fluorophenyl)-6-methyl-5-(3-methyl-1-((1-propyl-1H-pyrazol-4-yl)sulfonyl)piperidin-4-yl)-1H-indazole Intermediate X: 1-(4-fluorophenyl)-6-methyl-5-(3-methylpyridin-4-yl)-1H-indazole

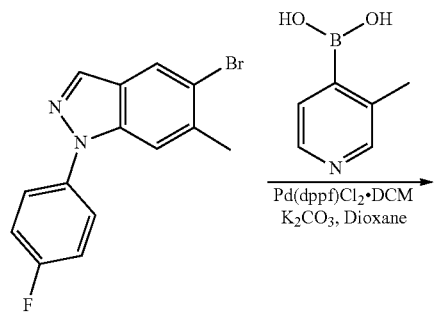

To a suspension of 5-bromo-1-(4-fluorophenyl)-6-methyl-1H-indazole (Prepared using the method described for Intermediate D) (0.5 g, 1.64 mmol), (3-methylpyridin-4-yl)boronic acid (0.25 g, 1.83 mmol), and Pd(dppl)Cl$_2$·DCM (0.1 g, 0.122 mmol) in dioxane (5 mL) was added a solution of potassium carbonate (0.75 g, 5.43 mmol) in water (2 mL). The mixture was evacuated and back filled with nitrogen (3×) then heated to 90° C. for 3 hours. The mixture was cooled to room temperature and diluted with ethyl acetate (10 mL). The organic phase was separated and absorbed directly on to silica gel. The crude product was purified by chromatography on silica gel (24 g cartridge, 0-100% EtOAc/isohexane) to afford 1-(4-fluorophenyl)-6-methyl-5-(3-methylpyridin-4-yl)-1H-indazole (Intermediate X) (324 mg, 0.99 mmol, 60% yield) as a pale brown semi-solid; R$^t$ 1.03 min (Method 1); m/z 3018.3 (M+H)$^+$ (ES$^+$); δ$_H$ (DMSO-d6, 500 MHz) δ 8.56 (s, 1H), 8.48 (d, J=4.9 Hz, 1H), 8.34 (s, 1H), 7.87-7.82 (m, 2H), 7.78 (s, 1H), 7.62 (s, 1H), 7.49-7.43 (m, 2H), 7.18 (d, J=4.9 Hz, 1H), 2.14 (s, 3H), 2.04 (s, 3H).

Intermediate Y: 1-(4-fluorophenyl)-6-methyl-5-(3-methylpiperidin-4-yl)-1H-indazole

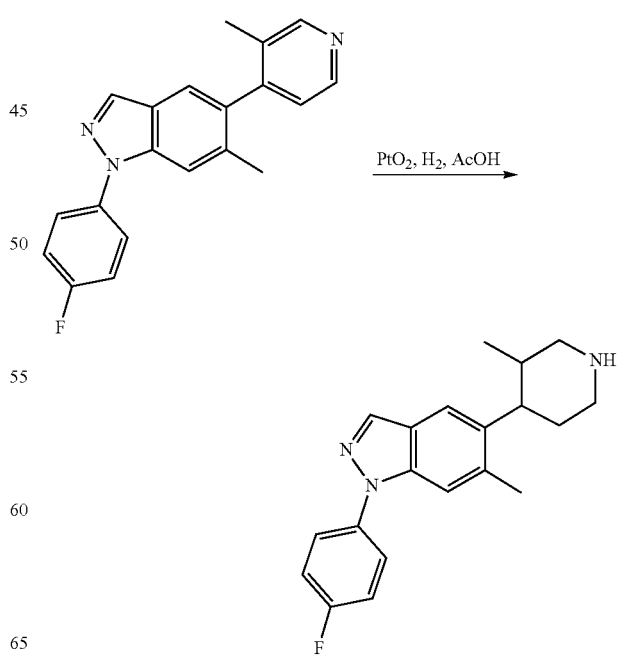

1-(4-fluorophenyl)-6-methyl-5-(3-methylpyridin-4-yl)-1H-indazole (Intermediate X) (100 mg, 0.315 mmol) was dissolved in acetic acid (2 mL). Platinum oxide (IV) (50 mg, 0.220 mmol) was added and the mixture was stirred under 5 bar hydrogen pressure at 50° C. for 16 hours. The mixture was filtered through a short plug of Celite eluting with methanol (5×10 mL). The filtrate was treated with SCX (3 g) and stirred for 15 minutes. The SCX was washed with methanol (100 mL) then the product was eluted with 0.7 M ammonia in methanol (5×10 mL). The combined fractions were concentrated in vacuo to give 1-(4-fluorophenyl)-6-methyl-5-((3R,4R)-3-methylpiperidin-4-yl)-1H-indazole (Intermediate Y) (92 mg, 0.284 mmol, 90% yield) as a yellow oil. The material was taken through crude into the final step.

Example 26: 1-(4-fluorophenyl)-6-methyl-5-(3-methyl-1-((1-propyl-1H-pyrazol-4-yl)sulfonyl)piperidin-4-yl)-1H-indazole

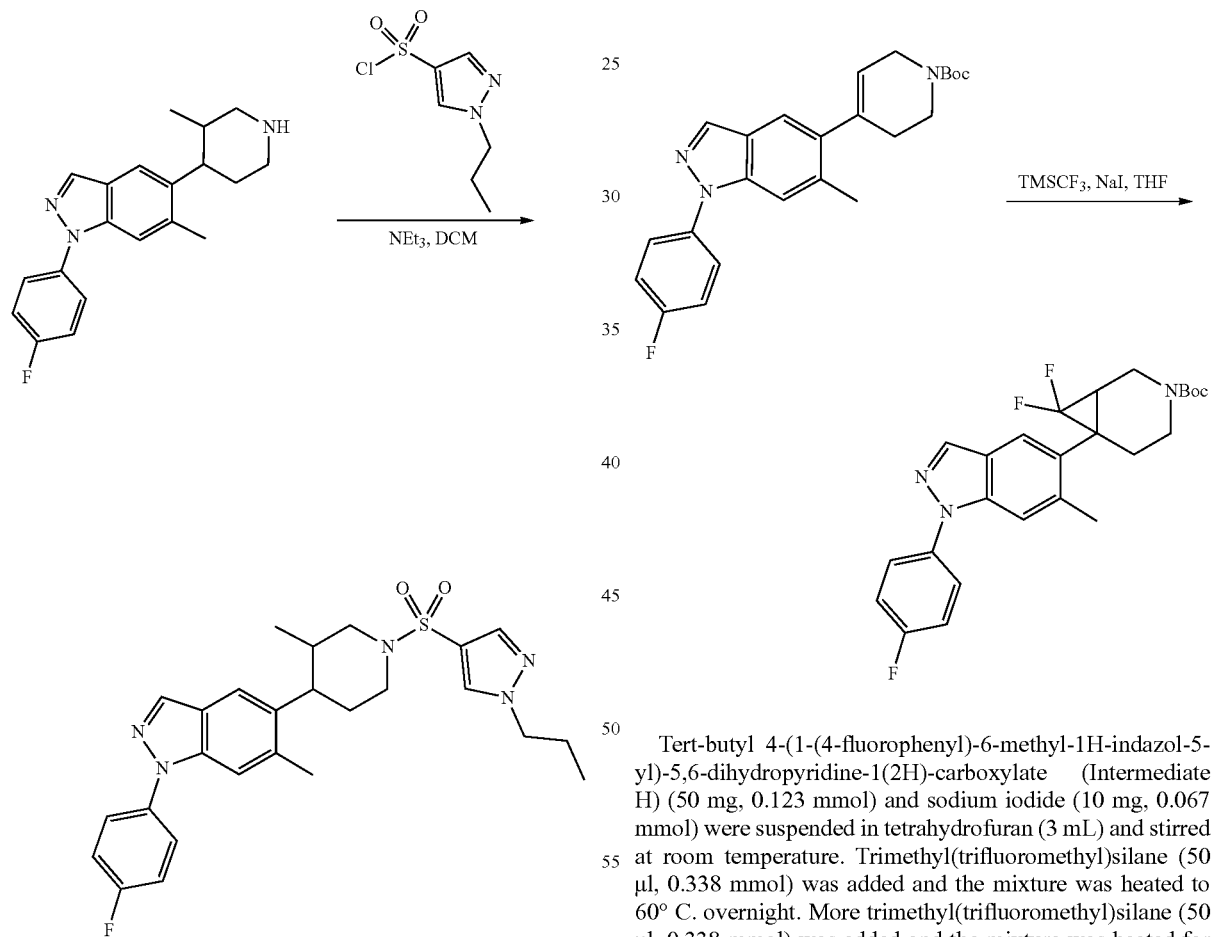

1-(4-fluorophenyl)-6-methyl-5-(3-methylpiperidin-4-yl)-1H-indazole (Intermediate Y) (92 mg, 0.284 mmol) was dissolved in dichloromethane (3 mL). 1-propyl-1H-pyrazole-4-sulfonyl chloride (89 mg, 0.427 mmol) was added as a solution in dichloromethane (1 mL) followed by triethylamine (100 µl, 0.717 mmol). The mixture was stirred at room temperature for 3 hours then purified directly by chromatography on silica gel (24 g cartridge, 0-100% EtOAc/isohexane) to afford 1-(4-fluorophenyl)-6-methyl-5-((3R,4R)-3-methyl-1-((1-propyl-1H-pyrazol-4-yl)sulfonyl)piperidin-4-yl)-1H-indazole (Example 26) (31 mg, 0.059 mmol, 21% yield) as a colourless solid; $R^t$ 1.81 min (Method 1); m/z 496.4 (M+H)$^+$ (ES$^+$); $\delta_H$ (DMSO-d6, 500 MHz) $\delta$ 8.40 (s, 1H), 8.26 (s, 1H), 7.83 (s, 1H), 7.82-7.75 (m, 2H), 7.61 (s, 1H), 7.57 (s, 1H), 7.45-7.38 (m, 2H), 4.17 (t, J=6.9 Hz, 2H), 3.82-3.76 (m, 1H), 3.53-3.48 (m, 1H), 3.08-3.01 (m, 1H), 2.58-2.53 (m, 1H), 2.43 (s, 3H), 2.41-2.33 (m, 2H), 2.16-2.08 (m, 1H), 1.84 (h, J=7.2 Hz, 2H), 1.64-1.58 (m, 1H), 0.84 (t, J=7.4 Hz, 3H), 0.78 (d, J=7.0 Hz, 3H).

Example 27: 5-(7,7-difluoro-3-((1-propyl-1H-pyrazol-4-yl)sulfonyl)-3-azabicyclo[4.1.0]heptan-6-yl)-1-(4-fluorophenyl)-6-methyl-1H-indazole Intermediate Z: tert-butyl 7,7-difluoro-6-(1-(4-fluorophenyl)-6-methyl-1H-indazol-5-yl)-3-azabicyclo[4.1.0]heptane-3-carboxylate

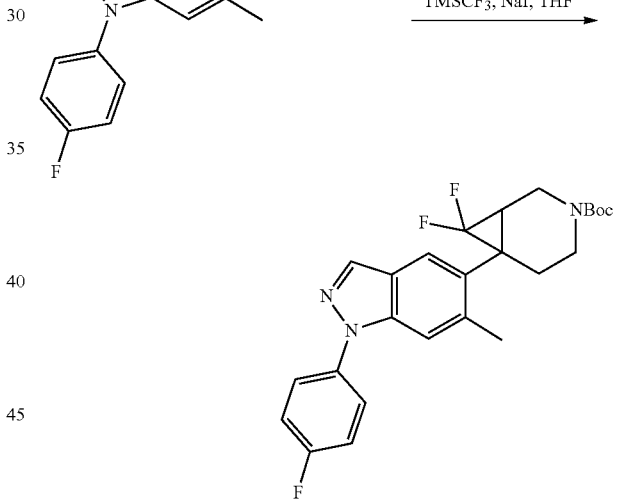

Tert-butyl 4-(1-(4-fluorophenyl)-6-methyl-1H-indazol-5-yl)-5,6-dihydropyridine-1(2H)-carboxylate (Intermediate H) (50 mg, 0.123 mmol) and sodium iodide (10 mg, 0.067 mmol) were suspended in tetrahydrofuran (3 mL) and stirred at room temperature. Trimethyl(trifluoromethyl)silane (50 µl, 0.338 mmol) was added and the mixture was heated to 60° C. overnight. More trimethyl(trifluoromethyl)silane (50 µl, 0.338 mmol) was added and the mixture was heated for a further 24 hours. The mixture was cooled to room temperature, absorbed on to silica gel and purified by chromatography on silica gel (12 g cartridge, 0-50% EtOAc/isohexane) to afford tert-butyl 7,7-difluoro-6-(1-(4-fluorophenyl)-6-methyl-1H-indazol-5-yl)-3-azabicyclo[4.1.0]heptane-3-carboxylate (Intermediate Z) (42 mg, 0.083 mmol, 67% yield) as a pale yellow oil; $R^t$ 1.99 min (Method 1); m/z 458.4 (M+H)$^+$ (ES$^+$); This was used directly in the next step as the NMR is rotameric.

Example 27: 5-(7,7-difluoro-3-((1-propyl-1H-pyrazol-4-yl)sulfonyl)-3-azabicyclo[4.1.0]heptan-6-yl)-1-(4-fluorophenyl)-6-methyl-1H-indazole

Example 28: 1-(1-(4-fluorophenyl)-6-methyl-1H-indazol-5-yl)-N-methylpyrrolidine-3-sulfonamide

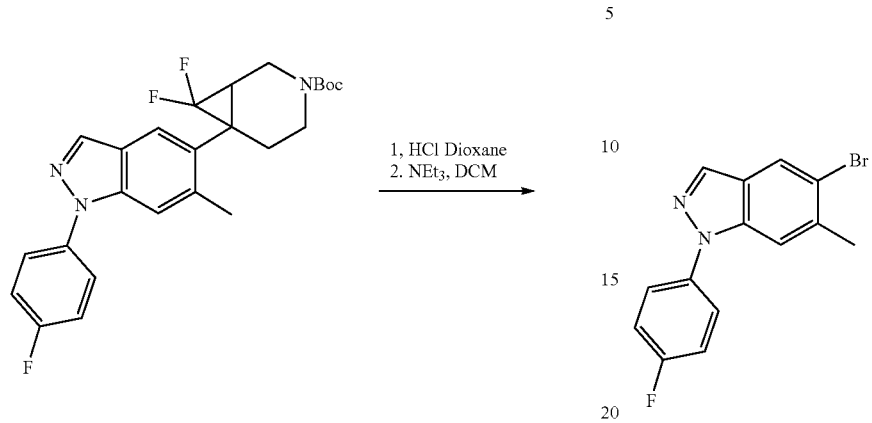

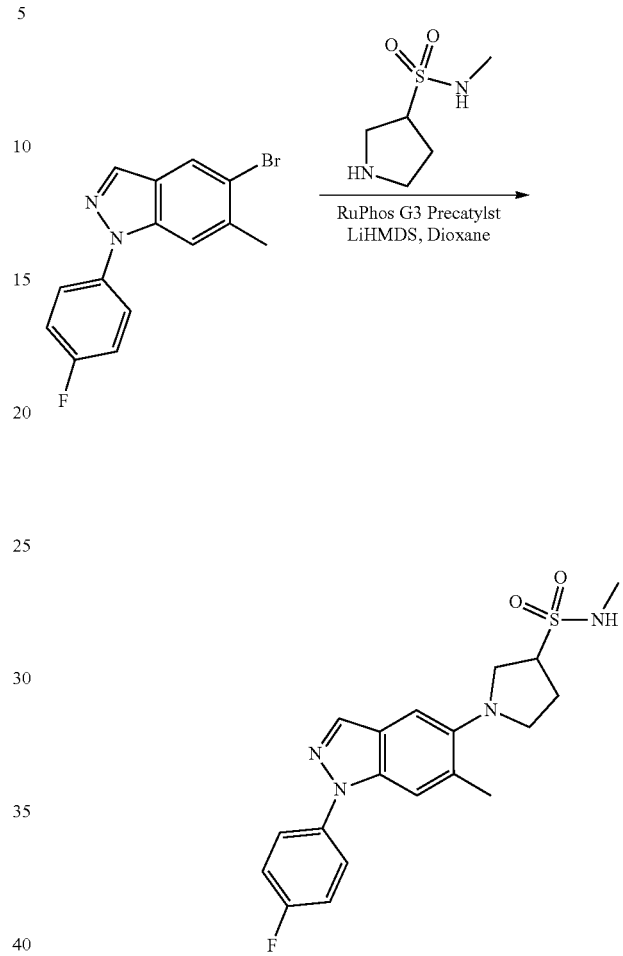

Step A: Tert-butyl 7,7-difluoro-6-(1-(4-fluorophenyl)-6-methyl-1H-indazol-5-yl)-3-azabicyclo[4.1.0]heptane-3-carboxylate (Intermediate Z) (40 mg, 0.087 mmol) was dissolved in HCl (4M in dioxane) (3 mL, 12.00 mmol) and stirred at room temperature for 1 hour. The solvent was removed in vacuo and the oily residue was triturated with diethyl ether (3 mL) to give 5-(7,7-difluoro-3-azabicyclo[4.1.0]heptan-6-yl)-1-(4-fluorophenyl)-6-methyl-1H-indazole, HCl (32 mg, 0.081 mmol, 93% yield) as a colourless solid.

Step B: 5-(7,7-difluoro-3-azabicyclo[4.1.0]heptan-6-yl)-1-(4-fluorophenyl)-6-methyl-1H-indazole, HCl (15 mg, 0.038 mmol) was suspended in dichloromethane (2 mL). 1-propyl-1H-pyrazole-4-sulfonyl chloride (12 mg, 0.058 mmol) was added followed by triethylamine (20 µl, 0.143 mmol). The mixture was stirred at room temperature for 1 hour then purified directly by chromatography on silica gel (4 g cartridge, 0-100% EtOAc/isohexane) to afford 5-(7,7-difluoro-3-((1-propyl-1H-pyrazol-4-yl)sulfonyl)-3-azabicyclo[4.1.0]heptan-6-yl)-1-(4-fluorophenyl)-6-methyl-1H-indazole (Example 27) (17 mg, 0.030 mmol, 80% yield) as a colourless solid foam; $R^t$ 1.78 min (Method 1); m/z 530.4 (M+H)$^+$ (ES$^+$); $\delta_H$ (DMSO-d6, 500 MHz) δ 8.48 (s, 1H), 8.24 (s, 1H), 7.91 (s, 1H), 7.81-7.75 (m, 2H), 7.65 (s, 1H), 7.57 (s, 1H), 7.47-7.39 (m, 2H), 4.18 (t, J=6.9 Hz, 2H), 3.61-3.54 (m, 1H), 3.45-3.37 (m, 1H), 3.18-3.10 (m, 1H), 2.71-2.63 (m, 1H), 2.44 (s, 3H), 2.35-2.25 (m, 1H), 1.96-1.87 (m, 1H), 1.87-1.78 (m, 2H), 0.83 (t, J=7.4 Hz, 3H), one proton obscured by residual DMSO.

A vial containing RuPhos G3 Precatalyst (13.70 mg, 0.016 mmol), N-methylpyrrolidine-3-sulfonamide hydrochloride (65.8 mg, 0.328 mmol), 5-bromo-1-(4-fluorophenyl)-6-methyl-1H-indazole (Prepared using the method described for Intermediate D) (50 mg, 0.164 mmol) in 1,4-dioxane (2 mL) was evacuated and backfilled with N$_2$ (×3). A 1M solution of LiHMDS (655 µl, 0.655 mmol) in tetrahydrofuran (1 mL) was added and the resultant orange solution was stirred at room temperature for 18 hours. The reaction mixture was quenched with a saturated solution of sodium bicarbonate (5 mL) and extracted with ethyl acetate (3×10 mL). The organic layers were combined and passed through a hydrophobic frit. The solvent was removed under reduced pressure to afford a black oil. The crude product was purified by chromatography on silica gel (24 g cartridge, 0-100% EtOAc/isohexane) to afford 1-(1-(4-fluorophenyl)-6-methyl-1H-indazol-5-yl)-N-methylpyrrolidine-3-sulfonamide (Example 28) (32 mg, 0.078 mmol, 48% yield) as a pale yellow solid; $R^t$ 1.46 min (Method 1); m/z 389.3 (M+H)$^+$ (ES$^+$); $\delta_H$ (DMSO-d6, 500 MHz) δ 8.20 (d, J=0.9 Hz, 1H), 7.81-7.75 (m, 2H), 7.63 (s, 1H), 7.45-7.39 (m, 3H), 7.09 (q, J=4.8 Hz, 1H), 4.02 (tt, J=9.2, 5.7 Hz, 1H), 3.40-3.33 (m, 2H), 3.18 (t, J=6.6 Hz, 2H), 2.65 (d, J=4.9 Hz, 3H), 2.44 (d, J=0.9 Hz, 3H), 2.34-2.18 (m, 2H).

Example 29: 1-(1-(4-fluorophenyl)-6-methyl-1H-indazol-5-yl)-N-methyl-N-(1-propyl-1H-pyrazol-4-yl)pyrrolidine-3-sulfonamide Intermediate AA: tert-butyl 3-(N-(1-propyl-1H-pyrazol-4-yl)sulfamoyl)pyrrolidine-1-carboxylate

Example 29: 1-(1-(4-fluorophenyl)-6-methyl-1H-indazol-5-yl)-N-(1-propyl-1H-pyrazol-4-yl)pyrrolidine-3-sulfonamide

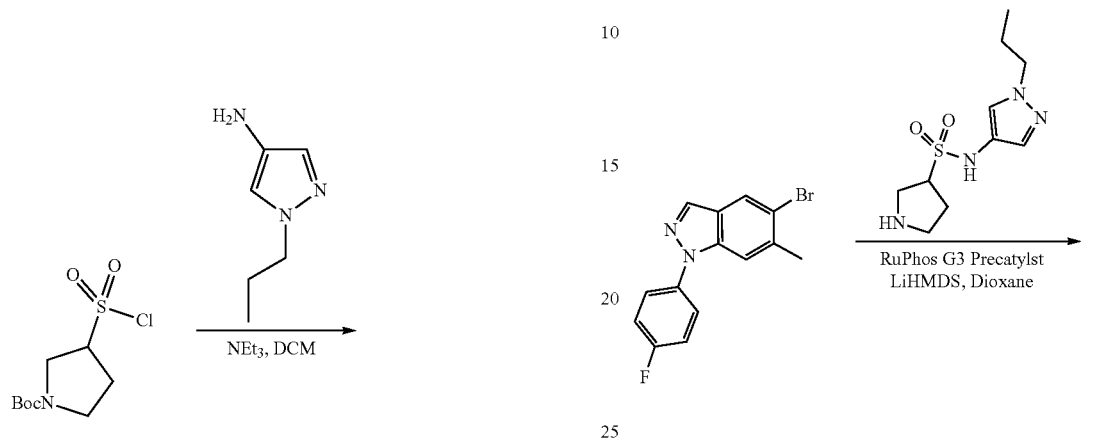

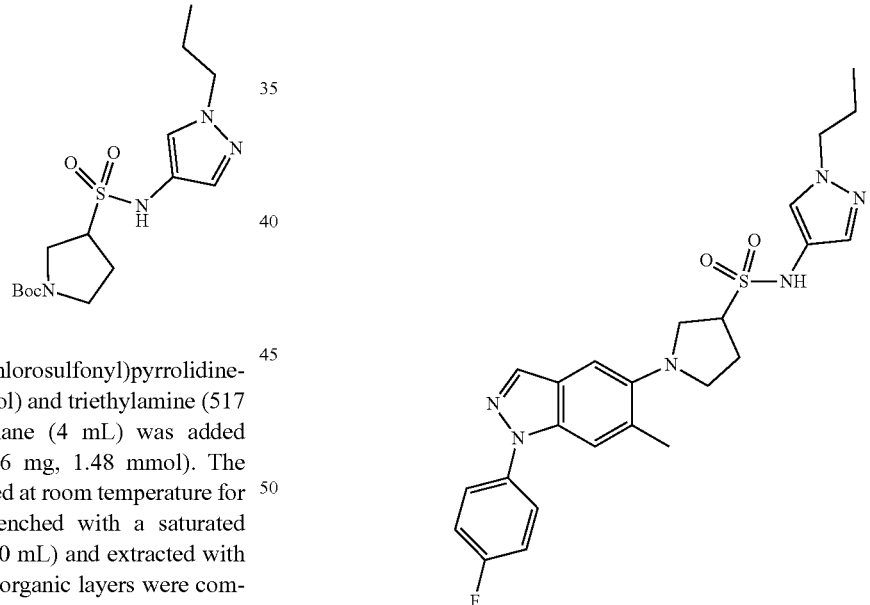

To a solution of tert-butyl 3-(chlorosulfonyl)pyrrolidine-1-carboxylate (200 mg, 0.741 mmol) and triethylamine (517 µl, 3.71 mmol) in dichloromethane (4 mL) was added 1-propyl-1H-pyrazol-4-amine (186 mg, 1.48 mmol). The resultant yellow solution was stirred at room temperature for 18 hours. The reaction was quenched with a saturated solution of sodium bicarbonate (10 mL) and extracted with dichloromethane (3×10 mL). The organic layers were combined and passed through a hydrophobic frit. The solvent was removed in vacuo to afford a dark oil. The crude product was purified by chromatography on silica gel (24 g cartridge, 0-100% EtOAc/isohexane) to afford tert-butyl 3-(N-(1-propyl-1H-pyrazol-4-yl)sulfamoyl)pyrrolidine-1-carboxylate (Intermediate AA) (115 mg, 0.305 mmol, 41% yield) as a pale purple oil; R$^t$ 1.19 min (Method 1); m/z 381.4 (M+H)$^+$ (ES$^+$); (DMSO-d6, 500 MHz) δ 9.39 (s, 1H), 7.67 (s, 1H), 7.30 (s, 1H), 3.99 (t, J=7.0 Hz, 2H), 3.80 (d, J=26.6 Hz, 1H), 3.53 (d, J=7.5 Hz, 2H), 3.40 (dt, J=10.3, 7.2 Hz, 1H), 2.18 (q, J=7.8, 7.4 Hz, 3H), 1.75 (h, J=7.2 Hz, 2H), 1.40 (s, 9H), 0.81 (t, J=7.4 Hz, 3H).

The compound was prepared by similar methods to those described for Example 29; Rt 1.57 min (Method 1); m/z 483.4 (M+H)+ (ES+). δH (DMSO-d6, 500 MHz) δ 9.30 (s, 1H), 8.20 (d, J=0.9 Hz, 1H), 7.81-7.75 (m, 2H), 7.70 (s, 1H), 7.63 (s, 1H), 7.44-7.37 (m, 3H), 7.33 (d, J=0.7 Hz, 1H), 3.99 (t, J=7.0 Hz, 2H), 3.90 (tt, J=8.8, 6.0 Hz, 1H), 3.42 (dd, J=10.3, 5.6 Hz, 1H), 3.29 (dd, J=10.3, 8.5 Hz, 1H), 3.18 (t, J=6.6 Hz, 2H), 2.41 (br s, 3H), 2.27 (m, 2H), 1.74 (h, J=7.3 Hz, 2H), 0.79 (t, J=7.4 Hz, 3H).

Example 30: 1-(1-(4-fluorophenyl)-6-methyl-1H-indazol-5-yl)-N-methyl-N-(1-propyl-1H-pyrazol-4-yl)pyrrolidine-3-sulfonamide

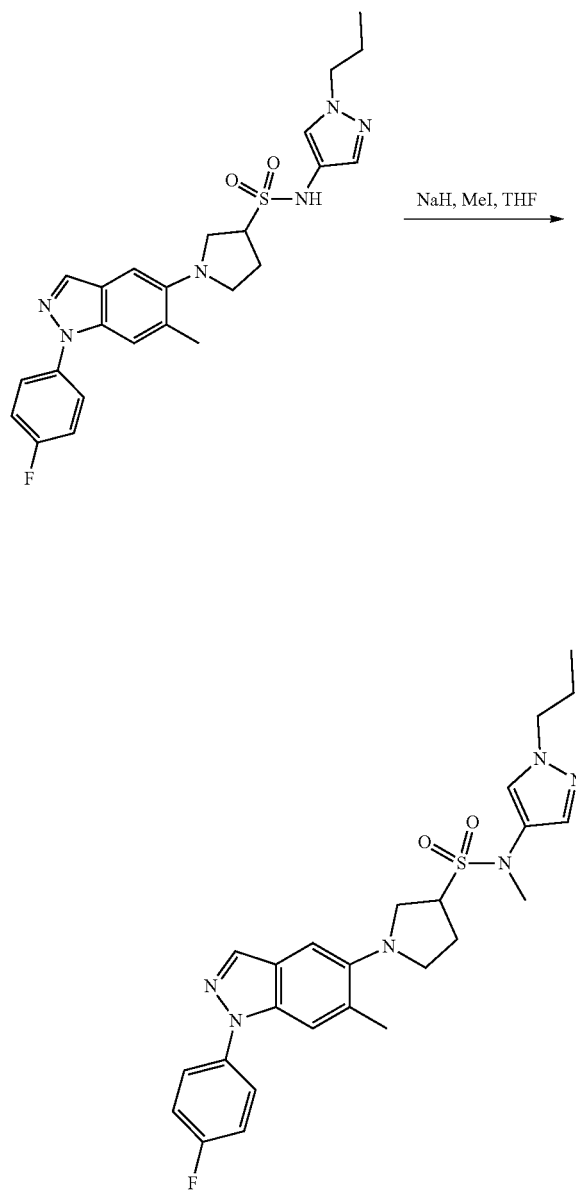

To a solution of 1-(1-(4-fluorophenyl)-6-methyl-1H-indazol-5-yl)-N-(1-propyl-1H-pyrazol-4-yl)pyrrolidine-3-sulfonamide (Example 29) (30 mg, 0.062 mmol) in dimethylformamide (2 mL) at 0° C. was added sodium hydride (2.98 mg, 0.075 mmol) in one portion. The resultant yellow solution was stirred at 0° C. for 30 minutes and methyl iodide (7.77 µl, 0.124 mmol) was added. The resultant white solution was stirred at room temperature for 2 hours. The reaction mixture was quenched with a saturated solution of sodium bicarbonate (10 mL) and extracted with ethyl acetate (3×10 mL). The organic layers were combined and passed through a hydrophobic frit. The solvent was removed under reduced pressure to afford a pale yellow residue. The crude product was purified by chromatography on silica gel (12 g cartridge, 0-50% EtOAc/isohexane) to afford 1-(1-(4-fluorophenyl)-6-methyl-1H-indazol-5-yl)-N-methyl-N-(1-propyl-1H-pyrazol-4-yl)pyrrolidine-3-sulfonamide (Example 30) (10 mg, 0.020 mmol, 32% yield) as a pale yellow solid; Rt 1.70 min (Method 1); m/z 497.4 (M+H)+ (ES+). δH (DMSO-d6, 500 MHz) δ 8.18 (d, J=0.9 Hz, 1H), 7.88 (d, J=0.8 Hz, 1H), 7.80-7.75 (m, 2H), 7.62 (s, 1H), 7.54 (d, J=0.8 Hz, 1H), 7.45-7.39 (m, 2H), 7.38 (s, 1H), 4.18-4.08 (m, 1H), 4.01 (t, J=6.9 Hz, 2H), 3.30 (m, 1H, overlapped with water signal), 3.24 (s, 3H), 3.23-3.14 (m, 2H), 3.10 (m, 1H), 2.37 (d, J=0.9 Hz, 3H), 2.31 (m, 1H), 2.18 (dq, J=13.6, 6.9 Hz, 1H), 1.75 (h, J=7.2 Hz, 2H), 0.79 (t, J=7.4 Hz, 3H).

Example 31: 4-(1-(4-fluorophenyl)-6-methyl-1H-indazol-5-yl)-N-phenylpiperidine-1-carboxamide

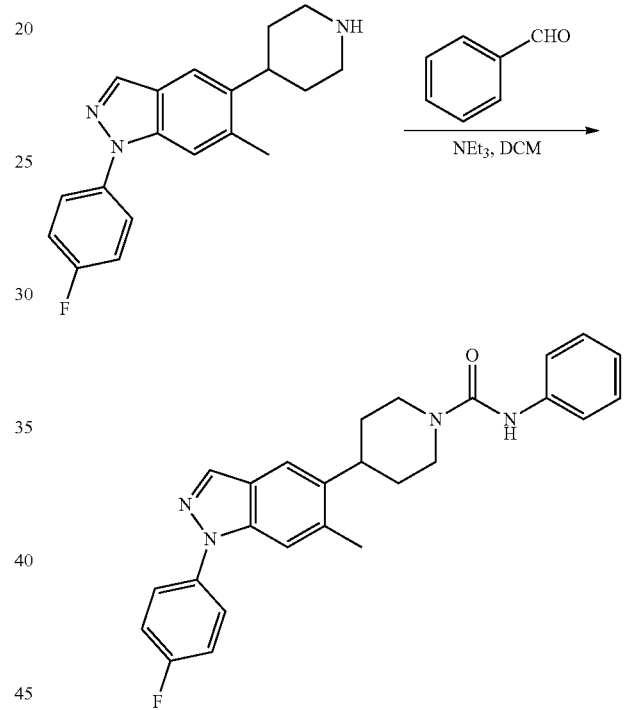

1-(4-fluorophenyl)-6-methyl-5-(piperidin-4-yl)-1H-indazole, HCl (Deprotection of Intermediate I) (30 mg, 0.087 mmol) was suspended in dichloromethane (2 mL). triethylamine (50 µl, 0.359 mmol) was added followed by phenyl isocyanate (20 µl, 0.183 mmol). The mixture was stirred for 2 hours at room temperature then concentrated in vacuo. The residue was dissolved in DMSO (2 mL) then purified by preparative HPLC (Waters, Acidic (0.1% Formic acid), Acidic, Waters X-Select Prep-C18, 5 µm, 19×50 mm column, 35-65% MeCN in 0.1% aq. formic acid) to afford 4-(1-(4-fluorophenyl)-6-methyl-1H-indazol-5-yl)-N-phenylpiperidine-1-carboxamide (Example 31) (9.8 mg, 0.022 mmol, 26% yield) as a colourless solid; Rt 1.71 min (Method 1); m/z 429.5 (M+H)+ (ES+). δH (DMSO-d6, 500 MHz) δ 8.54 (s, 1H), 8.23 (s, 1H), 7.81-7.77 (m, 2H), 7.71 (s, 1H), 7.63 (s, 1H), 7.53-7.48 (m, 2H), 7.46-7.40 (m, 2H), 7.27-7.21 (m, 2H), 6.94 (t, J=7.3 Hz, 1H), 4.37-4.28 (m, 2H), 3.09-3.00 (m, 1H), 3.00-2.91 (m, 2H), 2.52 (s, 3H), 1.86-1.79 (m, 2H), 1.69-1.57 (m, 2H).

Example 32: 4-(1-(4-fluorophenyl)-6-methyl-1H-indazol-5-yl)-N-isopropylpiperidine-1-carboxamide

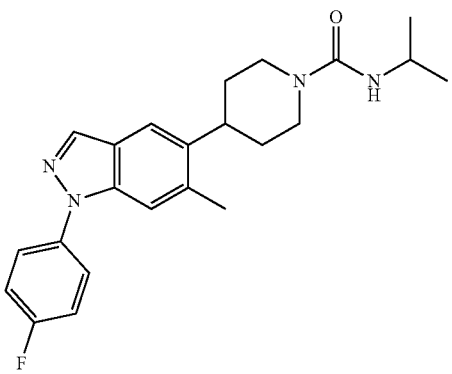 [SMILES: Cc1cc2c(cnn2-c2ccc(F)cc2)cc1C1CCN(C(=O)NC(C)C)CC1]

The compound was prepared by similar methods to those described for Example 31; Rt 1.59 min (Method 1); m/z 395.4 (M+H)+ (ES+). δH (DMSO-d6, 500 MHz) δ 8.23 (s, 1H), 7.82-7.74 (m, 2H), 7.66 (s, 1H), 7.61 (s, 1H), 7.45-7.39 (m, 2H), 6.17 (d, J=7.6 Hz, 1H), 4.19-4.15 (m, 2H), 3.85-3.73 (m, 1H), 3.00-2.90 (m, 1H), 2.82-2.71 (m, 2H), 2.49 (s, 3H), 1.77-1.70 (m, 2H), 1.59-1.47 (m, 2H), 1.09 (d, J=6.6 Hz, 6H).

Example 33: 1-(4-fluorophenyl)-6-methyl-5-(4-((1-methyl-1H-pyrazol-4-yl)sulfonyl)piperidin-1-yl)-1H-indazole Intermediate AB: tert-butyl 4-((1-methyl-1H-pyrazol-4-yl)sulfonyl)piperidine-1-carboxylate

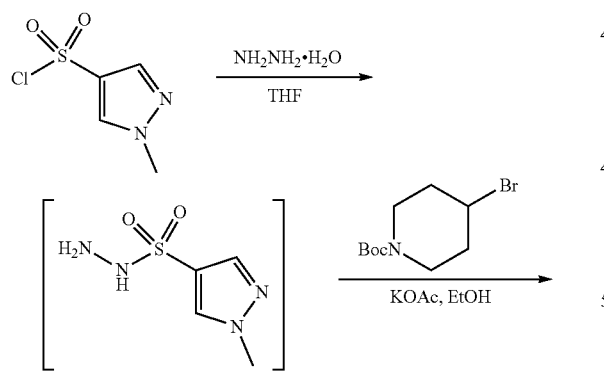

To a solution of 1-methyl-1H-pyrazole-4-sulfonyl chloride (1.66 g, 9.19 mmol) in tetrahydrofuran (25 mL) at 0° C. was added hydrazine hydrate (1.3 ml, 26.1 mmol). The mixture was allowed to reach room temperature over 1 hour. The mixture was diluted with dichloromethane (50 mL) and water (10 mL). The aqueous was washed with 10% methanol in dichloromethane (3×20 mL). The combined organics were dried by passing through a hydrophobic frit then concentrated in vacuo to give 1-methyl-1H-pyrazole-4-sulfonohydrazide (668 mg, 3.79 mmol, 41% yield) as a colourless solid. The solid was dissolved in ethanol (10 mL). potassium acetate (4.51 g, 46.0 mmol) and tert-butyl 4-bromopiperidine-1-carboxylate (2.43 g, 9.19 mmol) were added and the mixture was heated to reflux for 3 days. The mixture was cooled to room temperature and the crude product purified by chromatography on silica gel (24 g cartridge, 0-100% EtOAc/isohexane) to afford tert-butyl 4-((1-methyl-1H-pyrazol-4-yl)sulfonyl)piperidine-1-carboxylate (Intermediate AB) (78 mg, 0.189 mmol, 2% yield) as a clear colourless oil; Very poor chromophore so UPLC analysis was inconclusive. (DMSO-d6, 500 MHz) δ 8.38 (s, 1H), 7.83 (s, 1H), 4.09-3.95 (m, 2H), 3.91 (s, 3H), 3.32-3.27 (m, 1H), 2.73 (s, 2H), 1.95-1.88 (m, 2H), 1.38 (s, 9H), 1.35-1.24 (m, 2H).

Intermediate AC: 4-((1-methyl-1H-pyrazol-4-yl)sulfonyl)piperidine

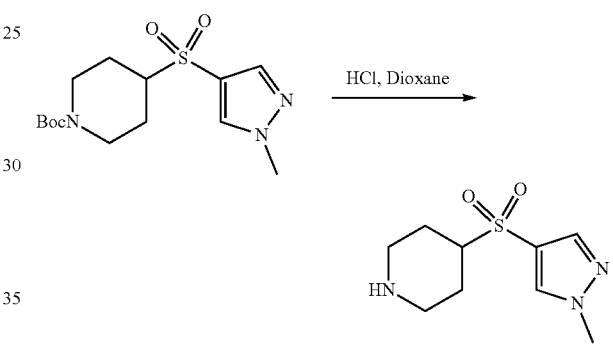

To a solution of tert-butyl 4-((1-methyl-1H-pyrazol-4-yl)sulfonyl)piperidine-1-carboxylate (Intermediate AB) (40 mg, 0.097 mmol) in dichloromethane (1 mL) was added HCl (4 M in dioxane) (1 mL, 4.00 mmol) in a single portion and the mixture was stirred for 1 hour at room temperature. The solvent was removed in vacuo and the solid formed was dried in vacuo for 1 hour at 40° C. to give 4-((1-methyl-1H-pyrazol-4-yl)sulfonyl)piperidine·HCl (Intermediate AC) which was used in the next step without further purification.

Example 33: 1-(4-fluorophenyl)-6-methyl-5-(4-((1-methyl-1H-pyrazol-4-yl)sulfonyl)piperidin-1-yl)-1H-indazole

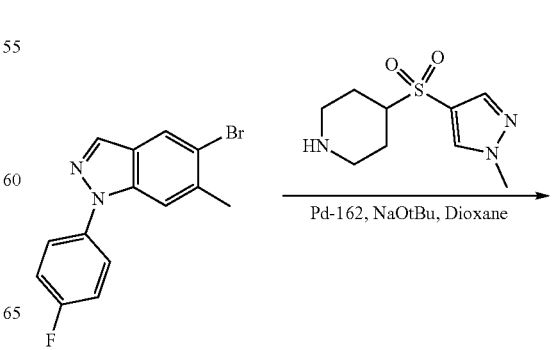

255
-continued

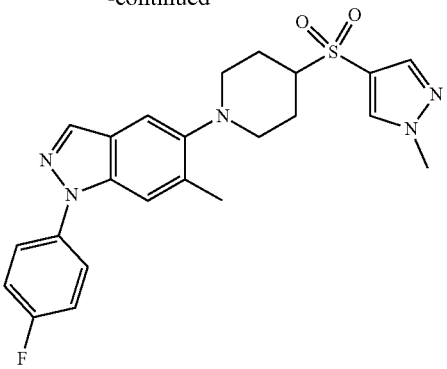

A stirred suspension of 5-bromo-1-(4-fluorophenyl)-1H-indazole (prepared using the method described for Intermediate D) (27 mg, 0.093 mmol), 4-((1-methyl-1H-pyrazol-4-yl)sulfonyl)piperidine, HCl (Intermediate AC) (26 mg, 0.098 mmol), sodium tert-butoxide (25 mg, 0.260 mmol), and Pd-162 (5 mg, 0.013 mmol) in dioxane (2 mL) was evacuated and backfilled with nitrogen (3×) was then heated to 90° C. for 16 hours. The mixture was cooled to room temperature and then absorbed directly onto silica gel. The crude product was purified by chromatography on silica gel (12 g cartridge, 0-100% EtOAc/isohexane) to afford 1-(4-fluorophenyl)-5-(4-((1-methyl-1H-pyrazol-4-yl)sulfonyl)piperidin-1-yl)-1H-indazole (Example 33) (5 mg, 0.001 mmol, 12% yield) as a pale yellow foam; R$^r$ 1.31 min (Method 1); m/z 440.4 (M+H)$^+$ (ES$^+$); δ$_H$ (DMSO-d6, 500 MHz) δ 8.42 (s, 1H), 8.20 (s, 1H), 7.86 (s, 1H), 7.80-7.74 (m, 2H), 7.68 (d, J=9.2 Hz, 1H), 7.43-7.38 (m, 2H), 7.30 (dd, J=9.2, 2.3 Hz, 1H), 7.23 (d, J=2.3 Hz, 1H), 3.93 (s, 3H), 3.77-3.70 (m, 2H), 2.75-2.68 (m, 2H), 2.07-2.01 (m, 2H), 1.72-1.61 (m, 2H), one proton obscured by residual water in DMSO solvent.

Examples 34-96

TABLE 3

The examples shown in the table below were prepared by similar methods to those described for Example 1

| Example | Structure | LC-MS Analysis |
| --- | --- | --- |
| 34 | (R)-5-(2-benzyl-4-((1-methy-1H-pyrazol-4-yl)sulfonyl)piperazin-1-yl)-1-(4-fluorophenyl)-1H-indazole | R$^r$ 1.78 min (Method 1): m/z 530.97 (M + H)$^+$ (ES$^+$) |
| 35 | (R)-5-(4-(cyclopentylsulfonyl)-2-methylpiperazin-1-yl)-1-(4-fluorophenyl)-1H-indazole | R$^r$ 1.71 min (Method 1); m/z 443.27 (M + H)$^+$ (ES$^+$) |

TABLE 3-continued

The examples shown in the table below were prepared by similar methods to those described for Example 1

| Example | Structure | LC-MS Analysis |
|---|---|---|
| 36 | 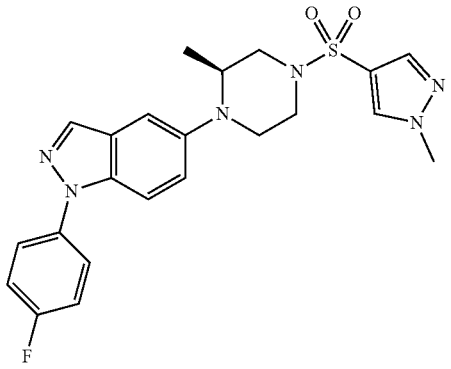<br>(S)-1-(4-fluorophenyl)-5-(2-methyl-4-((1-methyl-1H-pyrazol-4-yl)sulfonyl)piperazin-1-yl)-1H-indazole | R$^t$ 1.48 min (Method 1); m/z 455.45 (M + H)$^+$ (ES$^+$) |
| 37 | 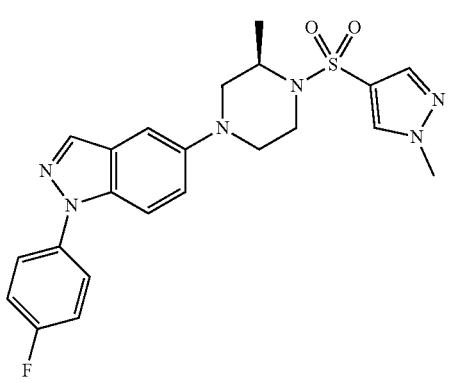<br>(R)-1-(4-fluorophenyl)-5-(3-methyl-4-((1-methyl-1H-pyrazol-4-yl)sulfonyl)piperazin-1-yl)-1H-indazole | R$^t$ 1.54 min (Method 1); m/z 455.46 (M + H)$^+$ (ES$^+$) |
| 38 | 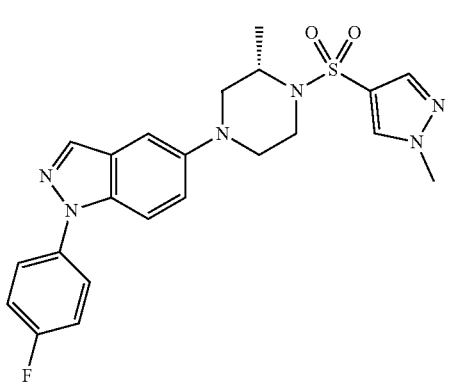<br>(R)-1-(4-fluorophenyl)-5-(3-methyl-4-((1-methyl-1H-pyrazol-4-yl)sulfonyl)piperazin-1-yl)-1H-indazole | R$^t$ 1.54 min (Method 1); m/z 455.34 (M + H)$^+$ (ES$^+$) |

TABLE 3-continued

The examples shown in the table below were prepared by similar methods to those described for Example 1

| Example | Structure | LC-MS Analysis |
| --- | --- | --- |
| 39 | 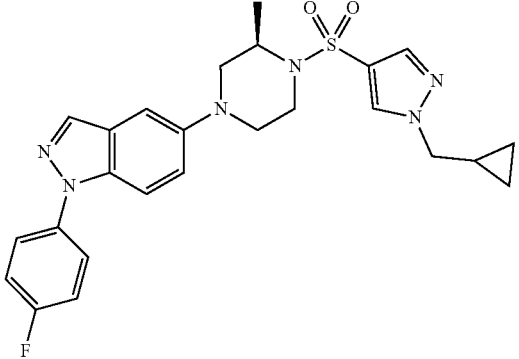<br>(R)-5-(4-((1-(cyclopropylmethyl)-1H-pyrazol-4-yl)sulfonyl)-3-methylpiperazin-1-yl)-1-(4-fluorophenyl)-1H-indazole | R$^t$ 1.71 min (Method 1); m/z 495.41 (M + H)$^+$ (ES$^+$) |
| 40 | 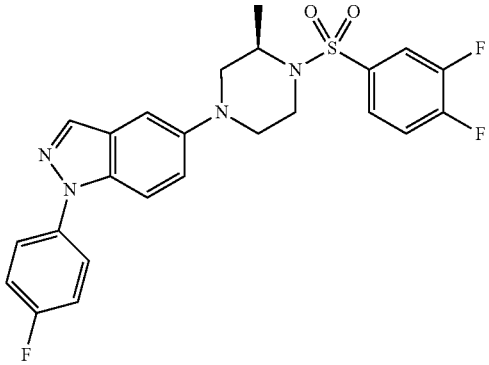<br>(R)-5-(4-((3,4-difluorophenyl)sulfonyl)-3-methylpiperazin-1-yl)-1-(4-fluorophenyl)-1H-indazole | R$^t$ 1.88 min (Method 1); m/z 487.32 (M + H)$^+$ (ES$^+$) |
| 41 | 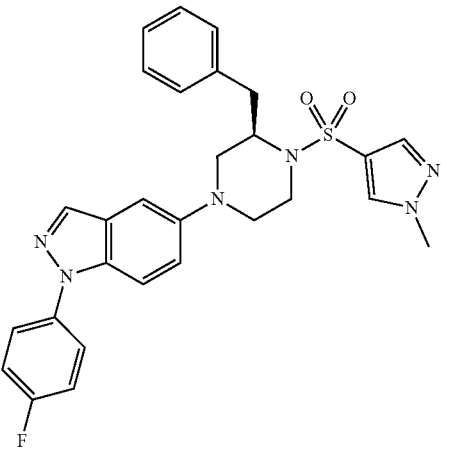<br>(R)-5-(3-benzyl-4-((1-methyl-1H-pyrazol-4-yl)sulfonyl)piperazin-1-yl)-1-(4-fluorophenyl)-1H-indazole | R$^t$ 1.78 min (Method 1); m/z 531.67 (M + H)$^+$ (ES$^+$) |

TABLE 3-continued

The examples shown in the table below were prepared by similar methods to those described for Example 1

| Example | Structure | LC-MS Analysis |
|---|---|---|
| 42 | 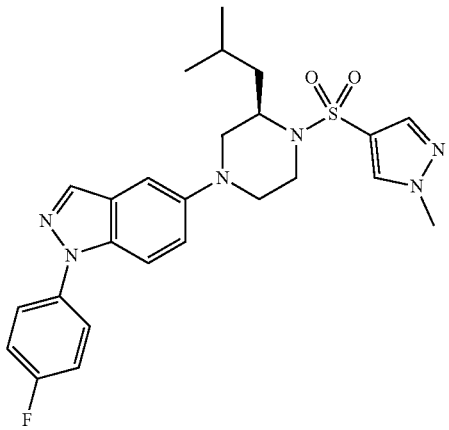<br>(R)-1-(4-fluorophenyl)-5-(3-isobutyl-4-((1-methyl-1H-pyrazol-4-yl)sulfonyl)piperazin-1-yl)-1H-indazole | $R^t$ 1.79 min (Method 1); m/z 497.21 $(M + H)^+$ $(ES^+)$ |
| 43 | 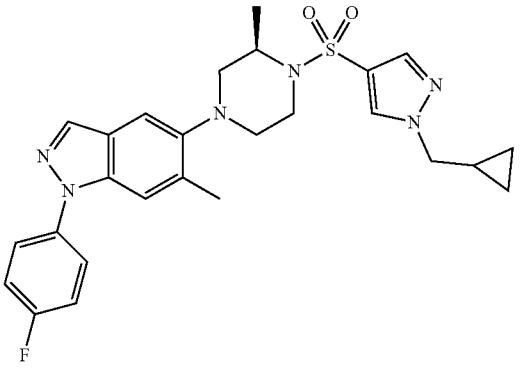<br>(R)-5-(4-((1-(cyclopropylmethyl)-1H-pyrazol-4-yl)sulfonyl)-3-methylpiperazin-1-yl)-1-(4-fluorophenyl)-6-methyl-1H-indazole | $R^t$ 1.82 min (Method 1); m/z 509.49 $(M + H)^+$ $(ES^+)$ |
| 44 | 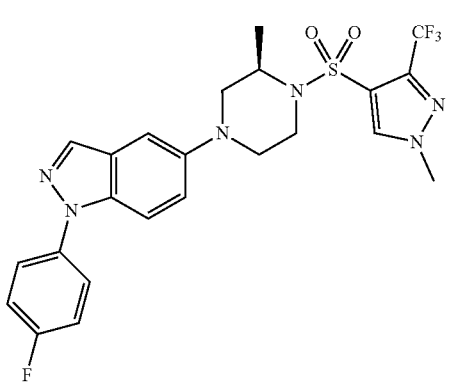<br>(R)-1-(4-fluorophenyl)-5-(3-methyl-4-((1-methyl-3-(trifluoromethyl)-1H-pyrazol-4-yl)sulfonyl)piperazin-1-yl)-1H-indazole | $R^t$ 1.78 min (Method 1); m/z 534.4 $(M + H)^+$ $(ES^+)$ |

TABLE 3-continued

The examples shown in the table below were prepared by similar methods to those described for Example 1

| Example | Structure | LC-MS Analysis |
|---|---|---|
| 45 | 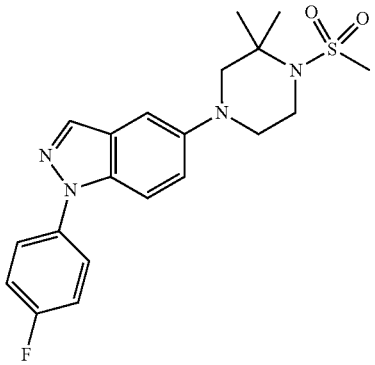<br>5-(3,3-dimethyl-4-(methylsulfonyl)piperazin-1-yl)-1-(4-fluorophenyl)-1H-indazole | $R^t$ 1.61 min (Method 1); m/z 403.42 $(M + H)^+$ $(ES^+)$ |
| 46 | 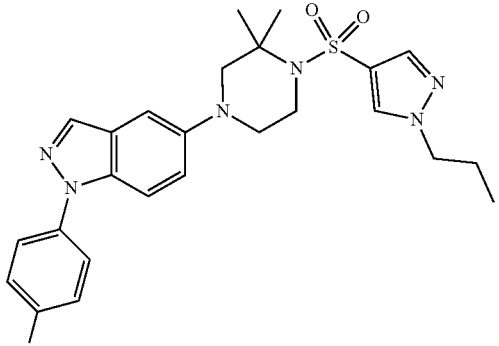<br>5-(3,3-dimethyl-4-((1-propyl-1H-pyrazol-4-yl)sulfonyl)piperazin-1-yl)-1-(4-fluorophenyl)-1H-indazole | $R^t$ 1.77 min (Method 1); m/z 497.74 $(M + H)^+$ $(ES^+)$ |
| 47 | 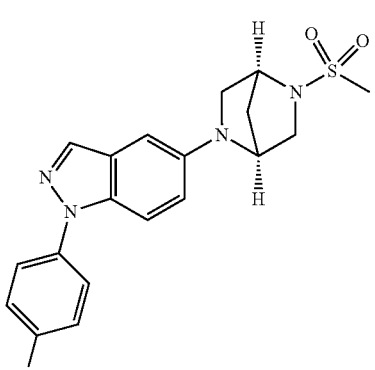<br>1-(4-fluorophenyl)-5-((1S,4S)-5-(methylsulfonyl)-2,5-diazabicyclo[2.2.1]heptan-2-yl)-1H-indazole | $R^t$ 1.38 min (Method 1); m/z 387.66 $(M + H)^+$ $(ES^+)$ |

TABLE 3-continued

The examples shown in the table below were prepared by similar methods to those described for Example 1

| Example | Structure | LC-MS Analysis |
|---|---|---|
| 48 | 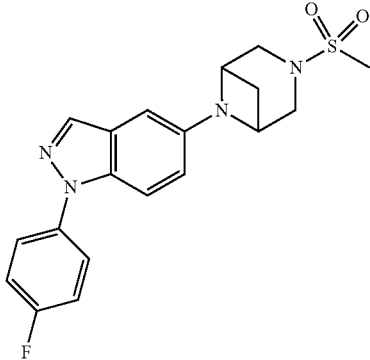<br>6-(1-(4-fluorophenyl)-1H-indazol-5-yl)-3-(methylsulfonyl)-3,6-diazabicyclo[3.1.1]heptane | $R^t$ 1.44 min (Method 1); m/z 387.37 (M + H)$^+$ (ES$^+$) |
| 49 | 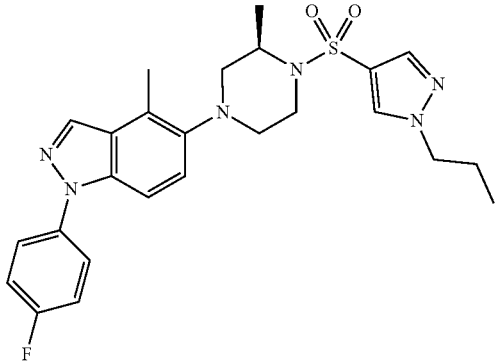<br>(R)-1-(4-fluorophenyl)-4-methyl-5-(3-methyl-4-((1-propyl-1H-pyrazol-4-yl)sulfonyl)piperazin-1-yl)-1H-indazole | $R^t$ 1.81 min (Method 1); m/z 497.46 (M + H)$^+$ (ES$^+$) |
| 50 | 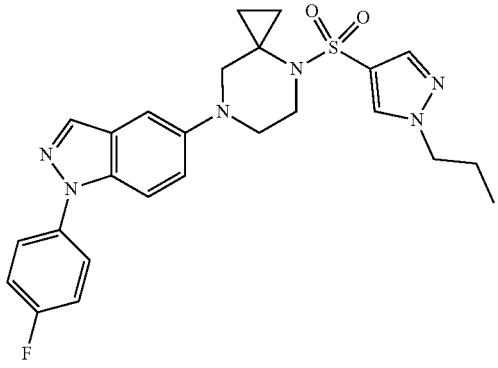<br>1-(4-fluorophenyl)-5-(4-((1-propyl-1H-pyrazol-4-yl)sulfonyl)-4,7-diazaspiro[2.5]octan-7-yl)-1H-indazole | $R^t$ 1.66 min (Method 1); m/z 495.45 (M + H)$^+$ (ES$^+$) |

TABLE 3-continued

The examples shown in the table below were prepared by similar methods to those described for Example 1

| Example | Structure | LC-MS Analysis |
|---|---|---|
| 51 | 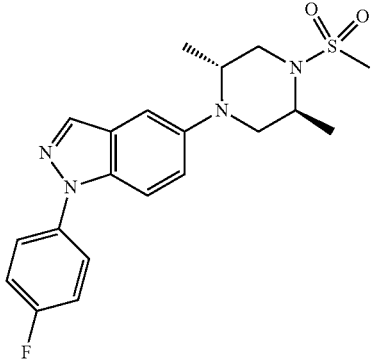<br>5-((2R,5S)-2,5-dimethyl-4-(methylsulfonyl)piperazin-1-yl)-1-(4-fluorophenyl)-1H-indazole | $R^t$ 1.58 min (Method 1); m/z 403.38 (M + H)$^+$ (ES$^+$) |
| 52 | 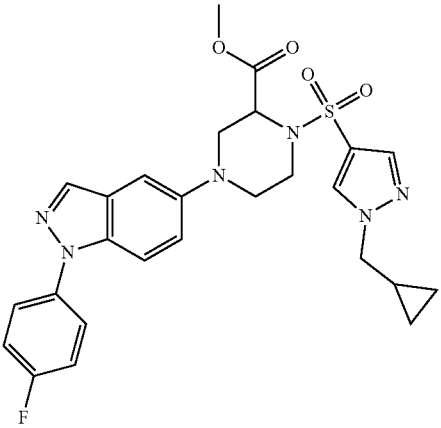<br>methyl 1-((1-(cyclopropylmethyl)-1H-pyrazol-4-yl)sulfonyl)-4-(1-(4-fluorophenyl)-1H-indazol-5-yl)piperazine-2-carboxamide | $R^t$ 1.66 min (Method 1); m/z 539.4 (M + H)$^+$ (ES$^+$) |
| 53 | 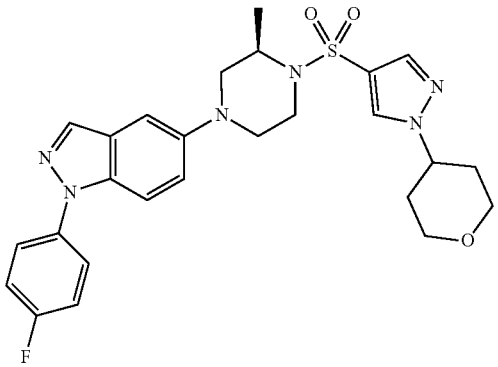<br>(R)-1-(4-fluorophenyl)-5-(3-methyl-4-((1-(tetrahydro-2H-pyran-4-yl)-1H-pyrazol-4-yl)sulfonyl)piperazin-1-yl)-1H-indazole | $R^t$ 1.60 min (Method 1); m/z 525.4 (M + H)$^+$ (ES$^+$) |

TABLE 3-continued

The examples shown in the table below were prepared by similar methods to those described for Example 1

| Example | Structure | LC-MS Analysis |
|---|---|---|
| 54 | 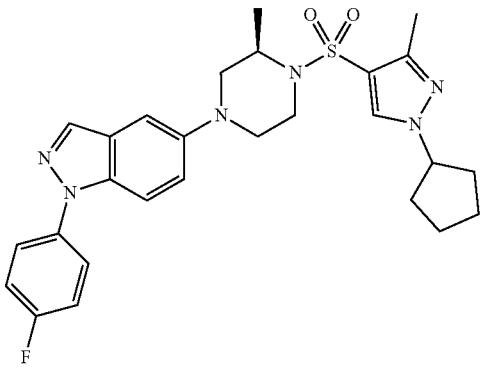<br>(R)-5-(4-((1-cyclopentyl-3-methyl-1H-pyrazol-4-yl)sulfonyl)-3-methylpiperazin-1-yl)-1-(4-fluorophenyl)-1H-indazole | $R^t$ 1.87 min (Method 1); m/z 523.5 $(M + H)^+$ $(ES^+)$ |
| 55 | 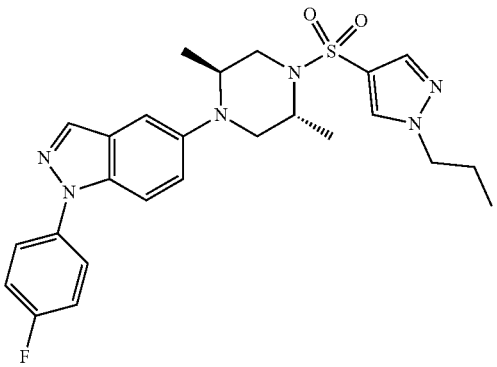<br>5-((2S,5R)-2,5-dimethyl-4-((1-propyl-1H-pyrazol-4-yl)sulfonyl)piperazin-1-yl)-1-(4-fluorophenyl)-1H-indazole | $R^t$ 1.75 min (Method 1); m/z 497.20 $(M + H)^+$ $(ES^+)$ |
| 56 | 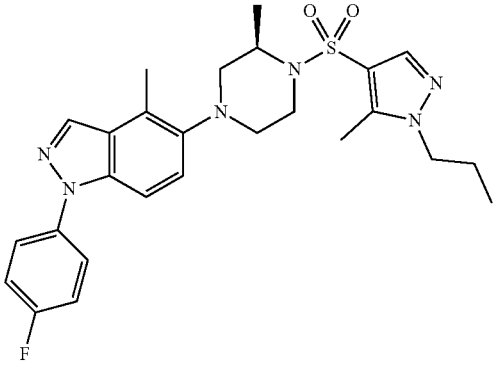<br>(R)-1-(4-fluorophenyl)-5-(3-methyl-4-((5-methyl-1-propyl-1H-pyrazol-4-yl)sulfonyl)piperazin-1-yl)-1H-indazole | $R^t$ 1.75 min (Method 1); m/z 497.72 $(M + H)^+$ $(ES^+)$ |

TABLE 3-continued

The examples shown in the table below were prepared by similar methods to those described for Example 1

| Example | Structure | LC-MS Analysis |
|---|---|---|
| 57 | 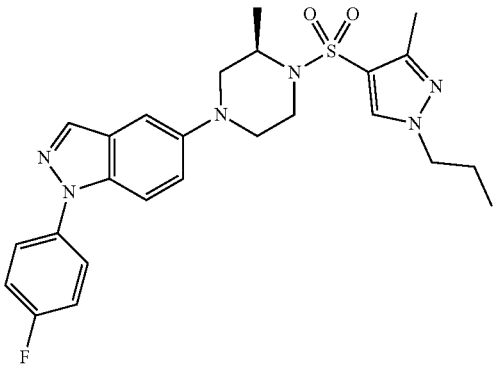<br>(R)-1-(4-fluorophenyl)-5-(3-methyl-4-((3-methyl-1-propyl-1H-pyrazol-4-yl)sulfonyl)piperazin-1-yl)-1H-indazole | $R^t$ 1.74 min (Method 1); m/z 497.45 $(M + H)^+$ $(ES^+)$ |
| 58 | 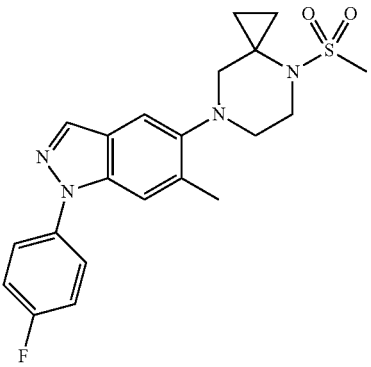<br>1-(4-fluorophenyl)-6-methyl-5-(4-(methylsulfonyl)-4,7-diazaspiro[2.5]octan-7-yl)-1H-indazole | $R^t$ 1.70 min (Method 1); m/z 415.42 $(M + H)^+$ $(ES^+)$ |
| 59 | 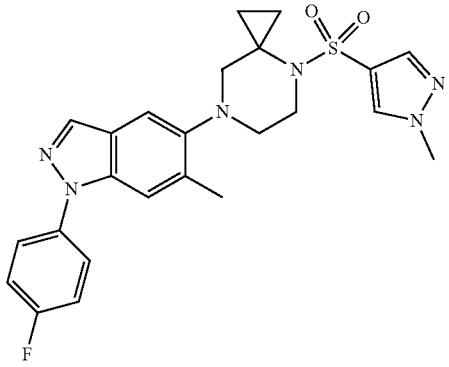<br>1-(4-fluorophenyl)-6-methyl-5-(4-((1-methyl-1H-pyrazol-4-yl)sulfonyl)-4,7-diazaspiro[2.5]octan-7-yl)-1H-indazole | $R^t$ 1.71 min (Method 1); m/z 481.43 $(M + H)^+$ $(ES^+)$ |

TABLE 3-continued

The examples shown in the table below were prepared by similar methods to those described for Example 1

| Example | Structure | LC-MS Analysis |
|---|---|---|
| 60 | 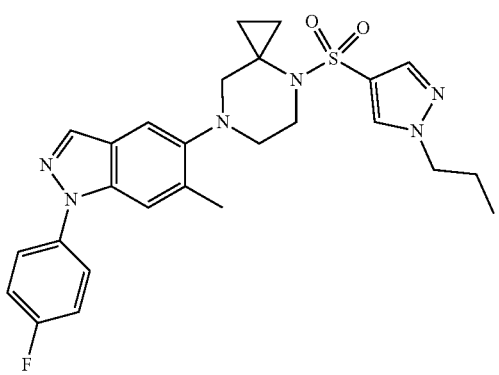  1-(4-fluorophenyl)-6-methyl-5-(4-((1-propyl-1H-pyrazol-4-yl)sulfonyl)-4,7-diazaspiro[2.5]octan-7-yl)-1H-indazole | $R^t$ 1.85 min (Method 1); m/z 509.44 $(M + H)^+$ $(ES^+)$ |
| 61 | 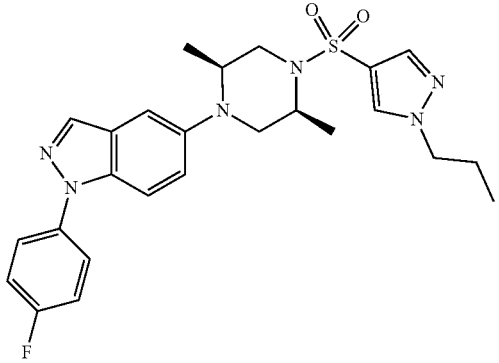  5-((2S,5S)-2,5-dimethyl-4-((1-propyl-1H-pyrazol-4-yl)sulfonyl)piperazin-1-yl)-1-(4-fluorophenyl)-1H-indazole | $R^t$ 1.77 min (Method 1); m/z 497.40 $(M + H)^+$ $(ES^+)$ |
| 62 | 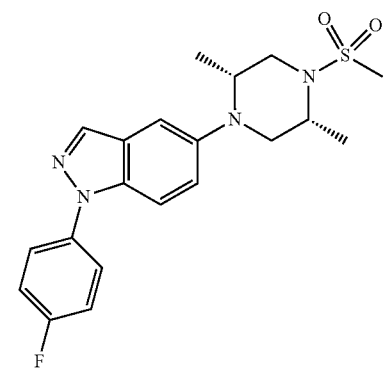  5-((2R,5R)-2,5-dimethyl-4-(methylsulfonyl)piperazin-1-yl)-1-(4-fluorophenyl)-1H-indazole | $R^t$ 1.61 min (Method 1); m/z 403.45 $(M + H)^+$ $(ES^+)$ |

TABLE 3-continued

The examples shown in the table below were prepared by similar methods to those described for Example 1

| Example | Structure | LC-MS Analysis |
|---|---|---|
| 63 | 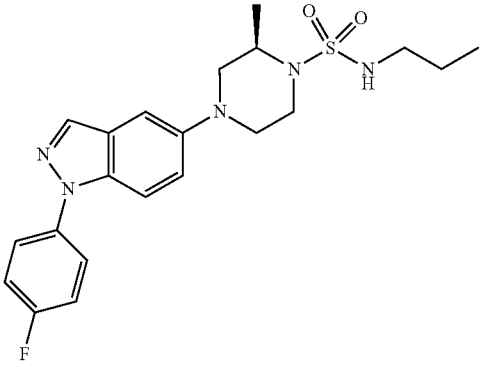<br>(R)-4-(1-(4-fluorophenyl)-1H-indazol-5-yl)-2-methyl-N-propylpiperazine-1-sulfonamide | $R^t$ 1.67 min (Method 1); m/z 432.3 (M + H)$^+$ (ES$^+$) |
| 64 | 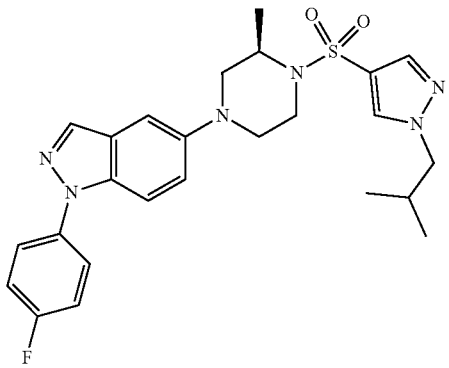<br>(R)-1-(4-fluorophenyl)-5-(4-((1-isobutyl-1H-pyrazol-4-yl)sulfonyl)-3-methylpiperazin-1-yl)-1H-indazole | $R^t$ 1.75 min (Method 1); m/z 497.3 (M + H)$^+$ (ES$^+$) |
| 65 | 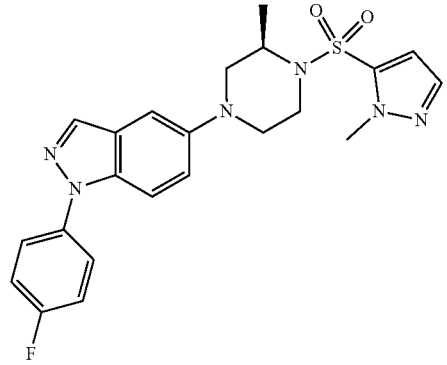<br>(R)-1-(4-fluorophenyl)-5-(3-methyl-4-((1-methyl-1H-pyrazol-5-yl)sulfonyl)piperazin-1-yl)-1H-indazole | $R^t$ 1.66 min (Method 1); m/z 455.2 (M + H)$^+$ (ES$^+$) |

TABLE 3-continued

The examples shown in the table below were prepared by similar methods to those described for Example 1

| Example | Structure | LC-MS Analysis |
|---|---|---|
| 66 | 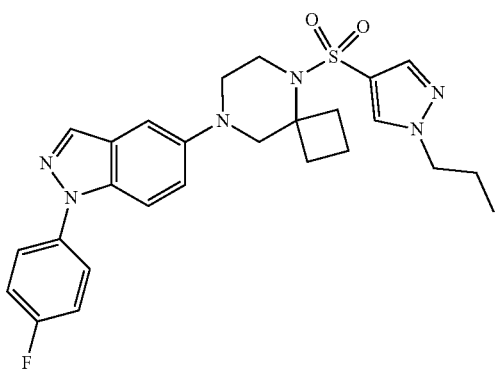

8-(1-(4-fluorophenyl)-1H-indazol-5-yl)-5-((1-propyl-1H-pyrazol-4-yl)sulfonyl)-5,8-diazaspiro[3.5]nonane | $R^t$ 1.80 min (Method 1); m/z 509.10 $(M + H)^+$ $(ES^+)$ |
| 67 | 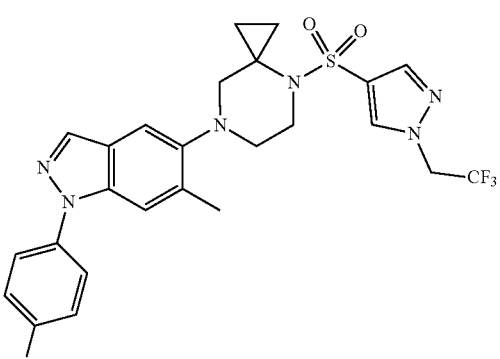

1-(4-fluorophenyl)-6-methyl-4-(4-((1-(2,2,2-trifluoroethyl)-1H-pyrazol-4-yl)sulfonyl)-4,7-diazaspiro[2.5]octan-7-yl)-1H-indazole | $R^t$ 1.83 min (Method 1); m/z 549.3 $(M + H)^+$ $(ES^+)$ |
| 68 | 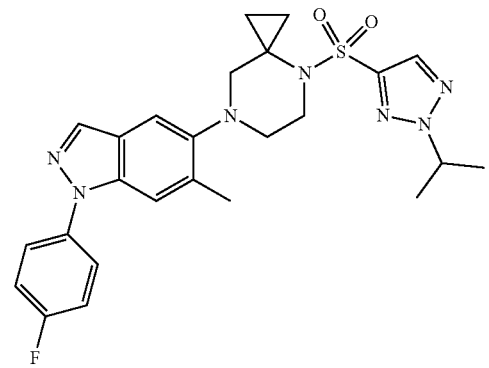

1-(4-fluorophenyl)-5-(4-((2-isopropyl-2H-1,2,3-triazol-4-yl)sulfonyl)-4,7-diazaspiro[2.5]octan-7-yl)-6-methyl-1H-indazole | $R^1$ 1.94 min (Method 1); m/z 510.5 $(M + H)^+$ $(ES^+)$ |

TABLE 3-continued

The examples shown in the table below were prepared by similar methods to those described for Example 1

| Example | Structure | LC-MS Analysis |
|---|---|---|
| 69 | 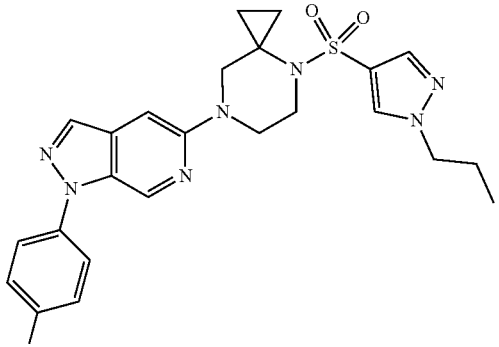<br>1-(4-fluorophenyl)-5-(4-((1-propyl-1H-pyrazol-4-yl)sulfonyl)-4,7-diazaspiro[2.5]octan-7-yl)-1H-pyrazolo[3,4-c]pyridine | R$^t$ 1.64 min (Method 1); m/z 496.37 (M + H)$^+$ (ES$^+$) |
| 70 | 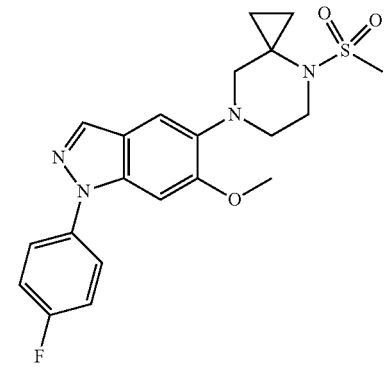<br>1-(4-fluorophenyl)-6-methoxy-5-(4-(methylsulfonyl)-4,7-diazaspiro[2.5]octan-7-yl)-1H-indazole | R$^t$ 1.42 min (Method 1); m/z 431.43 (M + H)$^+$ (ES$^+$) |
| 71 | 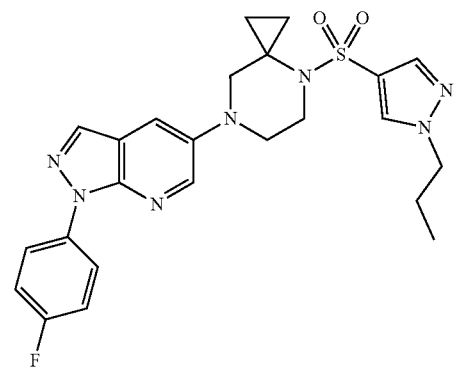<br>1-(4-fluorophenyl)-5-(4-((1-propyl-1H-pyrazol-4-yl)sulfonyl)-4,7-diazaspiro[2.5]octan-7-yl)-1H-pyrazolo[3,4-b]pyridine | R$^t$ 1.68 min (Method 1); m/z 496.44 (M + H)$^+$ (ES$^+$) |

TABLE 3-continued

The examples shown in the table below were prepared by similar methods to those described for Example 1

| Example | Structure | LC-MS Analysis |
|---|---|---|
| 72 | 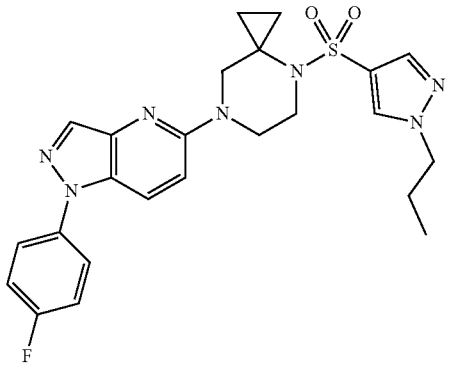<br>1-(4-fluorophenyl)-5-(4-((1-propyl-1H-pyrazol-4-yl)sulfonyl)-4,7-diazaspiro[2.5]octan-7-yl)-1H-pyrazolo[4,3-b]pyridine | $R^t$ 1.53 min (Method 1); m/z 496.37 $(M + H)^+$ $(ES^+)$ |
| 73 | 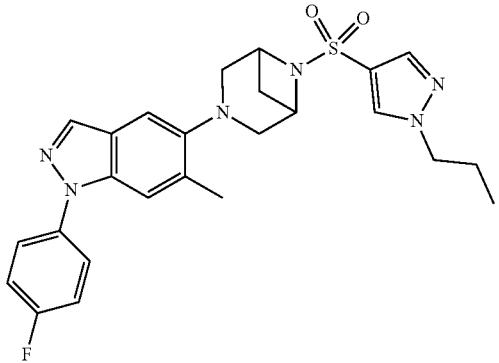<br>3-(1-(4-fluorophenyl)-6-methyl-1H-indazol-5-yl)-6-((1-propyl-1H-pyrazol-4-yl)sulfonyl)-3,6-diazabicyclo[3.1.1]heptane | $R^t$ 1.74 min (Method 1); m/z 495.4 $(M + H)^+$ $(ES^+)$ |
| 74 | 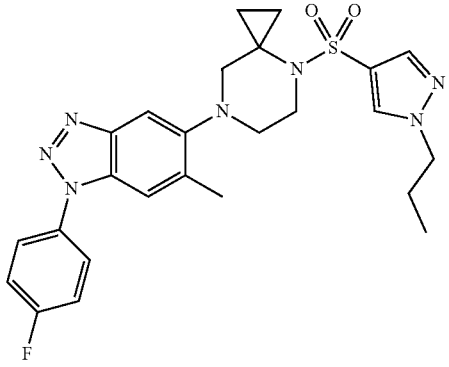<br>1-(4-fluorophenyl)-6-methyl-5-(4-((1-propyl-1H-pyrazol-4-yl)sulfonyl)-4,7-diazaspiro[2.5]octan-7-yl)-1H-benzo[d][1,2,3]triazole | $R^t$ 1.73 min (Method 1); m/z 510.35 $(M + H)^+$ $(ES^+)$ |

TABLE 3-continued

The examples shown in the table below were prepared by similar methods to those described for Example 1

| Example | Structure | LC-MS Analysis |
|---|---|---|
| 75 | 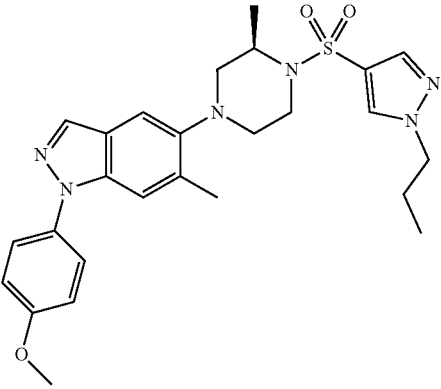<br>(R)-1-(4-methoxyphenyl)-6-methyl-5-(3-methyl-4-((1-propyl-1H-pyrazol-4-yl)sulfonyl)piperazin-1-yl)-1H-indazole | $R^t$ 1.75 min (Method 1); m/z 509.4 $(M + H)^+$ $(ES^+)$ |
| 76 | 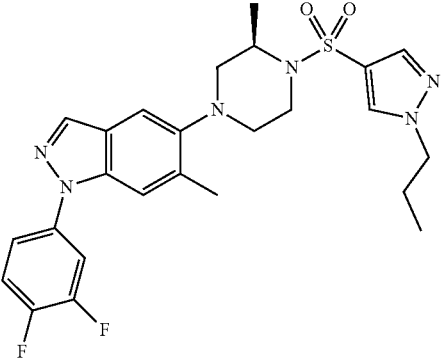<br>(R)-1-(3,4-difluorophenyl)-6-methyl-5-(3-methyl-4-((1-propyl-1H-pyrazol-4-yl)sulfonyl)piperazin-1-yl)-1H-indazole | $R^t$ 1.86 min (Method 1); m/z 515.3 $(M + H)^+$ $(ES^+)$ |
| 77 | 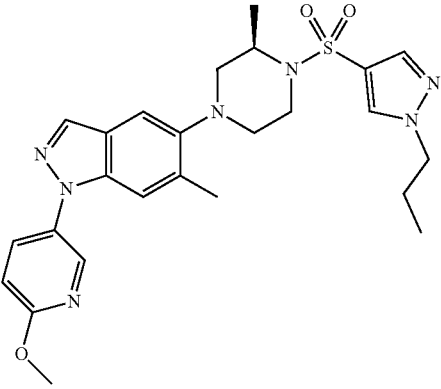<br>(R)-1-(6-methoxypyridin-3-yl)-6-methyl-5-(3-methyl-4-((1-propyl-1H-pyrazol-4-yl)sulfonyl)piperazin-1-yl)-1H-indazole | $R^t$ 1.70 min (Method 1); m/z 510.4 $(M + H)^+$ $(ES^+)$ |

TABLE 3-continued

The examples shown in the table below were prepared by similar methods to those described for Example 1

| Example | Structure | LC-MS Analysis |
| --- | --- | --- |
| 78 | 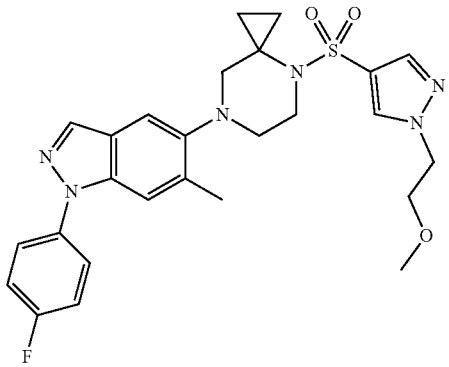<br>1-(4-fluorophenyl)-5-(4-((1-(2-methoxyethyl)-1H-pyrazol-4-yl)sulfonyl)-4,7-diazaspiro[2.5]octan-7-yl)-6-methyl-1H-indazole | $R^t$ 1.73 min (Method 1); m/z 525.27 $(M + H)^+$ $(ES^+)$ |
| 79 | 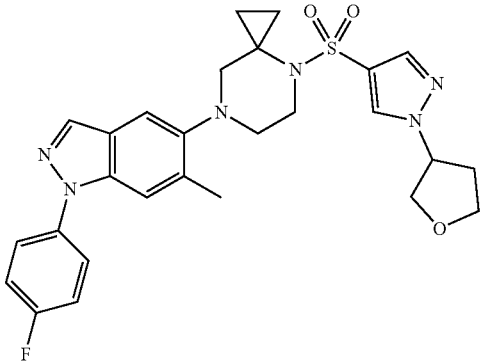<br>1-(4-fluorophenyl)-6-methyl-5-(4-((1-(tetrahydrofuran-3-yl)-1H-pyrazol-4-yl)sulfonyl)-4,7-diazaspiro[2.5]octan-7-yl)-1H-indazole | $R^t$ 1.73 min (Method 1); m/z 537.29 $(M + H)^+$ $(ES^+)$ |
| 80 | 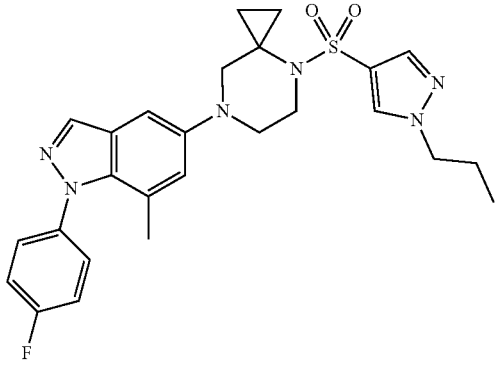<br>1-(4-fluorophenyl)-7-methyl-5-(4-((1-propyl-1H-pyrazol-4-yl)sulfonyl)-4,7-diazaspiro[2.5]octan-7-yl)-1H-indazole | $R^t$ 1.63 min (Method 1); m/z 509.4 $(M + H)^+$ $(ES^+)$ |

TABLE 3-continued

The examples shown in the table below were prepared by similar methods to those described for Example 1

| Example | Structure | LC-MS Analysis |
|---|---|---|
| 81 | 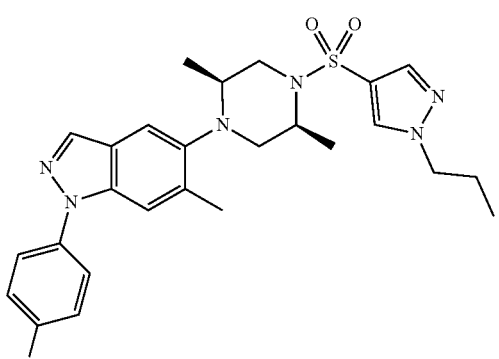<br>5-((2S,5S)-2,5-dimethyl-4-((1-propyl-1H-pyrazol-4-yl)sulfonyl)piperazin-1-yl)-1-(4-fluorophenyl)-6-methyl-1H-indazole | $R^t$ 1.90 min (Method 1); m/z 511.2 $(M + H)^+$ $(ES^+)$ |
| 82 | 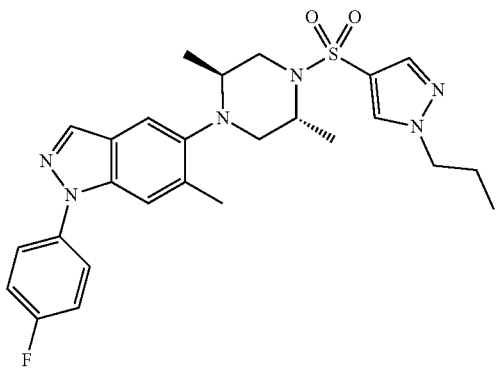<br>5-((2S,5R)-2,5-dimethyl-4-((1-propyl-1H-pyrazol-4-yl)sulfonyl)piperazin-1-yl)-1-(4-fluorophenyl)-6-methyl-1H-indazole | $R^t$ 1.86 min (Method 1); m/z 511.2 $(M + H)^+$ $(ES^+)$ |
| 83 | 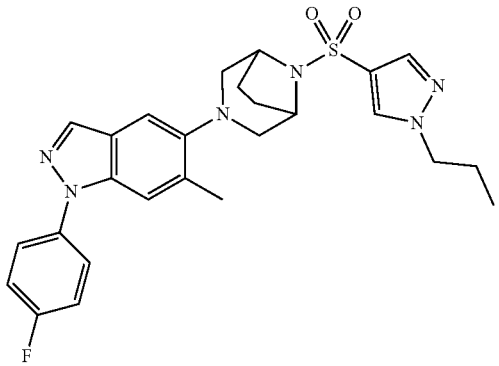<br>1-(4-fluorophenyl)-6-methyl-5-(8-((1-propyl-1H-pyrazol-4-yl)sulfonyl)-3,8-diazabicyclo[3.2.1]octan-3-yl)-1H-indazole | $R^t$ 2.73 min (Method 2); m/z 509.0 $(M + H)^+$ $(ES^+)$ |

TABLE 3-continued

The examples shown in the table below were prepared by similar methods to those described for Example 1

| Example | Structure | LC-MS Analysis |
|---|---|---|
| 84 | 3-(6-methyl-5-(4-((1-propyl-1H-pyrazol-4-yl)sulfonyl)-4,7-diazaspiro[2.5]octan-7-yl)-1H-indazol-1-yl)-N-(tetrahydrofuran-3-yl)benzamide | R$^t$ 1.52 min (Method 1); m/z 604.5 (M + H)$^+$ (ES$^+$) |
| 85 | 3-(6-methyl-5-(4-(methylsulfonyl)-4,7-diazaspiro[2.5]octan-7-yl)-1H-indazol-1-yl)-N-(tetrahydrofuran-3-yl)benzamide | R$^t$ 1.36 min (Method 1); m/z 510.5 (M + H)$^+$ (ES$^+$) |
| 86 | 1-(4-fluorophenyl)-6-methyl-5-(2-phenyl-4-((1-propyl-1H-pyrazol-4-yl)sulfonyl)piperazin-1-yl)-1H-indazole | R$^t$ 1.87 min (Method 1); m/z 559.4 (M + H)$^+$ (ES$^+$) |

TABLE 3-continued

The examples shown in the table below were prepared by similar methods to those described for Example 1

| Example | Structure | LC-MS Analysis |
|---|---|---|
| 87 | 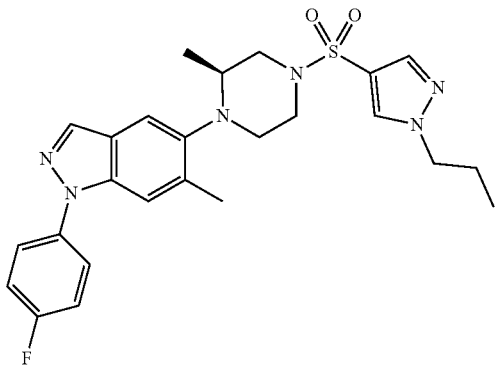<br>(S)-1-(4-fluorophenyl)-6-methyl-5-(2-methyl-4-((1-propyl-1H-pyrazol-4-yl)sulfonyl)piperazin-1-yl)-1H-indazole | $R^t$ 1.84 min (Method 1); m/z 497.4 (M + H)$^+$ (ES$^+$) |
| 88 | 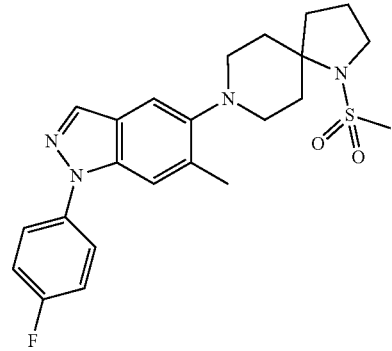<br>8-(1-(4-fluorophenyl)-6-methyl-1H-indazol-5-yl)-1-(methylsulfonyl)-1,8-diazaspiro[4.5]decane | $R^t$ 2.50 min (Method 2); m/z 443.0 (M + H)$^+$ (ES$^+$) |
| 89 | 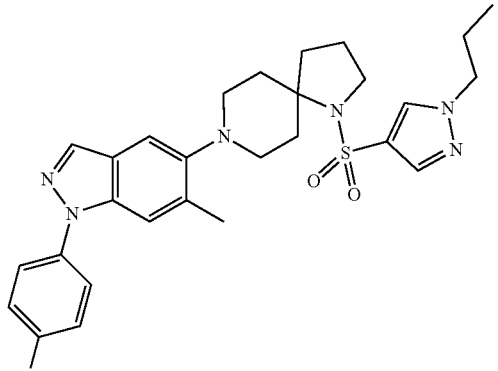<br>8-(1-(4-fluorophenyl)-6-methyl-1H-indazol-5-yl)-1-((1-propyl-1H-pyrazol-4-yl)sulfonyl)-1,8-diazaspiro[4.5]decane | $R^t$ 2.77 min (Method 2); m/z 537.20 (M + H)$^+$ (ES$^+$) |

TABLE 3-continued

The examples shown in the table below were prepared by similar methods to those described for Example 1

| Example | Structure | LC-MS Analysis |
|---|---|---|
| 90 | 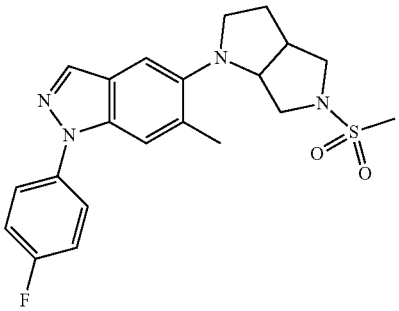<br>1-(4-fluorophenyl)-6-methyl-5-(5-(methylsulfonyl)hexahydropyrrolo[3,4-b]pyrrol-1(2H)-yl)-1H-indazole | R$^t$ 1.60 min (Method 1); m/z 415.47 (M + H)$^+$ (ES$^+$) |
| 91 | 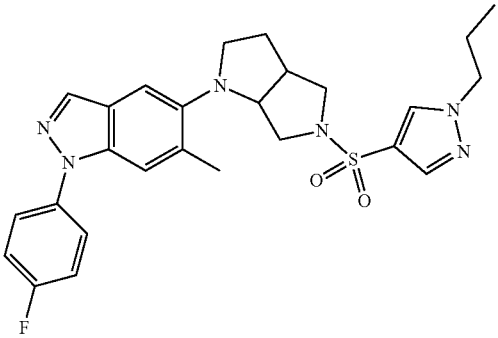<br>1-(4-fluorophenyl)-6-methyl-5-(5-((1-propyl-1H-pyrazol-4-yl)sulfonyl)hexahydropyrrolo[3,4-b]pyrrol-1(2H)-yl)-1H-indazole | R$^t$ 1.77 min (Method 1); m/z 509.44 (M + H)$^+$ (ES$^+$) |
| 92 | 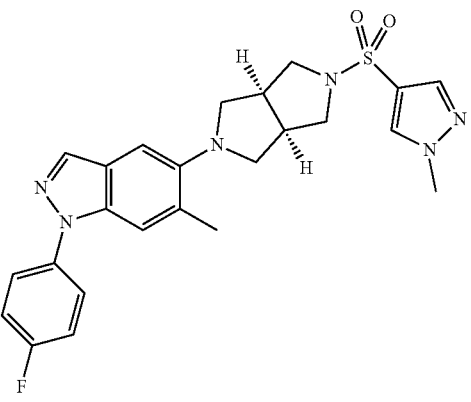<br>1-(4-fluorophenyl)-6-methyl-5-((3aR,6aS)-5-((1-methyl-1H-pyrazol-4-yl)sulfonyl)hexahydropyrrolo[3,4-c]pyrrol-2(1H)-yl)-1H-indazole | R$^t$ 1.57 min (Method 1); m/z 481.37 (M + H)$^+$ (ES$^+$) |

TABLE 3-continued

The examples shown in the table below were prepared by similar methods to those described for Example 1

| Example | Structure | LC-MS Analysis |
|---------|-----------|----------------|
| 93 | 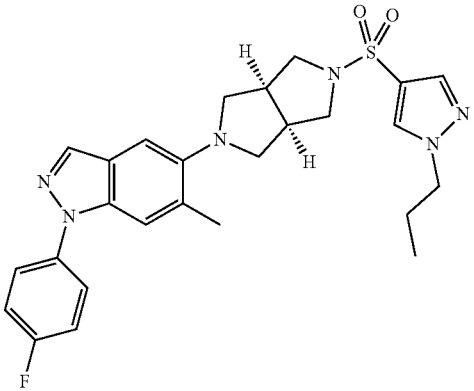<br>1-(4-fluorophenyl)-6-methyl-5-((3aR,6aS)-5-((1-propyl-1H-pyrazol-4-yl)sulfonyl)hexahydropyrrolo[3,4-c]pyrrol-2(1H)-yl)-1H-indazole | $R^t$ 1.73 min (Method 1); m/z 509.40 $(M + H)^+$ $(ES^+)$ |
| 94 | 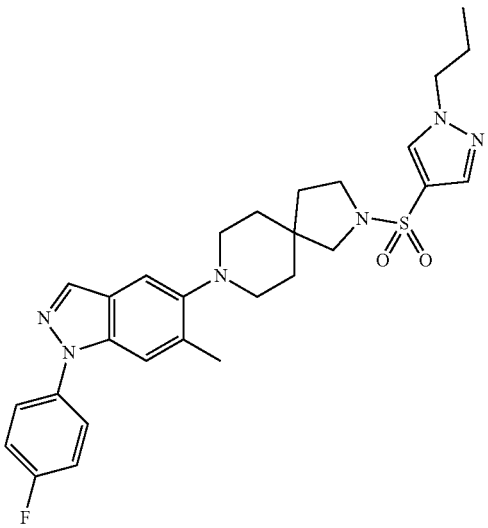<br>8-(1-(4-fluorophenyl)-6-methyl-1H-indazol-5-yl)-2-((1-propyl-1H-pyrazol-4-yl)sulfonyl)-2,8-diazaspiro[4.5]decane | $R^t$ 1.84 min (Method 1); m/z 537.45 $(M + H)^+$ $(ES^+)$ |
| 95 | 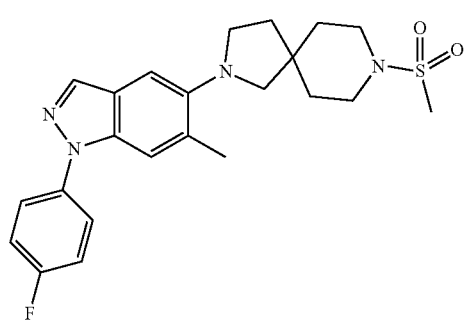<br>2-(1-(4-fluorophenyl)-6-methyl-1H-indazol-5-yl)-8-(methylsulfonyl)-2,8-diazaspiro[4.5]decane | $R^t$ 1.64 min (Method 1); m/z 443.40 $(M + H)^+$ $(ES^+)$ |

TABLE 3-continued

The examples shown in the table below were prepared by similar methods to those described for Example 1

| Example | Structure | LC-MS Analysis |
|---|---|---|
| 96 | 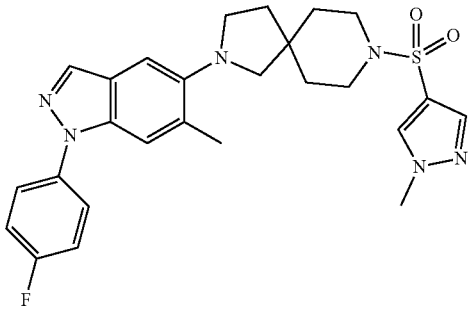\n\n2-(1-(4-fluorophenyl)-6-methyl-1H-indazol-5-yl)-8-((1-methyl-1H-pyrazol-4-yl)sulfonyl)-2,8-diazaspiro[4.5]decane | $R^t$ 1.67 min (Method 1); m/z 509.43 $(M + H)^+$ $(ES^+)$ |

Examples 97-103

TABLE 4

The examples shown in the table below were prepared by similar methods to those described for Example 2.

| Example | Structure | LC-MS Analysis |
|---|---|---|
| 97 | 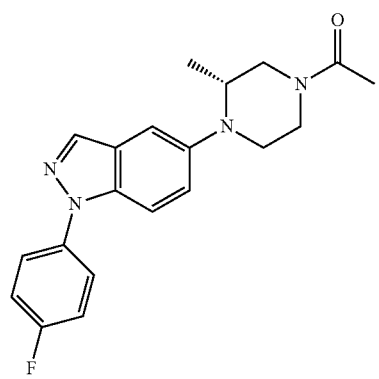\n\n(R)-1-(4-(1-(4-fluorophenyl)-1H-indazol-5-yl)-3-methylpiperazin-1-yl)ethan-1-one | $R^t$ 1.17 min (Method 1); m/z 353.41 $(M + H)^+$ $(ES^+)$ |

TABLE 4-continued

The examples shown in the table below were prepared by similar methods to those described for Example 2.

| Example | Structure | LC-MS Analysis |
|---|---|---|
| 98 | 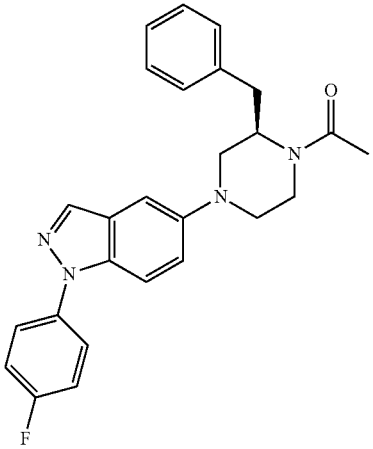<br>(R)-1-(2-benzyl-4-(1-(4-fluorophenyl)-1H-indazol-5-yl)piperazin-1-yl)ethan-1-one | $R^t$ 1.69 min (Method 1); m/z 429.49 (M + H)$^+$ (ES$^+$) |
| 99 | 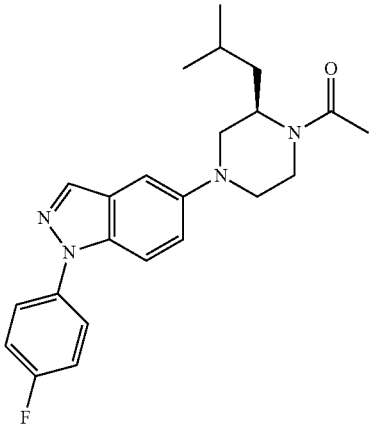<br>(R)-1-(4-(1-(4-fluorophenyl)-1H-indazol-5-yl)-2-isobutylpiperazin-1-yl)ethan-1-one | $R^t$ 1.70 min (Method 1); m/z 395.46 (M + H)$^+$ (ES$^+$) |
| 100 | 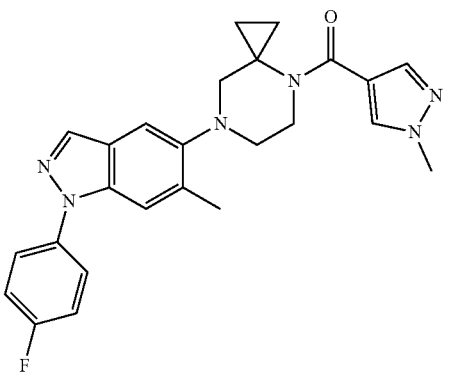<br>(7-(1-(4-fluorophenyl)-6-methyl-1H-indazol-5-yl)-4,7-diazaspiro[2.5]octan-4-yl)(1-methyl-1H-pyrazol-4-yl)methanone | $R^t$ 1.53 min (Method 1); m/z 445.4 (M + H)$^+$ (ES$^+$) |

TABLE 4-continued

The examples shown in the table below were prepared by similar methods to those described for Example 2.

| Example | Structure | LC-MS Analysis |
|---|---|---|
| 101 | 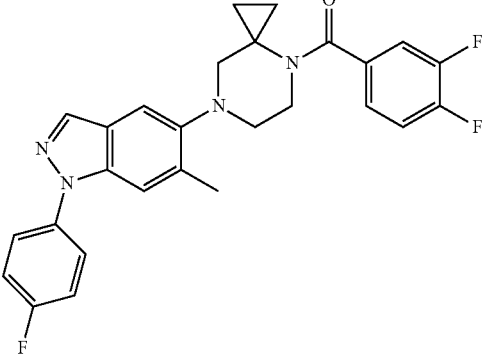<br>(3,4-difluorophenyl)(7-(1-(4-fluorophenyl)-6-methyl-1H-indazol-5-yl)-4,7-diazaspiro[2.5]octan-4-yl)methanone | $R^t$ 1.88 min (Method 1); m/z 477.5 $(M + H)^+$ $(ES^+)$ |
| 102 | 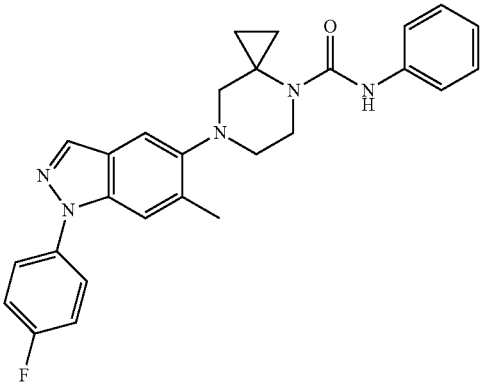<br>7-(1-(4-fluorophenyl)-6-methyl-1H-indazol-5-yl)-N-phenyl-4,7-diazaspiro[2.5]octane-4-carboxamide | $R^t$ 1.82 min (Method 1); m/z 456.3 $(M + H)^+$ $(ES^+)$ |
| 103 | 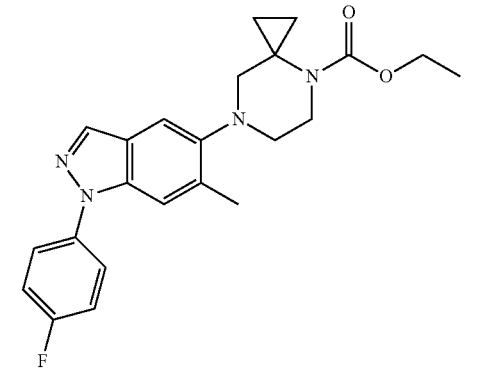<br>ethyl 7-(1-(4-fluorophenyl)-6-methyl-1H-indazol-5-yl)-4,7-diazaspiro[2.5]octane-4-carboxylate | $R^t$ 1.90 min (Method 1); m/z 409.3 $(M + H)^+$ $(ES^+)$ |

Example 104: (R)-1-(4-fluorophenyl)-5-(3-methyl-4-(propylsulfonyl)piperazin-1-yl)-1H-indazole

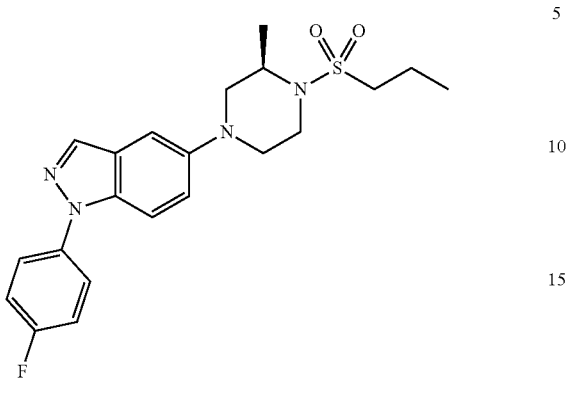

The compound was prepared by similar methods to those described for Example 3. $R^t$ 1.71 min (Method 1); m/z 417.43 (M+H)$^+$ (ES$^+$).

Examples 105-133

TABLE 5

The examples shown in the table below were prepared by similar methods to those described for Example 5.

| Example | Structure | LC-MS Analysis |
|---|---|---|
| 105 | (S)-N-(1-(1-(4-fluorophenyl)-1H-indazol-5-yl)pyrrolidin-3-yl)methanesulfonamide | $R^t$ 1.39 min (Method 1); m/z 375.36 (M + H)$^+$ (ES$^+$) |
| 106 | N-(1-(1-(4-fluorophenyl)-6-methyl-1H-indazol-5-yl)piperidin-4-yl)methanesulfonamide | $R^t$ 1.43 min (Method 1); m/z 403.2 (M + H)$^+$ (ES$^+$) |

TABLE 5-continued

The examples shown in the table below were prepared by similar methods to those described for Example 5.

| Example | Structure | LC-MS Analysis |
|---|---|---|
| 107 | 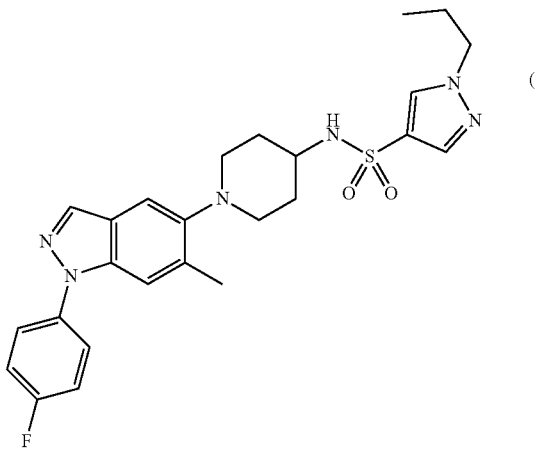<br>N-(1-(1-(4-fluorophenyl)-6-methyl-1H-indazol-5-yl)piperidin-4-yl)-1-propyl-1H-pyrazole-4-sulfonamide | R$^t$ 1.65 min (Method 1); m/z 497.3 (M + H)$^+$ (ES$^+$) |
| 108 | 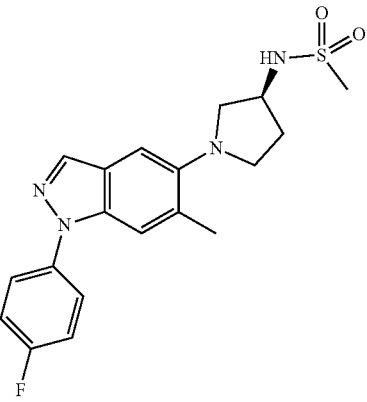<br>(S)-N-(1-(1-(4-fluorophenyl)-6-methyl-1H-indazol-5-yl)pyrrolidin-3-yl)methanesulfonamide | R$^t$ 1.40 min (Method 1); m/z 389.4 (M + H)$^+$ (ES$^+$) |
| 109 | 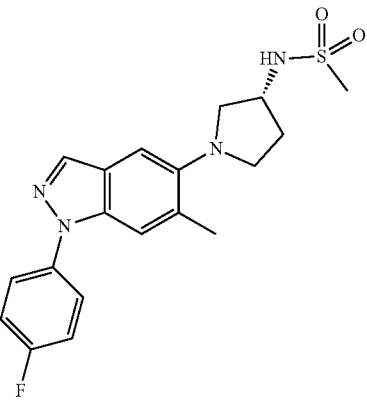<br>(R)-N-(1-(1-(4-fluorophenyl)-6-methyl-1H-indazol-5-yl)pyrrolidin-3-yl)methanesulfonamide | R$^t$ 1.41 min (Method 1); m/z 389.3 (M + H)$^+$ (ES$^+$) |

TABLE 5-continued

The examples shown in the table below were prepared by similar methods to those described for Example 5.

| Example | Structure | LC-MS Analysis |
|---------|-----------|----------------|
| 110 | 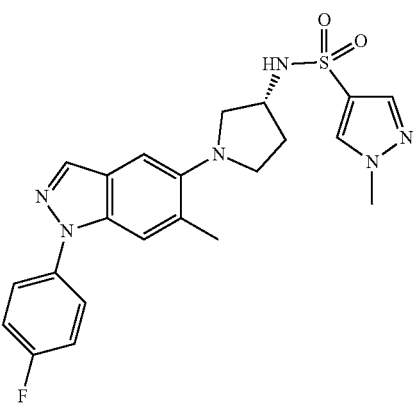<br>(R)-N-(1-(1-(4-fluorophenyl)-6-methyl-1H-indazol-5-yl)pyrrolidin-3-yl)-1-methyl-1H-pyrazole-4-sulfonamide | $R^t$ 1.44 min (Method 1); m/z 455.4 $(M + H)^+$ $(ES^+)$ |
| 111 | 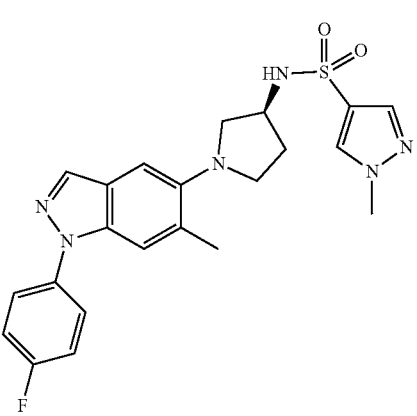<br>(S)-N-(1-(1-(4-fluorophenyl)-6-methyl-1H-indazol-5-yl)pyrrolidin-3-yl)-1-methyl-1H-pyrazole-4-sulfonamide | $R^t$ 1.45 min (Method 1); m/z 455.4 $(M + H)^+$ $(ES^+)$ |
| 112 | 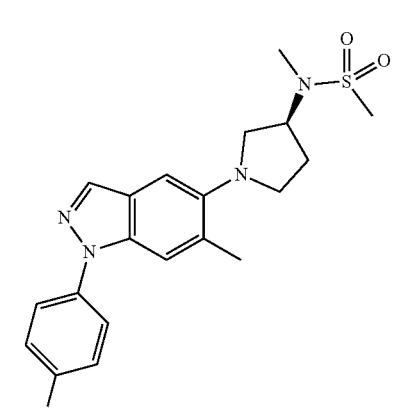<br>(S)-N-(1-(1-(4-fluorophenyl)-6-methyl-1H-indazol-5-yl)pyrrolidin-3-yl)-N-methylmethanesulfonamide | $R^t$ 1.58 min (Method 1); m/z 403.4 $(M + H)^+$ $(ES^+)$ |

TABLE 5-continued

The examples shown in the table below were prepared by similar methods to those described for Example 5.

| Example | Structure | LC-MS Analysis |
|---|---|---|
| 113 | 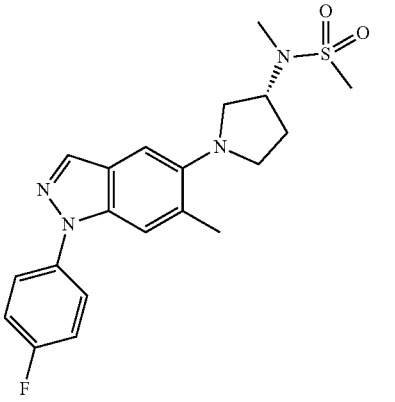<br>(R)-N-(1-(1-(4-fluorophenyl)-6-methyl-1H-indazol-5-yl)pyrrolidin-3-yl)-N-methylmethanesulfonamide | R$^t$ 1.59 min (Method 1); m/z 403.4 (M + H)$^+$ (ES$^+$) |
| 114 | 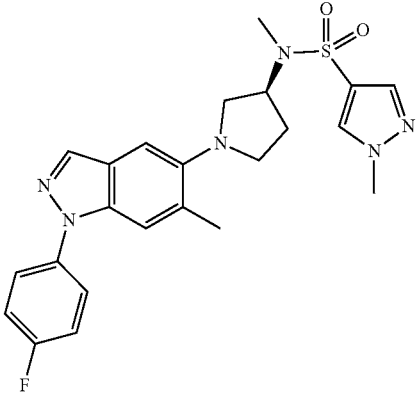<br>(S)-N-(1-(1-(4-fluorophenyl)-6-methyl-1H-indazol-5-yl)pyrrolidin-3-yl)-N,1-dimethyl-1H-pyrazole-4-sulfonamide | R$^t$ 1.61 min (Method 1); m/z 469.3 (M + H)$^+$ (ES$^+$) |
| 115 | 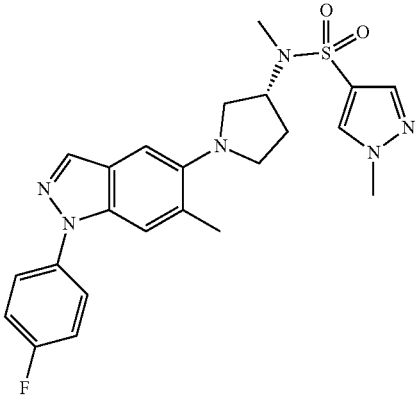<br>(R)-N-(1-(1-(4-fluorophenyl)-6-methyl-1H-indazol-5-yl)pyrrolidin-3-yl)-N,1-dimethyl-1H-pyrazole-4-sulfonamide | R$^t$ 1.61 min (Method 1); m/z 469.4 (M + H)$^+$ (ES$^+$) |

TABLE 5-continued

The examples shown in the table below were prepared by similar methods to those described for Example 5.

| Example | Structure | LC-MS Analysis |
|---------|-----------|----------------|
| 116 | N-(1-(1-(4-fluorophenyl)-6-methyl-1H-indazol-5-yl)piperidin-4-yl)-N-methylmethanesulfonamide | $R^t$ 1.63 min (Method 1); m/z 417.2 $(M + H)^+$ $(ES^+)$ |
| 117 | N-(1-(1-(4-fluorophenyl)-6-methyl-1H-indazol-5-yl)piperidin-4-yl)-N-methyl-1-propyl-1H-pyrazole-4-sulfonamide | $R^t$ 1.81 min (Method 1); m/z 511.3 $(M + H)^+$ $(ES^+)$ |
| 118 | (S)-N-(1-(1-(4-fluorophenyl)-6-methoxy-1H-indazol-5-yl)pyrrolidin-3-yl)-N-methyl-1-propyl-1H-pyrazole-4-sulfonamide | $R^t$ 1.61 min (Method 1); m/z 513.4 $(M + H)^+$ $(ES^+)$ |

TABLE 5-continued

The examples shown in the table below were prepared by similar methods to those described for Example 5.

| Example | Structure | LC-MS Analysis |
|---|---|---|
| 119 | N-(1-(1-(4-fluorophenyl)-6-methyl-1H-indazol-5-yl)-3-methylpyrrolidin-3-yl)-N-methyl-1-propyl-1H-pyrazole-4-sulfonamide | R$^t$ 1.83 min (Method 1); m/z 511.4 (M + H)$^+$ (ES$^+$) |
| 120 | 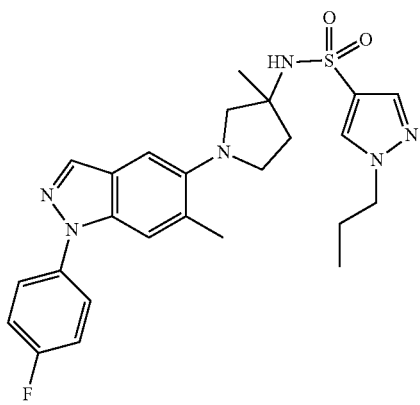 N-(1-(4-fluorophenyl)-6-methyl-1H-indazol-5-yl)-3-methylpyrrolidin-3-yl)-1-propyl-1H-pyrazole-4-sulfonamide | R$^t$ 1.69 min (Method 1); m/z 497.4 (M + H)$^+$ (ES$^+$) |

TABLE 5-continued

The examples shown in the table below were prepared by similar methods to those described for Example 5.

| Example | Structure | LC-MS Analysis |
|---|---|---|
| 121 | 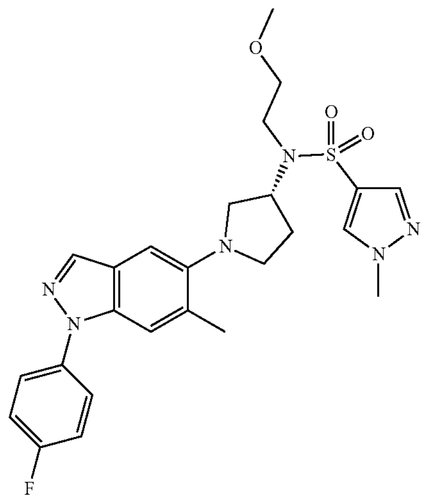 | R$^t$ 1.62 min (Method 1); m/z 513.39 (M + H)$^+$ (ES$^+$) |

(R)-N-(1-(1-(4-fluorophenyl)-6-methyl-1H-indazol-5-yl)pyrrolidin-3-yl)-N-(2-methoxyethyl)-1-methyl-1H-pyrazole-4-sulfonamide

| 122 | 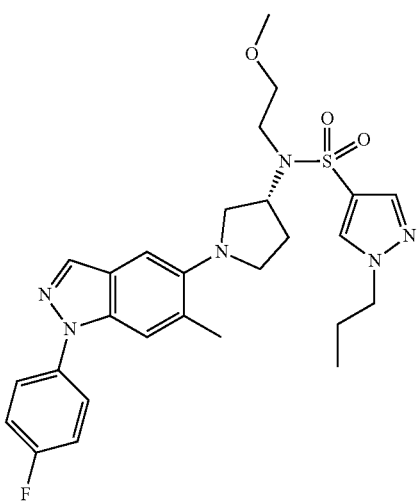 | R$^t$ 1.80 min (Method 1); m/z 541.4 (M + H)$^+$ (ES$^+$) |

(R)-N-(1-(1-(fluorophenyl)-6-methyl-1H-indazol-5-yl)pyrrolidin-3-yl)-N-(2-methoxyethyl)-1-propyl-1H-pyrazole-sulfonamide TABLE 5-continued The examples shown in the table below were prepared by similar methods to those described for Example 5.

| Example | Structure | LC-MS Analysis |
|---|---|---|
| 123 | 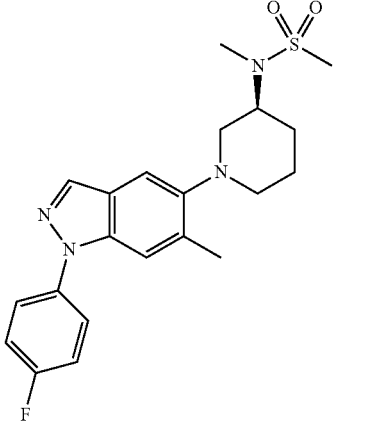<br>(S)-N-(1-(1-(4-fluorophenyl)-6-methyl-1H-indazol-5-yl)piperidin-3-yl)-N-methylmethanesulfonamide | $R^t$ 1.68 min (Method 1); m/z 417.00 $(M + H)^+$ $(ES^+)$ |
| 124 | 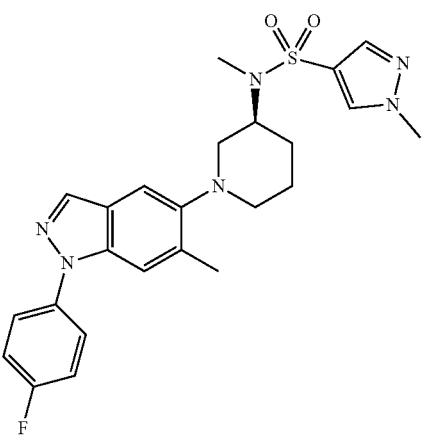<br>(S)-N-(1-(1-(4-fluorophenyl)-6-methyl-1H-indazol-5-yl)piperidin-3-yl)-N,1-dimethyl-1H-pyrazole-4-sulfonamide | $R^t$ 1.69 min (Method 1); m/z 483.00 $(M + H)^+$ $(ES^+)$ |
| 125 | 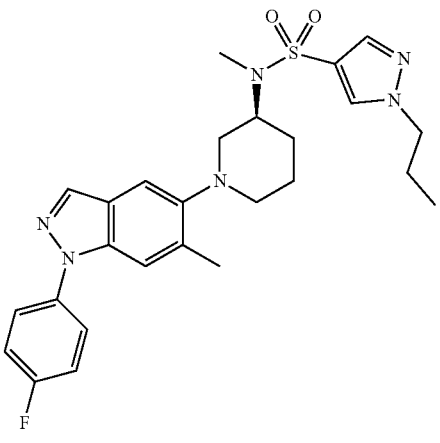<br>(S)-N-(1-(1-(4-fluorophenyl)-6-methyl-1H-indazol-5-yl)piperidin-3-yl)-N-methyl-1-propyl-1H-pyrazole-4-sulfonamide | $R^t$ 1.83 min (Method 1); m/z 511.20 $(M + H)^+$ $(ES^+)$ |

TABLE 5-continued

The examples shown in the table below were prepared by similar methods to those described for Example 5.

| Example | Structure | LC-MS Analysis |
|---|---|---|
| 126 | 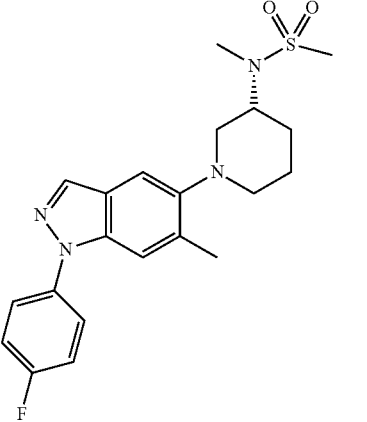<br>(R)-N-(1-(1-(4-fluorophenyl)-6-methyl-1H-indazol-5-yl)piperidin-3-yl)-N-methylmethanesulfonamide | $R^t$ 1.68 min (Method 1); m/z 417.00 $(M + H)^+$ $(ES^+)$ |
| 127 | 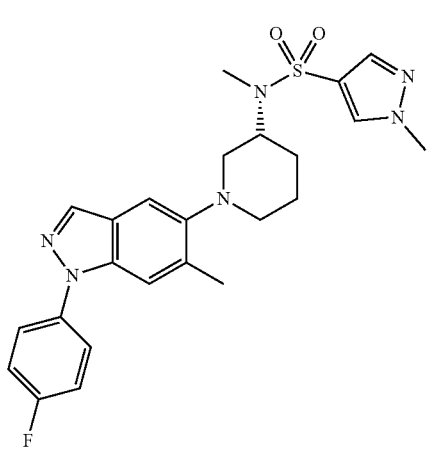<br>(R)-N-(1-(1-(4-fluorophenyl)-6-methyl-1H-indazol-5-yl)piperidin-3-yl)-N,1-dimethyl-1H-pyrazole-4-sulfonamide | $R^t$ 1.68 min (Method 1); m/z 483.00 $(M + H)^+$ $(ES^+)$ |
| 128 | 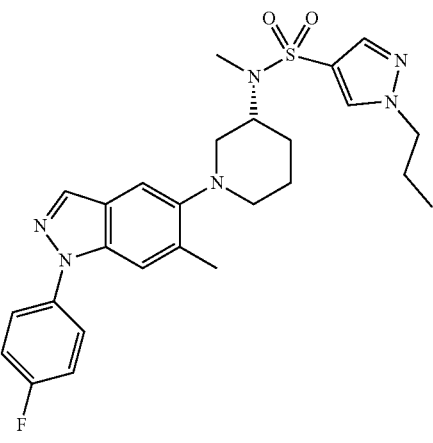<br>(R)-N-(1-(1-(4-fluorophenyl)-6-methyl-1H-indazol-5-yl)piperidin-3-yl)-N-methyl-1-propyl-1H-pyrazole-4-sulfonamide | $R^t$ 1.84 min (Method 1); m/z 511.20 $(M + H)^+$ $(ES^+)$ |

321

TABLE 5-continued

The examples shown in the table below were prepared by similar methods to those described for Example 5.

| Example | Structure | LC-MS Analysis |
|---|---|---|
| 129 | 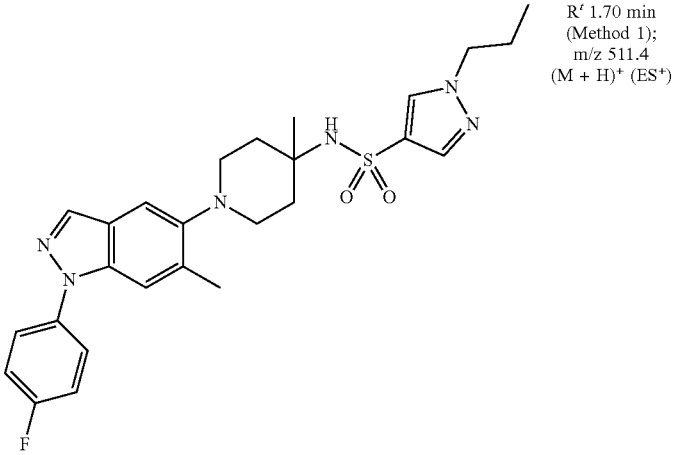<br>N-(1-(1-(4-fluorophenyl)-6-methyl-1H-indazol-5-yl)-4-methylpiperidin-4-yl)-1-propyl-1H-pyrazole-4-sulfonamide | $R^t$ 1.70 min (Method 1); m/z 511.4 $(M + H)^+$ $(ES^+)$ |
| 130 | 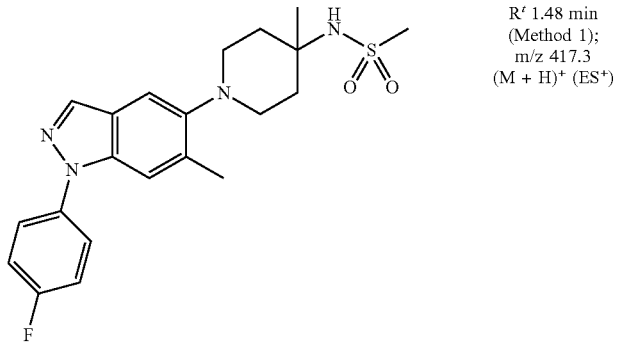<br>N-(1-(1-(4-fluorophenyl)-6-methyl-1H-indazol-5-yl)-4-methylpiperidin-4-yl)methanesulfonamide | $R^t$ 1.48 min (Method 1); m/z 417.3 $(M + H)^+$ $(ES^+)$ |
| 131 | 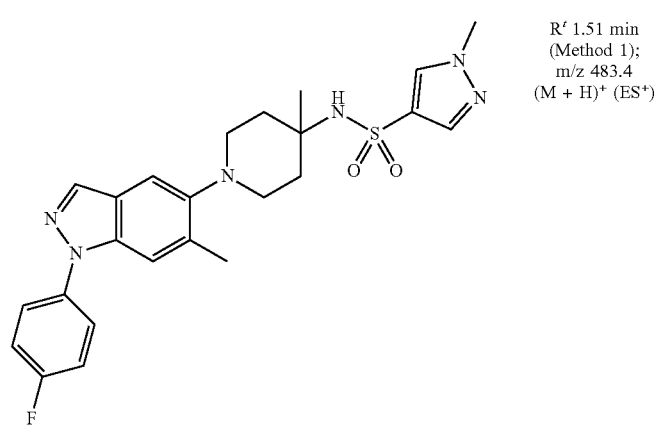<br>N-(1-(1-(4-fluorophenyl)-6-methyl-1H-indazol-5-yl)-4-methylpiperidin-4-yl)-1-methyl-1H-pyrazole-4-sulfonamide | $R^t$ 1.51 min (Method 1); m/z 483.4 $(M + H)^+$ $(ES^+)$ |

TABLE 5-continued

The examples shown in the table below were prepared by similar methods to those described for Example 5.

| Example | Structure | LC-MS Analysis |
| --- | --- | --- |
| 132 | 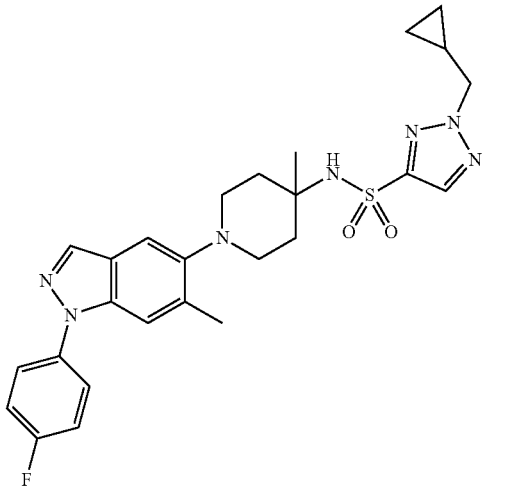  2-(cyclopropylmethyl)-N-(1-(1-(4-fluorophenyl)-6-methyl-1H-indazol-5-yl)-4-methylpiperidin-4-yl)-2H-1,2,3-triazole-4-sulfonamide | $R^t$ 1.87 min (Method 1); m/z 524.5 $(M + H)^+$ $(ES^+)$ |
| 133 | 1-(cyclopropylmethyl)-N-(1-(1-(4-fluorophenyl)-6-methyl-1H-indazol-5-yl)-4-methylpiperidin-4-yl)-1H-pyrazole-4-sulfonamide | $R^t$ 1.79 min (Method 1); m/z 523.5 $(M + H)^+$ $(ES^+)$ |

Examples 134-146

TABLE 6

The examples shown in the table below were prepared by similar methods to those described for Example 6.

| Example | Structure | LC-MS Analysis |
|---|---|---|
| 134 | 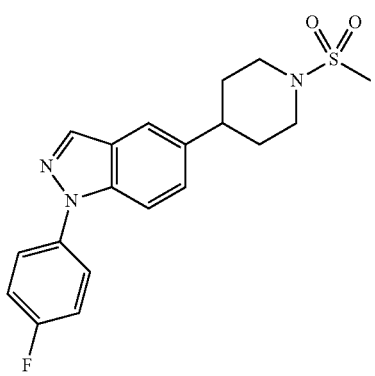<br>1-(4-fluorophenyl)-5-(1-(methylsulfonyl)piperidin-4-yl)-1H-indazole | $R^t$ 1.51 min (Method 1); m/z 374.2 $(M + H)^+$ $(ES^+)$ |
| 135 | 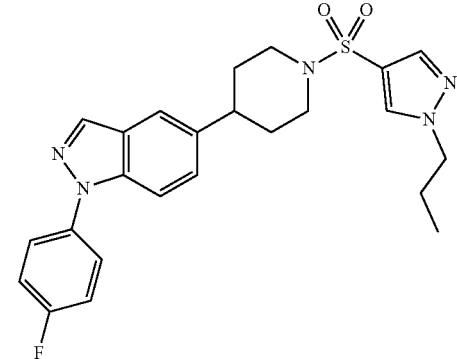<br>1-(4-fluorophenyl)-5-(1-((1-propyl-1H-pyrazol-4-yl)sulfonyl)piperidin-4-yl)-1H-indazole | $R^t$ 1.70 min (Method 1); m/z 468.3 $(M + H)^+$ $(ES^+)$ |
| 136 | 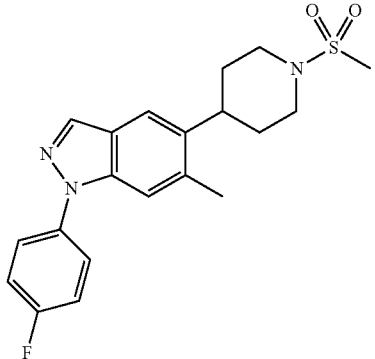<br>1-(4-fluorophenyl)-6-methyl-5-(1-(methylsulfonyl)piperidin-4-yl)-1H-indazole | $R^t$ 1.57 min (Method 1); m/z 388.5 $(M + H)^+$ $(ES^+)$ |

TABLE 6-continued

The examples shown in the table below were prepared by similar methods to those described for Example 6.

| Example | Structure | LC-MS Analysis |
|---|---|---|
| 137 | 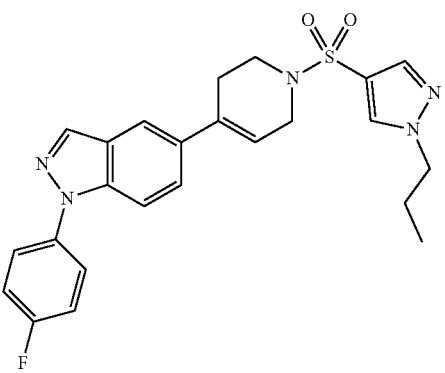<br>1-(4-fluorophenyl)-5-(1-((1-propyl-1H-pyrazole-4-yl)sulfonyl)-1,2,3,6-tetrahydropyridin-4-yl)-1H-indazole | $R^t$ 1.69 min (Method 1); m/z 466.3 $(M + H)^+$ $(ES^+)$ |
| 138 | 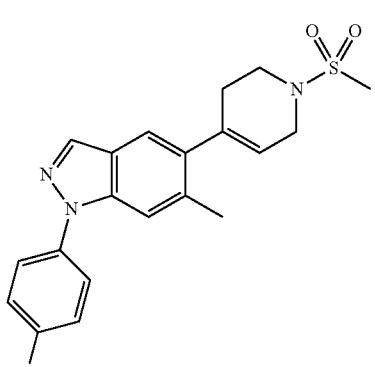<br>1-(4-fluorophenyl)-6-methyl-5-(1-(methylsulfonyl)-1,2,3,6-tetrahydro-pyridin-4-yl)-1H-indazole | $R^t$ 1.56 min (Method 1); m/z 386.2 $(M + H)^+$ $(ES^+)$ |
| 139 | 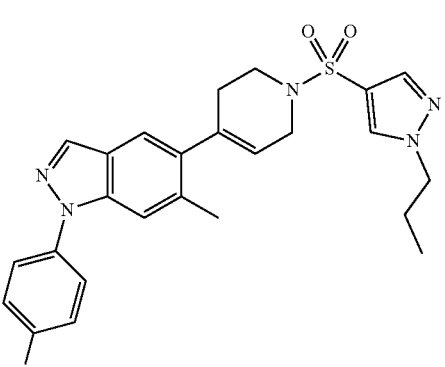<br>1-(4-fluorophenyl)-6-methyl-5-(1-((1-propyl-1H-pyrazol-4-yl)sulfonyl)-1,2,3,6-tetrahydro-pyridin-4-yl)-1H-indazole | $R^t$ 1.76 min (Method 1); m/z 480.3 $(M + H)^+$ $(ES^+)$ |

TABLE 6-continued

The examples shown in the table below were prepared by similar methods to those described for Example 6.

| Example | Structure | LC-MS Analysis |
|---|---|---|
| 140 | 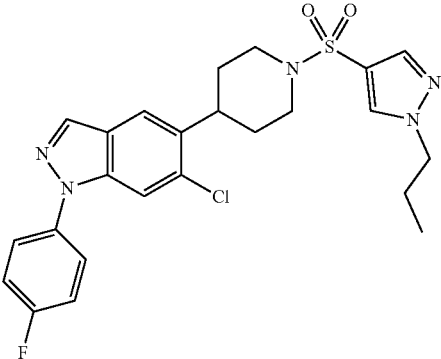<br>6-chloro-1-(4-fluorophenyl)-5-(1-((1-propyl-1H-pyrazole-4-yl)sulfonyl)piperidin-4-yl)-1H-indazole | $R^t$ 1.86 min (Method 1); m/z 502.3/504.3 (M + H/Chlorine isotope)$^+$ (ES$^+$) |
| 141 | 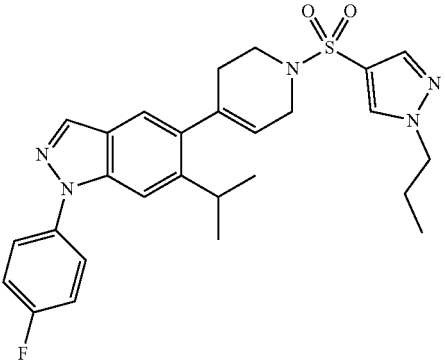<br>1-(4-fluorophenyl)-6-isopropyl-5-(1-((1-propyl-1H-pyrazol-4-yl)sulfonyl)-1,2,3,6-tetrahydropyridin-4-yl)-1H-indazole | $R^t$ 1.89 min (Method 1); m/z 508.36 (M + H)$^+$ (ES$^+$) |
| 142 | 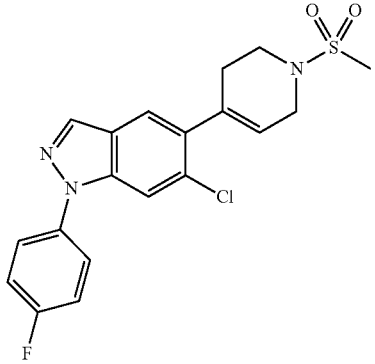<br>6-chloro-1-(4-fluorophenyl)-5-(1-(methylsulfonyl)-1,2,3,6-tetrahydropyridin-4-yl)-1H-indazole | $R^t$ 1.65 min (Method 1); m/z 406.14 (M + H)$^+$ (ES$^+$) |

TABLE 6-continued

The examples shown in the table below were prepared by similar methods to those described for Example 6.

| Example | Structure | LC-MS Analysis |
|---------|-----------|----------------|
| 143 | 6-chloro-1-(4-fluorophenyl)-5-(1-((1-propyl-1H-pyrazol-4-yl)sulfonyl)-1,2,3,6-tetrahydro-pyridin-4-yl)-1H-indazole | $R^t$ 1.83 min (Method 1); m/z 500.62 (M + H)$^+$ (ES$^+$) |
| 144 | 6-(difluoromethoxy)-1-(4-fluorophenyl)-5-(1-((1-propyl-1H-pyrazol-4-yl)sulfonyl)-1,2,3,6-tetrahydropyridin-4-yl)-1H-indazole | $R^t$ 1.74 min (Method 1); m/z 531.98 (M + H)$^+$ (ES$^+$) |
| 145 | 3-(6-methyl-5-(1-((1-propyl-1H-pyrazol-4-yl)sulfonyl)-1,2,3,6-tetrahydropyridin-4-yl)-1H-indazol-1-yl)-N-(tetrahydrofuran-3-yl)benzamide | $R^t$ 1.44 min (Method 1); m/z 575.5 (M + H)$^+$ (ES$^+$) |

TABLE 6-continued

The examples shown in the table below were prepared by similar methods to those described for Example 6.

| Example | Structure | LC-MS Analysis |
|---|---|---|
| 146 | 3-(6-methyl-5-(1-(methylsulfonyl)-1,2,3,6-tetrahydropyridin-4-yl)-1H-indazol-1-yl)-N-(tetrahydrofuran-3-yl)benzamide | $R^t$ 1.26 min (Method 1); m/z 481.4 (M + H)$^+$ (ES$^+$) |

Examples 147-189

TABLE 7

The examples shown in the table below were prepared by similar methods to those described for Example 16.

| Example | Structure | LC-MS Analysis |
|---|---|---|
| 147 | 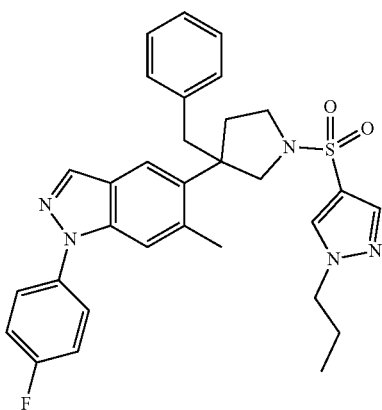 5-(3-benzyl-1-((1-propyl-1H-pyrazol-4-yl)sulfonyl)pyrrolidin-3-yl)-1-(4-fluorophenyl)-6-methy-1H-indazole | $R^t$ 1.89 min (Method 1); m/z 558.8 (M + H)$^+$ (ES$^+$) |

TABLE 7-continued

The examples shown in the table below were prepared by similar methods to those described for Example 16.

| Example | Structure | LC-MS Analysis |
|---|---|---|
| 148 | 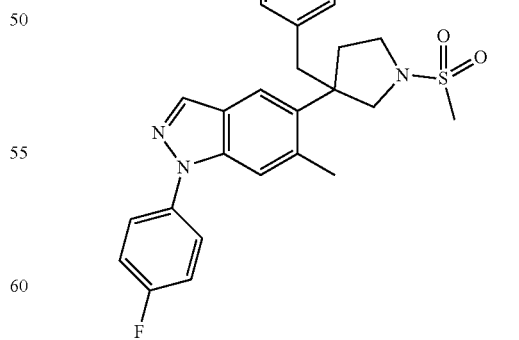 1-(4-fluorophenyl)-6-methyl-5-(1-(methylsulfonyl)-3-(pyridin-3-ylmethyl)pyrrolidin-3-yl)-1H-indazole | $R^t$ 1.03 min (Method 1); m/z 465.4 (M + H)$^+$ (ES$^+$) |

TABLE 7-continued

The examples shown in the table below were prepared by similar methods to those described for Example 16.

| Example | Structure | LC-MS Analysis |
|---|---|---|
| 149 | 1-(4-fluorophenyl)-6-methyl-5-(1-((1-propyl-1H-pyrazol-4-yl)sulfonyl)-3-(pyridin-3-ylmethyl)pyrrolidin-3-yl)-1H-indazole | $R^t$ 1.23 min (Method 1); m/z 559.4 $(M + H)^+$ $(ES^+)$ |
| 150 | 1-(4-fluorophenyl)-6-methyl-5-(1-(methylsulfonyl)-3-(pyridin-2-ylmethyl)pyrrolidin-3-yl)-1H-indazole | $R^t$ 1.13 min (Method 1); m/z 465.4 $(M + H)^+$ $(ES^+)$ |
| 151 | 1-(4-fluorophenyl)-6-methyl-5-(1-((1-methyl-1H-pyrazol-4-yl)sulfonyl)-3-(pyridin-2-ylmethyl)pyrrolidin-3-yl)-1H-indazole | $R^t$ 1.16 min (Method 1); m/z 531.4 $(M + H)^+$ $(ES^+)$ |
| 152 | 1-(4-fluorophenyl)-6-methyl-5-(1-((1-propyl-1H-pyrazol-4-yl)sulfonyl)-3-(pyridin-2-ylmethyl)pyrrolidin-3-yl)-1H-indazole | $R^t$ 1.34 min (Method 1); m/z 581.4 $(M + H)^+$ $(ES^+)$ |
| 153 | 5-(3-benzyl-1-((1-methyl-1H-pyrazol-4-yl)sulfonyl)pyrrolidin-3-yl)-1-(4-fluorophenyl)-6-methyl-1H-indazole | $R^t$ 1.76 min (Method 1); m/z 530.4 $(M + H)^+$ $(ES^+)$ |
| 154 | 5-((3-benzyl-3-(1-(4-fluorophenyl)-6-methyl-1H-indazol-5-yl)pyrrolidin-1-yl)sulfonyl)thiazole | $R^t$ 1.84 min (Method 1); m/z 533.4 $(M + H)^+$ $(ES^+)$ |

TABLE 7-continued

The examples shown in the table below were prepared by similar methods to those described for Example 16.

| Example | Structure | LC-MS Analysis |
|---|---|---|
| 155 | 5-(3-benzyl-1-(cyclopropylsulfonyl)pyrrolidin-3-yl)-1-(4-fluorophenyl)-6-methyl-1H-indazole | R$^t$ 1.85 min (Method 1); m/z 490.4 (M + H)$^+$ (ES$^+$) |
| 156 | 5-(3-benzyl-1-((tetrahydro-2H-pyran-4-yl)sulfonyl)pyrrolidin-3-yl)-1-(4-fluorophenyl)-6-methyl-1H-indazole | R$^t$ 1.81 min (Method 1); m/z 534.4 (M + H)$^+$ (ES$^+$) |
| 157 | 5-(3-benzyl-1-(methylsulfonyl)pyrrolidin-3-yl)-1-(4-fluorophenyl)-1H-indazole | R$^t$ 1.72 min (Method 1); m/z 450.4 (M + H)$^+$ (ES$^+$) |
| 158 | 5-(3-benzyl-1-((1-methyl-1H-pyrazol-4-yl)sulfonyl)pyrrolidin-3-yl)-1-(4-fluorophenyl)-1H-indazole | R$^t$ 1.72 min (Method 1); m/z 516.4 (M + H)$^+$ (ES$^+$) |
| 159 | 5-(3-benzyl-1-((1-propyl-1H-pyrazol-4-yl)sulfonyl)pyrrolidin-3-yl)-1-(4-fluorophenyl)-1H-indazole | R$^t$ 1.84 min (Method 1); m/z 544.4 (M + H)$^+$ (ES$^+$) |
| 160 | 5-(3-benzyl-1-(methylsulfonyl)pyrrolidin-3-yl)-1-(4-fluorophenyl)-6-methoxy-1H-indazole | R$^t$ 1.73 min (Method 1); m/z 480.4 (M + H)$^+$ (ES$^+$) |

TABLE 7-continued

The examples shown in the table below were prepared by similar methods to those described for Example 16.

| Example | Structure | LC-MS Analysis |
|---|---|---|
| 161 | 5-(3-benzyl-1-((1-methyl-1H-pyrazol-4-yl)sulfonyl)pyrrolidin-3-yl)-1-(4-fluorophenyl)-6-methoxy-1H-indazole | R$^t$ 1.72 min (Method 1); m/z 546.4 (M + H)$^+$ (ES$^+$) |
| 162 | 5-(3-benzyl-1-((1-propyl-1H-pyrazol-4-yl)sulfonyl)pyrrolidin-3-yl)-1-(4-fluorophenyl)-6-methoxy-1H-indazole | R$^t$ 1.84 min (Method 1); m/z 574.5 (M + H)$^+$ (ES$^+$) |
| 163 | 5-(3-benzyl-1-(methylsulfonyl)pyrrolidin-3-yl)-1-(4-fluorophenyl)-6-isopropyl-1H-indazole | R$^t$ 1.89 min (Method 1); m/z 492.4 (M + H)$^+$ (ES$^+$) |
| 164 | 5-(3-benzyl-1-((1-methyl-1H-pyrazol-4-yl)sulfonyl)pyrrolidin-3-yl)-1-(4-fluorophenyl)-6-isopropyl-1H-indazole | R$^t$ 1.89 min (Method 1); m/z 558.5 (M + H)$^+$ (ES$^+$) |
| 165 | 5-(3-benzyl-1-((1-propyl-1H-pyrazol-4-yl)sulfonyl)pyrrolidin-3-yl)-1-(4-fluorophenyl)-6-isopropyl-1H-indazole | R$^t$ 2.00 min (Method 1); m/z 586.5 (M + H)$^+$ (ES$^+$) |
| 166 | 5-(3-benzyl-1-(cyclopropylsulfonyl)pyrrolidin-3-yl)-1-(4-fluorophenyl)-6-methoxy-1H-indazole | R$^t$ 1.82 min (Method 1); m/z 506.4 (M + H)$^+$ (ES$^+$) |

TABLE 7-continued

The examples shown in the table below were prepared by similar methods to those described for Example 16.

| Example | Structure | LC-MS Analysis |
|---|---|---|
| 167 | 5-(3-ethyl-1-(methylsulfonyl)pyrrolidin-3-yl)-1-(4-fluorophenyl)-6-methyl-1H-indazole | R$^t$ 1.63 min (Method 1); m/z 402.4 (M + H)$^+$ (ES$^+$) |
| 168 | 5-(3-ethyl-1-((1-propyl-1H-pyrazol-4-yl)sulfonyl)pyrrolidin-3-yl)-1-(4-fluorophenyl)-6-methyl-1H-indazole | R$^t$ 1.78 min (Method 1); m/z 496.4 (M + H)$^+$ (ES$^+$) |
| 169 | 1-(4-fluorophenyl)-6-methyl-5-(1-((1-methyl-1H-pyrazol-4-yl)sulfonyl)-3-((5-(trifluoromethyl)pyridin-2-yl)methyl)pyrrolidin-3-yl)-1H-indazole | R$^t$ 1.71 min (Method 1); m/z 599.6 (M + H)$^+$ (ES$^+$) |
| 170 | 1-(4-fluorophenyl)-6-methyl-5-(1-((1-methyl-1H-pyrazol-4-yl)sulfonyl)-3-((6-(trifluoromethyl)pyridin-3-yl)methyl)pyrrolidin-3-yl)-1H-indazole | R$^t$ 1.69 min (Method 1); m/z 599.4 (M + H)$^+$ (ES$^+$) |
| 171 | 5-(3-((6-(difluoromethyl)pyridin-3-yl)methyl)-1-((1-methyl-1H-pyrazol-4-yl)sulfonyl)pyrrolidin-3-yl)-1-(4-fluorophenyl)-6-methyl-1H-indazole | R$^t$ 1.59 min (Method 1); m/z 581.3 (M + H)$^+$ (ES$^+$) |

TABLE 7-continued

The examples shown in the table below were prepared by similar methods to those described for Example 16.

| Example | Structure | LC-MS Analysis |
|---|---|---|
| 172 | 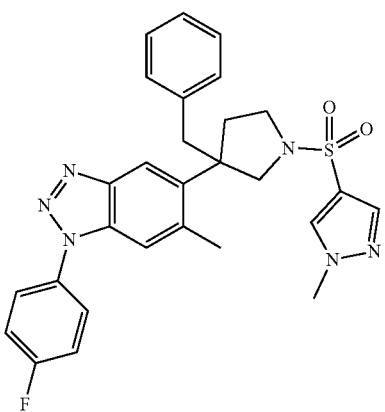<br>5-(3-benzyl-1-((1-methyl-1H-pyrazol-4-yl)sulfonyl)pyrrolidin-3-yl)-1-(4-fluorophenyl)-6-methyl-1H-benzo[d][1,2,3]triazole | R$^t$ 1.67 min (Method 1); m/z 531.0 (M + H)$^+$ (ES$^+$) |
| 173 | 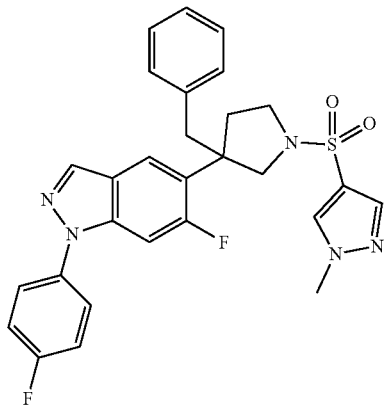<br>5-(3-benzyl-1-((1-methyl-1H-pyrazol-4-yl)sulfonyl)pyrrolidin-3-yl)-6-fluoro-1-(4-fluorophenyl)-1H-indazole | R$^t$ 1.76 min (Method 1); m/z 534.0 (M + H)$^+$ (ES$^+$) |
| 174 | 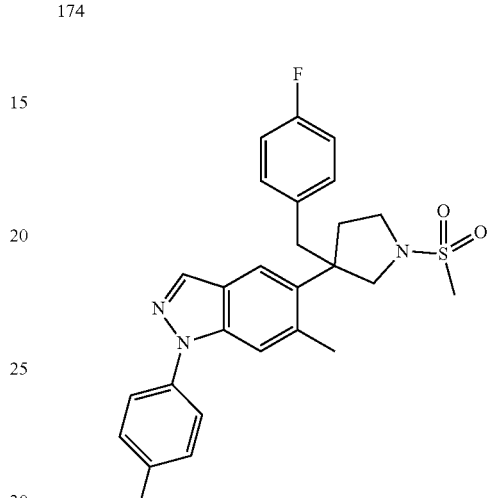<br>5-(3-(4-fluorobenzyl)-1-(methylsulfonyl)pyrrolidin-3-yl)-1-(4-fluorophenyl)-6-methyl-1H-indazole | R$^t$ 1.78 min (Method 1); m/z 482.4 (M + H)$^+$ (ES$^+$) |
| 175 | 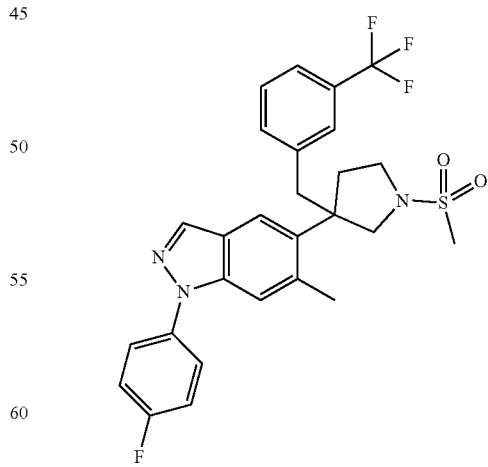<br>1-(4-fluorophenyl)-6-methyl-5-(1-(methylsulfonyl)-3-(3-(trifluoromethyl)benzyl)pyrrolidin-3-yl)-1H-indazole | R$^t$ 1.85 min (Method 1); m/z 532.2 (M + H)$^+$ (ES$^+$) |

TABLE 7-continued

The examples shown in the table below were prepared by similar methods to those described for Example 16.

| Example | Structure | LC-MS Analysis |
|---|---|---|
| 176 | 1-(4-fluorophenyl)-6-methyl-5-(1-((1-methyl-1H-pyrazol-4-yl)sulfonyl)-3-(3-(trifluoromethyl)benzyl)pyrrolidin-3-yl)-1H-indazole | $R^t$ 1.85 min (Method 1); m/z 598.4 $(M + H)^+$ $(ES^+)$ |
| 177 | 1-(4-fluorophenyl)-6-methyl-5-(1-(methylsulfonyl)-3-(4-(trifluoromethyl)benzyl)pyrrolidin-3-yl)-1H-indazole | $R^t$ 1.89 min (Method 1); m/z 532.4 $(M + H)^+$ $(ES^+)$ |
| 178 | 1-(4-fluorophenyl)-6-methyl-5-(1-((1-methyl-1H-pyrazol-4-yl)sulfonyl)-3-(4-(trifluoromethyl)benzyl)pyrrolidin-3-yl)-1H-indazole | $R^t$ 1.89 min (Method 1); m/z 598.6 $(M + H)^+$ $(ES^+)$ |
| 179 | 5-((3-(1-(4-fluorophenyl)-6-methyl-1H-indazol-5-yl)-1-((1-methyl-1H-pyrazol-4-yl)sulfonyl)pyrrolidin-3-yl)methyl)thiazole | $R^t$ 1.47 min (Method 1); m/z 537.3 $(M + H)^+$ $(ES^+)$ |

TABLE 7-continued

The examples shown in the table below were prepared by similar methods to those described for Example 16.

| Example | Structure | LC-MS Analysis |
|---|---|---|
| 180 | 5-((3-(1-(4-fluorophenyl)-6-methyl-1H-indazol-5-yl)-1-(methylsulfonyl)pyrrolidin-3-yl)methyl)thiazole | R$^t$ 1.45 min (Method 1); m/z 471.3 (M + H)$^+$ (ES$^+$) |
| 181 | 5-(3-benzyl-1-(methylsulfonyl)pyrrolidin-3-yl)-6-fluoro-1-(4-fluorophenyl)-1H-indazole | R$^t$ 1.77 min (Method 1); m/z 468.4 (M + H)$^+$ (ES$^+$) |
| 182 | 5-(3-(4-fluorobenzyl)-1-((1-methyl-1H-pyrazol-4-yl)sulfonyl)pyrrolidin-3-yl)-1-(4-fluorophenyl)-6-methyl-1H-indazole | R$^t$ 1.79 min (Method 1); m/z 547.6 (M + H)$^+$ (ES$^+$) |
| 183 | 5-((3-(1-(4-fluorophenyl)-6-methyl-1H-indazol-5-yl)-1-(methylsulfonyl)pyrrolidin-3-yl)methyl)-1-methyl-1H-benzo[d][1,2,3]triazole | R$^t$ 1.52 min (Method 1); m/z 519.3 (M + H)$^+$ (ES$^+$) |
| 184 | 1-(4-fluorophenyl)-6-methyl-5-(1-(methylsulfonyl)-3-(prop-2-yn-1-yl)pyrrolidin-3-yl)-1H-indazole | R$^t$ 4.48 min (Method 5); m/z 412.3 (M + H)$^+$ (ES$^+$) |

TABLE 7-continued

The examples shown in the table below were prepared by similar methods to those described for Example 16.

| Example | Structure | LC-MS Analysis |
|---|---|---|
| 185 | 1-(4-fluorophenyl)-6-methyl-5-(1-((1-methyl-1H-pyrazol-4-yl)sulfonyl)-3-(prop-2-yn-1-yl)pyrrolidin-3-yl)-1H-indazole | R$^t$ 4.59 min (Method 5); m/z 478.4 (M + H)$^+$ (ES$^+$) |
| 186 | 1-(4-fluorophenyl)-6-methyl-5-(3-(prop-2-yn-1-yl)-1-((1-propyl-1H-pyrazol-4-yl)sulfonyl)pyrrolidin-3-yl)-1H-indazole | R$^t$ 5.16 min (Method 5); m/z 506.4 (M + H)$^+$ (ES$^+$) |
| 187 | 2-((3-(1-(4-fluorophenyl)-6-methyl-1H-indazol-5-yl)-1-(methylsulfonyl)pyrrolidin-3-yl)methyl)thiazole | R$^t$ 1.49 min (Method 1); m/z 471.3 (M + H)$^+$ (ES$^+$) |
| 188 | 2-((3-(1-(4-fluorophenyl)-6-methyl-1H-indazol-5-yl)-1-((1-methyl-1H-pyrazol-4-yl)sulfonyl)pyrrolidin-3-yl)methyl)thiazole | R$^t$ 1.52 min (Method 1); m/z 537.3 (M + H)$^+$ (ES$^+$) |
| 189 | 2-((3-(1-(4-fluorophenyl)-6-methyl-1H-indazol-5-yl)-1-((1-propyl-1H-pyrazol-4-yl)sulfonyl)pyrrolidin-3-yl)methyl)thiazole | R$^t$ 1.64 min (Method 1); m/z 565.3 (M + H)$^+$ (ES$^+$) |

Examples 190-208

TABLE 8

The examples shown in the table below were prepared by similar methods to those described for Example 19.

| Example | Structure | LC-MS Analysis |
|---|---|---|
| 190 | 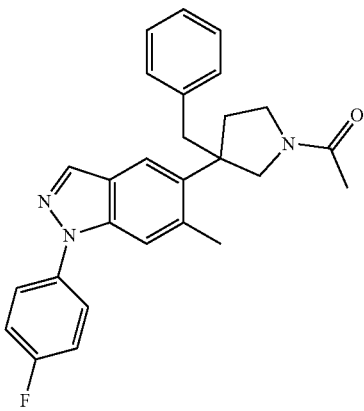 [SMILES: CC(=O)N1CCC(Cc2ccccc2)(c2cc3cnn(-c4ccc(F)cc4)c3cc2C)C1]  1-(3-benzyl-3-(1-(4-fluorophenyl)-6-methyl-1H-indazol-5-yl)pyrrolidin-1-yl)ethan-1-one | $R^t$ 1.65 min (Method 1); m/z 428.5 $(M + H)^+$ $(ES^+)$ |
| 191 | 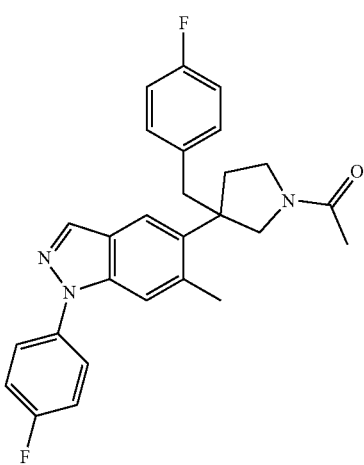 [SMILES: CC(=O)N1CCC(Cc2ccc(F)cc2)(c2cc3cnn(-c4ccc(F)cc4)c3cc2C)C1]  1-(3-(4-fluorobenzyl)-3-(1-(4-fluorophenyl)-6-methyl-1H-indazol-5-yl)pyrrolidin-1-yl)ethan-1-one | $R^t$ 1.68 min (Method 1); m/z 446.4 $(M + H)^+$ $(ES^+)$ |
| 192 | 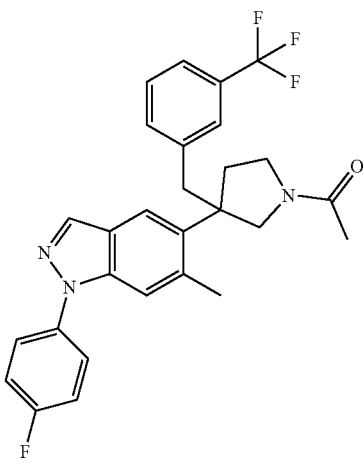 [SMILES: CC(=O)N1CCC(Cc2cccc(C(F)(F)F)c2)(c2cc3cnn(-c4ccc(F)cc4)c3cc2C)C1]  1-(3-(1-(4-fluorophenyl)-6-methyl-1H-indazol-5-yl)-3-(3-(trifluoromethyl)benzyl)pyrrolidin-1-yl)ethan-1-one | $R^t$ 1.74 min (Method 1); m/z 496.1 $(M + H)^+$ $(ES^+)$ |

TABLE 8-continued

The examples shown in the table below were prepared by similar methods to those described for Example 19.

| Example | Structure | LC-MS Analysis |
|---|---|---|
| 193 | 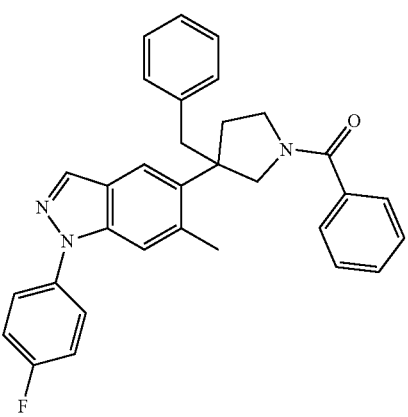 [SMILES: Cc1cc2c(cnn2-c2ccc(F)cc2)cc1C1(Cc2ccccc2)CCN(C(=O)c2ccccc2)C1]<br>(3-benzyl-3-(1-(4-fluorophenyl)-6-methyl-1H-indazol-5-yl)pyrrolidin-1-yl)(phenyl)methanone | $R^t$ 1.84 min (Method 4); m/z 490.4 $(M + H)^+$ $(ES^+)$ |
| 194 | 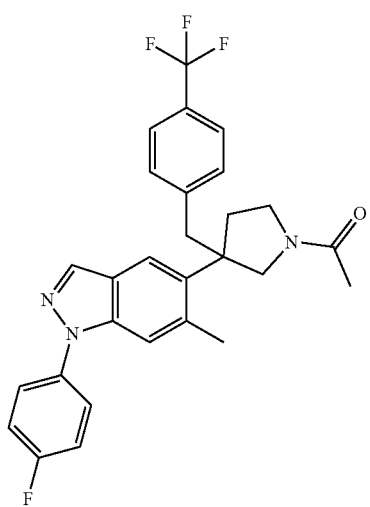 [SMILES: CC(=O)N1CCC(Cc2ccc(C(F)(F)F)cc2)(c2cc3cnn(-c4ccc(F)cc4)c3cc2C)C1]<br>1-(3-(1-(4-fluorophenyl)-6-methyl-1H-indazol-5-yl)-3-(4-(trifluoromethyl)benzyl)pyrrolidin-1-yl)ethan-1-one | $R^t$ 1.79 min (Method 1); m/z 496.4 $(M + H)^+$ $(ES^+)$ |
| 195 | 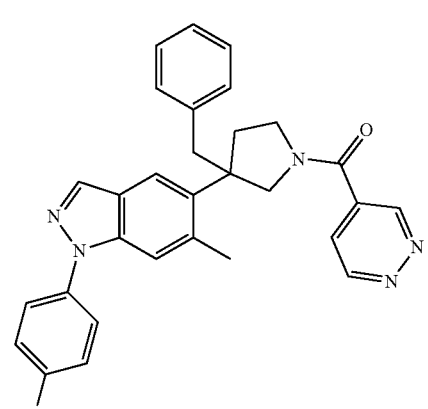<br>(3-benzyl-3-(1-(4-fluorophenyl)-6-methyl-1H-indazol-5-yl)pyrrolidin-1-yl)(pyridazin-4-yl)methanone | $R^t$ 1.59 min (Method 1); m/z 492.4 $(M + H)^+$ $(ES^+)$ |

TABLE 8-continued

The examples shown in the table below were prepared by similar methods to those described for Example 19.

| Example | Structure | LC-MS Analysis |
|---|---|---|
| 196 | 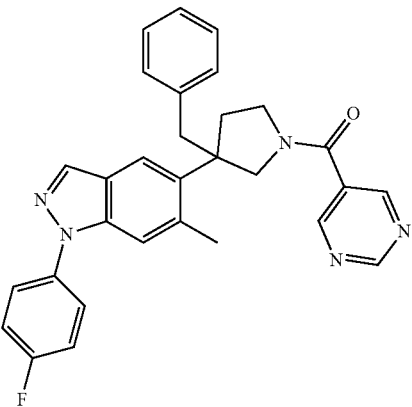 [SMILES: Cc1cc2c(cnn2-c2ccc(F)cc2)cc1C1(Cc2ccccc2)CCN(C(=O)c2cncnc2)C1]<br>(3-benzyl-3-(1-(4-fluorophenyl)-6-methyl-1H-indazol-5-yl)pyrrolidin-1-yl)(pyrimidin-5-yl)methanone | $R^t$ 1.63 min (Method 1); m/z 492.4 $(M + H)^+$ $(ES^+)$ |
| 197 | 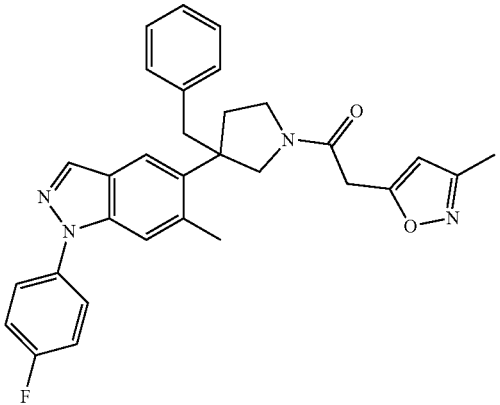 [SMILES: Cc1cc(CC(=O)N2CCC(Cc3ccccc3)(c3cc4cnn(-c5ccc(F)cc5)c4cc3C)C2)on1]<br>1-(3-benzyl-3-(1-(4-fluorophenyl)-6-methyl-1H-indazol-5-yl)pyrrolidin-1-yl)-2-(3-methylisoxazol-5-yl)ethan-1-one | $R^t$ 1.74 min (Method 1); m/z 509.4 $(M + H)^+$ $(ES^+)$ |
| 198 | 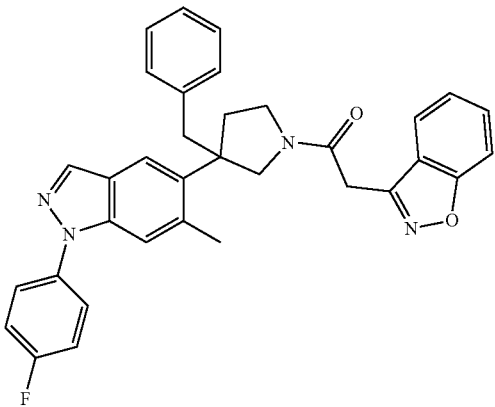<br>2-(benzo[d]isoxazol-3-yl)-1-(3-benzyl-3-(1-(4-fluorophenyl)-6-methyl-1H-indazol-5-yl)pyrrolidin-1-yl)ethan-1-one | $R^t$ 1.91 min (Method 1); m/z 545.1 $(M + H)^+$ $(ES^+)$ |

TABLE 8-continued

The examples shown in the table below were prepared by similar methods to those described for Example 19.

| Example | Structure | LC-MS Analysis |
|---|---|---|
| 199 | 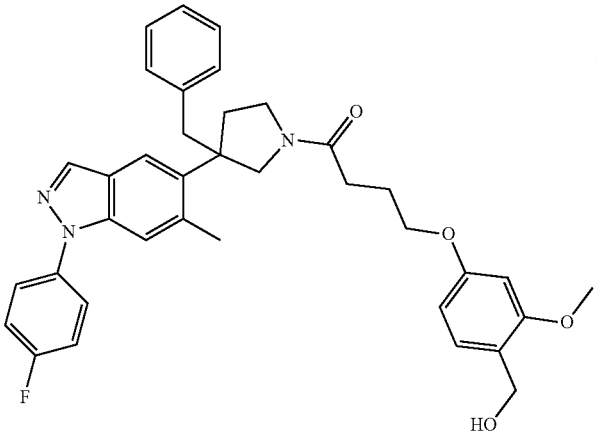 [SMILES: COc1cc(OCCCC(=O)N2CCC(Cc3ccccc3)(c3cc4cnn(-c5ccc(F)cc5)c4cc3C)C2)ccc1CO]<br>1-(3-benzyl-3-(1-(4-fluorophenyl)-6-methyl-1H-indazol-5-yl)pyrrolidin-1-yl)-4-(4-(hydroxymethyl)-3-methoxyphenoxy)butan-1-one | $R^t$ 1.76 min (Method 1); m/z 630.5 $(M + Na)^+$ $(ES^+)$ |
| 200 | 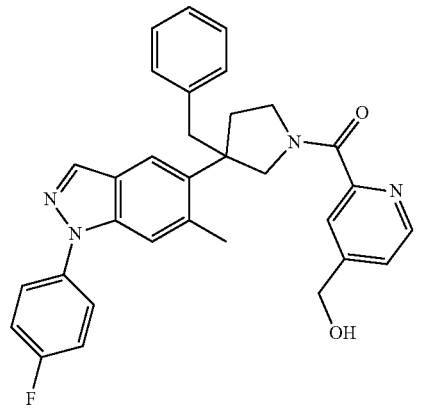 [SMILES: Cc1cc2c(cnn2-c2ccc(F)cc2)cc1C1(Cc2ccccc2)CCN(C(=O)c2cc(CO)ccn2)C1]<br>(3-benzyl-3-(1-(4-fluorophenyl)-6-methyl-1H-indazol-5-yl)pyrrolidin-1-yl)(4-(hydroxymethyl)pyridin-2-yl)methanone | $R^t$ 1.61 min (Method 1); m/z 521.4 $(M + H)^+$ $(ES^+)$ |
| 201 | 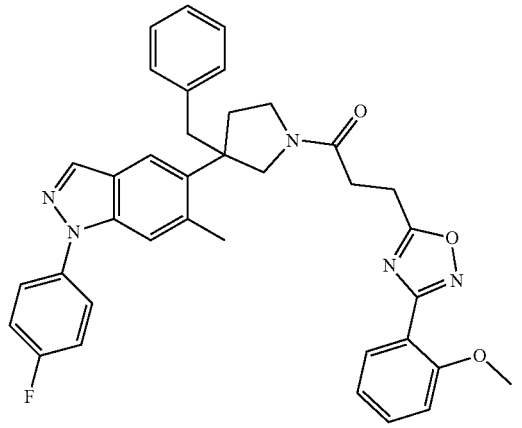 [SMILES: COc1ccccc1-c1noc(CCC(=O)N2CCC(Cc3ccccc3)(c3cc4cnn(-c5ccc(F)cc5)c4cc3C)C2)n1]<br>1-(3-benzyl-3-(1-(4-fluorophenyl)-6-methyl-1H-indazol-5-yl)pyrrolidin-1-yl)-3-(3-(2-methoxyphenyl)-1,2,4-oxadiazol-5-yl)propan-1-one | $R^t$ 1.90 min (Method 1); m/z 616.4 $(M + H)^+$ $(ES^+)$ |

TABLE 8-continued

The examples shown in the table below were prepared by similar methods to those described for Example 19.

| Example | Structure | LC-MS Analysis |
|---|---|---|
| 202 | 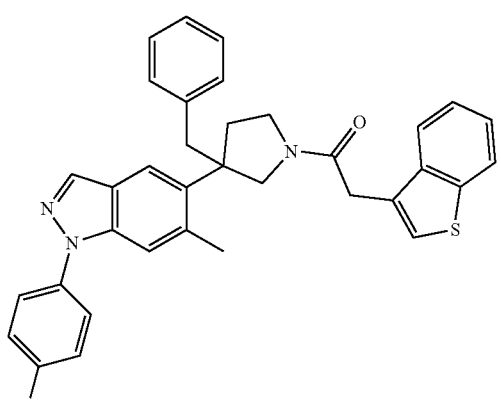<br>2-(benzo[b]thiophen-3-yl)-1-(3-benzyl-3-(1-(4-fluorophenyl)-6-methyl-1H-indazol-5-yl)pyrrolidin-1-yl)ethan-1-one | $R^t$ 2.04 min (Method 1); m/z 560.3 $(M + H)^+$ $(ES^+)$ |
| 203 | 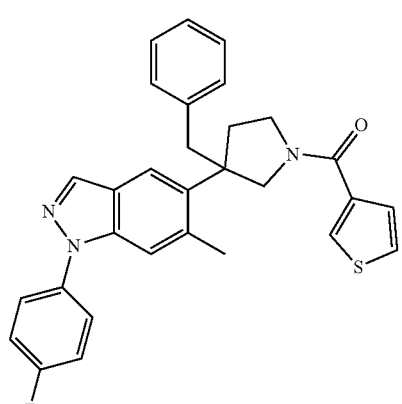<br>(3-benzyl-3-(1-(4-fluorophenyl)-6-methyl-1H-indazol-5-yl)pyrrolidin-1-yl)(thiophen-3-yl)methanone | $R^t$ 1.83 min (Method 1); m/z 496.4 $(M + H)^+$ $(ES^+)$ |
| 204 | 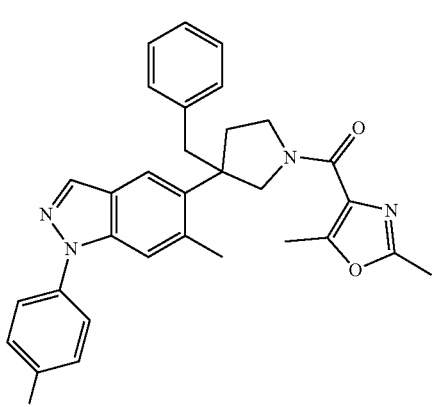<br>(3-benzyl-3-(1-(4-fluorophenyl)-6-methyl-1H-indazol-5-yl)pyrrolidin-1-yl)(2,5-dimethyloxazol-4-yl)methanone | $R^t$ 1.85 min (Method 1); m/z 508.2 $(M + H)^+$ $(ES^+)$ |

TABLE 8-continued

The examples shown in the table below were prepared by similar methods to those described for Example 19.

| Example | Structure | LC-MS Analysis |
|---|---|---|
| 205 | 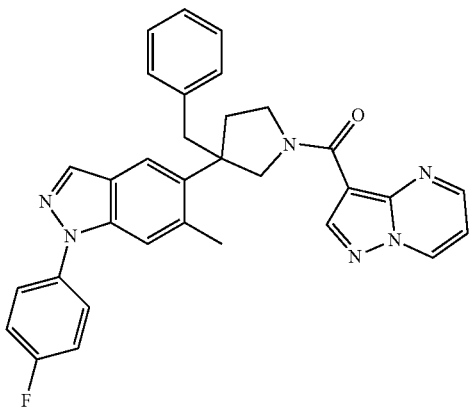 [SMILES: Cc1cc2c(cnn2-c2ccc(F)cc2)cc1C1(Cc2ccccc2)CCN(C(=O)c2cnn3cccnc23)C1]<br>(3-benzyl-3-(1-(4-fluorophenyl)-6-methyl-1H-indazol-5-yl)pyrrolidin-1-yl)(pyrazolo[1,5-a]pyrimidin-3-yl)methanone | $R^t$ 1.62 min (Method 1); m/z 530.2 $(M + H)^+$ $(ES^+)$ |
| 206 | 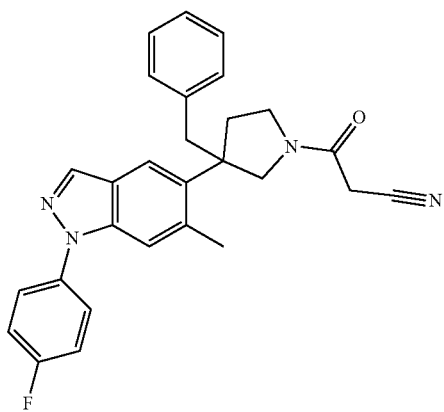 [SMILES: Cc1cc2c(cnn2-c2ccc(F)cc2)cc1C1(Cc2ccccc2)CCN(C(=O)CC#N)C1]<br>3-(3-benzyl-3-(1-(4-fluorophenyl)-6-methyl-1H-indazol-5-yl)pyrrolidin-1-yl)-3-oxopropanenitrile | $R^t$ 1.65 min (Method 1); m/z 452.2 $(M + H)^+$ $(ES^+)$ |

TABLE 8-continued

The examples shown in the table below were prepared by similar methods to those described for Example 19.

| Example | Structure | LC-MS Analysis |
|---|---|---|
| 207 | 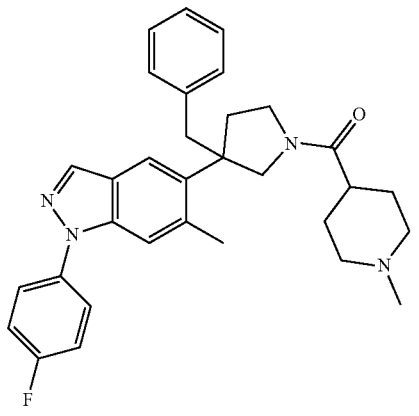 [SMILES: Cc1cc2c(cnn2-c2ccc(F)cc2)cc1C1(Cc2ccccc2)CCN(C(=O)C2CCN(C)CC2)C1]<br>(3-benzyl-3-(1-(4-fluorophenyl)-6-methyl-1H-indazol-5-yl)pyrrolidin-1-yl)(1-methylpiperidin-4-yl)methanone | $R^t$ 1.12 min (Method 1); m/z 510.3 (M + H)$^+$ (ES$^+$) |
| 208 | 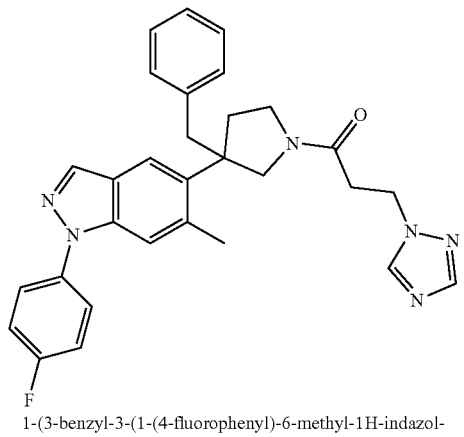<br>1-(3-benzyl-3-(1-(4-fluorophenyl)-6-methyl-1H-indazol-5-yl)pyrrolidin-1-yl)-3-(1H-1,2,4-triazol-1-yl)propan-1-one | $R^t$ 1.53 min (Method 1); m/z 508.2 (M + H)$^+$ (ES$^+$) |

Example 209: 1-(1-(4-fluorophenyl)-6-methyl-1H-indazol-5-yl)-4-((1-propyl-1H-pyrazol-4-yl)sulfonyl)piperazin-2-one

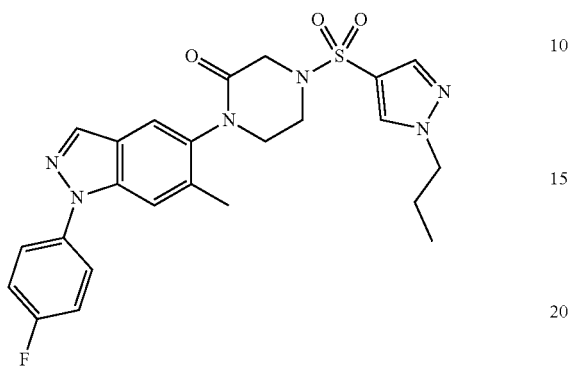

The compound was prepared by similar methods to those described for Example 7. $R^t$ 1.44 min (Method 1); m/z 497.3 (M+H)$^+$ (ES$^+$).

Examples 210-228

TABLE 9

The examples shown in the table below were prepared by similar methods to those described for Example 16.

| Example | Structure | LC-MS Analysis |
|---|---|---|
| 210 | 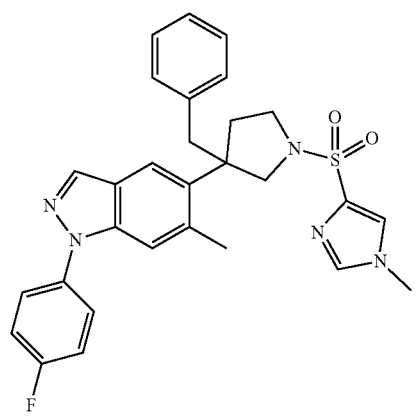 [SMILES: Cc1cc2c(cnn2-c2ccc(F)cc2)cc1C1(Cc2ccccc2)CCN(S(=O)(=O)c2cn(C)cn2)C1] 5-(3-benzyl-1-((1-methyl-1H-imidazol-4-yl)sulfonyl)pyrrolidin-3-yl)-1-(4-fluorophenyl)-6-methyl-1H-indazole | $R^t$ 1.69 min (Method 6); m/z 530.5 (M + H)$^+$ (ES$^+$) |

TABLE 9-continued

The examples shown in the table below were prepared by similar methods to those described for Example 16.

| Example | Structure | LC-MS Analysis |
|---|---|---|
| 211 | 1-(4-fluorophenyl)-6-methyl-5-(1-((1-methyl-1H-pyrazol-4-yl)sulfonyl)-3-(3-phenylprop-2-yn-1-yl)pyrrolidin-3-yl)-1H-indazole | $R^t$ 1.78 min (Method 6); m/z 554.4 (M + H)$^+$ (ES$^+$) |
| 212 | 5-(3-(4-fluorobenzyl)-1-((1-methyl-1H-pyrazol-4-yl)sulfonyl)pyrrolidin-3-yl)-1-(4-fluorophenyl)-6-methoxy-1H-indazole | $R^t$ 1.75 min (Method 6); m/z 524.69 (M + H)$^+$ (ES$^+$) |
| 213 | 5-(3-benzyl-1-((2-methyl-2H-1,2,3-triazol-4-yl)sulfonyl)pyrrolidin-3-yl)-1-(4-fluorophenyl)-6-methyl-1H-indazole | $R^t$ 1.81 min (Method 6); m/z 531.4 (M + H)$^+$ (ES$^+$) |

TABLE 9-continued

The examples shown in the table below were prepared by similar methods to those described for Example 16.

| Example | Structure | LC-MS Analysis |
|---|---|---|
| 215 | 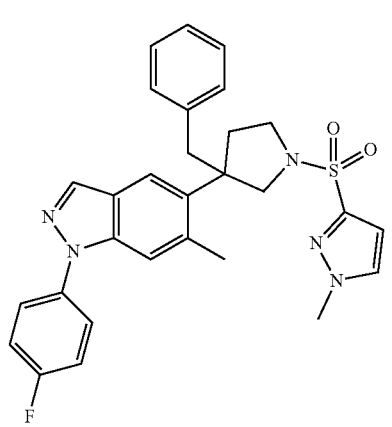 [SMILES: Cc1cc2c(cnn2-c2ccc(F)cc2)cc1C1(Cc2ccccc2)CCN(S(=O)(=O)c2ccn(C)n2)C1]<br>5-(3-benzyl-1-((1-methyl-1H-pyrazol-3-yl)sulfonyl)pyrrolidin-3-yl)-1-(4-fluorophenyl)-6-methyl-1H-indazole | R$^t$ 1.76 min (Method 6); m/z 530.4 (M + H)$^+$ (ES$^+$) |
| 216 | 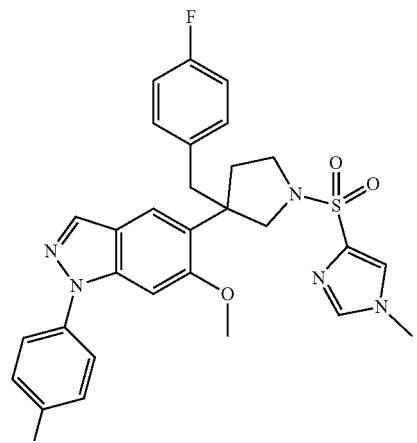<br>5-(3-(4-fluorobenzyl)-1-((1-methyl-1H-imidazol-4-yl)sulfonyl)pyrrolidin-3-yl)-1-(4-fluorophenyl)-6-methoxy-1H-indazole | R$^t$ 1.65 min (Method 6); m/z 564.3 (M + H)$^+$ (ES$^+$) |
| 217 | 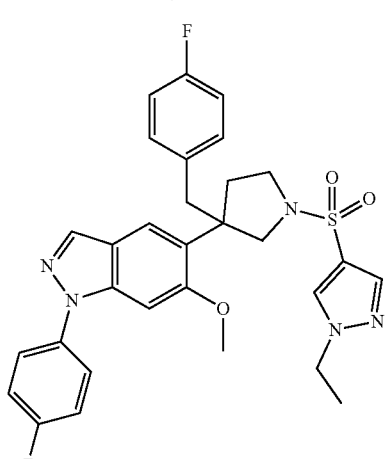<br>5-(1-((1-ethyl-1H-pyrazol-4-yl)sulfonyl)-3-(4-fluorobenzyl)pyrrolidin-3-yl)-1-(4-fluorophenyl)-6-methoxy-1H-indazole | R$^t$ 1.78 min (Method 6); m/z 578.7 (M + H)$^+$ (ES$^+$) |

TABLE 9-continued

The examples shown in the table below were prepared by similar methods to those described for Example 16.

| Example | Structure | LC-MS Analysis |
|---|---|---|
| 218 | 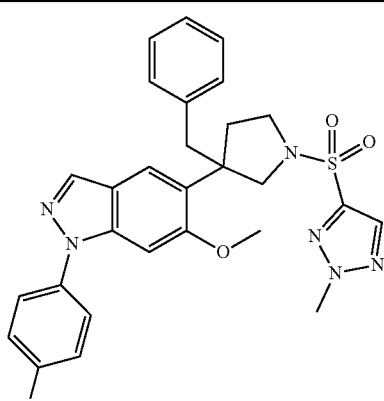<br>5-(3-benzyl-1-((2-methyl-2H-1,2,3-triazol-4-yl)sulfonyl)pyrrolidin-3-yl)-1-(4-fluorophenyl)-6-methoxy-1H-indazole | $R^t$ 1.80 min (Method 6); m/z 547.5 $(M + H)^+$ $(ES^+)$ |
| 219 | 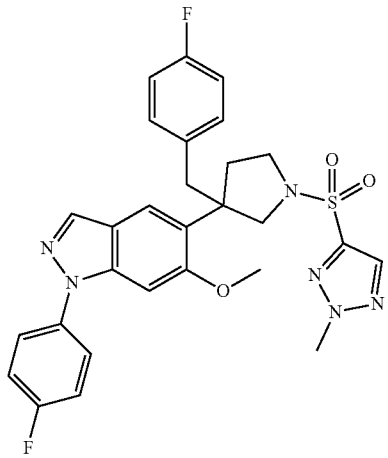 [SMILES: COc1cc2c(cnn2-c2ccc(F)cc2)cc1C1(Cc2ccc(F)cc2)CCN(S(=O)(=O)c2cnn(C)n2)C1]<br>5-(3-(4-fluorobenzyl)-1-((2-methyl-2H-1,2,3-triazol-4-yl)sulfonyl)pyrrolidin-3-yl)-1-(4-fluorophenyl)-6-methoxy-1H-indazole | $R^t$ 1.80 min (Method 6); m/z 565.7 $(M + H)^+$ $(ES^+)$ |
| 220 | 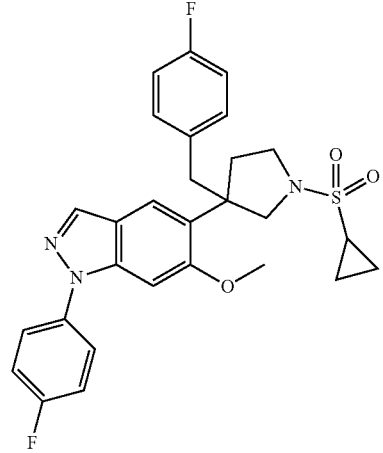 [SMILES: COc1cc2c(cnn2-c2ccc(F)cc2)cc1C1(Cc2ccc(F)cc2)CCN(S(=O)(=O)C2CC2)C1]<br>5-(1-(cyclopropylsulfonyl)-3-(4-fluorobenzyl)pyrrolidin-3-yl)-1-(4-fluorophenyl)-6-methoxy-1H-indazole | $R^t$ 1.8 min (Method 6); m/z 524.2 $(M + H)^+$ $(ES^+)$ |

TABLE 9-continued

The examples shown in the table below were prepared by similar methods to those described for Example 16.

| Example | Structure | LC-MS Analysis |
|---|---|---|
| 221 | 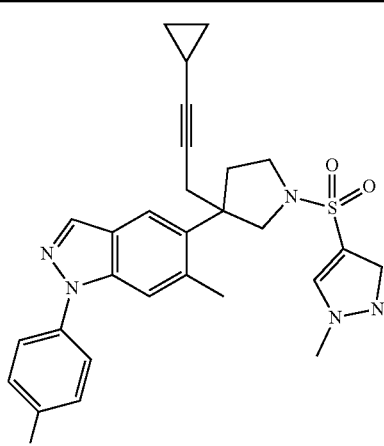<br>5-(3-(3-cyclopropylprop-2-yn-1-yl)-1-((1-methyl-1H-pyrazol-4-yl)sulfonyl)pyrrolidin-3-yl)-1-(4-fluorophenyl)-6-methyl-1H-indazole | $R^t$ 1.72 min (Method 2); m/z 518.2 (M + H)$^+$ (ES$^+$) |
| 222 | 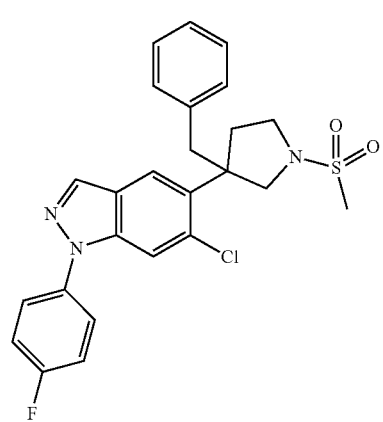 [SMILES: CS(=O)(=O)N1CCC(Cc2ccccc2)(c2cc3cnn(-c4ccc(F)cc4)c3cc2Cl)C1]<br>5-(3-benzyl-1-(methylsulfonyl)pyrrolidin-3-yl)-6-chloro-1-(4-fluorophenyl)-1H-indazole | $R^t$ 1.82 min (Method 6); m/z 484.4 (M + H)$^+$ (ES$^+$) |
| 223 | 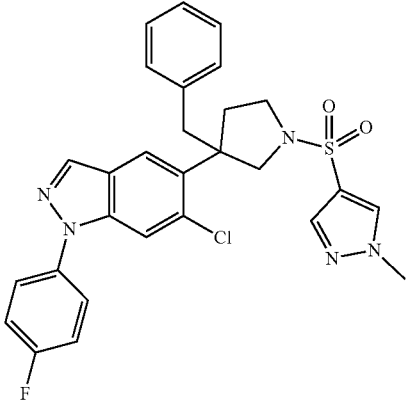 [SMILES: Cn1cc(S(=O)(=O)N2CCC(Cc3ccccc3)(c3cc4cnn(-c5ccc(F)cc5)c4cc3Cl)C2)cn1]<br>5-(3-benzyl-1-((1-methyl-1H-pyrazol-4-yl)sulfonyl)pyrrolidin-3-yl)-6-chloro-1-(4-fluorophenyl)-1H-indazole | $R^t$ 1.79 min (Method 1); m/z 550.6 (M + H)$^+$ (ES$^+$) |

TABLE 9-continued

The examples shown in the table below were prepared by similar methods to those described for Example 16.

| Example | Structure | LC-MS Analysis |
|---|---|---|
| 224 | 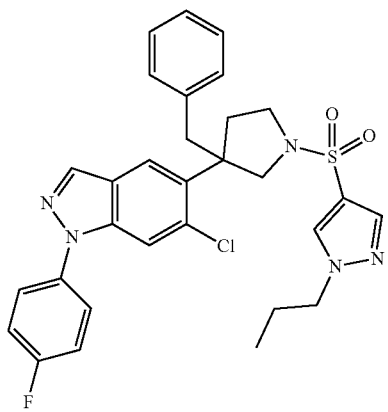 [SMILES: CCCn1cc(S(=O)(=O)N2CCC(Cc3ccccc3)(c3cc4cnn(-c5ccc(F)cc5)c4cc3Cl)C2)cn1]<br>5-(3-benzyl-1-((1-propyl-1H-pyrazol-4-yl)sulfonyl)pyrrolidin-3-yl)-6-chloro-1-(4-fluorophenyl)-1H-indazole | R$^t$ 1.72 min (Method 6); m/z 578.4 (M + H)$^+$ (ES$^+$) |
| 225 | 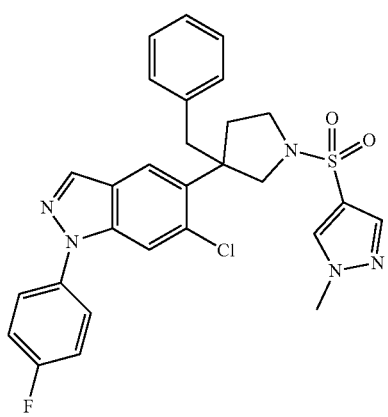 [SMILES: Cn1cc(S(=O)(=O)N2CCC(Cc3ccccc3)(c3cc4cnn(-c5ccc(F)cc5)c4cc3Cl)C2)cn1]<br>5-(3-benzyl-1-((1-methyl-1H-pyrazol-3-yl)sulfonyl)pyrrolidin-3-yl)-6-chloro-1-(4-fluorophenyl)-1H-indazole | R$^t$ 1.81 min (Method 6); m/z 550.2 (M + H)$^+$ (ES$^+$) |
| 226 | 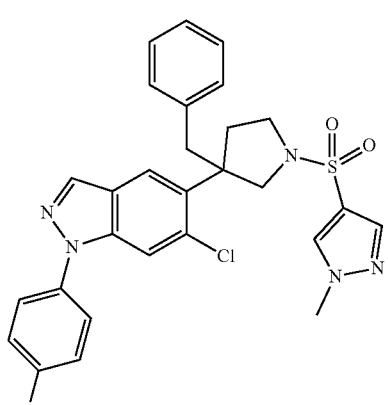<br>5-(3-benzyl-1-((2-methyl-2H-1,2,3-triazol-4-yl)sulfonyl)pyrrolidin-3-yl)-6-chloro-1-(4-fluorophenyl)-1H-indazole | R$^t$ 1.87 min (Method 6); m/z 551.3 (M + H)$^+$ (ES$^+$) |

TABLE 9-continued

The examples shown in the table below were prepared by similar methods to those described for Example 16.

| Example | Structure | LC-MS Analysis |
| --- | --- | --- |
| 227 | 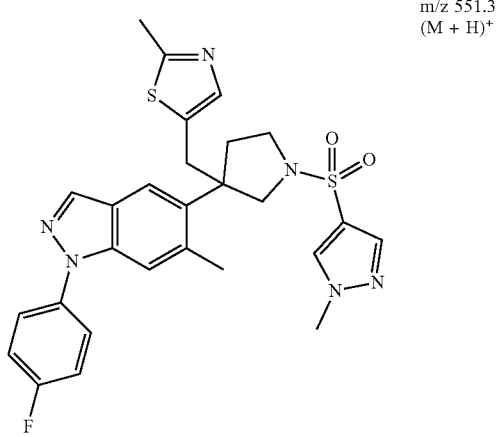<br>5-((3-(1-(4-fluorophenyl)-6-methyl-1H-indazol-5-yl)-1-((1-methyl-1H-pyrazol-4-yl)sulfonyl)pyrrolidin-3-yl)methyl)-2-methylthiazole | $R^t$ 1.45 min (Method 6); m/z 551.3 $(M + H)^+$ $(ES^+)$ |
| 228 | 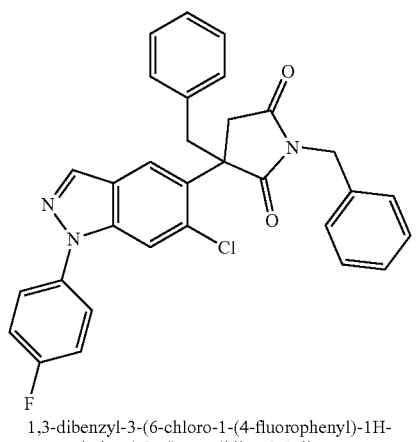<br>1,3-dibenzyl-3-(6-chloro-1-(4-fluorophenyl)-1H-indazol-5-yl)pyrrolidine-2,5-dione | $R^t$ 2.00 min (Method 6); m/z 524.4 $(M + H)^+$ $(ES^+)$ |

Examples 229-235

TABLE 10

The examples shown in the table below were prepared by similar methods to those described for Example 19.

| Example | Structure | LC-MS Analysis |
|---|---|---|
| 229 | 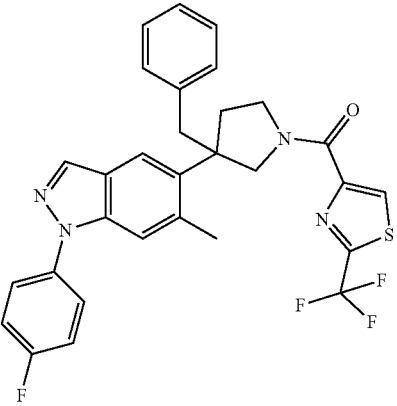 [SMILES: Cc1cc2c(cnn2-c2ccc(F)cc2)cc1C1(Cc2ccccc2)CCN(C(=O)c2csc(C(F)(F)F)n2)C1] (3-benzyl-3-(1-(4-fluorophenyl)-6-methyl-1H-indazol-5-yl)pyrrolidin-1-yl)(2-(trifluoromethyl)thiazol-4-yl)methanone | $R^t$ 2.00 min (Method 6); m/z 565.45 $(M + H)^+$ $(ES^+)$ |
| 230 | 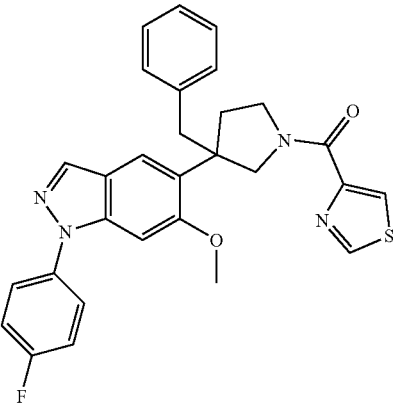 [SMILES: COc1cc2c(cnn2-c2ccc(F)cc2)cc1C1(Cc2ccccc2)CCN(C(=O)c2cscn2)C1] (3-benzyl-3-(1-(4-fluorophenyl)-6-methoxy-1H-indazol-5-yl)pyrrolidin-1-yl)(thiazol-4-yl)methanone | $R^t$ 2.60 min (Method 2); m/z 513.0 $(M + H)^+$ $(ES^+)$ |
| 231 | 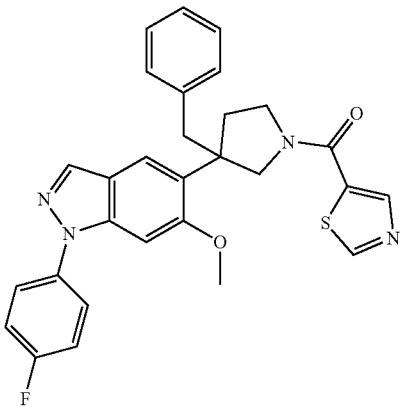 [SMILES: COc1cc2c(cnn2-c2ccc(F)cc2)cc1C1(Cc2ccccc2)CCN(C(=O)c2cncs2)C1] (3-benzyl-3-(1-(4-fluorophenyl)-6-methoxy-1H-indazol-5-yl)pyrrolidin-1-yl)(thiazol-5-yl)methanone | $R^t$ 2.53 min (Method 2); m/z 513.0 $(M + H)^+$ $(ES^+)$ |

TABLE 10-continued

The examples shown in the table below were prepared by similar methods to those described for Example 19.

| Example | Structure | LC-MS Analysis |
|---|---|---|
| 232 | 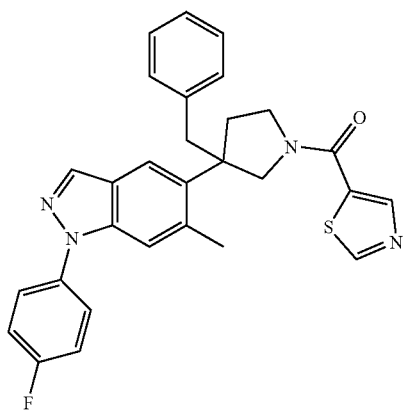 [SMILES: Cc1cc2c(cnn2-c2ccc(F)cc2)cc1C1(Cc2ccccc2)CCN(C(=O)c2cncs2)C1]<br>(3-benzyl-3-(1-(4-fluorophenyl)-6-methyl-1H-indazol-5-yl)pyrrolidin-1-yl)(thiazol-5-yl)methanone | $R^t$ 2.58 min (Method 2); m/z 496.8 $(M + H)^+$ $(ES^+)$ |
| 233 | 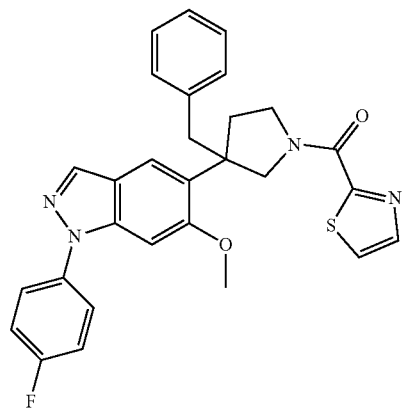 [SMILES: COc1cc2c(cnn2-c2ccc(F)cc2)cc1C1(Cc2ccccc2)CCN(C(=O)c2nccs2)C1]<br>(3-benzyl-3-(1-(4-fluorophenyl)-6-methoxy-1H-indazol-5-yl)pyrrolidin-1-yl)(thiazol-2-yl)methanone | $R^t$ 1.84 min (Method 2); m/z 512.9 $(M + H)^+$ $(ES^+)$ |
| 234 | 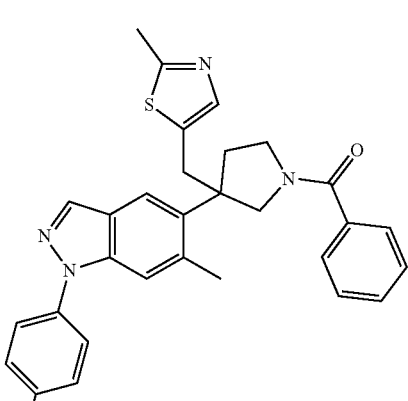<br>(3-(1-(4-fluorophenyl)-6-methyl-1H-indazol-5-yl)-3-((2-methylthiazol-5-yl)methyl)pyrrolidin-1-yl)(phenyl)methanone | $R^t$ 1.56 min (Method 1); m/z 511.3 $(M + H)^+$ $(ES^+)$ |

TABLE 10-continued

The examples shown in the table below were prepared by similar methods to those described for Example 19.

| Example | Structure | LC-MS Analysis |
|---|---|---|
| 235 | ((3-benzyl-3-(1-(4-fluorophenyl)-6-methyl-1H-indazol-5-yl)pyrrolidin-1-yl)(thiazol-4-yl)methanone | $R^t$ 1.77 min (Method 1); m/z 497.1 $(M + H)^+$ $(ES^+)$ |

Example 236: 5-(3-benzyl-1-((2-methyl-2H-1,2,3-triazol-4-yl)sulfonyl)pyrrolidin-3-yl)-1-(6-methoxy-pyridin-3-yl)-6-methyl-1H-indazole Intermediate AD: 6-methyl-1-(tetrahydro-2H-pyran-2-yl)-5-(4,4,5,5-tetramethyl-1,3,2-dioxaborolan-2-yl)-1H-indazole

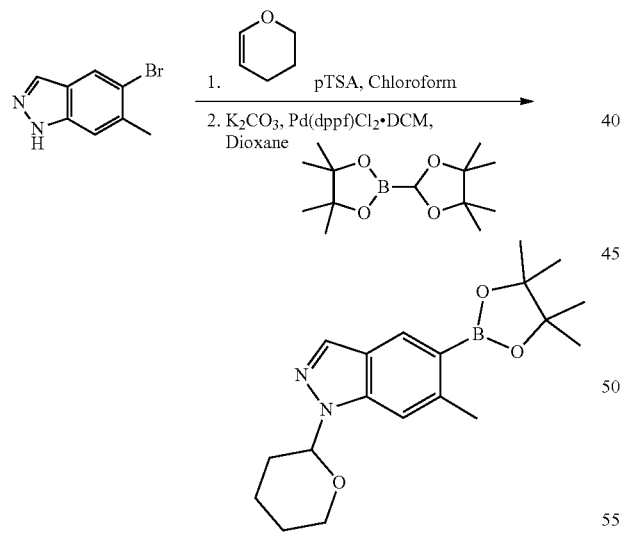

To a solution of 5-bromo-6-methyl-1H-indazole (25.00 g, 118.4 mmol) and dihydropyran (19.93 g, 21.5 mL, 236.9 mmol) in chloroform (400 mL) was added p-toluenesulfonic acid monohydrate (2.253 g, 1.817 mL, 11.84 mmol). The brown suspension was stirred at room temperature for 48 hours. The reaction mixture was washed with sodium bicarbonate (2×200 mL), the organic layer was dried using anhydrous sodium sulphate and the solvent was removed under reduced pressure to give 5-bromo-6-methyl-1-(tetrahydro-2H-pyran-2-yl)-1H-indazole (39 g, 0.12 mol, 97%) as brown oil. A suspension of 5-bromo-6-methyl-1-(tetrahydro-2H-pyran-2-yl)-1H-indazole (39 g, 87.3% Wt, 0.12 mol), 4,4,4',4',5,5,5',5'-octamethyl-2,2'-bi(1,3,2-dioxaborolane) (35 g, 0.14 mol) and potassium acetate (51 g, 0.52 mol) in 1,4-dioxane (250 mL) was sparged with $N_2$ for 15 minutes. PdCl2(dppf)-CH2Cl2adduct (4.7 g, 5.8 mmol) was added and the solution was sparged with $N_2$ for 15 minutes, heated to 80° C. and stirred for 3.5 hours. The reaction mixture was allowed to cool to room temperature overnight and partitioned between EtOAc (500 mL) and 1:1 brine/$H_2O$ (250 mL), the layers were separated, and the aqueous layer extracted with EtOAc (300 mL). The combined organics were washed with sodium hydrogen carbonate solution (2×250 mL), dried over $MgSO_4$, filtered and concentrated in vacuo to afford 6-methyl-1-(tetrahydro-2H-pyran-2-yl)-5-(4,4,5,5-tetramethyl-1,3,2-dioxaborolan-2-yl)-1H-indazole (45 g, 0.11 mol, 94%) (Intermediate AD) as a dark brown oil which was used crude in the next step.

Intermediate AE: 1-benzyl-3-(6-methyl-1-(tetrahydro-2H-pyran-2-yl)-1H-indazol-5-yl)pyrrolidine-2,5-dione

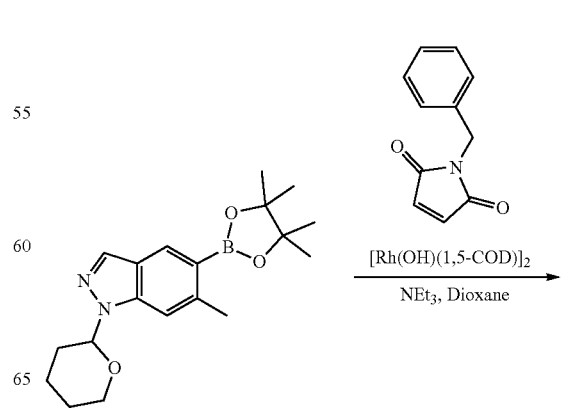

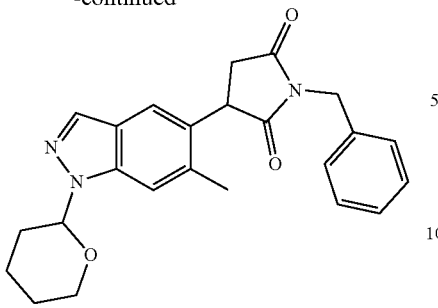

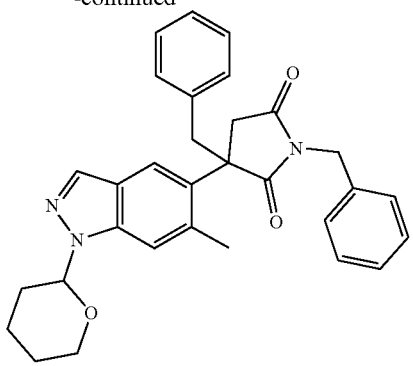

A solution of 6-methyl-1-(tetrahydro-2H-pyran-2-yl)-5-(4,4,5,5-tetramethyl-1,3,2-dioxaborolan-2-yl)-1H-indazole (Intermediate AD) (45 g, 82.5% Wt, 0.11 mol), 1-benzyl-1H-pyrrole-2,5-dione (24 g, 0.13 mol) and triethylamine (16 g, 23 mL, 0.16 mol) in 1,4-dioxane (300 mL) and water (33.3 mL) was sparged with $N_2$ for 10 minutes. Hydroxy(cyclooctadiene)rhodium(I) dimer (1.5 g, 3.3 mmol) was added and the solution was sparged with $N_2$ for 5 minutes and then heated at 80° C. and stirred for 1 hour. The reaction was cooled and concentrated to low volume (~150 mL). The reaction mixture was partitioned between EtOAc (300 mL) and water (150 mL), the layers were separated, and the organic layer washed with half saturated brine (100 mL). The organics were dried over $MgSO_4$, filtered and concentrated in vacuo to give a dark brown oil. The crude product was purified by chromatography on silica gel (330 g cartridge, 0-65% EtOAc/isohexane) to afford 1-benzyl-3-(6-methyl-1-(tetrahydro-2H-pyran-2-yl)-1H-indazol-5-yl)pyrrolidine-2,5-dione (Intermediate AE) (32 g, 78 mmol, 72%) as a sticky tan gum; Rt 1.93 min (Method 7); m/z 404.3 (M+H)+ (ES+). $\delta_H$ (400 MHz, DMSO-$d_6$) δ 7.97 (s, 1H), 7.57 (s, 1H), 7.48 (d, J=2.3 Hz, 1H), 7.40-7.20 (m, 5H), 5.83-5.72 (m, 1H), 4.66 (s, 2H), 4.55 (m, 1H), 3.87 (m, 1H), 3.77-3.67 (m, 1H), 3.40-3.32 (m, 1H), 2.77 (ddd, J=18.2, 5.1, 2.7 Hz, 1H), 2.41 (m, 4H), 1.99 (m, 1H), 1.93 (m, 1H), 1.80-1.65 (m, 1H), 1.61-1.5 (m, 2H).

Intermediate AF: 1,3-dibenzyl-3-(6-methyl-1-(tetrahydro-2H-pyran-2-yl)-1H-indazol-5-yl)pyrrolidine-2,5-dione A solution of 1-benzyl-3-(6-methyl-1-(tetrahydro-2H-pyran-2-yl)-1H-indazol-5-yl)pyrrolidine-2,5-dione (Intermediate AE) (6.10 g, 74% Wt, 11.2 mmol) in THF (55.0 mL) was sparged with $N_2$ for 10 minutes whilst it was cooled to 0° C. Sodium hydride (685 mg, 60% Wt, 17.1 mmol) was added in one portion and the resulting solution was stirred at 0° C. for 30 minutes. (Bromomethyl)benzene (3.83 g, 2.66 mL, 22.4 mmol) was added and the reaction mixture was allowed to warm to 20° C. and stirred for 23 hours. The reaction mixture was quenched with water (40 mL) and the aqueous phase was extracted with EtOAc (3×60 mL). The combined organic phase was dried over $MgSO_4$, filtered, and concentrated in vacuo. The crude product was purified by chromatography on silica gel (120 g cartridge, 0-50% EtOAc/isohexane) to afford 1,3-dibenzl-3-(6-methyl-1-(tetrahydro-2H-pyran-2-yl)-1H-indazol-5-yl)pyrrolidine-2,5-dione (Intermediate AF) (5.47 g, 9.42 mmol, 55.7%) as a white solid; $\delta_H$ (400 MHz, DMSO-d6) δ 8.06 (s, 1H), 7.97 (s, 1H), 7.57 (d, J=2.8 Hz, 1H), 7.30-7.17 (m, 8H), 7.15-7.08 (m, 2H), 5.77 (dd, J=10.1, 2.9 Hz, 1H), 4.32 (dd, J=14.4, 4.0 Hz, 1H), 4.23 (dd, J=14.4, 5.2 Hz, 1H), 3.90-3.83 (m, 1H), 3.76-3.67 (m, 1H), 3.57 (dd, J=12.7, 5.4 Hz, 1H), 3.37 (d, J=12.7 Hz, 1H), 3.18 (d, J=18.8 Hz, 1H), 3.03 (d, J=18.8 Hz, 1H), 2.46-2.34 (m, 1H), 2.19 (d, J=5.3 Hz, 3H), 2.09-1.99 (m, 1H), 1.98-1.89 (m, 1H), 1.80-1.65 (m, 2H).

Intermediate AG: 5-(1,3-dibenzylpyrrolidine-3-yl)-6-methyl-1-(tetrahydro-2H-pyran-2-yl)-1H-indazole

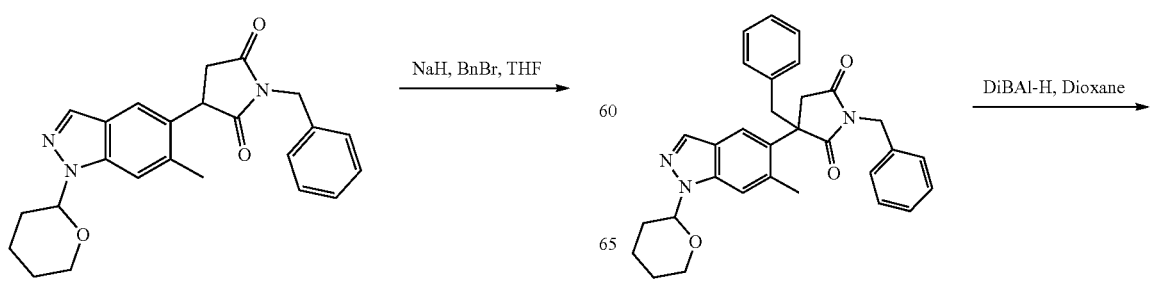

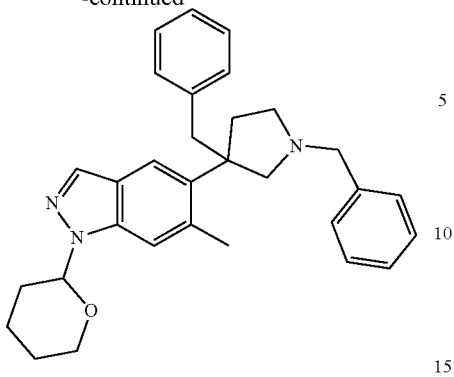

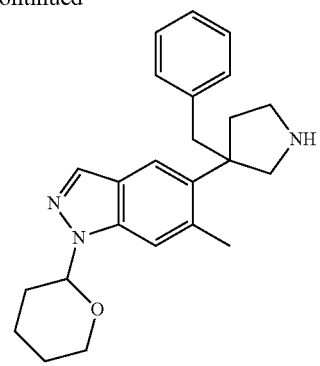

To a 3-neck round-bottomed flask with bubbler, a solution of 1,3-dibenzyl-3-(6-methyl-1-(tetrahydro-2H-pyran-2-yl)-1H-indazol-5-yl)pyrrolidine-2,5-dione (Intermediate AF) (6.40 g, 85% Wt, 11.0 mmol) in 1,4-dioxane (44.0 mL) was sparged with N₂ for 10 minutes then cooled to 0° C. DIBAL-H (1 molar in hexanes) (11.7 g, 82.0 mL, 1 molar, 82.0 mmol) was added and then the resulting solution was allowed to warm to 20° C. and stirred for 18 hours. The reaction was cooled to 0° C. and water (3.3 mL), 2 M NaOH (3.3 mL) and water (8.2 mL) were added sequentially very slowly. The reaction mixture was allowed to warm to room temperature, MgSO₄ (excess) was added and then the reaction mixture was stirred for 15 minutes. The slurry was filtered, washed with EtOAc (2×50 mL) and concentrated in vacuo. The crude product was purified by chromatography on silica gel (120 g cartridge, 0-50% EtOAc/isohexane) to afford 5-(1,3-dibenzylpyrrolidine-3-yl)-6-methyl-1-(tetrahydro-2H-pyran-2-yl)-1H-indazole (Intermediate AG) (3.96 g, 7.99 mmol, 72.5%) as a pale yellow foam; δ$_H$ (400 MHz, DMSO-d6) δ 7.84-7.79 (m, 1H), 7.50 (s, 1H), 7.46-7.42 (m, 2H), 7.42-7.36 (m, 2H), 7.34-7.26 (m, 1H), 7.00-6.92 (m, 1H), 6.87 (td, J=7.5, 3.5 Hz, 2H), 6.75 (d, J=7.3 Hz, 1H), 6.41-6.33 (m, 2H), 5.80-5.71 (m, 1H), 3.95-3.83 (m, 1H), 3.79-3.69 (m, 2H), 3.61-3.53 (m, 1H), 3.22-3.01 (m, 4H), 2.55-2.51 (m, 3H), 2.42-2.31 (m, 4H), 2.20-2.09 (m, 1H), 2.07-1.99 (m, 1H), 1.97-1.87 (m, 1H), 1.80-1.67 (m, 1H), 1.62-1.53 (m, 2H).

Intermediate AH: 5-(3-benzylpyrrolidin-3-yl)-6-methyl-1-(tetrahydro-2H-pyran-2-yl)-1H-indazole

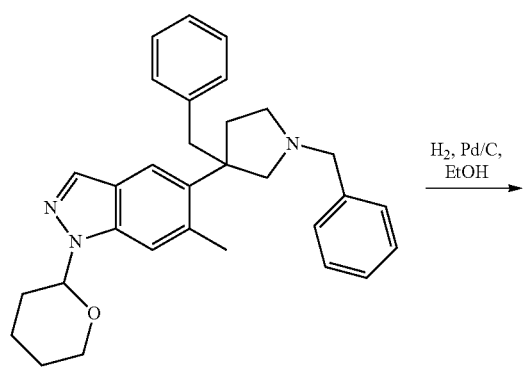

10% palladium on carbon (1.06 g, 4% Wt, 400 μmol) in EtOH (2.0 mL) was added to a solution of 5-(1,3-dibenzylpyrrolidin-3-yl)-6-methyl-1-(tetrahydro-2H-pyran-2-yl)-1H-indazole (Intermediate AG) (3.96 g, 94% Wt, 7.99 mmol) in EtOH (15.0 mL). The reaction mixture was stirred under an atmosphere of H₂ (5 bar) at 20° C. for 23 hours. The reaction mixture was filtered through a glass microfiber filter, washed with EtOH (3×25 mL) and concentrated in vacuo to afford 5-(3-benzylpyrrolidin-3-yl)-6-methyl-1-(tetrahydro-2H-pyran-2-yl)-1H-indazole (Intermediate AH) (3.04 g, 7.3 mmol, 91%) as a light brown oil; Rt 1.29 min (Method 7); m/z 376.3 (M+H)+ (ES+).

Intermediate AI: 5-(3-benzyl-1-((2-methyl-2H-1,2,3-triazol-4-yl)sulfonyl)pyrrolidin-3-yl)-6-methyl-1H-indazole

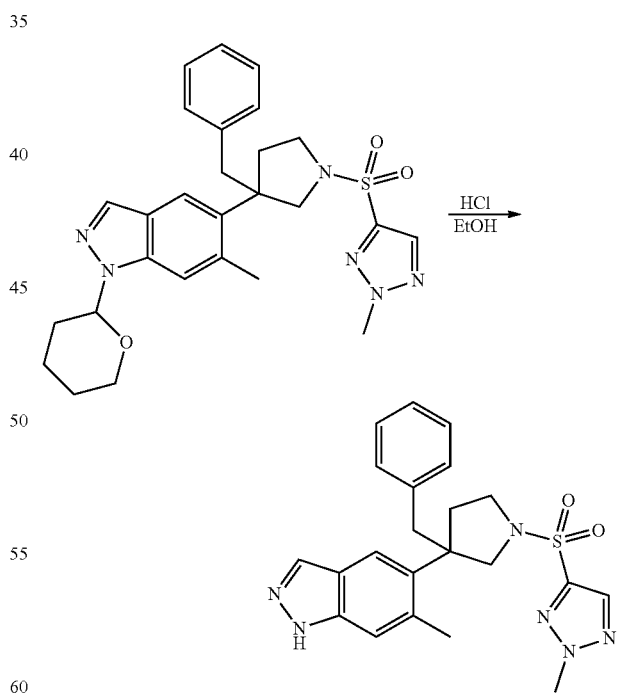

To a suspension of 5-(3-benzyl-1-((2-methyl-2H-1,2,3-triazol-4-yl)sulfonyl)pyrrolidin-3-yl)-6-methyl-1-(tetrahydro-2H-pyran-2-yl)-1H-indazole (prepared using a similar method described for Example 16) (1.17 g, 92% Wt, 2.07 mmol) in ethanol (15.0 mL) was added HCl (4 M in dioxane) (2.2 g, 15 mL, 4 molar, 60 mmol). The reaction mixture was stirred at 20° C. for 18 hours. The reaction mixture was concentrated in vacuo and the residue partitioned between dichloromethane (30 mL) and saturated aqueous NaHCO₃ (30 mL). The layers were separated and then the aqueous phase was extracted with dichloromethane (2×10 mL). The combined organic phase was dried over MgSO₄, filtered, and concentrated in vacuo. The crude product was purified by chromatography on silica gel (40 g cartridge, 0-100% (3:1 EtOAc/EtOH)/isohexane) to afford 5-(3-benzyl-1-((2-methyl-2H-1,2,3-triazol-4-yl)sulfonyl)pyrrolidin-3-yl)-O-methyl-1H-indazole (1.20 g, 2.4 mmol, 60%) (Intermediate AI) as a pale yellow solid; Rt 1.78 min (Method 7); m/z 437.2 (M+H)+ (ES+). δ$_H$ (400 MHz, DMSO-d6) δ 12.81 (s, 1H), 8.35 (s, 1H), 7.82 (d, J=1.2 Hz, 1H), 7.29 (s, 1H), 7.10-7.04 (m, 1H), 7.03-6.97 (m, 2H), 6.92 (s, 1H), 6.50-6.43 (m, 2H), 4.16 (s, 3H), 3.94 (d, J=9.6 Hz, 1H), 3.68-3.59 (m, 1H), 3.53-3.45 (m, 1H), 3.34 (d, J=9.8 Hz, 1H), 2.98 (d, J=13.4 Hz, 1H), 2.71 (d, J=13.4 Hz, 1H), 2.44-2.34 (m, 4H), 2.11-2.00 (m, 1H).

Example 236: 5-(3-benzyl-1-((2-methyl-2H-1,2,3-triazol-4-yl)sulfonyl)pyrrolidin-3-yl)-1-(6-methoxy-pyridin-3-yl)-6-methyl-1H-indazole

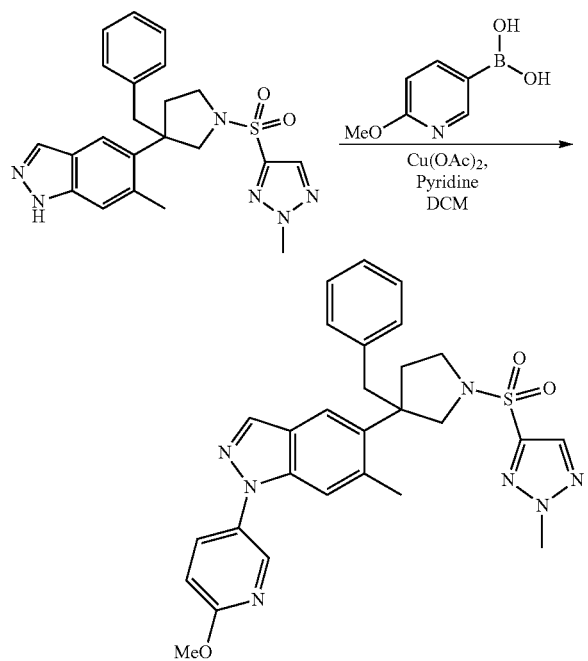 [SMILES: Cc1cc2[nH]ncc2cc1C1(Cc2ccccc2)CCN(S(=O)(=O)c2cnn(C)n2)C1 ; COc1ccc(B(O)O)cn1 ; COc1ccc(-n2ncc3cc(C4(Cc5ccccc5)CCN(S(=O)(=O)c5cnn(C)n5)C4)c(C)cc32)cn1]

Pyridine (130 mg, 0.13 mL, 1.65 mmol) was added to a solution of 5-(3-benzyl-1-((2-methyl-2H-1,2,3-triazol-4-yl)sulfonyl)pyrrolidin-3-yl)-6-methyl-1H-indazole (360 mg, 825 μmol) (Intermediate AI), (6-methoxypyridin-3-yl)boronic acid (252 mg, 1.65 mmol) and copper (II) acetate (150 mg, 825 μmol) in dichloromethane (10 mL) and stirred in an open vessel overnight. The reaction was adsorbed onto silica and was purified by chromatography on silica gel (24 g cartridge, 0-80% EtOAc/isohexane) to afford 5-(3-benzyl-1-((2-methyl-2H-1,2,3-triazol-4-yl)sulfonyl)pyrrolidin-3-yl)-1-(6-methoxypyridin-3-yl)-6-methyl-1H-indazole (26 mg, 47 μmol, 5.7%) (Example 236) as a white solid; Rt 1.75 min (Method 6); m/z 544.4 (M+H)+ (ES+). δ$_H$ (DMSO-d6, 500 MHz) δ 8.59-8.57 (m, 1H), 8.34 (s, 1H), 8.15 (d, J 0.9, 1H), 8.09 (dd, J 8.8, 2.8, 1H), 7.58 (s, 1H), 7.12-7.02 (m, 5H), 6.54-6.51 (m, 2H), 4.16 (s, 3H), 3.97 (d, J 9.8, 1H), 3.94 (s, 3H), 3.68-3.61 (m, 1H), 3.54-3.47 (m, 1H), 3.41-3.36 (m, 1H), 3.02 (d, J 13.4, 1H), 2.75 (d, J 13.5, 1H), 2.45-2.38 (m, 4H), 2.12-2.03 (m, 1H).

Example 237: 5-(5-(3-benzyl-1-((2-methyl-2H-1,2,3-triazol-4-yl)sulfonyl)pyrrolidin-3-yl)-6-methyl-1H-indazol-1-yl)-1,3-dimethylpyridin-2(1H)-one

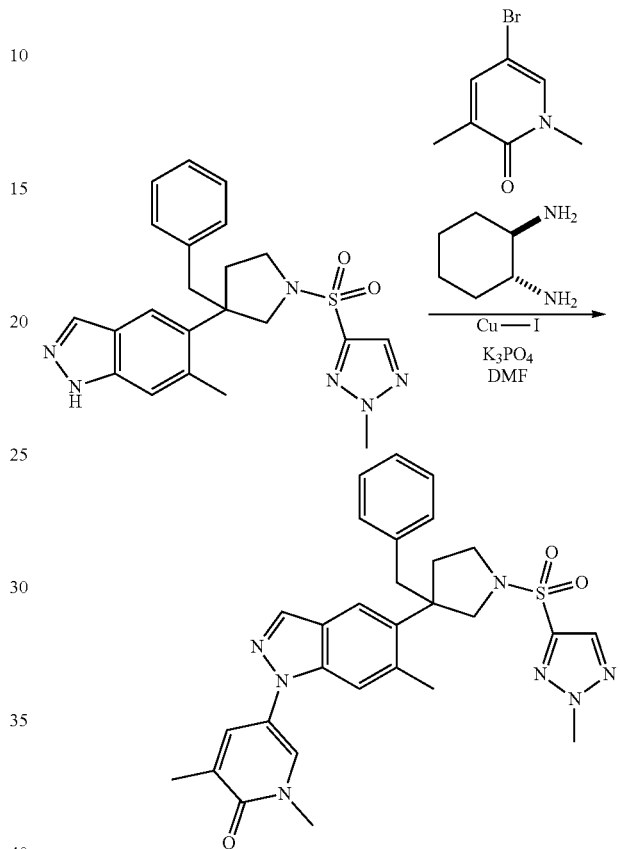

A suspension of 5-(3-benzyl-1-((2-methyl-2H-1,2,3-triazol-4-yl)sulfonyl)pyrrolidin-3-yl)-6-methyl-1H-indazole (52.0 mg, 94% Wt, 112 μmol), (1R,2R)-cyclohexane-1,2-diamine (14.3 mg, 15.0 μL, 125 μmol) (Intermediate AI), 5-bromo-1,3-dimethylpyridin-2(1H)-one (51.0 mg, 252 μmol) and potassium phosphate (64.0 mg, 302 μmol) in DMF (2.00 mL) was sparged with N₂ for 5 minutes before copper(I) iodide (12.0 mg, 63.0 μmol) was added. The reaction mixture was sparged with N₂ for 5 minutes and then the reaction mixture was heated at 120° C. for 21 hours. The reaction mixture was allowed to cool to room temperature, diluted with 5% LiCl(aq) solution (10 mL) and extracted with EtOAc (4×5 mL). The combined organic phase was washed with 1:1 saturated brine (aq)/water (2×10 mL), dried over MgSO₄, filtered, and concentrated in vacuo. The crude product was purified by preparative HPLC (Waters, Acidic (0.1% formic acid in water), Acidic, Waters X-Select CSH C18 ODB prep column, 30-60% MeCN in Water) to afford 5-(5-(3-benzyl-1-((2-methyl-2H-1,2,3-triazol-4-yl)sulfonyl)pyrrolidin-3-yl)-6-methyl-1H-indazol-1-yl)-1,3-dimethylpyridin-2(1H)-one (Example 237) (32.3 mg, 56.8 μmol, 50.7%) as a tan solid; Rt 1.97 min (Method 6); m/z 558.3 (M+H)+ (ES+). δ$_H$ (400 MHz, DMSO-d6) δ 8.35 (s, 1H), 8.09-8.04 (m, 2H), 7.66 (dd, J=2.9, 1.3 Hz, 1H), 7.48 (s, 1H), 7.12-6.99 (m, 4H), 6.54-6.47 (m, 2H), 4.17 (s, 3H), 3.97 (d, J=9.7 Hz, 1H), 3.70-3.60 (m, 1H), 3.56 (s, 3H), 3.53-3.46 (m, 1H), 3.36 (d, J=9.8 Hz, 1H), 3.01 (d, J=13.4 Hz, 1H), 2.73 (d, J=13.5 Hz, 1H), 2.45-2.37 (m, 4H), 2.13-2.01 (m, 4H).

Examples 238-243

TABLE 11

The examples shown in the table below were prepared by similar methods to those described for Example 236

| Example | Structure | LC-MS Analysis |
|---|---|---|
| 238 | 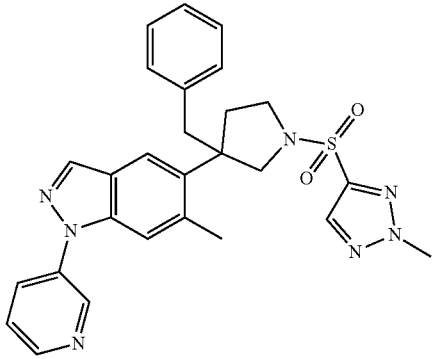 [SMILES: Cc1cc2c(cnn2-c2cccnc2)cc1C1(Cc2ccccc2)CCN(S(=O)(=O)c2cnn(C)n2)C1]<br>5-(3-benzyl-1-((2-methyl-2H-1,2,3-triazol-4-yl)sulfonyl)pyrrolidin-3-yl)-6-methyl-1-(pyridin-3-yl)-1H-indazole | $R^t$ 1.45 min (Method 6); m/z 514.6 $(M + H)^+$ $(ES^+)$ |
| 239 | 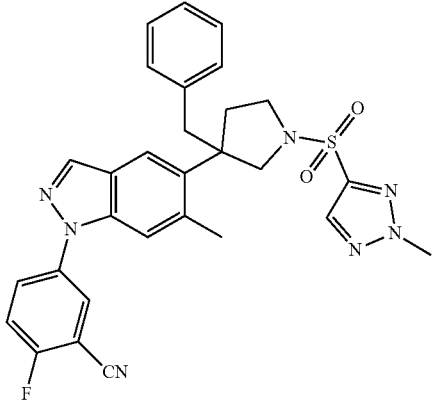 [SMILES: Cc1cc2c(cnn2-c2ccc(F)c(C#N)c2)cc1C1(Cc2ccccc2)CCN(S(=O)(=O)c2cnn(C)n2)C1]<br>5-(5-(3-benzyl-1-((2-methyl-2H-1,2,3-triazol-4-yl)sulfonyl)pyrrolidin-3-yl)-6-methyl-1H-indazol-1-yl)-2-fluorobenzonitrile | $R^t$ 1.77 min (Method 6); m/z 556.6 $(M + H)^+$ $(ES^+)$ |
| 240 | 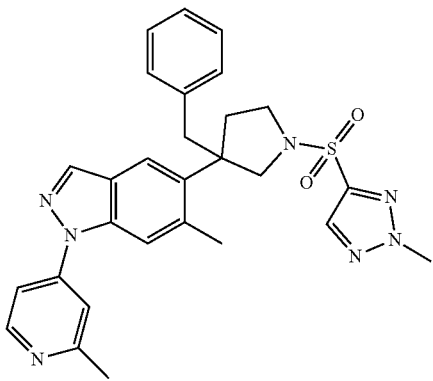 [SMILES: Cc1cc(-n2ncc3cc(C4(Cc5ccccc5)CCN(S(=O)(=O)c5cnn(C)n5)C4)c(C)cc32)ccn1]<br>5-(3-benzyl-1-((2-methyl-2H-1,2,3-triazol-4-yl)sulfonyl)pyrrolidin-3-yl)-6-methyl-1-(2-methylpyridin-4-yl)-1H-indazole | $R^t$ 1.06 min (Method 6); m/z 528.4 $(M + H)^+$ $(ES^+)$ |

TABLE 11-continued

The examples shown in the table below were prepared by similar methods to those described for Example 236

| Example | Structure | LC-MS Analysis |
|---|---|---|
| 241 | 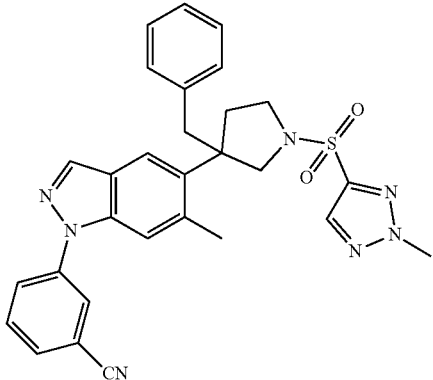 [SMILES: Cc1cc2c(cnn2-c2cccc(C#N)c2)cc1C1(Cc2ccccc2)CCN(S(=O)(=O)c2cnn(C)n2)C1]
3-(5-(3-benzyl-1-((2-methyl-2H-1,2,3-triazol-4-yl)sulfonyl)pyrrolidin-3-yl)-6-methyl-1H-indazol-1-yl)benzonitrile | $R^t$ 1.76 min (Method 6); m/z 538.4 (M + H)$^+$ (ES$^+$) |
| 242 | 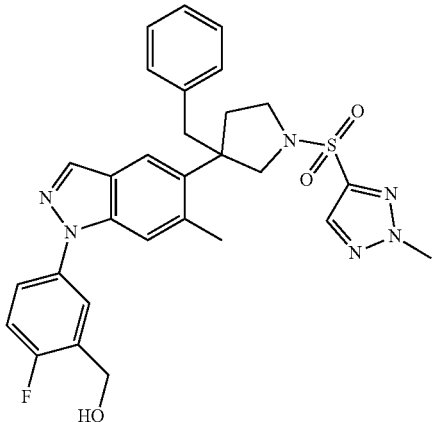 [SMILES: Cc1cc2c(cnn2-c2ccc(F)c(CO)c2)cc1C1(Cc2ccccc2)CCN(S(=O)(=O)c2cnn(C)n2)C1]
(5-(5-(3-benzyl-1-((2-methyl-2H-1,2,3-triazol-4-yl)sulfonyl)pyrrolidin-3-yl)-6-methyl-1H-indazol-1-yl)-2-fluorophenyl)methanol | $R^t$ 2.00 min (Method 7); m/z 561.3 (M + H)$^+$ (ES$^+$) |
| 243 | 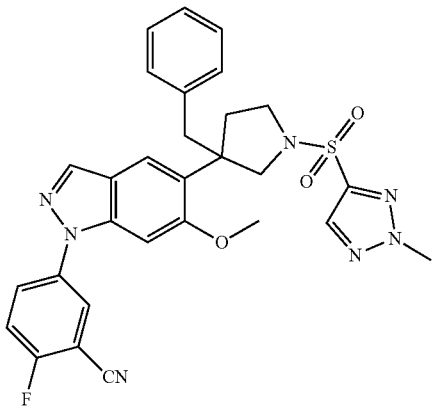 [SMILES: COc1cc2c(cnn2-c2ccc(F)c(C#N)c2)cc1C1(Cc2ccccc2)CCN(S(=O)(=O)c2cnn(C)n2)C1]
5-(5-(3-benzyl-1-((2-methyl-2H-1,2,3-triazol-4-yl)sulfonyl)pyrrolidin-3-yl)-6-methoxy-1H-indazol-1-yl)-2-fluorobenzonitrile | $R^t$ 2.28 min (Method 6); m/z 572.0 (M + H)$^+$ (ES$^+$) |

Examples 244-274

TABLE 12

The examples shown in the table below were prepared by similar methods to those described for Example 237

| Example | Structure | LC-MS Analysis |
|---|---|---|
| 244 | 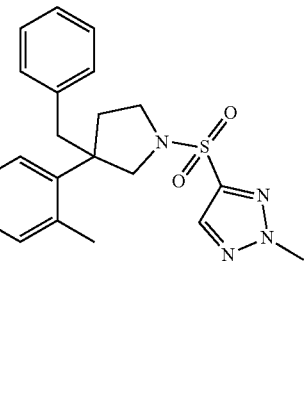<br>4-(5-(3-benzyl-1-((2-methyl-2H-1,2,3-triazol-4-yl)sulfonyl)pyrrolidin-3-yl)-6-methyl-1H-indazol-1-yl)-1-methylpyridin-2(1H)-one | $R^t$ 4.09 min (Method 5); m/z 544.3 $(M + H)^+$ $(ES^+)$ |
| 245 | 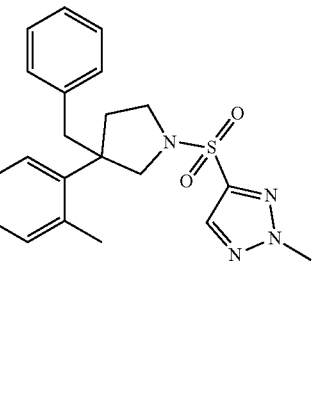<br>5-(5-(3-benzyl-1-((2-methyl-2H-1,2,3-triazol-4-yl)sulfonyl)pyrrolidin-3-yl)-6-methyl-1H-indazol-1-yl)-1-methyl-2-oxo-1,2-dihydropyridine-3-carbonitrile | $R^t$ 1.49 min (Method 8); m/z 569.1 $(M + H)^+$ $(ES^+)$ |
| 246 | 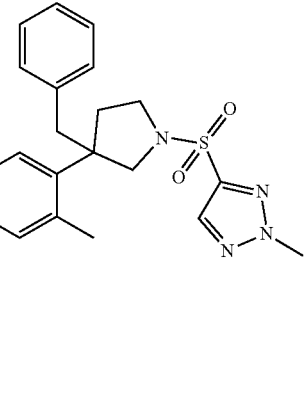<br>5-(5-(3-benzyl-1-((2-methyl-2H-1,2,3-triazol-4-yl)sulfonyl)pyrrolidin-3-yl)-6-methyl-1H-indazol-1-yl)-3-fluoro-1-methylpyridin-2(1H)-one | $R^t$ 1.48 min (Method 8); m/z 562.4 $(M + H)^+$ $(ES^+)$ |

TABLE 12-continued

The examples shown in the table below were prepared by similar methods to those described for Example 237

| Example | Structure | LC-MS Analysis |
|---|---|---|
| 247 | 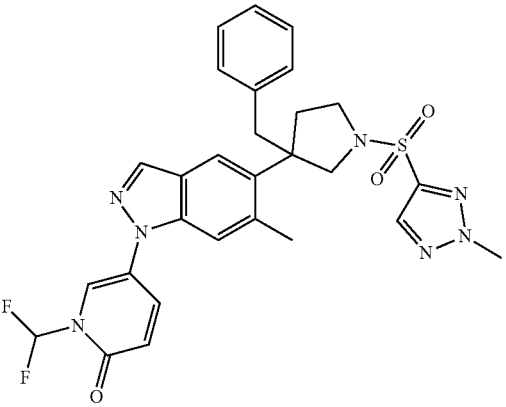 [SMILES: Cc1cc2c(cnn2-c2ccc(=O)n(C(F)F)c2)cc1C1(Cc2ccccc2)CCN(S(=O)(=O)c2cnn(C)n2)C1]<br>5-(5-(3-benzyl-1-((2-methyl-2H-1,2,3-triazol-4-yl)sulfonyl)pyrrolidin-3-yl)-6-methyl-1H-indazol-1-yl)-1-(difluoromethyl)pyridin-2(1H)-one | $R^t$ 2.09 min (Method 8); m/z 580.0 $(M + H)^+$ $(ES^+)$ |
| 248 | 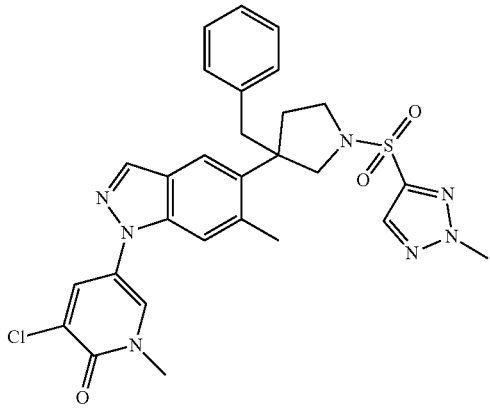 [SMILES: Cc1cc2c(cnn2-c2cc(Cl)c(=O)n(C)c2)cc1C1(Cc2ccccc2)CCN(S(=O)(=O)c2cnn(C)n2)C1]<br>5-(5-(3-benzyl-1-((2-methyl-2H-1,2,3-triazol-4-yl)sulfonyl)pyrrolidin-3-yl)-6-methyl-1H-indazol-1-yl)-3-chloro-1-methylpyridin-2(1H)-one | $R^t$ 2.01 min (Method 1); m/z 578.0 $(M + H)^+$ $(ES^+)$ |
| 249 | 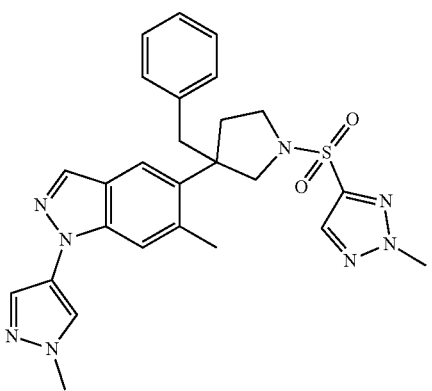 [SMILES: Cc1cc2c(cnn2-c2cnn(C)c2)cc1C1(Cc2ccccc2)CCN(S(=O)(=O)c2cnn(C)n2)C1]<br>5-(3-benzyl-1-((2-methyl-2H-1,2,3-triazol-4-yl)sulfonyl)pyrrolidin-3-yl)-6-methyl-1-(1-methyl-1H-pyrazol-4-yl)-1H-indazole | $R^t$ 2.00 min (Method 1); m/z 517.2 $(M + H)^+$ $(ES^+)$ |

TABLE 12-continued

The examples shown in the table below were prepared by similar methods to those described for Example 237

| Example | Structure | LC-MS Analysis |
|---|---|---|
| 250 | 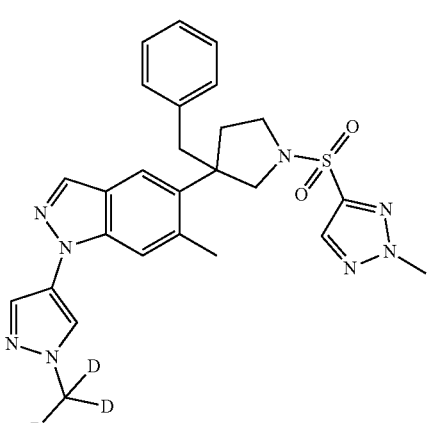<br>5-(3-benzyl-1-((2-methyl-2H-1,2,3-triazol-4-yl)sulfonyl)pyrrolidin-3-yl)-6-methyl-1-(1-(methyl-d3)-1H-pyrazol-4-yl)-1H-indazole | $R^t$ 1.99 min (Method 1); m/z 520.3 (M + H)$^+$ (ES$^+$) |
| 251 | 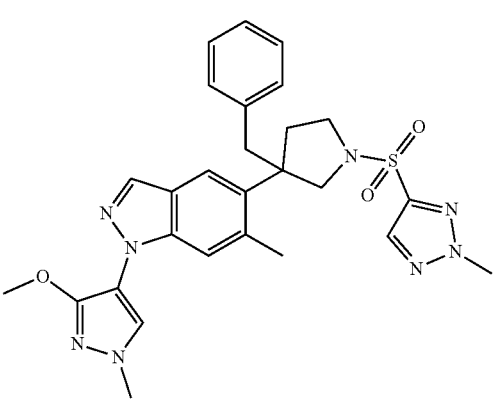<br>5-(3-benzyl-1-((2-methyl-2H-1,2,3-triazol-4-yl)sulfonyl)pyrrolidin-3-yl)-1-(3-methoxy-1-methyl-1H-pyrazol-4-yl)-6-methyl-1H-indazole | $R^t$ 1.92 min (Method 7); m/z 547.4 (M + H)$^+$ (ES$^+$) |
| 252 | 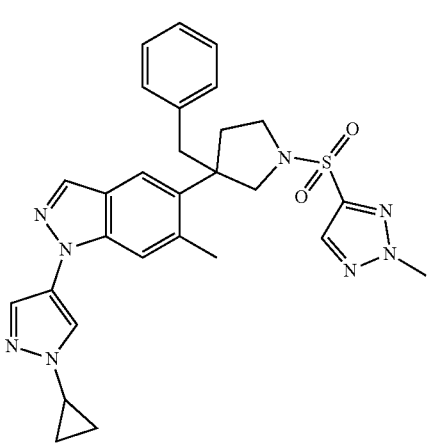 [SMILES: Cc1cc2c(cnn2-c2cnn(C3CC3)c2)cc1C1(Cc2ccccc2)CCN(S(=O)(=O)c2cnn(C)n2)C1]<br>5-(3-benzyl-1-((2-methyl-2H-1,2,3-triazol-4-yl)sulfonyl)pyrrolidin-3-yl)-1-(1-cyclopropyl-1H-pyrazol-4-yl)-6-methyl-1H-indazole | $R^t$ 2.03 min (Method 7); m/z 543.2 (M + H)$^+$ (ES$^+$) |

TABLE 12-continued

The examples shown in the table below were prepared by similar methods to those described for Example 237

| Example | Structure | LC-MS Analysis |
| --- | --- | --- |
| 253 | 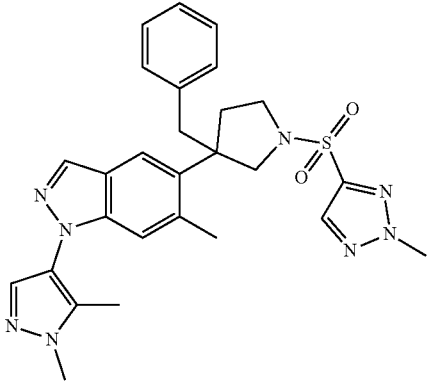 [SMILES: Cc1cc2c(cnn2-c2cnn(C)c2C)cc1C1(Cc2ccccc2)CCN(S(=O)(=O)c2cnn(C)n2)C1]<br>5-(3-benzyl-1-((2-methyl-2H-1,2,3-triazol-4-yl)sulfonyl)pyrrolidin-3-yl)-1-(1,5-dimethyl-1H-pyrazol-4-yl)-6-methyl-1H-indazole | $R^t$ 1.88 min (Method 7); m/z 531.2 $(M + H)^+$ $(ES^+)$ |
| 254 | 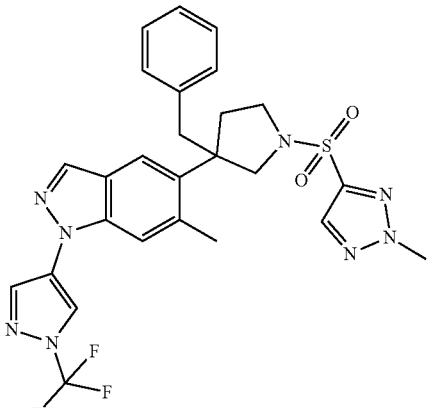<br>5-(3-benzyl-1-((2-methyl-2H-1,2,3-triazol-4-yl)sulfonyl)pyrrolidin-3-yl)-6-methyl-1-(1-(trifluoromethyl)-1H-pyrazol-4-yl)-1H-indazole | $R^t$ 2.22 min (Method 7); m/z 571.5 $(M + H)^+$ $(ES^+)$ |
| 255 | 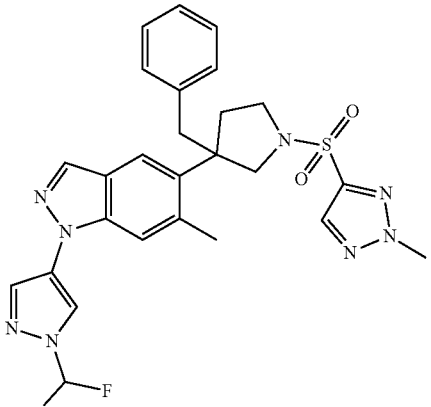<br>5-(3-benzyl-1-((2-methyl-2H-1,2,3-triazol-4-yl)sulfonyl)pyrrolidin-3-yl)-1-(1-(difluoromethyl)-1H-pyrazol-4-yl)-6-methyl-1H-indazole | $R^t$ 2.07 min (Method 7); m/z 553.1 $(M + H)^+$ $(ES^+)$ |

TABLE 12-continued

The examples shown in the table below were prepared by similar methods to those described for Example 237

| Example | Structure | LC-MS Analysis |
|---|---|---|
| 256 | 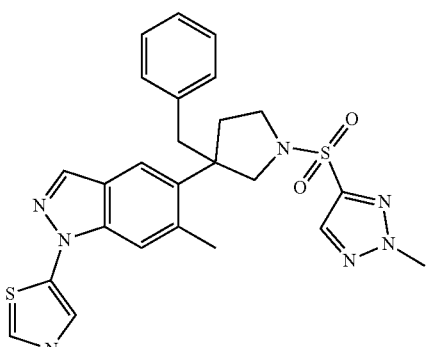<br>4-(5-(3-benzyl-1-((2-methyl-2H-1,2,3-triazol-4-yl)sulfonyl)pyrrolidin-3-yl)-6-methyl-1H-indazol-1-yl)thiazole | $R^t$ 2.14 min (Method 7); m/z 520.1 $(M + H)^+$ $(ES^+)$ |
| 257 | 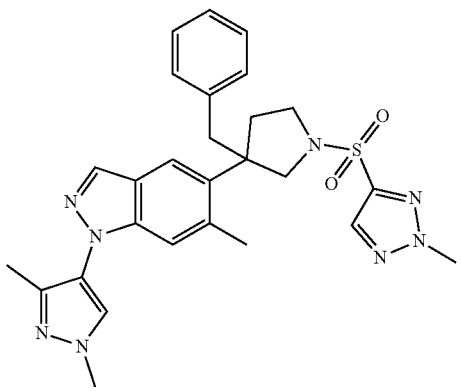<br>5-(3-benzyl-1-((2-methyl-2H-1,2,3-triazol-4-yl)sulfonyl)pyrrolidin-3-yl)-1-(1,3-dimethyl-1H-pyrazol-4-yl)-6-methyl-1H-indazole | $R^t$ 1.91 min (Method 7); m/z 531.2 $(M + H)^+$ $(ES^+)$ |
| 258 | 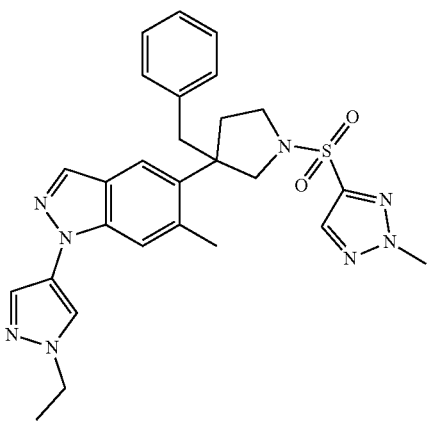 [SMILES: CCn1cc(-n2ncc3cc(C4(Cc5ccccc5)CCN(S(=O)(=O)c5cnn(C)n5)C4)c(C)cc32)cn1]<br>5-(3-benzyl-1-((2-methyl-2H-1,2,3-triazol-4-yl)sulfonyl)pyrrolidin-3-yl)-1-(1-ethyl-1H-pyrazol-4-yl)-6-methyl-1H-indazole | $R^t$ 1.99 min (Method 7); m/z 531.3 $(M + H)^+$ $(ES^+)$ |

TABLE 12-continued

The examples shown in the table below were prepared by similar methods to those described for Example 237

| Example | Structure | LC-MS Analysis |
|---|---|---|
| 259 | 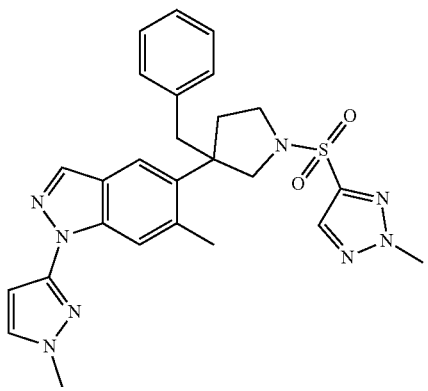 [SMILES: Cc1cc2c(cnn2-c2ccn(C)n2)cc1C1(Cc2ccccc2)CCN(S(=O)(=O)c2cnn(C)n2)C1]<br>5-(3-benzyl-1-((2-methyl-2H-1,2,3-triazol-4-yl)sulfonyl)pyrrolidin-3-yl)-6-methyl-1-(1-methyl-1H-pyrazol-3-yl)-1H-indazole | $R^t$ 2.03 min (Method 7); m/z 517.3 $(M + H)^+$ $(ES^+)$ |
| 260 | 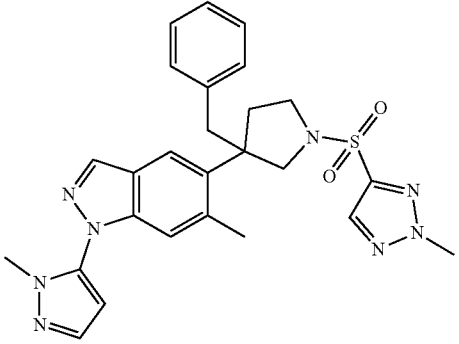<br>5-(3-benzyl-1-((2-methyl-2H-1,2,3-triazol-4-yl)sulfonyl)pyrrolidin-3-yl)-6-methyl-1-(1-methyl-1H-pyrazol-5-yl)-1H-indazole | $R^t$ 1.96 min (Method 7); m/z 517.3 $(M + H)^+$ $(ES^+)$ |
| 261 | 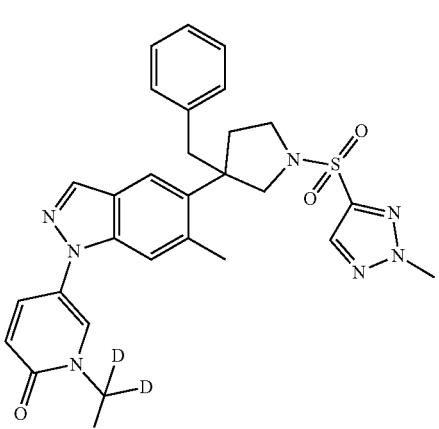<br>5-(5-(3-benzyl-1-((2-methyl-2H-1,2,3-triazol-4-yl)sulfonyl)pyrrolidin-3-yl)-6-methyl-1H-indazol-1-yl)-1-(methyl-d3)pyridin-2(1H)-one | $R^t$ 1.87 min (Method 1); m/z 547.0 $(M + H)^+$ $(ES^+)$ |

TABLE 12-continued

The examples shown in the table below were prepared by similar methods to those described for Example 237

| Example | Structure | LC-MS Analysis |
|---|---|---|
| 262 | 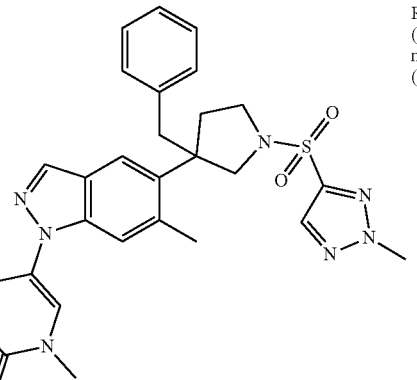<br>5-(5-(3-benzyl-1-((2-methyl-2H-1,2,3-triazol-4-yl)sulfonyl)pyrrolidin-3-yl)-6-methyl-1H-indazol-1-yl)-3-cyclopropyl-1-methylpyridin-2(1H)-one | $R^t$ 1.61 min (Method 7); m/z 584.3 $(M + H)^+$ $(ES^+)$ |
| 263 | 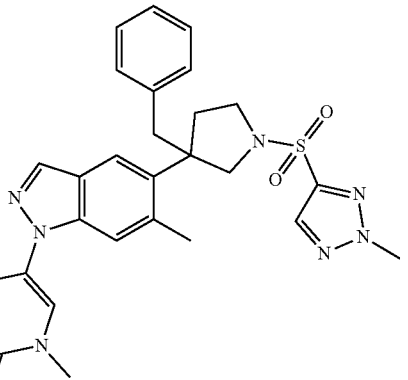<br>5-(5-(3-benzyl-1-((2-methyl-2H-1,2,3-triazol-4-yl)sulfonyl)pyrrolidin-3-yl)-6-methyl-1H-indazol-1-yl)-3-ethyl-1-methylpyridin-2(1H)-one | $R^t$ 1.94 min (Method 7); m/z 572.6 $(M + H)^+$ $(ES^+)$ |
| 264 | 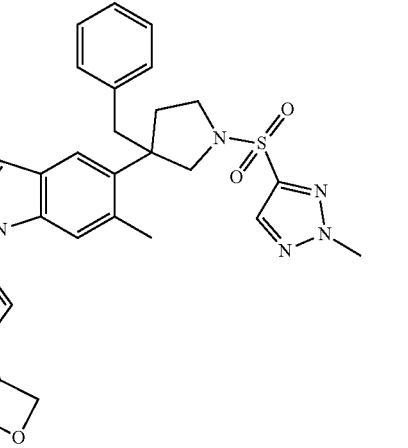<br>5-(3-benzyl-1-((2-methyl-2H-1,2,3-triazol-4-yl)sulfonyl)pyrrolidin-3-yl)-6-methyl-1-(1-(oxetan-3-yl)-1H-pyrazol-4-yl)-1H-indazole | $R^t$ 1.87 min (Method 7); m/z 559.2 $(M + H)^+$ $(ES^+)$ |

TABLE 12-continued

The examples shown in the table below were prepared by similar methods to those described for Example 237

| Example | Structure | LC-MS Analysis |
|---|---|---|
| 265 | 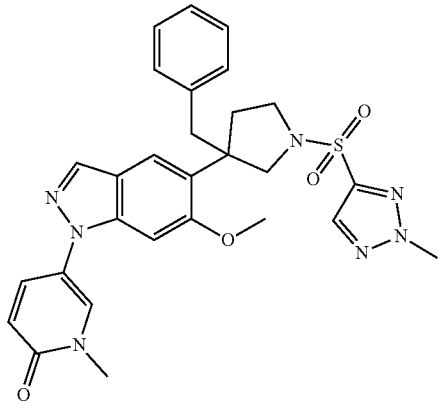 [SMILES: COc1cc2c(cnn2-c2ccc(=O)n(C)c2)cc1C1(Cc2ccccc2)CCN(S(=O)(=O)c2cnn(C)n2)C1]<br>5-(5-(3-benzyl-1-((2-methyl-2H-1,2,3-triazol-4-yl)sulfonyl)pyrrolidin-3-yl)-6-methoxy-1H-indazol-1-yl)-1-methylpyridin-2(1H)-one | $R^t$ 1.87 min (Method 1); m/z 560.2 $(M + H)^+$ $(ES^+)$ |
| 266 | 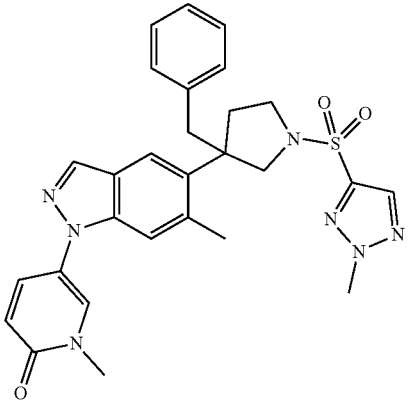 [SMILES: Cc1cc2c(cnn2-c2ccc(=O)n(C)c2)cc1C1(Cc2ccccc2)CCN(S(=O)(=O)c2cnn(C)n2)C1]<br>5-(5-(3-benzyl-1-((2-methyl-2H-1,2,3-triazol-4-yl)sulfonyl)pyrrolidin-3-yl)-6-methyl-1H-indazol-1-yl)-1-methylpyridin-2(1H)-one | $R^t$ 1.38 min (Method 1); m/z 544.5 $(M + H)^+$ $(ES^+)$ |
| 267 | 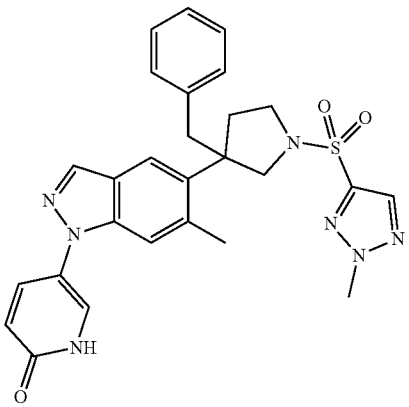 [SMILES: Cc1cc2c(cnn2-c2ccc(=O)[nH]c2)cc1C1(Cc2ccccc2)CCN(S(=O)(=O)c2cnn(C)n2)C1]<br>5-(5-(3-benzyl-1-((2-methyl-2H-1,2,3-triazol-4-yl)sulfonyl)pyrrolidin-3-yl)-6-methyl-1H-indazol-1-yl)pyridin-2(1H)-one | $R^t$ 1.30 min (Method 1); m/z 530.4 $(M + H)^+$ $(ES^+)$ |

TABLE 12-continued

The examples shown in the table below were prepared by similar methods to those described for Example 237

| Example | Structure | LC-MS Analysis |
|---|---|---|
| 268 | 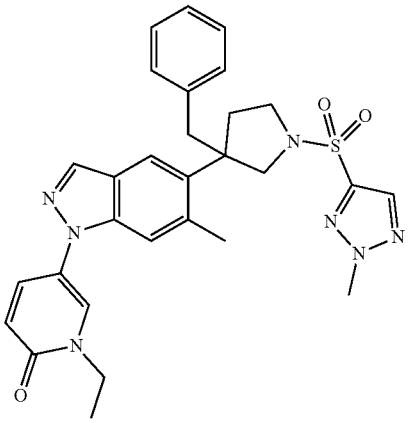 [SMILES: CCn1cc(-n2ncc3cc(C4(Cc5ccccc5)CCN(S(=O)(=O)c5cnn(C)n5)C4)c(C)cc32)ccc1=O]<br>5-(5-(3-benzyl-1-((2-methyl-2H-1,2,3-triazol-4-yl)sulfonyl)pyrrolidin-3-yl)-6-methyl-1H-indazol-1-yl)-1-ethylpyridin-2(1H)-one | $R^t$ 1.93 min (Method 1); m/z 558.2 $(M + H)^+$ $(ES^+)$ |
| 269 | 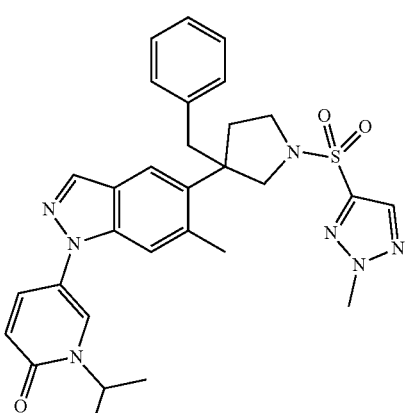<br>5-(5-(3-benzyl-1-((2-methyl-2H-1,2,3-triazol-4-yl)sulfonyl)pyrrolidin-3-yl)-6-methyl-1H-indazol-1-yl)-1-isopropylpyridin-2(1H)-one | $R^t$ 1.50 min (Method 1); m/z 572.2 $(M + H)^+$ $(ES^+)$ |
| 270 | 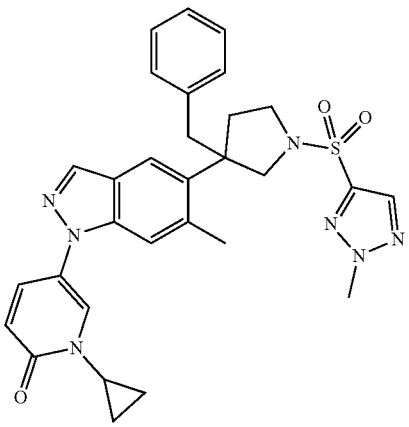 [SMILES: Cc1cc2c(cnn2-c2ccc(=O)n(C3CC3)c2)cc1C1(Cc2ccccc2)CCN(S(=O)(=O)c2cnn(C)n2)C1]<br>5-(5-(3-benzyl-1-((2-methyl-2H-1,2,3-triazol-4-yl)sulfonyl)pyrrolidin-3-yl)-6-methyl-1H-indazol-1-yl)-1-cyclopropylpyridin-2(1H)-one | $R^t$ 1.48 min (Method 1); m/z 570.3 $(M + H)^+$ $(ES^+)$ |

TABLE 12-continued

The examples shown in the table below were prepared by similar methods to those described for Example 237

| Example | Structure | LC-MS Analysis |
|---|---|---|
| 271 | 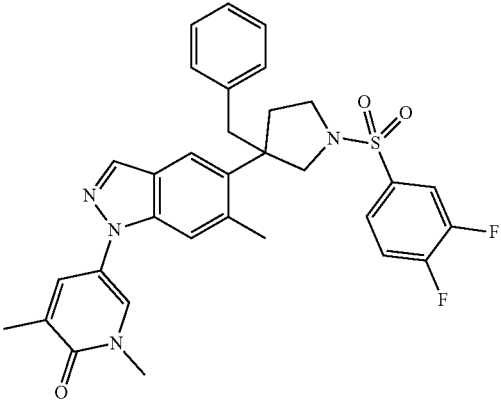 [SMILES: Cc1cc2c(cnn2-c2cc(C)c(=O)n(C)c2)cc1C1(Cc2ccccc2)CCN(S(=O)(=O)c2ccc(F)c(F)c2)C1]<br>5-(5-(3-benzyl-1-((3,4-difluorophenyl)sulfonyl)pyrrolidin-3-yl)-6-methyl-1H-indazol-1-yl)-1,3-dimethylpyridin-2(1H)-one | $R^t$ 2.10 min (Method 6); m/z 589.2 $(M + H)^+$ $(ES^+)$ |
| 272 | 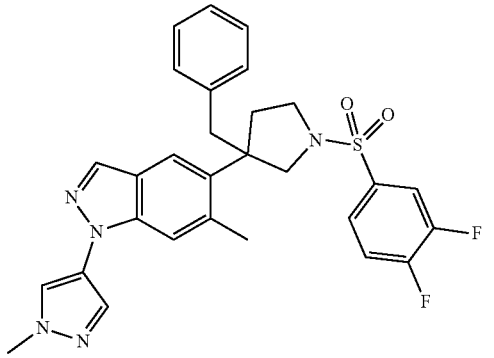 [SMILES: Cc1cc2c(cnn2-c2cnn(C)c2)cc1C1(Cc2ccccc2)CCN(S(=O)(=O)c2ccc(F)c(F)c2)C1]<br>5-(3-benzyl-1-((3,4-difluorophenyl)sulfonyl)pyrrolidin-3-yl)-6-methyl-1-(1-methyl-1H-pyrazol-4-yl)-1H-indazole | $R^t$ 2.12 min (Method 6); m/z 548.2 $(M + H)^+$ $(ES^+)$ |
| 273 | 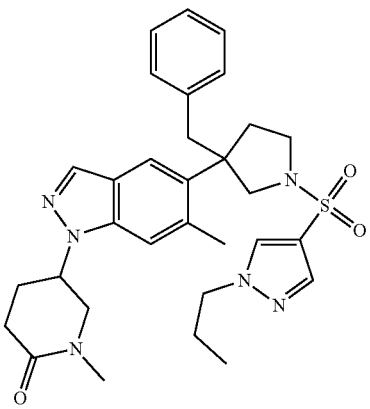 [SMILES: CCCn1cc(S(=O)(=O)N2CCC(Cc3ccccc3)(c3cc4cnn(C5CCC(=O)N(C)C5)c4cc3C)C2)cn1]<br>5-(5-(3-benzyl-1-((1-propyl-1H-pyrazol-4-yl)sulfonyl)pyrrolidin-3-yl)-6-methyl-1H-indazol-1-yl)-1-methylpiperidin-2-one | $R^t$ 1.43 min (Method 6); m/z 575.8 $(M + H)^+$ $(ES^+)$ |

TABLE 12-continued

The examples shown in the table below were prepared by similar methods to those described for Example 237

| Example | Structure | LC-MS Analysis |
|---|---|---|
| 274 | 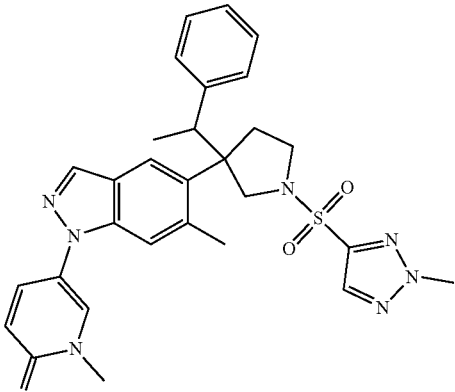<br>1-methyl-5-(6-methyl-5-(1-((2-methyl-2H-1,2,3-triazol-4-yl)sulfonyl)-3-(1-phenylethyl)pyrrolidin-3-yl)-1H-indazol-1-yl)pyridin-2(1H)-one | $R^t$ 1.84 min (Method 6); m/z 558.2 (M + H)$^+$ (ES$^+$) |

Example 275: 5-(5-(3-benzyl-1-((1-methyl-1H-1,2,3-triazol-4-yl)sulfonyl)pyrrolidin-3-yl)-6-methyl-1H-indazol-1-yl)-1-methylpyridin-2(1H)-one Intermediate AJ: 5-bromo-6-methyl-1-((2-(trimethylsilyl)ethoxy)methyl)-1H-indazole To a solution of 5-bromo-6-methyl-1H-indazole (25.00 g, 118.4 mmol) in dichloromethane (500 mL) were added tetrabutylammonium bromide (381.9 mg, 1.184 mmol) and 50% wt/wt potassium hydroxide (30 g, 20 mL, 1 molar, 20 mmol) before the addition of SEM-Cl (21.72 g, 23.1 mL, 130.3 mmol) over 5 minutes. The reaction was then stirred at room temperature overnight. The reaction was partitioned between water (200 mL), the phases were separated and the aqueous phase further extracted with and dichloromethane (2×100 mL), the organics were then washed with brine (100 mL) before being dried over MgSO$_4$ and concentrated in vacuo to give the crude product. The crude product was purified by chromatography on silica gel (330 g cartridge, 0-50% EtOAc/isohexane) to afford 5-bromo-6-methyl-1-((2-(trimethylsilyl)ethoxy)methyl)-1H-indazole (Intermediate AJ) (29.2 g, 85.6 mmol, 72.2%, 100% Purity) as a yellow oil; Rt 1.75 min (Method 6); m/z 341.1/343.0 (M+H)+ (ES+). $\delta_H$ (500 MHz, DMSO-d$_6$) δ 8.06 (br. s, 2H), 7.77-7.75 (m, 1H), 5.71 (s, 2H), 3.53-3.43 (m, 2H), 2.48 (s, 3H), 0.81-0.74 (m, 2H), −0.11 (s, 9H)

Intermediate AK: 5-(1,3-dibenzylpyrrolidin-3-yl)-6-methyl-1-((2-(trimethylsilyl)ethoxy)methyl)-1H-indazole

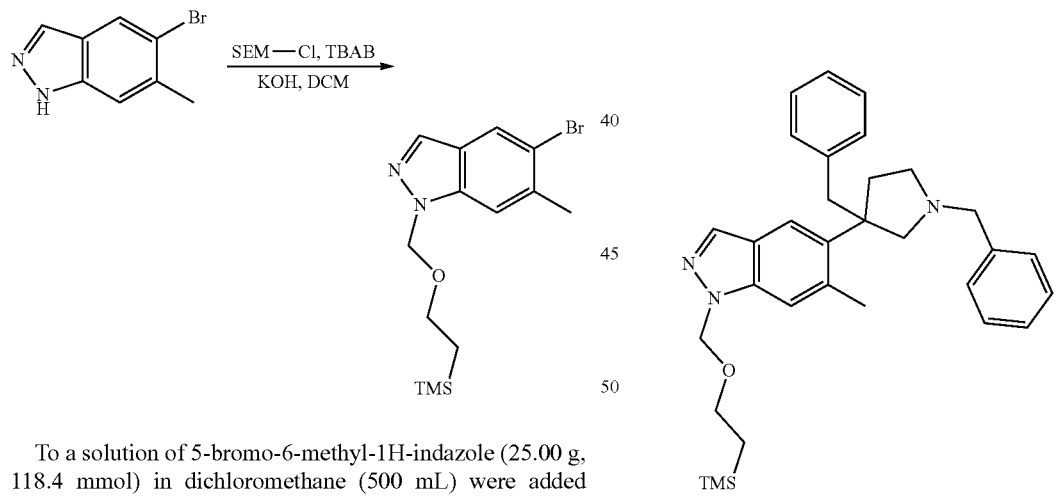

The compound was prepared by similar methods to those described for Example 16, to afford 5-(1,3-dibenzylpyrrolidin-3-yl)-6-methyl-1-((2-(trimethylsilyl)ethoxy)methyl)-1H-indazole (Intermediate AK); Rt 1.23 min (Method 6); m/z 512.2 (M+H)+ (ES+). $\delta_H$ (400 MHz, DMSO-d6) δ 7.84 (d, J=0.9 Hz, 1H), 7.51 (s, 1H), 7.47-7.35 (m, 4H), 7.33-7.26 (m, 1H), 6.99-6.90 (m, 1H), 6.83 (t, J=7.5 Hz, 2H), 6.74 (s, 1H), 6.38-6.24 (m, 2H), 5.67 (s, 2H), 3.75 (d, J=12.8 Hz, 1H), 3.60-3.53 (m, 1H), 3.49 (t, J=7.9 Hz, 2H), 3.25-3.13 (m, 2H), 3.10 (d, J=8.8 Hz, 1H), 3.03 (d, J=12.9 Hz, 1H), 2.52 (s, 3H), 2.41-2.29 (m, 3H), 2.17 (ddd, J=12.2, 9.4, 5.7 Hz, 1H), 0.79 (td, J=7.7, 2.6 Hz, 2H), −0.11 (s, 9H)

417

Intermediate AL: 5-(1,3-dibenzylpyrrolidin-3-yl)-6-methyl-1H-indazole

418

Intermediate AM: 5-(5-(3-benzylpyrrolidin-3-yl)-6-methyl-1H-indazol-1-yl)-1-methylpyridin-2(1H)-one

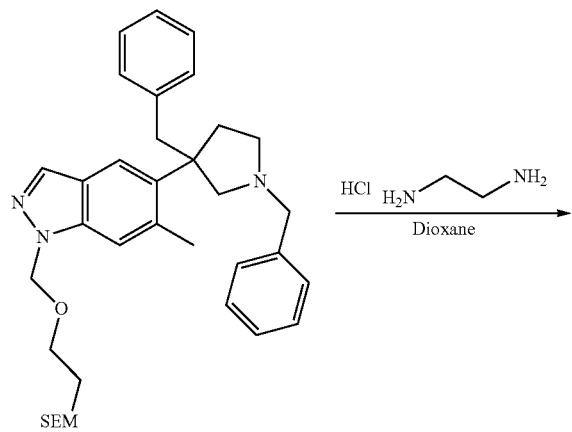

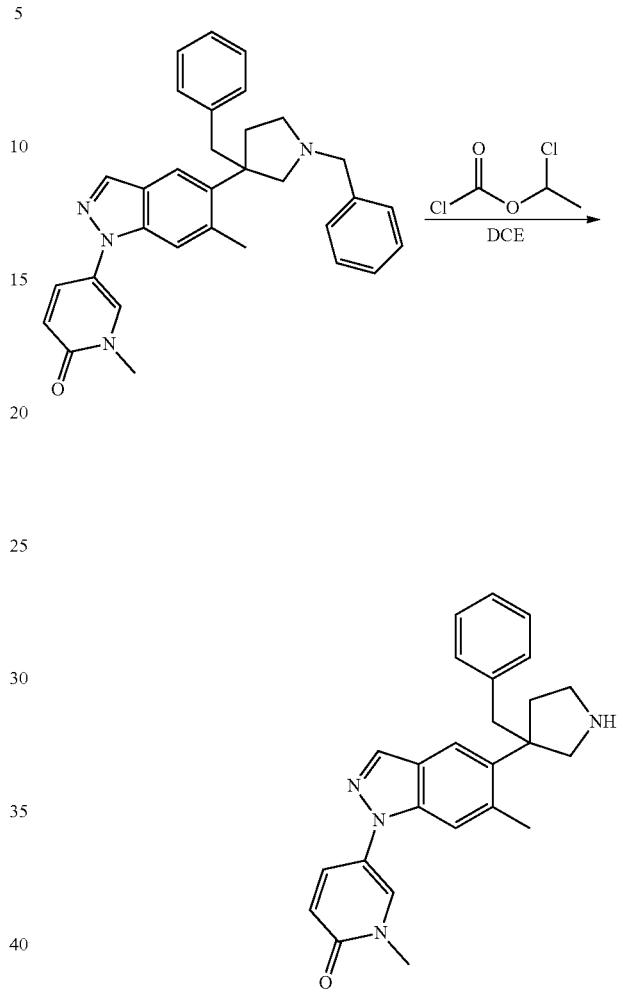

To a solution of 5-(1,3-dibenzylpyrrolidin-3-yl)-6-methyl-1-((2-(trimethylsilyl)ethoxy)methyl)-1H-indazole (Intermediate AK) (5.00 g, 9.77 mmol) in 1,4-dioxane (22 mL) was added HCl (4 M in 1,4-dioxane) (5.34 g, 36.6 mL, 4 molar, 147 mmol) and the reaction mixture stirred at room temperature for 2 days. The reaction mixture was concentrated in vacuo. The resulting purple residue was redissolved in dichloromethane (60 mL) and treated with ethane-1,2-diamine (5.8 g, 6.5 mL, 97 mmol), upon which the solution turned orange. The reaction mixture was stirred at room temperature for 90 minutes, then quenched with water (40 mL). The layers were separated, and the aqueous layer extracted with dichloromethane (2×20 mL). The combined organic extracts were dried over MgSO$_4$ and concentrated in vacuo. The crude product was purified by chromatography on silica gel (80 g cartridge, 0-50% EtOAc/heptane) to afford 5-(1,3-dibenzylpyrrolidin-3-yl)-6-methyl-1H-indazole (Intermediate AL) (3.03 g, 7.5 mmol, 77%) as a white solid; Rt 0.62 min (Method 7); m/z 382.2 (M+H)+ (ES+). $\delta_H$ (400 MHz, DMSO-d6) δ 12.73 (s, 1H), 7.77 (s, 1H), 7.48-7.37 (m, 4H), 7.33-7.27 (m, 2H), 6.99-6.91 (m, 1H), 6.85 (t, J=7.6 Hz, 2H), 6.73 (s, 1H), 6.44-6.23 (m, 2H), 3.75 (d, J=12.8 Hz, 1H), 3.57 (d, J=12.8 Hz, 1H), 3.20-2.98 (m, 4H), 2.49 (obs s, 3H), 2.41-2.30 (m, 3H), 2.22-2.09 (m, 1H).

To a solution of 5-(5-(1,3-dibenzylpyrrolidin-3-yl)-6-methyl-1H-indazol-1-yl)-1-methylpyridin-2(1H)-one (2.15 g, 4.40 mmol) (prepared using a similar method to Example 237) in dichloroethane (30 mL) was added 1-chloroethyl carbonochloridate (1.26 g, 949 μL, 8.80 mmol) and the reaction mixture stirred at 80° C. for 3 days. The reaction mixture was concentrated in vacuo and the residue redissolved in MeOH (30 mL). The reaction mixture was stirred at 60° C. for 2 hours and then cooled to room temperature and concentrated onto silica gel. The crude product was purified by chromatography on silica gel (24 g cartridge, 0-10% (0.7 M Ammonia/MeOH)/DCM) to afford 5-(5-(3-benzylpyrrolidin-3-yl)-6-methyl-1H-indazol-1-yl)-1-methylpyridin-2(1H)-one (Intermediate AM) (571 mg, 1.2 mmol, 28%) as tan solid; Rt 1.08 min (Method 6); m/z 399.2 (M+H)+ (ES+). $\delta_H$ (400 MHz, DMSO-d6) δ 8.21 (d, J=3.0 Hz, 1H), 8.09 (d, J=0.9 Hz, 1H), 7.76 (dd, J=9.6, 3.0 Hz, 1H), 7.52 (s, 1H), 7.16-6.96 (m, 4H), 6.67-6.52 (m, 3H), 3.68 (d, J=11.2 Hz, 1H), 3.55 (s, 3H), 3.35 (m, 4H), 3.17 (d, J=11.2 Hz, 1H), 3.07 (d, J=13.6 Hz, 1H), 2.99 (d, J=13.5 Hz, 1H), 2.45 (s, 3H), 2.10 (q, J=10.0 Hz, 1H).

Example 275: 5-(5-(3-benzyl-1-((1-methyl-1H-1,2,3-triazol-4-yl)sulfonyl)pyrrolidin-3-yl)-6-methyl-1H-indazol-1-yl)-1-methylpyridin-2(1H)-one

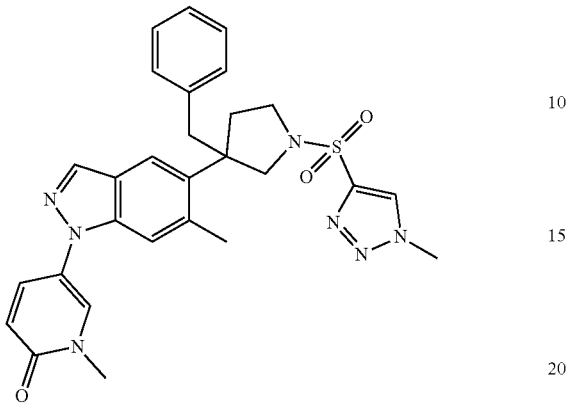

The compound was prepared by similar methods to those described for Example 16, using intermediate AM to afford 5-(5-(3-benzyl-1-((1-methyl-1H-1,2,3-triazol-4-yl)sulfonyl)pyrrolidin-3-yl)-6-methyl-1H-indazol-1-yl)-1-methylpyridin-2(1H)-one (Example 275); Rt 1.78 min (Method 6); m/z 544.0 (M+H)+ (ES+). $\delta_H$ (500 MHz, DMSO-d6) δ 8.81 (s, 1H), 8.21 (d, J=2.9 Hz, 1H), 8.08 (d, J=0.9 Hz, 1H), 7.75 (dd, J=9.6, 3.0 Hz, 1H), 7.49 (s, 1H), 7.12-7.07 (m, 1H), 7.06-6.99 (m, 3H), 6.56 (d, J=9.6 Hz, 1H), 6.54-6.49 (m, 2H), 4.06 (s, 3H), 3.99 (d, J=9.6 Hz, 1H), 3.74-3.64 (m, 1H), 3.54 (s, 4H), 3.38 (d, J=9.6 Hz, 1H), 3.01 (d, J=13.4 Hz, 1H), 2.77 (d, J=13.2 Hz, 1H), 2.41 (m, 4H), 2.00 (q, J=9.9 Hz, 1H)

Examples 276-325

TABLE 13

The examples shown in the table below were prepared by similar methods to those described for Example 16.

| Example | Structure | LC-MS Analysis |
|---------|-----------|----------------|
| 276 | 5-(5-(3-benzyl-1-((1-methyl-1H-pyrazol-3-yl)sulfonyl)pyrrolidin-3-yl)-6-methyl-1H-indazol-1-yl)-1-methylpyridin-2(1H)-one | R$^t$ 2.05 min (Method 2); m/z 543.0 (M + H)+ (ES+) |

TABLE 13-continued

The examples shown in the table below were prepared by similar methods to those described for Example 16.

| Example | Structure | LC-MS Analysis |
| --- | --- | --- |
| 277 | 5-(5-(3-benzyl-1-((2-methyl-2H-1,2,3-triazol-4-yl)sulfonyl)pyrrolidin-3-yl)-6-chloro-1H-indazol-1-yl)-1-methylpyridin-2(1H)-one | $R^t$ 1.49 min (Method 1); m/z 564.3 $(M + H)^+ (ES^+)$ |
| 278 | 5-(5-(3-benzyl-1-((1-(2,2,2-trifluoroethyl)-1H-pyrazol-4-yl)sulfonyl)pyrrolidin-3-yl)-6-methyl-1H-indazol-1-yl)-1-methylpyridin-2(1H)-one | $R^t$ 1.42 min (Method 1); m/z 611.5 $(M + H)^+ (ES^+)$ |
| 279 | 5-(5-(3-benzyl-1-((1-cyclobutyl-1H-pyrazol-4-yl)sulfonyl)pyrrolidin-3-yl)-6-methyl-1H-indazol-1-yl)-1-methylpyridin-2(1H)-one | $R^t$ 1.45 min (Method 1); m/z 583.5 $(M + H)^+ (ES^+)$ |

TABLE 13-continued

The examples shown in the table below were prepared by similar methods to those described for Example 16.

| Example | Structure | LC-MS Analysis |
| --- | --- | --- |
| 280 | 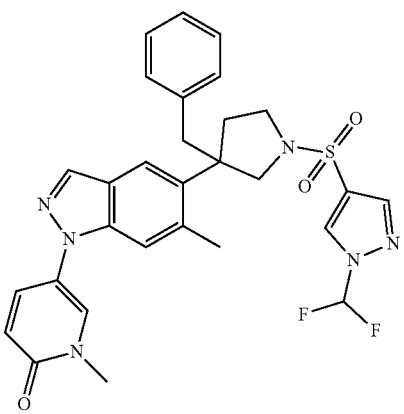 [SMILES: Cc1cc2c(cnn2-c2ccc(=O)n(C)c2)cc1C1(Cc2ccccc2)CCN(S(=O)(=O)c2cnn(C(F)F)c2)C1]<br>5-(5-(3-benzyl-1-((1-(difluoromethyl)-1H-pyrazol-4-yl)sulfonyl)pyrrolidin-3-yl)-6-methyl-1H-indazol-1-yl)-1-methylpyridin-2(1H)-one | $R^t$ 1.41 min (Method 1); m/z 579.4 $(M + H)^+$ $(ES^+)$ |
| 281 | 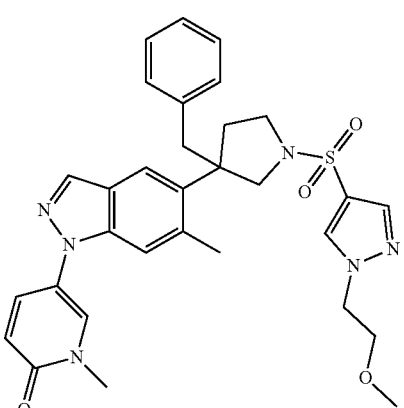<br>5-(5-(3-benzyl-1-((1-(2-methoxyethyl)-1H-pyrazol-4-yl)sulfonyl)pyrrolidin-3-yl)-6-methyl-1H-indazol-1-yl)-1-methylpyridin-2(1H)-one | $R^t$ 1.32 min (Method 1); m/z 587.4 $(M + H)^+$ $(ES^+)$ |
| 282 | 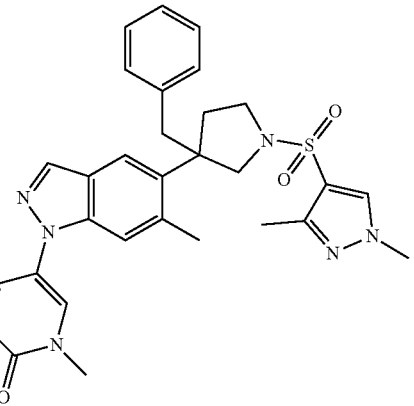<br>5-(5-(3-benzyl-1-((1,3-dimethyl-1H-pyrazol-4-yl)sulfonyl)pyrrolidin-3-yl)-6-methyl-1H-indazol-1-yl)-1-methylpyridin-2(1H)-one | $R^t$ 1.84 min (Method 1); m/z 557.1 $(M + H)^+$ $(ES^+)$ |

TABLE 13-continued

The examples shown in the table below were prepared by similar methods to those described for Example 16.

| Example | Structure | LC-MS Analysis |
| --- | --- | --- |
| 283 | 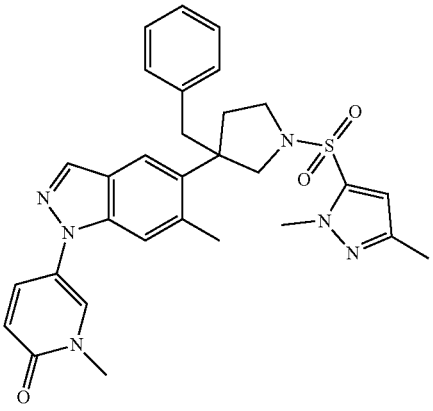 [SMILES: Cc1cc(S(=O)(=O)N2CCC(Cc3ccccc3)(c3cc4cnn(-c5ccc(=O)n(C)c5)c4cc3C)C2)n(C)n1] 5-(5-(3-benzyl-1-((1,3-dimethyl-1H-pyrazol-5-yl)sulfonyl)pyrrolidin-3-yl)-6-methyl-1H-indazol-1-yl)-1-methylpyridin-2(1H)-one | $R^t$ 1.98 min (Method 1); m/z 557.0 $(M + H)^+$ $(ES^+)$ |
| 284 | 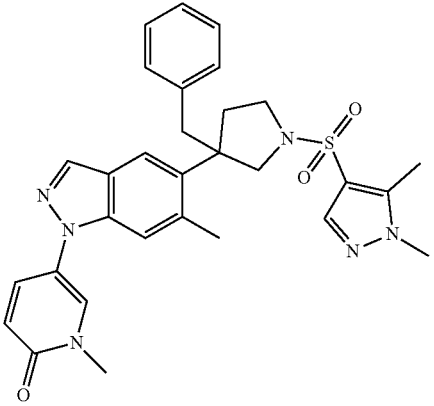 [SMILES: Cc1cc2c(cnn2-c2ccc(=O)n(C)c2)cc1C1(Cc2ccccc2)CCN(S(=O)(=O)c2cnn(C)c2C)C1] 5-(5-(3-benzyl-1-((1,5-dimethyl-1H-pyrazol-4-yl)sulfonyl)pyrrolidin-3-yl)-6-methyl-1H-indazol-1-yl)-1-methylpyridin-2(1H)-one | $R^t$ 1.84 min (Method 1); m/z 557.0 $(M + H)^+$ $(ES^+)$ |
| 285 | 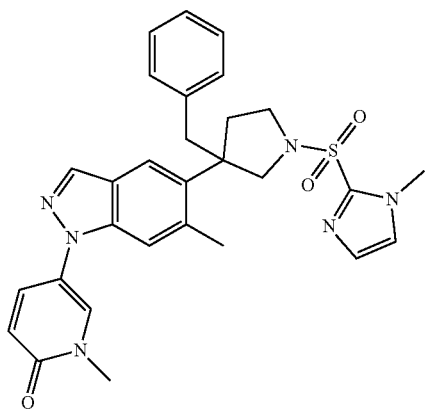 [SMILES: Cc1cc2c(cnn2-c2ccc(=O)n(C)c2)cc1C1(Cc2ccccc2)CCN(S(=O)(=O)c2nccn2C)C1] 5-(5-(3-benzyl-1-((1-methyl-1H-imidazol-2-yl)sulfonyl)pyrrolidin-3-yl)-6-methyl-1H-indazol-1-yl)-1-methylpyridin-2(1H)-one | $R^t$ 1.45 min (Method 1); m/z 543.0 $(M + H)^+$ $(ES^+)$ |

TABLE 13-continued

The examples shown in the table below were prepared by similar methods to those described for Example 16.

| Example | Structure | LC-MS Analysis |
|---|---|---|
| 286 | 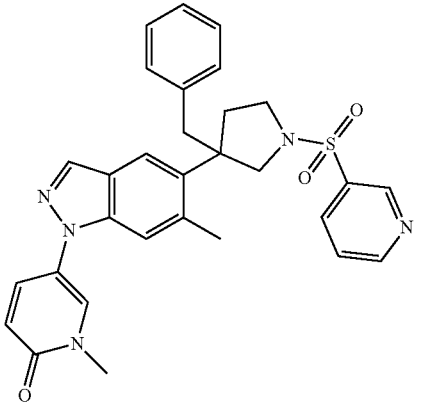 [SMILES: Cc1cc2c(cnn2-c2ccc(=O)n(C)c2)cc1C1(Cc2ccccc2)CCN(S(=O)(=O)c2cccnc2)C1]<br>5-(5-(3-benzyl-1-(pyridin-3-ylsulfonyl)pyrrolidin-3-yl)-6-methyl-1H-indazol-1-yl)-1-methylpyridin-2(1H)-one | $R^t$ 1.86 min (Method 1); m/z 540.2 $(M + H)^+$ $(ES^+)$ |
| 287 | 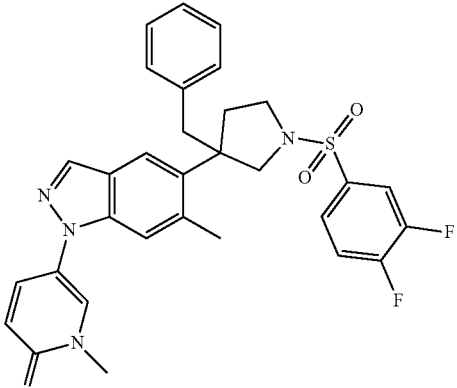<br>5-(5-(3-benzyl-1-((3,4-difluorophenyl)sulfonyl)pyrrolidin-3-yl)-6-methyl-1H-indazol-1-yl)-1-methylpyridin-2(1H)-one | $R^t$ 2.12 min (Method 1); m/z 575.0 $(M + H)^+$ $(ES^+)$ |
| 288 | 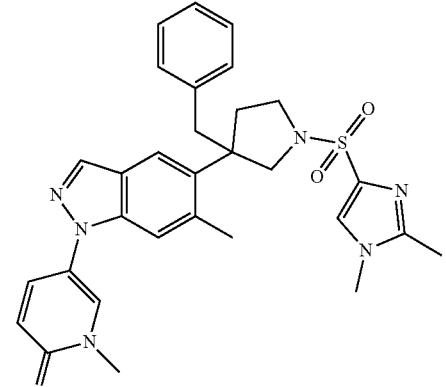<br>5-(5-(3-benzyl-1-((1-methyl-1H-imidazol-4-yl)sulfonyl)pyrrolidin-3-yl)-6-methyl-1H-indazol-1-yl)-1-methylpyridin-2(1H)-one | $R^t$ 1.70 min (Method 1); m/z 557.2 $(M + H)^+$ $(ES^+)$ |

TABLE 13-continued

The examples shown in the table below were prepared by similar methods to those described for Example 16.

| Example | Structure | LC-MS Analysis |
|---|---|---|
| 289 | 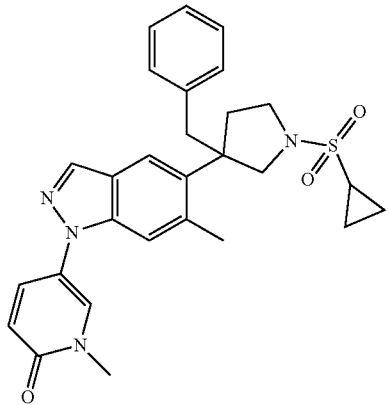 [SMILES: Cc1cc2c(cnn2-c2ccc(=O)n(C)c2)cc1C1(Cc2ccccc2)CCN(S(=O)(=O)C2CC2)C1]<br>5-(5-(3-benzyl-1-(cyclopropylsulfonyl)pyrrolidin-3-yl)-6-methyl-1H-indazol-1-yl)-1-methylpyridin-2(1H)-one | $R^t$ 1.87 min (Method 1); m/z 503.0 $(M + H)^+$ $(ES^+)$ |
| 290 | 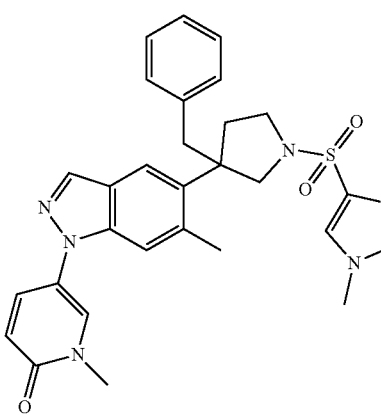<br>5-(5-(3-benzyl-1-((1-methyl-1H-imidazol-4-yl)sulfonyl)pyrrolidin-3-yl)-6-methyl-1H-indazol-1-yl)-1-methylpyridin-2(1H)-one | $R^t$ 1.70 min (Method 1); m/z 543.0 $(M + H)^+$ $(ES^+)$ |
| 291 | 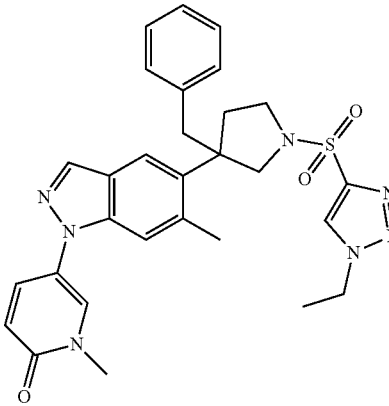<br>5-(5-(3-benzyl-1-((1-ethyl-1H-1,2,3-triazol-4-yl)sulfonyl)pyrrolidin-3-yl)-6-methyl-1H-indazol-1-yl)-1-methylpyridin-2(1H)-one | $R^t$ 1.85 min (Method 1); m/z 558.0 $(M + H)^+$ $(ES^+)$ |

TABLE 13-continued

The examples shown in the table below were prepared by similar methods to those described for Example 16.

| Example | Structure | LC-MS Analysis |
|---|---|---|
| 292 | 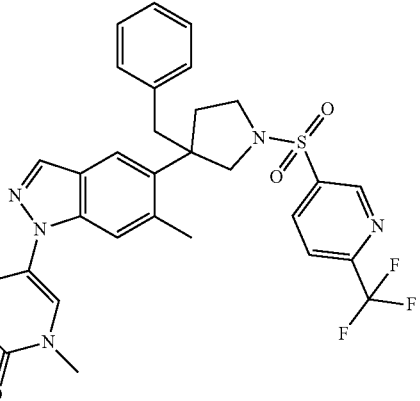<br>5-(5-(3-benzyl-1-((6-(trifluoromethyl)pyridin-3-yl)sulfonyl)pyrrolidin-3-yl)-6-methyl-1H-indazol-1-yl)-1-methylpyridin-2(1H)-one | $R^t$ 1.53 min (Method 1); m/z 608.2 $(M + H)^+$ $(ES^+)$ |
| 293 | 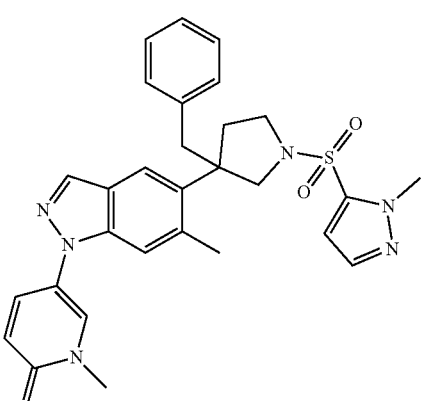<br>5-(5-(3-benzyl-1-((1-methyl-1H-pyrazol-5-yl)sulfonyl)pyrrolidin-3-yl)-6-methyl-1H-indazol-1-yl)-1-methylpyridin-2(1H)-one | $R^t$ 1.45 min (Method 7); m/z 543.3 $(M + H)^+$ $(ES^+)$ |
| 294 | 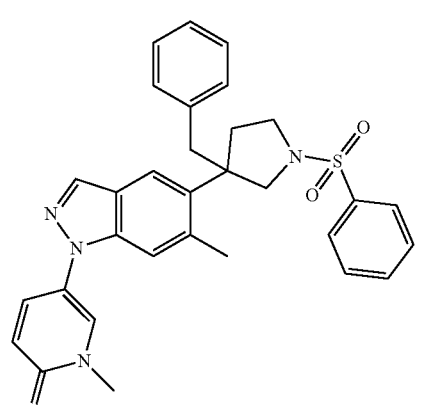<br>5-(5-(3-benzyl-1-(phenylsulfonyl)pyrrolidin-3-yl)-6-methyl-1H-indazol-1-yl)-1-methylpyridin-2(1H)-one | $R^t$ 1.65 min (Method 1); m/z 539.2 $(M + H)^+$ $(ES^+)$ |

TABLE 13-continued

The examples shown in the table below were prepared by similar methods to those described for Example 16.

| Example | Structure | LC-MS Analysis |
|---|---|---|
| 295 | 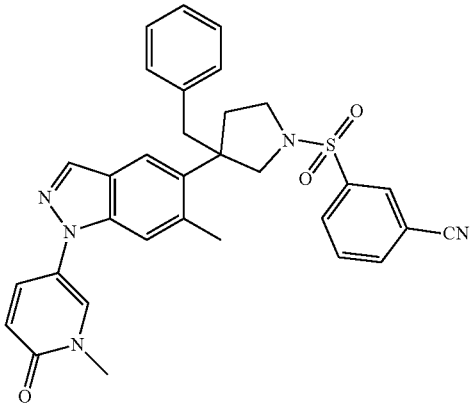 [SMILES: Cc1cc2c(cnn2-c2ccc(=O)n(C)c2)cc1C1(Cc2ccccc2)CCN(S(=O)(=O)c2cccc(C#N)c2)C1]<br>3-((3-benzyl-3-(6-methyl-1-(1-methyl-6-oxo-1,6-dihydropyridin-3-yl)-1H-indazol-5-yl)pyrrolidin-1-yl)sulfonyl)benzonitrile | $R^t$ 1.51 min (Method 7); m/z 564.3 $(M + H)^+$ $(ES^+)$ |
| 296 | 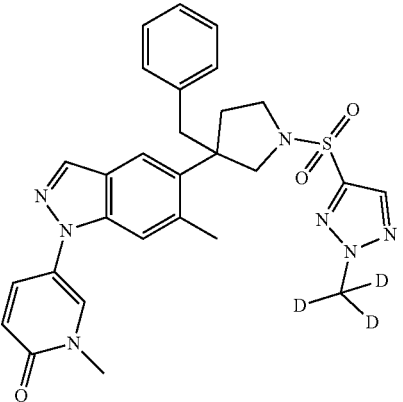 [SMILES: [2H]C([2H])([2H])n1ncc(S(=O)(=O)N2CCC(Cc3ccccc3)(c3cc4cnn(-c5ccc(=O)n(C)c5)c4cc3C)C2)n1]<br>5-(5-(3-benzyl-1-((2-(methyl-d3)-2H-1,2,3-triazol-4-yl)sulfonyl)pyrrolidin-3-yl)-6-methyl-1H-indazol-1-yl)-1-methylpyridin-2(1H)-one | $R^t$ 1.41 min (Method 1); m/z 547.3 $(M + H)^+$ $(ES^+)$ |
| 297 | 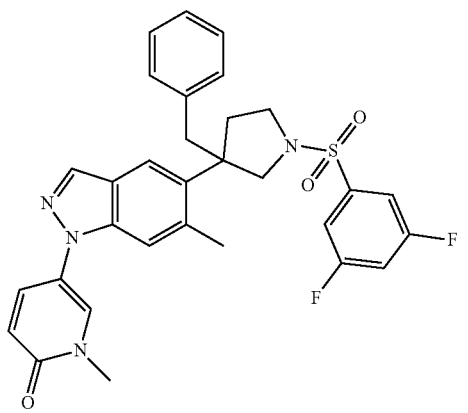 [SMILES: Cc1cc2c(cnn2-c2ccc(=O)n(C)c2)cc1C1(Cc2ccccc2)CCN(S(=O)(=O)c2cc(F)cc(F)c2)C1]<br>5-(5-(3-benzyl-1-((3,5-difluorophenyl)sulfonyl)pyrrolidin-3-yl)-6-methyl-1H-indazol-1-yl)-1-methylpyridin-2(1H)-one | $R^t$ 1.62 min (Method 7); m/z 575.3 $(M + H)^+$ $(ES^+)$ |

TABLE 13-continued

The examples shown in the table below were prepared by similar methods to those described for Example 16.

| Example | Structure | LC-MS Analysis |
|---|---|---|
| 298 | 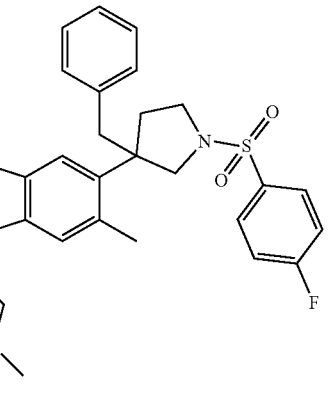 5-(5-(3-benzyl-1-((4-fluorophenyl)sulfonyl)pyrrolidin-3-yl)-6-methyl-1H-indazol-1-yl)-1-methylpyridin-2(1H)-one | $R^t$ 1.56 min (Method 7); m/z 557.3 $(M + H)^+$ $(ES^+)$ |
| 299 | 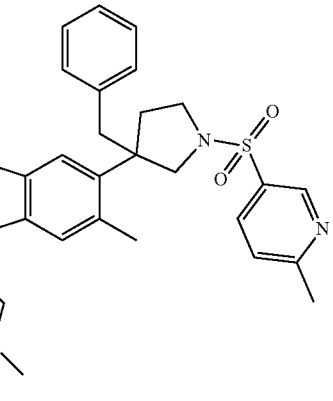 5-(5-(3-benzyl-1-((6-methylpyridin-3-yl)sulfonyl)pyrrolidin-3-yl)-6-methyl-1H-indazol-1-yl)-1-methylpyridin-2(1H)-one | $R^t$ 1.78 min (Method 7); m/z 554.2 $(M + H)^+$ $(ES^+)$ |
| 300 | 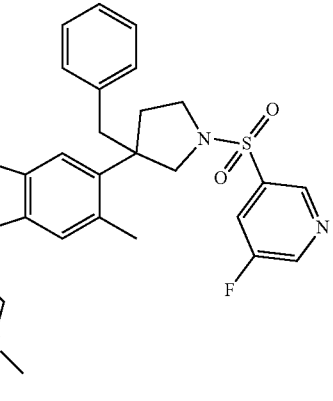 5-(5-(3-benzyl-1-((5-fluoropyridin-3-yl)sulfonyl)pyrrolidin-3-yl)-6-methyl-1H-indazol-1-yl)-1-methylpyridin-2(1H)-one | $R^t$ 1.84 min (Method 7); m/z 558.4 $(M + H)^+$ $(ES^+)$ |

TABLE 13-continued

The examples shown in the table below were prepared by similar methods to those described for Example 16.

| Example | Structure | LC-MS Analysis |
|---|---|---|
| 301 | 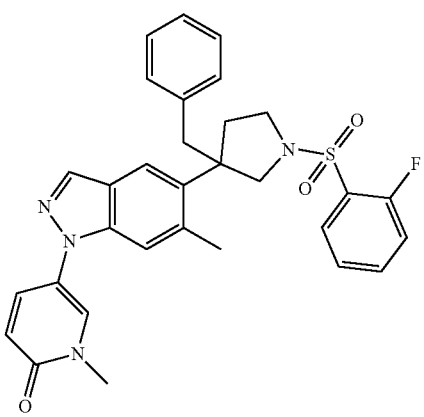 [SMILES: Cc1cc2c(cnn2-c2ccc(=O)n(C)c2)cc1C1(Cc2ccccc2)CCN(S(=O)(=O)c2ccccc2F)C1]<br>5-(5-(3-benzyl-1-((2-fluorophenyl)sulfonyl)pyrrolidin-3-yl)-6-methyl-1H-indazol-1-yl)-1-methylpyridin-2(1H)-one | R$^t$ 1.95 min (Method 7); m/z 557.1 (M + H)$^+$ (ES$^+$) |
| 302 | 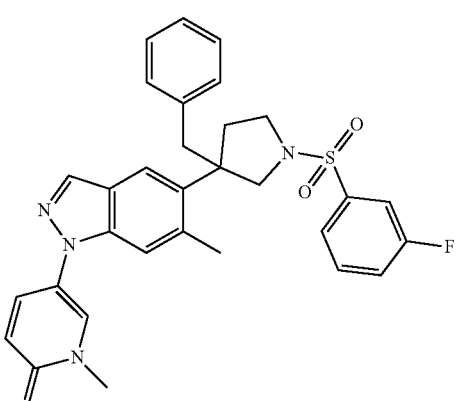<br>5-(5-(3-benzyl-1-((3-fluorophenyl)sulfonyl)pyrrolidin-3-yl)-6-methyl-1H-indazol-1-yl)-1-methylpyridin-2(1H)-one | R$^t$ 1.98 min (Method 7); m/z 557.3 (M + H)$^+$ (ES$^+$) |
| 303 | 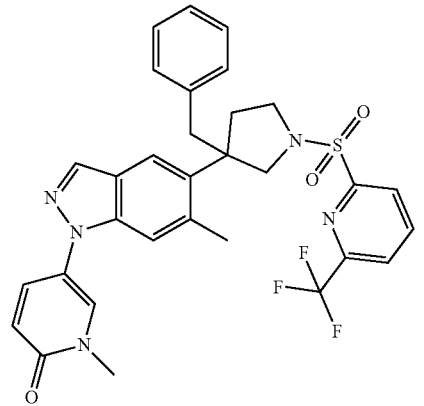 [SMILES: Cc1cc2c(cnn2-c2ccc(=O)n(C)c2)cc1C1(Cc2ccccc2)CCN(S(=O)(=O)c2cccc(C(F)(F)F)n2)C1]<br>5-(5-(3-benzyl-1-((6-(trifluoromethyl)pyridin-2-yl)sulfonyl)pyrrolidin-3-yl)-6-methyl-1H-indazol-1-yl)-1-methylpyridin-2(1H)-one | R$^t$ 1.96 min (Method 7); m/z 608.2 (M + H)$^+$ (ES$^+$) |

TABLE 13-continued

The examples shown in the table below were prepared by similar methods to those described for Example 16.

| Example | Structure | LC-MS Analysis |
|---|---|---|
| 304 | 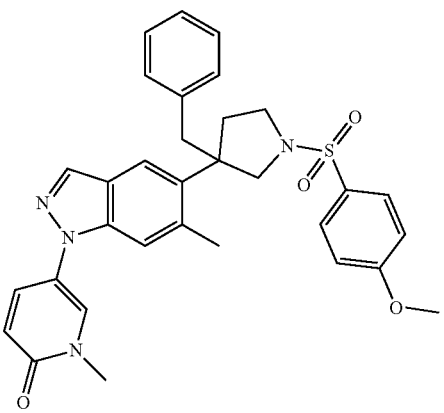 5-(5-(3-benzyl-1-((4-methoxyphenyl)sulfonyl)pyrrolidin-3-yl)-6-methyl-1H-indazol-1-yl)-1-methylpyridin-2(1H)-one | $R^t$ 1.90 min (Method 7); m/z 569.1 (M + H)$^+$ (ES$^+$) |
| 305 | 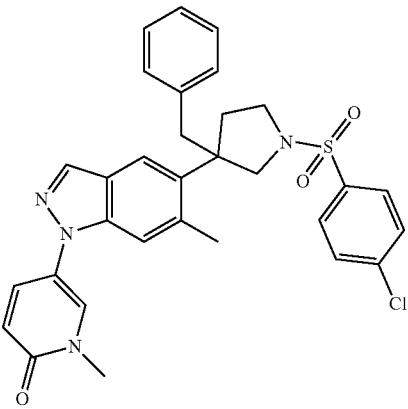 5-(5-(3-benzyl-1-((4-chlorophenyl)sulfonyl)pyrrolidin-3-yl)-6-methyl-1H-indazol-1-yl)-1-methylpyridin-2(1H)-one | $R^t$ 2.03 min (Method 7); m/z 573.1 (M + H)$^+$ (ES$^+$) |
| 306 | 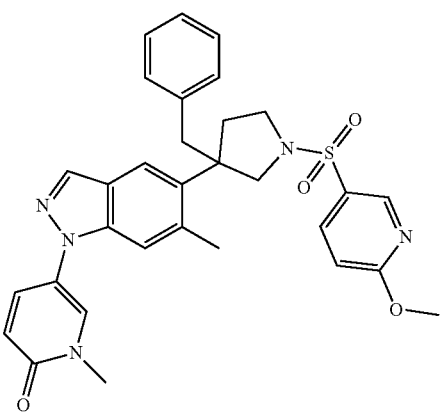 [SMILES: COc1ccc(S(=O)(=O)N2CCC(Cc3ccccc3)(c3cc4cnn(-c5ccc(=O)n(C)c5)c4cc3C)C2)cc1] 5-(5-(3-benzyl-1-((6-methoxypyridin-3-yl)sulfonyl)pyrrolidin-3-yl)-6-methyl-1H-indazol-1-yl)-1-methylpyridin-2(1H)-one | $R^t$ 1.87 min (Method 7); m/z 570.3 (M + H)$^+$ (ES$^+$) |

TABLE 13-continued

The examples shown in the table below were prepared by similar methods to those described for Example 16.

| Example | Structure | LC-MS Analysis |
|---|---|---|
| 307 | 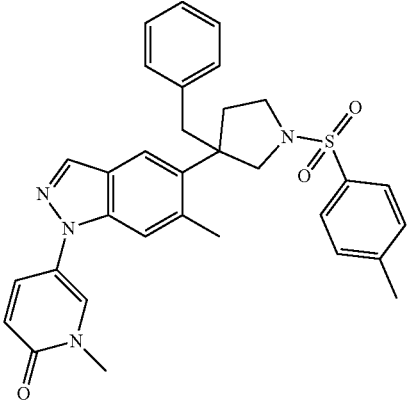 [SMILES: Cc1ccc(S(=O)(=O)N2CCC(Cc3ccccc3)(c3cc4cnn(-c5ccc(=O)n(C)c5)c4cc3C)C2)cc1]<br>5-(5-(3-benzyl-1-tosylpyrrolidin-3-yl)-6-methyl-1H-indazol-1-yl)-1-methylpyridin-2(1H)-one | $R^t$ 1.99 min (Method 7); m/z 553.3 $(M + H)^+$ $(ES^+)$ |
| 308 | 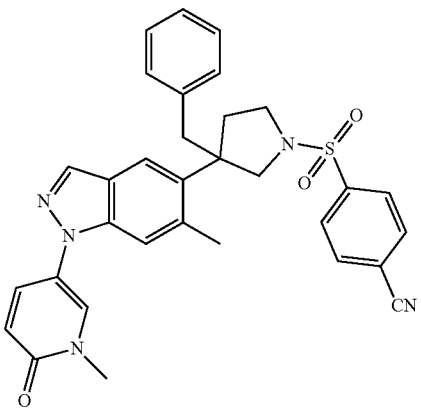 [SMILES: Cc1cc2c(cnn2-c2ccc(=O)n(C)c2)cc1C1(Cc2ccccc2)CCN(S(=O)(=O)c2ccc(C#N)cc2)C1]<br>4-((3-benzyl-3-(6-methyl-1-(1-methyl-6-oxo-1,6-dihydropyridin-3-yl)-1H-indazol-5-yl)pyrrolidin-1-yl)sulfonyl)benzonitrile | $R^t$ 1.88 min (Method 7); m/z 564.3 $(M + H)^+$ $(ES^+)$ |
| 309 | 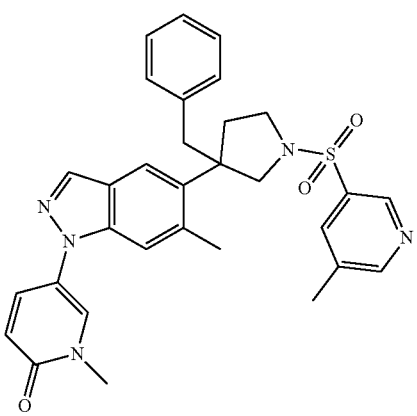 [SMILES: Cc1cncc(S(=O)(=O)N2CCC(Cc3ccccc3)(c3cc4cnn(-c5ccc(=O)n(C)c5)c4cc3C)C2)c1]<br>5-(5-(3-benzyl-1-((5-methylpyridin-3-yl)sulfonyl)pyrrolidin-3-yl)-6-methyl-1H-indazol-1-yl)-1-methylpyridin-2(1H)-one | $R^t$ 1.78 min (Method 7); m/z 554.4 $(M + H)^+$ $(ES^+)$ |

TABLE 13-continued

The examples shown in the table below were prepared by similar methods to those described for Example 16.

| Example | Structure | LC-MS Analysis |
|---|---|---|
| 310 | 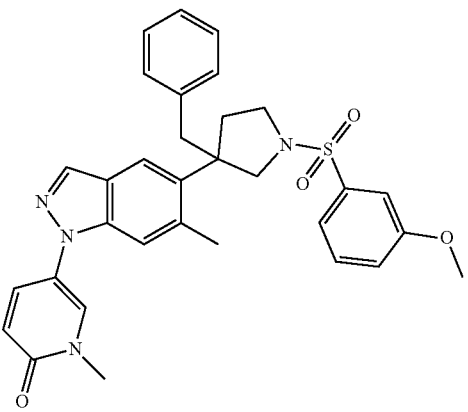 [SMILES: COc1cccc(S(=O)(=O)N2CCC(Cc3ccccc3)(c3cc4cnn(-c5ccc(=O)n(C)c5)c4cc3C)C2)c1]<br>5-(5-(3-benzyl-1-((3-methoxyphenyl)sulfonyl)pyrrolidin-3-yl)-6-methyl-1H-indazol-1-yl)-1-methylpyridin-2(1H)-one | $R^t$ 1.94 min (Method 7); m/z 569.4 $(M + H)^+$ $(ES^+)$ |
| 311 | 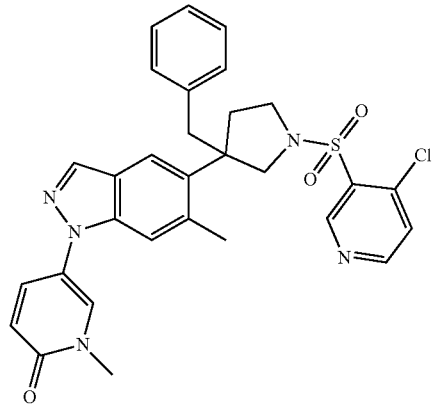 [SMILES: Cc1cc2c(cnn2-c2ccc(=O)n(C)c2)cc1C1(Cc2ccccc2)CCN(S(=O)(=O)c2cnccc2Cl)C1]<br>5-(5-(3-benzyl-1-((4-chloropyridin-3-yl)sulfonyl)pyrrolidin-3-yl)-6-methyl-1H-indazol-1-yl)-1-methylpyridin-2(1H)-one | $R^t$ 1.82 min (Method 7); m/z 574.3 $(M + H)^+$ $(ES^+)$ |
| 312 | 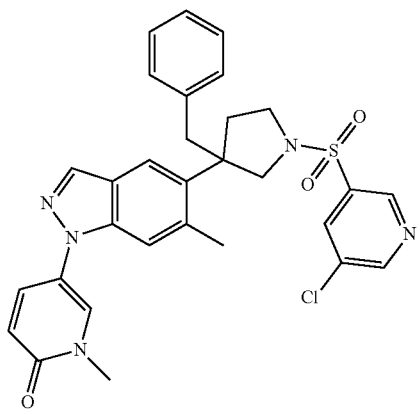 [SMILES: Cc1cc2c(cnn2-c2ccc(=O)n(C)c2)cc1C1(Cc2ccccc2)CCN(S(=O)(=O)c2cncc(Cl)c2)C1]<br>5-(5-(3-benzyl-1-((5-chloropyridin-3-yl)sulfonyl)pyrrolidin-3-yl)-6-methyl-1H-indazol-1-yl)-1-methylpyridin-2(1H)-one | $R^t$ 1.90 min (Method 7); m/z 574.3 $(M + H)^+$ $(ES^+)$ |

TABLE 13-continued

The examples shown in the table below were prepared by similar methods to those described for Example 16.

| Example | Structure | LC-MS Analysis |
|---|---|---|
| 313 | 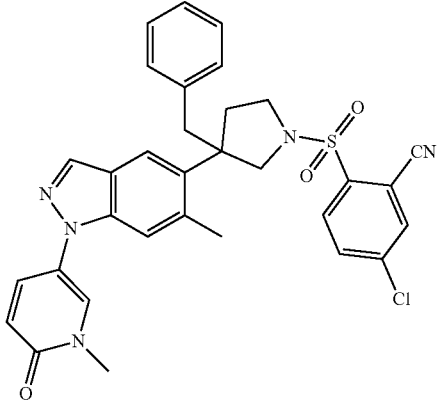 [SMILES: Cc1cc2c(cnn2-c2ccc(=O)n(C)c2)cc1C1(Cc2ccccc2)CCN(S(=O)(=O)c2ccc(Cl)cc2C#N)C1]<br>2-((3-benzyl-3-(6-methyl-1-(1-methyl-6-oxo-1,6-dihydropyridin-3-yl)-1H-indazol-5-yl)pyrrolidin-1-yl)sulfonyl)-5-chlorobenzonitrile | $R^t$ 1.99 min (Method 7); m/z 598.3 $(M + H)^+$ $(ES^+)$ |
| 314 | 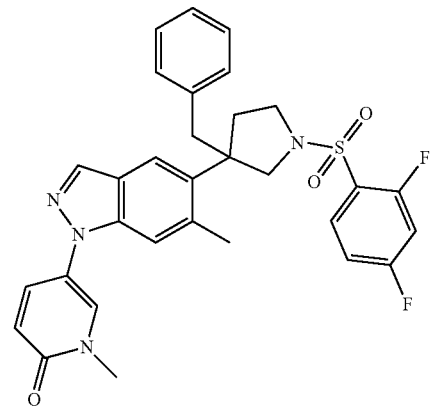 [SMILES: Cc1cc2c(cnn2-c2ccc(=O)n(C)c2)cc1C1(Cc2ccccc2)CCN(S(=O)(=O)c2ccc(F)cc2F)C1]<br>5-(5-(3-benzyl-1-((2,4-difluorophenyl)sulfonyl)pyrrolidin-3-yl)-6-methyl-1H-indazol-1-yl)-1-methylpyridin-2(1H)-one | $R^t$ 1.96 min (Method 7); m/z 575.2 $(M + H)^+$ $(ES^+)$ |
| 315 | 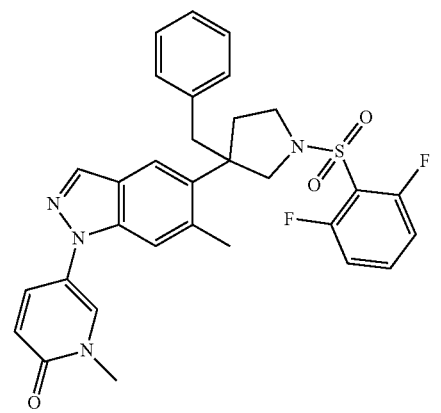 [SMILES: Cc1cc2c(cnn2-c2ccc(=O)n(C)c2)cc1C1(Cc2ccccc2)CCN(S(=O)(=O)c2c(F)cccc2F)C1]<br>5-(5-(3-benzyl-1-((2,6-difluorophenyl)sulfonyl)pyrrolidin-3-yl)-6-methyl-1H-indazol-1-yl)-1-methylpyridin-2(1H)-one | $R^t$ 1.92 min (Method 7); m/z 575.3 $(M + H)^+$ $(ES^+)$ |

TABLE 13-continued

The examples shown in the table below were prepared by similar methods to those described for Example 16.

| Example | Structure | LC-MS Analysis |
|---------|-----------|----------------|
| 316 | 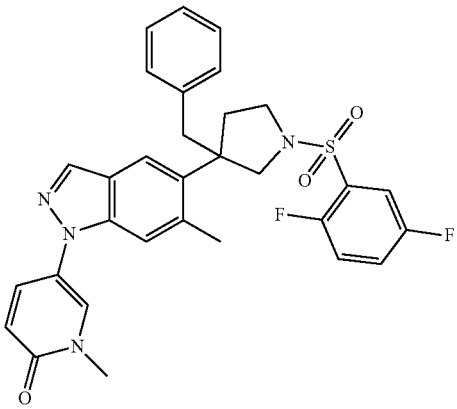 [SMILES: Cc1cc2c(cnn2-c2ccc(=O)n(C)c2)cc1C1(Cc2ccccc2)CCN(S(=O)(=O)c2cc(F)ccc2F)C1]<br>5-(5-(3-benzyl-1-((2,5-difluorophenyl)sulfonyl)pyrrolidin-3-yl)-6-methyl-1H-indazol-1-yl)-1-methylpyridin-2(1H)-one | $R^t$ 1.98 min (Method 7); m/z 575.3 (M + H)$^+$ (ES$^+$) |
| 317 | 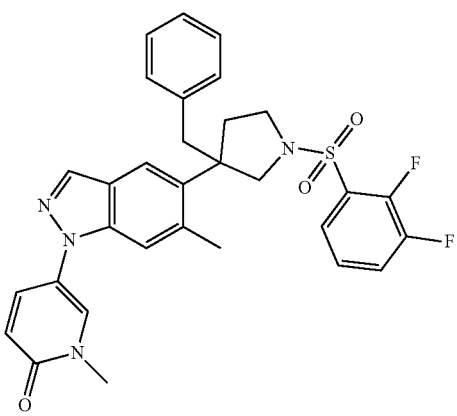 [SMILES: Cc1cc2c(cnn2-c2ccc(=O)n(C)c2)cc1C1(Cc2ccccc2)CCN(S(=O)(=O)c2cccc(F)c2F)C1]<br>5-(5-(3-benzyl-1-((2,3-difluorophenyl)sulfonyl)pyrrolidin-3-yl)-6-methyl-1H-indazol-1-yl)-1-methylpyridin-2(1H)-one | $R^t$ 1.98 min (Method 7); m/z 575.2 (M + H)$^+$ (ES$^+$) |
| 318 | 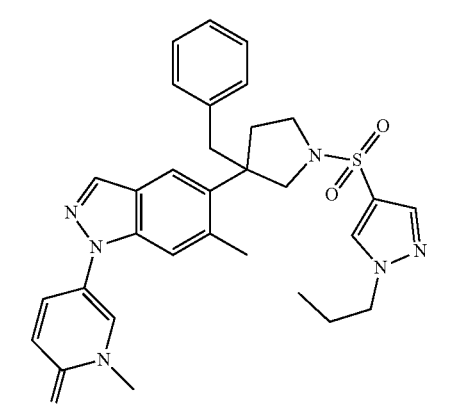<br>5-(5-(3-benzyl-1-((1-propyl-1H-pyrazol-4-yl)sulfonyl)pyrrolidin-3-yl)-6-methyl-1H-indazol-1-yl)-1-methylpyridin-2(1H)-one | $R^t$ 1.41 min (Method 1); m/z 571.3 (M + H)$^+$ (ES$^+$) |

TABLE 13-continued

The examples shown in the table below were prepared by similar methods to those described for Example 16.

| Example | Structure | LC-MS Analysis |
|---------|-----------|----------------|
| 319 | 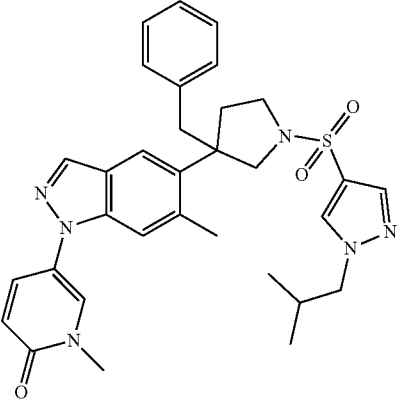 [SMILES: Cc1cc2c(cnn2-c2ccc(=O)n(C)c2)cc1C1(Cc2ccccc2)CCN(S(=O)(=O)c2cnn(CC(C)C)c2)C1]<br>5-(5-(3-benzyl-1-((1-isobutyl-1H-pyrazol-4-yl)sulfonyl)pyrrolidin-3-yl)-6-methyl-1H-indazol-1-yl)-1-methylpyridin-2(1H)-one | $R^t$ 1.47 min (Method 1); m/z 585.5 $(M + H)^+$ $(ES^+)$ |
| 320 | 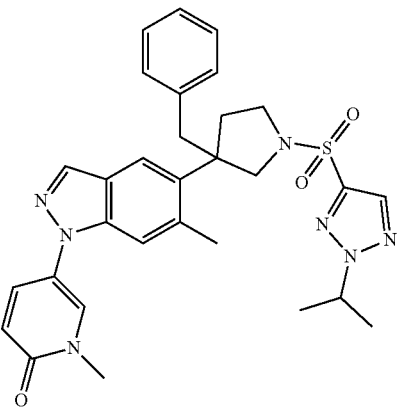<br>5-(5-(3-benzyl-1-((2-isopropyl-2H-1,2,3-triazol-4-yl)sulfonyl)pyrrolidin-3-yl)-6-methyl-1H-indazol-1-yl)-1-methylpyridin-2(1H)-one | $R^t$ 1.96 min (Method 7); m/z 575.2 $(M + H)^+$ $(ES^+)$ |
| 321 | 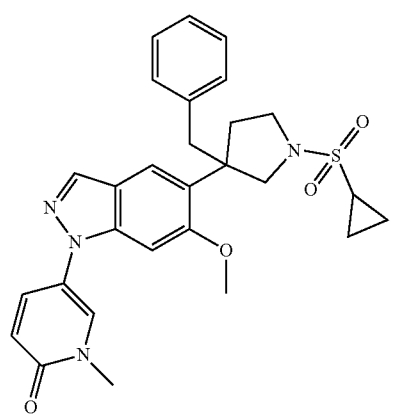 [SMILES: COc1cc2c(cnn2-c2ccc(=O)n(C)c2)cc1C1(Cc2ccccc2)CCN(S(=O)(=O)C2CC2)C1]<br>5-(5-(3-benzyl-1-(cyclopropylsulfonyl)pyrrolidin-3-yl)-6-methyl-1H-indazol-1-yl)-1-methylpyridin-2(1H)-one | $R^t$ 1.84 min (Method 1); m/z 519.2 $(M + H)^+$ $(ES^+)$ |

TABLE 13-continued

The examples shown in the table below were prepared by similar methods to those described for Example 16.

| Example | Structure | LC-MS Analysis |
|---|---|---|
| 322 | 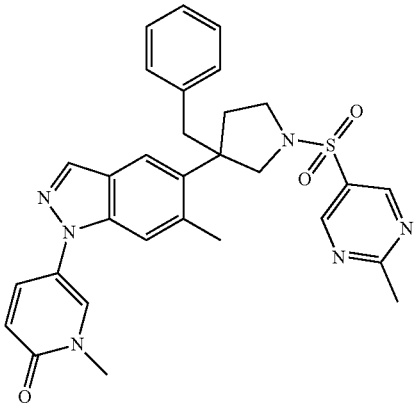 [SMILES: Cc1ncc(S(=O)(=O)N2CCC(Cc3ccccc3)(c3cc4cnn(-c5ccc(=O)n(C)c5)c4cc3C)C2)cn1]<br>5-(5-(3-benzyl-1-((2-methylpyrimidin-5-yl)sulfonyl)pyrrolidin-3-yl)-6-methyl-1H-indazol-1-yl)-1-methylpyridin-2(1H)-one | $R^t$ 1.75 min (Method 7); m/z 555.2 $(M + H)^+$ $(ES^+)$ |
| 323 | 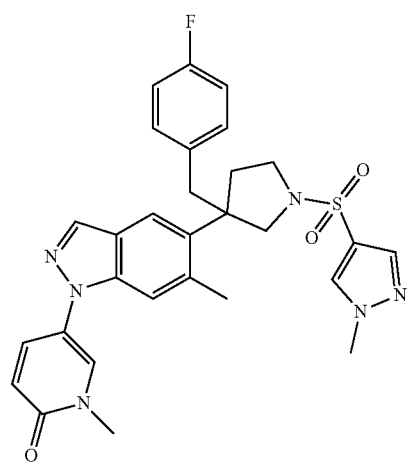 [SMILES: Cc1cc2c(cnn2-c2ccc(=O)n(C)c2)cc1C1(Cc2ccc(F)cc2)CCN(S(=O)(=O)c2cnn(C)c2)C1]<br>5-(5-(3-(4-fluorobenzyl)-1-((1-methyl-1H-pyrazol-4-yl)sulfonyl)pyrrolidin-3-yl)-6-methyl-1H-indazol-1-yl)-1-methylpyridin-2(1H)-one | $R^t$ 1.67 min (Method 7); m/z 561.3 $(M + H)^+$ $(ES^+)$ |
| 324 | 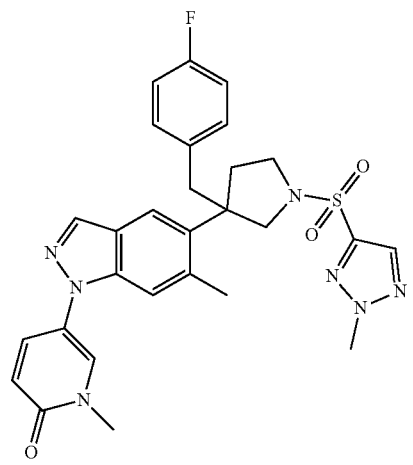 [SMILES: Cc1cc2c(cnn2-c2ccc(=O)n(C)c2)cc1C1(Cc2ccc(F)cc2)CCN(S(=O)(=O)c2cnn(C)n2)C1]<br>5-(5-(3-(4-fluorobenzyl)-1-((2-methyl-2H-1,2,3-triazol-4-yl)sulfonyl)pyrrolidin-3-yl)-6-methyl-1H-indazol-1-yl)-1-methylpyridin-2(1H)-one | $R^t$ 1.77 min (Method 7); m/z 562.2 $(M + H)^+$ $(ES^+)$ |

TABLE 13-continued

The examples shown in the table below were prepared by similar methods to those described for Example 16.

| Example | Structure | LC-MS Analysis |
|---|---|---|
| 325 | 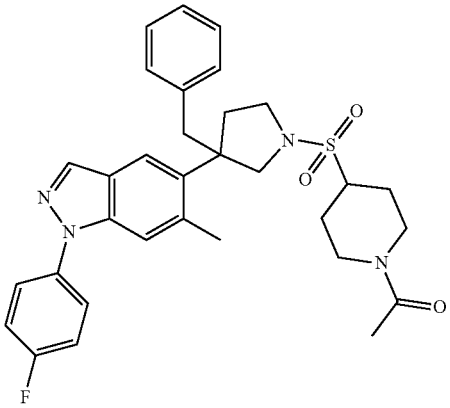 [SMILES: CC(=O)N1CCC(S(=O)(=O)N2CCC(Cc3ccccc3)(c3cc4cnn(-c5ccc(F)cc5)c4cc3C)C2)CC1]<br>1-(4-((3-benzyl-3-(1-(4-fluorophenyl)-6-methyl-1H-indazol-5-yl)pyrrolidin-1-yl)sulfonyl)piperidin-1-yl)ethan-1-one | $R^t$ 2.08 min (Method 7); m/z 575.5 $(M + H)^+$ $(ES^+)$ |

Examples 326-332

TABLE 14

The examples shown in the table below were prepared by similar methods to those described for Example 19.

| Example | Structure | LC-MS Analysis |
|---|---|---|
| 326 | 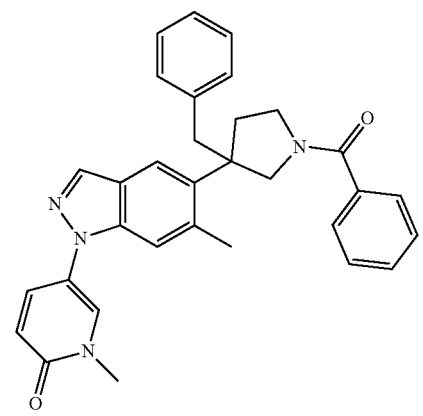 [SMILES: Cc1cc2c(cnn2-c2ccc(=O)n(C)c2)cc1C1(Cc2ccccc2)CCN(C(=O)c2ccccc2)C1]<br>5-(5-(1-benzoyl-3-benzylpyrrolidin-3-yl)-6-methyl-1H-indazol-1-yl)-1-methylpyridin-2(1H)-one | $R^t$ 1.37 min (Method 1); m/z 503.4 $(M + H)^+$ $(ES^+)$ |

TABLE 14-continued

The examples shown in the table below were prepared by similar methods to those described for Example 19.

| Example | Structure | LC-MS Analysis |
|---|---|---|
| 327 | 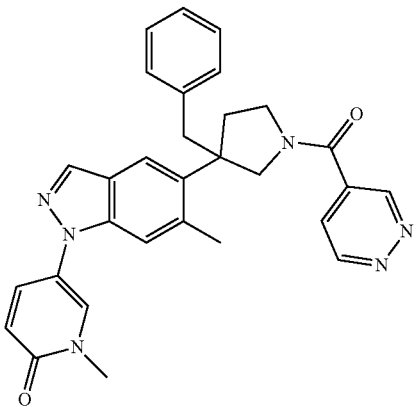 [SMILES: Cc1cc2c(cnn2-c2ccc(=O)n(C)c2)cc1C1(Cc2ccccc2)CCN(C(=O)c2ccnnc2)C1]<br>5-(5-(3-benzyl-1-(pyridazine-4-carbonyl)pyrrolidin-3-yl)-6-methyl-1H-indazol-1-yl)-1-methylpyridin-2(1H)-one | $R^t$ 1.60 min (Method 7); m/z 505.0 $(M + H)^+$ $(ES^+)$ |
| 328 | 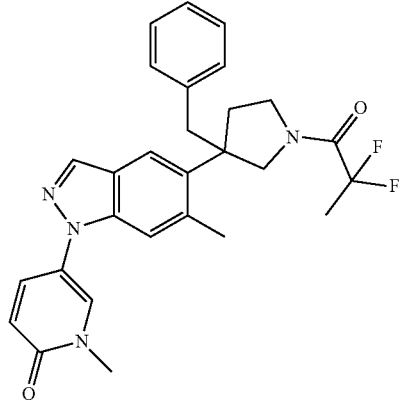 [SMILES: Cc1cc2c(cnn2-c2ccc(=O)n(C)c2)cc1C1(Cc2ccccc2)CCN(C(=O)C(C)(F)F)C1]<br>5-(5-(3-benzyl-1-(2,2-difluoropropanoyl)pyrrolidin-3-yl)-6-methyl-1H-indazol-1-yl)-1-methylpyridin-2(1H)-one | $R^t$ 1.93 min (Method 1); m/z 491.0 $(M + H)^+$ $(ES^+)$ |
| 329 | 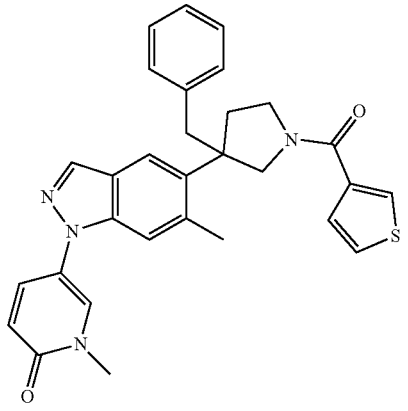 [SMILES: Cc1cc2c(cnn2-c2ccc(=O)n(C)c2)cc1C1(Cc2ccccc2)CCN(C(=O)c2ccsc2)C1]<br>5-(5-(3-benzyl-1-(thiophene-3-carbonyl)pyrrolidin-3-yl)-6-methyl-1H-indazol-1-yl)-1-methylpyridin-2(1H)-one | $R^t$ 1.85 min (Method 1); m/z 509.0 $(M + H)^+$ $(ES^+)$ |

TABLE 14-continued

The examples shown in the table below were prepared by similar methods to those described for Example 19.

| Example | Structure | LC-MS Analysis |
| --- | --- | --- |
| 330 | 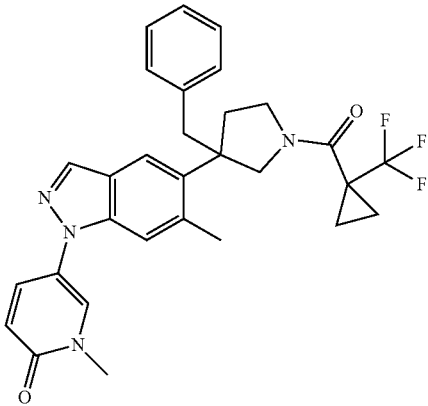 [SMILES: Cc1cc2c(cnn2-c2ccc(=O)n(C)c2)cc1C1(Cc2ccccc2)CCN(C(=O)C2(C(F)(F)F)CC2)C1]<br>5-(5-(3-benzyl-1-(1-(trifluoromethyl)cyclopropane-1-carbonyl)pyrrolidin-3-yl)-6-methyl-1H-indazol-1-yl)-1-methylpyridin-2(1H)-one | $R^t$ 1.93 min (Method 1); m/z 535.0 $(M + H)^+$ $(ES^+)$ |
| 331 | 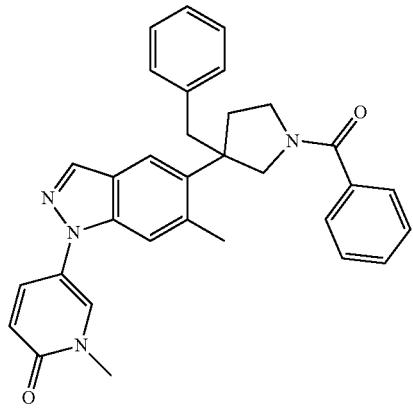<br>5-(5-(3-benzyl-1-(2-methylcyclopropane-1-carbonyl)pyrrolidin-3-yl)-6-methyl-1H-indazol-1-yl)-1-methylpyridin-2(1H)-one | $R^t$ 1.77 min (Method 7); m/z 481.3 $(M + H)^+$ $(ES^+)$ |
| 332 | 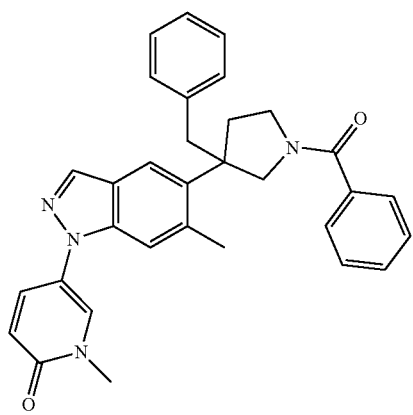<br>5-(5-(3-benzyl-1-(cyclopropanecarbonyl)pyrrolidin-3-yl)-6-methyl-1H-indazol-1-yl)-1-methylpyridin-2(1H)-one | $R^t$ 1.37 min (Method 7); m/z 467.4 $(M + H)^+$ $(ES^+)$ |

Example 333: 5-(5-(3-benzyl-1-((2-methyl-2H-1,2,3-triazol-4-yl)sulfonyl)pyrrolidin-3-yl)-6-ethyl-1H-indazol-1-yl)-1-methylpyridin-2(1H)-one

Intermediate AN: 5-(1,3-dibenzylpyrrolidin-3-yl)-1-((2-(trimethylsilyl)ethoxy)methyl)-6-vinyl-1H-indazole

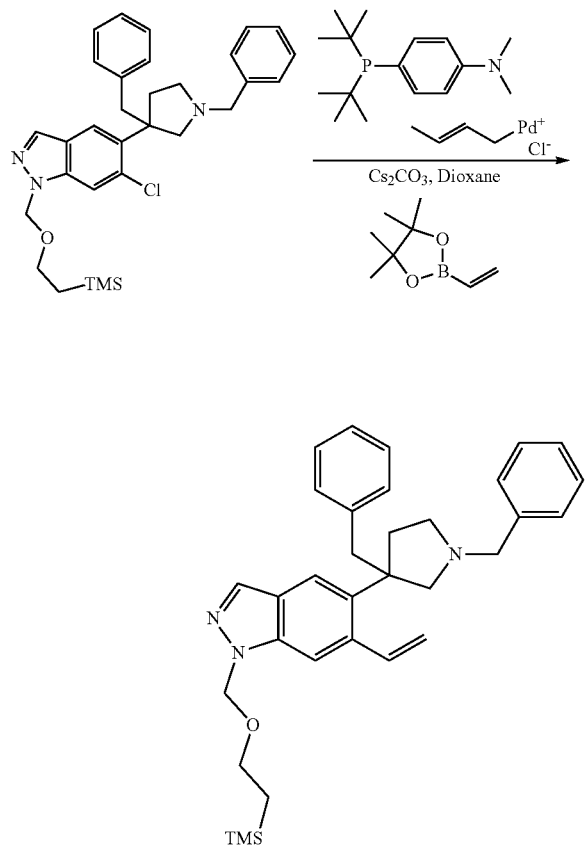

A vial containing 6-chloro-5-(1,3-dibenzylpyrrolidin-3-yl)-1-((2-(trimethylsilyl)ethoxy)methyl)-1H-indazole (prepared using a similar method to those described for Example 275) (300 mg, 90% Wt, 507 μmol), cesium carbonate (496 mg, 1.52 mmol), 4,4,5,5-tetramethyl-2-vinyl-1,3,2-dioxaborolane (156 mg, 1.01 mmol) and Pd-161 (46.9 mg, 101 μmol) was evacuated under vacuum and refilled with N$_2$ (×3). 1,4-Dioxane (5 mL) was added, and the resultant solution was heated at 90° C. for 18 hours. The reaction mixture was cooled to room temperature and then quenched with a saturated solution of NaHCO$_3$ (20 mL) and extracted with EtOAc (3×20 mL). The combined organic was washed with brine (10 mL), dried over MgSO$_4$ and filtered. The solvent was removed under reduced pressure to afford a yellow oil. The crude product was purified by chromatography on silica gel (24 g cartridge, 0-50% EtOAc/isohexane) to afford 5-(1,3-dibenzylpyrrolidin-3-yl)-1-((2-(trimethylsilyl)ethoxy)methyl)-6-vinyl-1H-indazole (Intermediate AN) (300 mg, 462 μmol, 91.0%) as a sticky yellow oil; Rt 1.35 min (Method 6); m/z 524.6 (M+H)+ (ES+).

Intermediate AO: 5-(3-benzylpyrrolidin-3-yl)-6-ethyl-1-((2-(trimethylsilyl)ethoxy)methyl)-1H-indazole

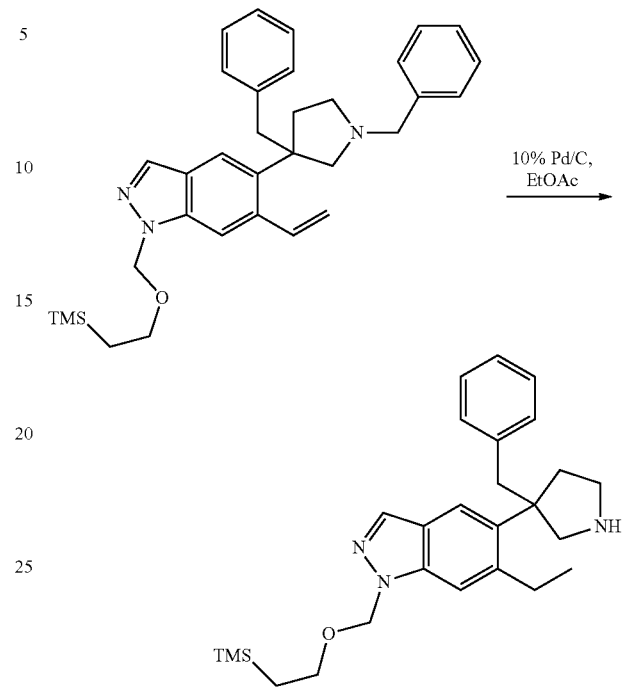

To a solution of 5-(1,3-dibenzylpyrrolidin-3-yl)-1-((2-(trimethylsilyl)ethoxy)methyl)-6-vinyl-1H-indazole (300 mg, 573 μmol) in EtOAc (6 mL) was added 10% palladium on charcoal (type 39) (61.0 mg, 10% Wt, 57.3 μmol) and the reaction mixture was stirred under 5 bars of hydrogen for 3 days. Further palladium on charcoal (type 39) (3.05 mg, 28.6 μmol) was added and the reaction mixture was heated at 50° C. under 5 bars of hydrogen for 18 hours. The reaction mixture was filtered through a Whatman GF/F filter pad and rinsed with EtOH (3×1 mL). The combined filtrate was concentrated in vacuo to afford 5-(3-benzylpyrrolidin-3-yl)-6-ethyl-1-((2-(trimethylsilyl)ethoxy)methyl)-1H-indazole (Intermediate AO) (215 mg, 0.30 mmol, 53%) as an orange oil which was used crude in the next step; Rt 0.55 min (Method 6); m/z 436.5 (M+H)+ (ES+).

Intermediate AP: 5-(3-benzyl-1-((2-methyl-2H-1,2,3-triazol-4-yl)sulfonyl)pyrrolidin-3-yl)-6-ethyl-1-((2-(trimethylsilyl)ethoxy)methyl)-1H-indazole

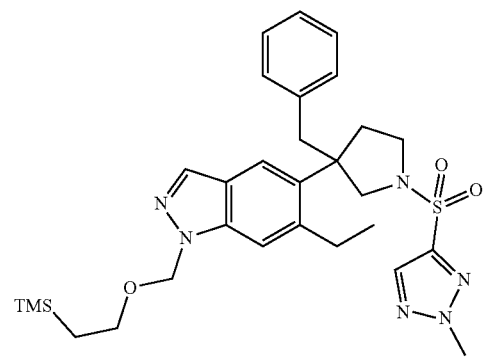 [SMILES: CCc1cc2c(cnn2COCC[Si](C)(C)C)cc1C1(Cc2ccccc2)CCN(S(=O)(=O)c2cnn(C)n2)C1]

461

The compound was prepared by similar methods to those described for Example 16, to afford 5-(3-benzyl-1-((2-methyl-2H-1,2,3-triazol-4-yl)sulfonyl)pyrrolidin-3-yl)-6-ethyl-1-((2-(trimethylsilyl)ethoxy)methyl)-1H-indazole (Intermediate AP); Rt 1.93 min (Method 6); m/z 581.5 (M+H)+ (ES+).

Intermediate AQ: 5-(3-benzyl-1-((2-methyl-2H-1,2,3-triazol-4-yl)sulfonyl)pyrrolidin-3-yl)-6-ethyl-1H-indazole

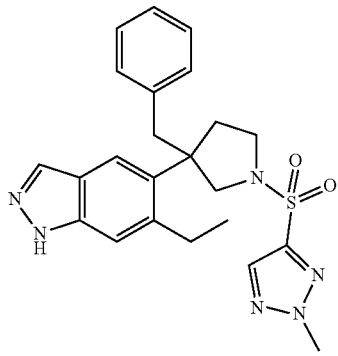 [SMILES: CCc1cc2[nH]ncc2cc1C1(Cc2ccccc2)CCN(S(=O)(=O)c2cnn(C)n2)C1]

The compound was prepared by similar methods to those described for Example 275, to afford 5-(3-benzyl-1-((2-methyl-2H-1,2,3-triazol-4-yl)sulfonyl)pyrrolidin-3-yl)-6-ethyl-1H-indazole (Intermediate AQ); Rt 1.45 min (Method 6); m/z 451.5 (M+H)+ (ES+).

462

Example 333: 5-(5-(3-benzyl-1-((2-methyl-2H-1,2,3-triazol-4-yl)sulfonyl)pyrrolidin-3-yl)-6-ethyl-1H-indazol-1-yl)-1-methylpyridin-2(1H)-one

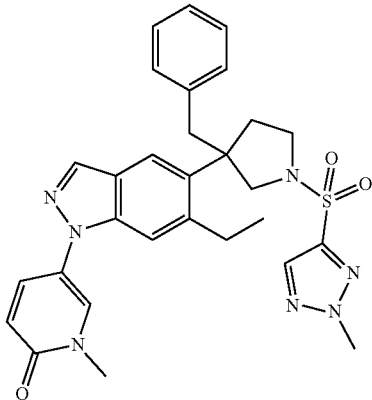 [SMILES: CCc1cc2c(cnn2-c2ccc(=O)n(C)c2)cc1C1(Cc2ccccc2)CCN(S(=O)(=O)c2cnn(C)n2)C1]

The compound was prepared by similar methods to those described for Example 237, to afford 5-(5-(3-benzyl-1-((2-methyl-2H-1,2,3-triazol-4-yl)sulfonyl)pyrrolidin-3-yl)-6-ethyl-1H-indazol-1-yl)-1-methylpyridin-2(1H)-one (Example 333); Rt 1.44 min (Method 6); m/z 558.1 (M+H)+ (ES+). 5H (500 MHz, DMSO-$d_6$) δ 8.31 (s, 1H), 8.21 (d, J=2.9 Hz, 1H), 8.08 (d, J=0.9 Hz, 1H), 7.77 (dd, 0.7=9.6, 3.0 Hz, 1H), 7.51 (s, 1H), 7.11-7.00 (m, 4H), 6.58 (d, J=9.6 Hz, 1H), 6.55-6.51 (m, 2H), 4.13 (s, 3H), 3.92 (d, J=9.8 Hz, 1H), 3.61 (q, J=8.4 Hz, 1H), 3.55 (s, 3H), 3.46 (t, J=9.2 Hz, 1H), 3.43-3.36 (m, 1H), 3.04 (d, J=13.5 Hz, 1H), 2.87-2.74 (m, 3H),[(3)] 2.43-2.33 (m, 1H), 2.14-2.04 (m, 1H), 1.29 (t, J=7.3 Hz, 3H).

Example 334: 5-(3-benzyl-1-((2-methyl-2H-1,2,3-triazol-4-yl)sulfonyl)pyrrolidin-3-yl)-1-(4-fluorophenyl)-1H-indazole-6-carbonitrile Intermediate AR: 5-(1,3-dibenzylpyrrolidin-3-yl)-1-((2-(trimethylsilyl)ethoxy)methyl)-1H-indazole-6-carbonitrile

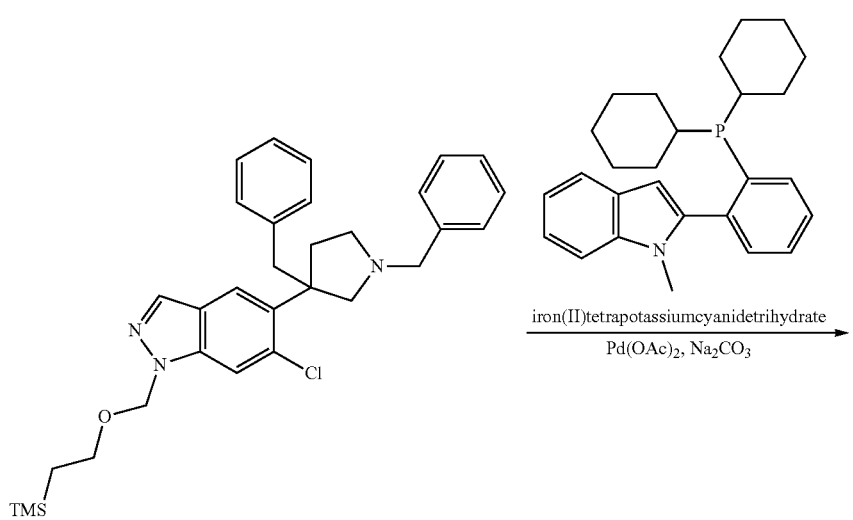

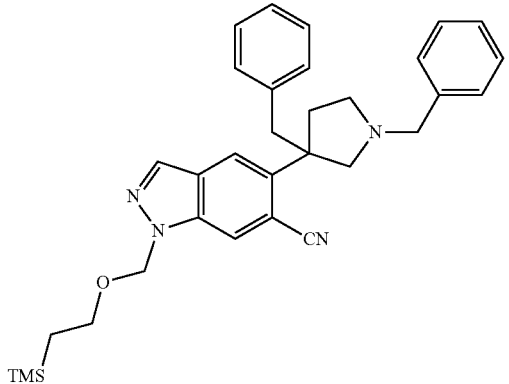

A vial containing sodium carbonate (155 mg, 1.47 mmol), palladium diacetate (21.9 mg, 97.7 μmol), iron(II) tetrapotassium cyanide trihydrate (413 mg, 977 μmol), 2-(2-(dicyclohexylphosphaneyl)phenyl)-1-methyl-1H-indole (78.9 mg, 195 μmol) and 6-chloro-5-(1,3-dibenzylpyrrolidin-3-yl)-1-((2-(trimethylsilyl)ethoxy)methyl)-1H-indazole (520 mg, 977 μmol) (prepared using a similar method to those described for Example 275) was evacuated under vacuum and refilled with nitrogen (×3). 1,4-Dioxane (4 mL) and water (4 mL) were added and the solution was degassed with nitrogen for 10 minutes and heated at 130° C. in a microwave for 12 hours. The reaction mixture was quenched with a saturated solution of NaHCO$_3$ (10 mL) and extracted with EtOAc (3×10 mL). The combined organic was passed through a hydrophobic frit and the solvent was removed under reduced pressure to afford a pale yellow residue. The crude product was purified by chromatography on silica gel (40 g cartridge, 0-100% (0.7 M Ammonia/MeOH)/DCM) to afford 5-(1,3-dibenzylpyrrolidin-3-yl)-1-((2-(trimethylsilyl)ethoxy)methyl)-1H-indazole-6-carbonitrile (430 mg, 587 μmol, 60.1%, 74.4% Purity) as a sticky yellow oil; Rt 1.28 min (Method 6); m/z 523.2 (M+H)+ (ES+).

Intermediate AS: 5-(3-benzyl-1-((2-methyl-2H-1,2,3-triazol-4-yl)sulfonyl)pyrrolidin-3-yl)-1H-indazole-6-carbonitrile

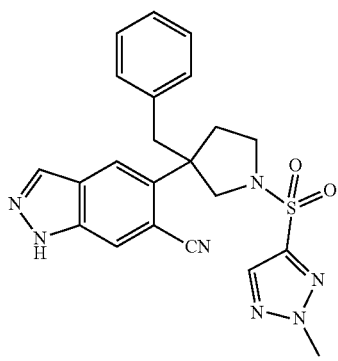 [SMILES: Cn1ncc(S(=O)(=O)N2CCC(Cc3ccccc3)(c3cc4cn[nH]c4cc3C#N)C2)n1]

The compound was prepared by similar methods to those described for Example 275, to afford 5-(3-benzyl-1-((2-methyl-2H-1,2,3-triazol-4-yl)sulfonyl)pyrrolidin-3-yl)-1H-indazole-6-carbonitrile (Intermediate AR); Rt 1.45 min (Method 6); m/z 451.5 (M+H)+ (ES+).

Example 334: 5-(3-benzyl-1-((2-methyl-2H-1,2,3-triazol-4-yl)sulfonyl)pyrrolidin-3-yl)-1-(4-fluorophenyl)-1H-indazole-6-carbonitrile

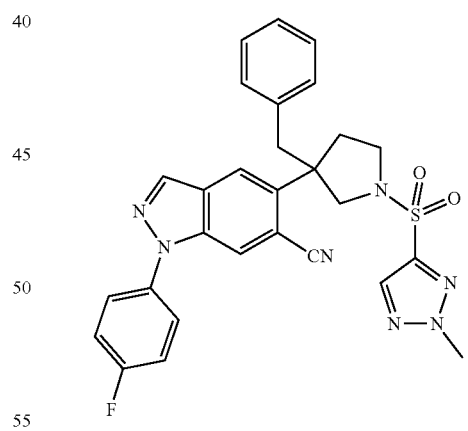

The compound was prepared by similar methods to those described for Example 16, to afford 5-(3-benzyl-1-((2-methyl-2H-1,2,3-triazol-4-yl)sulfonyl)pyrrolidin-3-yl)-1-(4-fluorophenyl)-1H-indazole-6-carbonitrile (Example 334); Rt 1.65 min (Method 8); m/z 542.2 (M+H)+ (ES+). $\delta_H$ (400 MHz, Methanol-d$_4$) δ 8.29 (s, 1H), 8.24 (d, J=1.0 Hz, 1H), 8.04 (s, 1H), 7.86-7.79 (m, 2H), 7.45-7.36 (m, 3H), 7.14-7.04 (m, 3H), 6.71-6.65 (m, 2H), 4.19-4.10 (m, 1H), 4.08 (s, 3H), 3.84 (d, J=10.4 Hz, 1H), 3.76 (dt, J=10.1, 7.4 Hz, 1H), 3.64-3.53 (m, 1H), 3.39 (d, J=13.8 Hz, 1H), 3.11 (d, J=13.8 Hz, 1H), 2.68-2.58 (m, 1H), 2.46-2.35 (m, 1H).

Example 335: 5-(5-(3-benzyl-4-methyl-1-((2-methyl-2H-1,2,3-triazol-4-yl)sulfonyl)pyrrolidin-3-yl)-6-methyl-1H-indazol-1-yl)-1-methylpyridin-2(1H)-one Intermediate AT: 1,3-dibenzyl-4-methyl-3-(6-methyl-1-((2-(trimethylsilyl)ethoxy)methyl)-1H-indazol-5-yl)pyrrolidine-2,5-dione

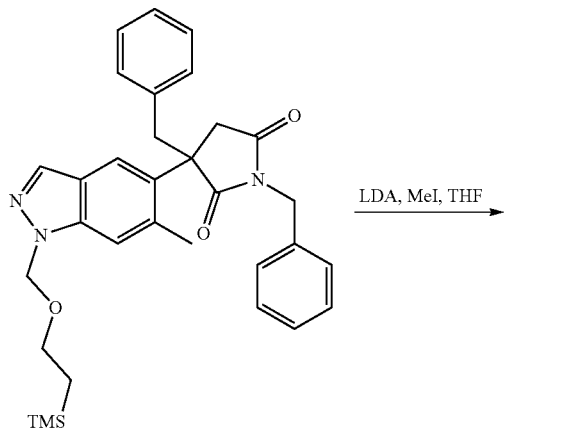

LDA, MeI, THF

Example 335: 5-(5-(3-benzyl-4-methyl-1-((2-methyl-2H-1,2,3-triazol-4-yl)sulfonyl)pyrrolidin-3-yl)-6-methyl-1H-indazol-1-yl)-1-methylpyridin-2(1H)-one

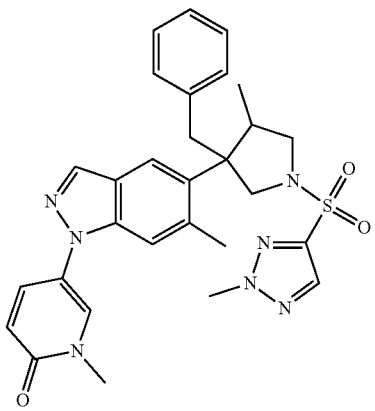

The compound was prepared by similar methods to those described for Example 275 to afford 5-(5-(3-benzyl-4-methyl-1-((2-methyl-2H-1,2,3-triazol-4-yl)sulfonyl)pyrrolidin-3-yl)-6-methyl-1H-indazol-1-yl)-1-methylpyridin-2(1H)-one (Example 335) (59.75 mg, 0.10 mmol, 67%) as a yellow solid. Rt 1.76 min (Method 7); m/z 558.2 (M+H)+ (ES+). $\delta_H$ (400 MHz, DMSO-$d_6$) δ 8.29 (s, 1H), 8.10 (d, J=2.9 Hz, 1H), 8.01 (d, J=1.0 Hz, 1H), 7.72 (dd, J=9.6, 3.0 Hz, 1H), 7.48 (s, 1H), 7.09-7.04 (m, 1H), 7.01 (dd, J=8.1, 6.4 Hz, 2H), 6.85 (s, 1H), 6.55 (d, J=9.6 Hz, 1H), 6.52-6.49 (m, 2H), 4.24 (s, 3H), 4.00 (dd, J=10.3, 6.3 Hz, 1H), 3.77 (d, J=9.4 Hz, 1H), 3.56 (s, 3H), 3.48 (d, J=9.1 Hz, 1H), 3.28 (d, J=10.2 Hz, 1H), 3.14 (d, J=13.5 Hz, 1H), 2.98-2.91 (m, 1H), 2.55 (s, 3H), 0.53 (d, J=7.0 Hz, 3H)-one CH obscured by water.

Example 336: 1,3-dibenzyl-3-(1-(4-fluorophenyl)-6-methyl-1H-indazol-5-yl)-5-hydroxypyrrolidin-2-one To a solution of 1,3-dibenzyl-3-(6-methyl-1-((2-(trimethylsilyl)ethoxy)methyl)-1H-indazol-5-yl)pyrrolidine-2,5-dione (4.12 g, 87% Wt, 6.64 mmol) (prepared using similar methods to those described in Example 16 and Example 275) in THF (60 mL) at 0° C. was added lithium diisopropylamide (2 M in THF) (1.1 g, 5.0 mL, 2.0 molar, 10 mmol) and the resulting solution was stirred at this temperature for 30 minutes. Iodomethane (1.89 g, 827 µL, 13.3 mmol) was added and the reaction mixture was allowed to warm to room temperature and stirred overnight. The reaction was quenched with saturated aqueous NaHCO₃ solution (50 mL) and extracted with EtOAc (3×50 mL). The combined organic layers were dried using MgSO₄, filtered, and concentrated under reduced pressure. The crude product was purified by chromatography on silica gel (220 g cartridge, 0-40% EtOAc/isohexane) to afford 1,3-dibenzyl-4-methyl-3-(6-methyl-1-((2-(trimethylsilyl)ethoxy)methyl)-1H-indazol-5-yl)pyrrolidine-2,5-dione (Intermediate AT) (3.02 g, 4.6 mmol, 70%) as a sticky yellow oil, which solidified to a yellow solid upon standing overnight; Rt 2.61 min (Method 7); m/z 542.2 (M+H)+ (ES+)

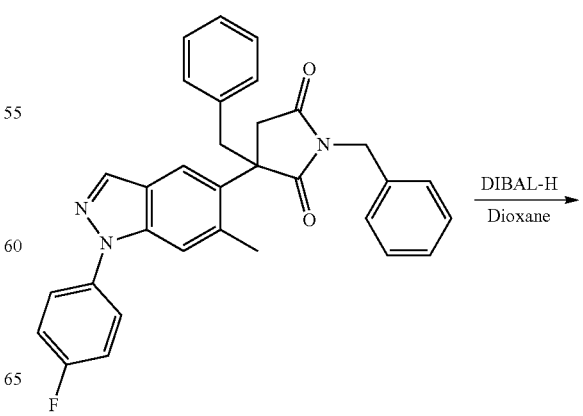

DIBAL-H
Dioxane

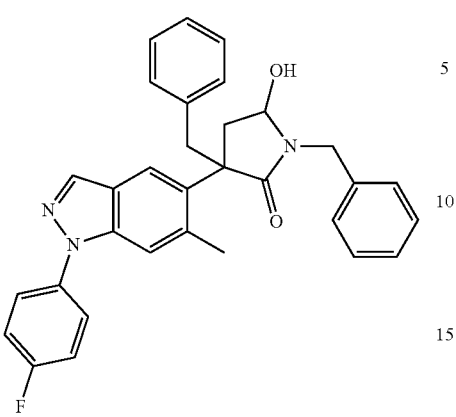

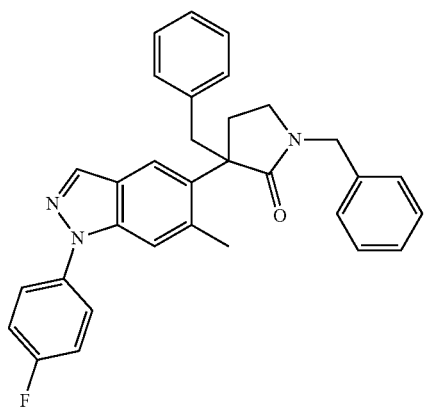

To a solution of 1,3-dibenzyl-3-(1-(4-fluorophenyl)-6-methyl-1H-indazol-5-yl)pyrrolidine-2,5-dione (Intermediate O) (0.105 g, 209 μmol) in dioxane (3 mL) was added DIBAL-H in hexane (29.7 mg, 209 μL, 1 molar, 209 μmol) and the reaction stirred at room temperature overnight. The reaction was quenched with NaHCO₃ (10 mL) and extracted with EtOAc (2×10 mL), the organics were dried over MgSO₄ and concentrated in vacuo to give the crude product. The crude product was purified by chromatography on silica gel (24 g cartridge, 0-100% EtOAc/isohexane) to afford 5-(1,3-dibenzylpyrrolidin-3-yl)-1-(4-fluorophenyl)-6-methyl-1H-indazole (example xx) as a yellow solid (Example 336) (52 mg, 0.21 mmol, 48%); Rt 1.76 min (Method 7); m/z 558.2 (M+H)+ (ES+).

Example 337: 1,3-dibenzyl-3-(1-(4-fluorophenyl)-6-methyl-1H-indazol-5-yl)pyrrolidin-2-one To a solution of 1,3-dibenzyl-3-(1-(4-fluorophenyl)-6-methyl-1H-indazol-5-yl)-5-hydroxypyrrolidin-2-one (0.052 g, 0.10 mmol) (Example 336) in TFA (1 mL) was added triethylsilane (0.12 g, 0.16 mL, 1.0 mmol) and the reaction stirred at room temperature for 1 hour. The reaction was quenched with NaHCO₃ (10 mL) and then EtOAc (2×10 mL) was added, the organics were combined and then dried over MgSO₄ and concentrated in vacuo to give the crude product. The crude product was purified by chromatography on silica gel (12 g cartridge, 0-100% EtOAc/isohexane) to afford 1,3-dibenzyl-3-(1-(4-fluorophenyl)-6-methyl-1H-indazol-5-yl)pyrrolidin-2-one (0.016 g, 32 μmol, 31%) (Example 337) as a light yellow solid. Rt 3.00 min (Method 2); m/z 490.0 (M+H)+ (ES+). $\delta_H$ (500 MHz, DMSO-$d_6$) δ 8.32 (s, 1H), 8.02 (s, 1H), 7.94-7.74 (m, 2H), 7.68 (s, 1H), 7.43 (t, J=8.8 Hz, 2H), 7.37-7.20 (m, 8H), 7.18-6.97 (m, 2H), 4.49 (d, J=14.5 Hz, 1H), 4.03 (d, J=14.5 Hz, 1H), 3.45-3.28 (m, 2H), 3.2 (s, 3H), 2.99-2.81 (m, 1H), 2.34-2.14 (m, 3H).

Example 338: 3-benzyl-3-(1-(4-fluorophenyl)-1H-indazol-5-yl)-1-(methylsulfonyl) pyrrolidin-2-one Intermediate AU: 3-(1-(4-fluorophenyl)-1H-indazol-5-yl)-1-(4-methoxybenzyl) pyrrolidine-2,5-dione

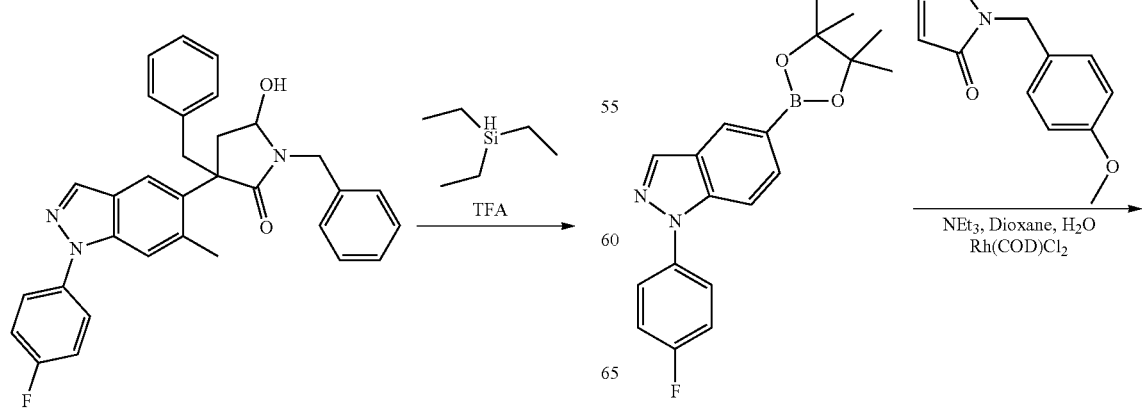

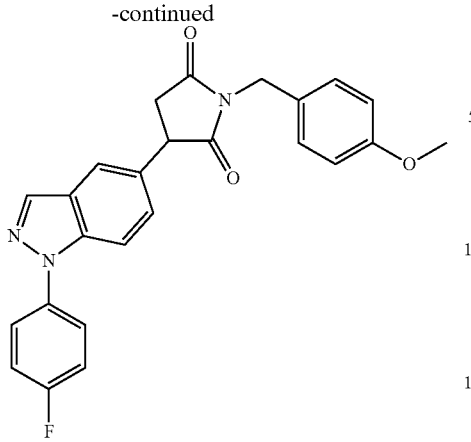
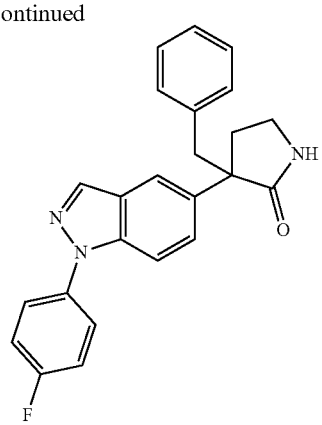

To a solution of 1-(4-fluorophenyl)-5-(4,4,5,5-tetramethyl-1,3,2-dioxaborolan-2-yl)-1H-indazole (0.672 g, 87% Wt, 1.73 mmol) (prepared using a similar method to those described in Example 16) in dioxane (10 mL) and water (1 mL) which was degassed with nitrogen for 10 minutes was added 1-(4-methoxybenzyl)-1H-pyrrole-2,5-dione (413 mg, 1.90 mmol), triethylamine (262 mg, 361 μL, 2.59 mmol) and hydroxy(cyclooctadiene)rhodium(I) dimer (39.4 mg, 86.4 μmol) before being heated to 80° C. overnight. The reaction was cooled, partitioned between EtOAc (2×20 mL) and water (20 mL) and then the organics were dried over MgSO$_4$ and concentrated in vacuo to give the crude product. The crude product was purified by chromatography on silica gel (40 g cartridge, 0-100% EtOAc/isohexane) to afford 3-(1-(4-fluorophenyl)-1H-indazol-5-yl)-1-(4-methoxybenzyl)pyrrolidine-2,5-dione (Intermediate AU) (0.651 g, 1.5 mmol, 87%) as a yellow solid. Rt 2.49 min (Method 2); m/z 429.8 (M+H)+ (ES+).

Intermediate AV: 3-benzyl-3-(1-(4-fluorophenyl)-1H-indazol-5-yl)pyrrolidin-2-one To a solution of 3-benzyl-3-(1-(4-fluorophenyl)-1H-indazol-5-yl)-1-(4-methoxybenzyl)pyrrolidin-2-one (0.131 g, 259 μmol) (prepared using similar methods to those described for Example 337) in MeCN (3 mL) was added ceric ammonium nitrate (284 mg, 518 μmol) and the reaction was left to stir at room temperature overnight. A further portion of ceric ammonium nitrate (142 mg, 259 μmol) was added and the reaction stirred overnight at room temperature. The reaction was partitioned between EtOAc (2×20 mL) and NaHCO$_3$ (20 mL), the organics were dried over MgSO$_4$ and concentrated in vacuo to give the crude product. The crude product was purified by chromatography on silica gel (12 g cartridge, 0-100% EtOAc/isohexane) to afford 3-benzyl-3-(1-(4-fluorophenyl)-1H-indazol-5-yl)pyrrolidin-2-one (Intermediate AV) (0.028 g, 70 μmol, 27%) as a yellow solid. Rt 2.40 min (Method 2); m/z 385.8 (M+H)+ (ES+). δ$_H$ (500 MHz, DMSO-d$_6$) δ 8.34 (d, J=0.8 Hz, 1H), 7.93 (d, J=1.7 Hz, 1H), 7.84-7.70 (m, 5H), 7.47-7.39 (m, 2H), 7.23-7.13 (m, 3H), 7.12-7.04 (m, 2H), 3.18-3.07 (m, 2H), 3.01-2.92 (m, 1H), 2.88 (t, J=8.0 Hz, 1H), 2.43 (ddd, J=10.1, 6.8, 3.4 Hz, 1H), 2.32 (dt, J=13.1, 8.1 Hz, 1H).

Example 338: 3-benzyl-3-(1-(4-fluorophenyl)-1H-indazol-5-yl)-1-(methylsulfonyl)pyrrolidin-2-one

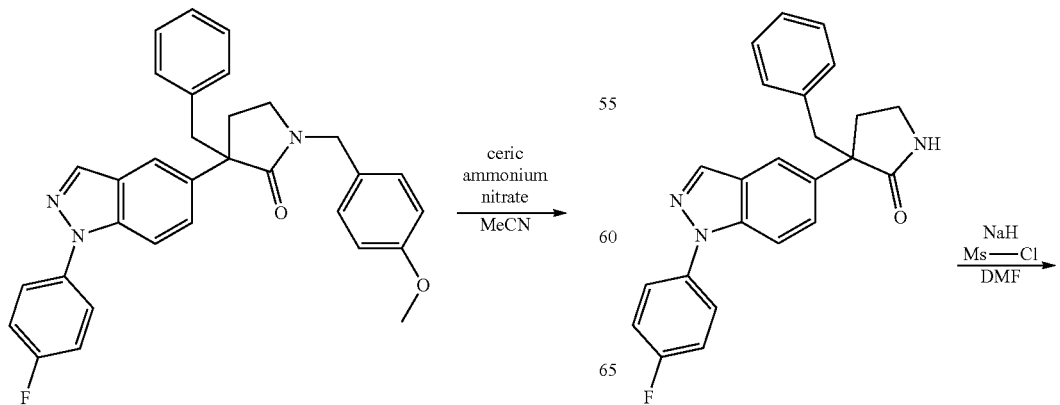

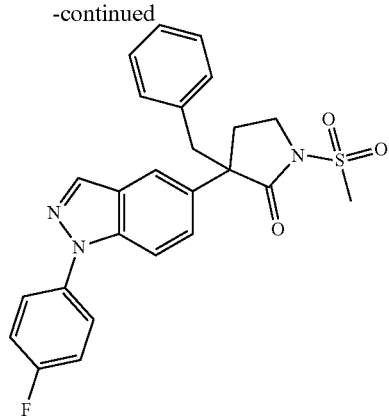

To a solution of 3-benzyl-3-(1-(4-fluorophenyl)-1H-indazol-5-yl)pyrrolidin-2-one (0.027 g, 70 μmol) in DMF (3 mL) at 0° C. was added sodium hydride (5.1 mg, 60% Wt, 0.13 mmol) and the reaction was stirred for 10 minutes before the addition of methanesulfonyl chloride (15 mg, 10 μL, 0.13 mmol) and the reaction was warmed to room temperature and left to stir overnight. The reaction was cooled to 0° C. again, sodium hydride (10 mg, 0.42 mmol) was added and the reaction mixture stirred for 10 minutes and then methanesulfonyl chloride (24 mg, 16 μL, 0.21 mmol) was added and the reaction left overnight again. The reaction was quenched by slow addition of NaHCO$_3$ (10 mL) and then EtOAc (15 mL), the aqueous was extracted with EtOAc (15 mL) again and then the organics were combined washed with brine (15 mL) and then dried over MgSO$_4$ and concentrated in vacuo to give the crude product. The crude product was purified by chromatography on silica gel (12 g cartridge, 0-50% EtOAc/isohexane) to afford 3-benzyl-3-(1-(4-fluorophenyl)-1H-indazol-5-yl)-1-(methylsulfonyl)pyrrolidin-2-one (0.005 g, 0.01 mmol, 20%, 98%) (Example 338) as a light yellow solid. Rt 2.64 min (Method 2); m/z 463.8 (M+H)+ (ES+). $\delta_H$ (500 MHz, DMSO-d$_6$) δ 8.36 (d, J=0.9 Hz, 1H), 7.90-7.86 (m, 1H), 7.85-7.78 (m, 3H), 7.67 (dd, J=9.0, 1.9 Hz, 1H), 7.47-7.40 (m, 2H), 7.21-7.16 (m, 3H), 7.01-6.95 (m, 2H), 3.60-3.50 (m, 2H), 3.28 (s, 3H), 3.25 (s, 2H), 2.57 (ddd, J=13.2, 6.7, 4.4 Hz, 1H), 2.49-2.40 (m, 1H).

Example 339: 3-benzyl-3-(1-(4-fluorophenyl)-6-methyl-1H-indazol-5-yl)-1-(methylsulfonyl)pyrrolidin-2-one

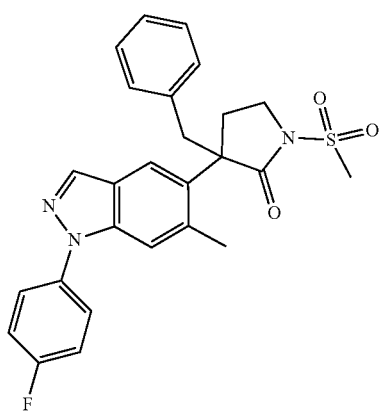 [SMILES: Cc1cc2c(cnn2-c2ccc(F)cc2)cc1C1(Cc2ccccc2)CCN(S(C)(=O)=O)C1=O]

The compound was prepared by similar methods to those described for Example 338 to afford 3-benzyl-3-(1-(4-fluorophenyl)-6-methyl-1H-indazol-5-yl)-1-(methylsulfonyl)pyrrolidin-2-one (Example 339); R$^t$ 1.70 min (Method 1); m/z 478.3 (M+H)$^+$ (ES$^+$). $\delta_H$ (500 MHz, Chloroform-d) δ 8.15 (d, J=0.9 Hz, 1H), 7.97 (s, 1H), 7.70-7.64 (m, 2H), 7.55 (q, J=0.9 Hz, 1H), 7.38-7.31 (m, 5H), 7.27-7.22 (m, 2H), 3.65-3.56 (m, 2H), 3.47 (d, J=13.1 Hz, 1H), 3.13 (s, 3H), 2.96-2.90 (m, 1H), 2.61 (d, J=0.8 Hz, 3H), 2.56-2.51 (m, 2H).

Example 340: 1-(4-fluorophenyl)-5-(3-(methoxymethyl)-1-((1-methyl-1H-pyrazol-4-yl)sulfonyl)pyrrolidin-3-yl)-6-methyl-1H-indazole Intermediate AW: tert-butyl 3-(1-(4-fluorophenyl)-6-methyl-1H-indazol-5-yl)-3-((4,4,5,5-tetramethyl-1,3,2-dioxaborolan-2-yl)methyl)pyrrolidine-1-carboxylate

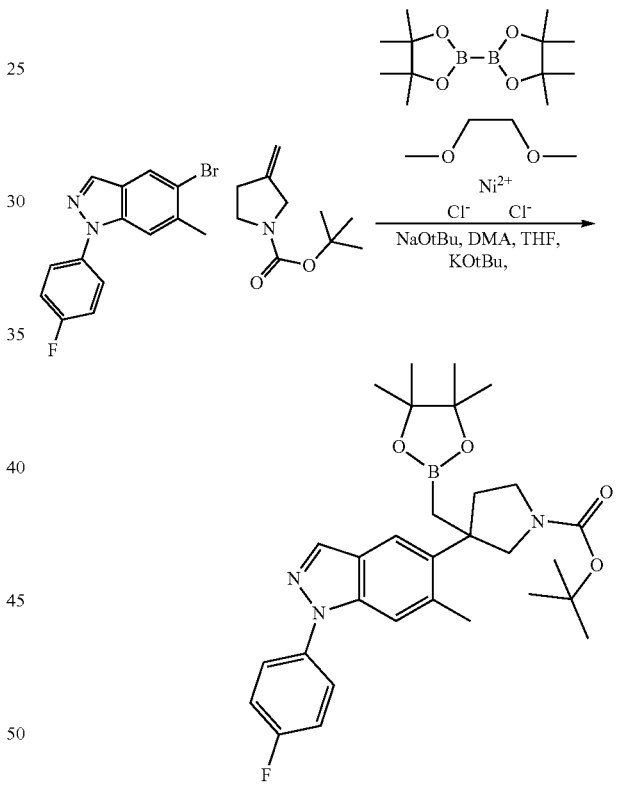

In a microwave vial containing nickel chloride, dimethoxyethane adduct (230 mg, 1.05 mmol) was added DMA (7 mL). The blue solution was submitted to a vacuum/nitrogen cycle (×3) and stirred at room temperature for 5 minutes. In the meantime, to a solution of bis(pinacolato)diborane (1.66 g, 6.55 mmol) and 5-bromo-1-(4-fluorophenyl)-6-methyl-1H-indazole (Intermediate D) (2.50 g, 8.19 mmol) in THF (15 mL) and dimethylacetamide (2 mL) were added tert-butyl 3-methylenepyrrolidine-1-carboxylate (600 mg, 594 μL, 3.27 mmol), sodium t-butoxide (2 M THF) (283 mg, 1.47 mL, 2 molar, 2.95 mmol) and potassium t-butoxide (1 M THF) (220 mg, 1.96 mL, 1 molar, 1.96 mmol). The colourless solution was submitted to a vacuum/nitrogen cycle (×3) and nickel chloride dimethoxyethane adduct (144 mg, 4.37 mL, 0.15 molar, 655 µmol) was added. The resultant cloudy solution was heated at 50° C. for 16 hours. The reaction mixture was quenched by adding a saturated aqueous solution of NaHCO$_3$ (50 mL) and the product was extracted with EtOAc (3×50 mL). The organic layers were combined and passed through a phase separator. The solvent was removed under reduced pressure to afford a yellow oil. The crude product was purified by chromatography on silica gel (80 g cartridge, 0-50% EtOAc/isohexane) to afford tert-butyl 3-(1-(4-fluorophenyl)-6-methyl-1H-indazol-5-yl)-3-((4,4,5,5-tetramethyl-1,3,2-dioxaborolan-2-yl)methyl)pyrrolidine-1-carboxylate (Intermediate AW) (900 mg, 1.6 mmol, 49%) as a white solid. R$^t$ 2.12 min (Method 1); m/z 536.5 (M+H)$^+$ (ES$^+$). δ$_H$ (500 MHz, DMSO-d$_6$) δ 8.22 (d, J=1.0 Hz, 1H), 7.83-7.72 (m, 2H), 7.64 (s, 1H), 7.57 (q, J=0.8 Hz, 1H), 7.43-7.32 (m, 2H), 3.96 (br. d, J=10.5 Hz, 1H), 3.55 (d, J=10.6 Hz, 1H), 3.46-3.35 (m, 2H), 2.61 (d, J=0.9 Hz, 3H), 2.55-2.52 (m, 1H), 2.30-2.21 (m, 1H), 1.46 (s, 9H), 1.32 (d, J=2.1 Hz, 2H), 0.96 (s, 6H), 0.94 (s, 6H).

Intermediate AX: 1-(4-fluorophenyl)-6-methyl-5-(3-((4,4,5,5-tetramethyl-1,3,2-dioxaborolan-2-yl)methyl)pyrrolidin-3-yl)-1H-indazole

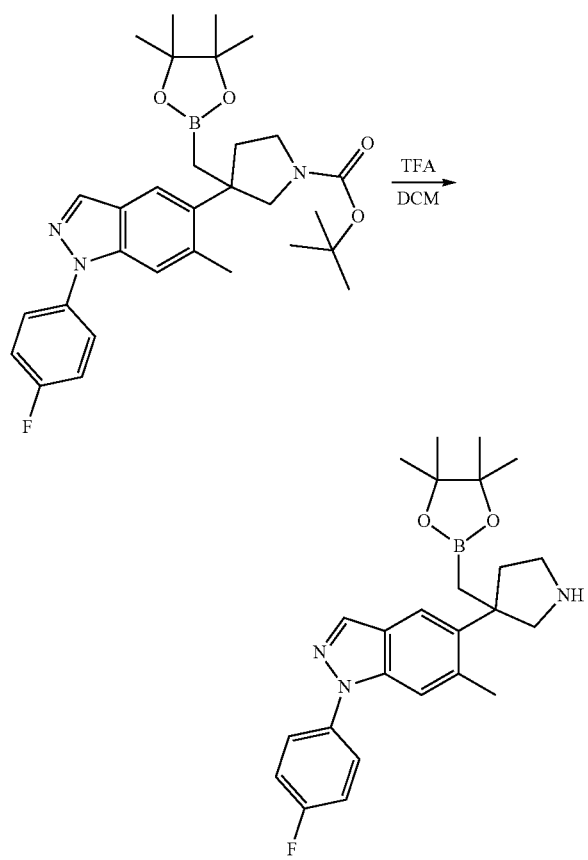

To a solution of tert-butyl 3-(1-(4-fluorophenyl)-6-methyl-1H-indazol-5-yl)-3-((4,4,5,5-tetramethyl-1,3,2-dioxaborolan-2-yl)methyl)pyrrolidine-1-carboxylate (760 mg, 1.42 mmol) in dichloromethane (15 mL) was added 2,2,2-trifluoroacetic acid (1.62 g, 1.09 mL, 14.2 mmol). The resultant mixture was stirred at room temperature for 18 hours. The mixture was concentrated to dryness under reduced pressure to afford 1-(4-fluorophenyl)-6-methyl-5-(3-((4,4,5,5-tetramethyl-1,3,2-dioxaborolan-2-yl)methyl)pyrrolidin-3-yl)-1H-indazole, trifluoracetate (Intermediate AX) (800 mg, 1.41 mmol, 99.6%) as an orange oil. R$^t$ 1.43 min (Method 8); m/z 436.5 (M+H)$^+$ (ES$^+$).

Intermediate AY: (3-(1-(4-fluorophenyl)-6-methyl-1H-indazol-5-yl)-1-((1-methyl-1H-pyrazol-4-yl)sulfonyl)pyrrolidin-3-yl)methanol

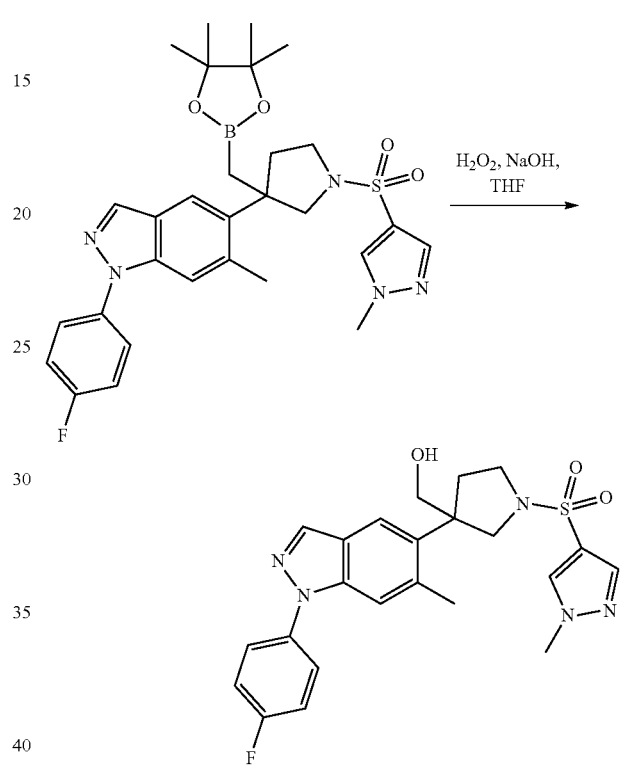

To a solution of 1-(4-fluorophenyl)-6-methyl-5-(1-((1-methyl-1H-pyrazol-4-yl)sulfonyl)-3-((4,4,5,5-tetramethyl-1,3,2-dioxaborolan-2-yl)methyl)pyrrolidin-3-yl)-1H-indazole (215 mg, 371 µmol) (prepared by similar methods to those described for Example 16)) in THF (5 mL) at 0° C. was added a 2 M solution of sodium hydroxide (74.2 mg, 928 µL, 2 molar, 1.86 mmol) followed by hydrogen peroxide (30% aqueous) (84.1 mg, 75.8 µL, 30% Wt, 742 µmol). The resultant solution was stirred at 0° C. for 2 hours. The reaction was quenched with a saturated solution of Na$_2$S$_2$O$_3$ (10 mL) and extracted with EtOAc (3×20 mL). The organic layers were dried using anhydrous sodium sulfate and the solvent was removed under reduced pressure. The crude product was purified by chromatography on silica gel (40 g cartridge, 0-100% EtOAc/isohexane) to afford (3-(1-(4-fluorophenyl)-6-methyl-1H-indazol-5-yl)-1-((1-methyl-1H-pyrazol-4-yl)sulfonyl)pyrrolidin-3-yl)methanol (Intermediate AY) (180 mg, 345 µmol, 93.1%) as a white solid; R$^t$ 1.33 min (Method 1); m/z 470.4 (M+H)$^+$ (ES$^+$). δ$_H$ (500 MHz, DMSO-d$_6$) δ 8.40 (s, 1H), 8.26 (d, J=0.9 Hz, 1H), 7.88 (d, J=0.7 Hz, 1H), 7.80-7.74 (m, 2H), 7.55 (d, J=12.2 Hz, 2H), 7.46-7.39 (m, 2H), 4.79 (t, J=5.5 Hz, 1H), 3.87 (d, J=9.9 Hz, 1H), 3.85 (s, 3H), 3.43 (dd, J=10.9, 5.6 Hz, 1H), 3.31-3.25 (m, 3H), 3.23 (d, J=9.8 Hz, 1H), 2.57-2.52 (m, 1H) 2.50 (m, 3H) 2.07-1.99 (m, 1H).

Example 340: 1-(4-fluorophenyl)-5-(3-(methoxymethyl)-1-((1-methyl-1H-pyrazol-4-yl)sulfonyl)pyrrolidin-3-yl)-6-methyl-1H-indazole

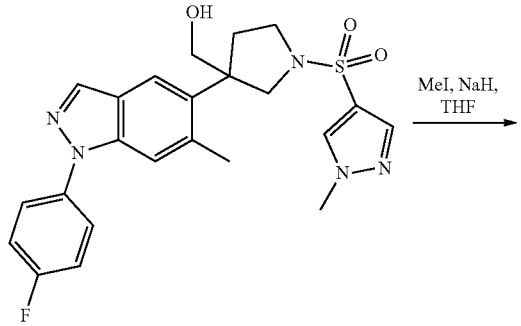

MeI, NaH, THF

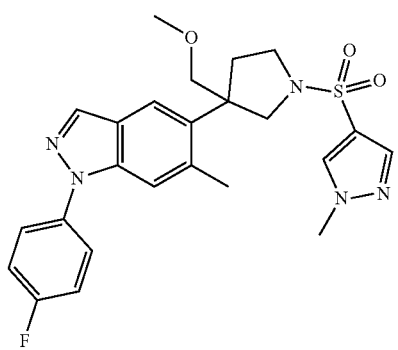

To a solution of (3-(1-(4-fluorophenyl)-6-methyl-1H-indazol-5-yl)-1-((1-methyl-1H-pyrazol-4-yl)sulfonyl)pyrrolidin-3-yl)methanol (Intermediate AY) (15 mg, 32 µmol) in THF (1 mL) at 0° C. was added sodium hydride (60% dispersion in mineral oil) (1.5 mg, 60% Wt, 38 µmol). The resultant solution was stirred at 0° C. for 30 minutes before methyl iodide (6.8 mg, 3.0 µL, 48 µmol) was added. The reaction mixture was stirred at 0° C. for 2 hours and was allowed to warm up to room temperature for 16 hours. The reaction mixture was quenched with a saturated solution of NaHCO$_3$ (5 mL) and extracted with EtOAc (3×10 mL). The organic layers were combined and passed through a hydrophobic frit. The solvent was removed under reduced pressure to afford a colourless residue. The crude product was purified by chromatography on silica gel (4 g cartridge, 0-100% EtOAc/isohexane) to afford 1-(4-fluorophenyl)-5-(3-(methoxymethyl)-1-((1-methyl-1H-pyrazol-4-yl)sulfonyl)pyrrolidin-3-yl)-6-methyl-1H-indazole (Example 340) (10 mg, 20 µmol, 63%) as a white solid. R$^t$ 1.55 min (Method 1); m/z 484.4 (M+H)$^+$ (ES$^+$). δ$_H$ (500 MHz, DMSO-d$_6$) δ 8.42 (s, 1H), 8.25 (d, J=0.9 Hz, 1H), 7.90 (d, J=0.7 Hz, 1H), 7.81-7.74 (m, 2H), 7.57 (d, J=2.8 Hz, 2H), 7.46-7.37 (m, 2H), 3.90 (d, J=10.0 Hz, 1H), 3.86 (s, 3H), 3.31-3.25 (m, 4H)$^{(4)}$, 3.20 (d, J=9.5 Hz, 1H), 3.00 (s, 3H), 2.55-2.51 (m, 4H), 2.16-2.04 (m, 1H).

Example 341: 5-(3-((benzyloxy)methyl)-1-((1-methyl-1H-pyrazol-4-yl)sulfonyl)pyrrolidin-3-yl)-1-(4-fluorophenyl)-6-methyl-1H-indazole

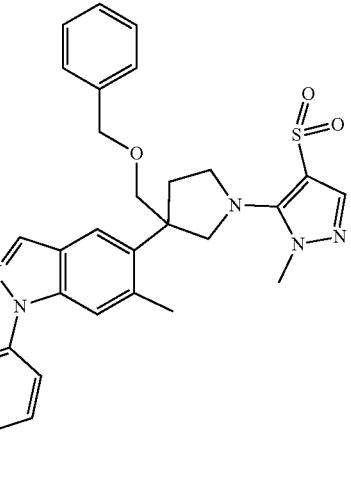

The compound was prepared by similar methods to those described for Example 340, to afford 5-(3-((benzyloxy)methyl)-1-((1-methyl-1H-pyrazol-4-yl)sulfonyl)pyrrolidin-3-yl)-1-(4-fluorophenyl)-6-methyl-1H-indazole (Example 341); R$^t$ 1.76 min (Method 1); m/z 560.4 (M+H)$^+$ (ES$^+$). δ$_H$ (500 MHz, DMSO-d$_6$) δ 8.41 (s, 1H), 8.26 (d, J=0.9 Hz, 1H), 7.89 (d, J=0.7 Hz, 1H), 7.81-7.76 (m, 2H), 7.63 (s, 1H), 7.57 (s, 1H), 7.45-7.38 (m, 2H), 7.26-7.19 (m, 3H), 7.07-7.02 (m, 2H), 4.29-4.17 (m, 2H), 3.95 (d, J=9.9 Hz, 1H), 3.83 (s, 3H), 3.42 (d, J=9.5 Hz, 1H), 3.31-3.21 (m, 4H) 2.59-2.53 (m, 1H), 2.48 (s, 3H), 2.16-2.06 (m, 1H).

Example 342: (E)-1-(4-fluorophenyl)-6-methyl-5-(1-((1-methyl-1H-pyrazol-4-yl)sulfonyl)-3-styrylpyrrolidin-3-yl)-1H-indazole Intermediate AZ: 3-(1-(4-fluorophenyl)-6-methyl-1H-indazol-5-yl)-1-((1-methyl-1H-pyrazol-4-yl)sulfomyl)pyrrolidine-3-carbaldehyde

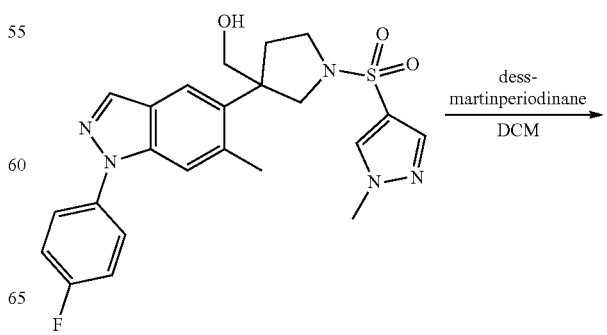

dess-martinperiodinane
DCM

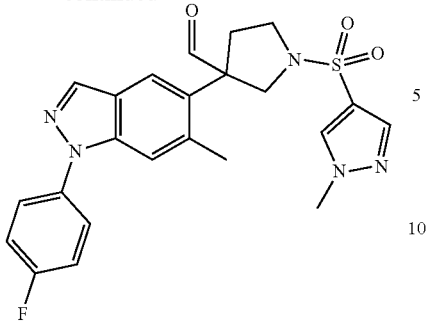

To a solution (3-(1-(4-fluorophenyl)-6-methyl-1H-indazol-5-yl)-1-((1-methyl-1H-pyrazol-4-yl)sulfonyl)pyrrolidin-3-yl)methanol (30 mg, 64 μmol) (Intermediate AY) in dichloromethane (2 mL) at 0° C. was added dess-martinperiodinane (54 mg, 0.13 mmol). The resultant colourless solution was stirred at 0° C. for 2 hours. The reaction mixture was partitioned between EtOAc (10 mL) and a saturated solution of NaHCO$_3$ (10 mL) and the phases were separated. The organic layer was dried over MgSO$_4$ and filtered. The solvent was removed under reduced pressure to afford a colourless oil. The crude product was purified by chromatography on silica gel (12 g cartridge, 0-100% EtOAc/isohexane) to afford 3-(1-(4-fluorophenyl)-6-methyl-1H-indazol-5-yl)-1-((1-methyl-1H-pyrazol-4-yl)sulfonyl)pyrrolidine-3-carbaldehyde (Intermediate AZ) (30 mg, 60 μmol, 94%) as a white solid; R$^t$ 1.45 min (Method 1); m/z 468.4 (M+H)$^+$ (ES$^+$). δ$_H$ (500 MHz, DMSO-d$_6$) δ 9.34 (s, 1H), 8.39-8.31 (m, 2H), 7.86-7.82 (m, 2H), 7.81-7.77 (m, 2H), 7.65 (s, 1H), 7.46-7.39 (m, 2H), 4.23 (d, J=10.3 Hz, 1H), 3.81 (s, 3H), 3.36-3.33 (m, 2H), 3.15-3.05 (m, 1H), 2.75 (ddd, J=11.6, 7.0, 3.7 Hz, 1H), 2.31 (dt, J=12.9, 8.4 Hz, 1H), 2.26 (s, 3H).

Example 342: (E)-1-(4-fluorophenyl)-6-methyl-5-(1-((1-methyl-1H-pyrazol-4-yl)sulfonyl)-3-styrylpyrrolidin-3-yl)-1H-indazole

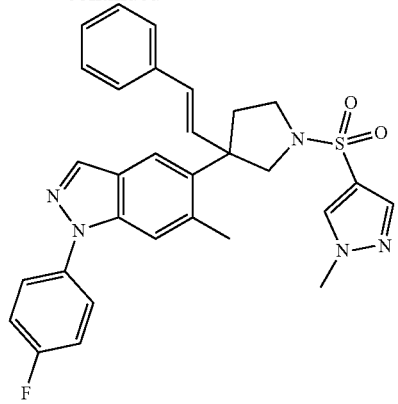

To a solution of diethoxyphosphorylmethylbenzene (37 mg, 33 μL, 0.16 mmol) in THF (1 mL) at 0° C. was added sodium hydride (60% dispersion in mineral oil) (6.4 mg, 60% Wt, 0.16 mmol). The reaction mixture was stirred at 0° C. for 1 hour before a solution of 3-(1-(4-fluorophenyl)-6-methyl-1H-indazol-5-yl)-1-((1-methyl-1H-pyrazol-4-yl)sulfonyl)pyrrolidine-3-carbaldehyde (25 mg, 53 μmol) (Intermediate AZ) in THF (1 mL) was added. The resultant solution was allowed to warm up to room temperature and stirred at for 4 hours. The reaction mixture was quenched by adding a saturated solution of NaHCO$_3$ (10 mL) and extracted by EtOAc (3×10 mL). The organic layers were combined and dried over MgSO$_4$. The solvent was removed to afford a colourless residue. The crude product was purified by chromatography on silica gel (12 g cartridge, 0-100% EtOAc/isohexane) to afford (E)-1-(4-fluorophenyl)-6-methyl-5-(1-((1-methyl-1H-pyrazol-4-yl)sulfonyl)-3-styrylpyrrolidin-3-yl)-1H-indazole (10 mg, 18 μmol, 34%) (Example 342) as a white solid; R$^t$ 1.81 min (Method 1); m/z 542.4 (M+H)$^+$ (ES$^+$). δ$_H$ (500 MHz, DMSO-d$_6$) δ 8.39 (s, 1H), 8.31 (d, J=0.9 Hz, 1H), 7.91 (d, J=0.7 Hz, 1H), 7.83-7.77 (m, 3H), 7.61 (s, 1H), 7.45-7.40 (m, 2H), 7.30-7.24 (m, 2H), 7.22-7.17 (m, 3H), 6.26 (d, J=16.2 Hz, 1H), 5.99 (d, J=16.2 Hz, 1H), 3.97 (d, J=10.2 Hz, 1H), 3.74 (s, 3H), 3.47 (d, J=10.3 Hz, 1H), 3.45-3.40 (m, 1H), 3.33 (m, 1H), 2.50 (m, 1H), 2.44-2.40 (m, 3H), 2.40-2.36 (m, 1H).

Example 343: 1-(4-fluorophenyl)-6-methyl-5-(1-((1-methyl-1H-pyrazol-4-yl)sulfonyl)-3-phenethylpyrrolidin-3-yl)-1H-indazole

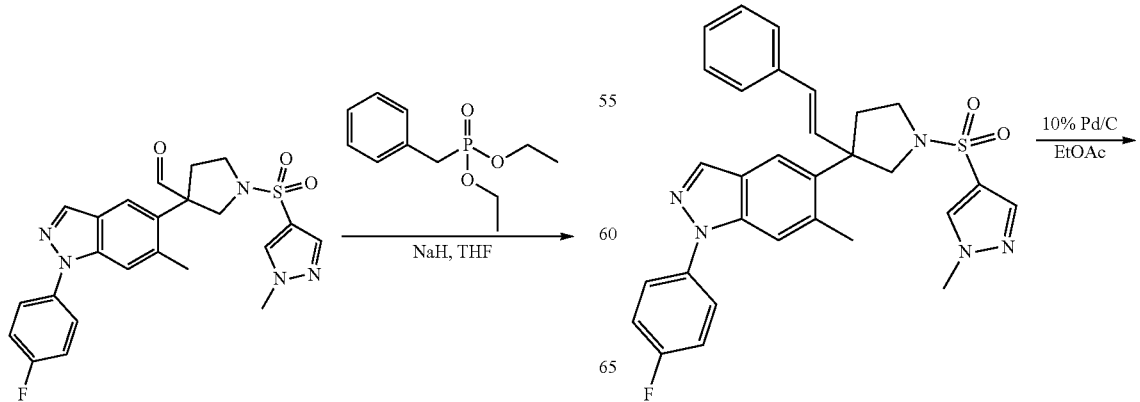

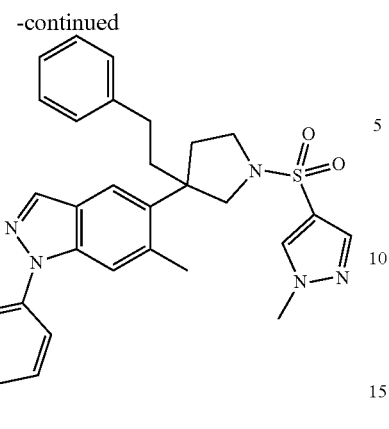

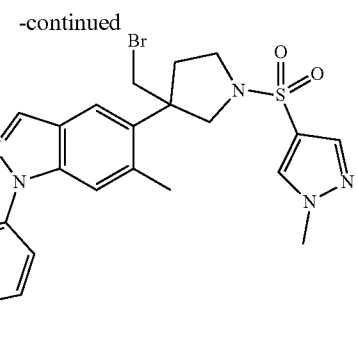

To a solution of (E)-1-(4-fluorophenyl)-6-methyl-5-(1-((1-methyl-1H-pyrazol-4-yl)sulfonyl)-3-styrylpyrrolidin-3-yl)-1H-indazole (Example 342) (6 mg, 0.01 mmol) in EtOAc (1 mL) was added palladium on carbon (type 39) (1 mg, 10% Wt, 1 μmol) and the reaction mixture was stirred under 2 bars of hydrogen (hydrogenation vessel) for 150 minutes. The reaction mixture was filtered through a Whatman GF/F filter pad and rinsed with EtOAc (3×1 mL). The combined filtrate was concentrated in vacuo to afford a colourless oil. The crude product was purified by chromatography on silica gel (200 mg cartridge, 20-80% EtOAc/isohexane) to afford 1-(4-fluorophenyl)-6-methyl-5-(1-((1-methyl-1H-pyrazol-4-yl)sulfonyl)-3-phenethylpyrrolidin-3-yl)-1H-indazole (Example 343) (4.0 mg, 7.2 μmol, 65%, 97.6%) as a white solid; $R^t$ 1.83 min (Method 1); m/z 544.1 (M+H)$^+$ (ES$^+$). $\delta_H$ (500 MHz, DMSO-d$_6$) δ 8.40 (s, 1H), 8.29 (d, J=0.9 Hz, 1H), 7.89 (d, J=0.7 Hz, 1H), 7.84-7.75 (m, 2H), 7.64 (d, J=12.8 Hz, 2H), 7.47-7.39 (m, 2H), 7.19 (dd, J=8.2, 6.8 Hz, 2H), 7.14-7.07 (m, 1H), 6.93-6.87 (m, 2H), 3.84 (d, J=10.1 Hz, 1H), 3.73 (s, 3H), 3.41-3.34 (m, 2H), 3.31-3.27 (m, 1H), 2.56 (s, 4H), 2.29-2.15 (m, 2H), 2.02-1.93 (m, 1H), 1.83 (td, J=13.3, 4.7 Hz, 1H), 1.61-1.51 (m, 1H).

Example 344: 1-(4-fluorophenyl)-6-methyl-5-(1-((1-methyl-1H-pyrazol-4-yl)sulfonyl)-3-(phenoxymethyl)pyrrolidin-3-yl)-1H-indazole Intermediate BA: 5-(3-(bromomethyl)-1-((1-methyl-1H-pyrazol-4-yl)sulfonyl)pyrrolidin-3-yl)-1-(4-fluorophenyl)-6-methyl-1H-indazole To a solution of (3-(1-(4-fluorophenyl)-6-methyl-1H-indazol-5-yl)-1-((1-methyl-1H-pyrazol-4-yl)sulfonyl)pyrrolidin-3-yl)methanol (30 mg, 64 μmol) (Intermediate AY) and triphenylphosphine (20 mg, 77 μmol) in dichloromethane (2 mL) at 0° C. was added carbon tetrabromide (25 mg, 77 μmol). The resultant colourless solution was stirred at 0° C. for 2 hours and allowed to warm up to room temperature and stirred for 16 hours. Further carbon tetrabromide (32 mg, 96 μmol) and triphenylphosphine (25 mg, 96 μmol) were added and the pale yellow solution was heated at 35° C. for 20 hours. The reaction was quenched with a saturated solution of NaHCO$_3$ (10 mL) and extracted with EtOAc (3×10 mL). The organic layers were combined and washed with brine (10 mL) and passed through a phase separator. The solvent was removed under reduced pressure to afford a colourless residue. The crude product was purified by chromatography on silica gel (12 g cartridge, 0-100% EtOAc/isohexane) to afford 5-(3-(bromomethyl)-1-((1-methyl-1H-pyrazol-4-yl)sulfonyl)pyrrolidin-3-yl)-1-(4-fluorophenyl)-6-methyl-1H-indazole (Intermediate BA) (23 mg, 37 μmol, 57%) as a white solid; $R^t$ 1.61 min (Method 1); m/z 532.4/534.4 (M+H)$^+$ (ES$^+$). $\delta_H$ (500 MHz, DMSO-d$_6$) δ 8.41 (s, 1H), 8.29 (d, J=0.9 Hz, 1H), 7.91 (d, J=0.7 Hz, 1H), 7.81-7.77 (m, 2H), 7.61 (s, 1H), 7.58 (s, 1H), 7.45-7.40 (m, 2H), 3.95 (d, J=10.2 Hz, 1H), 3.83 (s, 4H), 3.72 (d, J=10.8 Hz, 1H), 3.42-3.36 (m, 2H), 3.26 (dt, J=9.9, 4.8 Hz, 1H), 2.63-2.56 (m, 1H), 2.54 (s, 3H), 2.31-2.26 (m, 1H).

Example 344: 1-(4-fluorophenyl)-6-methyl-5-(1-((1-methyl-1H-pyrazol-4-yl)sulfonyl)-3-(phenoxymethyl)pyrrolidin-3-yl)-1H-indazole

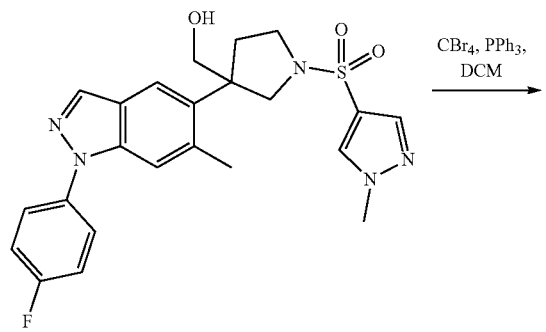 →(CBr$_4$, PPh$_3$, DCM)→ 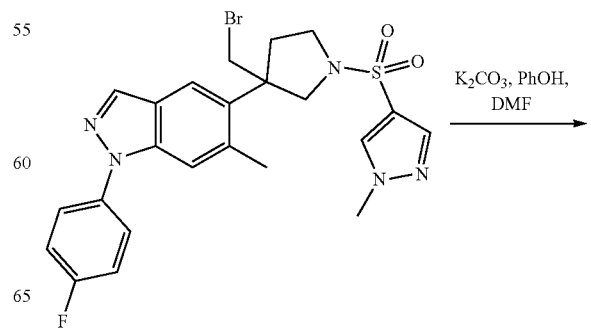 →(K$_2$CO$_3$, PhOH, DMF)→

481
-continued

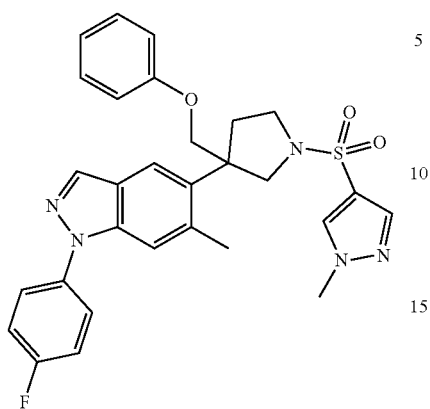

To a solution of of 5-(3-(bromomethyl)-1-((1-methyl-1H-pyrazol-4-yl)sulfonyl)pyrrolidin-3-yl)-1-(4-fluorophenyl)-6-methyl-1H-indazole (Intermediate BA) (10 mg, 19 µmol) and phenol (5.3 mg, 56 µmol) in DMF (1 mL) was added potassium carbonate (13 mg, 94 µmol). The reaction mixture was heated at 80° C. for 4 days. The reaction mixture was quenched by adding a saturated solution of NaHCO$_3$ (10 mL) and extracted with EtOAc (3×10 mL). The organic layers were combined and passed through a hydrophobic frit. The solvent was removed under reduced pressure to afford a yellow residue. The crude product was purified by chromatography on silica gel (4 g cartridge, 0-100% EtOAc/isohexane) and by reversed phase preparative HPLC on a Waters X-Select CSH column C18, 5 µm 30×100 mm, flow rate 40 mL min$^{-1}$ eluting with a 0.1% Formic Acid in water-MeCN gradient over 12 mins using UV detection across all wavelengths with PDA as well as an ELS Detector. At-Column dilution pump gives 2 mL min$^{-1}$ MeCN over the entire method, which is included in the following MeCN percentages. Gradient information: 0.0-0.5 min, 40% MeCN; 0.5-10.5 min, ramped from 40% MeCN to 70% MeCN; 10.5-10.6 min, ramped from 70% MeCN to 100% MeCN; 10.6-12 min, held at 100% MeCN. The clean fractions were evaporated in a genevac and the residues were suspended in acetonitrile and MeOH, pooled, and evaporated on a V10. The solid was further dried in a vacuum oven at 30° C./5 mbar for 4h to afford 1-(4-fluorophenyl)-6-methyl-5-(1-((1-methyl-1H-pyrazol-4-yl)sulfonyl)-3-(phenoxymethyl)pyrrolidin-3-yl)-1H-indazole (5.0 mg, 8.9 µmol, 47%) (Example 344) as a white solid; R$^t$ 1.73 min (Method 1); m/z 546.4 (M+H)$^+$ (ES$^+$). $\delta_H$ (500 MHz, DMSO-d$_6$) δ 8.40 (s, 1H), 8.28 (d, J=0.9 Hz, 1H), 7.92 (d, J=0.7 Hz, 1H), 7.79-7.74 (m, 2H), 7.72 (s, 1H), 7.58 (s, 1H), 7.43-7.37 (m, 2H), 7.23-7.17 (m, 2H), 6.88 (tt, 0.7=7.3, 1.1 Hz, 1H), 6.71-6.66 (m, 2H), 4.10 (d, J=10.3 Hz, 1H), 3.83 (d, J=9.6 Hz, 1H), 3.73 (d, J=9.7 Hz, 1H), 3.71 (s, 3H), 3.42 (d, J=10.3 Hz, 1H), 3.39-3.33 (m, 2H),$^{(4)}$ 2.74-2.67 (m, 1H), 2.61 (s, 3H), 2.25 (dt, J=12.5, 9.5 Hz, 1H).

482

Example 345: (3-(1-(4-fluorophenyl)-6-methyl-1H-indazol-5-yl)-1-((1-methyl-1H-pyrazol-4-yl)sulfonyl)pyrrolidin-3-yl)(phenyl)methanone Intermediate BB: (3-(1-(4-fluorophenyl)-6-methyl-1H-indazol-5-yl)-1-((1-methyl-1H-pyrazol-4-yl)sulfonyl)pyrrolidin-3-yl)(phenyl)methanol

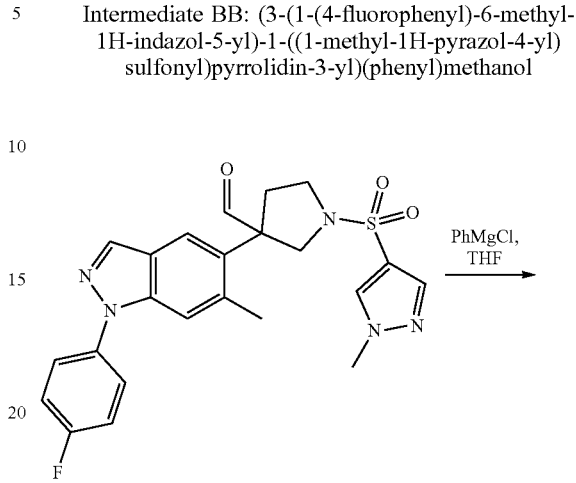

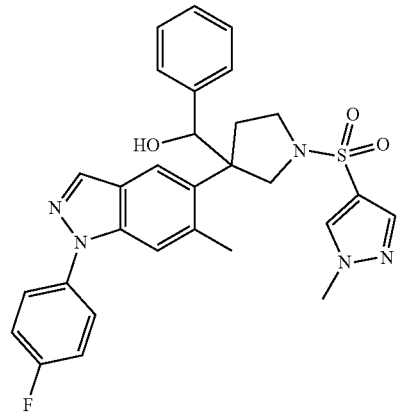

To a solution of 3-(1-(4-fluorophenyl)-6-methyl-1H-indazol-5-yl)-1-((1-methyl-1H-pyrazol-4-yl)sulfonyl)pyrrolidine-3-carbaldehyde (Intermediate AZ) (65 mg, 0.14 mmol) in THF (2 mL) at 0° C. was added phenylmagnesium chloride (2 M in THF) (38 mg, 0.14 mL, 2 molar, 0.28 mmol). The resultant solution was stirred at 0° C. for 2 hours. The reaction mixture was quenched with a saturated solution of NaHCO$_3$ (15 mL) and extracted with EtOAc (3×15 mL). The organic layers were combined and passed through a hydrophobic frit. The solvent was removed under reduced pressure to afford a colourless residue. The crude product was purified by chromatography on silica gel (12 g cartridge, 0-100% EtOAc/isohexane) to afford (3-(1-(4-fluorophenyl)-6-methyl-1H-indazol-5-yl)-1-((1-methyl-1H-pyrazol-4-yl)sulfonyl)pyrrolidin-3-yl)(phenyl)methanol (Intermediate BB) (45 mg, 77 µmol, 55%) as a white solid; R$^t$ 1.73 min (Method 1); m/z 546.4 (M+H)$^+$ (ES$^+$).

Example 345: (3-(1-(4-fluorophenyl)-6-methyl-1H-indazol-5-yl)-1-((1-methyl-1H-pyrazol-4-yl)sulfonyl)pyrrolidin-3-yl)(phenyl)methanone

Example 346: 1-(4-fluorophenyl)-6-methyl-5-(1-((1-methyl-1H-pyrazol-4-yl)sulfonyl)-3-(3-phenylpropyl)pyrrolidin-3-yl)-1H-indazole

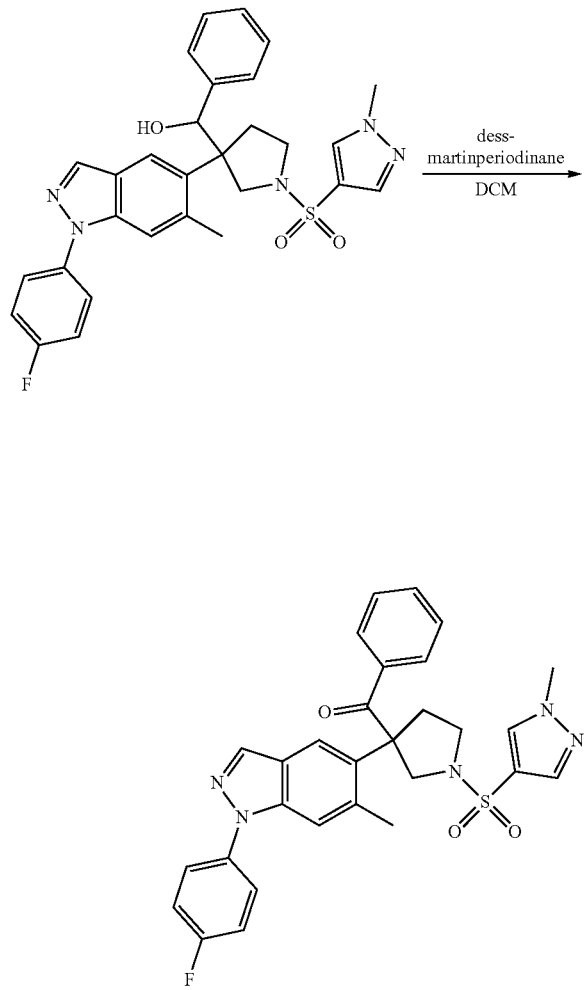

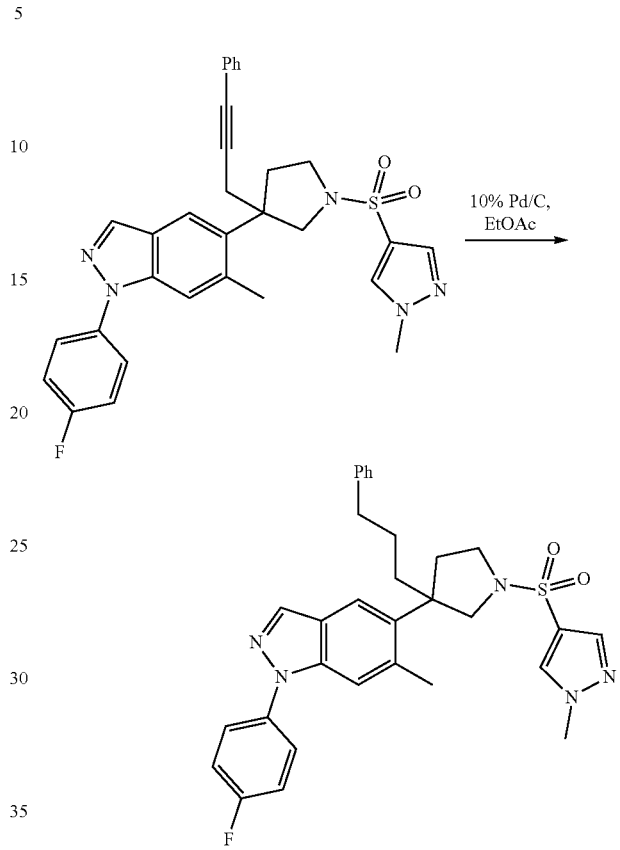

To a solution (3-(1-(4-fluorophenyl)-6-methyl-1H-indazol-5-yl)-1-((1-methyl-1H-pyrazol-4-yl)sulfonyl)pyrrolidin-3-yl)(phenyl)methanol (15 mg, 27 μmol) (Intermediate BB) in DCM (2 mL) at 0° C. was added dess-martinperiodinane (23 mg, 55 μmol). The resultant colourless solution was stirred at 0° C. for 2 hours. The reaction mixture was partitioned between EtOAc (10 mL) and a saturated solution of NaHCO₃ (10 mL) and the phases were separated. The organic layer was dried over MgSO₄ and filtered. The solvent was removed under reduced pressure to afford a colourless oil. The crude product was purified by chromatography on silica gel (12 g cartridge, 0-100% EtOAc/ isohexane) to afford (3-(1-(4-fluorophenyl)-6-methyl-1H-indazol-5-yl)-1-((1-methyl-1H-pyrazol-4-yl)sulfonyl) pyrrolidin-3-yl)(phenyl)methanone (Example 345) (9.0 mg, 16 μmol, 58%) as a white solid; R$^r$ 1.64 min (Method 1); m/z 544.3 (M+H)$^+$ (ES$^+$). δ$_H$ (500 MHz, DMSO-d$_6$) δ 8.37 (d, J=0.9 Hz, 1H), 8.30 (s, 1H), 8.10 (s, 1H), 7.81 (s, 1H), 7.79-7.74 (m, 2H), 7.65-7.60 (m, 2H), 7.54 (s, 1H), 7.47-7.42 (m, 1H), 7.42-7.36 (m, 2H), 7.31-7.26 (m, 2H), 4.10-3.94 (m, 1H), 3.76 (s, 3H), 3.44-3.34 (m, 2H), 3.07 (s, 1H), 2.65-2.55 (m, 2H), 2.12 (d, J=0.9 Hz, 3H).

To a solution of 1-(4-fluorophenyl)-6-methyl-5-(1-((1-methyl-1H-pyrazol-4-yl)sulfonyl)-3-(3-phenylprop-2-yn-1-yl)pyrrolidin-3-yl)-1H-indazole (10 mg, 94% Wt, 17 μmol) (Example 211) in EtOAc (2 mL) was added was added Pd/C (type 39) (1.8 mg, 10% Wt, 1.7 μmol) and the reaction mixture was stirred under 2 bars of hydrogen (hydrogenation vessel) for 150 minutes. The reaction mixture was filtered through a Whatman GF/F filter pad and rinsed with EtOAc (3×10 mL). The combined filtrate was concentrated in vacuo to afford a colourless oil. The crude product was purified by chromatography on silica gel (4 g cartridge, 0-50% EtOAc/ isohexane) to afford 1-(4-fluorophenyl)-6-methyl-5-(1-((1-methyl-1H-pyrazol-4-yl)sulfonyl)-3-(3-phenylpropyl)pyrrolidin-3-yl)-1H-indazole (Example 346) (5.0 mg, 8.5 μmol, 50%) as a white solid; R$^r$ 1.86 min (Method 1); m/z 558.4 (M+H)$^+$ (ES$^+$). δ$_H$ (500 MHz, DMSO-d$_6$) δ 8.40 (s, 1H), 8.22 (d, J=1.0 Hz, 1H), 7.88 (d, J=0.7 Hz, 1H), 7.81-7.75 (m, 2H), 7.56 (d, J=10.2 Hz, 2H), 7.45-7.38 (m, 2H), 7.20-7.15 (m, 2H), 7.13-7.08 (m, 1H), 7.00-6.95 (m, 2H), 3.83 (s, 3H), 3.75 (d, J=9.9 Hz, 1H), 3.32-3.28 (m, 2H), 3.28-3.22 (m, 1H), 2.44 (s, 3H), 2.42-2.36 (m, 1H),[2] 2.31 (t, J=7.6 Hz, 2H), 2.11-2.02 (m, 1H), 1.64-1.55 (m, 1H), 1.48-1.37 (m, 1H), 1.31-1.15 (m, 1H), 1.06-1.00 (m, 1H).

Example 347: GR Binding Assay

Binding of test compounds to the glucocorticoid receptor (GR) is determined using a fluorescence polarisation (FP) assay utilising a recombinant ligand binding domain (LBD)

of GR. The test compounds are assessed by their ability to displace a fluorescently tagged ligand and detection of the resulting decrease in fluorescence polarisation. Fluorescence polarisation values are converted to % inhibition using the high (1% DMSO only) and low (1 µM CORT125134, (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone of U.S. Pat. No. 8,859,774) controls and $IC_{50}$ values are calculated from non-linear regression curves fitted using Dotmatics software.

Example 348: Hep G2 TAT Ki

Glucocorticoid mediated activation of TAT occurs by transactivation of glucocorticoid response elements in the TAT promoter by glucocorticoid receptor-agonist complex. The following protocol describes an assay for measuring induction of TAT by dexamethasone in HepG2 cells (a human liver hepatocellular carcinoma cell line; ECACC, UK).

TAT activity was measured as outlined in the literature by A. Ah et al., J. Med. Chem., 2004, 47, 2441-2452. Dexamethasone induced TAT production with an average $EC_{50}$ value (half-maximal effect) of 20 nM.

HepG2 cells were cultured using MEME media supplemented with 10% (v/v) foetal bovine serum; 2 mM L-glutamine and 1% (v/v) NEAA at 37° C., 5%/95% (v/v) $CO_2$/air. The HepG2 cells were counted and adjusted to yield a density of $0.125 \times 10^6$ cells/ml in RPMI 1640 without phenol red, 10% (v/v) charcoal stripped FBS, 2 mM L-glutamine and seeded at 25,000 cells/well in 200 µl into 96 well, sterile, tissue culture micro titre plates, and incubated at 37° C., 5% $CO_2$ for 24 hours Growth media was removed and replaced with assay media {RPMI 1640 without phenol red, 2 mM L-glutamine+ 10 µM forskolin}. Test compounds were screened against a challenge of 100 nM dexamethasone. Compounds were serially half log diluted in 100% (v/v) dimethylsulphoxide from a 10 mM stock. Then an 8-point half-log dilution curve was generated followed by a 1:100 dilution into assay media to give a 10× final assay [compound]: this resulted in final assay [compound] that ranged 10 to 0.003 µM in 0.1% (v/v) dimethylsulfoxide.

Test compounds were pre-incubated with cells in microtitre plates for 30 minutes at 37° C., 5/95 (v/v) $CO_2$/air, before the addition of 100 nM dexamethasone and then subsequently for 20 hours to allow optimal TAT induction.

HepG2 cells were then lysed with 30 µl of cell lysis buffer containing a protease inhibitor cocktail for 15 minutes at 4° C. 155 µl of substrate mixture was then added containing 5.4 mM Tyrosine sodium salt, 10.8 mM alpha ketoglutarate and 0.06 mM pyridoxal 5' phosphate in 0.1M potassium phosphate buffer (pH 7.4). After 2 hours incubation at 37° C. the reaction was terminated by the addition of 15 µl of 10M aqueous potassium hydroxide solution, and the plates incubated for a further 30 minutes at 37° C. The TAT activity product was measured by absorbance at λ 340 nm.

$IC_{50}$ values were calculated by plotting % inhibition (normalised to 100 nM dexamethasone TAT stimulation) v. [compound] and fitting the data to a 4 parameter logistic equation. $IC_{50}$ values were converted to Ki (equilibrium dissociation constant) using the Cheng and Prusoff equation, assuming the antagonists were competitive inhibitors with respect to dexamethasone.

TABLE 15

Activity Data

| Example No. | Mean GR Binding $IC_{50}$ (nM) | Hep G2TATKi (nM) |
| --- | --- | --- |
| 1 | 930 | 594 |
| 2 | 1940 | |
| 3 | 206 | 10000 |
| 4 | 2 | |
| 5 | 126 | |
| 6 | 148 | 118 |
| 7 | 6114 | |
| 8 | 214 | 238 |
| 9 | 527 | |
| 10 | 214 | 238 |
| 11 | 258 | |
| 12 | 236 | |
| 13 | 82 | |
| 14 | 357 | 10000 |
| 15 | 455 | 10000 |
| 16 | 8 | 32 |
| 17 | 52 | 23 |
| 18 | 24 | 9 |
| 19 | | 142 |
| 20 | 8 | 236 |
| 21 | 884 | |
| 22 | 857 | |
| 23 | 1300 | 10000 |
| 24 | 84 | 1514 |
| 25 | 67 | 29 |
| 26 | | 50 |
| 27 | | 759 |
| 28 | 114 | 1062 |
| 29 | 9 | 210 |
| 30 | | 206 |
| 31 | 1357 | |
| 32 | 70 | 400 |
| 33 | 67 | 660 |
| 34 | 1104 | 10000 |
| 35 | 1813 | |
| 36 | 3550 | |
| 37 | 396 | 10000 |
| 38 | 1953 | |
| 39 | 81 | 242 |
| 40 | 546 | 10000 |
| 41 | 937 | |
| 42 | 2315 | |
| 43 | 95 | 467 |
| 44 | 1564 | |
| 45 | 562 | |
| 46 | 1133 | |
| 47 | 1411 | |
| 48 | 4051 | |
| 49 | 8225 | |
| 50 | 27 | 480 |
| 51 | 360 | 10000 |
| 52 | 700 | |
| 53 | 244 | 10000 |
| 54 | 142 | 10000 |
| 55 | 21 | 10000 |
| 56 | 80 | 1294 |
| 57 | 249 | 10000 |
| 58 | 32 | 321 |
| 59 | 19 | 246 |
| 60 | 8 | 39 |
| 61 | 25 | 205 |
| 62 | 431 | |
| 63 | 215 | |
| 64 | 151 | 10000 |
| 65 | 334 | 1482 |
| 66 | 429 | |
| 67 | 18 | 33 |
| 68 | 35 | 30 |
| 69 | 1158 | |
| 70 | 28 | 1583 |
| 71 | 238 | |
| 72 | 3745 | |
| 73 | 151 | 306 |
| 74 | 66 | |
| 75 | 325 | |

TABLE 15-continued

Activity Data

| Example No. | Mean GR Binding IC$_{50}$ (nM) | Hep G2TATKi (nM) |
|---|---|---|
| 76 | 83 | |
| 77 | 1045 | |
| 78 | | 70 |
| 79 | | 84 |
| 80 | | 536 |
| 81 | | 58 |
| 82 | | 65 |
| 83 | 515 | |
| 84 | 10 | 103 |
| 85 | 163 | 1420 |
| 86 | 162 | 864 |
| 87 | | 42 |
| 88 | 7230 | |
| 89 | 434 | |
| 90 | 45 | 343 |
| 91 | 227 | 336 |
| 92 | | 495 |
| 93 | | 216 |
| 94 | 52 | 95 |
| 95 | 612 | |
| 96 | 2556 | |
| 97 | 1813 | |
| 98 | 749 | |
| 99 | 898 | |
| 100 | 233 | 1196 |
| 101 | 118 | 823 |
| 102 | 267 | 10000 |
| 103 | 135 | 1707 |
| 104 | 270 | 10000 |
| 105 | 320 | |
| 106 | 9 | |
| 107 | 3 | |
| 108 | 7 | |
| 109 | 48 | |
| 110 | 46 | |
| 111 | 3 | |
| 112 | 249 | |
| 113 | 52 | |
| 114 | 304 | |
| 115 | 21 | |
| 116 | 72 | |
| 117 | 57 | |
| 118 | | 1640 |
| 119 | | 251 |
| 120 | 3 | 218 |
| 121 | 40 | 120 |
| 122 | 14 | 155 |
| 123 | 73 | 284 |
| 124 | 58 | 216 |
| 125 | 208 | |
| 126 | 190 | |
| 127 | 174 | |
| 128 | 590 | |
| 129 | 5 | 66 |
| 130 | 8 | 144 |
| 131 | 4 | 98 |
| 132 | 13 | 34 |
| 133 | 7 | 50 |
| 134 | 3379 | |
| 135 | 473 | |
| 136 | 102 | 10000 |
| 137 | 308 | |
| 138 | 101 | |
| 139 | 218 | |
| 140 | | 50 |
| 141 | 4225 | 487 |
| 142 | 429 | 715 |
| 143 | 384 | 32 |
| 144 | 265 | 180 |
| 145 | | 208 |
| 146 | | 942 |
| 147 | 42 | 12 |
| 148 | 24 | 331 |
| 149 | 13 | 108 |
| 150 | 13 | 169 |
| 151 | 17 | 161 |
| 152 | 13 | 63 |
| 153 | 11 | 26 |
| 154 | 269 | 14 |
| 155 | 13 | 16 |
| 156 | 11 | 36 |
| 157 | | 257 |
| 158 | | 161 |
| 159 | | 101 |
| 160 | 5 | 24 |
| 161 | 11 | 39 |
| 162 | 18 | 16 |
| 163 | 106 | 60 |
| 164 | 189 | 89 |
| 165 | 72 | 37 |
| 166 | 14 | 26 |
| 167 | 8 | 256 |
| 168 | 6 | 67 |
| 169 | 217 | 159 |
| 170 | 123 | 104 |
| 171 | 67 | 171 |
| 172 | 58 | 83 |
| 173 | 66 | 69 |
| 174 | 9 | 28 |
| 175 | 24 | 20 |
| 176 | 60 | 33 |
| 177 | 212 | 28 |
| 178 | 197 | 30 |
| 179 | | 331 |
| 180 | | 809 |
| 181 | | 165 |
| 182 | | 24 |
| 183 | | 182 |
| 184 | | 252 |
| 185 | | 164 |
| 186 | | 37 |
| 187 | | 199 |
| 188 | | 173 |
| 189 | 11 | 91 |
| 190 | 5 | 55 |
| 191 | 6 | 61 |
| 192 | 14 | 72 |
| 193 | 28 | 25 |
| 194 | 109 | 102 |
| 195 | | 70 |
| 196 | | 79 |
| 197 | | 65 |
| 198 | | 30 |
| 199 | | 33 |
| 200 | | 59 |
| 201 | | 48 |
| 202 | | 67 |
| 203 | | 21 |
| 204 | | 71 |
| 205 | | 109 |
| 206 | | 59 |
| 207 | | 594 |
| 208 | | 152 |
| 209 | 3900 | |
| 210 | | 41 |
| 211 | | 47 |
| 212 | 9 | 19 |
| 213 | 17 | 13 |
| 215 | 10 | 10 |
| 216 | | 53 |
| 217 | 17 | 14 |
| 218 | 14 | 10 |
| 219 | 26 | 13 |
| 220 | | 24 |
| 221 | 56 | 45 |
| 222 | 11 | 39 |
| 223 | 14 | 38 |
| 224 | | 21 |
| 225 | | 15 |
| 226 | 21 | 13 |

TABLE 15-continued

Activity Data

| Example No. | Mean GR Binding IC$_{50}$ (nM) | Hep G2TATKi (nM) |
|---|---|---|
| 227 | | 350 |
| 228 | | 28 |
| 229 | | 210 |
| 230 | | 74 |
| 231 | 13 | 48 |
| 232 | 10 | 37 |
| 233 | 70 | 52 |
| 234 | | 150 |
| 235 | 12 | 34 |
| 236 | | 81 |
| 237 | 4.8 | 22 |
| 238 | | 64 |
| 239 | 28 | 36 |
| 240 | | 73 |
| 241 | | 44 |
| 242 | 18 | 44 |
| 243 | 65 | 38 |
| 244 | | 840 |
| 245 | | 190 |
| 246 | 6.3 | 49 |
| 247 | 55 | 240 |
| 248 | 55 | 260 |
| 249 | 4.8 | 39 |
| 250 | 4.1 | 26 |
| 251 | 27 | 180 |
| 252 | 29 | 94 |
| 253 | 24 | 240 |
| 254 | 87 | 44 |
| 255 | 27 | 44 |
| 256 | 990 | 170 |
| 257 | 52 | 220 |
| 258 | 31 | 76 |
| 259 | 180 | 540 |
| 260 | 150 | 350 |
| 261 | 2.9 | 44 |
| 262 | 280 | 190 |
| 263 | 110 | 100 |
| 264 | 26 | 210 |
| 265 | 16 | 120 |
| 266 | 4.7 | 40 |
| 267 | 5.6 | 93 |
| 268 | | 160 |
| 269 | | 1300 |
| 270 | | 600 |
| 271 | 20 | 55 |
| 272 | 22 | 29 |
| 273 | | 280 |
| 274 | 81 | 290 |
| 275 | 18 | 70 |
| 276 | 5.4 | 52 |
| 277 | | 54 |
| 278 | | 44 |
| 279 | | 50 |
| 280 | | 42 |
| 281 | | 75 |
| 282 | | 120 |
| 283 | | 64 |
| 284 | | 58 |
| 285 | | 82 |
| 286 | 11 | 52 |
| 287 | 6.7 | 25 |
| 288 | 33 | 110 |
| 289 | 13 | 69 |
| 290 | 62 | 200 |
| 291 | | 110 |
| 292 | 14 | 110 |
| 293 | 6.1 | 100 |
| 294 | 4 | 41 |
| 295 | 6.3 | 62 |
| 296 | 6.9 | 44 |
| 297 | 10 | 36 |
| 298 | 3.6 | 37 |
| 299 | 8.8 | 48 |
| 300 | 4.6 | 36 |
| 301 | 4.8 | 25 |
| 302 | 12 | 27 |
| 303 | 4.4 | 24 |
| 304 | 7.5 | 48 |
| 305 | 3 | 32 |
| 306 | 11 | 56 |
| 307 | 8.8 | 89 |
| 308 | 14 | 62 |
| 309 | 11 | 66 |
| 310 | 11 | 66 |
| 311 | 3 | 29 |
| 312 | 12 | 41 |
| 313 | 8.3 | 50 |
| 314 | 11 | 56 |
| 315 | 6.7 | 29 |
| 316 | 12 | 32 |
| 317 | 8.9 | 23 |
| 318 | 5.1 | 48 |
| 319 | | 46 |
| 320 | 12 | 46 |
| 321 | 14 | 270 |
| 322 | 24 | 77 |
| 323 | 12 | 97 |
| 324 | 7.5 | 64 |
| 325 | 28 | 110 |
| 326 | 44 | 57 |
| 327 | 170 | 540 |
| 328 | 18 | 110 |
| 329 | 10 | 140 |
| 330 | 16 | 200 |
| 331 | 15 | 100 |
| 332 | 20 | 160 |
| 333 | | 41 |
| 334 | | 52 |
| 335 | 11 | 46 |
| 336 | 180 | 120 |
| 337 | 250 | 110 |
| 338 | 26 | 120 |
| 339 | 44 | 120 |
| 340 | 57 | 820 |
| 341 | 390 | 170 |
| 342 | | 110 |
| 343 | | 120 |
| 344 | | 97 |
| 345 | | 220 |
| 346 | | 140 |

Although the foregoing invention has been described in some detail by way of illustration and Examples for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound having the structure of Formula IVa:

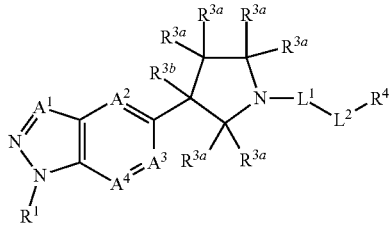

(IVa)

or a pharmaceutically acceptable salt thereof, wherein $R^1$ is heterocycloalkyl having 5 to 6 ring members and 1 to 2 heteroatoms each N, phenyl or a heteroaryl having 5 to 6 ring members and 1 to 2 heteroatoms each N or S, each substituted with 1 to 3 $R^{1a}$ groups;

each $R^{1a}$ is independently hydrogen, $C_{1-3}$ alkyl, $C_{1-3}$ deuteroalkyl, $C_{1-3}$ alkoxy, $C_{1-3}$ hydroxyalkyl, halogen, $C_{1-3}$ haloalkyl, oxo, —CN, $C_{3-6}$ cycloalkyl, or heterocycloalkyl having 3 to 5 ring members and 1 to 2 heteroatoms each N or O;

$A^1$, $A^2$, $A^3$ and $A^4$ are each independently =CR²— or =N—;

each $R^2$ is independently hydrogen, $C_{1-6}$ alkyl, $C_{1-6}$ alkoxy, $C_{2-6}$ alkoxyalkyl, halogen, $C_{1-6}$ haloalkyl, $C_{1-6}$ haloalkoxy, hydroxy or —CN;

each $R^{3a}$ is independently hydrogen, OH, or oxo;

$R^{3b}$ is $C_{1-6}$ alkyl, $C_{2-6}$ alkynyl, $C_{2-6}$ alkoxyalkyl, $C_{2-6}$ alkynyl-$C_{3-6}$ cycloalkyl, $C_{1-6}$ alkyl-$C_{6-12}$ aryl, $C_{2-6}$ alkenyl-$C_{6-12}$ aryl, $C_{2-6}$ alkynyl-$C_{6-12}$ aryl, $C_{1-6}$ alkyl-O-$C_{6-12}$ aryl, $C_{1-6}$ alkoxyalkyl-$C_{6-12}$ aryl, —C(O)—$C_{6-12}$ aryl, or $C_{1-6}$ alkyl-heteroaryl, wherein each heteroaryl has 5 to 10 ring members and 1 to 3 heteroatoms each independently N, O or S, and wherein each aryl and heteroaryl are substituted with 1 to 3 $R^{3b3}$ groups;

each $R^{3b3}$ is hydrogen, $C_{1-6}$ alkyl, $C_{1-6}$ alkoxy, $C_{2-6}$ alkoxyalkyl, $C_{1-6}$ hydroxyalkyl, halogen, $C_{1-6}$ haloalkyl, or $C_{1-6}$ haloalkoxy;

$R^4$ is $C_{1-6}$ alkyl, $C_{1-6}$ haloalkyl, —CN, $C_{3-8}$ cycloalkyl, 3 to 8 membered heterocycloalkyl having 1 to 3 heteroatoms each independently N, O or S, $C_{6-12}$ aryl, or 5 to 10 membered heteroaryl having 1 to 5 heteroatoms each independently N, O or S, wherein the cycloalkyl, heterocycloalkyl, aryl and heteroaryl are each independently substituted with 1 to 5 $R^{4a}$ groups;

each $R^{4a}$ is hydrogen, $C_{1-6}$ alkyl, $C_{1-6}$ deuteroalkyl, $C_{1-6}$ alkoxy, $C_{2-6}$ alkoxyalkyl, $C_{1-6}$ hydroxyalkyl, halogen, $C_{1-6}$ haloalkyl, —CN, —OH, oxo, —S(O)$_2$R$^{4b}$, —S(O)$_2$N(R$^{4b}$)(R$^{4c}$), $C_{3-6}$ cycloalkyl, $C_{6-12}$ aryl, $C_{6-12}$ aryl, wherein each aryl is optionally substituted with $C_{1-6}$ alkoxy;

each $R^{4b}$ and $R^{4c}$ is hydrogen or $C_{1-6}$ alkyl;

$L^1$ is absent; and $L^2$ is absent, —CH$_2$—, —C(O)—, —C(O)CH$_2$—, —C(O)CH$_2$CH$_2$—, —C(O)CH$_2$O—, —C(O)(CH$_2$)$_3$O—, or —S(O)$_2$.

2. The compound of claim 1, or a pharmaceutically acceptable salt thereof, wherein
$R^1$ is piperidine, pyridin-2-one, phenyl, pyridine, pyrazole, or thiazole, each substituted with 1 to $R^{1a}$ groups; and each $R^{1a}$ is hydrogen, methyl, ethyl, iso-propyl, —CD$_3$, methoxy, —CH$_2$OH, F, Cl, —CHF$_2$, —CF$_3$, oxo, —CN, cyclopropyl, or oxetane.

3. The compound of claim 2, or a pharmaceutically acceptable salt thereof, wherein $R^1$ is

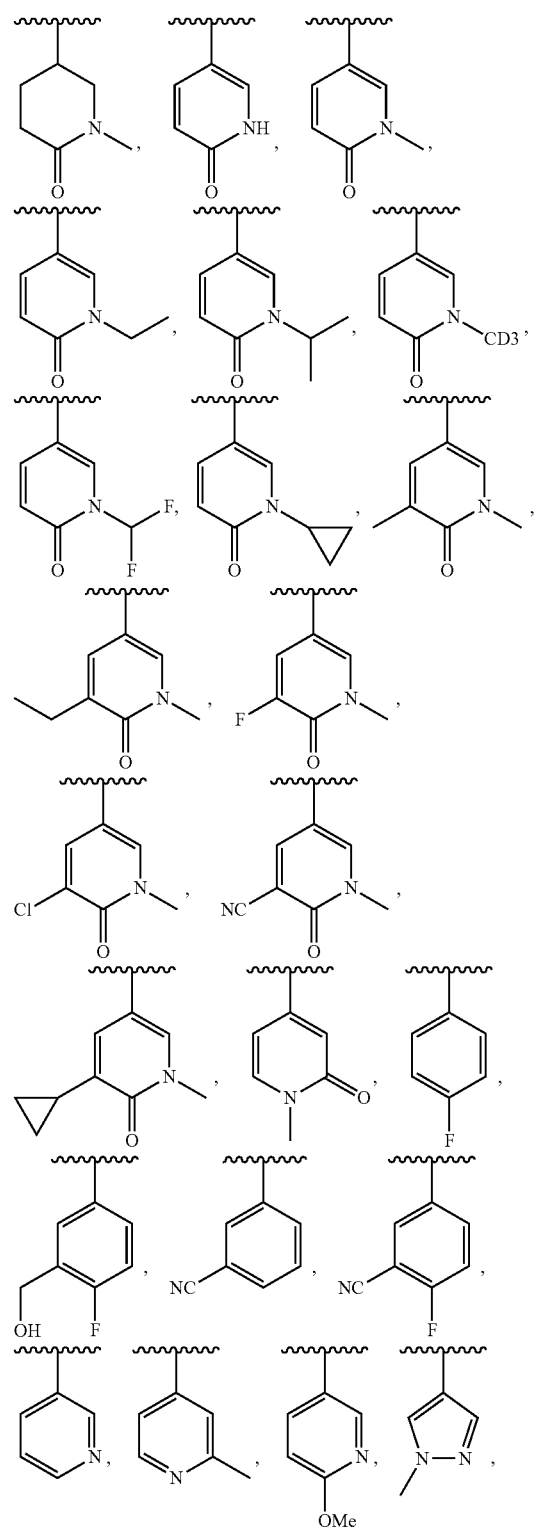

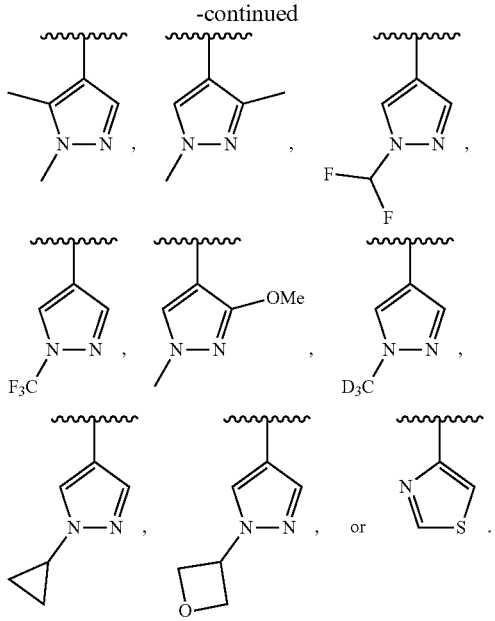

4. The compound of claim 1, or a pharmaceutically acceptable salt thereof, having the structure:

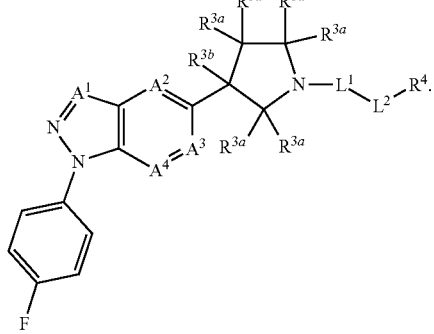

(IVb)

5. The compound of claim 4, or a pharmaceutically acceptable salt thereof, wherein $A^1$, $A^2$, $A^3$ and $A^4$ are each independently =$CR^2$— or =N—; and each $R^2$ is independently hydrogen, $C_{1-4}$ alkyl, $C_{1-4}$ alkoxy, halogen, or —CN.

6. The compound of claim 5, or a pharmaceutically acceptable salt thereof, wherein $A^1$, $A^2$, $A^3$ and $A^4$ are each independently =CH—, =C(Me)-, =C(Et)-, =C(iPr)-, =C(OMe)-, =C(F)-, =C(Cl)-, =C(CN)- or =N—.

7. The compound of claim 6, or a pharmaceutically acceptable salt thereof, wherein $A^1$ is =CH— or =N—;

$A^2$ and $A^4$ are each =CH—; and $A^3$ is =CH—, =C(Me)-, =C(Et)-, =C(iPr)-, =C(OMe)-, =C(F)—, =C(Cl)—, or =C(CN)—.

8. The compound of claim 7, or a pharmaceutically acceptable salt thereof, having the structure:

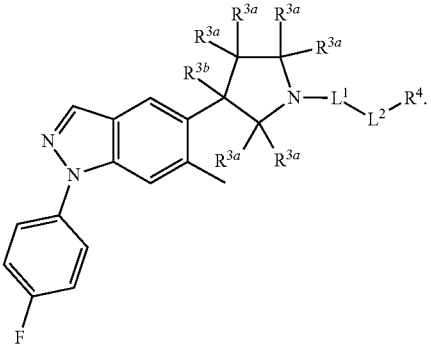

(IVc)

9. The compound of claim 8, or a pharmaceutically acceptable salt thereof, having the structure:

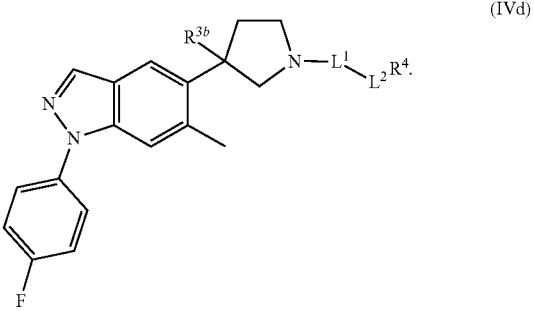

(IVd)

10. The compound of claim 9, or a pharmaceutically acceptable salt thereof, wherein $R^{3b}$ is $C_{1-3}$ alkyl, $C_{2-3}$ alkynyl, $C_{2-3}$ alkoxyalkyl, $C_{2-3}$ alkynyl-$C_{3-6}$ cycloalkyl, $C_{1-3}$ alkyl-$C_{6-12}$ aryl, $C_{2-3}$ alkenyl-$C_{6-12}$ aryl, $C_{2-3}$ alkynyl-$C_{6-12}$ aryl, $C_{1-3}$ alkyl-O—$C_{6-12}$ aryl, $C_{1-3}$ alkoxyalkyl-$C_{6-12}$ aryl, —C(O)—$C_{6-12}$ aryl, or $C_{1-3}$ alkyl-heteroaryl, wherein each heteroaryl has 5 to 10 ring members and 1 to 3 heteroatoms each independently N, O or S, and wherein each aryl and heteroaryl is substituted with 1 to 3 $R^{3b3}$ groups; and each $R^{3b3}$ is hydrogen, $C_{1-3}$ alkyl, $C_{1-3}$ hydroxyalkyl, halogen, or $C_{1-3}$ haloalkyl.

11. The compound of claim 10, or a pharmaceutically acceptable salt thereof, wherein $R^{3b3}$ is hydrogen, methyl, —CH₂OH, F, —CHF₂, or —CF₃.

12. The compound of claim 11, or a pharmaceutically acceptable salt thereof, wherein $R^{3b}$ is ethyl, —CH₂C≡CH, —CH₂OMe,

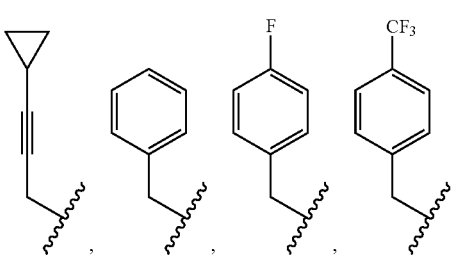

-continued

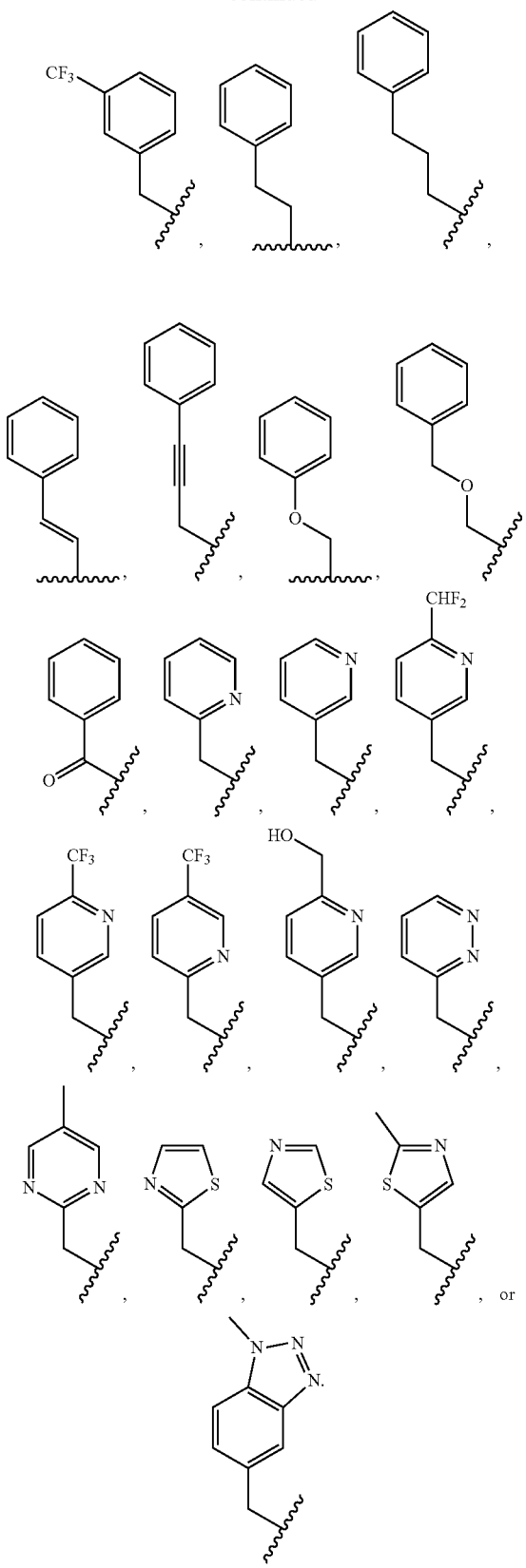

13. The compound of claim 12, or a pharmaceutically acceptable salt thereof, having the structure:

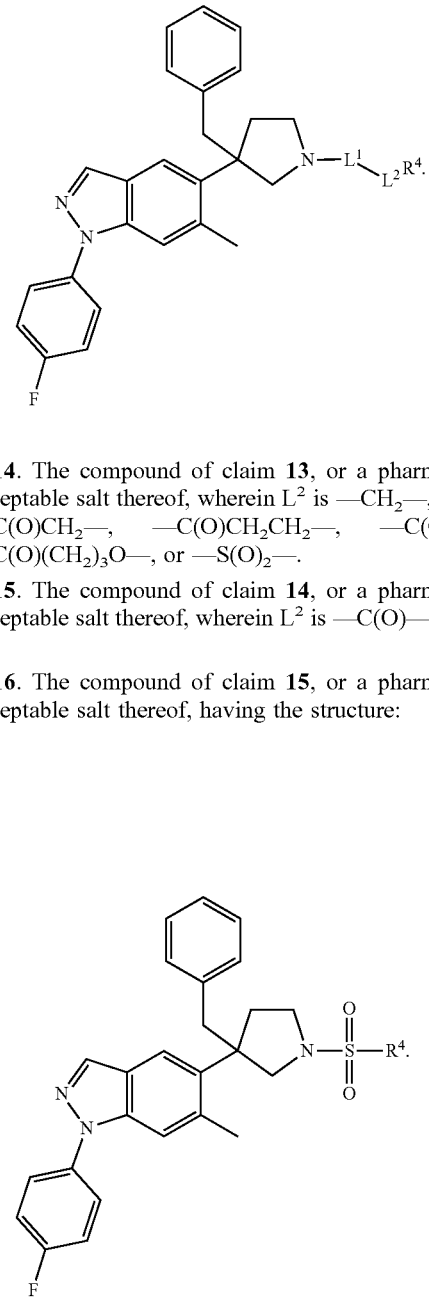

(IVe)

14. The compound of claim 13, or a pharmaceutically acceptable salt thereof, wherein $L^2$ is —CH$_2$—, —C(O)—, —C(O)CH$_2$—, —C(O)CH$_2$CH$_2$—, —C(O)CH$_2$O—, —C(O)(CH$_2$)$_3$O—, or —S(O)$_2$—.

15. The compound of claim 14, or a pharmaceutically acceptable salt thereof, wherein $L^2$ is —C(O)— or —S(O)$_2$—.

16. The compound of claim 15, or a pharmaceutically acceptable salt thereof, having the structure:

(IVf)

17. The compound of claim 16, or a pharmaceutically acceptable salt thereof, wherein $R^4$ is methyl, ethyl, —CF$_2$CH$_3$, —CN, cyclopropyl, cyclobutyl, piperidinyl, tetrahydropyranyl, pyrimidine-dione, phenyl, pyridinyl, pyridin-2-one, quinolinyl, pyrazolyl, imidazolyl, pyridazinyl, pyrimidinyl, indazolyl, triazolyl, pyrazolo-pyrimidine, tetrazolyl, oxazolyl, isoxazolyl, benzoisoxazolyl, oxadiazolyl, thiophenyl, benzothiophenyl, or thiazolyl; and each $R^{4a}$ is hydrogen, methyl, ethyl, n-propyl, iso-butyl, —CD$_3$, methoxy, —CH$_2$CH$_2$OCH$_3$, hydroxymethyl, F, Cl, —CHF$_2$, —CF$_3$, —CH$_2$CF$_3$, —CN, —OH, oxo, —S(O)$_2$Me, —S(O)$_2$NHMe, cyclobutyl, 2-methoxyphenyl or -OPh.

18. The compound of claim 17, or a pharmaceutically acceptable salt thereof, wherein
R⁴ is methyl, —CF$_2$CH$_3$, —CN,
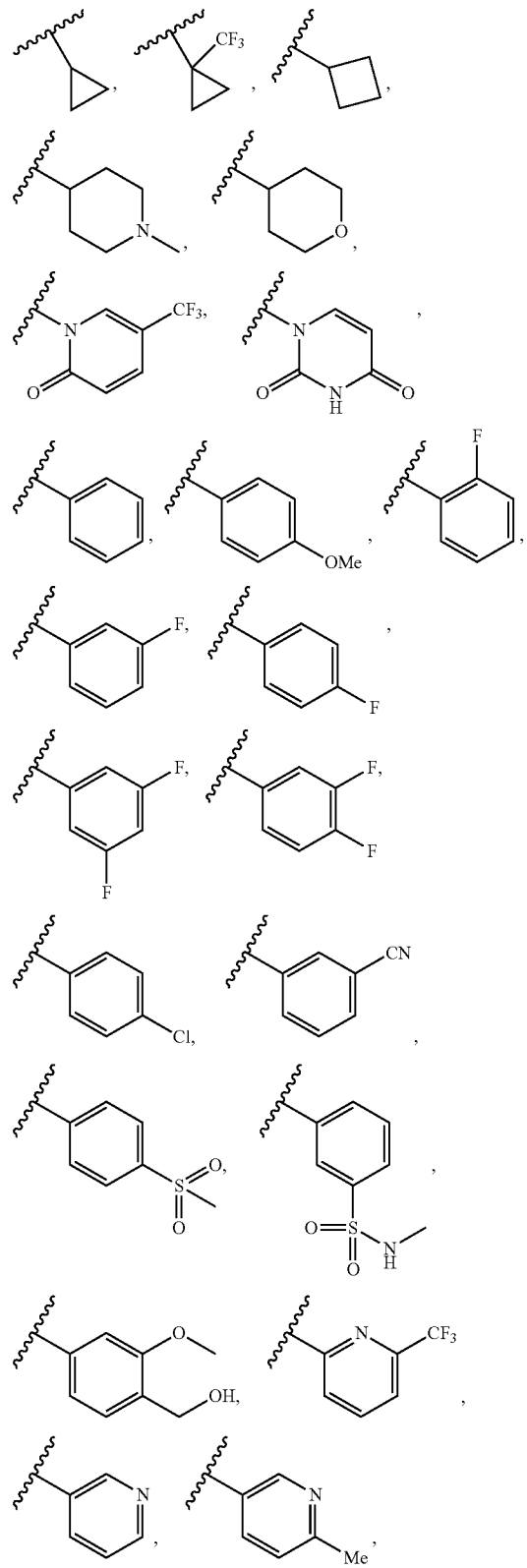
-continued
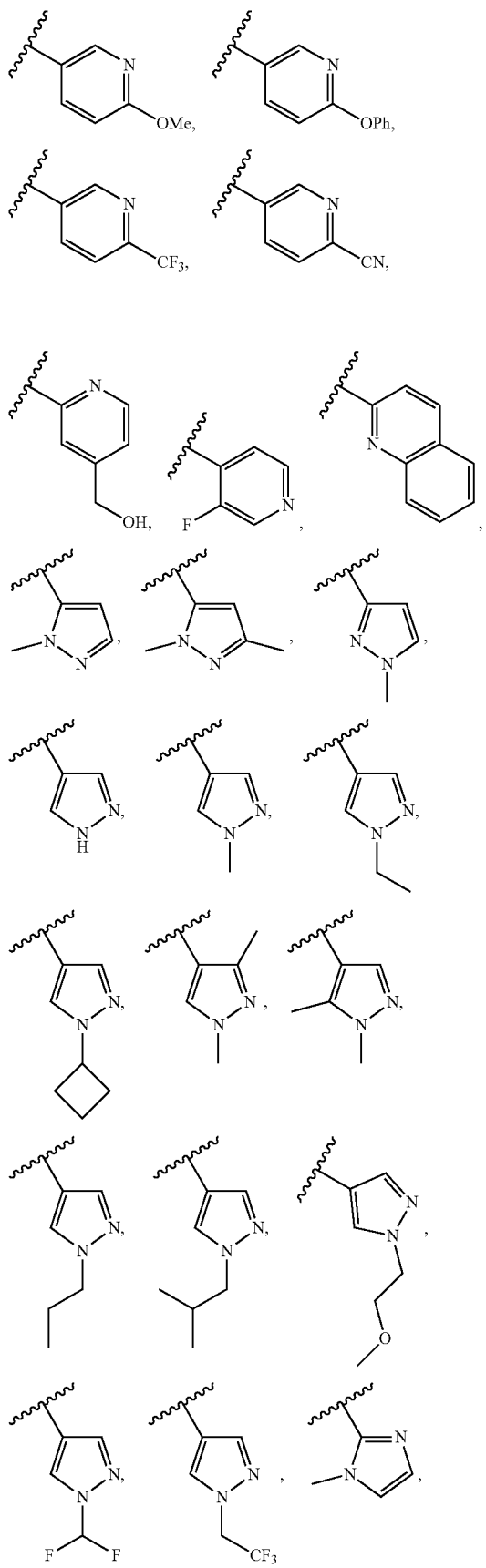

-continued
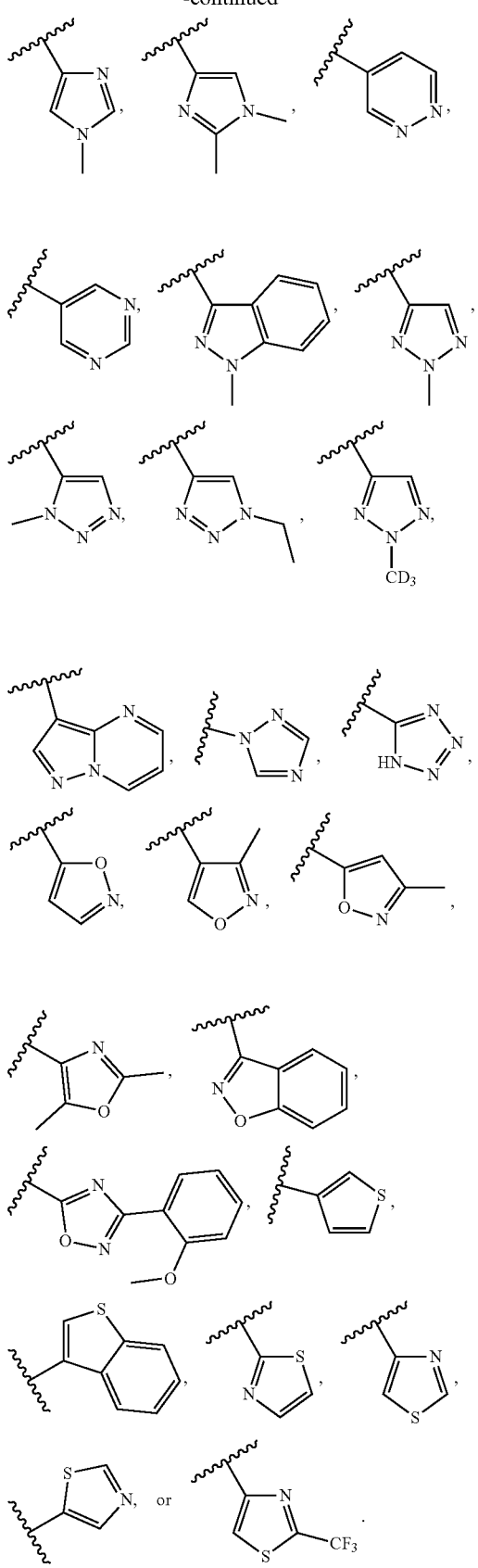
19. The compound of claim 1, or a pharmaceutically acceptable salt thereof, wherein
R$^1$ is
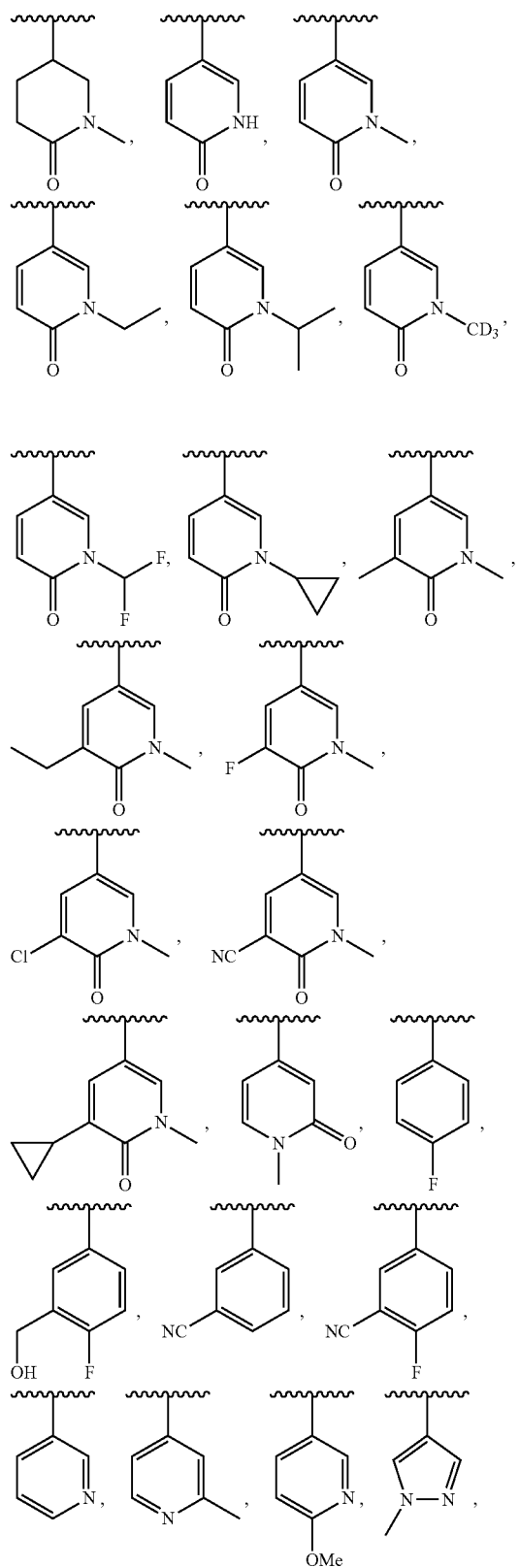

-continued
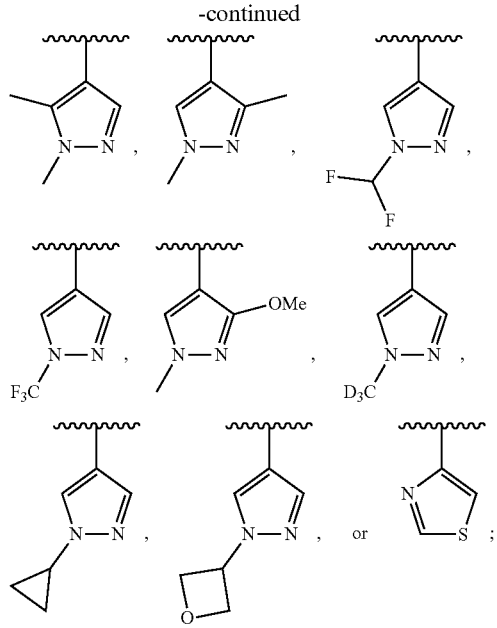
A¹ is =CH— or =N—;
A² and A⁴ are each =CH—;
A³ is =CH—, =C(Me)-, =C(Et)-, =C(iPr)-, =C(OMe)-, =C(F)—, =C(Cl)—, or =C(CN)—;
each R³ᵃ is hydrogen, —OH, or oxo;
R³ᵇ is ethyl, —CH₂C≡CH, —CH₂OMe,
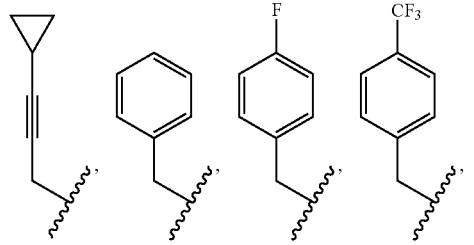
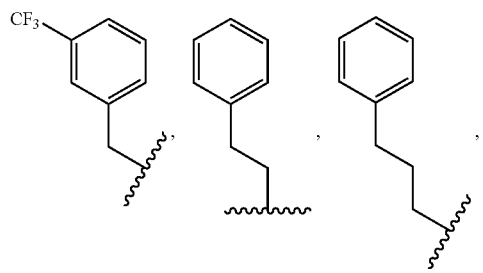
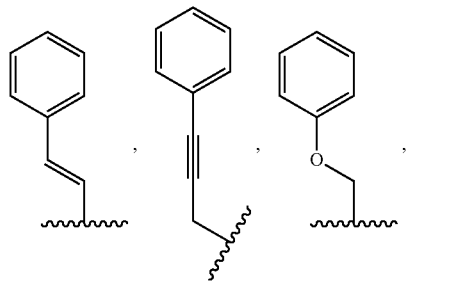
-continued
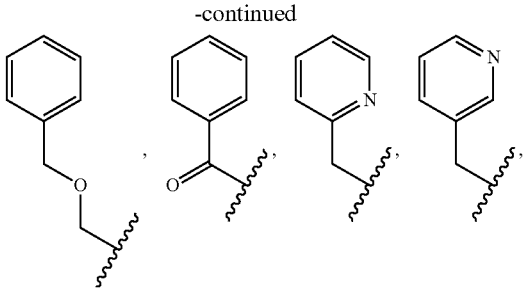
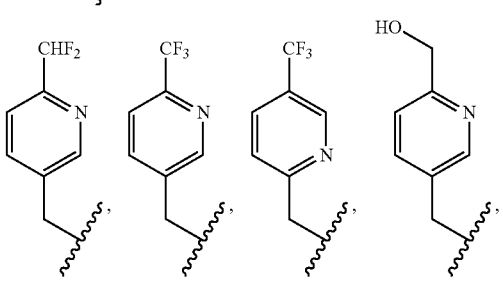
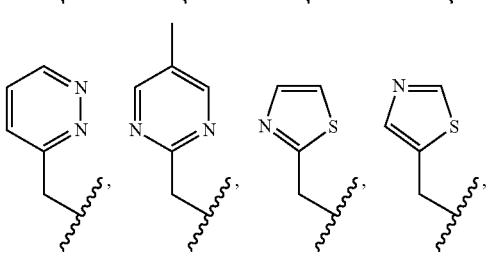
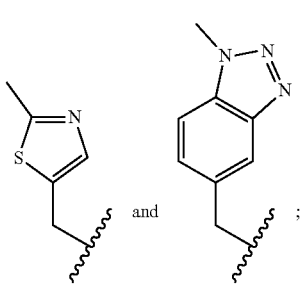
L¹ and L² together are absent, —CH₂—, —C(O)—, —C(O)CH₂—, —C(O)CH₂CH₂—, —C(O)CH₂O—, —C(O)(CH₂)₃O—, or —S(O)₂—; and
R⁴ is methyl, —CF₂CH₃, —CN,
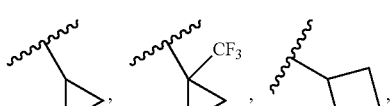
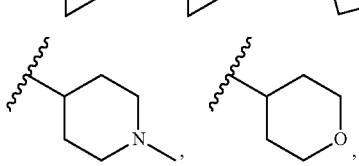
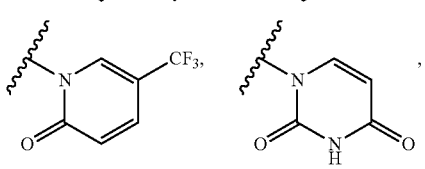

503
-continued
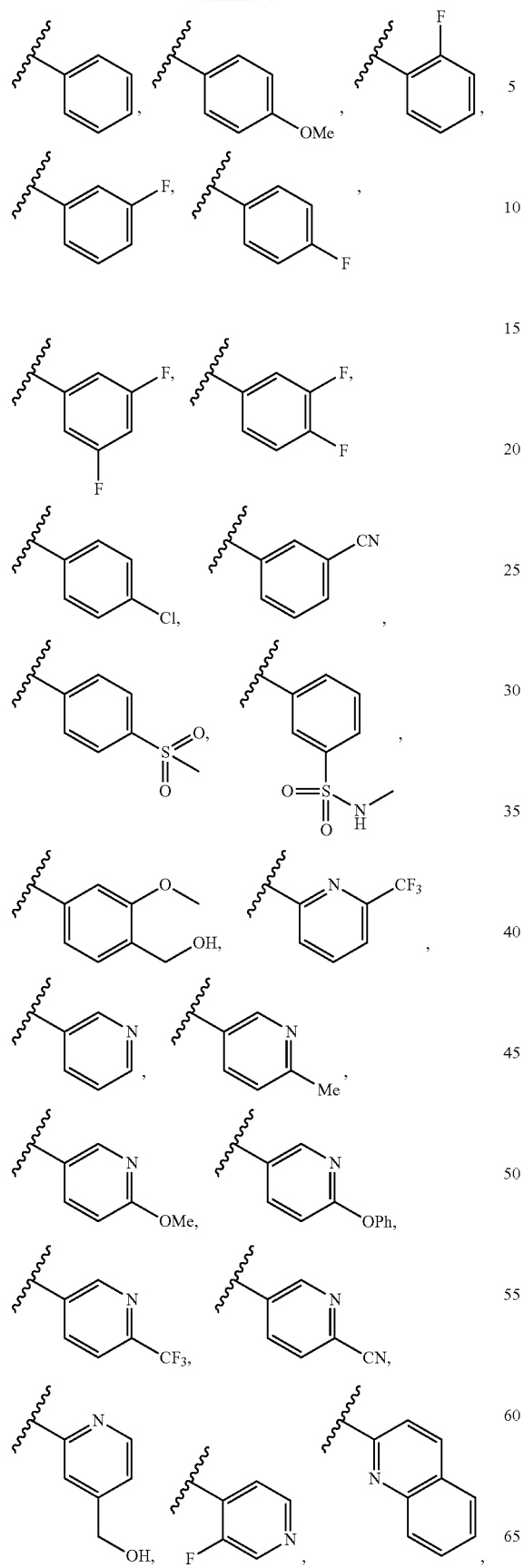
504
-continued
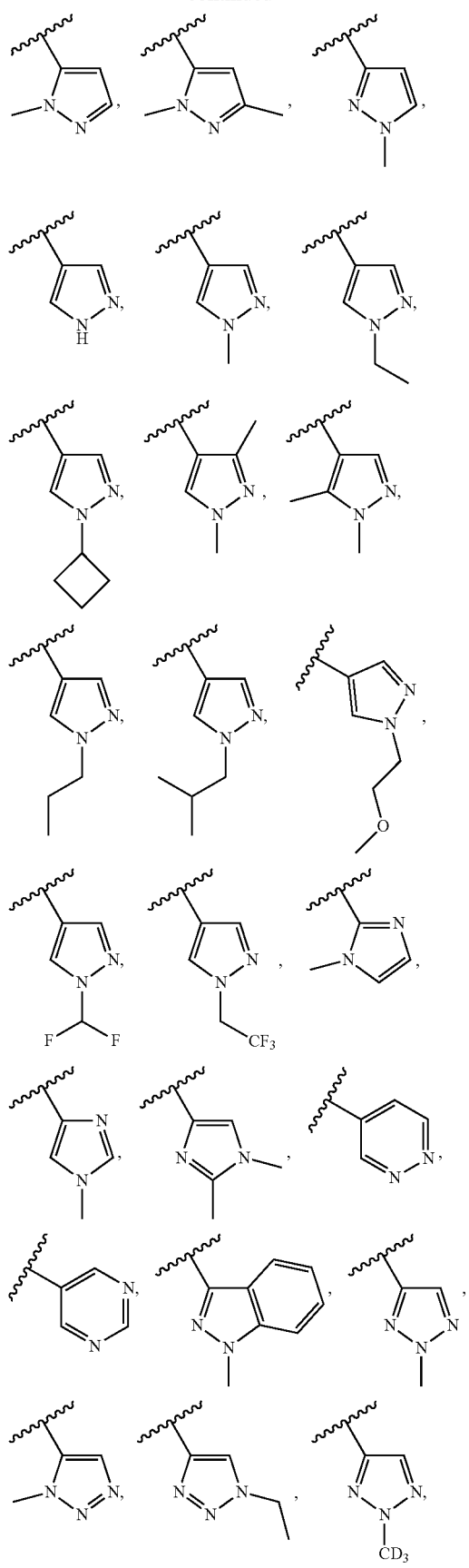

-continued
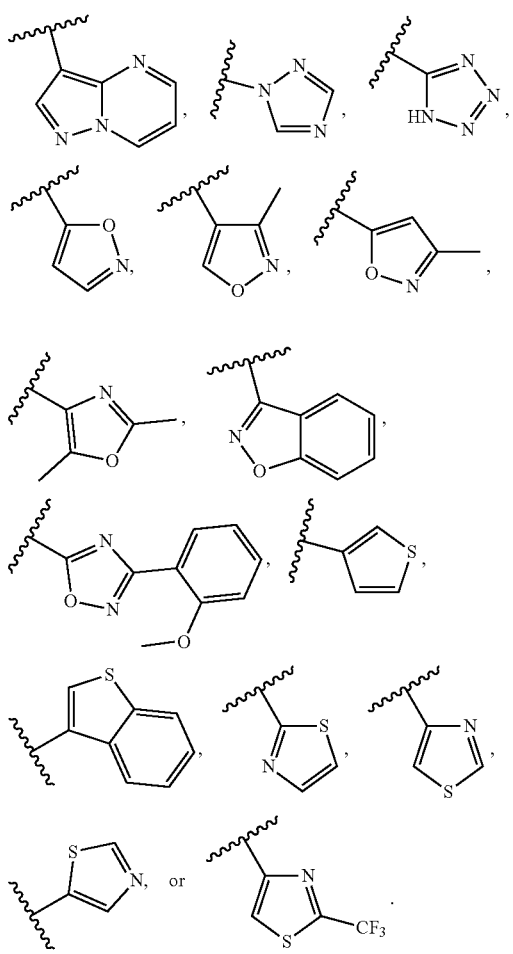
20. The compound of claim 1, or a pharmaceutically acceptable salt thereof, wherein
R$^1$ is
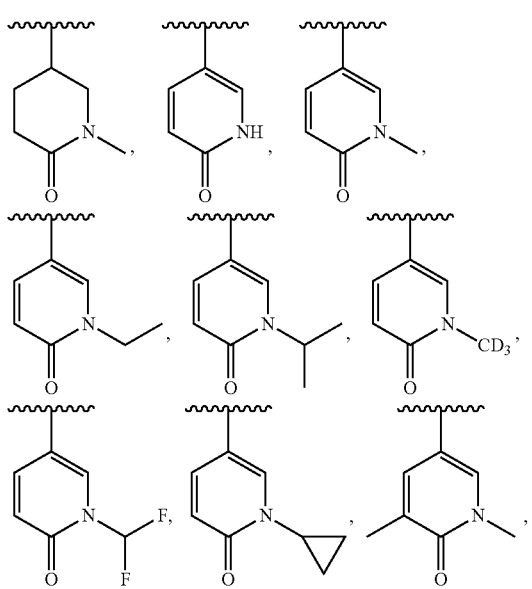
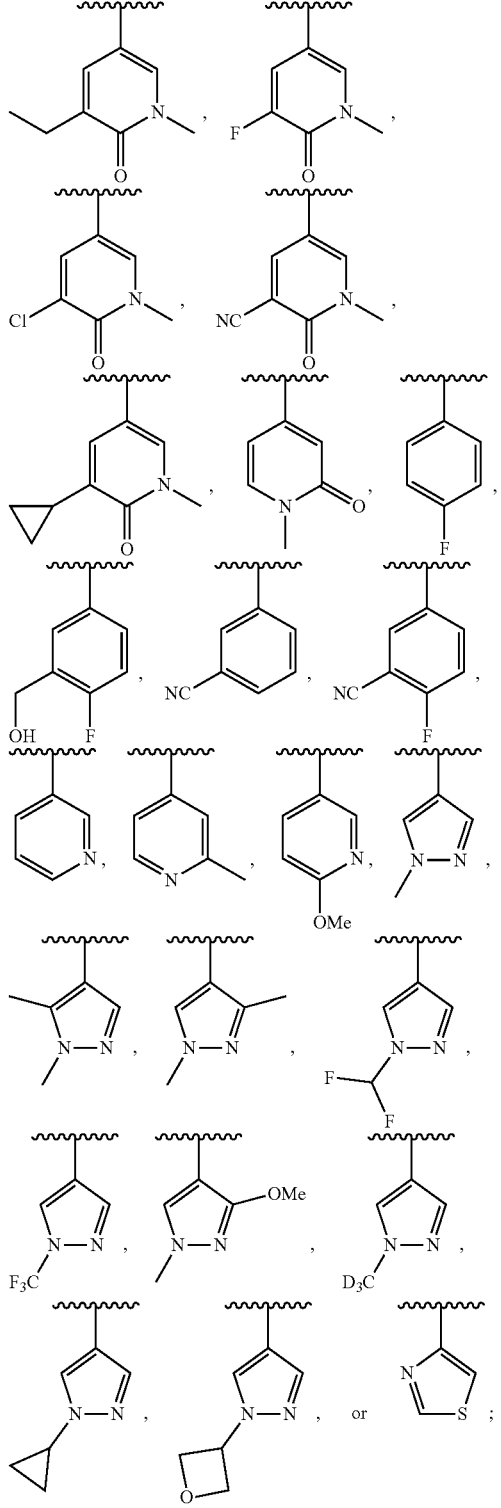
A$^1$ is =CH—;
A$^2$ and A$^4$ are each =CH—;
A$^3$ is =CH—, =C(Me)-, =C(Et)-, =C(OMe)-, =C(Cl)—, or =C(CN)—;
each R$^{3a}$ is hydrogen, —OH, or oxo;
R$^{3b}$ is —CH$_2$OMe,

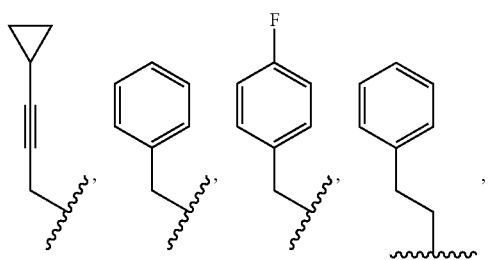
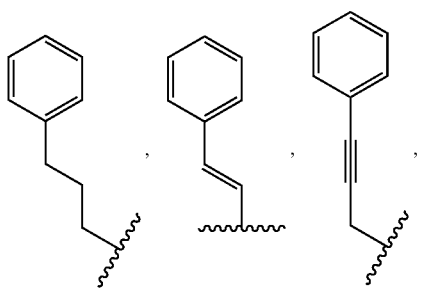
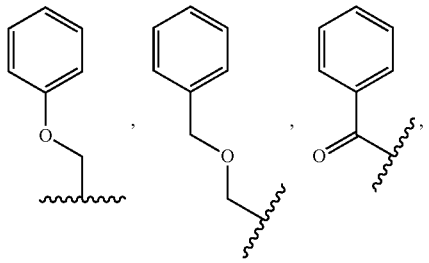
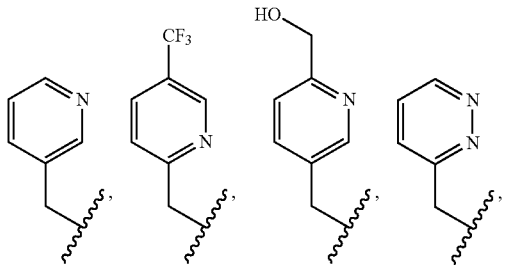
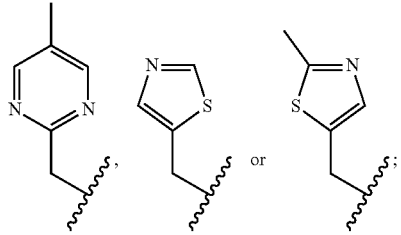
L¹ and L² together are —CH₂—, —C(O)—, —C(O)CH₂—, —C(O)CH₂CH₂—, —C(O)CH₂O—, or —S(O)₂—; and
R⁴ is methyl, —CF₂CH₃,
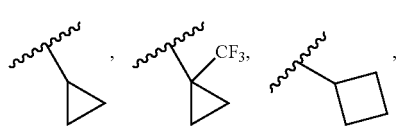
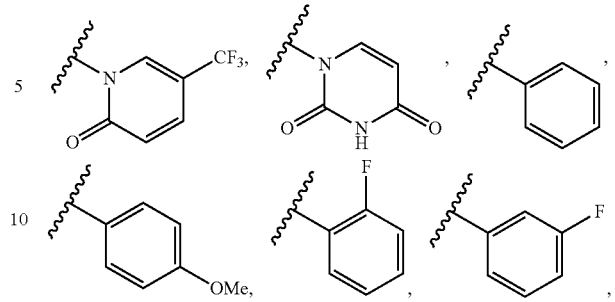
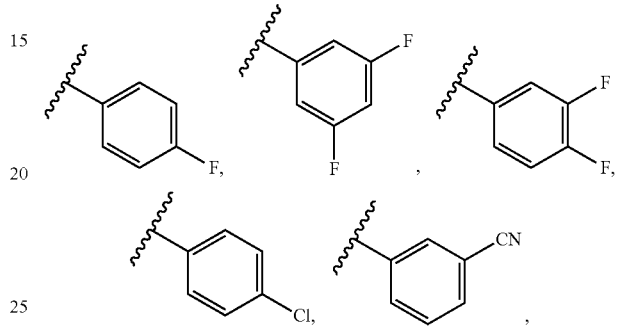
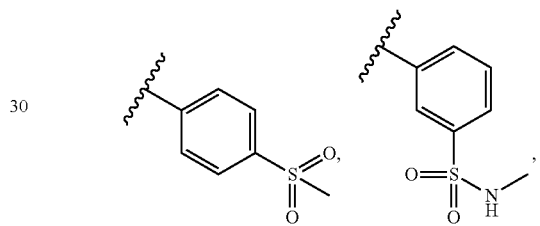
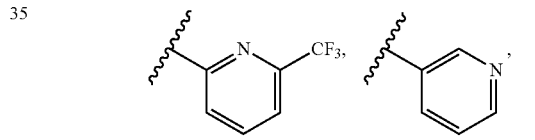
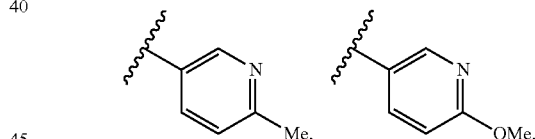
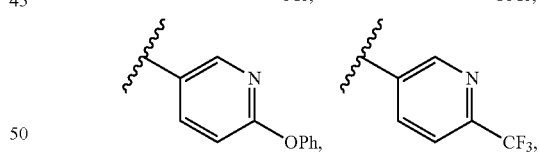
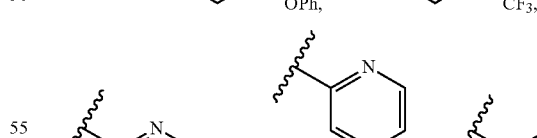
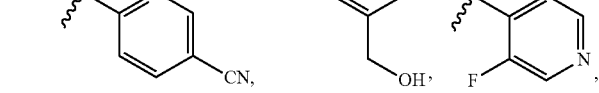

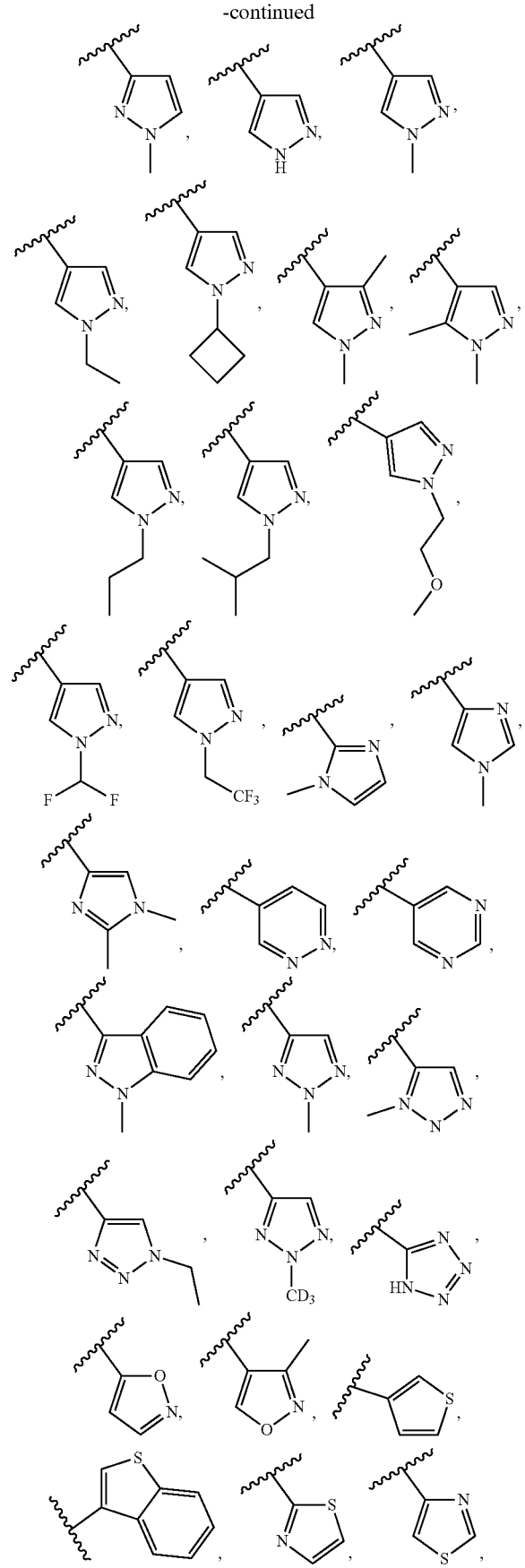
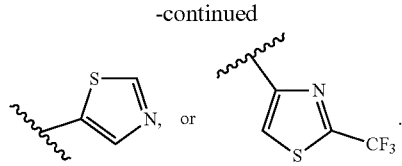
21. The compound of claim 1, or a pharmaceutically acceptable salt thereof, is the compound having the structure:
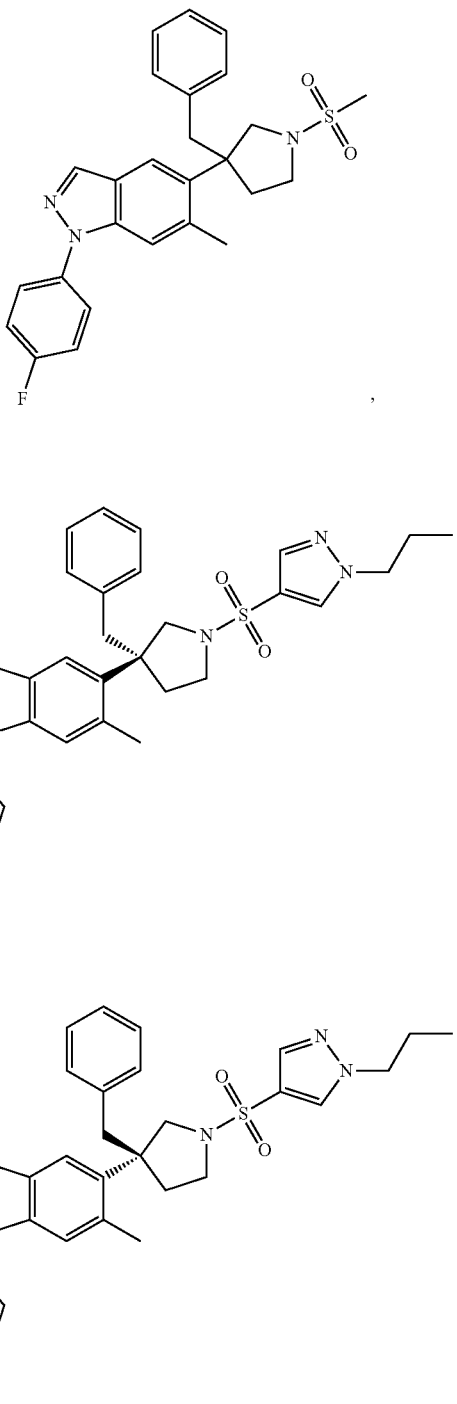

511
-continued
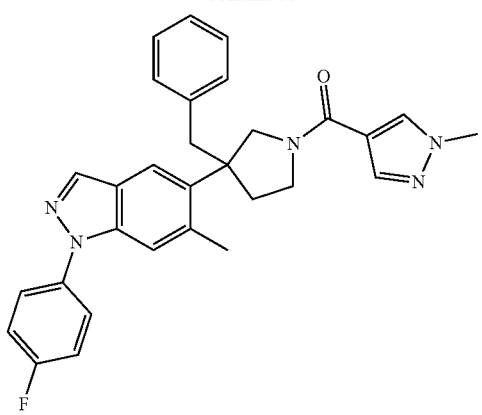
512
-continued
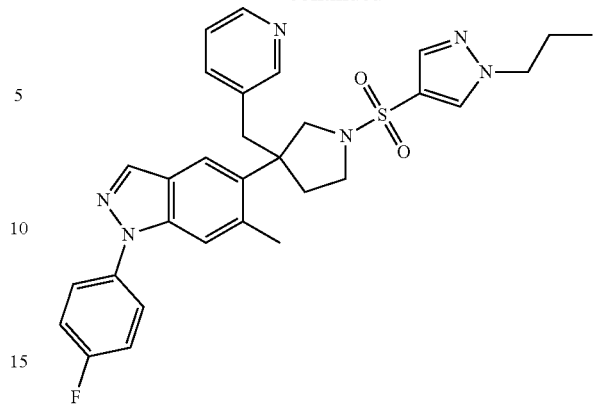
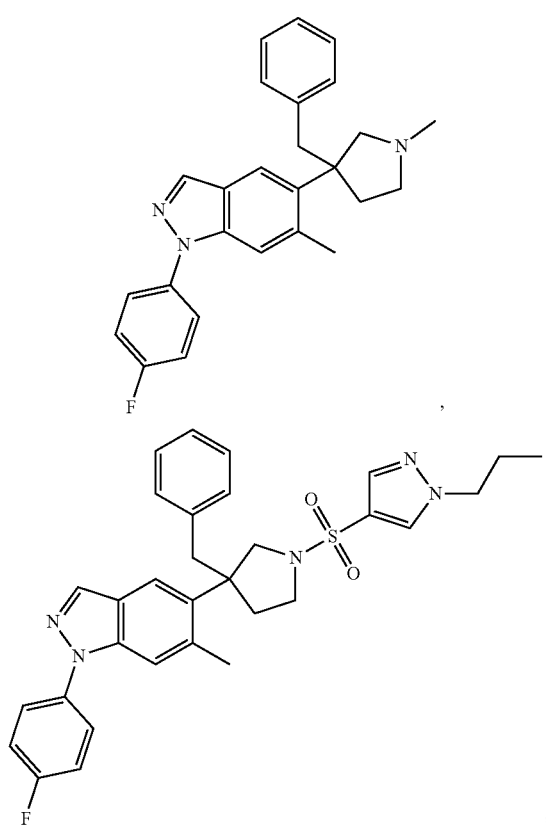
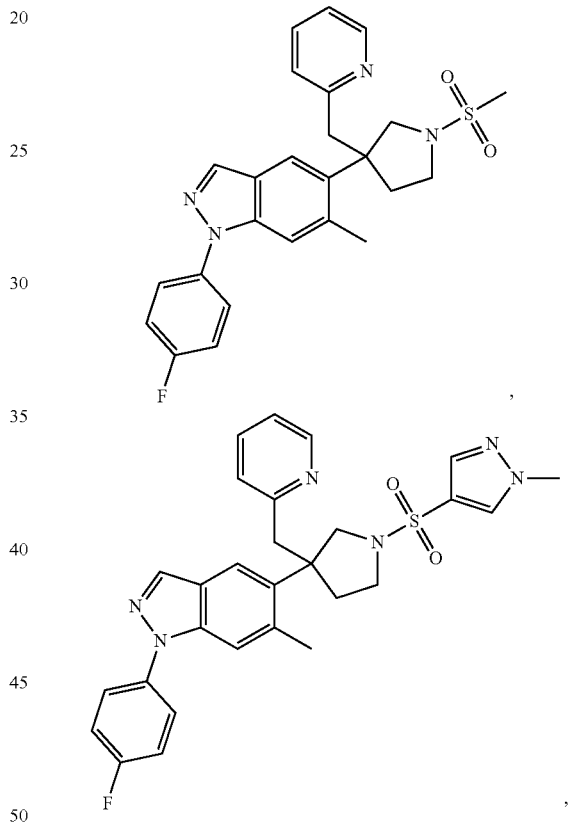
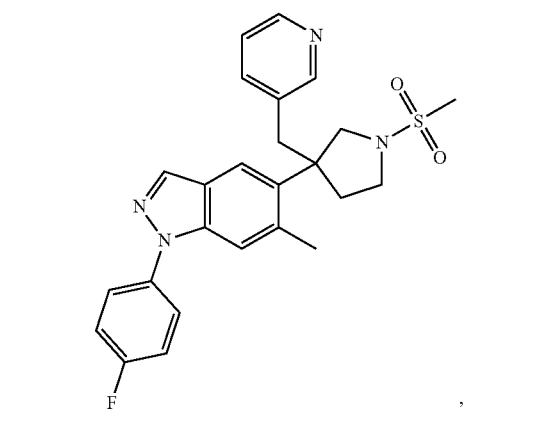
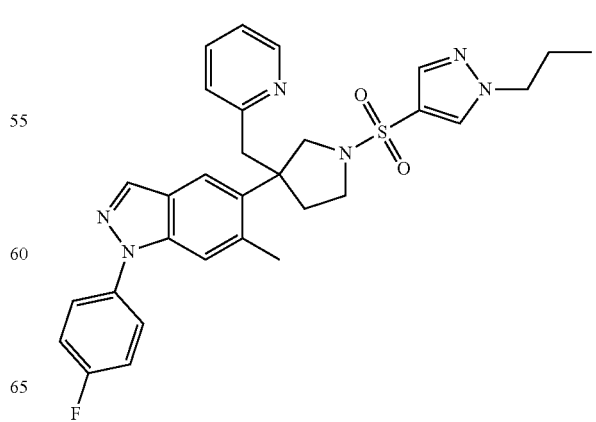

513
-continued
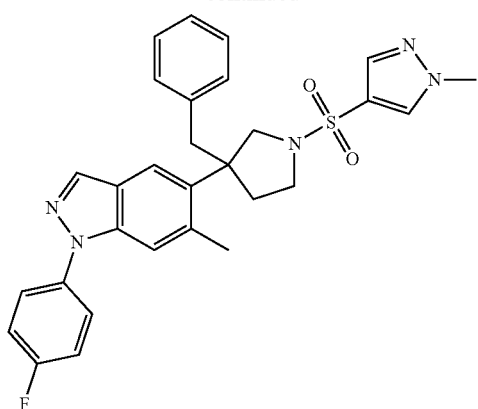
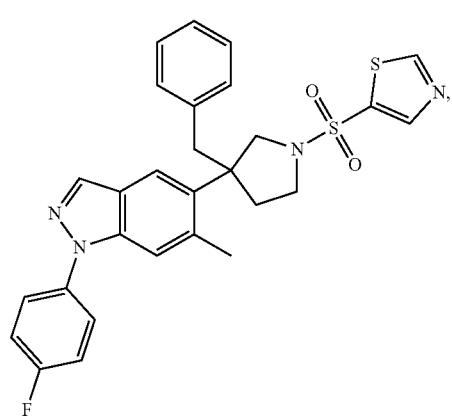
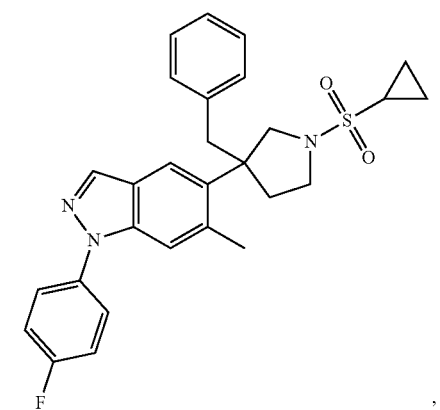
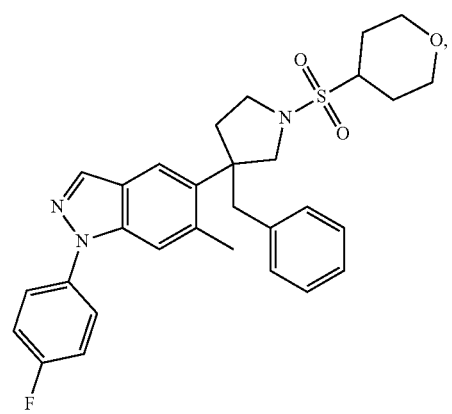
514
-continued
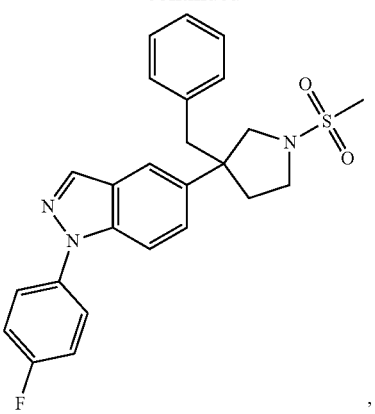
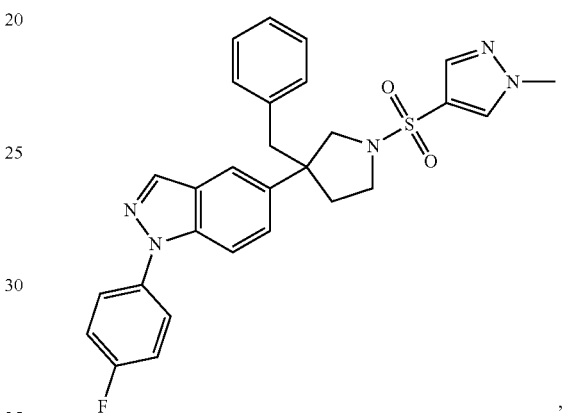
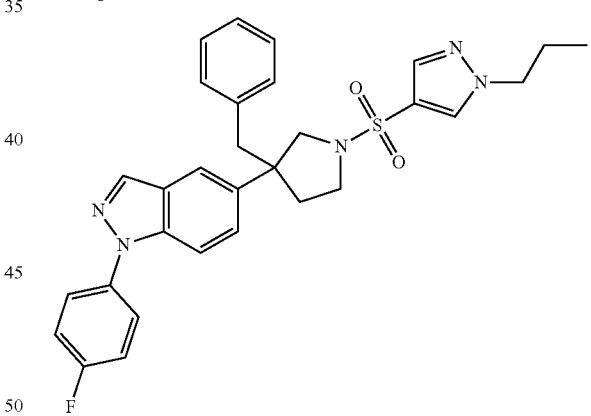
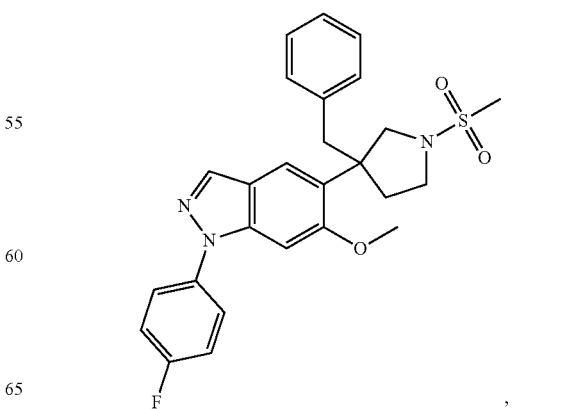

515
-continued
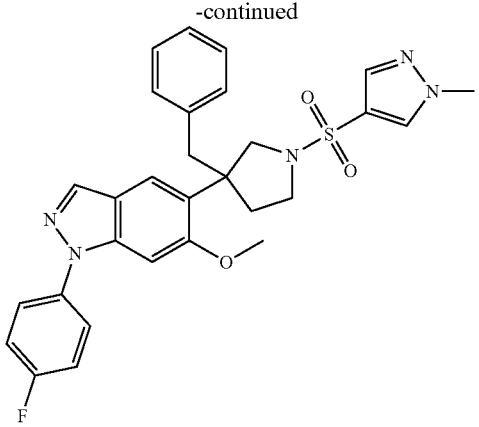
,
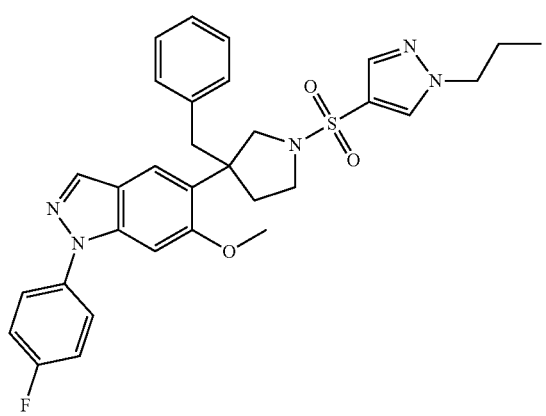
,
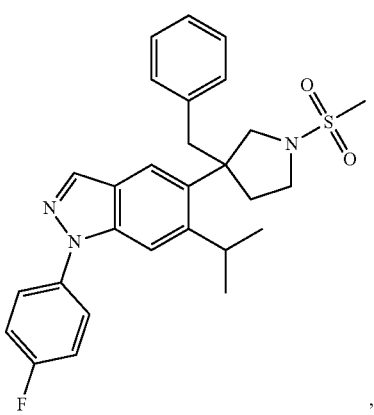
,
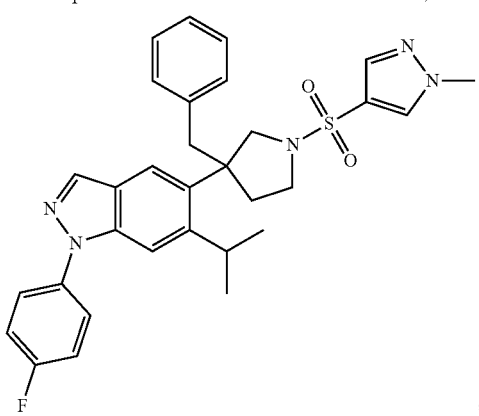
,
516
-continued
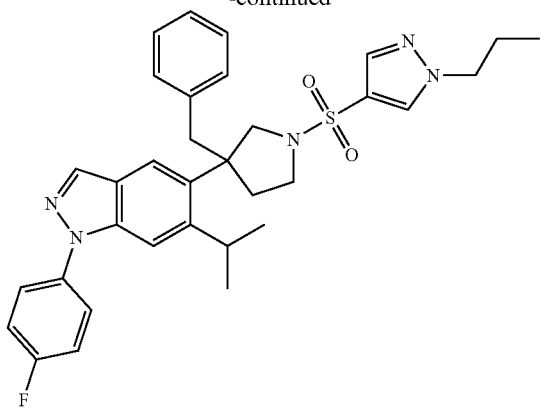
,
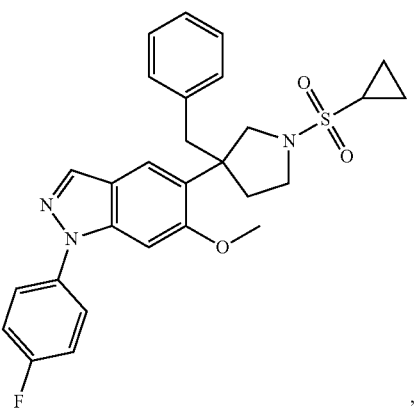
,
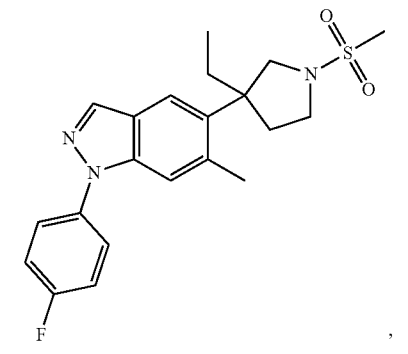
,
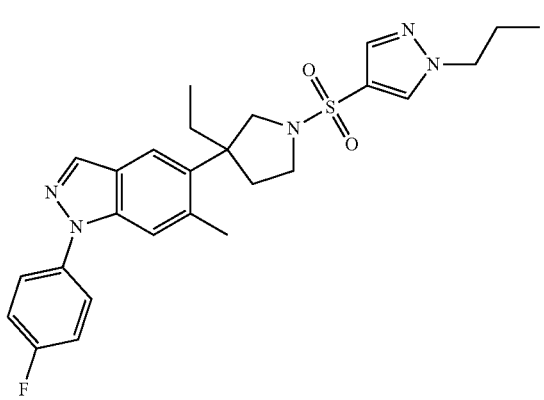
, 517
-continued
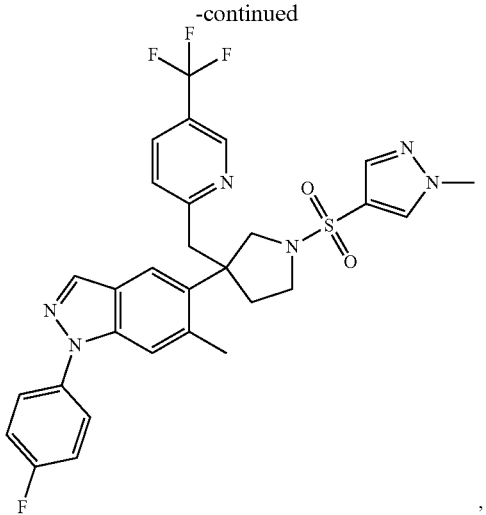
,
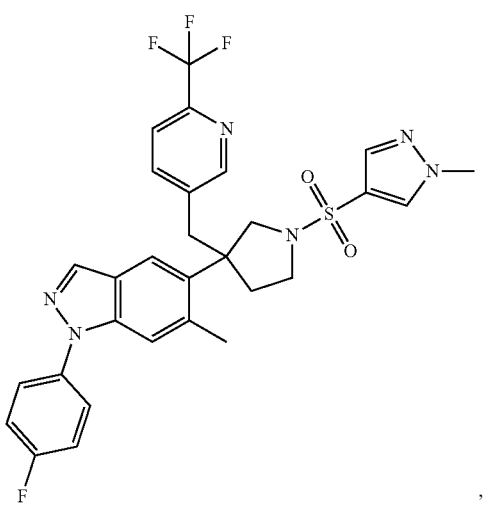
,
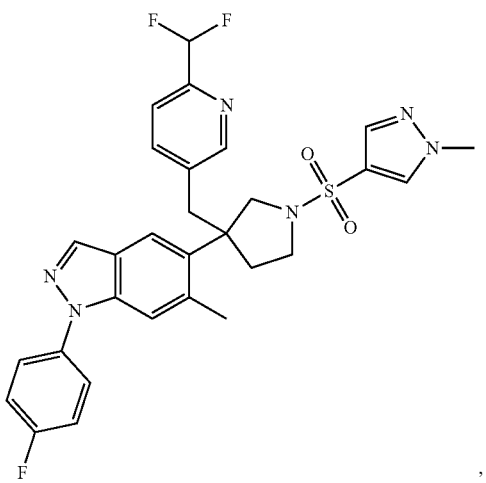
,
518
-continued
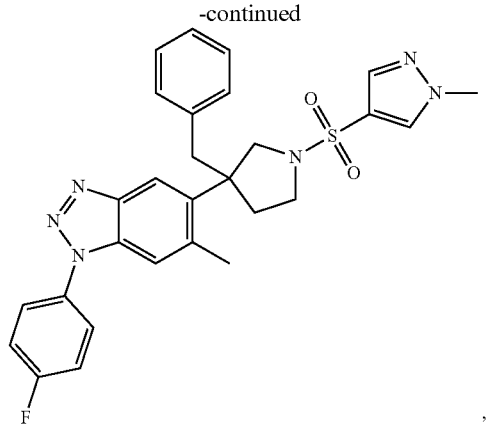
,
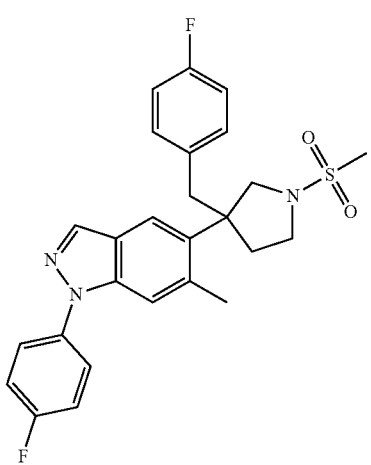
,
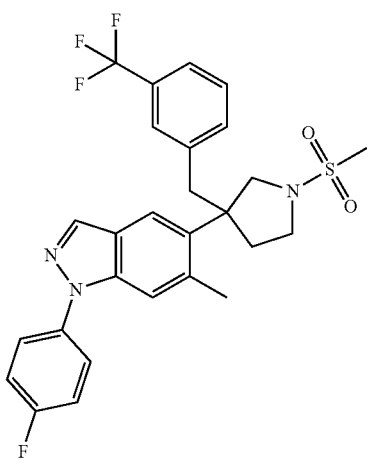
, 519
-continued
520
-continued
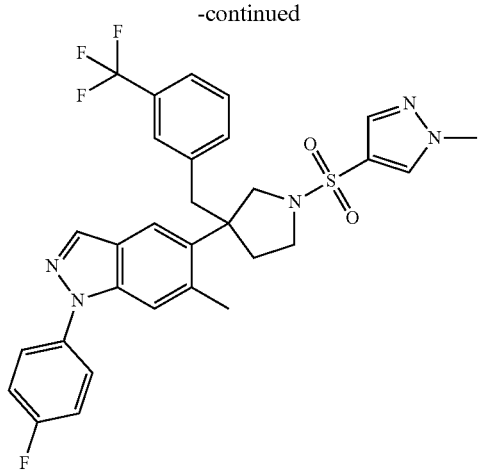
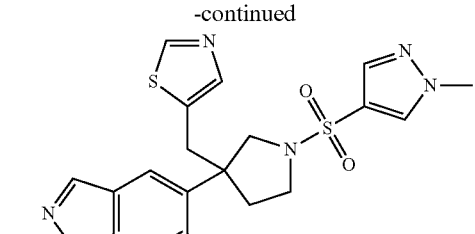

521
-continued
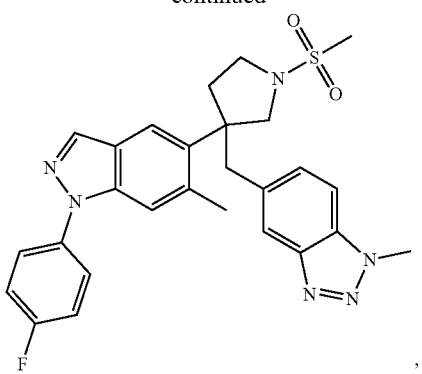
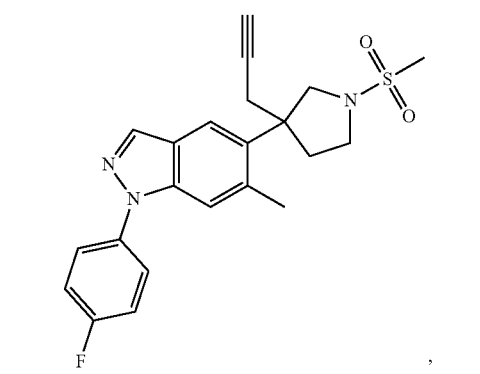
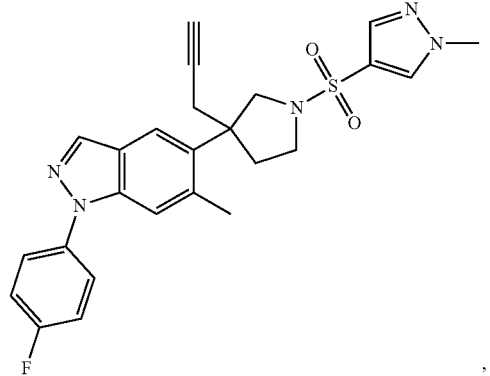
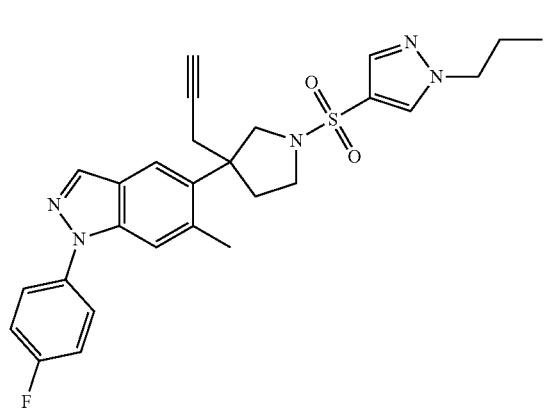
522
-continued
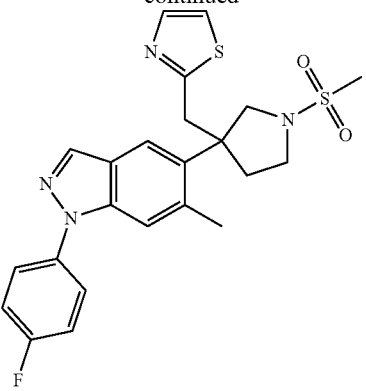
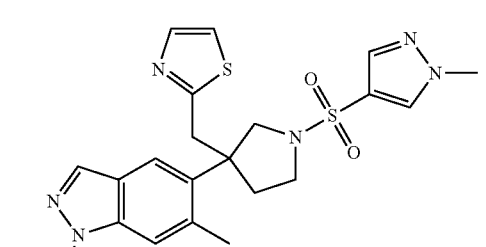
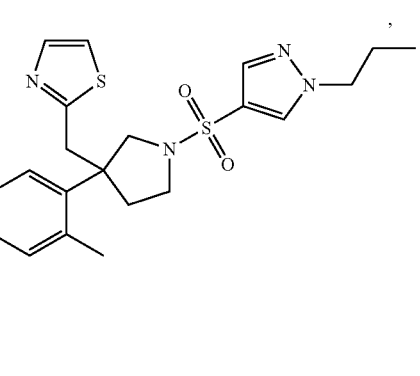
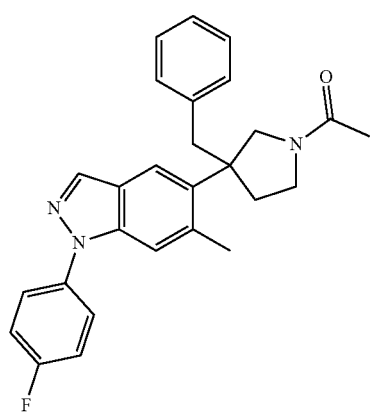

523
-continued
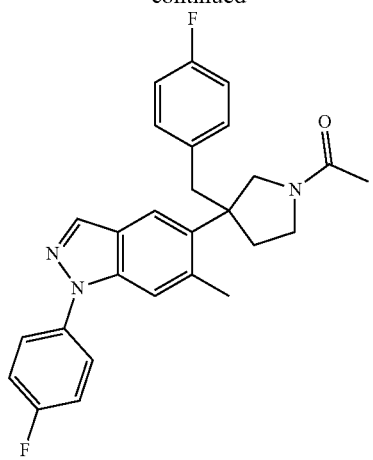
,
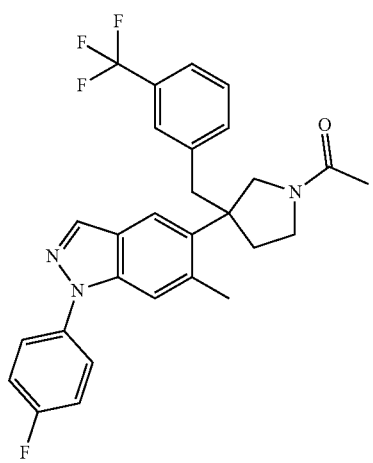
,
,
524
-continued
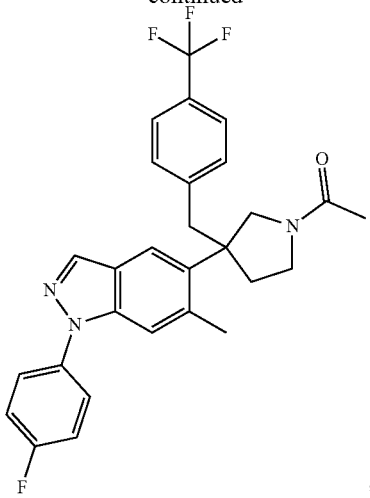
,
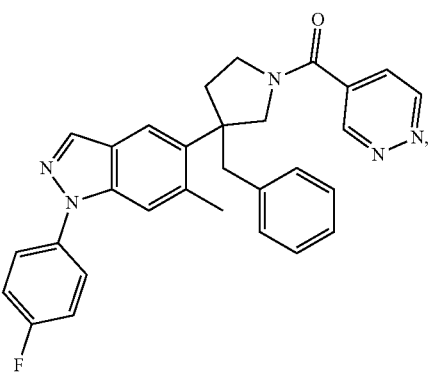 [SMILES: Cc1cc2c(cnn2-c2ccc(F)cc2)cc1C1(Cc2ccccc2)CCN(C(=O)c2ccccc2)C1]
,
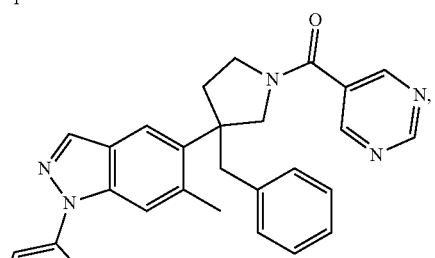
,
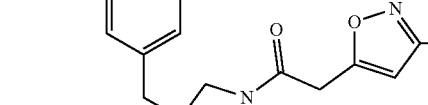
, 525
-continued
526
-continued
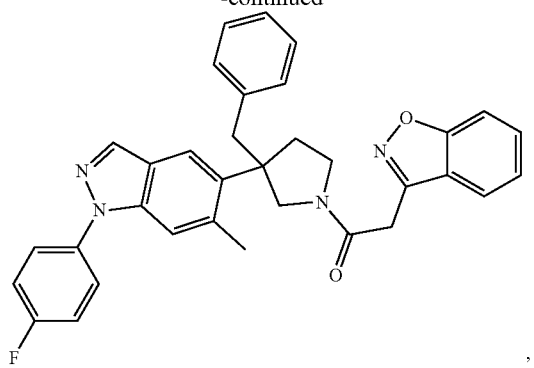
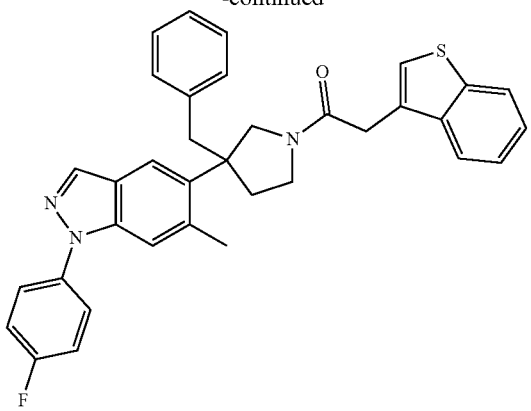

527
-continued
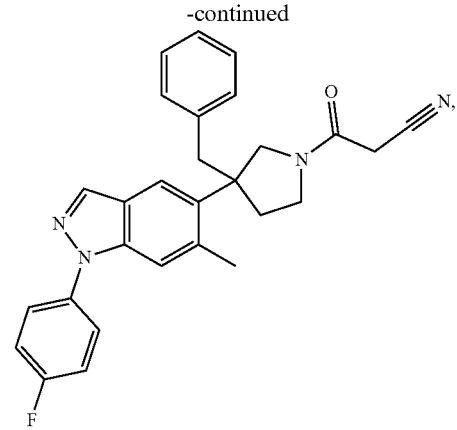
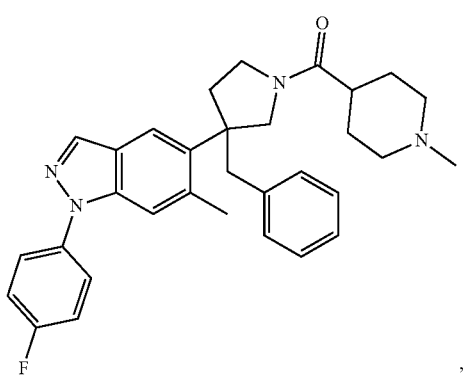
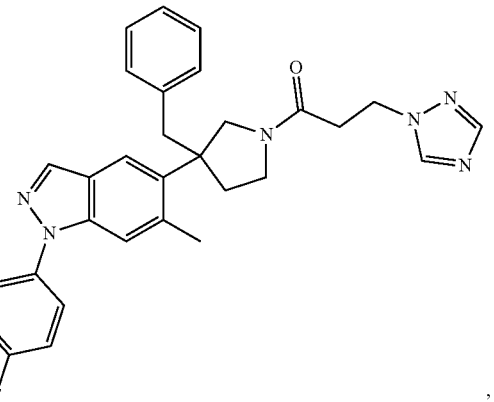
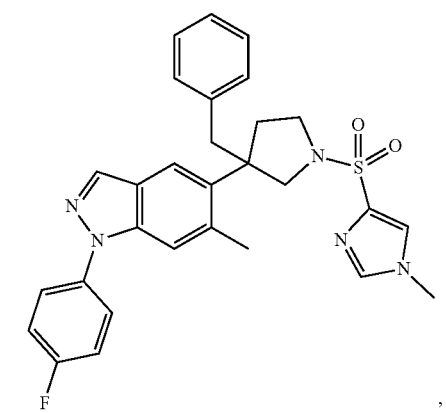
528
-continued
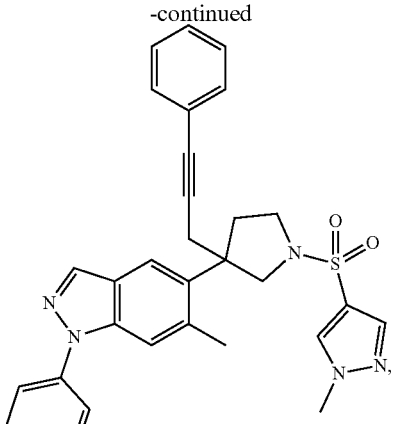
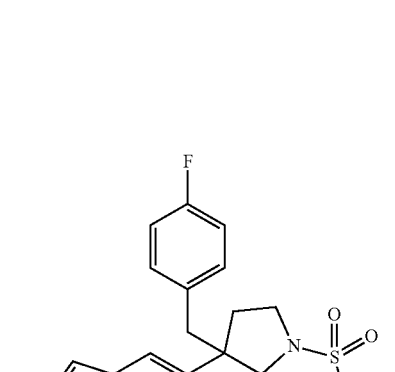
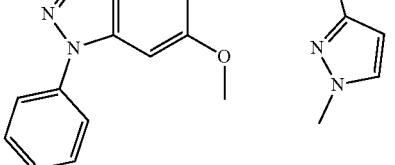

529
-continued
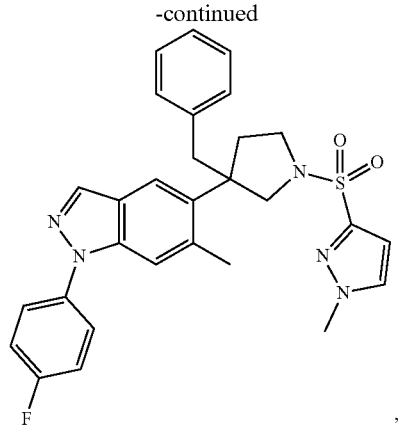
,
530
-continued
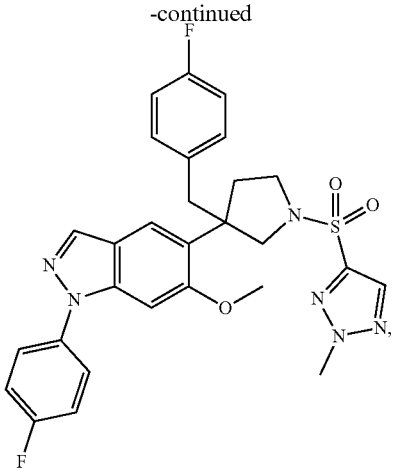
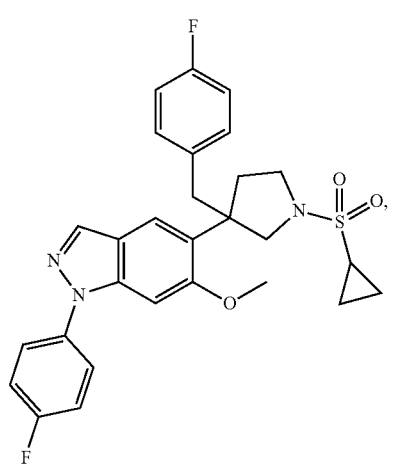
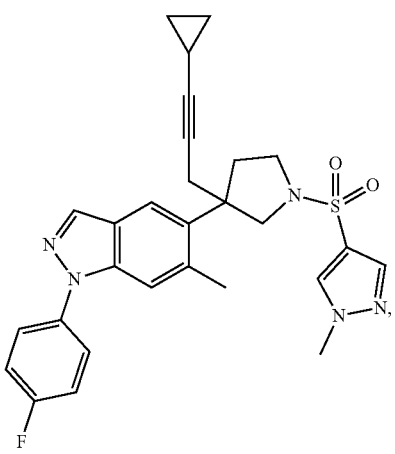

531
-continued
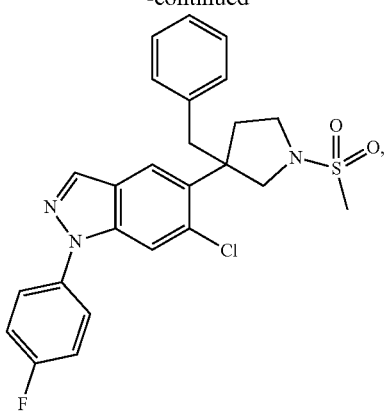
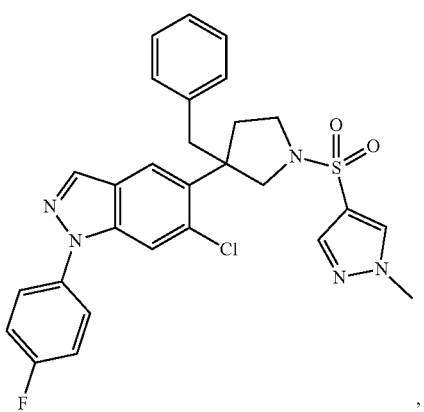
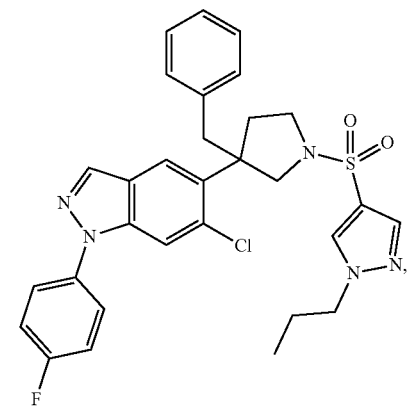
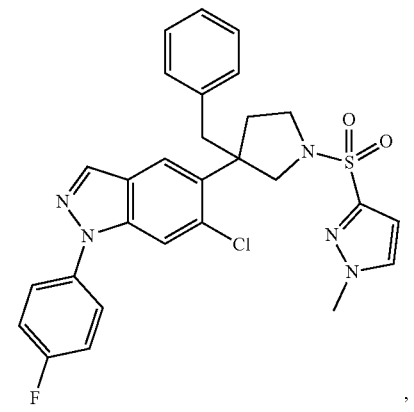
532
-continued
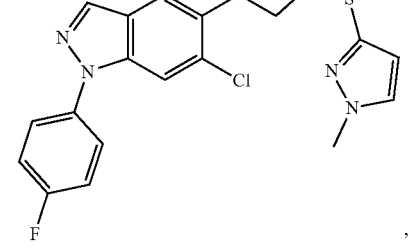

-continued
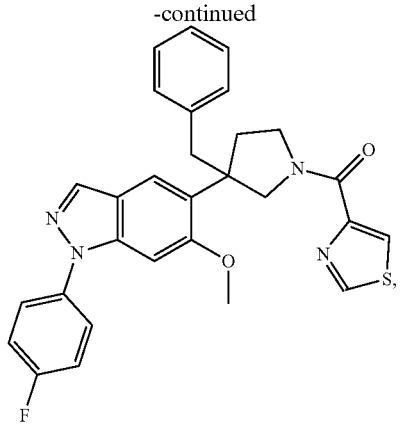
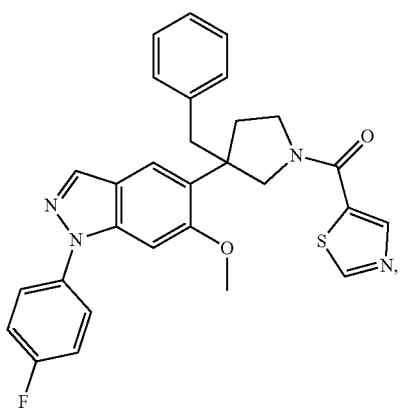
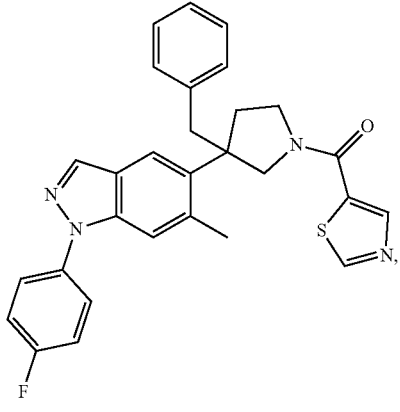
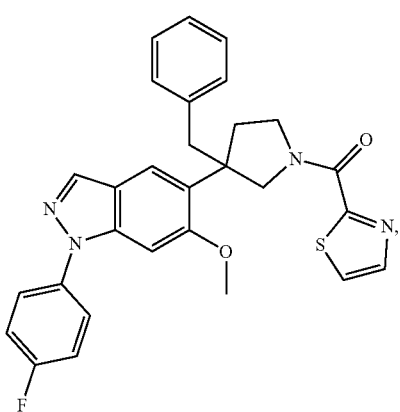
-continued
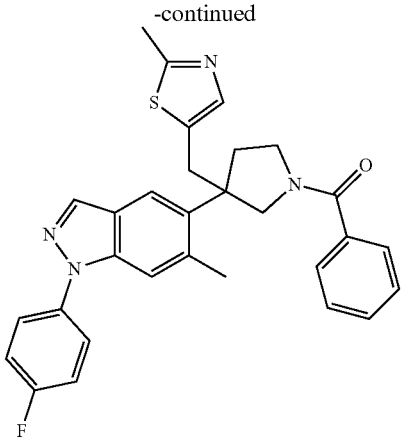
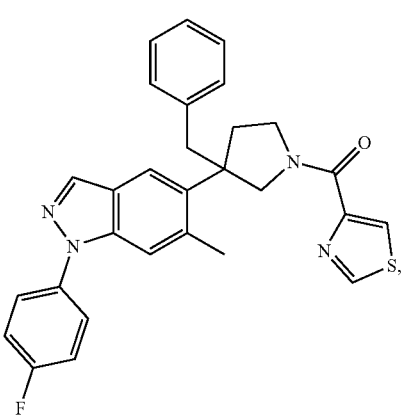
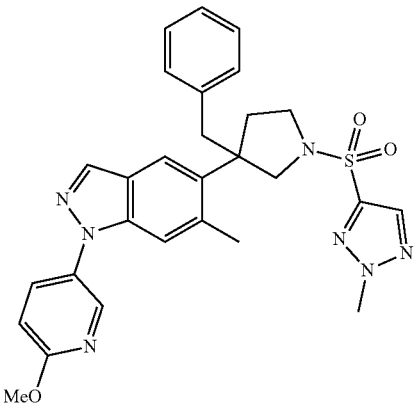
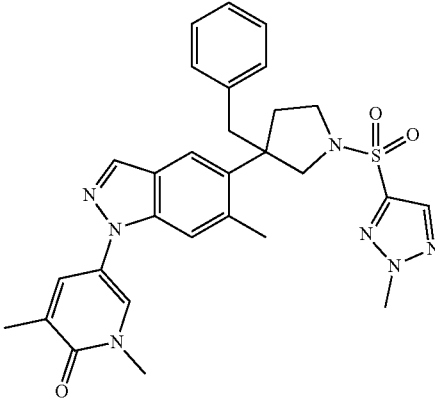

535
-continued
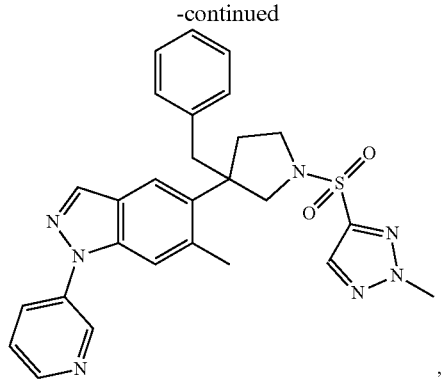
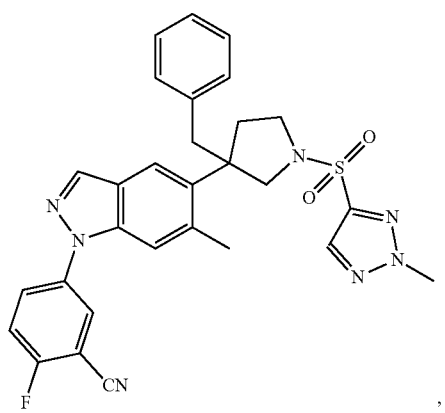
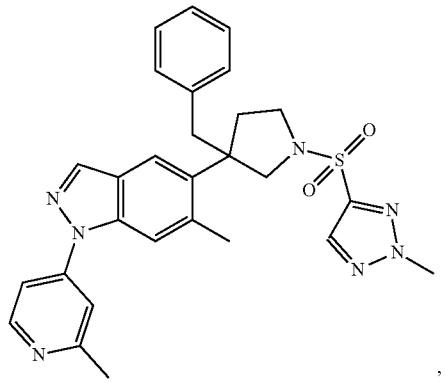
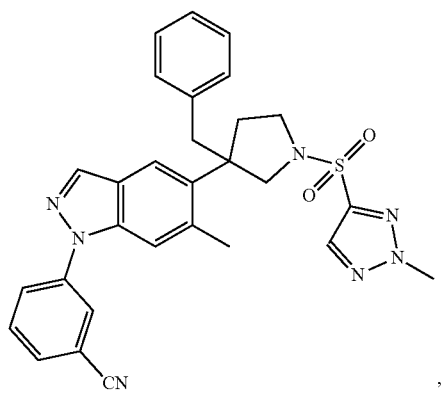
536
-continued
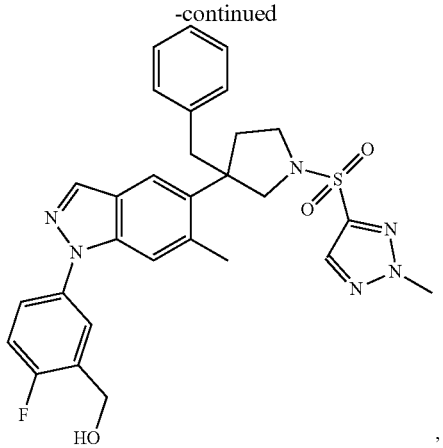
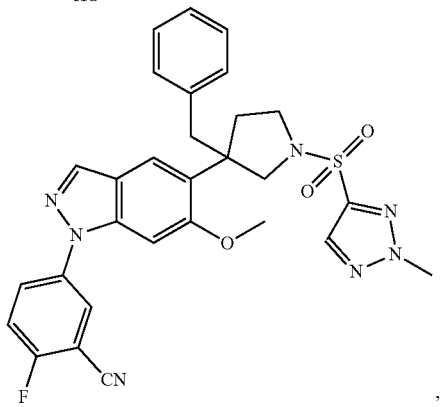
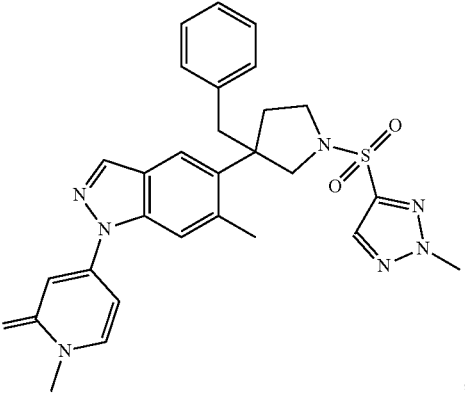
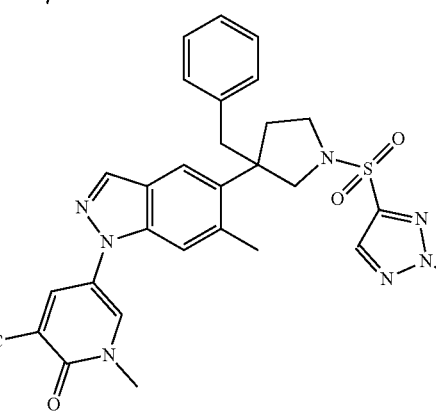

537
-continued
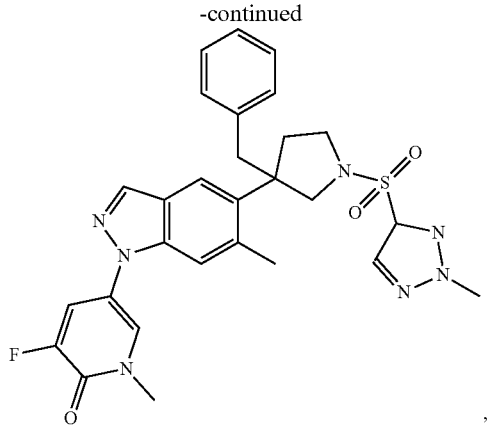
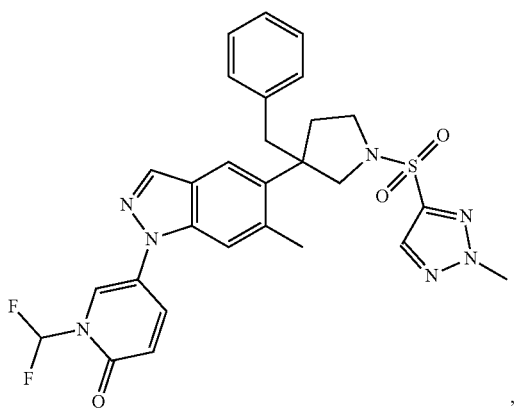
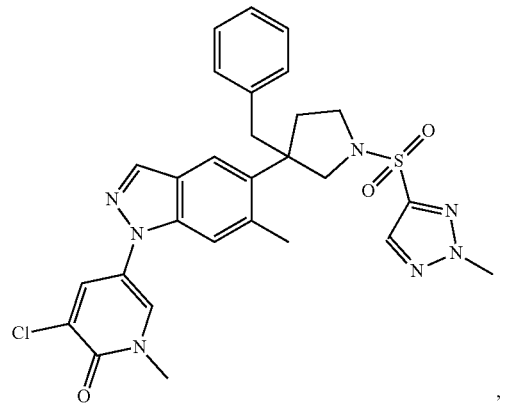
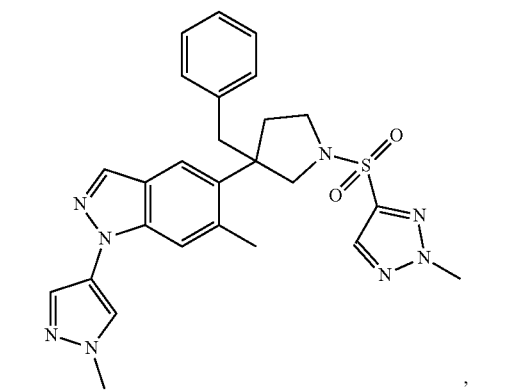
538
-continued
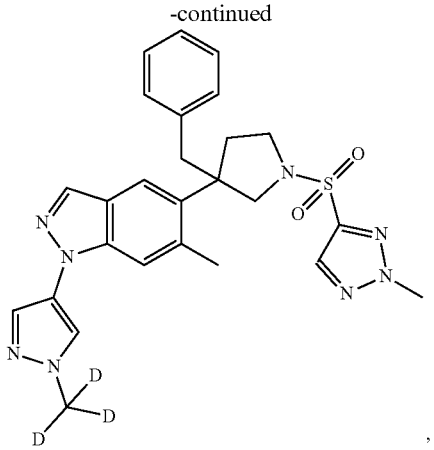
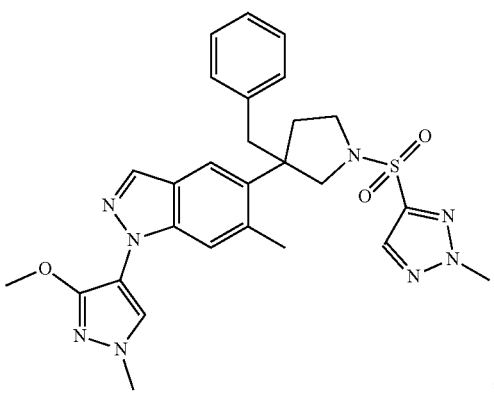
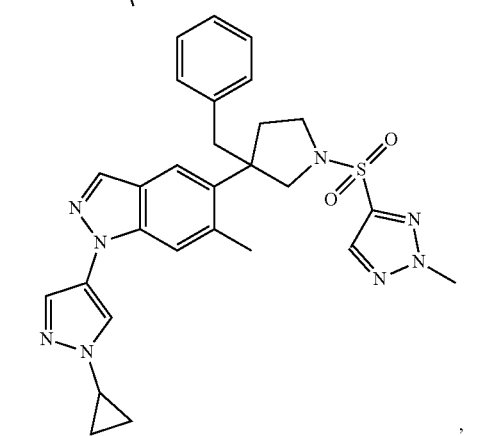
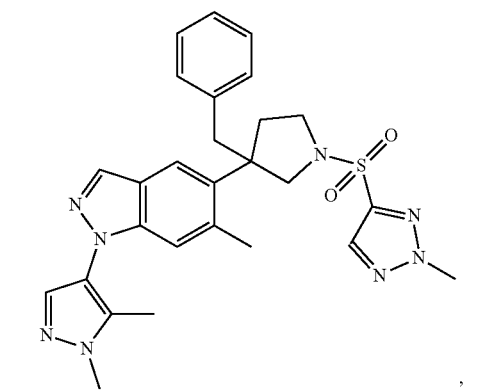

539
-continued
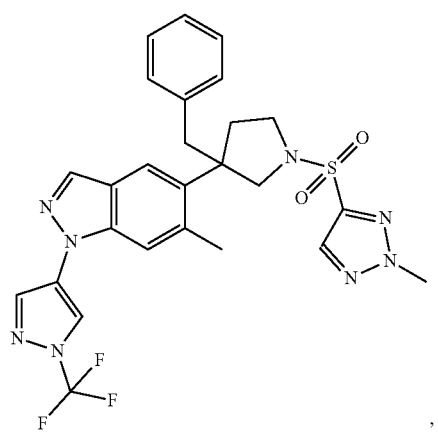
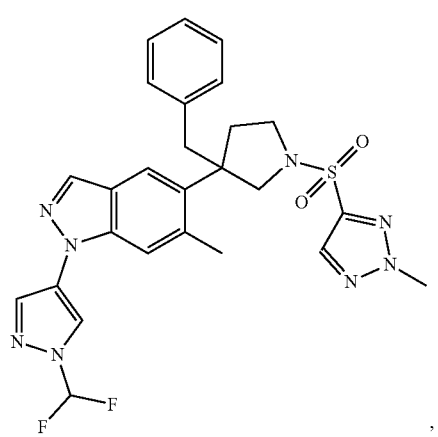
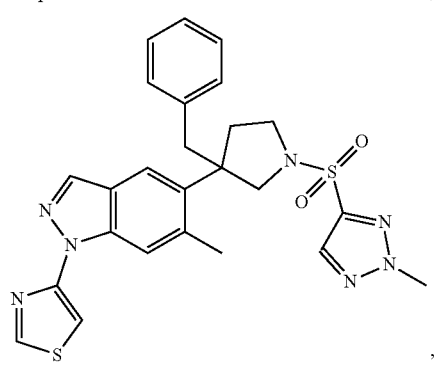
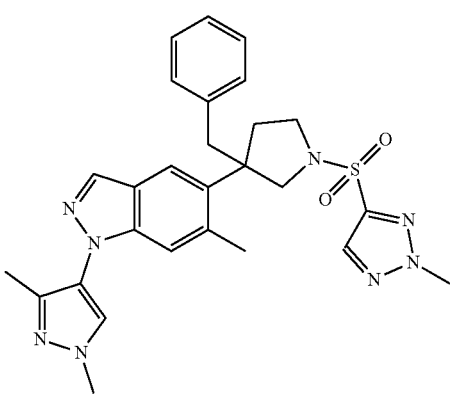
540
-continued
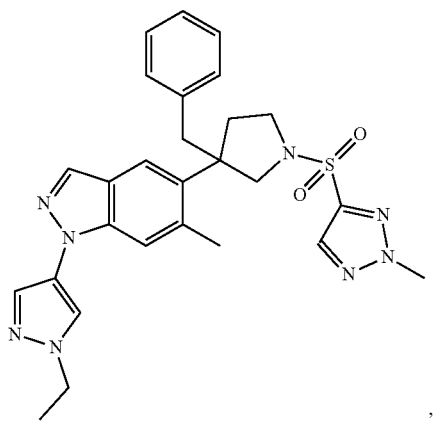
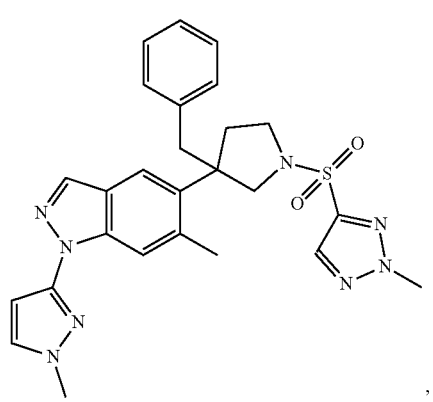
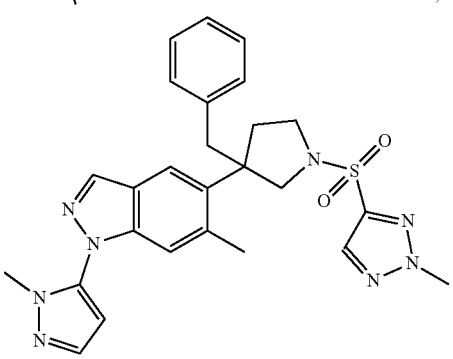
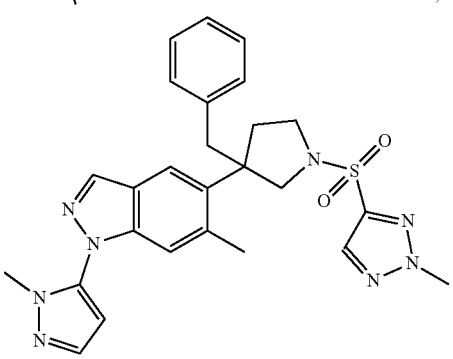

541
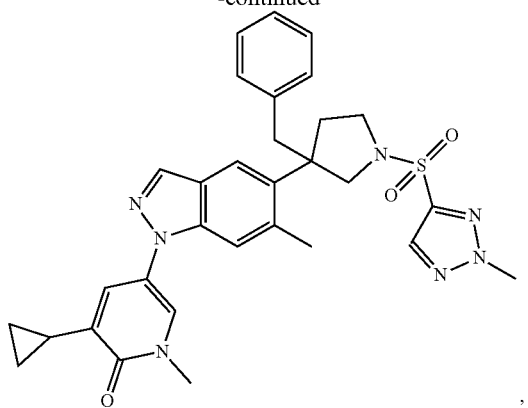
542
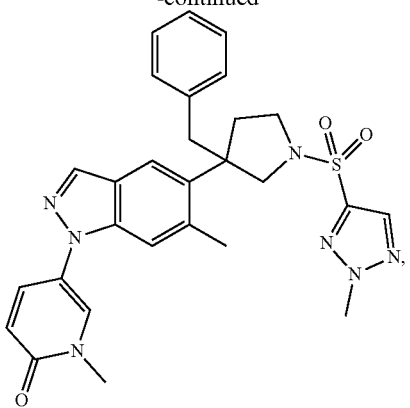

543
-continued
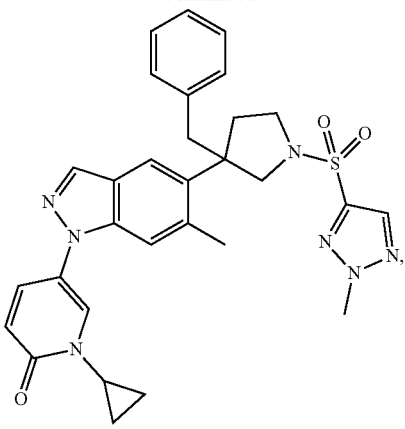
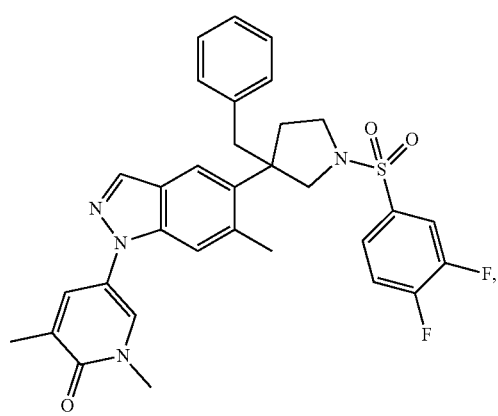
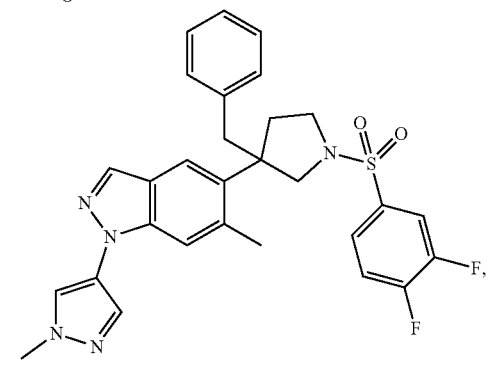
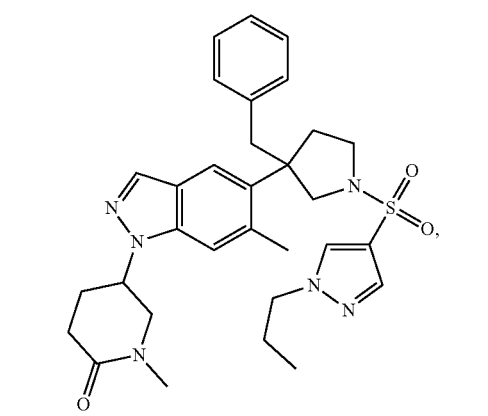
544
-continued
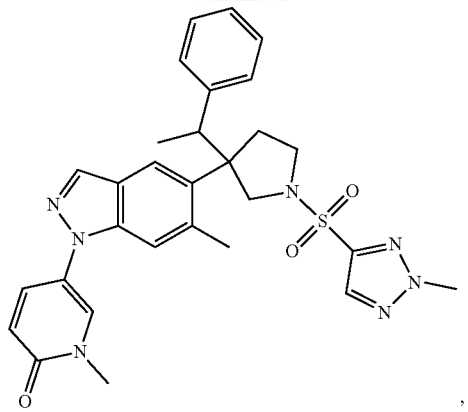
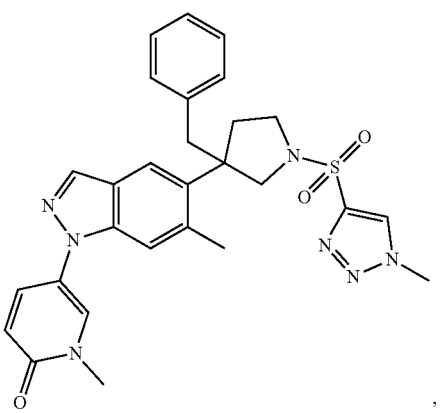
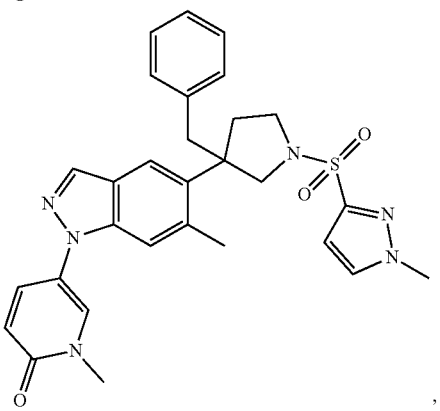
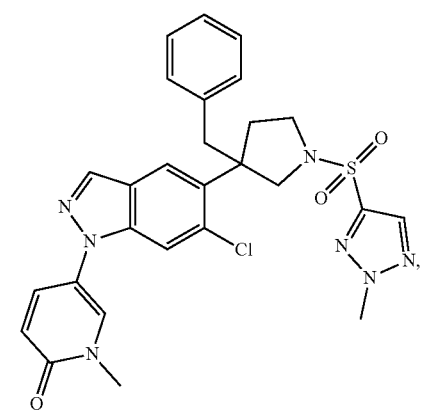

545
-continued
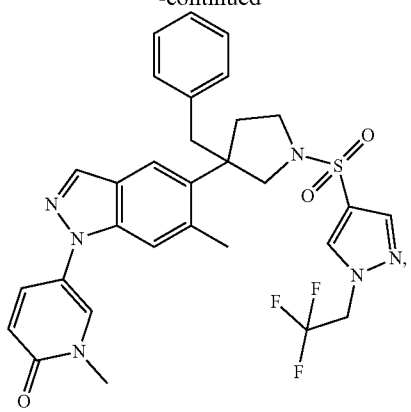
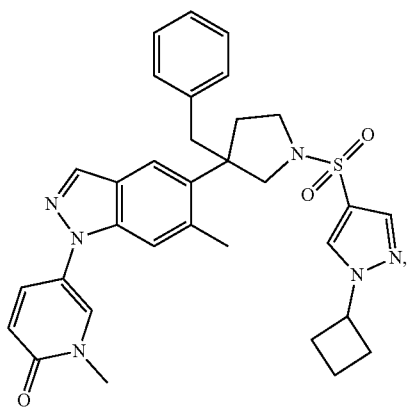
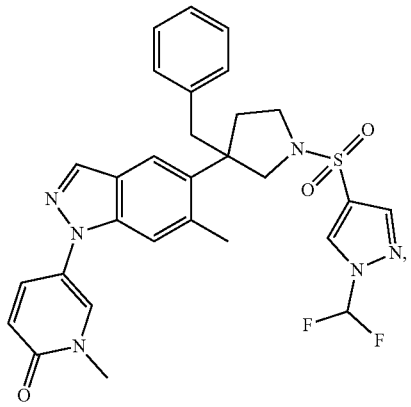
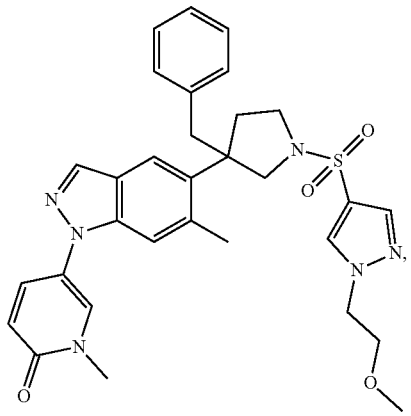
546
-continued
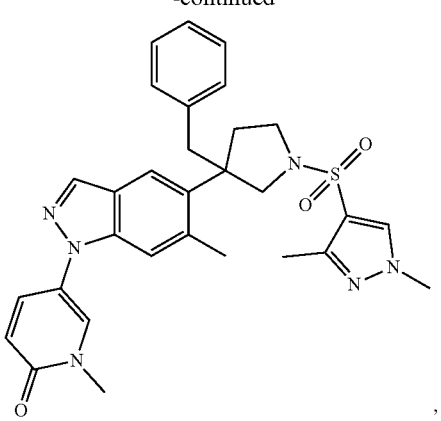
,
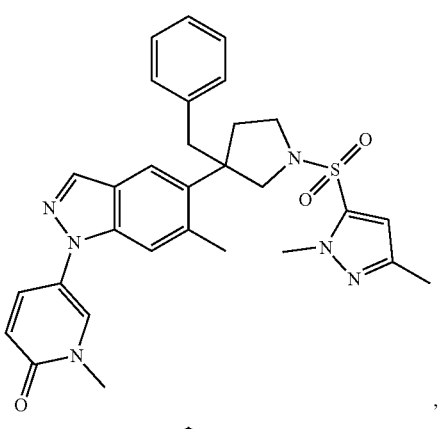
,
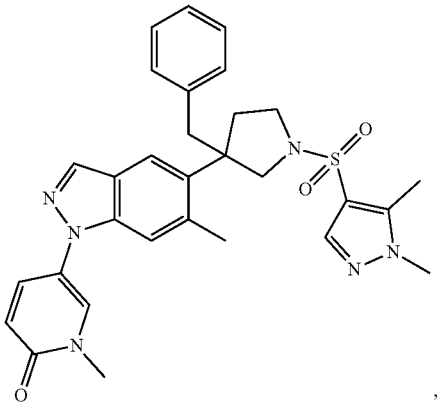
,
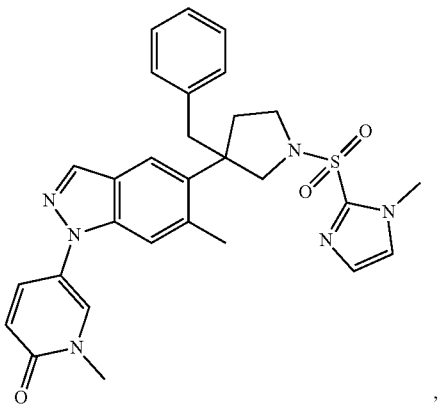
, 547
-continued
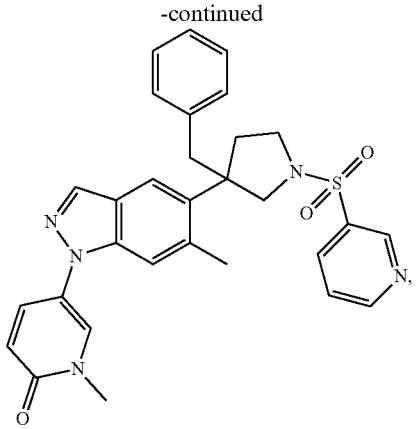
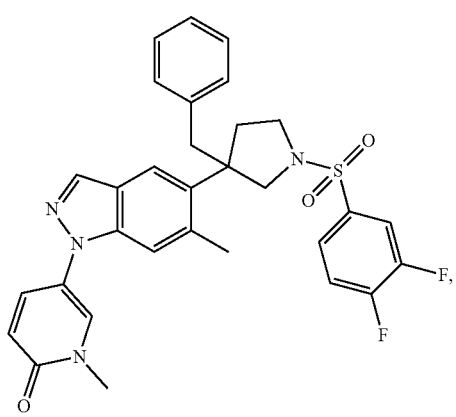
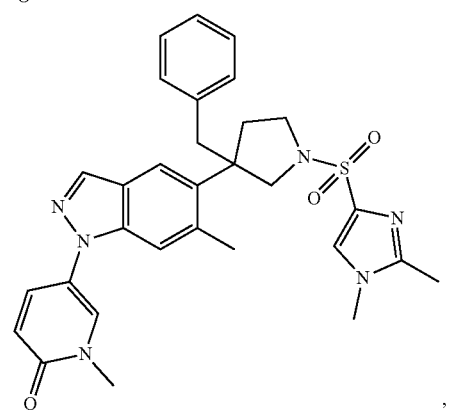
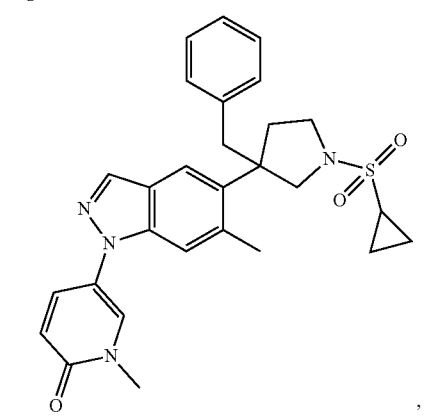
548
-continued
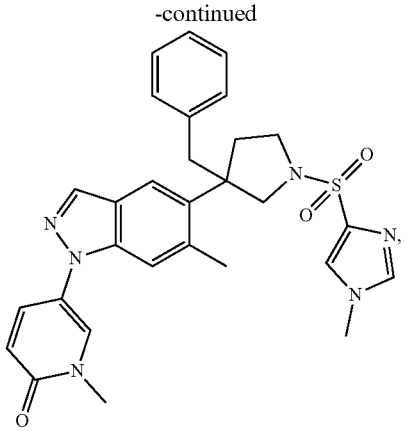
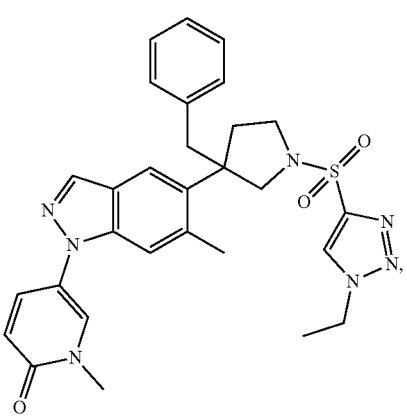
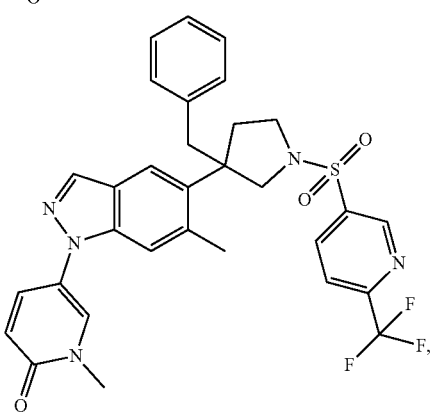
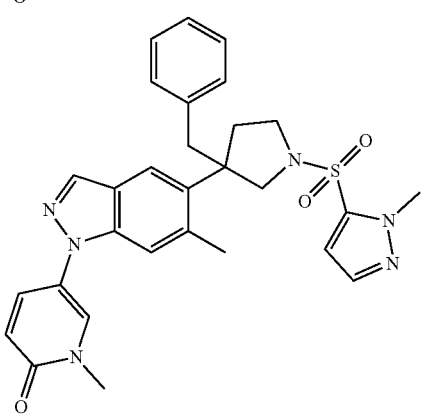

549
-continued
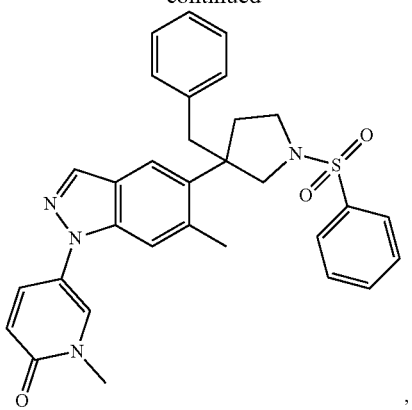
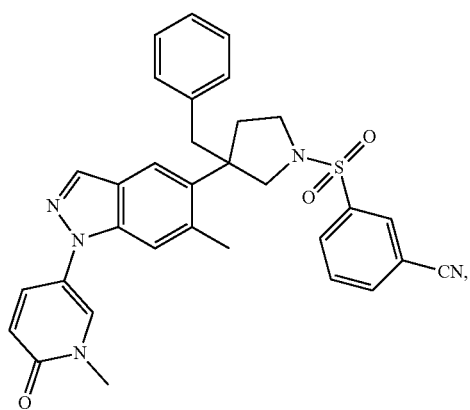
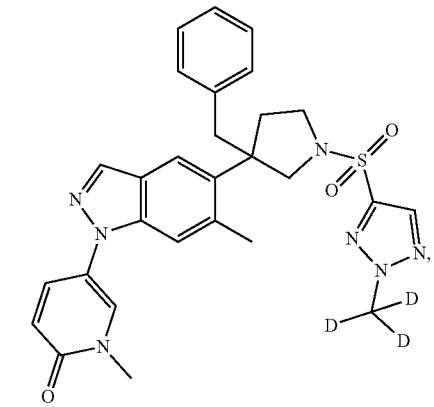
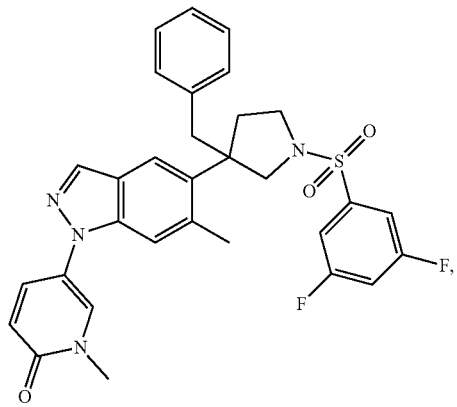
550
-continued
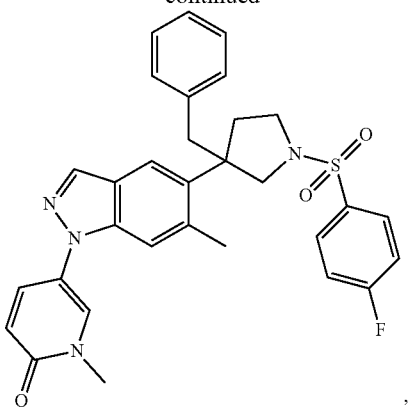
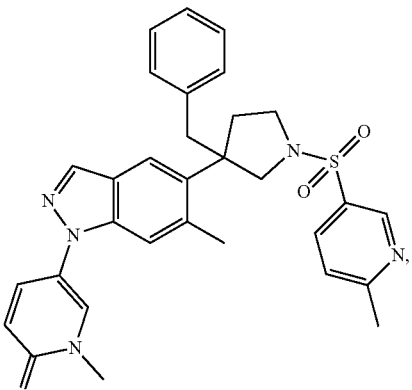
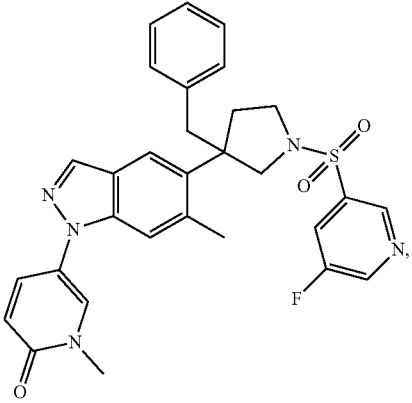
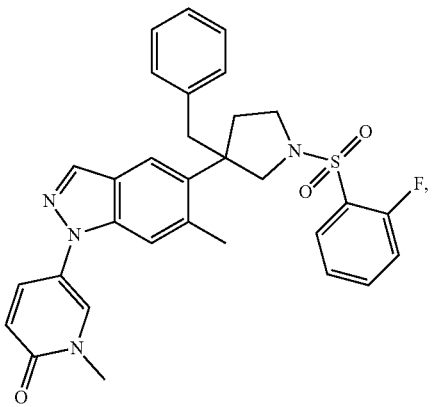

551
-continued
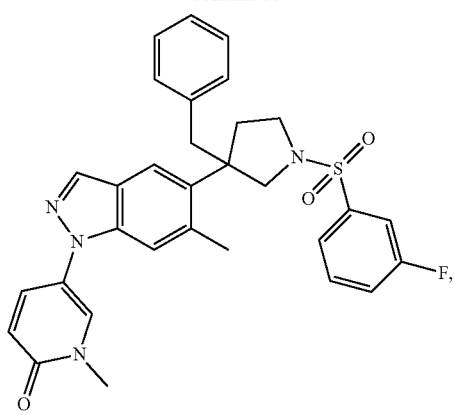
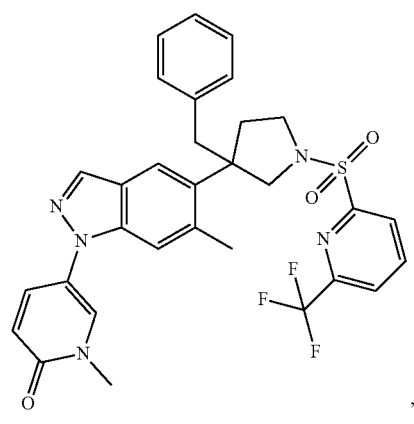
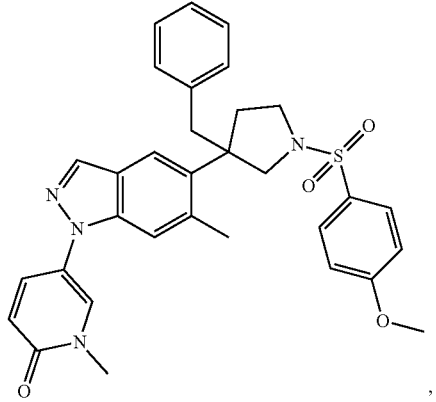
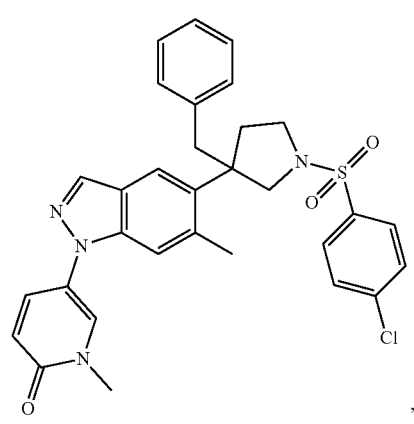
552
-continued
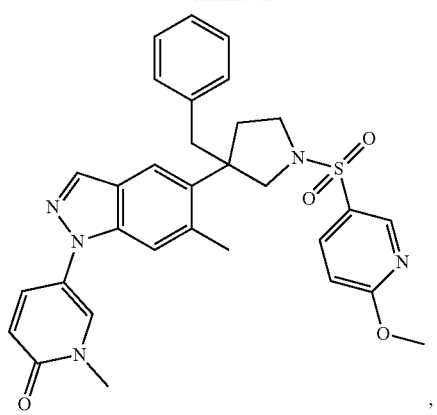
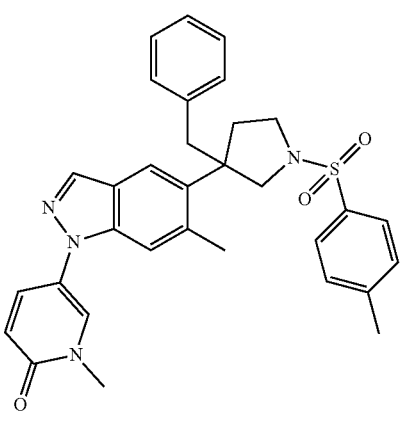
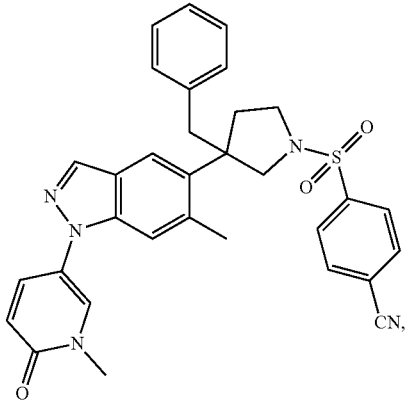
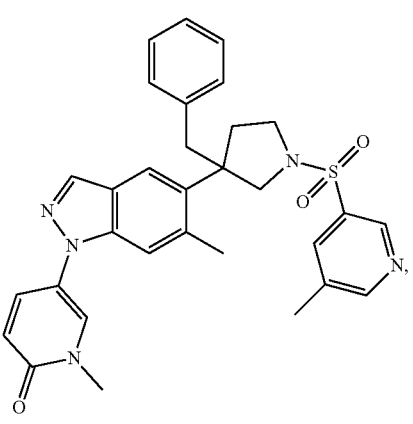

553
-continued
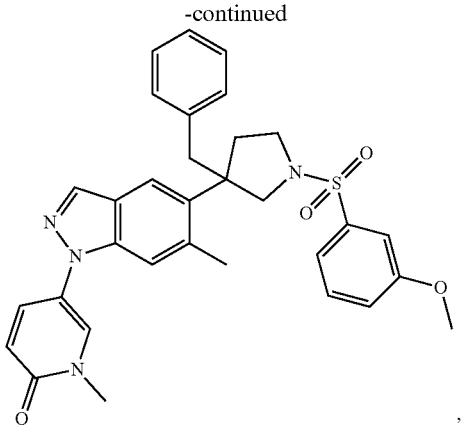
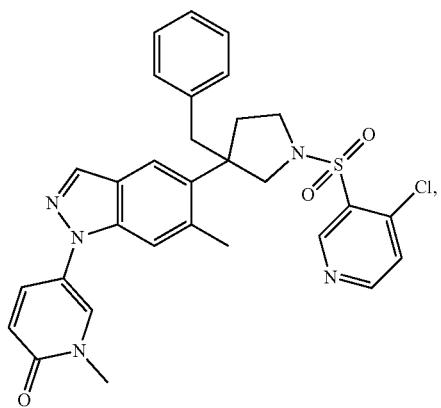
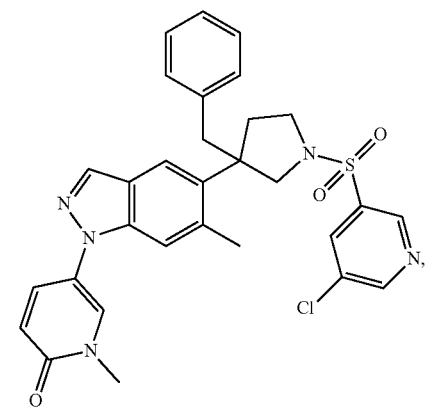
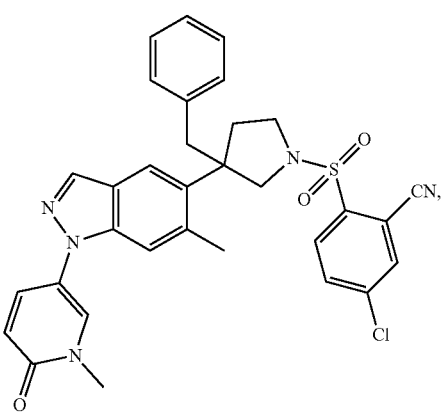
554
-continued
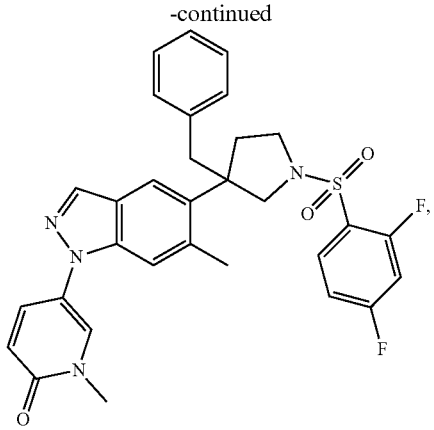
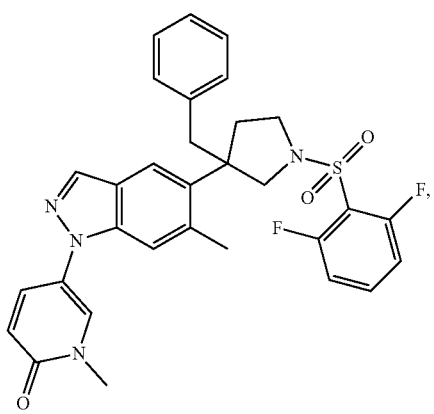
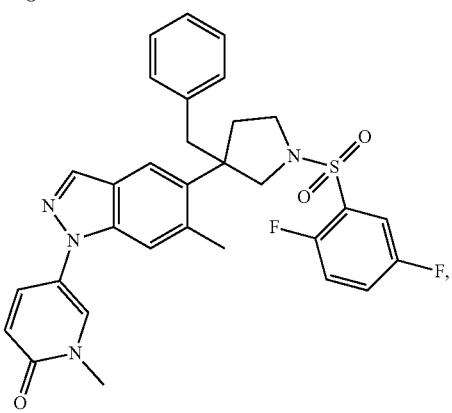
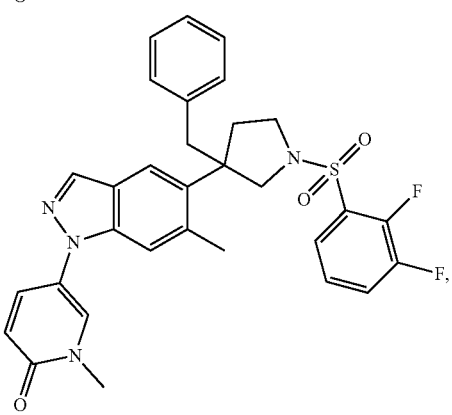

555
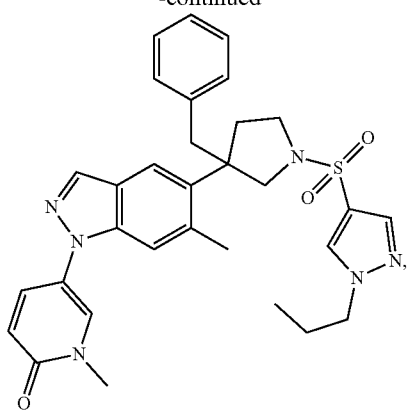
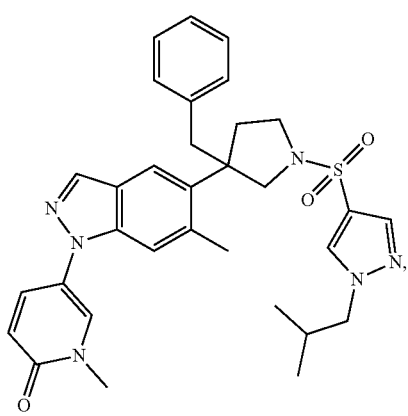
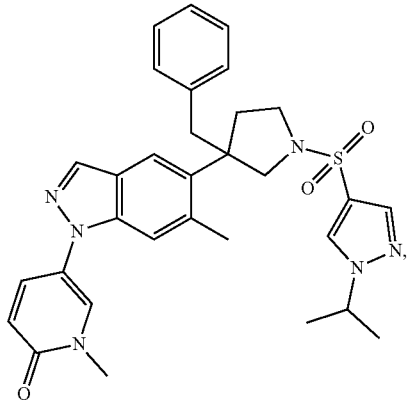
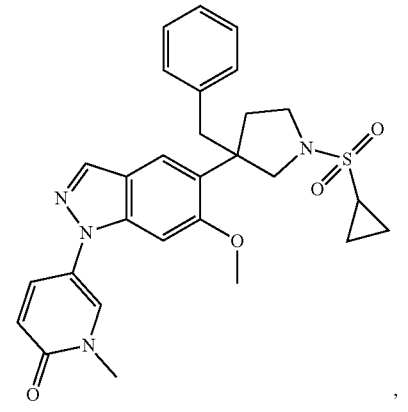
556
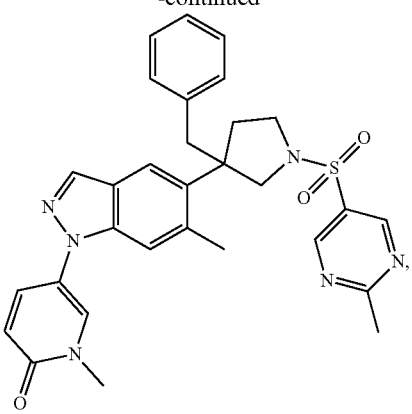
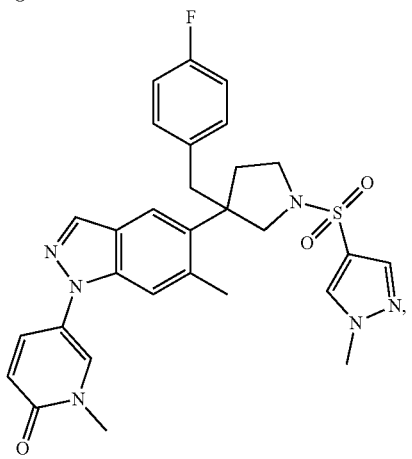
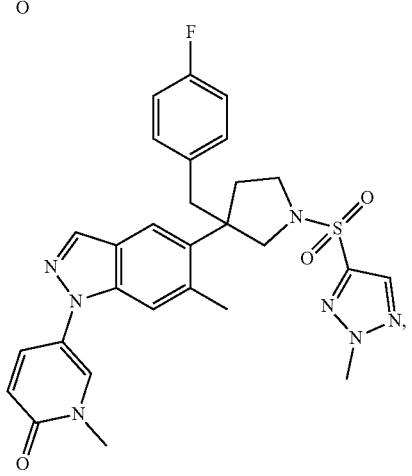
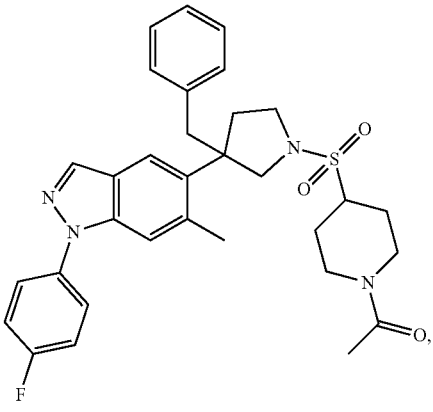

557
-continued
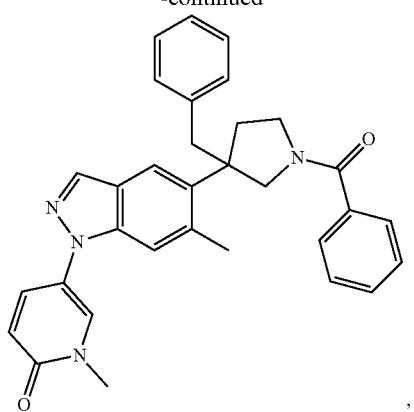
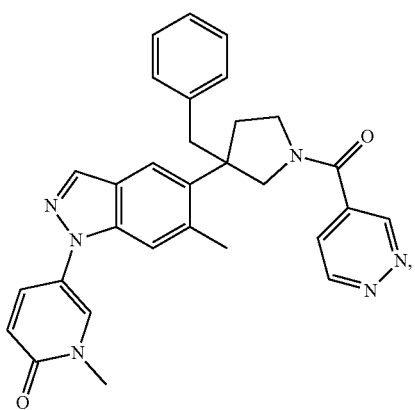
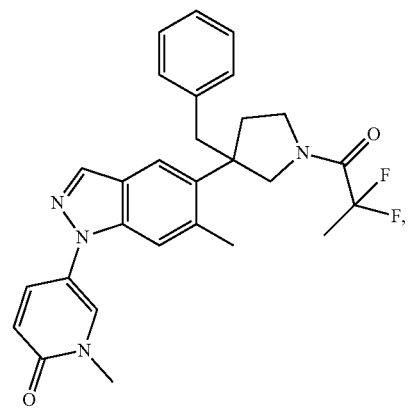
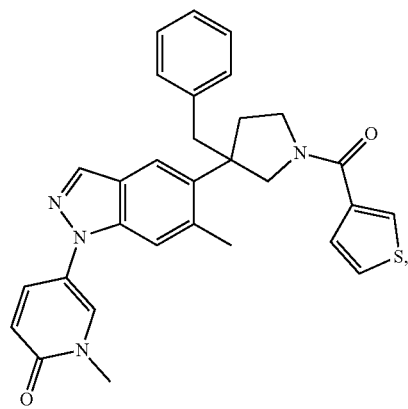
558
-continued
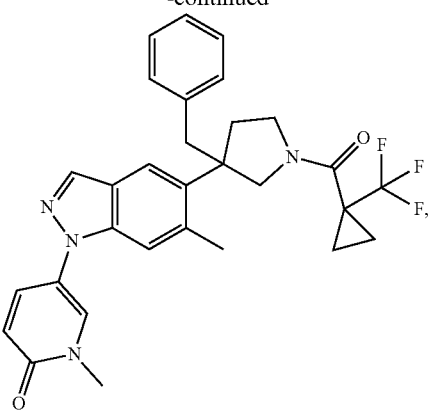
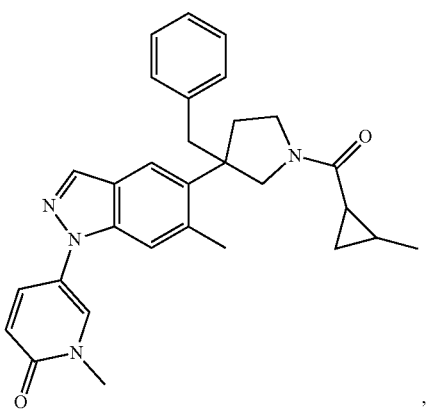
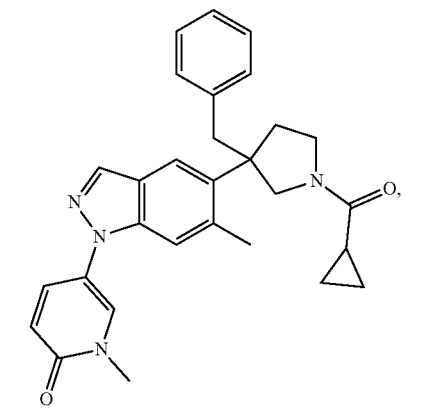
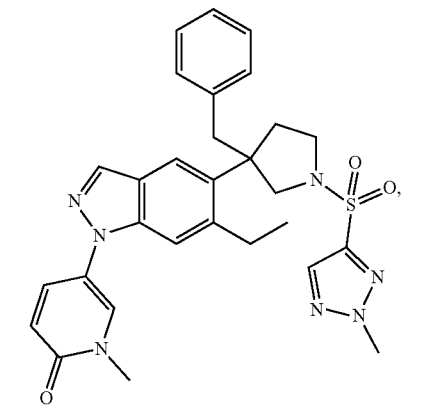

559
-continued
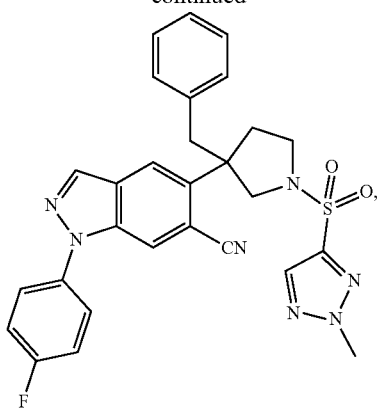
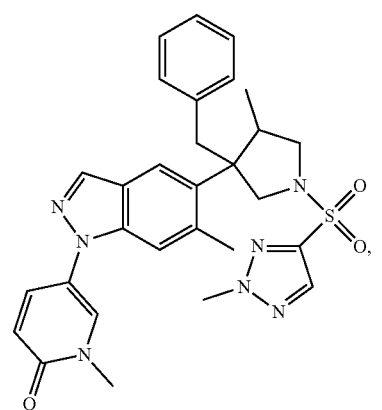
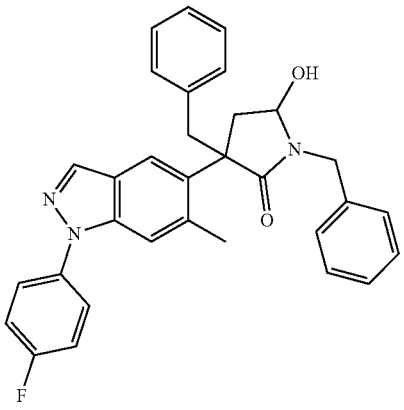
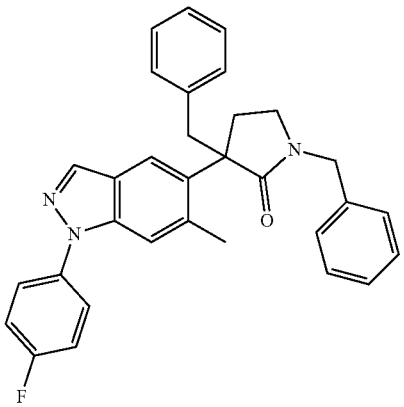
560
-continued
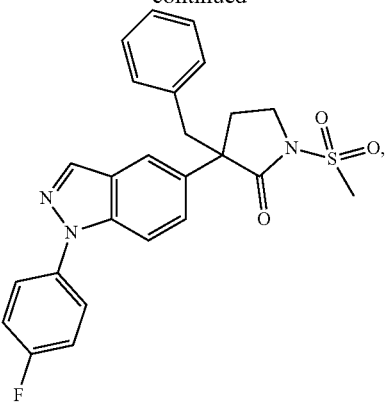

561
-continued

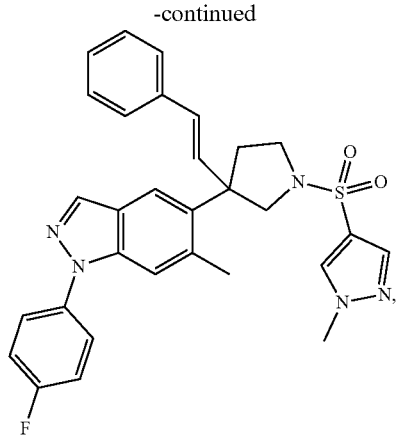

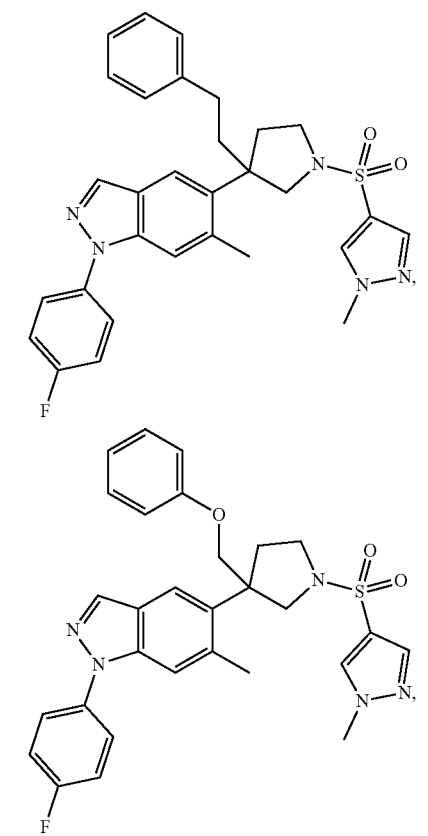

562
-continued

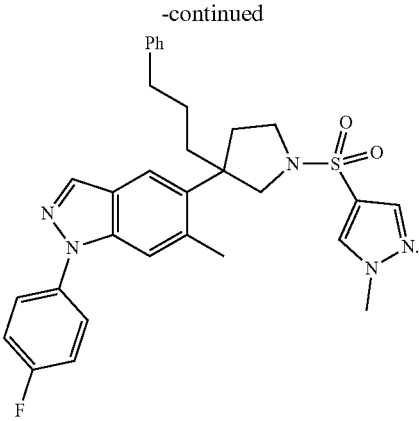

22. A pharmaceutical composition comprising a compound of claim 1, or a pharmaceutically acceptable salt thereof, and a pharmaceutically acceptable excipient.

23. The compound of claim 1, or a pharmaceutically acceptable salt thereof, having the structure:

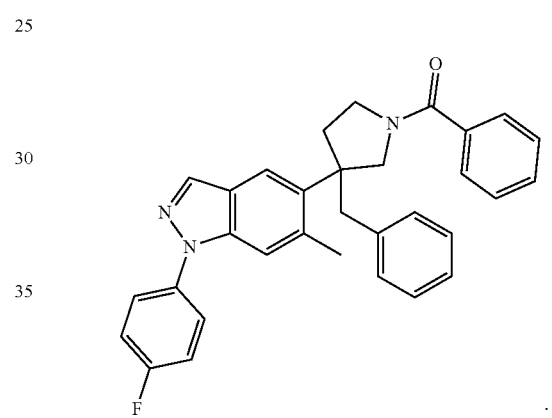

24. The compound of claim 1, or a pharmaceutically acceptable salt thereof, having the structure:

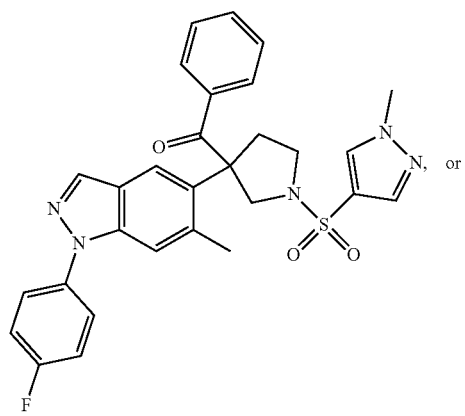

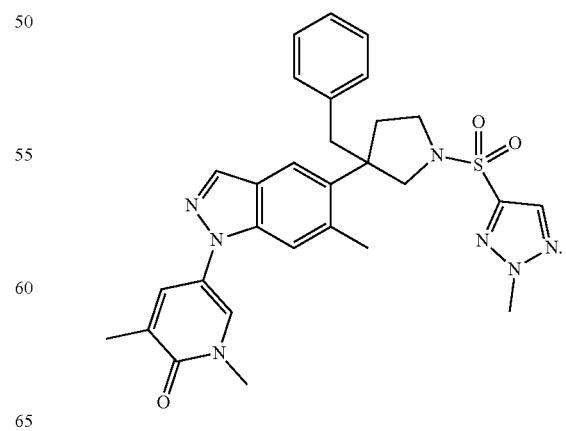

25. The compound of claim 1, or a pharmaceutically acceptable salt thereof, having the structure:

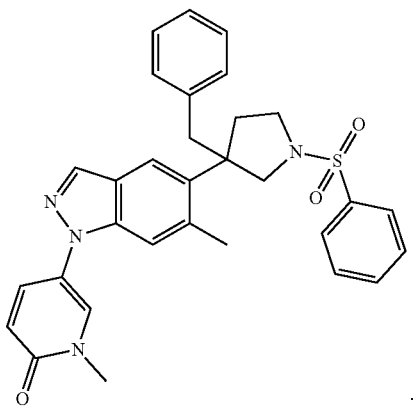 [SMILES: Cc1cc2c(cnn2-c2ccc(=O)n(C)c2)cc1C1(Cc2ccccc2)CCN(S(=O)(=O)c2ccccc2)C1]

26. The compound of claim 1, or a pharmaceutically acceptable salt thereof, having the structure:

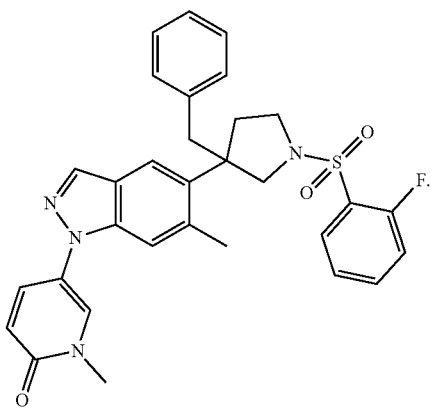 [SMILES: Cc1cc2c(cnn2-c2ccc(=O)n(C)c2)cc1C1(Cc2ccccc2)CCN(S(=O)(=O)c2ccccc2F)C1]

27. The compound of claim 1, or a pharmaceutically acceptable salt thereof, having the structure:

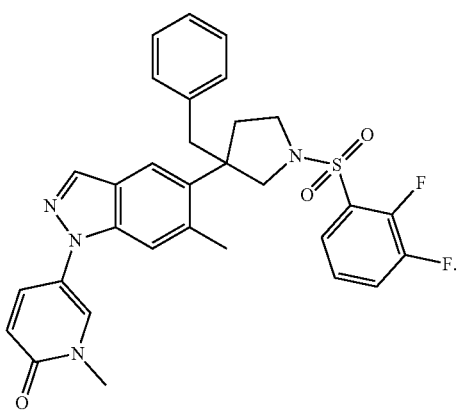 [SMILES: Cc1cc2c(cnn2-c2ccc(=O)n(C)c2)cc1C1(Cc2ccccc2)CCN(S(=O)(=O)c2cccc(F)c2F)C1]

28. The compound of claim 1, or a pharmaceutically acceptable salt thereof, having the structure:

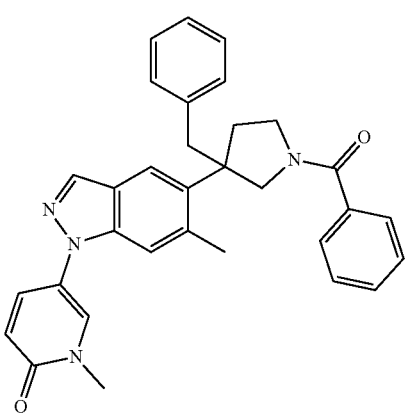

* * * * *